United States Patent
Borcherding et al.

(10) Patent No.: US 7,541,368 B2
(45) Date of Patent: Jun. 2, 2009

(54) PYRAZOLES AS INHIBITORS OF TUMOR NECROSIS FACTOR

(75) Inventors: David Roger Borcherding, Bangor, PA (US); Alexandre Gross, Jersey City, NJ (US); Patrick W. Shum, Flemington, NJ (US); Nicole Willard, Doylestown, PA (US); Brian S. Freed, Phillipsburg, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 226 days.

(21) Appl. No.: 11/264,063

(22) Filed: Nov. 1, 2005

(65) Prior Publication Data

US 2006/0063796 A1 Mar. 23, 2006

Related U.S. Application Data

(63) Continuation of application No. PCT/US2004/013875, filed on May 5, 2004.

(60) Provisional application No. 60/468,285, filed on May 6, 2003.

(51) Int. Cl.
*C07D 401/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)
*A01N 43/42* (2006.01)
*A01N 43/40* (2006.01)
*A61K 31/44* (2006.01)
*A61K 31/445* (2006.01)

(52) U.S. Cl. .................. 514/304; 514/326; 546/125; 546/208

(58) Field of Classification Search ............ 546/125, 546/208; 514/304, 326
See application file for complete search history.

(56) References Cited

FOREIGN PATENT DOCUMENTS

| WO | WO9932110 | 7/1999 |
| WO | WO0043384 | 7/2000 |

OTHER PUBLICATIONS

Dermer (Bio/Technology, 1994, 12:320).*
Freshney (Culture of Animal Cells, A Manual of Basic Technique, Alan R. Liss, Inc., 1983, New York, p. 4).*
Dumas et al., Bioorganic & Medicinal Chemistry Letters (2002), 12(12), 1559-1562.*
U.S. Appl. No. 09/909,966, filed Jul. 19, 2001, Goldstein, et al.

* cited by examiner

*Primary Examiner*—D. Margaret Seaman
*Assistant Examiner*—Niloofar Rahmani
(74) *Attorney, Agent, or Firm*—James W. Bolcsak

(57) ABSTRACT

The present invention provides compounds of Formula (I)

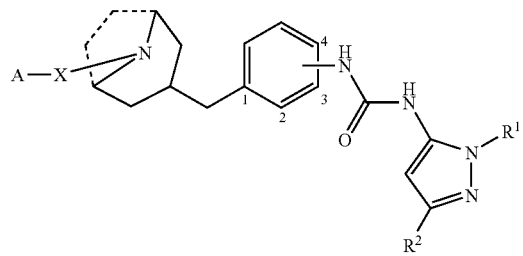

Formula (I)

and ester prodrugs, pharmaceutically acceptable salts or solvates of such compounds; or ester prodrugs of such salts or solvates; pharmaceutical compositions comprising such compounds, their preparation, and their pharmaceutical use in the treatment of disease states capable of being modulated by the inhibition of p38 kinase and/or tumor necrosis factor (TNF).

24 Claims, No Drawings

PYRAZOLES AS INHIBITORS OF TUMOR NECROSIS FACTOR

This invention is directed to a series of pyrazoles, their preparation, pharmaceutical compositions containing these compounds, and their pharmaceutical use in the treatment of disease states capable of being modulated by the inhibition of p38 kinase and/or tumor necrosis factor (TNF).

P38 kinase is a widely expressed mitogen/stress-activated protein kinase that is activated via a complex phosphorylation cascade by inflammatory and other stimuli. It plays an important role in regulating the production of TNF-alpha and other proinflammatory cytokines such as IL-1beta. Substantial evidence indicates that p38 regulates TNF-alpha release at the post-transcriptional level via regulatory elements that bind to the AU-rich 3'-untranslated region of the mRNA for TNF-alpha. As well as regulating inflammatory proteins, p38 also controls the expression of proteins that are involved in the transduction of pain responses in peripheral and central neurons. Thus, inhibitors of p38 kinase are useful for the treatment of inflammatory conditions associated with over-production of TNF-alpha and other pro-inflammatory cytokines as well as pain hypersensitivity.

Tumour necrosis factor (TNF) is an important pro-inflammatory cytokine which causes hemorrhagic necrosis of tumors and possesses other important biological activities. TNF is released by activated macrophages, activated T-lymphocytes, natural killer cells, mast cells and basophils, fibroblasts, endothelial cells and brain astrocytes among other cells.

The principal in vivo actions of TNF can be broadly classified as inflammatory and catabolic. It has been implicated as a mediator of endotoxic shock, inflammation of joints and of the airways, immune deficiency states, allograft rejection, and in the cachexia associated with malignant disease and some parasitic infections. In view of the association of high serum levels of TNF with poor prognosis in sepsis, graft versus host disease and adult respiratory distress syndrome, and its role in many other immunologic processes, this factor is regarded as an important mediator of general inflammation.

TNF primes or activates neutrophils, eosinophils, and endothelial cells to release tissue damaging mediators and increase the expression of adhesion molecules. In fibroblasts, TNF stimulates the production of collagenase, an enzyme implicated in the joint destruction in rheumatoid arthritis and other metalloproteinases. TNF also activates monocytes, macrophages and T-lymphocytes to cause the production of colony stimulating factors and other pro-inflammatory cytokines such IL-1, IL-6, IL-8 and GM-CSF, which in some cases mediate the end effects of TNF. The ability of TNF to activate T-lymphocytes, monocytes, macrophages and related cells has been implicated in the progression of Human Immunodeficiency Virus (HIV) infection. In order for these cells to become infected with HIV and for HIV replication to take place the cells must be maintained in an activated state. Cytokines such as TNF have been shown to activate HI replication in monocytes and macrophages. Features of endotoxic shock such as fever, metabolic acidosis, hypotension and intravascular coagulation are thought to be mediated through the actions of TNF. The cachexia associated with certain disease states is mediated through indirect effects on protein catabolism. TNF also promotes bone resorption and acute phase protein synthesis.

TNF-alpha inhibits surfactant protein C gene transcription, which may contribute to abnormalities of surfactant homeostasis associated with pulmonary injury and infection, induces mucin hypersecretion and mediates the recruitment of neutrophils and eosinophils during airway inflammation. Although TNF-alpha inhibits collagen synthesis in fibroblasts, a number of studies point to it being pro-fibrotic in vivo. Thus, by inhibiting TNF-alpha production, the compounds of the invention are useful in suppressing the inflammation and airways remodelling that occurs in asthma.

TNF-alpha is present in high concentration in the sputum of chronic obstructive pulmonary disease (COPD) patients particularly during exacerbations. TNF-alpha induces the production of several inflammatory proteins, including chemokines and proteases, in epithelial cells and macrophages. Serum concentrations of TNF-alpha and stimulated TNF-alpha production from peripheral blood monocytes are increased in weight-losing COPD patients, suggesting that it may play a role in the cachexia of severe COPD. Thus, the compounds of the invention through inhibition of TNF-alpha are useful in reversing the skeletal wasting seen in COPD as well as reducing the airway inflammatory response in this disease.

TNF-alpha inhibits the ability of insulin to stimulate glucose uptake in adipose tissue. In obesity the overproduction of TNF is thought to cause an insulin-resistant state. Thus, by blocking TNF release the compounds of the invention are useful in the treatment of diabetes.

TNF-alpha can induce angiogenesis in normally avascular tissue, possibly through up-regulation of other pro-inflammatory cytokines, upregulation of adhesion molecules, stimulation of matrix metalloproteinase expression and increased prostaglandin production. Thus, inhibition of TNF-alpha release by compounds of the invention will have benefit in angiogenesis dependent diseases including arthritis, diabetic retinopathies and cancer.

Tumor necrosis factor (TNF) and other cytokines (e.g., interleukin-1) play an important role in the pathogenesis of atherosclerotic lesions of the coronary artery, the acute ischemic event associated with myocardial infarction, the progression of myocardiopathies or the loss of myocardial function in congestive heart failure. Thus by inhibiting TNF-alpha and other inflammatory cytokines, the compounds of the invention will be useful for the treatment of heart disease, including myocardial infarction, thrombosis, angina and acute coronary syndrome.

TNF-alpha plays an important role in neuronal death that occurs in neurodegenerative diseases. Furthermore, p38 is implicated in neuronal apoptosis. Thus, the compounds of the invention, through inhibition of TNF-alpha or suppression of neuronal apoptosis are useful in the treatment of diseases such as Alzheimer's disease, Huntingdon's disease and Parkinson's disease as well as stroke.

The discussion herein relates to disease states associated with TNF including those disease states related to the production of TNF itself, and disease states associated with other cytokines, such as, but not limited to IL-1 or IL-6, that are modulated by association with TNF. For example, a IL-1 associated disease state, where IL-1 production or action is exacerbated or secreted in response to TNF, would therefore be considered a disease state associated with TNF. TNF-alpha and TNF-beta are also herein referred to collectively as "TNF" unless specifically delineated otherwise, since there is a close structural homology between TNF-alpha (cachectin) and TNF-beta (lymphotoxin) and each of them has a capacity to induce similar biological responses and bind to the same cellular receptor.

We have now found a novel group of pyrazoles which have valuable pharmaceutical properties, in particular the ability to regulate proteins that mediate cellular activity, for example p38 kinase and TNF.

Thus, in one aspect, the present invention is directed to compounds of Formula (I)

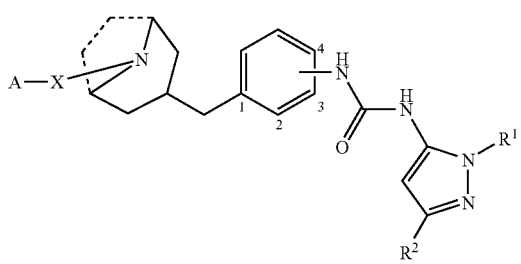

Formula (I)

wherein

is an optional ethylene bridge;

$R^1$ is alkyl, cycloalkyl, aryl or aryl substituted with one or more substituents selected from alkyl, alkoxy and amino, or $R^1$ is pyridyl or pyridyl substituted with one or more substituents selected from alkyl, alkoxy and amino;

$R^2$ is optionally substituted alkyl, alkoxyalkyl, optionally substituted cycloalkyl, optionally substituted cycloalkylalkyl, arylalkyl, or $R^2$ is arylalkyl substituted with one or more substituents selected from alkyl and alkoxy;

X is —C(O)—, —C(O)—CH$_2$—, —S(O)$_2$—, or —NH—C(O)—; and

A is optionally substituted alkenyl, optionally substituted alkoxy, optionally substituted alkoxyalkyl, optionally substituted alkyl, optionally substituted alkynyl, optionally substituted aryl, optionally substituted arylalkyl, optionally substituted arylalkoxy, optionally substituted arylalkoxyalkyl, optionally substituted aryloxy, optionally substituted aryloxyalkyl, optionally substituted cycloalkenyl, optionally substituted cycloalkyl, optionally substituted cycloalkylalkyl, optionally substituted cycloalkyloxy, optionally substituted cycloalkyloxyalkyl, optionally substituted cyclalkylalkoxy, optionally substituted cycloalkylalkoxyalkyl, optionally substituted heteroaryl, optionally substituted heteroarylalkyl, optionally substituted heteroaryloxy, optionally substituted heteroaryloxyalkyl, optionally substituted heteroarylalkoxy, optionally substituted heteroarylalkoxyalkyl, optionally substituted heterocycloalkyl, optionally substituted heterocycloalkylalkyl, optionally substituted heterocycloalkyloxy, optionally substituted heterocycloalkyloxyalkyl; or an ester prodrug, pharmaceutically acceptable salt or solvate of such compound; or an ester prodrug of such salt or solvate.

In the present specification, the term "compounds of the invention", and equivalent expressions, are meant to embrace compounds of Formulas (I) to (VI) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing one or more carbon-carbon double bonds and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl. "Optionally substituted alkenyl" means an alkenyl group which may be substituted by one or more alkyl group substituents.

"Alkoxy" means an alkyl-O— group in which the alkyl group is as described herein. Exemplary alkoxy groups include methoxy, ethoxy, n-propoxy, i-propoxy, n-butoxy and heptoxy.

"Optionally substituted alkoxy" means an alkoxy group which may be substituted on the alkyl portion by one or more alkyl group substituents.

"Alkoxyalkyl" means an alkyl-O-alkyl- group in which the alkyl group is as described herein. Exemplary alkoxymethyl groups include methoxymethyl and ethoxymethyl. "Optionally substituted alkoxyalkyl" means an alkoxyalkyl which may be substituted on the alkyl portions by one or more alkyl group substituents.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain. Particular alkyl groups have from 1 to about 6 carbon atoms. Exemplary alkyl groups include $C_{1-6}$alkyl groups such as methyl, ethyl, n-propyl, isopropyl, n-butyl, sec-butyl, isobutyl and t-butyl. "Optionally substituted alkyl" means an alkyl group which may be substituted by one or more alkyl group substituents, where "alkyl group substituent" includes, for example, includes, for example, acyl, acylamino, alkoxy, alkoxycarbonyl, alkylenedioxy, alkylsulfinyl, alkylsulfonyl, alkylthio, aroyl, aroylamino, aryl, arylalkyl, arylalkoxy, arylalkoxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyl, heteroarylalkoxy, heteroaroylamino, heteroaryloxy, hydroxy, nitro, oxo, trifluoromethyl, $Y^7Y^8N$—, $Y^7Y^8NCO$—, $Y^7Y^8NSO_2$—, where $Y^7$ and $Y^8$ are independently hydrogen, alkyl, aryl, arylalkyl, heteroaryl and heteroarylalkyl, or $Y^7$ and $Y^8$, together with the nitrogen atom to which they are attached, form a nitrogen-containing saturated alicyclic ring containing from 3 to 7 members, $Y^7Y^8N$—$C_{2-6}$alkylene-$Z^2$-, where $Z^2$ is O, $NR^5$ or $S(O)_n$, and where $R^5$ is hydrogen or alkyl, and n is 1 or 2, alkylC(=O)—$Y^7N$—, or alkylSO$_2$—$Y^7N$—.

"Alkylene" means a straight or branched bivalent hydrocarbon chain having from 1 to about 15 carbon atoms. Particular alkylene groups are the lower alkylene groups having from 1 to about 6 carbon atoms. Exemplary groups include methylene and ethylene.

"Alkylsulfinyl" means an alkyl-SO— group in which the alkyl group is as previously described. Preferred groups are those in which the alkyl group is $C_{1-6}$alkyl.

"Alkylsulfonyl" means an alkyl-$SO_2$— group in which the alkyl group is as previously described. Preferred groups are those in which the alkyl group is $C_{1-6}$alkyl.

"Alkylsulfonylcarbamoyl" means an alkyl-$SO_2$—NH—C(=O)— group in which the alkyl group is as previously described. Preferred alkylsulfonylcarbamoyl groups are those in which the alkyl group is $C_{1-6}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 6 carbon atoms in the chain. Exemplary alkynyl groups include ethynyl, propynyl, n-butynyl, i-butynyl, 3-methylbut-2-ynyl, and n-pentynyl. "Optionally substituted alkynyl" means an alkynyl group which may be substituted with one or more alkyl group substituents.

"Aroyl" means an aryl-CO— group in which the aryl group is as described herein. Exemplary groups include benzoyl and 1- and 2-naphthoyl.

"Aroylamino" is an aroyl-NH— group wherein aroyl is as previously defined.

"Aryl" as a group or part of a group denotes: (i) a monocyclic or multicyclic aromatic carbocyclic moiety of about 6 to about 14 carbon atoms, such as phenyl or naphthyl; or (ii) partially saturated multicyclic aromatic carbocyclic moiety in which an aryl and a cycloalkyl or cycloalkenyl group are fused together to form a cyclic structure, such as a tetrahydronaphthyl, indenyl or indanyl ring. "Optionally substituted aryl" groups may be substituted with one or more aryl group substituents which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyl, arylalkoxy, arylalkoxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyl, heteroarylalkoxy, heteroaroylamino, heteroaryloxy, hydroxy, nitro, trifluoromethyl, $Y^7Y^8N$—, $Y^7Y^8NCO$—, $Y^7Y^8NSO_2$—, where $Y^7$ and $Y^8$ are independently hydrogen, alkyl, aryl, arylalkyl, heteroaryl and heteroarylalkyl, or $Y^7$ and $Y^8$, together with the nitrogen atom to which they are attached, form a nitrogen-containing saturated alicyclic ring containing from 3 to 7 members, $Y^7Y^8N$—$C_{2-6}$alkylene-$Z^2$-, where $Z^2$ is O, $NR^5$ or $S(O)_n$, and where $R^5$ is hydrogen or al 1 or 2, alkylC(=O)—$Y^7N$—, or alkyl$SO_2$—$Y^7N$— or alkyl optionally substituted with aryl, cyano, heteroaryl, hydroxy, or $Y^7Y^8N$—.

"Arylalkyl" means an aryl-alkyl- group in which the aryl and alkyl moieties are as previously described. Preferred arylalkyl groups contain a $C_{1-6}$alkyl moiety. Exemplary arylalkyl groups include benzyl, 2-phenethyl and naphthlenemethyl. "Optionally substituted arylalkyl" means an arylalkyl group which may be substituted on the aryl portion by one or more aryl group substituents, and which may be substituted on the alkyl portion by one or more alkyl group substituents.

"Arylalkoxy" means an arylalkyl-O— group in which the arylalkyl group is as previously described. Exemplary arylalkoxy groups include benzyloxy and 1- or 2-naphthalenemethoxy. "Optionally substituted arylalkoxy" means an arylalkoxy group which may be substituted on the aryl portion by one or more aryl group substituents, and on the alkyl portion by one or more alkyl group substituents.

"Arylalkoxyalkyl" means an arylalkyl-O-alkyl- group in which the arylalkyl and alkyl groups are as previously described. Exemplary arylalkoxyalkyl groups include benzyloxymethyl and 1- or 2-naphthalenemethoxymethyl. "Optionally substituted arylalkoxyalkyl" means an arylalkoxyalkyl group which may be substituted on the aryl portion by one or more aryl group substituents, and on the alkyl portions by one or more alkyl group substituents.

"Arylalkoxycarbonyl" means an arylalkyl-O—CO— group in which the arylalkyl group is as previously described. An exemplary arylalkoxycarbonyl group is benzyloxycarbonyl.

"Aryloxyalkyl" means an aryl-O-alkyl group. An exemplary aryloxyalkyl group is phenoxymethyl. "Optionally substituted aryloxyalkyl" is an aryloxyalkyl group which may be substituted on the aryl portion by one or more aryl group substituents, and on the alkyl portion by one or more alkyl group substituents.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include optionally substituted phenoxy and naphthoxy. "Optionally substituted aryloxy" means an aryloxy group which may be substituted on the aryl portion by one or more aryl group substituents.

"Aryloxycarbonyl" means an aryl-O—CO— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylsulfonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Cycloalkenyl" means a non-aromatic monocyclic or multicyclic ring system containing at least one carbon-carbon double bond and having about 5 to about 10 carbon atoms. Exemplary monocyclic cycloalkenyl rings include cyclopentenyl, cyclohexenyl and cycloheptenyl. Exemplary multicyclic cycloalkenyl ring include norbornenyl. "Optionally substituted cycloalkenyl" means a cycloalkenyl group which may be substituted by one or more alkyl group substituents.

"Cycloalkoxyalkyl" means a cycloalkyl-O-alkyl- group in which the cycloalkyl group is as described hereinafter. Exemplary cycloalkoxyalkyl groups include cyclopropyloxymethyl and cyclopentyloxymethyl. "Optionally substituted cycloalkoxyalkyl" means a cycloalkoxyalkyl group which may be substituted by one or more alkyl group substituents.

"Cycloalkyl" means a non-aromatic monocyclic or multicyclic ring system of about 3 to about 10 carbon atoms. Exemplary monocyclic cycloalkyl rings include cyclopropyl, cyclopentyl, cyclohexyl and cycloheptyl. Exemplary multicyclic cycloalkyl rings include perhydronaphthyl, adamant- (1- or 2-)yl and norbornyl and spirocyclic groups e.g., spiro [4,4]non-2yl. "Optionally substituted cycloalkyl" means a cycloalkyl group which may be substituted by one or more alkyl group substituents.

"Cycloalkylalkyl" means a cycloalkyl-alkyl- group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl. "Optionally substituted cycloalkylalkyl" means a cycloalkylalkyl group which may be substituted by one or more alkyl group substituents.

"Cycloalkyloxy" means a cycloalkyl-O— group in which the cycloalkyl group is as described herein. Exemplary cycloalkyloxy groups include cyclopropyloxy, cyclopentyloxy, cyclohexyloxy and cycloheptyloxy. "Optionally substituted cycloalkyloxy" means a cycloalkyloxy group which may be substituted on the alkyl portion by one or more alkyl group substituents.

"Halo" or "halogen" means fluoro, chloro, bromo, or iodo. Preferred are fluoro or chloro.

"Heteroaroyl" means a heteroaryl-CO— group in which the heteroaryl group is as described herein. Exemplary groups include pyridylcarbonyl.

"Heteroaroylamino" means a heteroaroyl-NH— group in which the heteroaroyl moiety is as previously described.

"Heteroaryl" as a group or part of a group denotes an aromatic monocyclic or multicyclic organic moiety of about 5 to about 14 ring members in which one or more of the ring members is/are element(s) other than carbon, for example nitrogen, oxygen or sulfur. Examples of suitable heteroaryl groups include benzimidazolyl, benzofuryl, furyl, indolyl, imidazolyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups. "Optionally substituted heteroaryl" means a heteroaryl group which may be substituted by one or more aryl group substituents.

"Heteroarylalkyl" means a heteroaryl-alkyl- group in which the heteroaryl and alkyl moieties are as previously described. Preferred heteroarylalkyl groups contain a $C_{1-4}$alkyl moiety. Exemplary heteroarylalkyl groups include pyridylmethyl. "Optionally substituted heteroarylalkyl" means a heteroarylalkyl group which may be substituted on the heteroaryl portion by one or more aryl group substituents, and which may be substituted on the alkyl portion by one or more alkyl group substituents.

"Heteroarylalkoxy" means an heteroaryl-alkyl-O— group in which the heteroarylalkyl group is as previously described. Exemplary heteroaryloxy groups include pyridylmethoxy. "Optionally substituted heteroarylalkoxy" means a heteroarylalkoxy group which may be substituted on the heteroaryl portion by one or more aryl group substituents, and which may be substituted on the alkyl portion by one or more alkyl group substituents.

"Heteroarylalkoxyalkyl" means a heteroarylalkyl-O-alkyl- group in which the heteroarylalkyl and alkyl groups are as previously described. Exemplary heteroarylalkoxyalkyl groups include 4-pyridylmethoxymethyl and 3- or 4-quinolinemethoxymethyl. "Optionally substituted heteroarylalkoxyalkyl" means a heteroarylalkoxyalkyl group which may be substituted on the heteroaryl portion by one or more aryl group substituents, and on the alkyl portions by one or more alkyl group substituents.

"Heteroaryloxy" means an heteroaryl-O— group in which the heteroaryl group is as previously described. Exemplary heteroaryloxy groups include pyridyloxy. "Optionally substituted heteroaryloxy" means a heteroaryloxy group which may be substituted on the heteroaryl portion by one or more aryl group substituents.

"Heteroaryloxyalkyl" means a heteroaryl-O-alkyl group in which heteroaryl and alkyl are as described herein. "Optionally substituted heteroaryloxyalkyl" means a heteroaryloxyalkyl group which may be substituted on the heteroaryl portion by one or more aryl group substituents, and on the alkyl portion by one ore more alkyl group substituents.

"Heteroarylsulfonylcarbamoyl" means a heteroaryl-$SO_2$—NH—C(=O)— group in which the heteroaryl group is as previously described.

"Heterocycloalkyl" means a non-aromatic or partially aromatic monocyclic or multicyclic organic moiety of about 5 to about 14 ring members which contains one or more heteroatoms selected from O, S or $NY^7$. Exemplary heterocycloalkyl groups include 5-7 membered cyclic ethers such as tetrahydrofuran and perhydropyran. "Optionally substituted heterocycloalkyl" means a heterocycloalkyl group which may be substituted by one or more alkyl group substituents.

"Heterocycloalkylalkyl" means a heterocycloalkyl-alkyl-group in which the heterocycloalkyl and alkyl moieties are as previously described. "Optionally substituted heterocycloalkylalkyl" means a heterocycloalkylalkyl group which may be substituted by one or more alkyl group substituents.

"Heterocycloalkyloxy" means a heterocycloalkyl-O— group in which heterocycloalkyl is as previously defined. "Optionally substituted heterocycloalkyloxy" means a heterocycloalkyloxy group which may be substituted on the heterocycloalkyloxy portion by one or more alkyl group substituents.

"Heterocycloalkyloxyalkyl" means a heterocycloalkyl-O-alkyl group in which heterocycloalkyl is as previously defined. "Optionally substituted heterocycloalkyloxyalkyl" means a heterocycloalkyloxyalkyl group which may be substituted on the heterocycloalkyloxy portion or the alkyl portion by one or more alkyl group substituents.

"Hydroxyalkyl" means a HO-alkyl- group in which alkyl is as previously defined. Preferred hydroxyalkyl groups contain $C_{1-4}$alkyl. Exemplary hydroxyalkyl groups include hydroxymethyl and 2-hydroxyethyl.

"$Y^7Y^8N$—" means a substituted or unsubstituted amino group, wherein $Y^7$ and $Y^8$ are as previously described. Exemplary groups include amino ($H_2N$—), methylamino, ethylmethylamino, dimethylamino and diethylamino.

"$Y^7Y^8NCO$—" means a substituted or unsubstituted carbamoyl group, wherein $Y^7$ and $Y^8$ are as previously described. Exemplary groups are carbamoyl ($H_2NCO$—) and dimethylcarbamoyl ($Me_2NCO$—).

"$Y^7Y^8NSO_2$—" means a substituted or unsubstituted sulfamoyl group, wherein $Y^7$ and $Y^8$ are as previously described. Exemplary groups are sulfamoyl ($H_2NSO_2$—) and dimethylsulfamoyl ($Me_2NSO_2$—).

"Prodrug" means a compound which is convertible in vivo by metabolic means (e.g., by hydrolysis) to a compound of Formula (I), including N-oxides thereof. For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. An exemplary prodrug is the acetic acid ester of 1-(5-tert-butyl-2-p-tolyl-2H-pyrazol-3-yl)-3-{3-[1-(4-hydroxymethyl-benzoyl)-piperidin-4-ylmethyl]-phenyl}-urea, Compound A118.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates, methanolates, and the like.

Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of Formula (I) containing a carboxy group, are for example those described by F. J. Leinweber, Drug Metab. Res., 1987, 18, page 379.

An especially useful class of esters of compounds of Formula (I) containing a hydroxy group, may be formed from acid moieties selected from those described by Bundgaard et. al., J. Med. Chem., 1989, 3, pages 2503-2507, and include substituted (aminomethyl)-benzoates, for example dialkylamino-methylbenzoates in which the two alkyl groups may be joined together and/or interrupted by an oxygen atom or by an optionally substituted nitrogen atom, e.g., an alkylated nitrogen atom, more especially (morpholino-methyl)benzoates, e.g., 3- or 4-(morpholinomethyl)-benzoates, and (4-alkylpiperazin-1-yl)benzoates, e.g., 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g., hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be appreciated that compounds of the present invention may contain asymmetric centers. These asymmetric centers may independently be in either the R or S configuration. It will also be appreciated that compounds of formula (I) in which is an ethylene bridge can exist in either the exo- or endo-configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of Formula (I) hereinabove. Such isomers can be separated from their mixtures, by the application or adaptation of known methods, for example chromatographic techniques and recrystallisation techniques, or they are separately prepared from the appropriate isomers of their intermediates. Additionally, in situations where tautomers of the compounds of Formula (I) are possible, the present invention is intended to include all tautomeric forms of the compounds.

With reference to formula (I) above, the following are particular groupings:

X may particularly represent —C(O)— and A may particularly represent optionally substituted alkenyl, optionally substituted alkoxy, optionally substituted alkoxyalkyl, optionally substituted alkyl, optionally substituted alkynyl, optionally substituted aryl, optionally substituted arylalkyl, optionally substituted arylalkoxy, optionally substituted aryloxy, optionally substituted aryloxyalkyl, optionally substituted cycloalkenyl, optionally substituted cycloalkyl, optionally substituted cycloalkylalkyl, optionally substituted cycloalkyloxy, optionally substituted heteroaryl, optionally substituted heteroarylalkyl, optionally substituted heteroarylalkoxy, optionally substituted heterocycloalkyl or optionally substituted heterocycloalkylalkyl.

X may particularly also represent —C(O)—CH$_2$— and A may particularly represent optionally substituted aryl or optionally substituted heteroaryl.

X may particularly also represent —S(O)$_2$— and A may particularly represent optionally substituted alkenyl, optionally substituted alkyl, optionally substituted aryl or optionally substituted heteroaryl.

X may particularly also represent —NH—C(O)— and A may particularly represent optionally substituted alkenyl, optionally substituted aryl or optionally substituted heteroaryl.

R¹ may particularly represent aryl substituted with one or more substituents selected from alkyl, alkoxy and amino.

R² may particularly represent alkyl.

Preferred compounds of the invention are those of Formula (II)

Formula (II)

wherein A, X, R¹ and R² are as defined hereinabove.

Other preferred compounds of the invention are those of Formula (III)

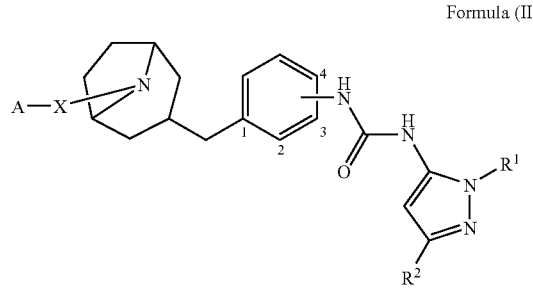

Formula (III)

wherein A, X, R¹ and R² are as defined hereinabove.

Still more preferred compounds of the present invention are those of Formula (I), Formula (II), or Formula (III) wherein A and X are as defined hereinabove, R¹ is p-tolyl, and R² is tert-butyl, i.e., compounds of Formulas (IV), (V) or (VI), respectively.

Formula (IV)

Formula (V)

Formula (VI)

A preferred embodiment of the present invention, are compounds of Formula (I), (II), (III), (IV), (V) or (VI) wherein A, R¹ and R² are as defined hereinabove, and X is —C(O)—.

Another preferred embodiment of the present invention, are compounds of Formula (I), (II), (III), (IV), (V) or (VI) wherein A, R¹ and R² are as defined hereinabove, and X is —C(O)—CH₂—.

Another preferred embodiment of the present invention, are compounds of Formula (I), (II), (III), (IV), (V) or (VI) wherein A, R¹ and R² are as defined hereinabove, and X is —S(O)₂.

Another preferred embodiment of the present invention, are compounds of Formula (I), (II), (III), (IV), (V) or (VI) wherein

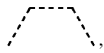

A, $R^1$ and $R^2$ are as defined hereinabove, and X is —NHC(O)—.

Especially preferred compounds of the present invention, are compounds of Formula (V) or (VI) wherein X is —C(O)—, and A is optionally substituted alkoxyalkyl, optionally substituted alkyl, optionally substituted aryl, optionally substituted arylalkyl, optionally substituted aryloxyalkyl, optionally substituted cycloalkyl, optionally substituted heteroaryl or optionally substituted heterocycloalkyl. Compounds of Formula (V) or (VI) in which X is —C(O)— and A is 4-acetoxymethylphenyl, acetylamino-methyl, 3-acetylaminophenyl, 3-amino-pyrazin-2-yl, 6-amino-pyridin-3-yl, benzoylaminomethyl, benzofuran-2-yl, benzyloxy, 5-chloro-6-hydroxy-pyridin-3-yl, 2-chloro-4-methansulfonylphenyl, 2-chloro-pyridin-3-yl, 5-chlorothiophen-2-yl, 3-(cyano-methyl-methyl)-phenyl, 2,4-difluorobenzyl, 4-difluoromethoxyphenyl, 4,5-dihydrobenzofuran-6-yl, 2,3-dimethoxyphenyl, 2,5-dimethoxyphenyl, 2,4-dimethoxyphenyl, 2,6-dimethoxypyridin-3-yl, 2,5-dimethylfuran-3-yl, 4,6-dimethylpyrimidin-2-yl, 2,4-dimethylthiazol-5-yl, 2-fluorobenzyl, furan-2-yl, furan-3-yl, 4-hydroxymethylphenyl, 6-hydroxy-pyridin-3-yl,indol-5-yl, indol-6-yl, isobutoxy, 2-isopropyl-5-methyl-cyclohexyloxy, 4-methoxybenzyl, methoxy-methyl, methoxycarbonylethyl, 4-methoxycarbonylphenoxy, 4-methoxyphenoxy, (methoxy)-(phenyl)-methyl, 4-methoxy-thiophen-3-yl, 5-methoxy-2-(1,1,1-trifluoroethoxy)-phenyl, methyl, 3-methyl-benzofuran-2-yl, 1-methyl-cyclopropyl, 2-methylfuran-3-yl, 3-methylfuran-2-yl, 2-methyl-4-methoxyphenyl, 6-methylpyridin2-yl, 2-methyl-pyridin-3-yl, 5-methyl-pyrazin-2-yl, 5-methyl-thiophen-2-yl, [1,8]naphthyridin-2-yl, 4-oxazol-5-yl-phenyl, 4-oxo-4,5,6,7-tetrahydro-benzofuran-3-yl, piperidine-3-yl, 2-phenoxy-ethyl, pyrazin-2-yl, pyridin-2-yl, pyridin-3-yl, pyridin-4-yl, 2-pyridin-3-yl-thiazol-4-yl, 2-pyridin-4-yl-thiazol-4-yl, quinolin-6-yl, [1,2,3]thiadiazol-4-yl, thiophen-3-yl and 2,4,6-trimethoxyphenyl are examples.

Especially preferred compounds of the present invention, are compounds of Formula (V) or (VI) wherein X is —S(O)$_2$— and A is optionally substituted alkyl, optionally substituted aryl or optionally substituted heteroaryl. Compounds of Formula (V) or (VI) in which X is —S(O)$_2$— and A is methyl, 2,5-dimethoxyphenyl, 2-methoxy-5-methylphenyl and 4-methyl-3,4-dihydro-2H-benzo[1,4]oxazine-7-yl are examples.

Especially preferred compounds of the present invention, are compounds of Formula (V) or (VI) wherein X is —NHC(O)— and A is optionally substituted alkenyl. Compounds of Formula (V) in which X is —NHC(O)— and A is 1-acetyl-3-oxo-3-phenyl-propenyl is an example.

Preferred compounds within the scope of the invention (that produce 50% inhibition in the LPS-induced TNF-alpha release in THP-1 cells assay at concentrations within the range 10 nanomolar to 500 nanomolar) are:

1-(5-tert-Butyl-2-p-tolyl-2H-pyrazol-3-yl)-3-{3-[1-((S)-2-methoxy-2-phenyl-acetyl)-piperidin-4-ylmethyl]-phenyl}-urea, Compound A4;

1-(5-tert-Butyl-2-p-tolyl-2H-pyrazol-3-yl)-3-{3-[1-([1,2,3] thiadiazole-4-carbonyl)-piperidin-4-ylmethyl]-phenyl}-urea, Compound A6;

1-(5-tert-Butyl-2-p-tolyl-2H-pyrazol-3-yl)-3-{3-[1-([1,6] naphthyridine-2-carbonyl)-piperidin-4-ylmethyl]-phenyl}-urea, Compound A7;

1-(5-tert-Butyl-2-p-tolyl-2H-pyrazol-3-yl)-3-{3-[1-([1,8] naphthyridine-2-carbonyl)-piperidin-4-ylmethyl]-phenyl}-urea, Compound A8;

1-(5-tert-Butyl-2-p-tolyl-2H-pyrazol-3-yl)-3-(3-{1-[1-(4-methoxy-phenyl)-cyclopropanrcarbonyl]-piperidin-4-ylmethyl}-phenyl)-urea, Compound A10;

1-(5-tert-Butyl-2-p-tolyl-2H-pyrazol-3-yl)-3-{3-[1-(isoquinoline-1-carbonyl)-piperidin-4-ylmethyl]-phenyl}-urea, Compound A13;

1-(5-tert-Butyl-2-p-tolyl-2H-pyrazol-3-yl)-3-{3-[1-(1-methyl-cyclopropanecarbonyl)-piperidin-4-ylmethyl]-phenyl}-urea, Compound A16;

1-(5-tert-Butyl-2-p-tolyl-2H-pyrazol-3-yl)-3-{3-[1-(2,3-dimethoxy-benzoyl)-piperidin-4-ylmethyl]-phenyl}-urea, Compound A2 1;

1-(5-tert-Butyl-2-p-tolyl-2H-pyrazol-3-yl)-3-(3-{1-[2-(2,3-dimethoxy-phenyl)-acetyl]-piperidin-4-ylmethyl}-phenyl)-urea, Compound A22;

1-(5-tert-Butyl-2-p-tolyl-2H-pyrazol-3-yl)-3-{3-[1-(2,4,6-trimethoxy-benzoyl)-piperidin-4-ylmethyl]-phenyl}-urea, Compound A24;

1-(5-tert-Butyl-2-p-tolyl-2H-pyrazol-3-yl)-3-(3-{1-[2-(2,4-difluoro-phenyl)-acetyl]-piperidin-4-ylmethyl}-phenyl)-urea, Compound A26;

1-(5-tert-Butyl-2-p-tolyl-2H-pyrazol-3-yl)-3-{3-[1-(2,4-dimethoxy-benzoyl)-piperidin-4-ylmethyl]-phenyl}-urea, Compound A27;

1-(5-tert-Butyl-2-p-tolyl-2H-pyrazol-3-yl)-3-{3-[1-(2,4-dimethyl-thiazole-5-carbonyl)-piperidin-4-ylmethyl]-phenyl}-urea, Compound A28;

1-(5-tert-Butyl-2-p-tolyl-2H-pyrazol-3-yl)-3-{3-[1-(2,5-dimethyl-furan-3-carbonyl)-piperidin-4-ylmethyl]-phenyl}-urea, Compound A29;

1-(5-tert-Butyl-2-p-tolyl-2H-pyrazol-3-yl)-3-{3-[1-(2-pyridin-3-yl-thiazole-4-carbonyl)-piperidin-4-ylmethyl]-phenyl}-urea, Compound A32;

1-(5-tert-Butyl-2-p-tolyl-2H-pyrazol-3-yl)-3-{3-[1-(2-pyridin-4-yl-thiazole-4-carbonyl)-piperidin-4-ylmethyl]-phenyl}-urea, Compound A34;

1-{3-[1-(2-Amino-pyridine-3-carbonyl)-piperidin-4-ylmethyl]-phenyl}-3-(5-tert-butyl-2-p-tolyl-2H-pyrazol-3-yl)-urea, Compound A39;

1-(5-tert-Butyl-2-p-tolyl-2H-pyrazol-3-yl)-3-{3-[1-(2-chloro-4-methanesulfonyl-benzoyl)-piperidin-4-ylmethyl]-phenyl}-urea, Compound A40;

1-(5-tert-Butyl-2-p-tolyl-2H-pyrazol-3-yl)-3-{3-[1-(2-chloro-pyridine-3-carbonyl)-piperidin-4-ylmethyl]-phenyl}-urea, Compound A42;

1-(5-tert-Butyl-2-p-tolyl-2H-pyrazol-3-yl)-3-(3-{1-[2-(2-fluoro-phenyl)-acetyl]-piperidin-4-ylmethyl}-phenyl)-urea, Compound A43;

1-(5-tert-Butyl-2-p-tolyl-2H-pyrazol-3-yl)-3-{3-[1-(furan-2-carbonyl)-piperidin-4-ylmethyl]-phenyl}-urea, Compound A45;

1-(5-tert-Butyl-2-p-tolyl-2H-pyrazol-3-yl)-3-(3-{1-[2-(2-methoxy-phenyl)-acetyl]-piperidin-4-ylmethyl}-phenyl)-urea, Compound A50;

1-(5-tert-Butyl-2-p-tolyl-2H-pyrazol-3-yl)-3-{3-[1-(2-methyl-furan-3-carbonyl)-piperidin-4-ylmethyl]-phenyl}-urea, Compound A52;

1-(5-tert-Butyl-2-p-tolyl-2H-pyrazol-3-yl)-3-{3-[1-(2-methyl-pyridine-3-carbonyl)-piperidin-4-ylmethyl]-phenyl}-urea, Compound A59;

1-(5-tert-Butyl-2-p-tolyl-2H-pyrazol-3-yl)-3-{3-[1-(pyrazine-2-carbonyl)-piperidin-4-ylmethyl]-phenyl}-urea, Compound A64;

1-(5-tert-Butyl-2-p-tolyl-2H-pyrazol-3-yl)-3-{3-[1-(tetrahydro-furan-2-carbonyl)-piperidin-4ylmethyl]-phenyl}-urea, Compound A66;

1-(5-tert-Butyl-2-p-tolyl-2H-pyrazol-3-yl)-3-(3-{1-[2-(3,4-dimethoxy-phenyl)-acetyl]-piperidin-4-ylmethyl}-phenyl)-urea, Compound A69;

1-{3-[1-(2-Benzo[1,3]dioxol-5-yl-acetyl)-piperidin-4-ylmethyl]-phenyl}-3-(5-tert-butyl-2-p-tolyl-2H-pyrazol-3-yl)-urea, Compound A70;

1-(5-tert-Butyl-2-p-tolyl-2H-pyrazol-3-yl)-3-{3-[1-(3,5-dimethoxy-benzoyl)-piperidin-4-ylmethyl]-phenyl}-urea, Compound A73;

1-(5-tert-Butyl-2-p-tolyl-2H-pyrazol-3-yl)-3-(3-{1-[3-(cyano-methyl-methyl)-benzoyl]-piperidin-4-ylmethyl}-phenyl)-urea, Compound A79;

1-(5-tert-Butyl-2-p-tolyl-2H-pyrazol-3-yl)-3-{3-[1-(3-furan-2-yl-propionyl)-piperidin-4-ylmethyl]-phenyl}-urea, Compound A81;

1-(5-tert-Butyl-2-p-tolyl-2H-pyrazol-3-yl)-3-(3-{1-[3-(2-methoxy-phenyl)-propionyl]-piperidin-4-ylmethyl}-phenyl)-urea, Compound A82;

1-(5-tert-Butyl-2-p-tolyl-2H-pyrazol-3-yl)-3-{3-[1-(3-thiophen-2-yl-propionyl)-piperidin-4-ylmethyl]-phenyl}-urea, Compound A83;

N-[3-(4-{3-[3-(5-tert-Butyl-2-p-tolyl-2H-pyrazol-3-yl)-ureido]-benzyl}-piperidine-1-carbonyl)-phenyl]-acetamide, Compound A88;

1-(5-tert-Butyl-2-p-tolyl-2H-pyrazol-3-yl)-3-{3-[1-(furan-3-carbonyl)-piperidin-4-ylmethyl]-phenyl}-urea, Compound A92;

1-(5-tert-Butyl-2-p-tolyl-2H-pyrazol-3-yl)-3-{3-[1-(3-methyl-furan-2-carbonyl)-piperidin-4-ylmethyl]-phenyl}-urea, Compound A95;

1-(5-tert-Butyl-2-p-tolyl-2H-pyrazol-3-yl)-3-{3-[1-(thiophene-3-carbonyl)-piperidin-4-ylmethyl]-phenyl}-urea, Compound A99;

1-(5-tert-Butyl-2-p-tolyl-2H-pyrazol-3-yl)-3-{3-[1-(4,5-dihydro-benzo[b]thiophene-6-carbonyl)-piperidin-4-ylmethyl]-phenyl}-urea, Compound A102;

1-(5-tert-Butyl-2-p-tolyl-2H-pyrazol-3-yl)-3-{3-[1-(4-oxazol-5-yl-benzoyl)-piperidin-4-ylmethyl]-phenyl}-urea, Compound A106;

1-(5-tert-Butyl-2-p-tolyl-2H-pyrazol-3-yl)-3-{3-[1-(4-difluoromethoxy-benzoyl)-piperidin-4-ylmethyl]-phenyl}-urea, Compound A111;

1-{3-[1-(4-Amino-3-trifluoromethoxy-benzoyl)-piperidin-4-ylmethyl]-phenyl}-3-(5-tert-butyl-2-p-tolyl-2H-pyrazol-3-yl)-urea, Compound A114;

1-(5-tert-Butyl-2-p-tolyl-2H-pyrazol-3-yl)-3-{3-[1-(4-hydroxymethyl-benzoyl)-piperidin-4-ylmethyl]-phenyl}-urea, Compound A118;

1-(5-tert-Butyl-2-p-tolyl-2H-pyrazol-3-yl)-3-{3-[1-(4-methoxy-2-methyl-benzoyl)-piperidin-4-ylmethyl]-phenyl}-urea, Compound A120;

1-(5-tert-Butyl-2-p-tolyl-2H-pyrazol-3-yl)-3-(3-{1-[2-(4-methoxy-phenoxy)-acetyl]-piperidin-4-ylmethyl}-phenyl)-urea, Compound A121;

1-(5-tert-Butyl-2-p-tolyl-2H-pyrazol-3-yl)-3-(3-{1-[2-(4-methoxy-phenyl)-acetyl]-piperidin-4-ylmethyl}-phenyl)-urea, Compound A122;

1-(5-tert-Butyl-2-p-tolyl-2H-pyrazol-3-yl)-3-{3-[1-(4-methoxy-thiophene-3-carbonyl)-piperidin-4-ylmethyl]-phenyl}-urea, Compound A123;

1-(5-tert-Butyl-2-p-tolyl-2H-pyrazol-3-yl)-3-{3-[1-(4-trifluoromethyl-pyridine-3-carbonyl)-piperidin-4-ylmethyl]-phenyl}-urea, Compound A126;

1-(5-tert-Butyl-2-p-tolyl-2H-pyrazol-3-yl)-3-{3-[1-(5-chloro-thiophene-2-carbonyl)-piperidin-4-ylmethyl]-phenyl}-urea, Compound A131;

1-(5-tert-Butyl-2-p-tolyl-2H-pyrazol-3-yl)-3-(3-{1-[5-methoxy-2-(2,2,2-trifluoro-ethoxy)-benzoyl]-piperidin-4-ylmethyl}-phenyl)-urea, Compound A132;

1-(5-tert-Butyl-2-p-tolyl-2H-pyrazol-3-yl)-3-{3-[1-(5-methyl-thiophene-2-carbonyl)-piperidin-4-ylmethyl]-phenyl}-urea, Compound A137;

1-(5-tert-Butyl-2-p-tolyl-2H-pyrazol-3-yl)-3-{3-[1-(5-methyl-pyrazine-2-carbonyl)-piperidin-4-ylmethyl]-phenyl}-urea, Compound A140;

1-{3-[1-(6-Amino-pyridine-3-carbonyl)-piperidin-4-ylmethyl]-phenyl}-3-(5-tert-butyl-2-p-tolyl-2H-pyrazol-3-yl)-urea, Compound A144;

1-(5-tert-Butyl-2-p-tolyl-2H-pyrazol-3-yl)-3-{3-[1-(6-methyl-pyridine-2-carbonyl)-piperidin-4-ylmethyl]-phenyl}-urea, Compound A146;

Acetic acid 4-(4-{3-[3-(5-tert-butyl-2-p-tolyl-2H-pyrazol-3-yl)-ureido]-benzyl}-piperidine-1-carbonyl)-benzyl ester, Compound A148;

1-{3-[1-(Benzothiazole-6-carbonyl)-piperidin-4-ylmethyl]-phenyl}-3-(5-tert-butyl-2-p-tolyl-2H-pyrazol-3-yl)-urea, Compound A150;

1-(5-tert-Butyl-2-p-tolyl-2H-pyrazol-3-yl)-3-{3-[1-(4-oxo-4,5,6,7-tetrahydro-benzofuran-3-carbonyl)-piperidin-4-ylmethyl]-phenyl}-urea, Compound A154;

N-[2-(4-{3-[3-(5-tert-butyl-2-p-tolyl-2H-pyrazol-3-yl)-ureido]-benzyl}-piperidin-1-yl)-2-oxo-ethyl]-benzamide, Compound A163;

1-(5-tert-Butyl-2-p-tolyl-2H-pyrazol-3-yl)-3-{3-[1-(1H-indazole-3-carbonyl)-piperidin-4-ylmethyl]-phenyl}-urea, Compound A167;

1-(5-tert-Butyl-2-p-tolyl-2H-pyrazol-3-yl)-3-{3-[1-(2-1H-indol-3-yl-acetyl)-piperidin-4-ylmethyl]-phenyl}-urea, Compound A168;

1-(5-tert-Butyl-2-p-tolyl-2H-pyrazol-3-yl)-3-{3-[1-(pyridine-4-carbonyl)-piperidin-4-ylmethyl]-phenyl}-urea, Compound A170;

1-(5-tert-Butyl-2-p-tolyl-2H-pyrazol-3-yl)-3-{3-[1-(2-methoxy-acetyl)-piperidin-4-ylmethyl]-phenyl}-urea, Compound A173;

N-[2-(4-{3-[3-(5-tert-Butyl-2-p-tolyl-2H-pyrazol-3-yl)-ureido]-benzyl}-piperidin-1-yl)-2-oxo-ethyl]-acetamide, Compound A179;

1-(5-tert-Butyl-2-p-tolyl-2H-pyrazol-3-yl)-3-{3-[1-(pyridine-3-carbonyl)-piperidin-4-ylmethyl]-phenyl}-urea, Compound A181;

1-(5-tert-Butyl-2-p-tolyl-2H-pyrazol-3-yl)-3-{3-[1-(2-o-tolyl-acetyl)-piperidin-4-ylmethyl]-phenyl}-urea, Compound A182;

1-(5-tert-Butyl-2-p-tolyl-2H-pyrazol-3-yl)-3-{3-[1-(quinoline-2-carbonyl)-piperidin-4-ylmethyl]-phenyl}-urea, Compound A184;

1-(5-tert-Butyl-2-p-tolyl-2H-pyrazol-3-yl)-3-{3-[1-(quinoline-4-carbonyl)-piperidin-4-ylmethyl]-phenyl}-urea, Compound A186;

1-(5-tert-Butyl-2-p-tolyl-2H-pyrazol-3-yl)-3-{3-[1-(2-thiophen-2-yl-acetyl)-piperidin-4-ylmethyl]-phenyl}-urea, Compound A189;

1-(5-tert-Butyl-2-p-tolyl-2H-pyrazol-3-yl)-3-{3-[1-(2-thiophen-3-yl-acetyl)-piperidin-4-ylmethyl]-phenyl}-urea, Compound A190;

1-(5-tert-Butyl-2-p-tolyl-2H-pyrazol-3-yl)-3-{4-[1-((S)-2-methoxy-2-phenyl-acetyl)-piperidin-4-ylmethyl]-phenyl}-urea, Compound A193;

1-(5-tert-Butyl-2-p-tolyl-2H-pyrazol-3-yl)-3-{4-[1-([1,2,3]thiadiazole-4-carbonyl)-piperidin-4-ylmethyl]-phenyl}-urea, Compound A196;

1-(5-tert-Butyl-2-p-tolyl-2H-pyrazol-3-yl)-3-{4-[1-([1,6]naphthyridine-2-carbonyl)-piperidin-4-ylmethyl]-phenyl}-urea, Compound A197;

1-(5-tert-Butyl-2-p-tolyl-2H-pyrazol-3-yl)-3-{4-[1-(1-methyl-cyclopropanecarbonyl)-piperidin-4-ylmethyl]-phenyl}-urea, Compound A206;

1-(5-tert-Butyl-2-p-tolyl-2H-pyrazol-3-yl)-3-{4-[1-(2,3-dimethoxy-benzoyl)-piperidin-4-ylmethyl]-phenyl}-urea, Compound A212;

1-(5-tert-Butyl-2-p-tolyl-2H-pyrazol-3-yl)-3-(4-{1-[2-(2,3-dimethoxy-phenyl)-acetyl]-piperidin-4-ylmethyl}-phenyl)-urea, Compound A213;

1-(5-tert-Butyl-2-p-tolyl-2H-pyrazol-3-yl)-3-{4-[1-(2,4,6-trimethoxy-benzoyl)-piperidin-4-ylmethyl]-phenyl}-urea, Compound A215;

1-(5-tert-Butyl-2-p-tolyl-2H-pyrazol-3-yl)-3-{4-[1-(2,4,6-trimethyl-benzoyl)-piperidin-4-ylmethyl]-phenyl}-urea, Compound A216;

1-(5-tert-Butyl-2-p-tolyl-2H-pyrazol-3-yl)-3-(4-{1-[2-(2,4-difluoro-phenyl)-acetyl]-piperidin-4-ylmethyl}-phenyl)-urea, Compound A217;

1-(5-tert-Butyl-2-p-tolyl-2H-pyrazol-3-yl)-3-{4-[1-(2,4-dimethoxy-benzoyl)-piperidin-4-ylmethyl]-phenyl}-urea, Compound A218;

1-(5-tert-Butyl-2-p-tolyl-2H-pyrazol-3-yl)-3-{4-[1-(2,4-dimethyl-thiazole-5-carbonyl)-piperidin-4-ylmethyl]-phenyl}-urea, Compound A219;

1-(5-tert-Butyl-2-p-tolyl-2H-pyrazol-3-yl)-3-{4-[1-(2,5-dimethoxy-benzoyl)-piperidin-4-ylmethyl]-phenyl}-urea, Compound A220;

1-(5-tert-Butyl-2-p-tolyl-2H-pyrazol-3-yl)-3-{4-[1-(2,5-dimethyl-furan-3-carbonyl)-piperidin-4-ylmethyl]-phenyl}-urea, Compound A222;

1-(5-tert-Butyl-2-p-tolyl-2H-pyrazol-3-yl)-3-{4-[1-(2,6-dimethoxy-pyridine-3-carbonyl)-piperidin-4-ylmethyl]-phenyl}-urea, Compound A224;

1-(5-tert-Butyl-2-p-tolyl-2H-pyrazol-3-yl)-3-{4-[1-(2-pyridin-3-yl-thiazole-4-carbonyl)-piperidin-4-ylmethyl]-phenyl}-urea, Compound A225;

1-(5-tert-Butyl-2-p-tolyl-2H-pyrazol-3-yl)-3-{4-[1-(2-pyridin-4-yl-thiazole-4-carbonyl)-piperidin-4-ylmethyl]-phenyl}-urea, Compound A227;

1-{4-[1-(2-Amino-pyridine-3-carbonyl)-piperidin-4-ylmethyl]-phenyl}-3-(5-tert-butyl-2-p-tolyl-2H-pyrazol-3-yl)-urea, Compound A231;

1-{4-[1-(Benzofuran-2-carbonyl)-piperidin-4-ylmethyl]-phenyl}-3-(5-tert-butyl-2-p-tolyl-2H-pyrazol-3-yl)-urea, Compound A232;

1-(5-tert-Butyl-2-p-tolyl-2H-pyrazol-3-yl)-3-{4-[1-(2-chloro-4-methanesulfonyl-benzoyl)-piperidin-4-ylmethyl]-phenyl}-urea, Compound A233;

1-(5-tert-Butyl-2-p-tolyl-2H-pyrazol-3-yl)-3-{4-[1-(2-chloro-pyridine-3-carbonyl)-piperidin-4-ylmethyl]-phenyl}-urea, Compound A235;

1-(5-tert-Butyl-2-p-tolyl-2H-pyrazol-3-yl)-3-(4-{1-[2-(2-fluoro-phenyl)-acetyl]-piperidin-4-ylmethyl}-phenyl)-urea, Compound A236;

1-(5-tert-Butyl-2-p-tolyl-2H-pyrazol-3-yl)-3-{4-[1-(furan-2-carbonyl)-piperidin-4-ylmethyl]-phenyl}-urea, Compound A237;

1-(5-tert-Butyl-2-p-tolyl-2H-pyrazol-3-yl)-3-[4-(1-hept-2-ynoyl-piperidin-4-ylmethyl)-phenyl]-urea, Compound A238;

1-(5-tert-Butyl-2-p-tolyl-2H-pyrazol-3-yl)-3-{4-[1-(2-hydroxy-quinoline-4-carbonyl)-piperidin-4-ylmethyl]-phenyl}-urea, Compound A240;

1-(5-tert-Butyl-2-p-tolyl-2H-pyrazol-3-yl)-3-{4-[1-(2-methyl-[1,6]naphthyridine-3-carbonyl)-piperidin-4-ylmethyl]-phenyl}-urea, Compound A243;

1-(5-tert-Butyl-2-p-tolyl-2H-pyrazol-3-yl)-3-{4-[1-(2-methyl-furan-3-carbonyl)-piperidin-4-ylmethyl]-phenyl}-urea, Compound A244;

1-(5-tert-Butyl-2-p-tolyl-2H-pyrazol-3-yl)-3-{4-[1-(2-methyl-[1,8]naphthyridine-3-carbonyl)-piperidin-4-ylmethyl]-phenyl}-urea, Compound A249;

1-(5-tert-Butyl-2-p-tolyl-2H-pyrazol-3-yl)-3-{4-[1-(2-methyl-pyridine-3-carbonyl)-piperidin-4-ylmethyl]-phenyl}-urea, Compound A251;

1-(5-tert-Butyl-2-p-tolyl-2H-pyrazol-3-yl)-3-{4-[1-(pyrazine-2-carbonyl)-piperidin-4-ylmethyl]-phenyl}-urea, Compound A256;

1-(5-tert-Butyl-2-p-tolyl-2H-pyrazol-3-yl)-3-{4-[1-(quinoxaline-2-carbonyl)-piperidin-4-ylmethyl]-phenyl}-urea, Compound A257;

1-(5-tert-Butyl-2-p-tolyl-2H-pyrazol-3-yl)-3-{4-[1-(tetrahydro-furan-2-carbonyl)-piperidin-4-ylmethyl]-phenyl}-urea, Compound A258;

1-(5-tert-Butyl-2-p-tolyl-2H-pyrazol-3-yl)-3-{4-[1-(3,4-dimethoxy-benzoyl)-piperidin-4-ylmethyl]-phenyl}-urea, Compound A261;

1-(5-tert-Butyl-2-p-tolyl-2H-pyrazol-3-yl)-3-(4-{1-[2-(3,4-dimethoxy-phenyl)-acetyl]-piperidin-4-ylmethyl}-phenyl)-urea, Compound A262;

1-{4-[1-(2-Benzo[1,3]dioxol-5-yl-acetyl)-piperidin-4-ylmethyl]-phenyl}-3-(5-tert-butyl-2-p-tolyl-2H-pyrazol-3-yl)-urea, Compound A263;

1-(5-tert-Butyl-2-p-tolyl-2H-pyrazol-3-yl)-3-{4-[1-(3,5-dimethoxy-benzoyl)-piperidin-4-ylmethyl]-phenyl}-urea, Compound A266;

1-(5-tert-Butyl-2-p-tolyl-2H-pyrazol-3-yl)-3-(4-{1-[3-(cyano-methyl-methyl)-benzoyl]-piperidin-4-ylmethyl}-phenyl)-urea, Compound A272;

1-(5-tert-Butyl-2-p-tolyl-2H-pyrazol-3-yl)-3-{4-[1-(3-furan-2-yl-propionyl)-piperidin-4-ylmethyl]-phenyl}-urea, Compound A274;

1-{4-[1-(3-Amino-pyrazine-2-carbonyl)-piperidin-4-ylmethyl]-phenyl}-3-(5-tert-butyl-2-p-tolyl-2H-pyrazol-3-yl)-urea, Compound A283;

1-(5-tert-Butyl-2-p-tolyl-2H-pyrazol-3-yl)-3-{4-[1-(furan-3-carbonyl)-piperidin-4-ylmethyl]-phenyl}-urea, Compound A286;

1-(5-tert-Butyl-2-p-tolyl-2H-pyrazol-3-yl)-3-(4-{1-[2-(3-methoxy-phenyl)-acetyl]-piperidin-4-ylmethyl}-phenyl)-urea, Compound A288;

1-(5-tert-Butyl-2-p-tolyl-2H-pyrazol-3-yl)-3-{4-[1-(3-methyl-furan-2-carbonyl)-piperidin-4-ylmethyl]-phenyl}-urea, Compound A289;

1-(5-tert-Butyl-2-p-tolyl-2H-pyrazol-3-yl)-3-{4-[1-(3-methyl-benzofuran-2-carbonyl)-piperidin-4-ylmethyl]-phenyl}-urea, Compound A290;

1-(5-tert-Butyl-2-p-tolyl-2H-pyrazol-3-yl)-3-{4-[1-(3-phenoxy-propionyl)-piperidin-4-ylmethyl]-phenyl}-urea, Compound A292;

1-(5-tert-Butyl-2-p-tolyl-2H-pyrazol-3-yl)-3-{4-[1-(thiophene-3-carbonyl)-piperidin-4-ylmethyl]-phenyl}-urea, Compound A294;

1-(5-tert-Butyl-2-p-tolyl-2H-pyrazol-3-yl)-3-{4-[1-(4,5-dimethyl-furan-2-carbonyl)-piperidin-4-ylmethyl]-phenyl}-urea, Compound A298;

1-(5-tert-Butyl-2-p-tolyl-2H-pyrazol-3-yl)-3-{4-[1-(4-oxazol-5-yl-benzoyl)-piperidin-4-ylmethyl]-phenyl}-urea, Compound A301;

1-(5-tert-Butyl-2-p-tolyl-2H-pyrazol-3-yl)-3-{4-[1-(4-difluoromethoxy-benzoyl)-piperidin-4-ylmethyl]-phenyl}-urea, Compound A306;

1-{4-[1-(4-Amino-3-trifluoromethoxy-benzoyl)-piperidin-4-ylmethyl]-phenyl}-3-(5-tert-butyl-2-p-tolyl-2H-pyrazol-3-yl)-urea, Compound A309;

1-(5-tert-Butyl-2-p-tolyl-2H-pyrazol-3-yl)-3-(4-{1-[2-(4-fluoro-phenyl)-acetyl]-piperidin-4-ylmethyl}-phenyl)-urea, Compound A314;

1-(5-tert-Butyl-2-p-tolyl-2H-pyrazol-3-yl)-3-{4-[1-(4-hydroxymethyl-benzoyl)-piperidin-4-ylmethyl]-phenyl}-urea, Compound A315;

1-(5-tert-Butyl-2-p-tolyl-2H-pyrazol-3-yl)-3-(4-{1-[2-(4-methoxy-phenyl)-acetyl]-piperidin-4-ylmethyl}-phenyl)-urea, Compound A319;

1-(5-tert-Butyl-2-p-tolyl-2H-pyrazol-3-yl)-3-{4-[1-(5-chloro-6-hydroxy-pyridine-3-carbonyl)-piperidin-4-ylmethyl]-phenyl}-urea, Compound A326;

1-(5-tert-Butyl-2-p-tolyl-2H-pyrazol-3-yl)-3-(4-{1-[2-(5-chloro-benzo[b]thiophen-3-yl)-acetyl]-piperidin-4-ylmethyl}-phenyl)-urea, Compound A327;

1-(5-tert-Butyl-2-p-tolyl-2H-pyrazol-3-yl)-3-{4-[1-(5-methyl-1-phenyl-1H-pyrazole-4-carbonyl)-piperidin-4-ylmethyl]-phenyl}-urea, Compound A331;

1-{4-[1-(6-Amino-pyridine-3-carbonyl)-piperidin-4-ylmethyl]-phenyl}-3-(5-tert-butyl-2-p-tolyl-2H-pyrazol-3-yl)-urea, Compound A331A;

1-(5-tert-Butyl-2-p-tolyl-2H-pyrazol-3-yl)-3-{4-[1-(6-chloro-pyridine-3-carbonyl)-piperidin-4-ylmethyl]-phenyl}-urea, Compound A332;

1-(5-tert-Butyl-2-p-tolyl-2H-pyrazol-3-yl)-3-{4-[1-(6-methyl-pyridine-2-carbonyl)-piperidin-4-ylmethyl]-phenyl}-urea, Compound A334;

Acetic acid 4-(4-{4-[3-(5-tert-butyl-2-p-tolyl-2H-pyrazol-3-yl)-ureido]-benzyl}-piperidin-1-carbonyl)-benzyl ester, Compound A336;

1-{4-[1-(Benzothiazole-6-carbonyl)-piperidin-4-ylmethyl]-phenyl}-3-(5-tert-butyl-2-p-tolyl-2H-pyrazol-3-yl)-urea, Compound A338;

1-(5-tert-Butyl-2-p-tolyl-2H-pyrazol-3-yl)-3-[4-(1-butyryl-piperidin-4-ylmethyl)-phenyl]-urea, Compound A343;

1-(5-tert-Butyl-2-p-tolyl-2H-pyrazol-3-yl)-3-{4-[1-(2-cyclopentyl-acetyl)-piperidin-4-ylmethyl]-phenyl}-urea, Compound A349;

N-[2-(4-{4-[3-(5-tert-Butyl-2-p-tolyl-2H-pyrazol-3-yl)-ureido]-benzyl}-piperidin-1-yl)-2-oxo-ethyl]-benzamide, Compound A352;

1-(5-tert-Butyl-2-p-tolyl-2H-pyrazol-3-yl)-3-{4-[1-(3-phenyl-propionyl)-piperidin-4-ylmethyl]-phenyl}-urea, Compound A354;

1-(5-tert-Butyl-2-p-tolyl-2H-pyrazol-3-yl)-3-{4-[1-(2-1H-indol-3-yl-acetyl)-piperidin-4-ylmethyl]-phenyl}-urea, Compound A358;

1-(5-tert-Butyl-2-p-tolyl-2H-pyrazol-3-yl)-3-{4-[1-(1H-indole-5-carbonyl)-piperidin-4-ylmethyl]-phenyl}-urea, Compound A361;

1-(5-tert-Butyl-2-p-tolyl-2H-pyrazol-3-yl)-3-{4-[1-(1H-indole-6-carbonyl)-piperidin-4-ylmethyl]-phenyl}-urea, Compound A362;

1-(5-tert-Butyl-2-p-tolyl-2H-pyrazol-3-yl)-3-{4-[1-(pyridine-4-carbonyl)-piperidin-4-ylmethyl]-phenyl}-urea, Compound A364;

1-(5-tert-Butyl-2-p-tolyl-2H-pyrazol-3-yl)-3-{4-[1-(2-methoxy-acetyl)-piperidin-4-ylmethyl]-phenyl}-urea, Compound A367;

1-(5-tert-Butyl-2-p-tolyl-2H-pyrazol-3-yl)-3-(4-{1-[3-(4,6-dimethyl-pyrimidin-2-ylamino)-benzoyl]-piperidin-4-ylmethyl}-phenyl)-urea, Compound A371;

N-[2-(4-{4-[3-(5-tert-Butyl-2-p-tolyl-2H-pyrazol-3-yl)-ureido]-benzyl}-piperidin-1-yl)-2-oxo-ethyl]-acetamide, Compound A375;

1-(5-tert-Butyl-2-p-tolyl-2H-pyrazol-3-yl)-3-{4-[1-(pyridine-3-carbonyl)-piperidin-4-ylmethyl]-phenyl}-urea, Compound A377;

1-(5-tert-Butyl-2-p-tolyl-2H-pyrazol-3-yl)-3-{4-[1-(pyridine-2-carbonyl)-piperidin-4-ylmethyl]-phenyl}-urea, Compound A380;

1-(5-tert-Butyl-2-p-tolyl-2H-pyrazol-3-yl)-3-{4-[1-(quinoline-2-carbonyl)-piperidin-4-ylmethyl]-phenyl}-urea, Compound A383;

1-(5-tert-Butyl-2-p-tolyl-2H-pyrazol-3-yl)-3-{4-[1-(quinoline-3-carbonyl)-piperidin-4-ylmethyl]-phenyl}-urea, Compound A384;

1-(5-tert-Butyl-2-p-tolyl-2H-pyrazol-3-yl)-3-{4-[1-(quinoline-4-carbonyl)-piperidin-4-ylmethyl]-phenyl}-urea, Compound A385;

1-(5-tert-Butyl-2-p-tolyl-2H-pyrazol-3-yl)-3-{4-[1-(quinoline-6-carbonyl)-piperidin-4-ylmethyl]-phenyl}-urea, Compound A386;

1-(5-tert-Butyl-2-p-tolyl-2H-pyrazol-3-yl)-3-{4-[1-(2-thiophen-2-yl-acetyl)-piperidin-4-ylmethyl]-phenyl}-urea, Compound A388;

1-(5-tert-Butyl-2-p-tolyl-2H-pyrazol-3-yl)-3-{4-[1-(2-thiophen-3-yl-acetyl)-piperidin-4-ylmethyl]-phenyl}-urea, Compound A389;

4-{3-[3-(5-tert-Butyl-2-p-tolyl-2H-pyrazol-3-yl)-ureido]-benzyl}-piperidine-1-carboxylic acid (4-acetyl-phenyl)-amide, Compound A403;

4-{4-[3-(5-tert-Butyl-2-p-tolyl-2H-pyrazol-3-yl)-ureido]-benzyl}-piperidine-1-carboxylic acid benzo[1,3]dioxol-5-ylamide, Compound A429;

4-{4-[3-(5-tert-Butyl-2-p-tolyl-2H-pyrazol-3-yl)-ureido]-benzyl}-piperidine-1-carboxylic acid (4-dimethylamino-phenyl)-amide, Compound A450;

1-(5-tert-Butyl-2-p-tolyl-2H-pyrazol-3-yl)-3-{4-[1-(2,5-dimethoxy-benzenesulfonyl)-piperidin-4-ylmethyl]-phenyl}-urea, Compound A564;

1-(5-tert-Butyl-2-p-tolyl-2H-pyrazol-3-yl)-3-{4-[1-(2-chloro-benzenesulfonyl)-piperidin-4-ylmethyl]-phenyl}-urea, Compound A567;

1-(5-tert-Butyl-2-p-tolyl-2H-pyrazol-3-yl)-3-{4-[1-(2-methoxy-5-methyl-benzenesulfonyl)-piperidin-4-ylmethyl]-phenyl}-urea, Compound A592;

1-(5-tert-Butyl-2-p-tolyl-2H-pyrazol-3-yl)-3-[4-(1-ethanesulfonyl-piperidin-4-ylmethyl)-phenyl]-urea, Compound A606;

1-(5-tert-Butyl-2-p-tolyl-2H-pyrazol-3-yl)-3-[4-(1-methanesulfonyl-piperidin-4-ylmethyl)-phenyl]-urea, Compound A608;

2-(4-{4-[3-(5-tert-Butyl-2-p-tolyl-2H-pyrazol-3-yl)-ureido]-benzyl}-piperidine-1-sulfonyl)-benzoic acid methyl ester, Compound A609;

1-(5-tert-Butyl-2-p-tolyl-2H-pyrazol-3-yl)-3-(3-{8-[2-(6-methoxy-benzofuran-3-yl)-acetyl]-8-aza-bicyclo[3.2.1]oct-3-ylmethyl}-phenyl)-urea, Compound A618;

1-(5-tert-Butyl-2-p-tolyl-2H-pyrazol-3-yl)-3-(3-{8-[2-(1-methyl-1H-indol-3-yl)-acetyl]-8-aza-bicyclo[3.2.1]oct-3-ylmethyl}-phenyl)-urea, Compound A641;

1-(5-tert-Butyl-2-p-tolyl-2H-pyrazol-3-yl)-3-(3-{8-[2-(3,4-difluoro-phenyl)-acetyl]-8-aza-bicyclo[3.2.1]oct-3-ylmethyl}-phenyl)-urea, Compound A719;

1-(5-tert-Butyl-2-p-tolyl-2H-pyrazol-3-yl)-3-(3-{8-[2-(2,4-difluoro-phenyl)-acetyl]-8-aza-bicyclo[3.2.1]oct-3-ylmethyl}-phenyl)-urea, Compound A720;

1-(5-tert-Butyl-2-p-tolyl-2H-pyrazol-3-yl)-3-(3-{8-[2-(2-fluoro-phenyl)-acetyl]-8-aza-bicyclo[3.2.1]oct-3-ylmethyl}-phenyl)-urea, Compound A761;

N-[2-(3-{3-[3-(5-tert-Butyl-2-p-tolyl-2H-pyrazol-3-yl)-ureido]-benzyl}-8-aza-bicyclo[3.2.1]oct-8-yl)-2-oxo-ethyl]-acetamide, Compound A766;

1-(5-tert-Butyl-2-p-tolyl-2H-pyrazol-3-yl)-3-{3-[8-(2,3-dimethoxy-benzoyl)-8-aza-bicyclo[3.2.1]oct-3-ylmethyl]-phenyl}-urea, Compound A786;

1-(5-tert-butyl-2-p-tolyl-2H-pyrazol-3-yl)-3-{2-[1-(2,4-dimethoxy-benzoyl)-piperidin-4-ylmethyl]-phenyl}-urea, Compound A1113;

1-(5-tert-Butyl-2-p-tolyl-2H-pyrazol-3-yl)-3-(4-{8-[2-(2,3-dimethoxy-phenyl)-acetyl]-8-aza-bicyclo[3.2.1]oct-3-ylmethyl}-phenyl)-urea, Compound A1312;

1-(5-tert-Butyl-2-p-tolyl-2H-pyrazol-3-yl)-3-(4-{8-[2-(2,4-difluoro-phenyl)-acetyl]-8-aza-bicyclo[3.2.1]oct-3-ylmethyl}-phenyl)-urea, Compound A1364;

1-(5-tert-Butyl-2-p-tolyl-2H-pyrazol-3-yl)-3-(4-{8-[2-(2-methoxy-phenyl)-acetyl]-8-aza-bicyclo[3.2.1]oct-3-ylmethyl}-phenyl)-urea, Compound A1404;

1-{4-[8-(4-Amino-5-chloro-2-methoxy-benzoyl)-8-aza-bicyclo[3.2.1]oct-3-ylmethyl]-phenyl}-3-(5-tert-butyl-2-p-tolyl-2H-pyrazol-3-yl)-urea, Compound A1441;

4-{4-[3-(5-tert-Butyl-2-p-tolyl-2H-pyrazol-3-yl)-ureido]-benzyl}-piperidine-1-carboxylic acid benzyl ester, Compound A1610;

4-{4-[3-(5-tert-Butyl-2-p-tolyl-2H-pyrazol-3-yl)-ureido]-benzyl}-piperidine-1-carboxylic acid isobutyl ester, Compound A1625;

1-(5-tert-Butyl-2-p-tolyl-2H-pyrazol-3-yl)-3-{3-[1-(2,5-dimethoxy-benzoyl)-piperidin-4-ylmethyl]-phenyl}-urea, Compound A1636;

1-(5-tert-Butyl-2-p-tolyl-2H-pyrazol-3-yl)-3-{4-[1-(4,5-dihydro-benzofuran-6-carbonyl)-piperidin-4-ylmethyl]-phenyl}-urea, Compound A1642;

1-(5-tert-Butyl-2-p-tolyl-2H-pyrazol-3-yl)-3-(3-{1-[2-(2,5-dimethoxy-phenyl)-acetyl]-piperidin-4-ylmethyl}-phenyl)-urea, Compound A1646; and 1-(5-tert-Butyl-2-p-tolyl-2H-pyrazol-3-yl)-3-{4-[8-(2,5-dimethoxy-benzoyl)-8-aza-bicyclo[3.2.1]oct-3-ylmethyl]-phenyl}-urea, Compound A1647.

Especially preferred compounds within the scope of the invention (that produce 50% inhibition in the p38 cascade assay at concentrations within the range 10 nanomolar to 100 nanomolar) are:

1-(5-tert-Butyl-2-p-tolyl-2H-pyrazol-3-yl)-3-{3-[1-(1-methyl-cyclopropanecarbonyl)-piperidin-4-ylmethyl]-phenyl}-urea, Compound A16;

1-(5-tert-Butyl-2-p-tolyl-2H-pyrazol-3-yl)-3-{3-[1-(2,4-dimethoxy-benzoyl)-piperidin-4-ylmethyl]-phenyl}-urea, Compound A27;

1-(5-tert-Butyl-2-p-tolyl-2H-pyrazol-3-yl)-3-{3-[1-(2,4-dimethyl-thiazole-5-carbonyl)-piperidin-4-ylmethyl]-phenyl}-urea, Compound A28;

1-(5-tert-Butyl-2-p-tolyl-2H-pyrazol-3-yl)-3-{3-[1-(2-pyridin-3-yl-thiazole-4-carbonyl)-piperidin-4-ylmethyl]-phenyl}-urea, Compound A32;

1-(5-tert-Butyl-2-p-tolyl-2H-pyrazol-3-yl)-3-{3-[1-(2-pyridin-4-yl-thiazole-4-carbonyl)-piperidin-4-ylmethyl]-phenyl}-urea, Compound A34;

1-(5-tert-Butyl-2-p-tolyl-2H-pyrazol-3-yl)-3-{3-[1-(2-chloro-pyridine-3-carbonyl)-piperidin-4-ylmethyl]-phenyl}-urea, Compound A42;

1-(5-tert-Butyl-2-p-tolyl-2H-pyrazol-3-yl)-3-(3-{1-[2-(2-fluoro-phenyl)-acetyl]-piperidin-4-ylmethyl}-phenyl)-urea, Compound A43;

1-(5-tert-Butyl-2-p-tolyl-2H-pyrazol-3-yl)-3-{3-[1-(2-methyl-pyridine-3-carbonyl)-piperidin-4-ylmethyl]-phenyl}-urea, Compound A59;

N-[3-(4-{3-[3-(5-tert-Butyl-2-p-tolyl-2H-pyrazol-3-yl)-ureido]-benzyl}-piperidine-1-carbonyl)-phenyl]-acetamide, Compound A88;

1-(5-tert-Butyl-2-p-tolyl-2H-pyrazol-3-yl)-3-{3-[1-(4-methoxy-2-methyl-benzoyl)-benzoyl)-piperidin-4-ylmethyl]-phenyl}-urea, Compound A120;

1-(5-tert-Butyl-2-p-tolyl-2H-pyrazol-3-yl)-3-{3-[1-(4-methoxy-thiophene-3-carbonyl)-piperidin-4-ylmethyl]-phenyl}-urea, Compound A123;

1-(5-tert-Butyl-2-p-tolyl-2H-pyrazol-3-yl)-3-{3-[1-(5-methyl-thiophene-2-carbonyl)-piperidin-4-ylmethyl]-phenyl}-urea, Compound A137;

N-[2-(4-{3-[3-(5-tert-Butyl-2-p-tolyl-2H-pyrazol-3-yl)-ureido]-benzyl}-piperidin-1-yl)-2-oxo-ethyl]-benzamide, Compound A163;

1-(5-tert-Butyl-2-p-tolyl-2H-pyrazol-3-yl)-3-{3-[1-(pyridine-4-carbonyl)-piperidin-4-ylmethyl]-phenyl}-urea, Compound A170;

1-(5-tert-Butyl-2-p-tolyl-2H-pyrazol-3-yl)-3-{3-[1-(2-methoxy-acetyl)-piperidin-4-ylmethyl]-phenyl}-urea, Compound A173;

4-(4-{3-[3-(5-tert-Butyl-2-p-tolyl-2H-pyrazol-3-yl)-ureido]-benzyl}-piperidin-1-yl)-4-oxo-butyric acid methyl ester, Compound A174;

N-[2-(4-3-[3-(5-tert-Butyl-2-p-tolyl-2H-pyrazol-3-yl)-ureido]-benzyl}-piperidin-1-yl)-2-oxo-ethyl]-acetamide, Compound A179;

1-(5-tert-Butyl-2-p-tolyl-2H-pyrazol-3-yl)-3-{3-[1-(pyridine-3-carbonyl)-piperidin-4-ylmethyl]-phenyl}-urea, Compound A181;

1-(5-tert-Butyl-2-p-tolyl-2H-pyrazol-3-yl)-3-(4-{1-[2-(2,4-difluoro-phenyl)-acetyl]-piperidin-4-ylmethyl}-phenyl)-urea, Compound A217;

1-(5-tert-Butyl-2-p-tolyl-2H-pyrazol-3-yl)-3-{4-[1-(2,4-dimethoxy-benzoyl)-piperidin-4-ylmethyl]-phenyl}-urea, Compound A218;

1-(5-tert-Butyl-2-p-tolyl-2H-pyrazol-3-yl)-3-{4-[1-(2,4-dimethyl-thiazole-5-carbonyl)-piperidin-4-ylmethyl]-phenyl}-urea, Compound A219;

1-(5-tert-Butyl-2-p-tolyl-2H-pyrazol-3-yl)-3-{4-[1-(2,5-dimethoxy-benzoyl)-piperidin-4-ylmethyl]-phenyl}-urea, Compound A220;

1-(5-tert-Butyl-2-p-tolyl-2H-pyrazol-3-yl)-3-{4-[1-(pyrazine-2-carbonyl)-piperidin-4-ylmethyl]-phenyl}-urea, Compound A256;

1-{4-[1-(3-Amino-pyrazine-2-carbonyl)-piperidin-4-ylmethyl]-phenyl}-3-(5-tert-butyl-2-p-tolyl-2H-pyrazol-3-yl)-urea, Compound A283;

1-(5-tert-Butyl-2-p-tolyl-2H-pyrazol-3-yl)-3-{4-[1-(3-methyl-furan-2-carbonyl)-piperidin-4-ylmethyl]-phenyl}-urea, Compound A289;

1-(5-tert-Butyl-2-p-tolyl-2H-pyrazol-3-yl)-3-{4-[1-(3-methyl-benzofuran-2-carbonyl)-piperidin-4-ylmethyl]-phenyl}-urea, Compound A290;

1-(5-tert-Butyl-2-p-tolyl-2H-pyrazol-3-yl)-3-{4-[1-(3-phenoxy-propionyl)-piperidin-4-ylmethyl]-phenyl}-urea, Compound A292;

1-(5-tert-Butyl-2-p-tolyl-2H-pyrazol-3-yl)-3-{4-[1-(thiophene-3-carbonyl)-piperidin-4-ylmethyl]-phenyl}-urea, Compound A294;

1-(5-tert-Butyl-2-p-tolyl-2H-pyrazol-3-yl)-3-{4-[1-(5-chloro-6-hydroxy-pyridine-3-carbonyl)-piperidin-4-ylmethyl]-phenyl}-urea, Compound A326;

1-(5-tert-Butyl-2-p-tolyl-2H-pyrazol-3-yl)-3-{4-[1-(5-methyl-pyrazine-2-carbonyl)-piperidin-4-ylmethyl]-phenyl}-urea, Compound A327;

1-(5-tert-Butyl-2-p-tolyl-2H-pyrazol-3-yl)-3-{4-[1-(6-hydroxy-pyridine-3-carbonyl)-piperidin-4-ylmethyl]-phenyl}-urea, Compound A333;

1-(5-tert-Butyl-2-p-tolyl-2H-pyrazol-3-yl)-3-{4-[1-(6-methyl-pyridine-2-carbonyl)-piperidin-4-ylmethyl]-phenyl}-urea, Compound A334;

Acetic acid 4-(4-{4-[3-(5-tert-butyl-2-p-tolyl-2H-pyrazol-3-yl)-ureido]-benzyl}-piperidine-1-carbonyl)-benzyl ester, Compound A336;

1-(5-tert-Butyl-2-p-tolyl-2H-pyrazol-3-yl)-3-{4-[1-(4-oxo-4,5,6,7-tetrahydro-benzofuran-3-carbonyl)-piperidin-4-ylmethyl]-phenyl}-urea, Compound A342;

N-[2-(4-{4-[3-(5-tert-Butyl-2-p-tolyl-2H-pyrazol-3-yl)-ureido]-benzyl}-piperidin-1-yl)-2-oxo-ethyl]-benzamide, Compound A352;

1-(5-tert-Butyl-2-p-tolyl-2H-pyrazol-3-yl)-3-{4-[1-(1H-indole-5-carbonyl)-piperidin-4-ylmethyl]-phenyl}-urea, Compound A361;

1-(5-tert-Butyl-2-p-tolyl-2H-pyrazol-3-yl)-3-{4-[1-(pyridine-4-carbonyl)-piperidin-4-ylmethyl]-phenyl}-urea, Compound A364;

1-(5-tert-Butyl-2-p-tolyl-2H-pyrazol-3-yl)-3-{4-[1-(2-methoxy-acetyl)-piperidin-4-ylmethyl]-phenyl}-urea, Compound A367;

N-[2-(4-{4-[3-(5-tert-Butyl-2-p-tolyl-2H-pyrazol-3-yl)-ureido]-benzyl}-piperidin-1-yl)-2-oxo-ethyl]-acetamide, Compound A375;

1-(5-tert-Butyl-2-p-tolyl-2H-pyrazol-3-yl)-3-{4-[1-(pyridine-3-carbonyl)-piperidin-4-ylmethyl]-phenyl}-urea, Compound A377;

1-(5-tert-Butyl-2-p-tolyl-2H-pyrazol-3-yl)-3-{4-[1-(quinoline-6-carbonyl)-piperidin-4-ylmethyl]-phenyl}-urea, Compound A386;

1-(5-tert-Butyl-2-p-tolyl-2H-pyrazol-3-yl)-3-[4-(1-methanesulfonyl-piperidin-4-ylmethyl)-phenyl]-urea, Compound A608;

N-[3-(3-{3-[3-(5-tert-Butyl-2-p-tolyl-2H-pyrazol-3-yl)-ureido]-benzyl}-8-aza-bicyclo[3.2.1]octane-8-carbonyl)-phenyl]-acetamide, Compound A707;

1-(5-tert-Butyl-2-p-tolyl-2H-pyrazol-3-yl)-3-{3-[8-(4-methyl-3,4-dihydro-2H-benzo[1,4]oxazine-7-sulfonyl)-8-aza-bicyclo[3.2.1]oct-3-ylmethyl]-phenyl}-urea, Compound A880;

4-{4-[3-(5-tert-Butyl-2-p-tolyl-2H-pyrazol-3-yl)-ureido]-benzyl}-piperidine-1-carboxylic acid 4-methoxy-phenyl ester, Compound A1605;

4-{4-[3-(5-tert-Butyl-2-p-tolyl-2H-pyrazol-3-yl)-ureido]-benzyl}-piperidine-1-carboxylic acid benzyl ester, Compound A1610;

4-{4-[3-(5-tert-Butyl-2-p-tolyl-2H-pyrazol-3-yl)-ureido]-benzyl}-piperidine-1-carboxylic acid isobutyl ester, Compound A1625;

1-(5-tert-Butyl-2-p-tolyl-2H-pyrazol-3-yl)-3-{3-[1-(2,5-dimethoxy-benzoyl)-piperidin-4-ylmethyl]-phenyl}-urea, Compound A1 636;

1-[4-(1-acetyl-piperidin-4-ylmethyl)-phenyl]-3-(5-tert-butyl-2-p-tolyl-2H-pyrazol-3-yl)-urea, Compound A1637;

1-{3-[1 benzofuran-2-carbonyl)-piperidin-4-ylmethyl]-phenyl}-3-(5-tert-butyl-2-p-tolyl-2H-pyrazol-3-yl)-urea, Compound A1638;

1-(5-tert-Butyl-2-p-tolyl-2H-pyrazol-3-yl)-3-{3-[1-(piperidine-4-carbonyl)-piperidin-4-ylmethyl]-phenyl}-urea, Compound A1639;

1-(5-tert-Butyl-2-p-tolyl-2H-pyrazol-3-yl)-3-{4-[8-(6-methyl-pyridine-2-carbonyl)-8-aza-bicyclo[3.2.1]oct-3-ylmethyl]-phenyl}-urea, Compound A1640;

4-{4-[3-(5-tert-Butyl-2-p-tolyl-2H-pyrazol-3-yl)-ureido]-benzyl}-piperidine-1-carboxylic acid (1-acetyl-3-oxo-3-phenyl-propenyl)-amide, Compound A1641; and 4-{4-[3-(5-tert-Butyl-2-p-tolyl-2H-pyrazol-3-yl)-ureido]-benzyl}-piperidin-1-carboxylic acid (1R,2S,5R)-2-isopropyl-5-methyl-cyclohexyl ester, Compound A1644.

Especially preferred compounds within the scope of the invention (that produce 50% inhibition in the LPS-induced TNF-alpha release in THP-1 cells assay at concentrations within the range 10 nanomolar to 100 nanomolar) are:

1-(5-tert-Butyl-2-p-tolyl-2H-pyrazol-3-yl)-3-{3-[1-((S)-2-methoxy-2-phenyl-acetyl)-piperidin-4-ylmethyl]-phenyl}-urea, Compound A4;

1-(5-tert-Butyl-2-p-tolyl-2H-pyrazol-3-yl)-3-{3-[1-([1,2,3]thiadiazole-4-carbonyl)-piperidin-4-ylmethyl]-phenyl}-urea, Compound A6;

1-(5-tert-Butyl-2-p-tolyl-2H-pyrazol-3-yl)-3-{3-[1-(2,3-diethoxy-benzoyl)-piperidin-4-ylmethyl]-phenyl}-urea, Compound A21;

1-(5-tert-Butyl-2-p-tolyl-2H-pyrazol-3-yl)-3-{3-[1-(2,4,6-trimethoxy-benzoyl)-piperidin-4-ylmethyl]-phenyl}-urea, Compound A24;

1-(5-tert-Butyl-2-p-tolyl-2H-pyrazol-3-yl)-3-{3-[1-(2,4-dimethoxy-benzoyl)-piperidin-4-ylmethyl]-phenyl}-urea, Compound A27;

1-(5-tert-Butyl-2-p-tolyl-2H-pyrazol-3-yl)-3-{3-[1-(2,4-dimethyl-thiazole-5-carbonyl)-piperidin-4-ylmethyl]-phenyl}-urea, Compound A28;

1-(5-tert-Butyl-2-p-tolyl-2H-pyrazol-3-yl)-3-{3-[1-(2,5-dimethyl-furan-3-carbonyl)-piperidin-4-ylmethyl]-phenyl}-urea, Compound A29;

1-(5-tert-Butyl-2-p-tolyl-2H-pyrazol-3-yl)-3-{3-[1-(2-chloro-4-methanesulfonyl-benzoyl)-piperidin-4-ylmethyl]-phenyl}-urea, Compound A40;

1-(5-tert-Butyl-2-p-tolyl-2H-pyrazol-3-yl)-3-{3-[1-(2-chloro-pyridine-3-carbonyl)-piperidin-4-ylmethyl]-phenyl}-urea, Compound A42;

1-(5-tert-Butyl-2-p-tolyl-2H-pyrazol-3-yl)-3-{3-[1-(furan-2-carbonyl)-piperidin-4-ylmethyl]-phenyl}-urea, Compound A45;

1-(5-tert-Butyl-2-p-tolyl-2H-pyrazol-3-yl)-3-{3-[1-(2-methyl-furan-3-carbonyl)-piperidin-4-ylmethyl]-phenyl}-urea, Compound A52;

N-[3-(4-{3-[3-(5-tert-Butyl-2-p-tolyl-2H-pyrazol-3-yl)-ureido]-benzyl}-piperidine-1-carbonyl)-phenyl]-acetamide, Compound A88;

1-(5-tert-Butyl-2-p-tolyl-2H-pyrazol-3-yl)-3-{3-[1-(furan-3-carbonyl)-piperidin-4-ylmethyl]-phenyl}-urea, Compound A92;

1-(5-tert-Butyl-2-p-tolyl-2H-pyrazol-3-yl)-3-{3-[1-(3-methyl-furan-2-carbonyl)-piperidin-4-ylmethyl]-phenyl}-urea, Compound A95;

1-(5-tert-Butyl-2-p-tolyl-2H-pyrazol-3-yl)-3-{3-[1-(thiophene-3-carbonyl)-piperidin-4-ylmethyl]-phenyl}-urea, Compound A99;

1-(5-tert-Butyl-2-p-tolyl-2H-pyrazol-3-yl)-3-{3-[1-(4-hydroxymethyl-benzoyl)-piperidin-4-ylmethyl]-phenyl}-urea, Compound A118;

1-(5-tert-Butyl-2-p-tolyl-2H-pyrazol-3-yl)-3-{3-[1-(4-methoxy-2-methyl-benzoyl)-piperidin-4-ylmethyl]-phenyl}-urea, Compound A120;

1-(5-tert-Butyl-2-p-tolyl-2H-pyrazol-3-yl)-3-{3-1-(4-methoxy-thiophene-3-carbonyl)-piperidin-4-ylmethyl]-phenyl}-urea, Compound A123;

1-(5-tert-Butyl-2-p-tolyl-2H-pyrazol-3-yl)-3-{3-[1-(5-chloro-thiophene-2-carbonyl)-piperidin-4-ylmethyl]-phenyl}-urea, Compound A131;

1-(5-tert-Butyl-2-p-tolyl-2H-pyrazol-3-yl)-3-(3-{1-[5-methoxy-2-(2,2,2-trifluoro-ethoxy)-benzoyl]-piperidin-4-ylmethyl}-phenyl)-urea, Compound A132;

1-(5-tert-Butyl-2-p-tolyl-2H-pyrazol-3-yl)-3-{3-[1-(5-methyl-thiophene-2-carbonyl)-piperidin-4-ylmethyl]-phenyl}-urea, Compound A137;

Acetic acid 4-(4-{3-[3-(5-tert-butyl-2-p-tolyl-2H-pyrazol-3-yl)-ureido]-benzyl}-piperidin-4-carbonyl)-benzyl ester, Compound A148;

1-(5-tert-Butyl-2-p-tolyl-2H-pyrazol-3-yl)-3-{4-[1-(1-methyl-cyclopropanecarbonyl)-piperidin-4-ylmethyl]-phenyl}-urea, Compound A206;

1-(5-tert-Butyl-2-p-tolyl-2H-pyrazol-3-yl)-3-{4-[1-(2,3-dimethoxy-benzoyl)-piperidin-4-ylmethyl]-phenyl}-urea, Compound A212;

1-(5-tert-Butyl-2-p-tolyl-2H-pyrazol-3-yl)-3-{4-[1-(2,4-dimethoxy-benzoyl)-piperidin-4-ylmethyl]-phenyl}-urea, Compound A218;

1-(5-tert-Butyl-2-p-tolyl-2H-pyrazol-3-yl)-3-{4-[1-(2,4-dimethyl-thiazole-5-carbonyl)-piperidin-4-ylmethyl]-phenyl}-urea, Compound A219;

1-(5-tert-Butyl-2-p-tolyl-2H-pyrazol-3-yl)-3-{4-[1-(2,5-dimethoxy-benzoyl)-piperidin-4-ylmethyl]-phenyl}-urea, Compound A220;

1-(5-tert-Butyl-2-p-tolyl-2H-pyrazol-3-yl)-3-{4-[1-(2,5-dimethyl-furan-3-carbonyl)-piperidin-4-ylmethyl]-phenyl}-urea, Compound A222;

1-(5-tert-Butyl-2-p-tolyl-2H-pyrazol-3-yl)-3-{4-[1-(2,6-dimethoxy-pyridine-3-carbonyl)-piperidin-4-ylmethyl]-phenyl}-urea, Compound A224;

1-(5-tert-Butyl-2-p-tolyl-2H-pyrazol-3-yl)-3-{4-[1-(2-pyridin-3-yl-thiazole-4-carbonyl)-piperidin-4-ylmethyl]-phenyl}-urea, Compound A225;

1-(5-tert-Butyl-2-p-tolyl-2H-pyrazol-3-yl)-3-{4-[1-(2-pyridin-4-yl-thiazole-4-carbonyl)-piperidin-4-ylmethyl]-phenyl}-urea, Compound A227;

1-(5-tert-Butyl-2-p-tolyl-2H-pyrazol-3-yl)-3-{4-[1-(2-chloro-pyridine-3-carbonyl)-piperidin-4-ylmethyl]-phenyl}-urea, Compound A235;

1-(5-tert-Butyl-2-p-tolyl-2H-pyrazol-3-yl)-3-{4-[1-(2-methyl-furan-3-carbonyl)-piperidin-4-ylmethyl]-phenyl}-urea, Compound A244;

1-(5-tert-Butyl-2-p-tolyl-2H-pyrazol-3-yl)-3-{4-[1-(2-methyl-[1,8naphthyridine-3-carbonyl)-piperidin-4-ylmethyl]-phenyl}-urea, Compound A249;

1-(5-tert-Butyl-2-p-tolyl-2H-pyrazol-3-yl)-3-{4-[1-(pyrazine-2-carbonyl)-piperidin-4-ylmethyl]-phenyl}-urea, Compound A256;

1-(5-tert-Butyl-2-p-tolyl-2H-pyrazol-3-yl)-3-(4-{1-[3-(cyano-methyl-methyl)-benzoyl]-piperidin-4-ylmethyl}-phenyl)-urea, Compound A272;

1-(5-tert-Butyl-2-p-tolyl-2H-pyrazol-3-yl)-3-{4-[1-(furan-3-carbonyl)-piperidin-4-ylmethyl]-phenyl}-urea, Compound A286;

1-(5-tert-Butyl-2-p-tolyl-2H-pyrazol-3-yl)-3-{4-[1-(3-methyl-furan-2-carbonyl)-piperidin-4-ylmethyl]-phenyl}-urea, Compound A289;

1-(5-tert-Butyl-2-p-tolyl-2H-pyrazol-3-yl)-3-{4-[1-(thiophene-3-carbonyl)-piperidin-4-ylmethyl]-phenyl}-urea, Compound A294;

1-(5-tert-Butyl-2-p-tolyl-2H-pyrazol-3-yl)-3-{4-[1-(4-oxazol-5-yl-benzoyl)-piperidin-4-ylmethyl]-phenyl}-urea, Compound A301;

1-(5-tert-Butyl-2-p-tolyl-2H-pyrazol-3-yl)-3-{4-[1-(4-difluoromethoxy-benzoyl)-piperidin-4-ylmethyl]-phenyl}-urea, Compound A306;

1-(5-tert-Butyl-2-p-tolyl-2H-pyrazol-3-yl)-3-{4-[1-(4-hydroxymethyl-benzoyl)-piperidin-4-ylmethyl]-phenyl}-urea, Compound A315;

1-(5-tert-Butyl-2-p-tolyl-2H-pyrazol-3-yl)-3-(4-{1-[2-(4-methoxy-phenyl)-acetyl]-piperidin-4-ylmethyl}-phenyl)-urea, Compound A319;

1-{4-[1-(6-Amino-pyridine-3-carbonyl)-piperidin-4-ylmethyl]-phenyl}-3-(5-tert-butyl-2-p-tolyl-2H-pyrazol-3-yl)-urea, Compound A331A;

1-(5-tert-Butyl-2-p-tolyl-2H-pyrazol-3-yl)-3-{4-[1-(6-methyl-pyridine-2-carbonyl)-piperidin-4-ylmethyl]-phenyl}-urea, Compound A334;

Acetic acid 4-(4-{4-[3-(5-tert-butyl-2-p-tolyl-2H-pyrazol-3-yl)-ureido]-benzyl}-piperidin-1-carbonyl)-benzyl ester, Compound A336;

N-[2-(4-{4-[3-(5-tert-Butyl-2-p-tolyl-2H-pyrazol-3-yl)-ureido]-benzyl}-piperidin-1-yl)-2-oxo-ethyl]-benzamide, Compound A352;

1-(5-tert-Butyl-2-p-tolyl-2H-pyrazol-3-yl)-3-{4-[1-(1H-indole-5-carbonyl)-piperidin-4-ylmethyl]-phenyl}-urea, Compound A361;

1-(5-tert-Butyl-2-p-tolyl-2H-pyrazol-3-yl)-3-{4-[1-(1H-indole-6-carbonyl)-piperidin-4-ylmethyl]-phenyl}-urea, Compound A362;

1-(5-tert-Butyl-2-p-tolyl-2H-pyrazol-3-yl)-3-{4-[1-(pyridine-4-carbonyl)-piperidin-4-ylmethyl]-phenyl}-urea, Compound A364;

1-(5-tert-Butyl-2-p-tolyl-2H-pyrazol-3-yl)-3-(4-{1-[3-(4,6-dimethyl-pyrimidin-2-ylamino)-benzoyl]-piperidin-4-ylmethyl}-phenyl)-urea, Compound A371;

1-(5-tert-Butyl-2-p-tolyl-2H-pyrazol-3-yl)-3-{4-[1-(pyridine-3-carbonyl)-piperidin-4-ylmethyl]-phenyl}-urea, Compound A377;

1-(5-tert-Butyl-2-p-tolyl-2H-pyrazol-3-yl)-3-{4-[1-(pyridine-2-carbonyl)-piperidin-4-ylmethyl]-phenyl}-urea, Compound A380;

1-(5-tert-Butyl-2-p-tolyl-2H-pyrazol-3-yl)-3-{4-[1-(quinoline-6-carbonyl)-piperidin-4-ylmethyl]-phenyl}-urea, Compound A386;

1-(5-tert-Butyl-2-p-tolyl-2H-pyrazol-3-yl)-3-{4-[1-(2,5-dimethoxy-benzenesulfonyl)-piperidin-4-ylmethyl]-phenyl}-urea, Compound A564;

1-(5-tert-Butyl-2-p-tolyl-2H-pyrazol-3-yl)-3-{4-[1-(2-methoxy-5-methyl-benzenesulfonyl)-piperidin-4-ylmethyl]-phenyl}-urea, Compound A592;

1-(5-tert-Butyl-2-p-tolyl-2H-pyrazol-3-yl)-3-[4-(1-methanesulfonyl-piperidin-4-ylmethyl)-phenyl]-urea, Compound A608;

1-(5-tert-Butyl-2-p-tolyl-2H-pyrazol-3-yl)-3-{3-[8-(2,3-dimethoxy-benzoyl)-8-aza-bicyclo[3.2.1]oct-3-ylmethyl]-phenyl}-urea, Compound A786;

1-(5-tert-butyl-2-p-tolyl-2H-pyrazol-3-yl)-3-{2-[1-(2,4-dimethoxy-benzoyl)-piperidin-4-ylmethyl]-phenyl}-urea, Compound A1113;
4-{4-[3-(5-tert-Butyl-2-p-tolyl-2H-pyrazol-3-yl)-ureido]-benzyl}-piperidine-1-carboxylic acid isobutyl ester, Compound A1625;
1-(5-tert-Butyl-2-p-tolyl-2H-pyrazol-3-yl)-3-{3-[1-(2,5-dimethoxy-benzoyl)-piperidin-4-ylmethyl]-phenyl}-urea, Compound A1636 and
1-(5-tert-Butyl-2-p-tolyl-2H-pyrazol-3-yl)-3-{4-[1-(4,5-dihydro-benzofuran-6-carbonyl)-piperidin-4-ylmethyl]-phenyl}-urea, Compound A1642.

The compounds of present invention and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0 (Beilstein Information Systems, Inc.). [For example, a compound of formula (I) wherein $R^1$ is p-tolyl, $R^2$ is tert-butyl, X is —C(O)—, A is 1-(2,4-dimethoxy-benzoyl)-piperidin-4-yl and the urea moiety is attached to position 4 of the substituted phenyl moiety; that is, a compound having the following structure:

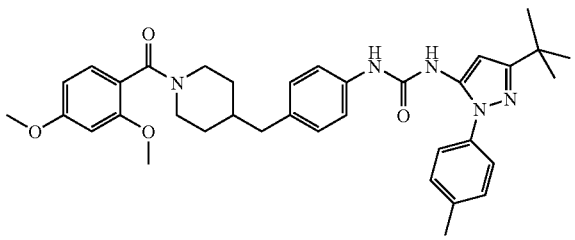

is named 1-(5-tert-butyl-2-p-tolyl-2H-pyrazol-3-yl)-3-{3-[1-(2,4-dimethoxy-benzoyl)-piperidin-4-ylmethyl]-phenyl}-urea. However, it is understood that, for a particular compound referred to by both a structural formula and a nomenclature name, if the structural formula and the nomenclature name are inconsistent with each other, the structural formula takes the precedence over the nomenclature name.

The compounds of the invention are p38 kinase inhibitors that inhibit the release of TNFα from mononuclear phagocytes and therefore have useful pharmacological activity. Accordingly, they are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention are inhibitors of the generation of tumour necrosis factor (TNF), especially TNF-alpha, according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of TNF, especially of TNF-alpha. For example, compounds of the present invention are useful in the treatment of joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, Lupus erythematosis, tuberculosis, atherosclerosis, acute coronary syndrome, myocardial infarction, stroke, muscle degeneration, cachexia, Reiter's syndrome, endotoxaemia, sepsis, septic shock, endotoxic shock, gram negative sepsis, gout, toxic shock syndrome, chronic pulmonary inflammatory diseases including asthma, adult respiratory distress syndrome, COPD, silicosis, pulmonary sarcoidosis, bone resorption diseases, osteoporosis, restenosis, heart failure and myocardial ischaemic syndromes, cardiac and renal reperfusion injury, thrombosis, glomerularnephritis, graft vs. host reaction, allograft rejection, Alzheimer's disease, Huntingdons's disease, Parkinson's disease and leprosy. Furthermore, the compounds are useful in the treatment of infections such as viral infections, for example HIV, cytomegalovirus (CMV), influenza, adenovirus and the Herpes group of viruses, parasitic infections, for example malaria such as cerebral malaria, and yeast and fungal infections, for example fungal meningitis; fever and myalgias due to infection; AIDS; AIDS related complex (ARC); cachexia secondary to infection or malignancy; cachexia secondary to acquired immune deficiency syndrome (AIDS) or to cancer, keloid and scar tissue formation, pyresis, diabetes, diabetic retinopathies, cancer and inflammatory bowel diseases such as Crohn's disease and ulcerative colitis; eczema; contact dermititis; psoriasis; sunburn and conjunctivitis. The compounds are also useful in the treatment of pain.

Compounds of the invention are also useful in the treatment of diseases of, or injury to, the brain in which overproduction of TNF-alpha has been implicated, such as multiple sclerosis, Alzheimers disease, trauma, stroke and other ischaemic conditions.

Compounds of the invention may also be useful in inhibiting diseases associated with over-production of other pro-inflammatory cytokines, IL-1, IL-6 and IL-8.

Compounds of the invention are also useful in the treatment of inflammatory and neuropathic pain.

A special embodiment of the therapeutic methods of the present invention is the treating of respiratory diseases including asthma and chronic obstructive pulmonary disease (COPD).

Another special embodiment of the therapeutic methods of the present invention is the treating of joint inflammation.

According to a further feature of the invention there is provided a method for the treatment of a human or animal patient suffering from, or subject to, conditions which can be ameliorated by the administration of an inhibitor of TNF, especially TNF-alpha, for example conditions as hereinbefore described, which comprises the administration to the patient of an effective amount of compound of the invention or a composition containing a compound of the invention. "Effective amount" is meant to describe an amount of compound of the present invention effective in inhibiting TNF and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts, *Protecting Groups in Organic Synthesis,* 3rd edition, John Wiley & Sons, Inc., 1999. Suitable amine protecting groups include sulfonyl (e.g., tosyl), acyl (e.g., benzyloxycarbonyl or t-butoxycarbonyl) and arylalkyl (e.g., benzyl), which may be removed by hydrolysis or hydrogenolysis as appropriate. Other suitable amine protecting groups include trifluoroacetyl [—C(=O)CF$_3$] which may be removed by base catalysed hydrolysis, or a solid phase resin bound benzyl group, such as a Merrifield resin bound 2,6-dimethoxybenzyl group (Ellman linker) or a 2,6-dimethoxy-4-[2-(polystyrylmethoxy)ethoxy]benzyl, which may be removed by acid catalysed hydrolysis, for example with trifluoroacetic acid.

Compounds of formula (I) in which

R$^1$, R2, X and A are as hereinbefore defined may be prepared by the reaction of amines of formula (X), wherein

X and A are as hereinbefore defined, with isocyanates of formula (XI), wherein R$^1$ and R$^2$ are as hereinbefore defined.

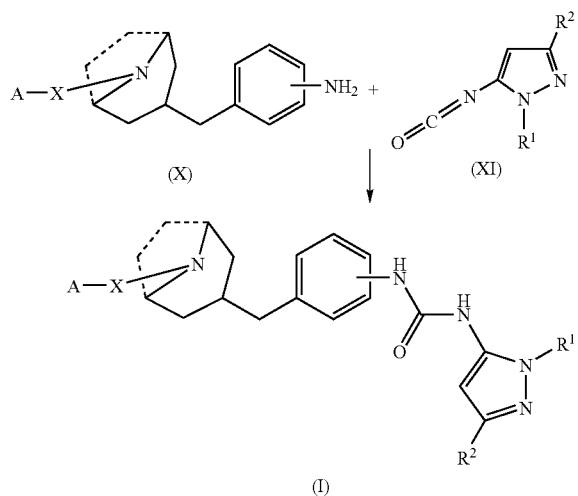

This reaction may conveniently be carried out in an inert solvent, such as dichloromethane, and at a temperature at about room temperature.

Compounds of formula (I) in which

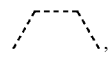

$R^1$, R2, X and A are as hereinbefore defined may also be prepared by the reaction of amines of formula (XIII), wherein

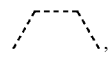

X and A are as hereinbefore defined, with isocyanates of formula (XII), wherein $R^1$ and $R^2$ are as hereinbefore defined.

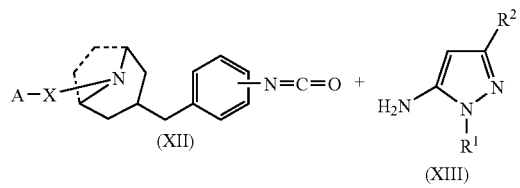

Compounds of formula (I) in which

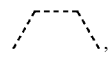

$R^1$ and $R^2$ are as hereinbefore defined, X is —C(O)— and A is optionally substituted alkoxyalkyl, optionally substituted alkenyl, optionally substituted alkyl, optionally substituted alkynyl, optionally substituted aryl, optionally substituted arylalkyl, optionally substituted arylalkoxyalkyl, optionally substituted aryloxyalkyl, optionally substituted cycloalkenyl, optionally substituted cycloalkyl, optionally substituted cycloalkylalkyl, optionally substituted cycloalkyloxyalkyl, optionally substituted cycloalkylalkoxyalkyl, optionally substituted heteroatyl, optionally substituted heteroarylalkyl, optionally substituted heteroaryloxyalkyl, optionally substituted heteroarylalkoxyalkyl, optionally substituted heterocycloalkyl, optionally substituted heterocycloalkylalkyl or optionally substituted heterocycloalkyloxyalkyl, may be prepared by the coupling of amines of formula (XIV), wherein

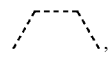

$R^1$ and $R^2$ are as hereinbefore defined,

with acids of formula (XV)

A-CO$_2$H         (XV)

wherein A is as defined immediately hereinabove. The condensation reaction can be effected using standard peptide coupling conditions such as treatment with an appropriate coupling agent [e.g., 1-(3-dimethylaminopropyl)-3-ethylcarbodiimide hydrochloride (EDCI), diisopropylcarbodiimide (DCI)] in an inert solvent, such as dichloromethane, and at ambient temperature. The coupling may also be carried out using resin technology, for example:

(i) treating tetrafluorophenol resin (PL-TFP 009) with acids of formula (XV), in the presence of diisopropylcarbodiimide, in an inert solvent, such as dimethylformamide, at a temperature at about room temperature, to give resin bound TFP active ester (XVI):

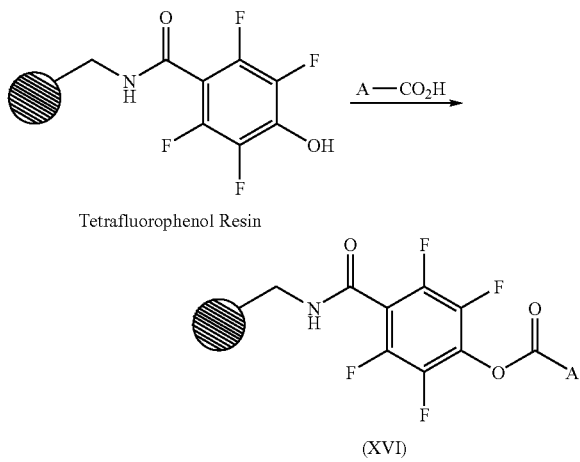

Tetrafluorophenol Resin

(XVI)

where

represents the polymeric core comprising polystyrene crosslinked with 1% divinylbenzene and A is as defined immediately hereinabove (ii) reaction of the resin bound TFP active ester (XVI) with amines of formula (XIV), wherein $R^1$ and $R^2$ are as defined hereinbefore, in dimethylformamide and at a temperature at about 50° C.

Compounds of formula (I) in which

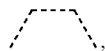

$R^1$ and $R^2$ are as hereinbefore defined, X is —C(O)— and A is optionally substituted alkoxy, optionally substituted arylalkoxy, optionally substituted aryloxy, optionally substituted cycloalkyloxy, optionally substituted cyclalkylalkoxy, optionally substituted heteroaryloxy, optionally substituted heteroarylalkoxy or optionally substituted heterocycloalkyloxy and is hereinafter defined as $R^f$, may be prepared by reaction of amines of formula (XIV), wherein

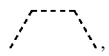

$R^1$ and $R^2$ are as hereinbefore defined, with chloroformates of formula (XVII)

A-O—C(O)—Cl        (XVII)

wherein A is as defined immediately hereinabove. The reaction may conveniently be carried out in the presence of a suitable base, such as pyridine, in an inert solvent, such as dichloromethane, and at ambient temperature. The carbamate formation reaction may also be carried out by treating (4-bromomethylphenoxy)methyl polystyrene with chloroformates of formula (XVII), in the presence of diisopropylethylamine, in an inert solvent, such as dimethylformamide, at a temperature at about room temperature, followed by reaction with tris-(2-aminoethyl)amine polystyrene.

Compounds of formula (I) in which

$R^1$ and $R^2$ are as hereinbefore defined, X is —C(O)—CH$_2$— and A is optionally substituted alkoxyalkyl, optionally substituted alkenyl, optionally substituted alkyl, optionally substituted alkynyl, optionally substituted aryl, optionally substituted arylalkyl, optionally substituted arylalkoxyalkyl, optionally substituted aryloxyalkyl, optionally substituted cycloalkenyl, optionally substituted cycloalkyl, optionally substituted cycloalkylalkyl, optionally substituted cycloalkyloxyalkyl, optionally substituted cycloalkylalkoxyalkyl, optionally substituted heteroaryl, optionally substituted heteroarylalkyl, optionally substituted heteroaryloxyalkyl, optionally substituted heteroarylalkoxyalkyl, optionally substituted heterocycloalkyl, optionally substituted heterocycloalkylalkyl or optionally substituted heterocycloalkyloxyalkyl may be prepared by the reaction of amines of formula (XIV) with alpha-halocarbonyl compounds of formula (XVIII)

A-COCH$_2$X$^1$        (XVIII)

wherein A is as defined immediately hereinabove and X$^1$ is bromo or chloro. The reaction may conveniently be carried out in an inert solvent, such as chloroform, in the presence of polymer-bound diisopropylamine at 50° C. under a nitrogen atmosphere followed by treatment with polymer-bound trisamine at room temperature. This method is particularly suitable for the prepared of compounds of formula (I) in which X is —C(O)—CH$_2$— and A is optionally substituted aryl or optionally substituted heteroaryl.

Compounds of formula (I) in which

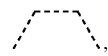

$R^1$ and $R^2$ are as hereinbefore defined, X is —NH—C(O)— and A is optionally substituted alkoxyalkyl, optionally substituted alkenyl, optionally substituted alkyl, optionally substituted alkynyl, optionally substituted aryl, optionally substituted arylalkyl, optionally substituted arylalkoxyalkyl, optionally substituted aryloxyalkyl, optionally substituted cycloalkenyl, optionally substituted cycloalkyl, optionally substituted cycloalkylalkyl, optionally substituted cycloalkyloxyalkyl, optionally substituted cycloalkylalkoxyalkyl, optionally substituted heteroaryl, optionally substituted heteroarylalkyl, optionally substituted heteroaryloxyalkyl, optionally substituted heteroarylalkoxyalkyl, optionally substituted heterocycloalkyl, optionally substituted heterocycloalkylalkyl or optionally substituted heterocycloalkyloxyalkyl may be prepared by the reaction of amines of formula (XIV) with isocyanates of formula (XIX)

A-NCO        (XIX)

wherein A is as defined immediately hereinabove. The reaction may conveniently be carried out in an inert solvent, such as chloroform, at room temperature under a nitrogen atmosphere followed by treatment of the reaction mixture with polymer-bound trisamine at room temperature. This method is particularly suitable for the prepared of compounds of formula (I) in which X is —NH—C(O)— and A is optionally substituted aryl or optionally substituted heteroaryl.

Compounds of formula (I) in which

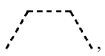

$R^1$ and $R^2$ are as hereinbefore defined, X is —S(O)$_2$— and A is optionally substituted alkenyl, optionally substituted alkyl, optionally substituted aryl or optionally substituted heteroaryl may be prepared by the reaction of amines of formula (XIV) with sulfonyl chlorides of formula (XX)

A-SO$_2$Cl (XX)

wherein A is as defined immediately hereinabove. The reaction may conveniently be carried out in the presence of a suitable base, such as pyridine, in an inert solvent, such as dichloromethane, and at a temperature at about room temperature. The reaction may also be carried out using resin technology, for example:

(i) treating tetrafluorophenol resin (PL-TFP 009) with sulfonyl chlorides of formula (XX), in the presence of diisopropylethylamine, in an inert solvent, such as dimethylformamide, at a temperature at about room temperature, to give resin bound TFP active sulfonyl ester (XXI):

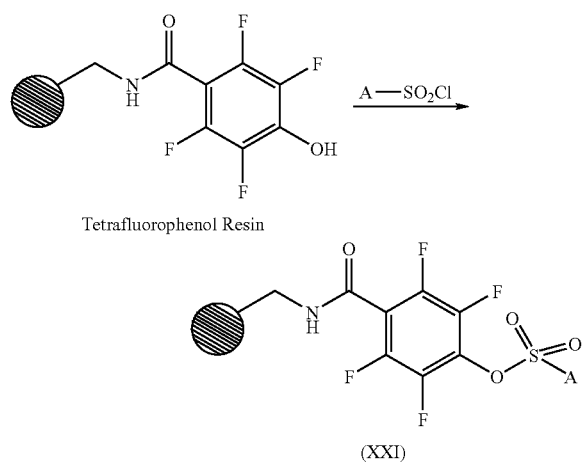

Tetrafluorophenol Resin (XXI)

where

represents the polymeric core comprising polystyrene crosslinked with 1% divinylbenzene and A is as defined immediately hereinabove (ii) reaction of the resin bound TFP active sulfonyl ester (XXI) with amines of formula (XIV), wherein $R^1$ and $R^2$ are as defined hereinbefore, in dimethylformamide and at a temperature at about 50° C.

Compounds of the invention may also be prepared by interconversion of other compounds of the invention.

Thus, for example, compounds of formula (I) containing a carboxy group may be prepared by hydrolysis of the corresponding esters. The hydrolysis may conveniently be carried out by alkaline hydrolysis using a base, such as an alkali metal hydroxide, e.g., lithium hydroxide, or an alkali metal carbonate, e.g., potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

Intermediate amines of formula (X), wherein

X and A are as hereinbefore defined may be prepared by the reduction of nitro compounds of formula (XXII)

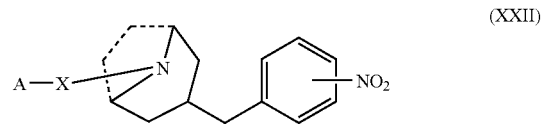

wherein

X and A are as hereinbefore defined. The reduction may conveniently be carried out using standard methods for the reduction of aromatic nitro compounds to the corresponding aromatic amines, for example (i) hydrogenation in the presence of a suitable catalyst, such as palladium on carbon, in an inert solvent, such as ethanol, at a temperature at about room temperature and optionally under pressure, (ii) treatment with sodium borohydride in the presence of a suitable catalyst, such as palladium on carbon, in an inert solvent, such as methanol, and at a temperature at about room temperature, (iii) treatment with tin chloride in an inert solvent, such as ethyl acetate or dimethylformamide, at a temperature at about 70° C. or (iii) treatment with tin in the presence of hydrochloric acid in ethanol at a temperature at about reflux temperature.

Nitro compounds of formula (XXII), wherein

X and A are as hereinbefore defined may be prepared by reaction of compounds of formula (XXIII) with the appropriate acids or acid chlorides, sulfonyl chlorides, isocyanates or chloroformates as described hereinabove.

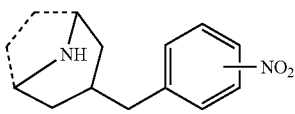

(XXIII)

Intermediates of formula (XII), wherein $R^1$ and $R^2$ are as hereinbefore defined, may be prepared from acids of formula (XXIV), wherein $R^2$ is as hereinbefore described:

Scheme A

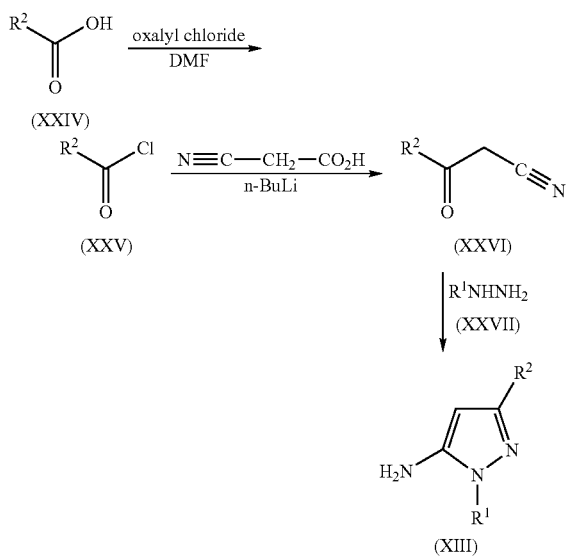

(i) acids of formula (XXIV) are treated with oxalyl chloride in the presence of dimethylformamide, an inert solvent, such as dichloromethane, and at a temperature at about room temperature to give acid chlorides of formula (XXV).

(ii) Acid chlorides of formula (XXV) are reacted with the dianion of cyanoacetic acid (generated by treatment with n-BuLi in an inert solvent, such as tetrahydrofuran, at a temperature at about −70° C.) to give ketoacetonitriles of formula (XXVI), (iii) ketoacetonitriles of formula (XXVI) are reacted with hydrazines of formula (XXVII), in an inert solvent, such as toluene, and at a temperature at about reflux temperature.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or an aqueous alcohol solution or other suitable solvents containing the appropriate acid and isolating the salt by evaporating the solution, or by reacting the free base and acid in an organic solvent, such as tetrahydrofuran, in which case the salt separates directly or can be obtained by concentration of the solution.

Compounds of this invention can be regenerated from their acid addition salts by the application or adaptation of known methods. For example, parent compounds of the invention can be regenerated from their acid addition salts by treatment with an alkali, e.g., aqueous sodium bicarbonate solution or aqueous ammonia solution.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

Compounds of this invention can be regenerated from their base addition salts by the application or adaptation of known methods. For example, parent compounds of the invention can be regenerated from their base addition salts by treatment with an acid, e.g., hydrochloric acid.

Compounds of the present invention may be conveniently prepared, or formed during the process of the invention, as solvates (e.g., hydrates). Hydrates of compounds of the present invention may be conveniently prepared by recrystallisation from an aqueous/organic solvent mixture, using organic solvents such as dioxan, tetrahydrofuran or methanol.

The starting materials and intermediates that are not commercially available may be prepared by the application or adaptation of known methods, for example methods as described in the Examples or their obvious chemical equivalents.

The present invention is further exemplified, but not limited by, the following illustrative Examples and Intermediates.

| Abbreviations: | |
|---|---|
| ATF-2 | Activating transcription factor-2 |
| ATP | Adenosine triphosphate |
| AU-rich | Adenine, uracil-rich |
| CBZ | Benzyloxy carbonyl |
| CIA | Collagen-induced arthritis |
| COPD | Chronic obstructive pulmonary disease |
| 9-BBN | 9-borabicyclo[3.3.1]nonane |
| DAST | (Diethylamino)sulfur trifluoride |
| DCM | Dichloromethane |
| DIC | N,N-diisopropylcarbodiimide |
| DMF | Dimethylformamide |
| DMSO | Dimethyl sulfoxide |
| DPPA | diphenylphosphoryl azide |
| DTT | Dithiothreitol |
| EDCI | N-(3-Dimethylaminopropyl)-N¢-ethylcarbodiimide hydrochloride |
| EDTA | Ethylenediaminetetraacetic acid |
| ELISA | Enzyme-linked immunosorbant assay |
| ELSD | evaporative light scattering detector |
| SI+ | electrospray ionization |
| EtOAc | Ethyl acetate |
| FCS | Fetal calf serum |
| GST | Glutathione S-transferase |
| HCl | hydrochloric acid |
| His | Histidine |
| HIV | Human immunodeficiency virus |
| HOBT | 1-Hydroxybenzotriazole hydrate |
| HPLC | high performance liquid chromatography |
| HTS | High throughput screening |
| IgG | Immunoglobulin G |
| IL- | Interleukin |
| JMC | Journal of Medicinal Chemistry |
| JOC | Journal of Organic Chemistry |
| LAH | lithium aluminum hydride |
| LPS | Lipopolysaccharide |
| MeOH | Methanol |

| | -continued |
|---|---|
| | Abbreviations: |
| MES | 2-Morpholinoethanesulfonic acid |
| MKK-6 | Mitogen activated protein kinase kinase-6 |
| NaBH4 | sodium borohydride |
| NH4Cl | ammonium chloride |
| PSI | pounds per square inch |
| PyBOP | (Benzotriazol-1-yloxy)tripyrrolidinophosphonium hexafluorophosphate |
| TEA | triethylamine |
| TFA | trifluoroacetic acid |
| THF | Tetrahydrofuran |
| TLC | thin layer chromatography |

Mass Spectra (MS) were recorded using a Micromass LCT mass spectrophotometer. The method was positive electrospray ionization, scanning mass m/z from 100 to 1000. Liquid chromatography was performed on an Agilent 1100 HPLC; stationary phase: phenomenex Synergi 2U Hydro-RP 20×4.0 mm column, mobile phase: A=0.1% formic acid (FA) in water, B=0.1% FA in acetonitrile. Flow is 1 mL/minute. Gradient is 10% B to 90% B in 3 minutes and 90% B to 100% B in 2 minutes.

Nuclear Magnetic Resonance Spectra (NMR) were recorded using VAST-NMR conditions (VAST=Versatile Automatic Sample Transportation) on a Varian Unity Inova 600 mhz NMR spectrophotometer. Spectral width is 15987 hz with 40,000 data points for digitizing. Relaxation delay was 2.0 seconds, with 128 transients in 7 minutes 28 seconds of acquisition time. Linear predication and solvent subtraction were applied for post-acquisition data processing. The samples were dissolved in $(CD_3)_2SO$ and transferred into the NMR probe via a Gilson-215 liquid handler. One 1 mL $(CD_3)_2SO$ rinse was performed for each sample change.

Intermediate 1 and Intermediate 2 [4-(4Amino-benzyl)-piperidin-1-yl]-(2,4-dimethoxy-phenyl)-methanone and [4(2-amino-benzyl)-piperidin-1-yl]-(2,4-dimethoxy-phenyl)-methanone To a mixture of 4-[4-nitrobenzyl]piperidine and 4-[2-nitrobenzyl]piperidine (1.0 g, 4.5 mmol, prepared as in WO199805292) and 2,4-dimethoxybenzoyl chloride (1.4 g, 6.8 mmol) in methylene chloride (25 mL) is added TEA (0.71 g, 7.0 mmol) and the reaction is stirred for 3 hours at room temperature. The reaction is extracted with dilute hydrochloric acid (HCl), sodium bicarbonate (NaHCO₃) (saturated), water and brine. The material is dried over sodium sulfate, filtered and concentrated to dryness. The material is purified on a 40 gram silica gel column eluted with ethyl acetate/heptane (1:1) to give 1.61 grams of product as a mixture. This product (1.61 g) is dissolved in methanol (100 mL) and 10% palladium on carbon (Pd/C) (300 mg) is added followed by the addition of small portions of sodium borohydride (NaBH₄) (2.0 g). The reaction evolved hydrogen and after 30 minutes the reaction is filtered through celite and concentrated to dryness. The residue is dissolved and the ortho and para isomers are separated on a 90 gram silica gel column using ethyl acetate/heptane (1:1) to give 545 mg of [4-(4-amino-benzyl)-piperidin-1-yl]-(2,4-dimethoxy-phenyl)-methanone, Intermediate 1, (MS M⁺¹ 355) and 300 mg of [4-(2-amino-benzyl)-piperidin-1-yl-(2,4-dimethoxy-phenyl)-methanone, Intermediate 2, (MS M⁺¹ 355).

Scheme 1:
Synthesis of Intermediate 1 and 2

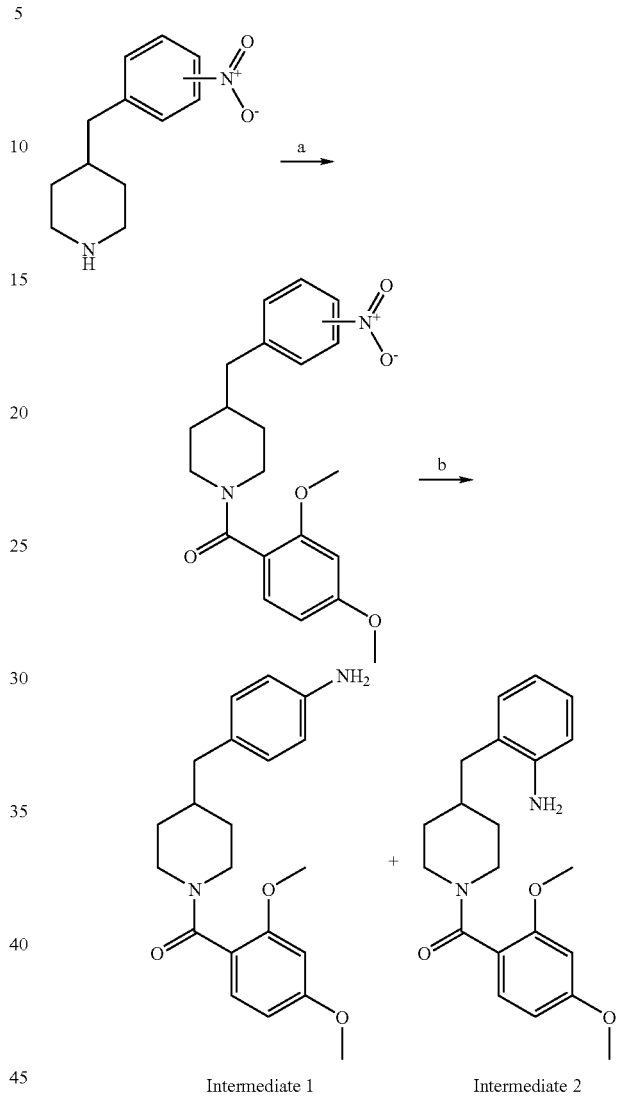

Intermediate 1    Intermediate 2
a. 2,4-dimethoxybenzoyl chloride, DCM, TEA;
b. Pd/C, NaBH4, MeOH Intermediate 3 1-(5-tert-Butyl-2-p-tolyl-2H-pyrazol-3-yl)-3-(3-piperidin-4-ylmethyl-phenyl)-urea hydrochloride The Weinreb amide (50 mmol) in tetrahydrofuran (THF) (100 mL) is cooled to 0° C. and 1M lithium aluminum hydride in THF (LAH/THF) (55 mL, 55 mmol) is added dropwise. The reaction is stirred for 1 hour at 0° C. and ethyl acetate (EtOAc) (55 mL) is carefully added to quench any unreacted LAH. The reaction is worked-up at 0° C. by the careful addition of H₂O, 15% aqueous (aqueous NaOH), H₂O(3×). The organic layer is stirred for 1 hour at room temperature and the solids that formed are filtered off. The filtrate is evaporated the residue is partitioned between methylene chloride and brine. The organic layer is dried (Magnesium Sulfate), filtered and evaporated. The material is chromatographed with silica gel using 15% ethyl acetate/methylene chloride to give 5.22 g of the aldehyde.

A solution of ethyl 3-iodobenzoate (40 mmol) in THF (40 mL) is cooled to −25 to −20° C. and 2M iso-propyl magnesium chloride in THF (iPrMgCl/THF) is added dropwise and the reaction is allowed to stir for 30 minutes. A solution of the aldehyde (35 mmol) in THF (35 mL) is then added while maintaining the temp from −25 to −20° C. The bath is removed and the stirring is continued overnight. The reaction is partitioned between ether-aqueous NH₄Cl. The organic layer is washed with brine, then dried over MgSO₄, filtered and evaporated. The residue is chromatographed on silica gel using 30% ethyl acetate/methylene chloride to yield 6.35 grams of the ester.

A mixture of the ester (18 mmol) and 20% Pd(OH)$_2$ (4.12 g) in ethyl alcohol (200 mL) is hydrogenated at 60-70 psi in a Parr apparatus overnight. The reaction is filtered through celite and evaporated to dryness. The residue is chromatographed on silica gel using 5% ethyl acetate/methylene chloride to yield 3.82 grams of reduced ester. The ester (20 mmol) in methanol (30 mL) is added 30 mL of 1N aqueous NaOH (30 mmol) and the reaction is heated in a 50° C. bath for 2 hours. The reaction is cooled to 0° C. and carefully acidified with 1N aqueous HCl. The reaction is extracted with ethyl acetate, dried over MgSO₄, filtered and concentrated to give quantitative yield of the acid.

To a solution of acid (20 mmol) in THF (100 mL) at room temp is added triethylamine (TEA) (22 mmol) followed by diphenylphosphoryl azide (DPPA) (22 mmol). The mixture is refluxed for 1 hour and the 3-amino-4-tert-butyl-2-tolylpyrazole (22 mmol) is added and the reaction is refluxed overnight. The reaction is cooled and partitioned between ether-aqueous NH₄Cl, and the organic layer is washed with brine, then dried over MgSO₄, filtered and evaporated. The residue is chromatographed on silica gel using 10-15% ethyl acetate/methylene chloride to yield 5.85 grams of the tert-butoxycarbonyl (BOC)-protected urea. The BOC-protected urea (10 mmol) is dissolved in methylene chloride (15 mL) under nitrogen at 0° C. and 4N HCl in dioxane (15 ml) is added. After 10 minutes the cooling bath is removed and the reaction is stirred for 3 hours at room temp. The solution is concentrated to a foam that solidified after stirring in ether for a few hours. The solid is filtered and air-dried to give a quantitative yield of 1(5-tert-Butyl-2-p-tolyl-2H-pyrazol-3-yl)-3-(3-piperidin-4-ylmethyl-phenyl)-urea hydrochloride, Intermediate 3, m/z MS M$^{+1}$ 446.

Scheme 2:
Synthesis of Intermediate 3

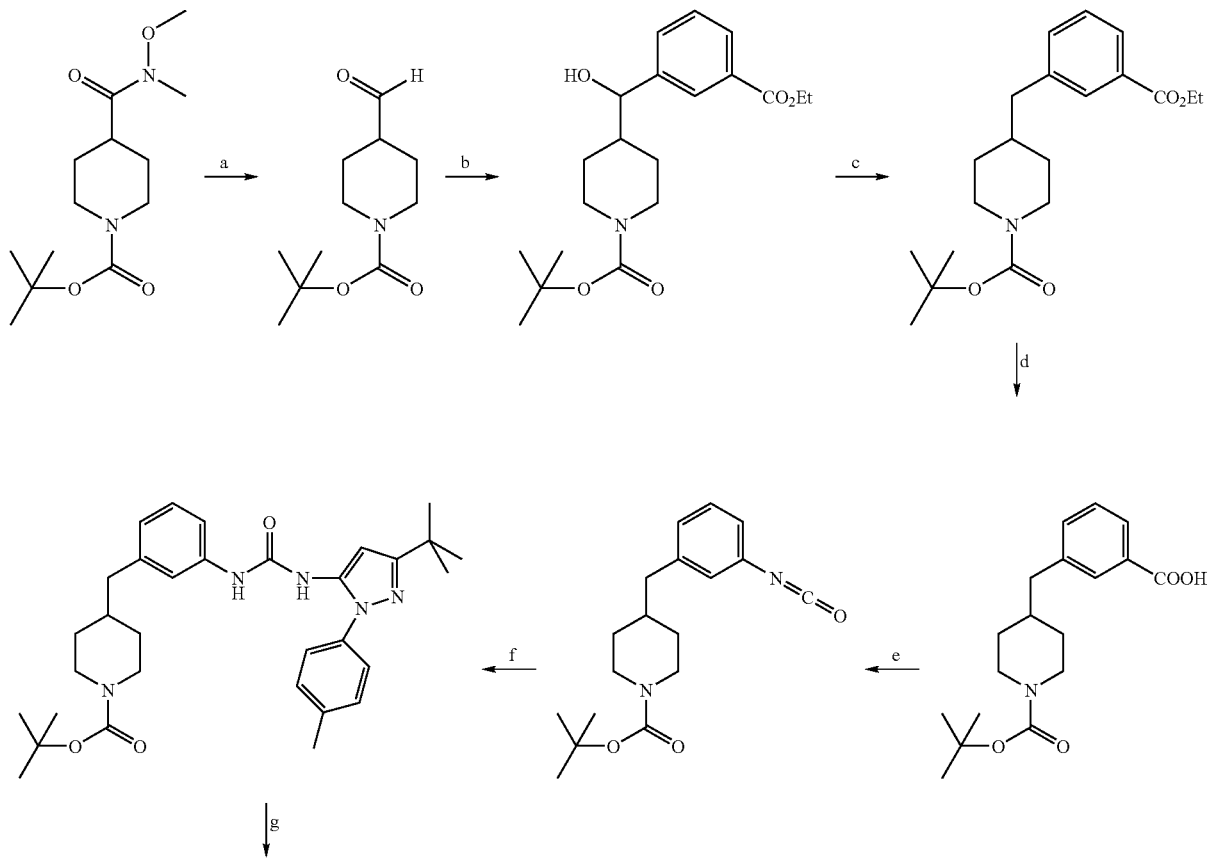

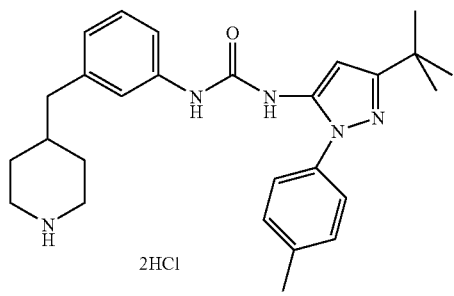

Intermediate 3 a. LAH, THF;
b. i-propMgCl, THF, ethyl 3-iodobenzoate;
c. Pd(OH)2, EtOH; d. MeOH, NaOH;
e. DPPA, TEA, THF;
f. 3-amino-5-t-butyl-2-tolylprazoie, DCM;
g. dioxane, HCl

Intermediate 4 1-(5tert-Butyl-2-tolyl-2H-pyrazol-3-yl)-3-(4-piperidin-4-ylmethyl-phenyl)-urea hydrochloride A solution of ethyl 4-iodobenzoate (5.52 g, 20 mmol) in THF (60 mL) is cooled to −20° C. and 2M iPrMgCl/THF (11 mL, 22 mmol) is added dropwise and the reaction is allowed to stir for 30 minutes. A solution of 4-formyl-piperidine-1-carboxylic acid tert-butyl ester (20 mmol) in THF (35 mL) is then added while maintaining the temp from −20° C. for 1 hour. The bath is removed and the reaction is allowed to come to room temperature and stir for 1 hour. The reaction is partitioned between ether-aqueous NH₄Cl. The organic layer is washed with brine, then dried over MgSO₄, filtered and evaporated. The residue is chromatographed on silica gel using 30% ethyl acetate/methylene chloride (1:4) to yield 5.05 grams of the ester. A mixture of this product (726 mg, 2 mmol) and 20% Pd(OH)₂ (726 mg) in ethyl alcohol (50 mL) is hydrogenated at 70 psi in a Parr apparatus for 2 hours. The reaction is filtered through celite and evaporated to dryness. The residue is chromatographed on silica gel using 5% ethyl acetate/methylene chloride to yield 485 mg of 4-[(4-ethoxycarbonyl-phenyl)hydroxy-methyl]-piperidine-1-carboxylic acid tert-butyl ester.

To a stirring solution of 4-[(4-ethoxycarbonyl-phenyl-)hydroxy-methyl]-piperidine-1-carboxylic acid tert-butyl ester (2.145 g, 6.18 mmol) in methanol (30 mL) is added 10 mL of 1N aqueous NaOH and the reaction is heated in a 50° C. bath for 1 hour. The reaction is cooled to 0° C. and carefully acidified with 1N aqueous HCl. The reaction is extracted with dichloromethane (DCM), dried over MgSO₄, filtered and concentrated to give 1.34 grams of 4-(carboxy-benzyl)-piperidine-1-carboxylic acid tert-butyl ester.

To a solution of 4-(carboxy-benzyl)-piperidine-1-carboxylic acid tert-butyl ester (1.595 g, 5.0 mmol) in THF (25 mL) at room temp is added TEA (0.77 mL, 5.5 mmol) followed by DPPA (1.18 mL, 5.5 mmol). The mixture is refluxed for 1 hour and 3-amino-4-tert-butyl-2-tolylpyrazole (1.26 g, 5.5 mmol) is added and the reaction is refluxed overnight. The reaction is cooled and partitioned between ether-aqueous NH₄Cl, and the organic layer is washed with brine, then dried over MgSO₄, filtered and evaporated. The residue is chromatographed on silica gel using ethyl acetate/heptane (3:7) chloride to yield 1.22 grams of 4-{4-[3-(5-tert-Butyl-2-p-tolyl-2H-pyrazol-3-yl)-ureido]-benzyl}-piperidine-1-carboxylic acid tert-butyl ester. 4-{4-[3-(5-tert-Butyl-2-p-tolyl-2H-pyrazol-3-yl)-ureido]-benzyl}-piperidine-1-carboxylic acid tert-butyl ester (3.24 g, 5.94 mmol) is dissolved in methylene chloride (20 mL) under nitrogen at 0° C. and 4N HCL in dioxane (3 ml) is added. After 10 minutes the cooling bath is removed and the reaction is stirred for 3 hours at room temp. The solution is concentrated to a foam which solidified after stirring in ether for a few hours. The solid is filtered and air dried to give 2.8 grams of 1-(5-tert-Butyl-2-p-tolyl-2H-pyrazol-3-yl)-3(4-piperidin-4-ylmethyl-phenyl)-urea hydrochloride. Intermediate 4, LCMS M$^{+1}$ 446, R$_T$=2.82 minutes.

Scheme 3:
Synthesis of Intermediate 4

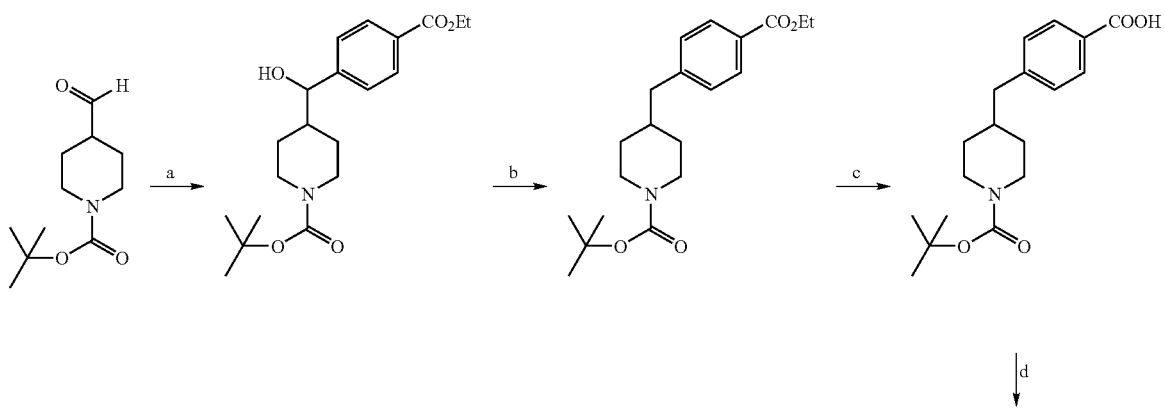

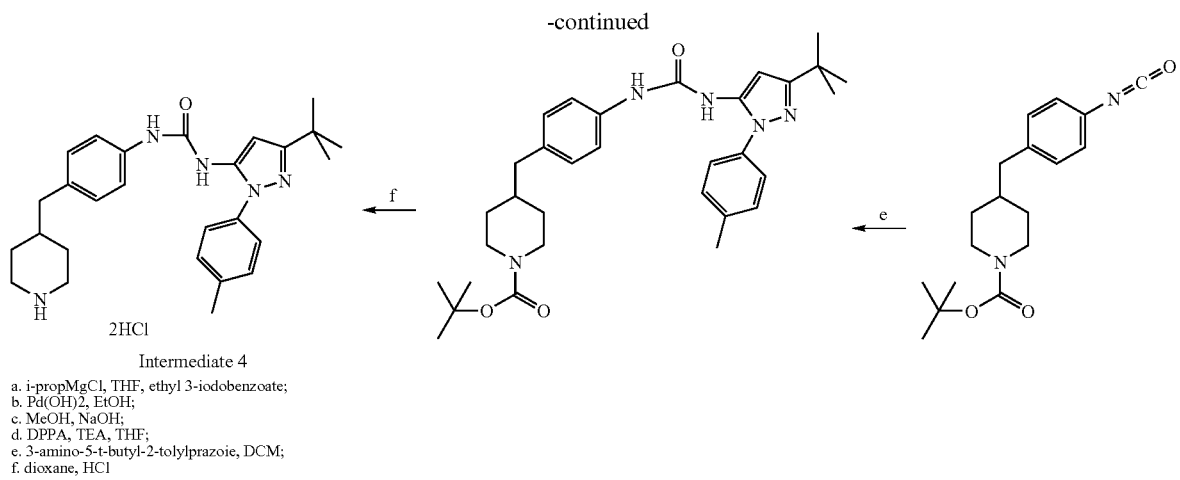

Intermediate 4 a. i-propMgCl, THF, ethyl 3-iodobenzoate;
b. Pd(OH)2, EtOH;
c. MeOH, NaOH;
d. DPPA, TEA, THF;
e. 3-amino-5-t-butyl-2-tolylprazoie, DCM;
f. dioxane, HCl

Intermediate 5 1-(5-tert-Butyl-2-p-tolyl-2H-pyrazol-3-yl)-3-(3-piperidin-4-ylmethyl-phenyl)-urea hydrochloride A solution of ethyl 2-iodobenzoate (1 eq) in THF (1.2 mL/g) is cooled to −25 to −20° C. and 2M iPrMgCl/THF (1.1 eq) is added dropwise and the reaction is allowed to stir for 30 minutes. A solution of the aldehyde (1 eq) in THF (1.8 mL/mmol) is then added while maintaining the temp from −25 to −20° C. The bath is removed and the stirring is continued overnight. The reaction is partitioned between ether-aqueous $NH_4Cl$. The organic layer is washed with brine, then dried over $MgSO_4$, filtered and evaporated. The residue is chromatographed on silica gel using 30% ethyl acetate/methylene chloride to yield the product. A mixture of product (1 eq) and 20% $Pd(OH)_2$ (1 wt eq) in ethyl alcohol (70 mL/g) is hydrogenated at 60-70 psi in a Parr apparatus overnight. The reaction is filtered through celite and evaporated to dryness. The residue is chromatographed on silica gel using 5% ethyl acetate/methylene chloride to yield the ester.

To a stirring solution of the ester (1 eq) in methanol (15 mL/g) is added 1N aqueous NaOH (1.7 eq) and the reaction is heated in a 50° C. bath for 2 hours. The reaction is cooled to 0° C. and carefully acidified with 1N aqueous HCL. The reaction is extracted with ethyl acetate, dried over $MgSO_4$, filtered and concentrated to yield the acid. To a solution of acid (1 eq) in THF (17 mL/g) at room temp is added TEA (1.1 eq) followed by DPPA (1.1 eq). The mixture is refluxed for 1 hour and the 3-amino-4-tert-butyl-2-tolylpyrazole (1.1 eq) is added and the reaction is refluxed overnight. The reaction is cooled and partitioned between ether-aqueous $NH_4Cl$, and the organic layer is washed with brine, then dried over $MgSO_4$, filtered and evaporated. The residue is chromatographed on silica gel using 10-15% ethyl acetate/methylene chloride to yield the BOC-protected urea The BOC-protected urea (1 eq) is dissolved in methylene chloride (6 mL/g) under nitrogen at 0° C. and 4N HCL in dioxane (2 eq) is added. After 10 minutes the cooling bath is removed and the reaction is stirred for 3 hours at room temp. The solution is concentrated to give 1-(5-tert-butyl-2-p-tolyl-2H-pyrazol-3-yl)-3-(3-piperidin-4-ylmethyl-phenyl)-urea hydrochloride, Intermediate 5.

Scheme 4:
Synthesis of Intermediate 5

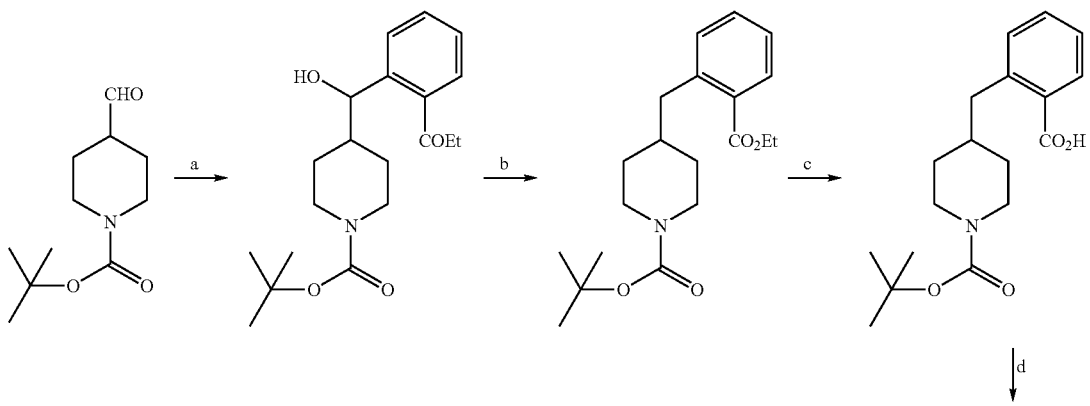

-continued

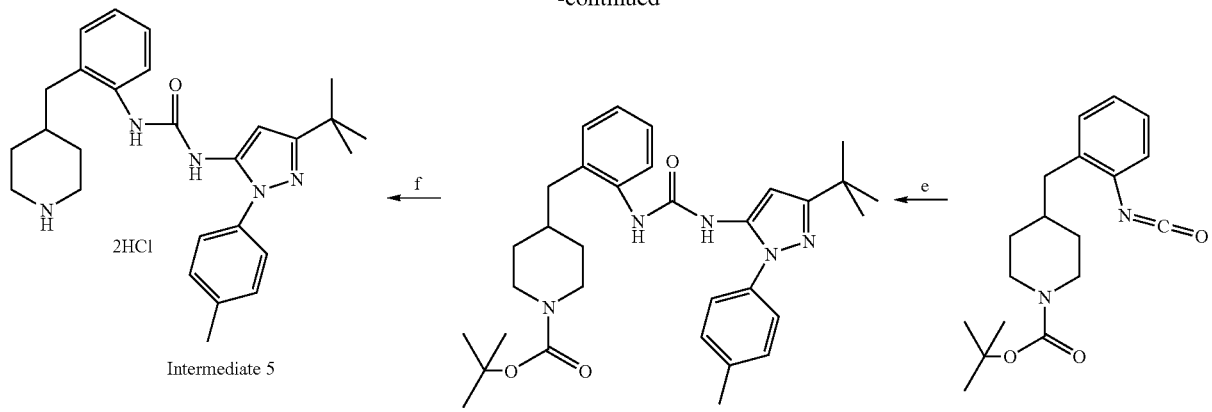

Intermediate 5 a. i-propMgCl, THF, ethyl 3-iodobenzoate;
b. Pd(OH)2, EtOH;
c. MeOH, NaOH;
d. DPPA, TEA, THF;
e. 3-amino-5-t-butyl-2-tolylprazoie, DCM;
f. dioxane, HCl Intermediate 6 1-[4-(8-Aza-bicyclo[3.2.1]oct-3-ylmethyl)-phenyl]-3-(5tert-butyl-2-p-tolyl-2H-pyrazol-3-yl)-urea dihydrochloride To a stirring 4.5M solution of NaHCO$_3$ is added 8-Aza-bicyclo[3.2.1]octan-3-one hydrochloride (9.0 g, 55 mmol, Scheme 5) followed by BOC anhydride (17.6 mL, 82.5 mmol). The reaction mixture is heated to 50° C. and stirred for 16 hours. Upon completion (TLC), the reaction mixture is cooled to room temperature and washed three times with ethyl acetate. Organics are combined washed with brine and dried over magnesium sulfate. Column chromatography (heptane/ethyl acetate, 9/1) gave a pale yellow oil as product (Yield: 6.2 g, 27.5 mmol).

To a suspension of methyl triphenylphosphonium bromide (15.95 g, 44.6 mmol) in 100 mL THF at 0° C. is added 45 mL of 1M potassium tert-butoxide/THF. The reaction mixture is stirred for 1 hour, whereupon a solution of 3-oxo-8-aza-bicyclo[3.2.1]octane-8-carboxylic acid tert-butyl ester (6.7 g, 30 mmol) in 50 mL THF is then added. The reaction mixture is gradually warmed to room temperature and stirred for 16 hours. Upon completion (TLC), the solution is washed three times with 100 mL ethyl acetate. Organics are combined and washed successively with ammonium chloride and brine, then dried over magnesium sulfate. Column chromatography (heptane/ethyl acetate, 8/1) gave product as a colorless oil (Yield: 4.0 g, 17 mmol).

3-Methylene-8-aza-bicyclo[3.2.1]octane-8-carboxylic acid tert-butyl ester (2.0 g, 8.97 mmol) is dissolved in a solution of 0.5M 9-borabicyclo[3.3.1]nonane (9-BBN) (0.5M THF, 17.9 mL, 8.97 mmol) and stirred at 65° C. for 1 hour under nitrogen. The reaction mixture is then added to a mixture containing p-bromoaniline (1.51 g, 8.51 mmol), dimethylformamide (DMF) (18 mL), H$_2$O (1.8 mL), K$_2$CO$_3$ (1.52 g) and dichloro[1,1'-bis(diphenylphosphino)ferrocene]-Palladium(II)Dichloromethane adduct (Pd(dppf)$_2$Cl$_2$·CH$_2$Cl$_2$) (600 mg). This reaction mixture is then allowed to stir overnight at 60° C. The reaction is diluted with ethyl acetate and water then the reaction pH is adjusted to 11 with 1N NaOH. The organic layer is washed with water, brine and dried over sodium sulfate. The solution is filtered and the volatiles are removed in vacuo, and the brown oil is purified by column chromatography (ethyl acetate/heptane; 1:1) to give product as a light brown oil. Yield: 1.45 g;. m/z (MS) M$^+$ 316.44.

A mixture of 4-[4-aminobenzyl]-8-aza-bicyclo[3.2.1]octane-8-carboxylic acid tert-butyl ester (1.41 g, 4.45 mmol) in 25 ml of DCM is added to 5-tert-butyl-2-[4-methylphenyl]-2H-pyrazole-isocyanate (1.53 g, 6.0 mmol) dissolved in DCM (10 mL) stirring at 0° C. The reaction is stirred at room temperature for 5 hours then is washed with 10% aqueous citric acid, water, brine and dried over sodium sulfate. The mixture is filtered and is concentrated in vacuo. The crude product is purified on silica gel using 5% to 10% ethyl acetate in DCM to give 1.0 g of pure product.

The urea (496 mg, 86 mmol) is dissolved in 4N HCl in dioxane (10 mL) and this is stirred for 15 minutes at 0° C. The reaction is allowed to come to room temperature and stir overnight. The reaction is concentrated and dissolved in a small amount of methanol and concentrated. The residue is mixed with ether (2×) and concentrated and repeated to give 1-[4-(8-aza-bicyclo[3.2.1]oct-3-ylmethyl)-phenyl]-3-(5-tert-butyl-2-p-tolyl-2H-pyrazol-3-yl)-urea dihydrochoride, Intermediate 6, (460 mg), as a white powder. LCMS M$^{+1}$ 472.33; R$_T$=2.53 minutes.

Scheme 5:
Synthesis of Intermediate 6

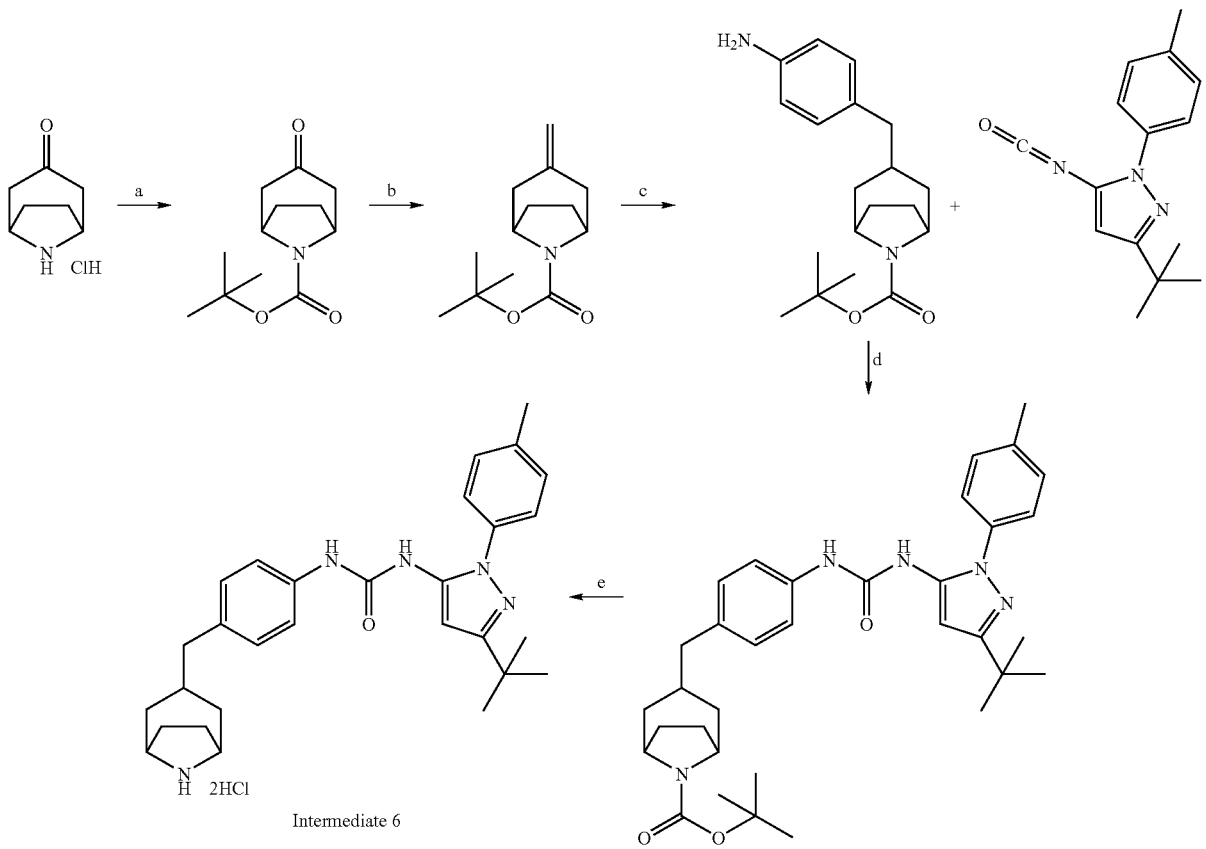

a. BOC$_2$O, NaHCO$_3$;
b. Ph$_3$PCH$_3$Br, t-BuOK, THF;
c. 9-BBN, THF, p-bromoaniline, Pd(dppf)$_2$Cl$_2$CH$_2$Cl$_2$, DMF, H$_2$O, K$_2$CO$_3$;
d. DCM; e. dioxane, HCl Intermediate 7 1-[3-(8Aza-bicyclo[3.2.1]oct-3-ylmethyl)-phenyl]-3-(5tert-butyl-2-p-tolyl-2H-pyrazol-3-yl)-urea dihydrochloride To a mixture of 3-methylene-8-aza-bicyclo[3.2.1]octane-8-carboxylic acid tert-butyl ester (1.59 g, 7.14 mmol) and NaBH$_4$ (0.92 g, 24.3 mmol) in THF (40 mL) at 0° C. under nitrogen is added dropwise borontrifluoride etherate (3.5 mL, 27.7 mmol). The mixture is stirred for 1 hour at 0° C. and allowed to stir overnight at room temperature. The reaction is cooled to 0° C. and water (5 mL) is added carefully to quench excess borane then 3N NaOH (10 mL) and 30% hydrogen peroxide are added and the mixture is heated in a 50° C. oil bath for 1 hour. The reaction is diluted with ethyl acetate and extracted with brine, dried over magnesium sulfate, filtered and evaporated to give the alcohol in quantitative yield of the alcohol and is used without further purification.

To a solution of oxalyl chloride (0.7 mL, 7.9 mmol) in DCM (35 mL) cooled to −70° C. is added dimethyl sulfoxide (DMSO) (0.84 mL, 14.4 mmol), then the reaction is allowed to stir for 10-15 minutes. The alcohol (1.73 g, 7.2 mmol) is dissolved in DCM and added to the reaction after stirring for 30 minutes at −70° C. TEA (5 ml) is added. The reaction is stirred for 15 minutes at −70° C. and then allowed to stir at room temperature for 1 hour. The reaction is quenched with saturated ammonium chloride and extracted with DCM and the organic layer is washed with brine, dried over magnesium sulfate, filtered and concentrated in vacuo. The residue is purified on silica gel using heptane/ethyl acetate (7:3) to give 1.07 grams of product.

A solution of ethyl 3-iodobenzoate (2.70 mL, 16 mmol) in THF (13 mL) is cooled to −20° C. and 2M iPrMgCl/THF (8 mL, 16 mmol) is added dropwise and the reaction is allowed to stir for 30 minutes. A solution of the aldehyde (12.62 mmol) in THF (16 mL) is then added while maintaining the temp from −20° C. for 1 hour. The bath is removed and the reaction is allowed to come to room temperature and stir for 1 hour. The reaction is partitioned between ether-aqueous NH$_4$Cl. The organic layer is washed with brine, then dried over MgSO$_4$, filtered and evaporated. The residue is chromatographed on silica gel using 30% ethyl acetate/methylene chloride (1:4) to yield 2.83 grams of the ester. A mixture of the ester (2.8 g, 7.2 mmol) and 20% Pd(OH)$_2$ (2.8 g, 20% over charcoal) in ethyl alcohol (100 mL) is hydrogenated in a Parr apparatus overnight. The reaction is filtered through celite and evaporated to dryness. The residue is chromatographed on silica gel using 5% ethyl acetate/methylene chloride to yield 2.1 g of the ester as a clear colorless liquid.

To a stirring solution of the ester (2.08 g, 5.57 mmol) in methanol (30 mL) is added 8 mL of 1N aqueous NaOH (8 mmol) and the reaction was stirred at room temperature for 3 days The solvent is removed by rotoevaporation and the residue is partitioned between water and ethyl acetate. The mixture is cooled to 0° C. and carefully acidified with 1N aqueous HCl to approximately pH 2. The two layers are separated and the organic layer is washed with water, brine and dried over magnesium sulfate. The solution is filtered and concentrated in vacuo to yield 1.7 grams of the desired acid as a white foam.

To a solution of acid (1.7 g, 4.9 mmol) in THF (25 mL) at room temp is added TEA (0.8 mL, 5.8 mmol) followed by DPPA (1.25 mL, 2.8 mmol). The mixture is refluxed for 1 hour and the 3-amino-4-tert-butyl-2-tolylpyrazole (1.3 g, 5.8 mmol) is added and the reaction is refluxed overnight. The reaction is cooled and partitioned between ether-aqueous NH$_4$Cl, and the organic layer is washed with brine, then dried over MgSO$_4$, filtered and evaporated. The residue is chromatographed on silica gel using DCM/heptane (9:1) to yield 1.67 grams of the BOC-protected urea. The BOC-protected urea (1.67 g, 2.92 mmol) is dissolved in methylene chloride (10 mL) under nitrogen at 0° C. and 4N HCL in dioxane (3.5 ml) is added. After 10 minutes the cooling bath is removed and the reaction is stirred for overnight at room temperature. The solution is concentrated to a foam which solidified after stirring in ether for a few hours. The solid is filtered and air dried to give 1.37 grams of 1-[3-(8-aza-bicyclo[3.2.1]oct-3-ylmethyl)-phenyl]-3-(5-tert-butyl-2-p-tolyl-2H-pyrazol-3-yl)-urea dihydrochloride, Intermediate 7. LCMS M$^{+1}$ 472.25, R$_T$=3.511 minutes Scheme 6:
Synthesis of Intermediate 7

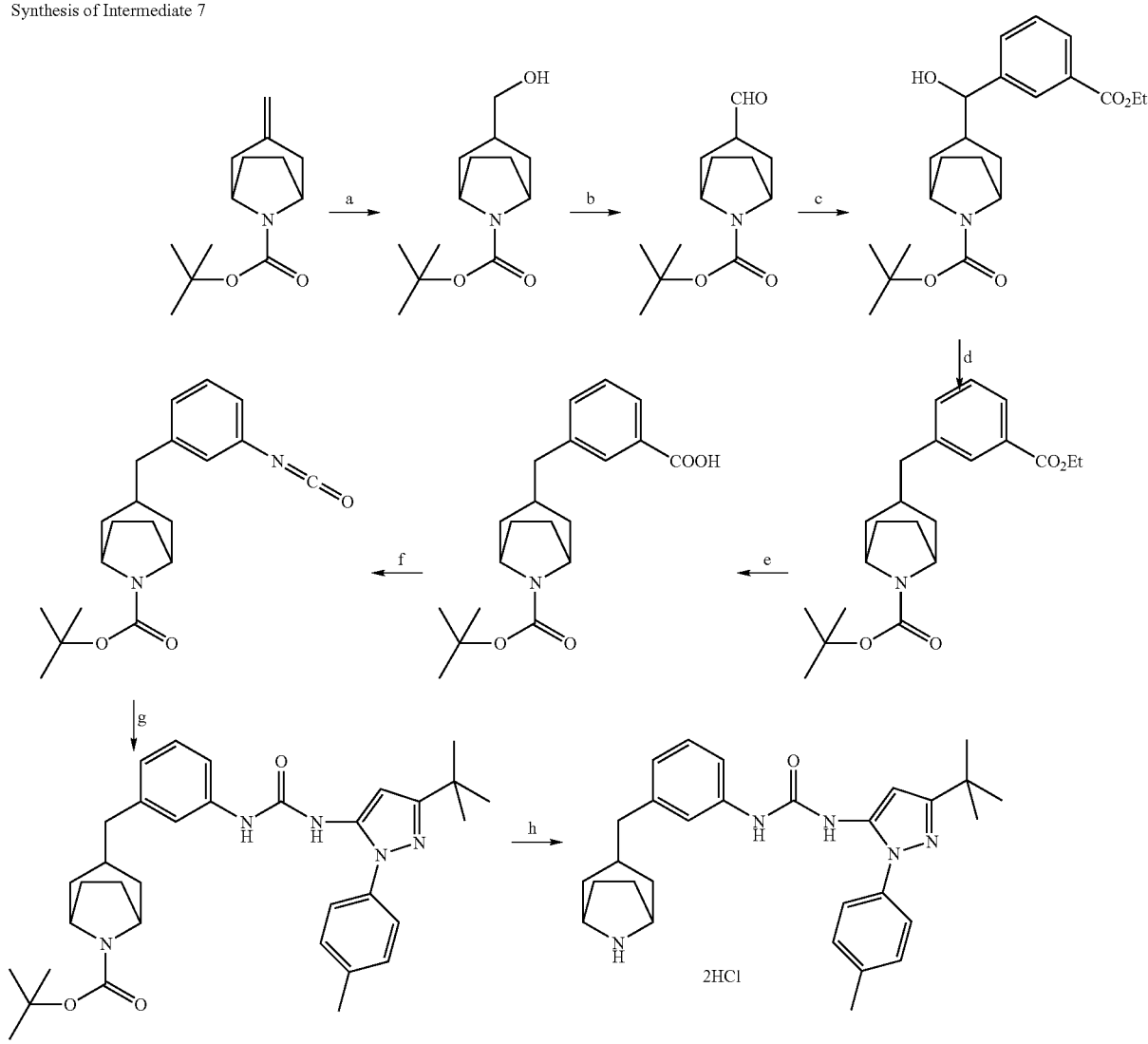

Intermediate 7 a. NaBH4, BF3-etherate, THF;
b. oxalylchloride, DMSO,, DCM;
c. i-propMgCl, THF, ethyl 3-iodobenzoate;
d. Pd(OH)2, EtOH;
e. MeOH, NaOH;
f. DPPA, TEA, THF;
g. 3-amino-5-t-butyl-2-tolylprazoie, DCM;
h. dioxane, HCl

Intermediate 8 1-(5tert-butyl-2-p-tolyl-2H-pyrazol-3-yl)-3-[2-(2-ethyl-6methyl-piperidin-4-ylmethyl)-phenyl]-urea dihydrochloride To a mixture of 3-Methylene-8-aza-bicyclo[3.2.1]octane-8-carboxylic acid tert-butyl ester (1.59 g, 7.14 mmol) and NaBH₄ (0.92 g, 24.3 mmol) in THF (40 mL) at 0° C. under nitrogen is added dropwise borontrifluoride etherate (3.5 mL, 27.7 mmol). The mixture is stirred for 1 hour at 0° C. and allowed to stir overnight at room temperature. The reaction is cooled to 0° C. and water (5 mL) is added carefully to quench excess borane then 3N NaOH (10 mL) and 30% hydrogen peroxide are added and the mixture is heated in a 50° C. oil bath for 1 hour. The reaction is diluted with ethyl acetate and extracted with brine, dried over magnesium sulfate, filtered and evaporated to give the alcohol in quantitative yield of the alcohol and is used without further purification.

To a solution of oxalyl chloride (0.7 mL, 7.9 mmol) in DCM (35 mL) cooled to −70° C. is added DMSO (0.84 mL, 14.4 mmol), then the reaction is allowed to stir for 10-15 minutes. The alcohol (1.73 g, 7.2 mmol) is dissolved in DCM and added to the reaction after stirring for 30 minutes at −70° C. TEA (5 ml) is added. The reaction is stirred for 15 minutes at −70° C. and then allowed to stir at room temperature for 1 hour. The reaction is quenched with saturated ammonium chloride and extracted with DCM and the organic layer is washed with brine, dried over magnesium sulfate, filtered and concentrated in vacuo. The residue is purified on silica gel using heptane/ethyl acetate (7:3) to give 1.07 grams of product.

A solution of ethyl 2-iodobenzoate (1 eq) in THF (2 mL/g) is cooled to −20° C. and 2M iPrMgCl/THF (1 eq) is added dropwise and the reaction is allowed to stir for 30 minutes. A solution of the aldehyde (0.75) in THF (2 mL/g) is then added while maintaining the temp from −20° C. for 1 hour. The bath is removed and the reaction is allowed to come to room temperature and stir for 1 hour. The reaction is partitioned between ether-aqueous NH₄Cl. The organic layer is washed with brine, then dried over MgSO₄, filtered and evaporated. The residue is chromatographed on silica gel using 30% ethyl acetate/methylene chloride (1:4) to yield the ester. A mixture of the ester (1 eq) and 20% Pd(OH)₂ (1 eq by wt, 20% over charcoal) in ethyl alcohol (100 mL) is hydrogenated in a Parr apparatus overnight. The reaction is filtered through celite and evaporated to dryness. The residue is chromatographed on silica gel using 5% ethyl acetate/methylene chloride to yield the ester.

To a stirring solution of the ester (1 eq) in methanol (15 mL/g) is added 1N aqueous NaOH (1.5 eq) and the reaction is stirred at room temperature for 3 days The solvent is removed by rotoevaporation and the residue is partitioned between water and ethyl acetate. The mixture is cooled to 0° C. and carefully acidified with 1N aqueous HCl to approximately pH 2. The two layers are separated and the organic layer is washed with water, brine and dried over magnesium sulfate. The solution is filtered and concentrated in vacuo to yield the desired acid.

To a solution of acid (1.75 eq) in THF (12 mL/g) at room temp is added TEA (0.8 mL, 5.8 mmol) followed by DPPA (1 eq). The mixture is refluxed for 1 hour and the 3-amino-4-tert-butyl-2-tolylpyrazole (1.2 eq) is added and the reaction is refluxed overnight. The reaction is cooled and partitioned between ether-aqueous NH₄Cl, and the organic layer is washed with brine, then dried over MgSO₄, filtered and evaporated. The residue is chromatographed on silica gel using DCM/heptane (9:1) to yield the BOC-protected urea. The BOC-protected urea (1 eq) is dissolved in methylene chloride (5 mL/g) under nitrogen at 0° C. and 4N HCL in dioxane (4 ml/g) is added. After 10 minutes the cooling bath is removed and the reaction is stirred for overnight at room temperature. The solution is concentrated to give 1-(5-tert-butyl-2-p-tolyl-2H-pyrazol-3-yl)-3-[2-(2-ethyl-6-methyl-piperidin-4-ylmethyl)-phenyl]-urea dihydrochloride, Intermediate 8.

Scheme 7:
Synthesis of Intermediate 8

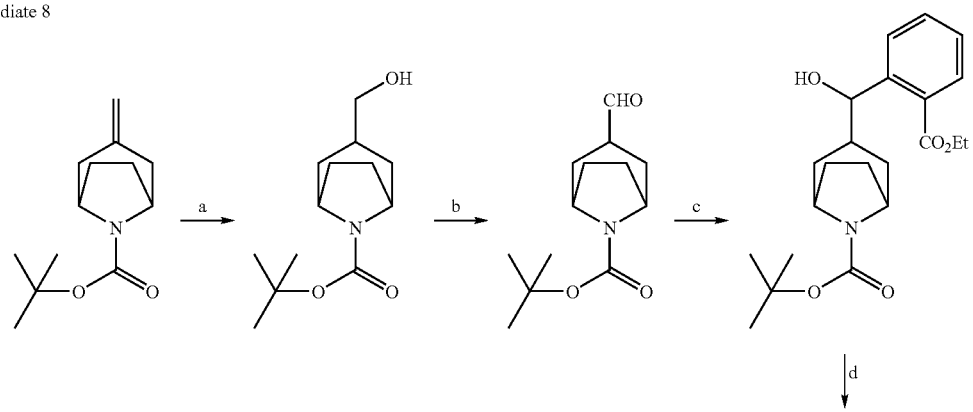

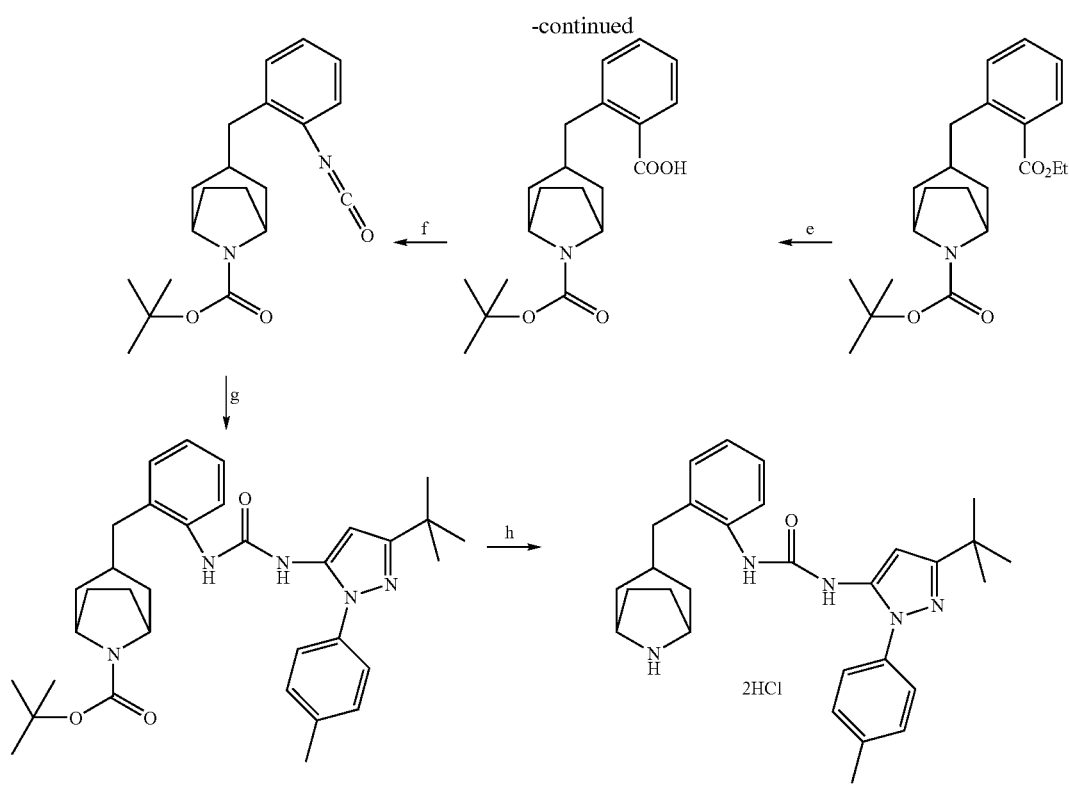

a. NaBH4, BF3-etherate, THF;
b. oxalylchloride, DMSO,, DCM;
c. i-propMgCl, THF, ethyl 3-iodobenzoate;
d. Pd(OH)2, EtOH;
e. MeOH, NaOH;
f. DPPA, TEA, THF;
g. 3-amino-5-t-butyl-2-tolylprazoie, DCM;
h. dioxane, HCl Intermediate 9 and Intermediate 10 endo 3-formyl-8-aza-bicyclo[3.2.1]octane-8carboxylic acid tert-butyl ester and exo 3-formyl-8-aza-bicyclo[3.2.1]octane-8-carboxylic acid tert-butyl ester To a mixture of 3-Methylene-8-aza-bicyclo[3.2.1]octane-8-carboxylic acid tert-butyl ester (1.59 g, 7.14 mmol) and NaBH$_4$ (0.92 g, 24.3 mmol) ii THF (40 mL) at 0° C. under nitrogen is added dropwise borontrifluoride etherate (3.5 mL, 27.7 mmol). The mixture is stirred for 1 hour at 0° C. and allowed to stir overnight at room temperature. The reaction is cooled to 0° C. and water (5 mL) is added carefully to quench excess borane then 3N NaOH (10 mL) and 30% hydrogen peroxide are added and the mixture is heated in a 50° C. oil bath for 1 hour. The reaction is diluted with ethyl acetate and extracted with brine, dried over magnesium sulfate, filtered and evaporated to give the alcohol in quantitative yield of the alcohol and is used without further purification.

To a solution of oxalyl chloride (0.7 mL, 7.9 mmol) in DCM (35 mL) cooled to −70° C. is added DMSO (0.84 mL, 14.4 mmol), then the reaction is allowed to stir for 10-15 minutes. The alcohol (1.73 g, 7.2 mmol) is dissolved in DCM and added to the reaction after stirring for 30 minutes at −70° C. TEA (5 ml) is added. The reaction is stirred for 15 minutes at −70° C. and then allowed to stir at room temperature for 1 hour. The reaction is quenched with saturated ammonium chloride and extracted with DCM and the organic layer is washed with brine, dried over magnesium sulfate, filtered and concentrated in vacuo. The endo and exo aldehydes are separated on silica gel using 7:3 heptane/ethylacetate to give endo 3-formyl-8-aza-bicyclo[3.2.1]octane-8-carboxylic acid tert-butyl ester, Intermediate 9 and exo 3-formyl-8-aza-bicyclo[3.2.1]octane-8-carboxylic acid tert-butyl ester, Intermediate 10.

Scheme 8:
Synthesis of Intermediate 9 and Intermediate 10

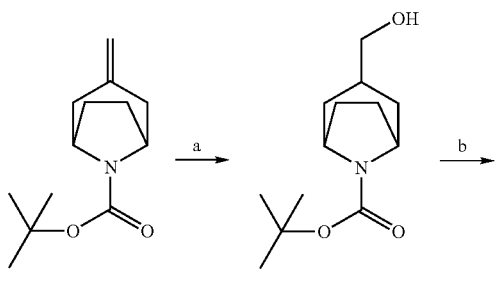

-continued

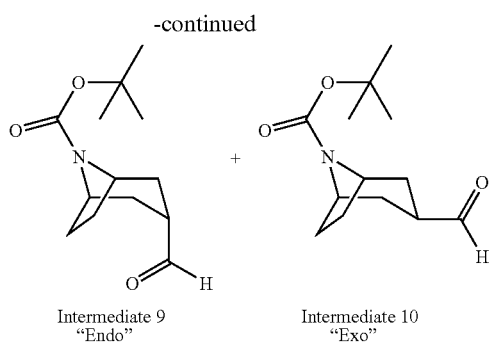

Intermediate 9 "Endo"   Intermediate 10 "Exo"

a. NaBH4, BF3-etherate, THF;
b. oxalylchloride, DMSO, DCM

Intermediate 11 endo 1-[2-(8-aza-bicyclo[3.2.1]oct-3-ylmethyl)-phenyl]-3-(5tert-butyl-2-p-tolyl-2H-pyrazol-3-yl)-urea dihydrochloride A solution of ethyl 2-iodobenzoate (1 eq) in THF (2 mL/g) is cooled to −20° C. and 2M iPrMgCl/THF (1 eq) is added dropwise and the reaction is allowed to stir for 30 minutes. A solution of endo 3-formyl-8-aza-bicyclo[3.2.1]octane-8-carboxylic acid tert-butyl ester, Intermediate 9, (0.75 g) in THF (2 mL/g) is then added while maintaining the temp from −20° C. for 1 hour. The bath is removed and the reaction is allowed to come to room temperature and stir for 1 hour. The reaction is partitioned between ether-aqueous $NH_4Cl$. The organic layer is washed with brine, then dried over $MgSO_4$, filtered and evaporated. The residue is chromatographed on silica gel using 30% ethylacetate/methylene chloride (1:4) to yield the ester. A mixture of the ester (1 eq) and 20% $Pd(OH)_2$ (1 eq by wt, 20% over charcoal) in ethyl alcohol (100 mL) is hydrogenated in a Parr apparatus overnight. The reaction is filtered through celite and evaporated to dryness. The residue is chromatographed on silica gel using 5% ethyl acetate/methylene chloride to yield the ester.

To a stirring solution of the ester (1 eq) in methanol (15 mL/g) is added 1N aqueous NaOH (1.5 eq) and the reaction is stirred at room temperature for 3 days The solvent is removed by rotoevaporation and the residue is partitioned between water and ethylacetate. The mixture is cooled to 0° C. and carefully acidified with 1N aqueous HCl to a solution of acid (1.75 eq) in THF (12 mL/g) at room temp is added TEA (0.8 mL, 5.8 mmol) followed by DPPA (1 eq). The mixture is refluxed for 1 hour and the 3-amino-4-tert-butyl-2-tolylpyrazole (1.2 eq) is added and the reaction is refluxed overnight. The reaction is cooled and partitioned between ether-aqueous $NH_4Cl$, and the organic layer is washed with brine, then dried over $MgSO_4$, filtered and evaporated. The residue is chromatographed on silica gel using DCM/heptane (9:1) to yield the BOC-protected urea. The BOC-protected urea (1 eq) is dissolved in methylene chloride (5 mL/g) under nitrogen at 0° C. and 4N HCL in dioxane (4 ml/g) is added. After 10 minutes the cooling bath is removed and the reaction is stirred for overnight at room temperature. The solution is concentrated to give endo 1-[2-(8-aza-bicyclo[3.2.1]oct-3-ylmethyl)-phenyl]-3-(5-tert-butyl-2-p-tolyl-2H-pyrazol-3-yl)-urea dihydrochloride, Intermediate 11.

Intermediate 12 endo 1-[3-(8-aza-bicyclo[3.2.1]oct-3-ylmethyl)-phenyl]-3-(5-tert-butyl-2-p-tolyl-2H-pyrazol-3-yl)-urea dihydrochloride A solution of ethyl 3-iodobenzoate (1 eq) in THF (2 mL/g) is cooled to −20° C. and 2M iPrMgCl/THF (1 eq) is added dropwise and the reaction is allowed to stir for 30 minutes. A solution of the Intermediate 9 (0.75) in THF (2 mL/g) is then added while maintaining the temp from −20° C. for 1 hour. The bath is removed and the reaction is allowed to come to room temperature and stir for 1 hour. The reaction is partitioned between ether-aqueous $NH_4Cl$. The organic layer is washed with brine, then dried over $MgSO_4$, filtered and evaporated. The residue is chromatographed on silica gel using 30% ethyl acetate/methylene chloride (1:4) to yield the ester. A mixture of the ester (1 eq) and 20% $Pd(OH)_2$ (1 eq by wt, 20% over charcoal) in ethyl alcohol (100 mL) is hydrogenated in a Parr apparatus overnight. The reaction is filtered through celite and evaporated to dryness. The residue is chromatographed on silica gel using 5% ethyl acetate/methylene chloride to yield the ester.

To a stirring solution of the ester (1 eq) in methanol (15 mL/g) is added 1N aqueous NaOH (1.5 eq) and the reaction is stirred at room temperature for 3 days The solvent is removed by rotoevaporation and the residue is partitioned between water and ethylacetate. The mixture is cooled to 0° C. and carefully acidified with 1N aqueous HCl to approximately pH 2. The two layers are separated and the organic layer is washed with water, brine and dried over magnesium sulfate. The solution is filtered and concentrated in vacuo to yield the desired acid.

To a solution of acid (1.75 eq) in THF (12 mL/g) at room temp is added TEA (0.8 mL, 5.8 mmol) followed by DPPA (1 eq). The mixture is refluxed for 1 hour and the 3-amino-4-tert-butyl-2-tolylpyrazole (1.2 eq) is added and the reaction is refluxed overnight. The reaction is cooled and partitioned between ether-aqueous $NH_4Cl$, and the organic layer is washed with brine, then dried over $MgSO_4$, filtered and evaporated. The residue is chromatographed on silica gel using DCM/heptane (9:1) to yield the BOC-protected urea. The BOC-protected urea (1 eq) is dissolved in methylene chloride (5 mL/g) under nitrogen at 0° C. and 4N HCL in dioxane (4 ml/g) is added. After 10 minutes the cooling bath is removed and the reaction is stirred for overnight at room temperature. The solution is concentrated to give endo 1-[3-(8-aza-bicyclo[3.2.1]oct-3-ylmethyl)-phenyl]-3-(5-tert-butyl-2-p-tolyl-2H-pyrazol-3-yl)-urea dihydrochloride, Intermediate 12.

Intermediate 13 endo 1-[4-(8-aza-bicyclo[3.2.1]oct-3-ylmethyl)-phenyl]-3-(5-tert-butyl-2-p-tolyl-2H-pyrazol-3-yl)-urea dihydrochloride A solution of ethyl 4-iodobenzoate (1 eq) in THF (2 mL/g) is cooled to −20° C. and 2M iPrMgCl/THF (1 eq) is added dropwise and the reaction is allowed to stir for 30 minutes. A solution of the Intermediate 9 (0.75) in THF (2 mL/g) is then added while maintaining the temp from −20° C. for 1 hour. The bath is removed and the reaction is allowed to come to room temperature and stir for 1 hour. The reaction is partitioned between ether-aqueous $NH_4Cl$. The organic layer is washed with brine, then dried over $MgSO_4$, filtered and evaporated. The residue is chromatographed on silica gel using 30% ethyl acetate/methylene chloride (1:4) to yield the ester. A mixture of the ester (1 eq) and 20% $Pd(OH)_2$ (1 eq by wt. 20% over charcoal) in ethyl alcohol (100 mL) is hydrogenated in a Parr apparatus overnight. The reaction is filtered through celite and evaporated to dryness. The residue is chromatographed on silica gel using 5% ethyl acetate/methylene chloride to yield the ester.

To a stirring solution of the ester (1 eq) in methanol (15 mL/g) is added 1N aqueous NaOH (1.5 eq) and the reaction is stirred at room temperature for 3 days The solvent is removed by rotoevaporation and the residue is partitioned between water and ethyl acetate. The mixture is cooled to 0° C. and carefully acidified with 1N aqueous HCl to approximately pH 2. The two layers are separated and the organic layer is washed with water, brine and dried over magnesium sulfate. The solution is filtered and concentrated in vacuo to yield the desired acid approximately pH 2. The two layers are separated and the organic layer is washed with water, brine and dried over magnesium sulfate. The solution is filtered and concentrated in vacuo to yield the desired acid.

To a solution of acid (1.75 eq) in THF (12 mL/g) at room temp is added TEA (0.8 mL, 5.8 mmol) followed by DPPA (1 eq). The mixture is refluxed for 1 hour and the 3-amino-4-tert-butyl-2-tolylpyrazole (1.2 eq) is added and the reaction is refluxed overnight. The reaction is cooled and partitioned between ether-aqueous NH$_4$Cl, and the organic layer is washed with brine, then dried over MgSO$_4$, filtered and evaporated. The residue is chromatographed on silica gel using DCM/heptane (9:1) to yield the BOC-protected urea. The BOC-protected urea (1 eq) is dissolved in methylene chloride (5 mL/g) under nitrogen at 0° C. and 4N HCL in dioxane (4 ml/g) is added. After 10 minutes the cooling bath is removed and the reaction is stirred for overnight at room temperature. The solution is concentrated to give endo 1-[4-(8-aza-bicyclo[3.2.1]oct-3-ylmethyl)-phenyl]-3-(5-tert-butyl-2-p-tolyl-2H-pyrazol-3-yl)-urea dihydrochloride, Intermediate 13.

Scheme 9:
Synthesis of Endo-Intermediates 11, 12 and 13

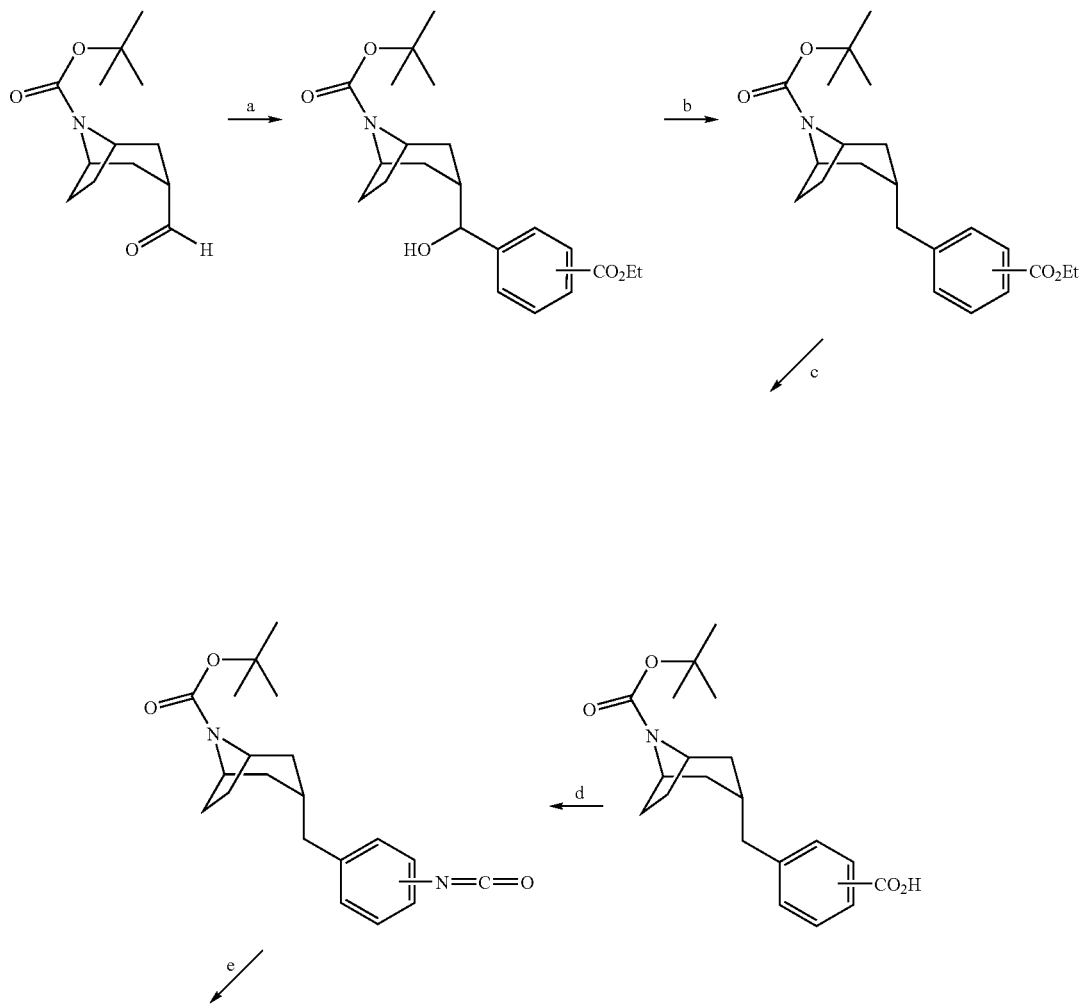

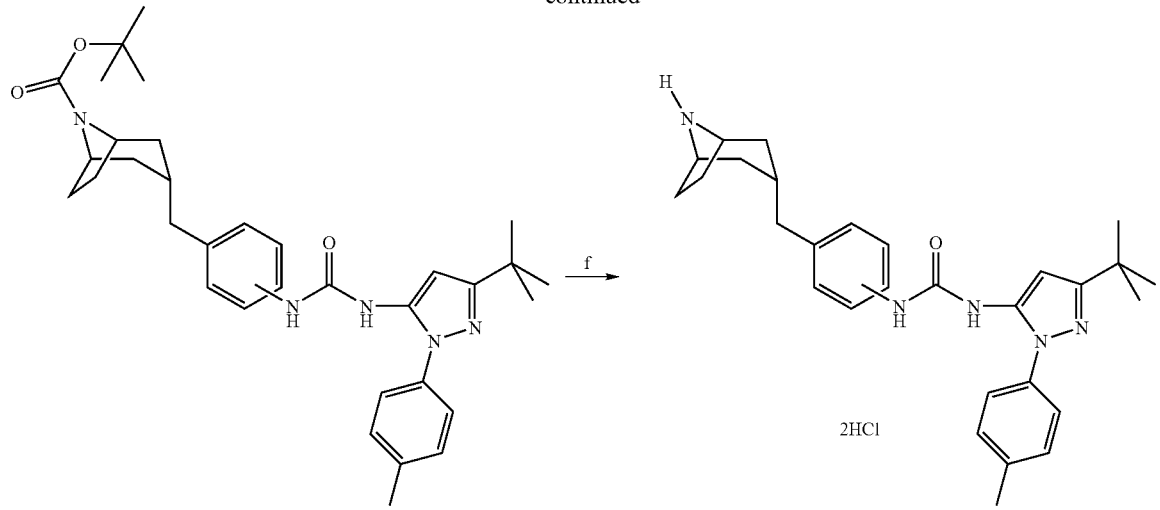

a. i-propMgCl, THF, ethyl 3-iodobenzoate;
b. Pd(OH)2, EtOH;
c. MeOH, NaOH;
d. DPPA, TEA, THF;
e. 3-amino-5-t-butyl-2-tolylprazoie, DCM;
f. dioxane, HCl Intermediate 11, 12 and 13

Intermediate 14 exo 1-[2-(8-aza-bicyclo[3.2.1]oct-3-ylmethyl)-phenyl]-3-(5tert-butyl-2-p-tolyl-2H-pyrazol-3-yl)-urea dihydrochloride A solution of ethyl 2-iodobenzoate (1 eq) in THF (2 mL/g) is cooled to −20° C. and 2M iPrMgCl/THF (1 eq) is added dropwise and the reaction is allowed to stir for 30 minutes. A solution of the Intermediate 10 (0.75) in THF (2 mL/g) is then added while maintaining the temp from −20° C. for 1 hour. The bath is removed and the reaction is allowed to come to room temperature and stir for 1 hour. The reaction is partitioned between ether-aqueous NH$_4$Cl. The organic layer is washed with brine, then dried over MgSO$_4$, filtered and evaporated. The residue is chromatographed on silica gel using 30% ethyl acetate/methylene chloride (1:4) to yield the ester. A mixture of the ester (1 eq) and 20% Pd(OH)$_2$ (1 eq by wt, 20% over charcoal) in ethyl alcohol (100 mL) is hydrogenated in a Parr apparatus overnight. The reaction is filtered through celite and evaporated to dryness. The residue is chromatographed on silica gel using 5% ethyl acetate/methylene chloride to yield the ester.

To a stirring solution of the ester (1 eq) in methanol (15 mL/g) is added 1N aqueous NaOH (1.5 eq) and the reaction is stirred at room temperature for 3 days The solvent is removed by rotoevaporation and the residue is partitioned between water and ethyl acetate. The mixture is cooled to 0° C. and carefully acidified with 1N aqueous HCl to a solution of acid (1.75 eq) in THF (12 mL/g) at room temp is added TEA (0.8 mL, 5.8 mmol) followed by DPPA (1 eq). The mixture is refluxed for 1 hour and the 3-amino-4-tert-butyl-2-tolylpyrazole (1.2 eq) is added and the reaction is refluxed overnight. The reaction is cooled and partitioned between ether-aqueous NH$_4$Cl, and the organic layer is washed with brine, then dried over MgSO$_4$, filtered and evaporated. The residue is chromatographed on silica using DCM/heptane (9:1) to yield the BOC-protected urea. The BOC-protected urea (1 eq) is dissolved in methylene chloride (5 mL/g) under nitrogen at 0° C. and 4N HCL in dioxane (4 ml/g) is added. After 10 minutes the cooling bath is removed and the reaction is stirred for overnight at room temperature. The solution is concentrated to give exo 1-[2-(8-aza-bicyclo[3.2.1]oct-3-ylmethyl)-phenyl]-3-(5-tert-butyl-2-p-tolyl-2H-pyrazol-3-yl)-urea dihydrochloride, Intermediate 14.

Intermediate 15 exo 1-[3-(8aza-bicyclo[3.2.1]oct-3-ylmethyl)-phenyl]-3-(5-tert-butyl-2-p-tolyl-2H-pyrazol-3-yl)-urea dihydrochloride A solution of ethyl 3-iodobenzoate (1 eq) in THF (2 mL/g) is cooled to −20° C. and 2M iPrMgCl/THF (1 eq) is added dropwise and the reaction is allowed to stir for 30 minutes. A solution of the Intermediate 10 (0.75) in THF (2 mL/g) is then added while maintaining the temp from −20° C. for 1 hour. The bath is removed and the reaction is allowed to come to room temperature and stir for 1 hour. The reaction is partitioned between ether-aqueous NH$_4$Cl. The organic layer is washed with brine, then dried over MgSO$_4$, filtered and evaporated. The residue is chromatographed on silica gel using 30% ethylacetate/methylene chloride (1:4) to yield the ester. A mixture of the ester (1 eq) and 20% Pd(OH)$_2$ (1 eq by wt, 20% over charcoal) in ethyl alcohol (100 mL) is hydrogenated in a Parr apparatus overnight. The reaction is filtered through celite and evaporated to dryness. The residue is chromatographed on silica gel using 5% ethyl acetate/methylene chloride to yield the ester.

To a stirring solution of the ester (1 eq) in methanol (15 mL/g) is added 1N aqueous NaOH (1.5 eq) and the reaction is stirred at room temperature for 3 days The solvent is removed by rotoevaporation and the residue is partitioned between water and ethylacetate. The mixture is cooled to 0° C. and carefully acidified with 1N aqueous HCl to approximately pH 2. The two layers are separated and the organic layer is washed with water, brine and dried over magnesium sulfate. The solution is filtered and concentrated in vacuo to yield the desired acid.

To a solution of acid (1.75 eq) in THF (12 mL/g) at room temp is added TEA (0.8 mL, 5.8 mmol) followed by DPPA (1 eq). The mixture is refluxed for 1 hour and the 3-amino-4-tert-butyl-2-tolylpyrazole (1.2 eq) is added and the reaction is refluxed overnight. The reaction is cooled and partitioned between ether-aqueous NH$_4$Cl, and the organic layer is washed with brine, then dried over MgSO$_4$, filtered and evaporated. The residue is chromatographed on silica gel using DCM/heptane (9:1) to yield the BOC-protected urea. The BOC-protected urea (1 eq) is dissolved in methylene chloride (5 mL/g) under nitrogen at 0° C. and 4N HCL in dioxane (4 ml/g) is added. After 10 minutes the cooling bath is removed and the reaction is stirred for overnight at room temperature. The solution is concentrated to give exo 1-[3-(8-aza-bicyclo[3.2.1]oct-3-ylmethyl)-phenyl]-3-(5-tert-butyl-2-p-tolyl-2H-pyrazol-3-yl)-urea dihydrochloride, Intermediate 15.

Intermediate 16 exo 1-[4-(8aza-bicyclo[3.2.1]oct-3-ylmethyl)-phenyl]-3-(5-tert-butyl-2-p-tolyl-2H-pyrazol-3-yl)-urea dihydrochloride A solution of ethyl 4-iodobenzoate (1 eq) in THF (2 mL/g) is cooled to −20° C. and 2M iPrMgCl/THF (1 eq) is added dropwise and the reaction is allowed to stir for 30 minutes. A solution of the Intermediate 10 (0.75) in THF (2 mL/g) is then added while maintaining the temp from −20° C. for 1 hour. The bath is removed and the reaction is allowed to come to room temperature and stir for 1 hour. The reaction is partitioned between ether-aqueous NH$_4$Cl. The organic layer is washed with brine, then dried over MgSO$_4$, filtered and evaporated. The residue is chromatographed on silica gel using 30% ethyl acetate/methylene chloride (1:4) to yield the ester. A mixture of the ester (1 eq) and 20% Pd(OH)$_2$ (1 eq by wt, 20% over charcoal) in ethyl alcohol (100 mL) is hydrogenated in a Parr apparatus overnight. The reaction is filtered through celite and evaporated to dryness. The residue is chromatographed on silica gel using 5% ethyl acetate/methylene chloride to yield the ester.

To a stirring solution of the ester (1 eq) in methanol (15 mL/g) is added 1N aqueous NaOH (1.5 eq) and the reaction is stirred at room temperature for 3 days The solvent is removed by rotoevaporation and the residue is partitioned between water and ethyl acetate. The mixture is cooled to 0° C. and carefully acidified with 1N aqueous HCl to approximately pH 2. The two layers are separated and the organic layer is washed with water, brine and dried over magnesium sulfate. The solution is filtered and concentrated in vacuo to yield the desired acid.

To a solution of acid (1.75 eq) in THF (12 mL/g) at room temp is added TEA (0.8 mL, 5.8 mmol) followed by DPPA (1 eq). The mixture is refluxed for 1 hour and the 3-amino-4-tert-butyl-2-tolylpyrazole (1.2 eq) is added and the reaction is refluxed overnight. The reaction is cooled and partitioned between ether-aqueous NH$_4$Cl, and the organic layer is washed with brine, then dried over MgSO$_4$, filtered and evaporated. The residue is chromatographed on silica gel using DCM/heptane (9:1) to yield the BOC-protected urea. The BOC-protected urea (1 eq) is dissolved in methylene chloride (5 mL/g) under nitrogen at 0° C. and 4N HCL in dioxane (4 ml/g) is added. After 10 minutes the cooling bath is removed and the reaction is stirred for overnight at room temperature. The solution is concentrated to give exo 1-[4-(8-aza-bicyclo[3.2.1]oct-3-ylmethyl)-phenyl]-3-(5-tert-butyl-2-p-tolyl-2H-pyrazol-3-yl)-urea dihydrochloride, Intermediate 16.

Scheme 10:
Synthesis of Exo-Intermediates 14, 15 and 16

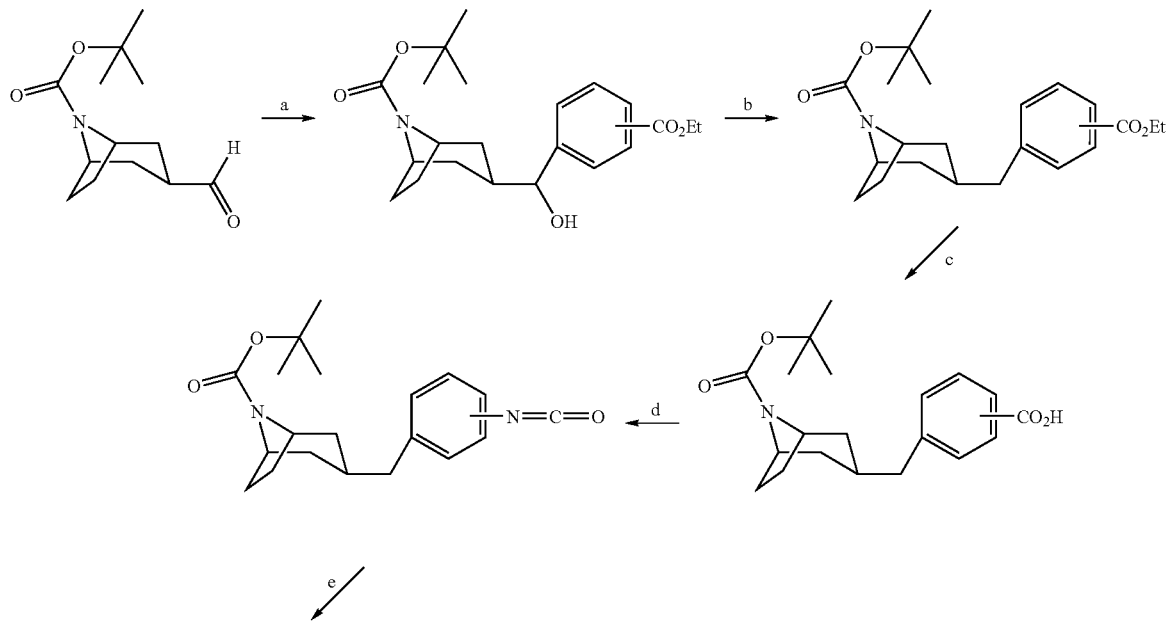

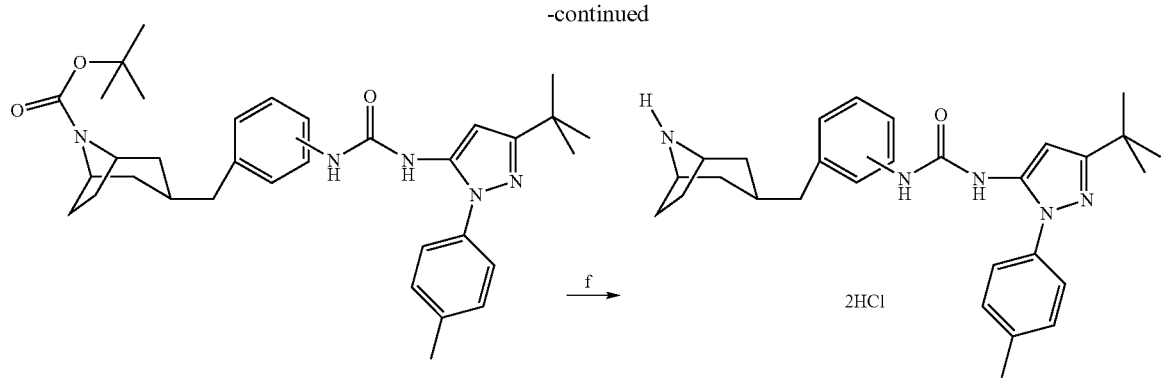

a. i-propMgCl, THF, ethyl 3-iodobenzoate;
b. Pd(OH)2, EtOH;
c. MeOH, NaOH;
d. DPPA, TEA, THF;
e. 3-amino-5-t-butyl-2-tolylprazoie, DCM;
f. dioxane, HCl Intermediate 14, 15 and 16

EXAMPLE 1

1-(5-tert-butyl-2-p-tolyl-2H-pyrazol-3-yl)-3-{4-[1-(2,4dimethoxy-benzoyl)-piperidin-4-ylmethyl]-phenyl]-urea, Compound A218

Intermediate 1 (255 mg) and 5-tert-butyl-2-[4-methylphenyl]-2H-pyrazole-isocyanate (400 mg, prepared as in J. Med. Chem. 45, 2994-3008, 2002) is dissolved in methylene chloride (30 mL) and allowed to stir overnight at room temperature. The reaction is concentrated and dissolved in a small amount of methylene chloride and applied to a 10 gram silica gel column that is eluted with ethyl acetate/heptane (1:1). The fractions containing product are concentrated and recrystallized from ethyl acetate/heptane to give 321 mg of 1-(5-tert-butyl-2-p-tolyl-2H-prazol-3-yl)-3-{4-[1(2,4-dimethoxy-benzoyl)-piperidin-4-ylmethyl]-phenyl}-urea, Compound A218, Example 1. m/z LCMS M$^{+1}$ 610, R$_T$=3.71 minutes.

Scheme 11:
Synthesis of Example 1

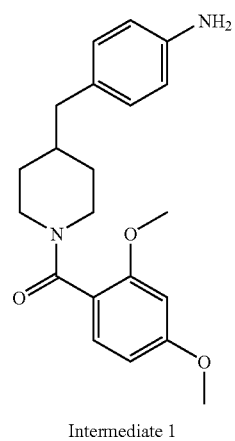

Intermediate 1

+

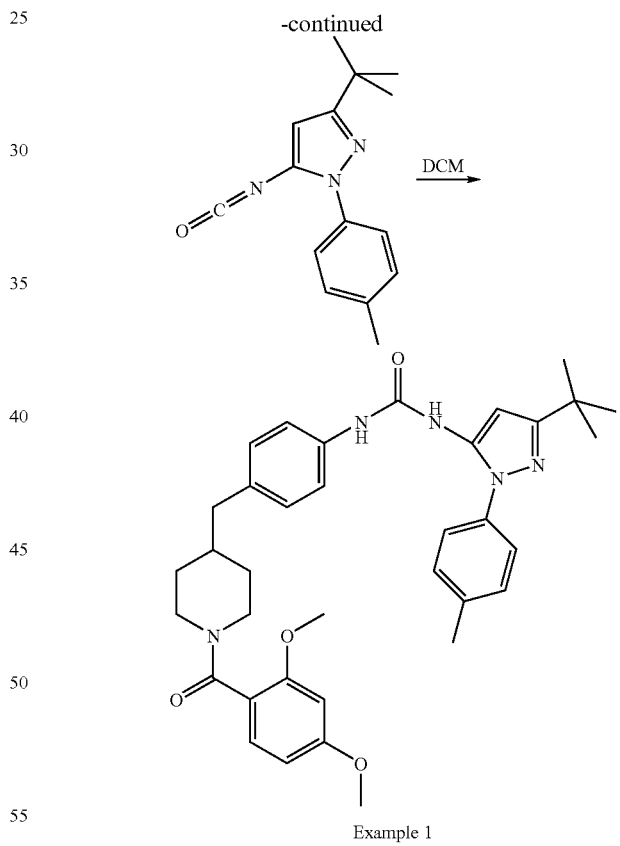

Example 1

EXAMPLE 2

1-(5-tert-butyl-2-p-tolyl-2H-pyrazol-3-yl)-3-{2-[1-(2,4-dimethoxy-benzoyl)-piperidin-4-ylmethyl]-phenyl]-urea, Compound A1113

Intermediate 2 (70 mg) and 5-tert-butyl-2-[4-methylphenyl]-2H-pyrazole-isocyanate (90 mg) is dissolved in methylene chloride (10 mL) and allowed to stir for 36 hours at room temperature. The reaction is concentrated and dissolved in a small amount of methylene chloride and applied to a 10 gram silica gel column that is eluted with ethyl acetate to give 115 mg of 1-(5-tert-butyl-2-p-tolyl-2H-pyrazol-3-yl)-3-{2-[1-(2, 4-dimethoxy-benzoyl)-piperidin-4-ylmethyl]-phenyl}-urea, Compound A1113, Example 2. m/z LCMS M$^{+1}$ 610, R$_T$=3.70 minutes.

Scheme 12:
Synthesis of Example 2

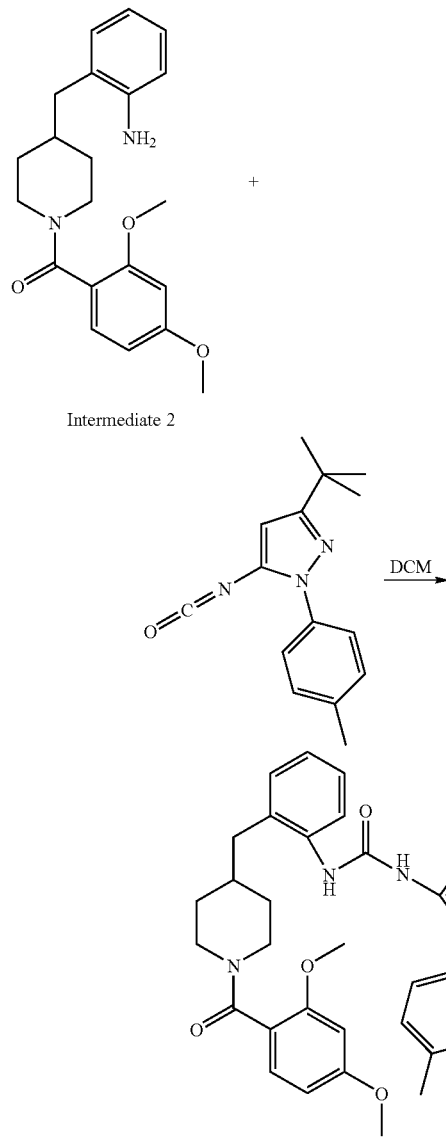

Example 2

EXAMPLE 3

1-(5-tert-butyl-2-tolyl-2H-pyrazol-3-yl)-3-{3-[1-(2, 4-dimethoxy-benzoyl)-piperidin-4-ylmethyl]-phenyl}-urea, Compound A27

To a stirring solution of 4-methylene-piperidine hydrochloride (1.00 g, 8.12 mmol, JOC 66,2487-2492,2001) in 10 mL anhydrous dichloromethane at room temperature is added 2,4-dimethoxybenzoyl chloride (1.63 g, 8.12 mmol) and TEA (4 g, 40 mmol). The reaction mixture is allowed to stir for 16 hours. Dichloromethane is removed in vacuo, and the resultant residue is purified through silica gel chromatography (95% DCM, 5% MeOH) to give (2,4-dimethoxy-phenyl)-(4-methylene-piperidin-1-yl)-methanone. Yield: 1.62 g, 6.23 mmol. m/z (MS) M$^{+1}$ 261.01.

(2,4-Dimethoxy-phenyl)-(4-methylene-piperidin-1-yl)-methanone (100 mg, 0.383 mmol) is reacted with a solution of 0.5M 9-BBN (0.766 mL, 0.383 mmol) and stirred at 68° C. for 1.5 hours. The reaction mixture is then added to a 4 mL vial containing m-bromoaniline (131 mg, 0.766 mmol), DMF (0.791 mL), H$_2$O (0.075 mL), K$_2$CO$_3$ (63 mg, 0.456 mmol) and Pd(dppf)$_2$Cl$_2$.CH$_2$Cl$_2$ (25 mg). This reaction mixture is then allowed to stir at 60° C. for 16 hours. The contents of the vial are then emptied into water adjusted to pH 11. Organics are extracted twice with 50 mL ethyl acetate, washed with sodium bicarbonate, water and brine, and dried over sodium sulfate. Volatiles are removed in vacuo, and the oily residue is purified via gradient chromatography (40% EtOAc in heptane to 5% MeOH in ethyl acetate) of 4-(3-amino-benzyl)-piperidin-1-yl]-(2,4-dimethoxy-phenyl)-methanone. Yield: 10 mg, 0.028 mmol. m/z (MS) M$^{+1}$ 354.19.

4-(3-Amino-benzyl)-piperidin-1-yl]-(2,4-dimethoxy-phenyl)-methanone (10 mg) and 5-tert-butyl-2-[4-methylphenyl]-2H-pyrazole-isocyanate (20 mg) are stirred in methylene chloride (10 mL) overnight at room temperature. The reaction is concentrated and purified on a 10 gram silica gel column using ethyl acetate/heptane (4:1) to give 17 mg of 1-(5-tert-butyl-2-p-tolyl-2H-pyrazol-3-yl)-3-{3-[1-(2,4-dimethoxy-benzoyl)-piperidin-4-ylmethyl]-phenyl}-urea, Compound A27, Example 3. LC/MS M$^{+1}$ 610, 305 R$_T$=3.71 minutes Scheme 13:
Synthesis of Example 3

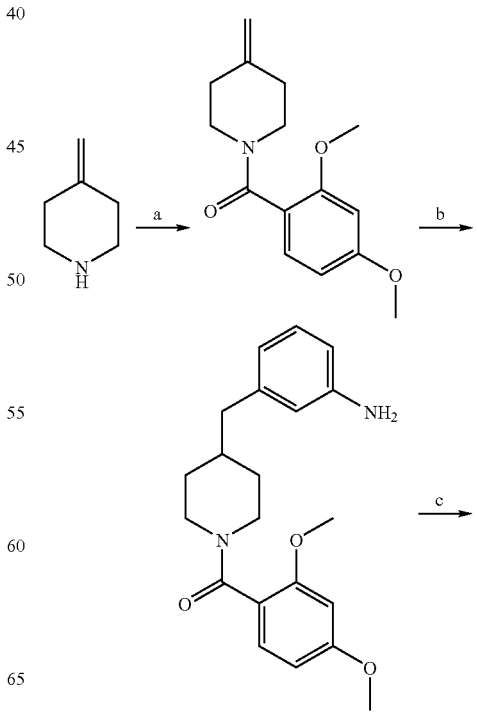

-continued

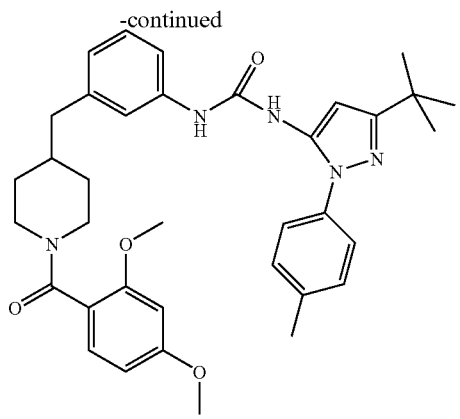

Example 3
a. 2,4-dimethoxybenzoyl chloride, DCM, TEA;
b. i. 9BBN, THF, ii. m-bromoaniline, Pd(dppf)2DMf, K2CO3;
c. isocyanate, DCM

EXAMPLE 4 AND EXAMPLE 5

1-(5-tert-Butyl-2-tolyl-2H-pyrazol-3-yl)-3-{4-[8-(2, 4dimethoxy-benzoyl)-8-aza-bicyclo[3.2.1]oct-3-ylmethyl]-phenyl}-urea, Compound A1429, and 1-(5tert-butyl-2p-tolyl-2H-pyrazol-3-yl)-3-{2-[8-(2, 4-dimethoxy-benzoyl)-8-aza-bicyclo[3.2.1]oct-3-ylmethyl]-phenyl}-urea, Compound A 1643

To a stirring solution of tropinone (10 g, 72 mmol) into 350 mL DCE at 0° C. was added 1-chloroethyl chloroformate (11.6 mL, 108 mmol). The reaction mixture was then heated to reflux and stirred for 16 hours. Upon completion (TLC), volatiles were removed in vacuo and the dark brown residue was washed with ether and filtered. The filtrate was concentrated under reduced pressure and the product formed a brown oil (Yield: 12.65 g, 54.7 mmol). The brown oil was dissolved in 100 mL MeOH and set to reflux for 2 hours. Upon completion (TLC), the methanol was removed in vacuo and the residue was dissolved in ether. Solid particulates were filtered, and the ether was removed under reduced pressure and 8-aza-bicyclo[3.2.1]octan-3-one hydrochloride formed as a beige solid (Yield: 5.0 g, 40 mmol). The product was used without any further purification.

A mixture of 8-Aza-bicyclo[3.2.1]octan-3-one hydrochloride (2.5 g, 20 mmol), TEA (4.2 mL, 30 mmol) and DMAP (cat.) in DCM (60 mL) was cooled to 0° C. and benzyl chloroformate (4.3 mL, 30 mmol) was added and stirred for 30 minutes, then the reaction was allowed to stir at room temperature for overnight. The reaction was extracted with saturated ammonium chloride, brine and dried over magnesium sulfate. The organic layer was concentrated and purified on silica gel using heptane/ethyl acetate (7:3) to give 2.62 grams of CBZ-protected 8-Aza-bicyclo[3.2.1]octan-3-one.

To a solution of benzylphosphonium bromide (10.5 g, 24.3 mmol) in THF (65 mL) was added at room temperature potassium t-butoxide (1M in THF, 24.3 mL, 24.3 mmol). The reaction was stirred for 30 minutes and the CBZ-protected 8-Aza-bicyclo[3.2.1]octan-3-one (3.5 g, 13.4 mmol) in THF was added and the reaction was refluxed for 48 hours. The mixture was extracted with saturated ammonium chloride, brine and dried over magnesium sulfate. The organic was concentrated and the residue was taken up in ether and the solid that formed was filtered and the filtrate was concentrated to a oil. This was purified on silica gel using DCM to obtain 3.77 grams of product as a light yellow oil. The oil (1.93 g, 5.8 mmol) was dissolved in ethanol (30 mL) and Pd/C (20%, 500 mg) was added and the reaction was hydrogenated at 50 PSI. The mixture was shaken over night and filtered through celite and concentrated. The residue was purified on silica gel using DCM/MeOH/NH$_4$OH (90:10:1) to give 1 gram of 4-benzyl-nortropane. LCMS M$^{+1}$ 202, R$_T$=2.914 minutes.

To a solution of 4-benzylnortropane (494 mg, 2.46 mmol) in TFA (1.84 mL) was added ammonium nitrate (207 mg, 2.58 mmol) at 0° C. The mixture was then allowed to come to room temperature and stir overnight, then the mixture was concentrated and partitioned between water and ethyl acetate. The organic layer was dried over magnesium sulfate, concentrated and purified on silica gel (90/10/1 DCM/MeOH, NH$_4$OH) to give a mixture of 2-nitro- and 4-nitro substituted 4-benzylnortropane trifluoroacetamide (127 mg, 0.37 mmol)). The trifluoroacetamide group was removed by dissolving it in methanol/water (5 mL, 1:1) followed by the addition of potassium carbonate (102 mg, 0.75 mmol) and stirring overnight at room temperature. The reaction was concentrated and partitioned between water and ethyl acetate, then the organic layer was extracted with saturated ammonium chloride. Product was in both layers and they were combined and concentrated to dryness. The residue was taken into methanol and the solids were removed and the methanol layer was concentrated to give 90 mg of product as a mixture of 4-nitro- and 2-nitro-benzylnortropane.

To the mixture of 4-[4-nitrobenzyl]nortropane and 4-[2-nitrobenzyl]nortropane (117 mg, 0.47 mmol) in methylene chloride (5 mL) was added TEA (0.07 mL) then the mixture was cooled to 0° C. followed by the addition of 2,4-dimethoxybenzoyl chloride (100 mg, 0.55 mmol). The reaction was stirred overnight at room temperature. The reaction was extracted with saturated ammonium chloride and dried over magnesium sulfate. The solution was concentrated and purified on silica gel column (95/5/1 DCM/MeOH, NH$_4$OH) to give 108 mg of product as a mixture. This product (108 mg) was dissolved in methanol (10 mL) and 10% Pd/C (300 mg) was added followed by the addition of NaBH$_4$ (100 mg). After 60 minutes the reaction was concentrated to dryness. The residue was dissolved in DCM and portioned with water. The organic layer was concentrated and the ortho and para isomers were purified on silica gel column using ethyl acetate/methanol (95:5) to give 50 mg of product as a mixture of regioisomers.

The mixture of regioisomers (50 mg) were dissolved in DCM (5 mL) and 5-tert-butyl-2-[4-methylphenyl]-2H-pyrazole-isocyanate (33.5 mg, 0.13 mmol, JMC 45,2994-3008, 2002) was added and the reaction was stirred for 2 hours at room temperature. The reaction was extracted with brine and the organic was concentrated to dryness to give 50 mg of crude product. The regioisomers were separated on a preparative HPLC to give 29 mg of 1-(5-tert-Butyl-2-p-tolyl-2H-pyrazol-3-yl)-3-{4-[8-(2,4-dimethoxy-benzoyl)-8-aza-bicyclo[3.2.1]oct-3-ylmethyl]-phenyl}-urea, Compound A 1429; Example 4 (LCMS M$^{+1}$ 636, R$_T$=3.68) and 10 mg of 1-(5-tert-butyl-2-p-tolyl-2H-pyrazol-3-yl)-3-{2-[8-(2,4-dimethoxy-benzoyl)-8-aza-bicyclo[3.2.1]oct-3-ylmethyl]-phenyl}-urea, Compound A 1643, Example 5 (LCMS M$^{+1}$=636, R$_T$=3.61). HPLC. 10-100% B over 18 min, A=0.1% TFA/H$_2$O, B=CH$_3$CN; C18 RP Metachem Monochrome 10 micron, 2in×15 cm column. 70 mL/minute or 20 mL/minute; 220 nm.

Scheme 14:
Synthesis of Example 4 and Example 5
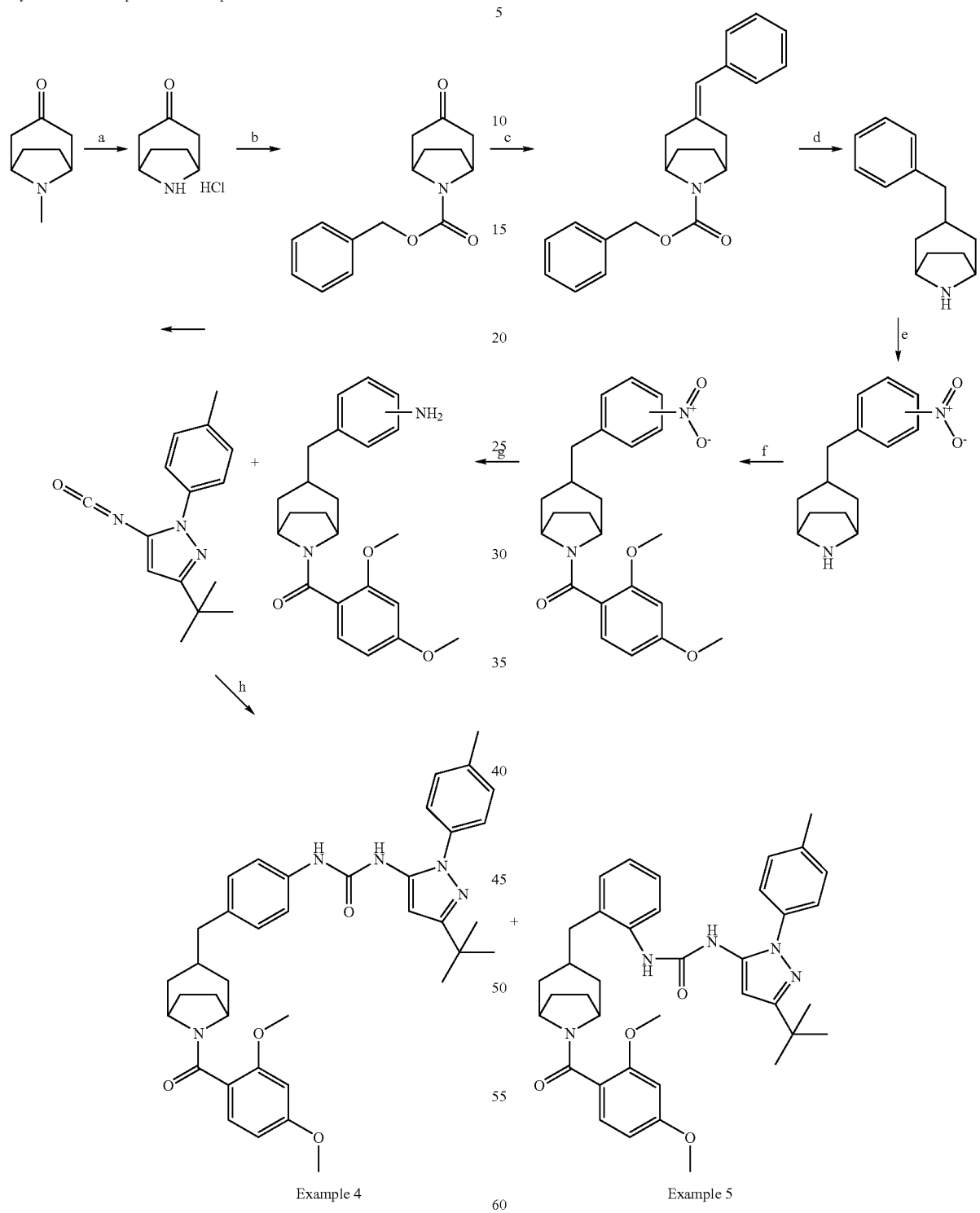
Example 4
Example 5
a. i. 1-chloro-ethyl chloroformate, DCE ii. methanol;
b. benzyl chloroformate, DMAP, TEA, DCM;
c. Ph3PCH2PhBr, t-BuOK, THF;
d. Pd/C, H2;
e. i. TFAA, sodium nitrate, ii. MeOH, K2CO3;
f. 2,4-dimethoxybenzoyl chloride, TEA, DCM;
g. Pd/C, MeOH, NaBH4;
h. DCM

EXAMPLE 6

1-{4-[8-(4-Amino-5-chloro-2-methoxy-benzoyl)-8-aza-bicyclo[3.2.1]oct-3-ylmethyl]-phenyl}-3-(5-tert-butyl-2-p-tolyl-2H-pyrazol-3-yl)-urea, Compound A1441

4-amino-5-chloro-2-methoxybenzoic acid (60 mg, 0.30 mmol) is dissolved in DCM and 1-(3-dimethylaminopropyl)-3-ethylcarbodiimide hydrochloride (EDCI) (64 mg, 0.30 mmol) is added followed by the addition of Intermediate 3 (130 mg, 0.28 mmol). The reaction is stirred at room temperature for overnight and the reaction is concentrated to dryness and purified on a 10 gram silica gel column using ethyl acetate/heptane (35%/65%) to give 60 mg of 1-{4-[8-(4-Amino-5-chloro-2-methoxy-benzoyl)-8-aza-bicyclo[3.2.1]oct-3-ylmethyl]-phenyl}-3-(5-tert-butyl-2-p-tolyl-2H-pyrazol-3-yl)-urea, Compound A1441, Example 6. m/z (LCMS) M$^{+1}$=636, R$_T$=3.47 minutes.

Scheme 15:
Synthesis of Example 6

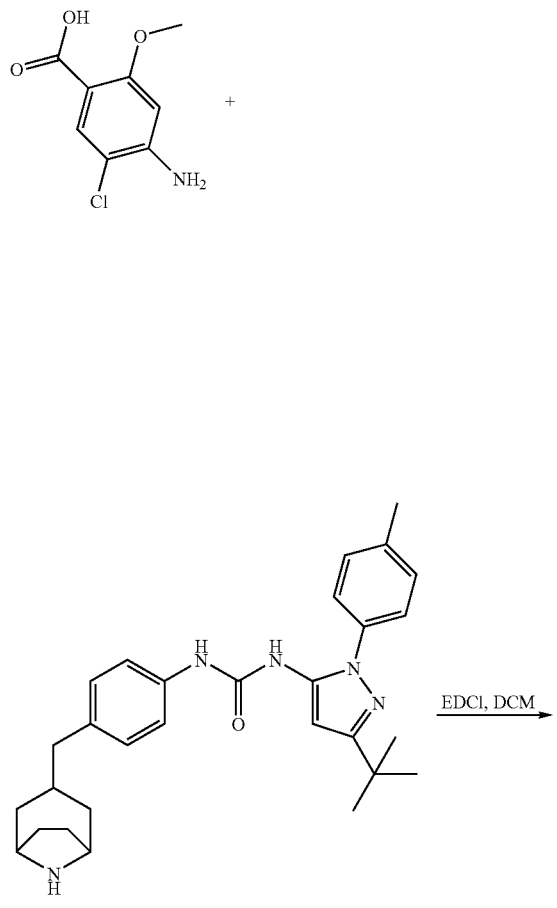

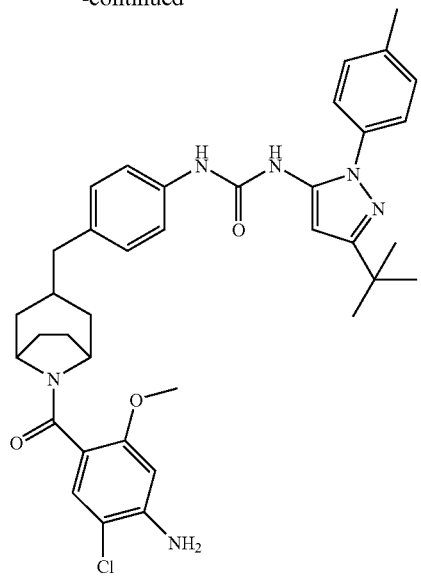

Example 6

EXAMPLE 7

General Procedure for Amide Formation

The following procedure is used for preparation of certain amides of the present invention, i.e., where X of Formulas (I) to (VI) is —C(O)—.

Weigh 0.125 mmol of tetrafluorophenol resin (PL-TFP 009) into fritted polypropylene syringe tubes. Add 1 mL N,N-dimethylformamide (DMF) to swell the resin. Add 0.250 mmol of both an appropriate carboxylic acid and N,N'-diisopropylcarbodiimide (DIC). Cap and shake on a platform shaker overnight at room temperature. Using a luer lock vacuum box, aspirate reaction liquor and wash 3× each with DMF and tetrahydrofuran (THF), and alternate dichloromethane (DCM) and methanol washes 3×, followed by one DCM and two DMF washes. Add 1 mL DMF and 0.075 mmol of one of the amine intermediates selected from Intermediates 3 to 8 or 11 to 16 to the acid-loaded resin. Cap and shake on a platform shaker overnight at 50° C. Collect the reaction liquor, rinse twice with DCM, collecting both rinses. Add 1% triethylamine (TEA) in DCM, cap and shake approx. 1 hour at room temperature on a platform shaker. Collect this wash and add to the original collection. Dry in a Genevac centrifugal evaporator.

Scheme 16:
General Amide Formation

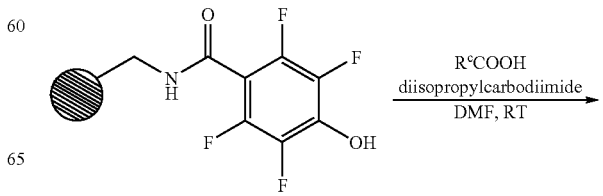

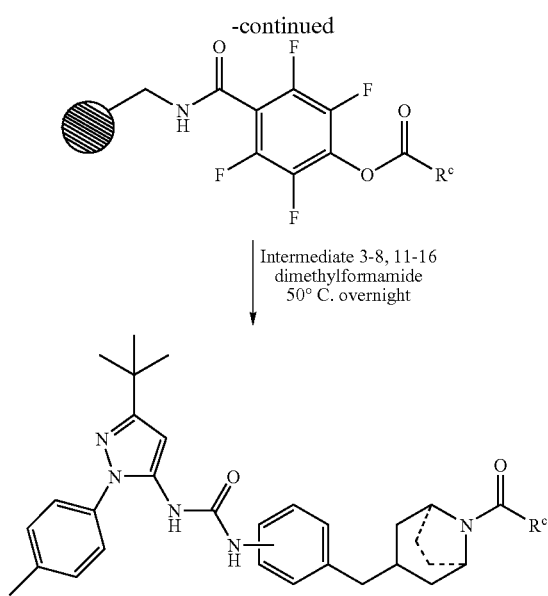

Intermediate 3-8, 11-16
dimethylformamide
50° C. overnight

Appropriate carboxylic acids, i.e. R$^c$COOH, which are used in the procedure of Example 7 to prepare compounds of the invention include:
3-Diethylamino-benzoic acid;
4-(2-Amino-ethyl)-benzoic acid;
4-(2-Acetylamino-ethyl)benzoic acid;
4-Methyl-3,4-dihydro-2H-benzo[1,4]oxazine-7-carboxylic acid;
4-Oxazol-5-yl-benzoic acid;
2-Hydroxy-6-methyl-isonicotinic acid;
(6-Methoxy-benzofuran-3-yl)-acetic acid;
(5-Chloro-2,4-dimethoxy-phenyl)-acetic acid;
4-Propionyl-benzoic acid;
4-(2-Methyl-allyl)-benzoic acid;
4-But-3-enyl-benzoic acid;
Terephthalamic acid;
[5-(4-Methoxy-phenyl)-thiophen-2-yl]-acetic acid;
4-Methyl-thiophene-3-carboxylic acid;
3-Methyl-thiophene-2,4-dicarboxylic acid 4-ethyl ester;
4-(2,2,2-Trifluoro-ethoxymethyl)-benzoic acid;
5-(2-Trifluoromethoxy-phenyl)-furan-2-carboxylic acid;
2-Methyl-5-(piperidine-1-sulfonyl)-furan-3-carboxylic acid;
1-Methyl-1H-imidazole-4-carboxylic acid;
2-(4-Methoxy-benzyl)-thiazole-4-carboxylic acid;
6-Methyl-imidazo[2,1-b]thiazole-5-carboxylic acid;
Pyrazolo[1,5-a]pyrimidine-3-carboxylic acid;
4-tert-Butoxymethyl-benzoic acid;
Furan-3-yl-acetic acid;
5-Methoxy-3-methyl-benzo[b]thiophene-2-carboxylic acid;
(4-Methyl-6,7-dihydro-4H-thieno[3,2-c]pyran-4-yl)-acetic acid;
3-Methyl-benzo[b]thiophene-2-carboxylic acid;
5-Methyl-4-morpholin-4-ylmethyl-furan-2-carboxylic acid;
3-(3-Allyl-thioureido)-benzoic acid;
5-Oxo-5,6,7,8-tetrahydro-naphthalene-2-carboxylic acid;
3,5-Difluoro-4-trifluoromethyl-benzoic acid;
2-Methyl-4-trifluoromethoxy-benzoic acid;
2-Methyl-5-thiophen-2-yl-furan-3-carboxylic acid;
4-(1H-Pyrazol-3-yl)-benzoic acid;
4-(2H-Tetrazol-5-yl)-benzoic acid;
4-Methyl-3-oxo-3,4-dihydro-2H-benzo[1,4]thiazine-6-carboxylic acid;
Benzofuran-4-yl-acetic acid;
Quinoxaline-6-carboxylic acid;
3-Methyl-isoxazole-4-carboxylic acid;
3-Methoxy-thiophene-2-carboxylic acid;
2-(2,3-Dihydro-benzofuran-5-yl)-thiazole-4-carboxylic acid;
4-Methoxy-2-trifluoromethyl-benzoic acid;
4-Acetoxymethyl-benzoic acid;
5-Methyl-isoxazole-4-carboxylic acid;
3-Butoxy-4-methoxy-benzoic acid;
Furan-2-yl-acetic acid;
2,2-Difluoro-benzo[1,3]dioxole-5-carboxylic acid;
4-Thiophen-2-yl-benzoic acid;
4-Fluoro-2-methoxy-benzoic acid;
2-Fluoro-4-methoxy-benzoic acid;
1,3-Dimethyl-1H-pyrazole-4-carboxylic acid;
5-Methoxy-1,2dimethyl-1H-indole-3-carboxylic acid;
4-(1H-Imidazol-2-yl)-benzoic acid;
4-(3,6-Dioxo-cyclohexa-1,4-dienyl)-benzoic acid;
5-Methyl-2-trifluoromethyl-furan-3-carboxylic acid;
3-Pyridin-3-yl-propionic acid;
5-Amino-N-(2,3-dihydroxy-propyl)-isophthalamic acid;
3-Amino-4-isopropenyl-benzoic acid;
2-Methyl-imidazo[1,2-a]pyridine-3-carboxylic acid;
3,4-Bis-acetylamino-benzoic acid;
4-(2-Oxo-propyl)benzoic acid;
4-Ethoxymethyl-benzoic acid;
4-Difluoromethoxy-benzoic acid;
2-Methyl-5-phenyl-furan-3-carboxylic acid;
5-Methoxy-2-(2,2,2-trifluoro-ethoxy)-benzoic acid;
3-Acetylamino-5-methoxy-benzoic acid;
1H-Indazole-3-carboxylic acid;
3-Methyl-5-trifluoromethyl-isoxazole-4-carboxylic acid;
4-Amino-3-trifluoromethoxy-benzoic acid;
3H-[1,2,3]Triazole-4-carboxylic acid;
4-Isobutyl-benzoic acid;
(2,4-Dimethoxy-phenyl)-acetic acid;
2-Chloro-6-methoxy-isonicotinic acid;
4-Methyl-2-pyridin-4-yl-thiazole-5-carboxylic acid;
4-Methyl-2-pyridin-3-yl-thiazole-5-carboxylic acid;
2-Pyridin-4-yl-thiazole-4-carboxylic acid;
1,3,5-Trimethyl-1H-pyrazole-4-carboxylic acid;
3,5-Dimethyl-1H-pyrazole-4-carboxylic acid;
4-(1,1,2,2-Tetrafluoro-ethoxy)benzoic acid;
3-(1,1,2,2-Tetrafluoro-ethoxy)-benzoic acid;
Benzo[b]thiophen-4-yl-acetic acid;
4-Guanidino-benzoic acid;
2-Fluoro-4-propoxy-benzoic acid;
2-Fluoro-4-isopropoxy-benzoic acid;
(1-Methyl-1H-indol-3-yl)-acetic acid;
4-Methyl-2-pyrazin-2-yl-thiazole-5-carboxylic acid;
Benzothiazole-6-carboxylic acid;
6-(2,2,2-Trifluoro-ethoxy)-nicotinic acid;
4-Oxo-2-phenyl-4H-chromene-6-carboxylic acid;
4-Ethylamino-benzoic acid;
5-Methoxymethyl-1-phenyl-1H-[1,2,3]triazole-4-carboxylic acid;
2-(2,3-Dihydro-benzo[1,4]dioxin-2-yl)-4-methyl-thiazole-5-carboxylic acid;
5-tert-Butyl-furan-2-carboxylic acid;
5-Chloro-furan-2-carboxylic acid;
5-Methyl-furan-2-carboxylic acid;
2-Methyl-furan-3-carboxylic acid;
4-(3-Methyl-ureido)-benzoic acid;
4-Methyl-thiophene-2-carboxylic acid;
Bicyclo[2.2.1]hept-5-ene-2-carboxylic acid;
2,6-Dioxo-hexahydro-pyrimidine-4-carboxylic acid;

4-[1,2,3]Thiadiazol-4-yl-benzoic acid;
4,5-Dimethyl-furan-2-carboxylic acid;
3-Methanesulfonyl-6,7-dihydro-benzo[c]thiophene-1-carboxylic acid;
2,3-Dihydro-benzofuran-5-carboxylic acid;
2-(2,3-Dihydro-benzo[1,4]dioxin-2-yl)-thiazole-4-carboxylic acid;
5-Chloro-thiophene-3-carboxylic acid;
4-Chloro-thiophene-2-carboxylic acid;
(3,5-Dimethyl-phenyl)-acetic acid;
Indan-2-yl-acetic acid;
1H-Imidazole-4-carboxylic acid;
2,5-Dimethyl-furan-3-carboxylic acid;
5-Methoxy-benzofuran-2-carboxylic acid;
2,6-Dimethoxy-nicotinic acid;
5,6-Dichloro-nicotinic acid;
(2-Methyl-1H-indol-3-yl)-acetic acid;
5-Methyl-pyrazine-2-carboxylic acid;
5-Chloro-4-methoxy-thiophene-3-carboxylic acid;
4-Methoxy-thiophene-3-carboxylic acid;
5-Methyl-1-phenyl-1H-pyrazole-4-carboxylic acid;
5-Oxo-pyrrolidine-2-carboxylic acid;
Methoxy-phenyl-acetic acid;
7-Methoxy-benzofuran-2-carboxylic acid;
3-Methyl-benzofuran-2-carboxylic acid;
3-Thioureido-benzoic acid;
(2,3-Dimethoxy-phenyl)-acetic acid;
3-(4-Fluoro-phenyl)-propionic acid;
4-Ethoxycarbonyloxy-benzoic acid;
5-Chloro-6-hydroxy-nicotinic acid;
2,4-Dimethyl-thiazole-5-carboxylic acid;
5-Pyridin-2-yl-thiophene-2-carboxylic acid;
4-(2,2,2-Trifluoro-acetyl)-benzoic acid;
(5-Chloro-benzo[b]thiophen-3-yl)-acetic acid;
2-Pyridin-3-yl-thiazole-4-carboxylic acid;
(5-Chloro-3-methyl-benzo[b]thiophen-2-yl)-acetic acid;
4-Oxo-4,5,6,7-tetrahydro-benzofuran-3-carboxylic acid;
[1,2,3]Thiadiazole-4-carboxylic acid;
3,5-Dimethyl-isoxazole-4-carboxylic acid;
5-Methyl-2-phenyl-2H-[1,2,3]triazole-4-carboxylic acid;
Benzo[b]thiophen-3-yl-acetic acid;
Benzo[b]thiophene-2-carboxylic acid;
Quinoline-6-carboxylic acid;
3-Thiophen-2-yl-propionic acid;
2-(4-Chloro-phenyl)propionic acid;
Furan-2-yl-oxo-acetic acid;
5-Chloro-thiophene-2-carboxylic acid;
3-(1H-Benzoimidazol-2-yl)propionic acid;
2-Acetylamino-propionic acid;
2-Hydroxy-quinoline-4-carboxylic acid;
6-Methyl-pyridine-2-carboxylic acid;
Tetrahydro-furan-2-carboxylic acid;
4-Oxo-2-phenyl-pentanoic acid;
2,2-Dimethyl-pentanoic acid;
4-Cyanomethyl-benzoic acid;
4-Carbamimidoyl-benzoic acid;
4-(2-Hydroxy-ethoxy)-benzoic acid;
4-Methoxy-2-methyl-benzoic acid;
1-(4-Methoxy-phenyl)-cyclopropanecarboxylic acid;
4-Hydroxymethyl-benzoic acid;
(3,5-Dimethoxy-phenyl)-acetic acid;
(2,4,6-Trimethoxy-phenyl)-acetic acid;
(2,3-Dimethyl-phenoxy)-acetic acid;
3-p-Tolyl-propionic acid;
2,4,6-Trimethoxy-benzoic acid;
Benzo[1,3]dioxol-5-yl-acetic acid;
Hept-2-ynoic acid;
(4-Methoxy-phenoxy)-acetic acid;
2-Methyl-2-phenyl-propionic acid;
3-Methyl-furan-2-carboxylic acid;
Phenylamino-acetic acid;
3-Acetylamino-benzoic acid;
2-Methyl-nicotinic acid;
Pyridin-4-yl-acetic acid hydrochloride;
Pyridin-3-yl-acetic acid hydrochloride;
(1H-Imidazol-4-yl)-acetic acid hydrochloride;
Dimethylamino-acetic acid hydrochloride;
Quinoxaline-2-carboxylic acid;
1H-Benzotriazole-5-carboxylic acid;
3,6-Dichloro-pyridazine-4-carboxylic acid;
5-Oxo-tetrahydro-furan-2-carboxylic acid;
1H-Pyrazole-4-carboxylic acid;
2,3-Dihydro-1H-indole-2-carboxylic acid;
(3,5-Difluoro-phenyl)acetic acid;
4-Aminomethyl-benzoic acid;
(3,4-Difluoro-phenyl)-acetic acid;
(2,4-Difluoro-phenyl)-acetic acid;
Phthalic acid dimethyl ester;
(4-Amino-phenyl)-acetic acid;
(4-Amino-benzoylamino)-acetic acid;
3-Amino-4-hydroxy-benzoic acid;
Isoquinoline-1-carboxylic acid;
Quinoline-4-carboxylic acid;
Quinoline-3-carboxylic acid;
Quinoline-2-carboxylic acid;
3-Piperidin-1-yl-propionic acid;
Isonicotinic acid;
Nicotinic acid;
6-Amino-nicotinic acid;
2-Amino-nicotinic acid
Pyridine-2-carboxylic acid;
6-Chloro-nicotinic acid;
2-Chloro-nicotinic acid;
3-Amino-pyrazine-2-carboxylic acid;
Pyrazine-2-carboxylic acid;
Piperidine-4-carboxylic acid;
1H-Indole-5-carboxylic acid;
3-(1H-Indol-3-yl)-propionic acid;
(1H-Indol-3-yl)-acetic acid;
(1H-Indol-3-yl)-oxo-acetic acid;
1H-Indole-3-carboxylic acid;
Thiophen-3-yl-acetic acid;
Thiophene-3-carboxylic acid;
Thiophen-2-yl-acetic acid;
5-Methyl-thiophene-2-carboxylic acid;
Furan-3-carboxylic acid;
3-Furan-2-yl-propionic acid;
5-Oxo-pyrrolidine-2-carboxylic acid;
(2,5-Dioxo-imidazolidin-4-yl)-acetic acid;
Heptanoic acid;
5-Oxo-5-phenyl-pentanoic acid;
4-(4-Methoxy-phenyl)-butyric acid;
4-Phenyl-butyric acid;
(4-Methoxy-phenyl)-acetic acid;
(4-Fluoro-phenyl)-acetic acid;
(3,4-Dimethoxy-phenyl)-acetic acid;
(3-Methoxy-phenyl)-acetic acid;
(3-Fluoro-phenyl)-acetic acid;
o-Tolyl-acetic acid;
(2-Methoxy-phenyl)acetic acid;
(2-Fluoro-phenyl)-acetic acid;
Methoxy-acetic acid;
Phenoxy-acetic acid;
Dimethylamino-acetic acid;

(N-Methyl-guanidino)-acetic acid;
Acetylamino-acetic acid;
Methoxy-phenyl-acetic acid;
2,2-Dimethyl-propionic acid;
Cycloheptanecarboxylic acid;
Naphthalen-2-yl-acetic acid;
Naphthalen-1-yl-acetic acid;
Furan-2-carboxylic acid;
5-Methyl-3-phenyl-isoxazole-4-carboxylic acid;
Butyric acid;
4-(4-Fluoro-phenyl)-4-oxo-butyric acid;
Succinic acid monomethyl ester;
3-(2-Methoxy-phenyl)-propionic acid;
3-Phenyl-propionic acid;
3-Phenoxy-propionic acid;
Benzoylamino-acetic acid;
2-Phenyl-propionic acid;
2-Oxo-3-phenyl-propionic acid;
2-Oxo-propionic acid;
3-(Cyano-methyl-methyl)benzoic acid;
3,5-Dimethoxy-benzoic acid;
2,4-Dimethoxy-benzoic acid;
2,3-Dimethoxy-benzoic acid;
1,2,3,4-Tetrahydro-naphthalene-2-carboxylic acid;
Cyclohexyl-acetic acid;
1-Methyl-cyclohexanecarboxylic acid;
Cyclohexanecarboxylic acid;
Cyclopentyl-acetic acid;
1-Phenyl-cyclopentanecarboxylic acid;
Cyclopentanecarboxylic acid;
Cyclobutanecarboxylic acid;
1-Methyl-cyclopropanecarboxylic acid;
3,5-Bis-trifluoromethyl-benzoic acid;
4-Amino-5-chloro-2-methoxy-benzoic acid;
Benzo[d]imidazo[2,1-b]thiazole-2-carboxylic acid;
[1,6]Naphthyridine-2-carboxylic acid;
2-Methyl-5-trifluoromethyl-oxazole-4-carboxylic acid;
4-(4-Chloro-phenyl)-thiophene-2-carboxylic acid;
2-Trifluoromethyl-[1,8]naphthyridine-3-carboxylic acid;
4-(4-Methoxy-phenyl)-thiophene-2-carboxylic acid;
2-(4,6-Dimethyl-pyrimidin-2-ylamino)-benzoic acid;
3-(4,6-Dimethyl-pyrimidin-2-ylamino)benzoic acid;
4-(4,6-Dimethyl-pyrimidin-2-ylamino)-benzoic acid;
3-(2,2-Difluoro-benzo[1,3]dioxol-5-yl)-acrylic acid;
2-Phenyl-5-trifluoromethyl-oxazole-4-carboxylic acid;
6-Trifluoromethyl-nicotinic acid;
2-(4,6-Dimethoxy-pyrimidin-2-ylsulfanyl)-benzoic acid;
3-(4,6-Dimethoxy-pyrimidin-2-yloxy)-benzoic acid;
2-Trifluoromethyl-[1,6]naphthyridine-3-carboxylic acid;
2-Chloro-4-methanesulfonyl-benzoic acid;
1H-Indole-6-carboxylic acid;
3-[(4,6-Dimethyl-pyrimidin-2-yl)-methyl-amino]-benzoic acid;
2-Methyl-[1,6]naphthyridine-3-carboxylic acid;
[1,8]Naphthyridine-2-carboxylic acid;
4,5-Dihydro-benzo[b]thiophene-6-carboxylic acid;
4,5-Dihydro-benzofuran-6-carboxylic acid;
2,5-Dimethyl-oxazole-4-carboxylic acid;
1-(5-Bromo-pyrimidin-2-yl)-piperidine-4-carboxylic acid;
2-(4,6-Dimethoxy-pyrimidin-2-yloxy)-benzoic acid;
1-(5-Bromo-pyrimidin-2-yl)-piperidine-3-carboxylic acid;
4-[(4,6-Dimethyl-pyrimidin-2-yl)-methyl-amino]-benzoic acid;
1H-Pyrrole-3-carboxylic acid hydrate;
4-Trifluoromethyl-nicotinic acid;
2-Methyl-[1,8]naphthyridine-3-carboxylic acid;
5-Methyl-pyrazine-2-carboxylic acid;

5-Nitro-1H-indole-2-carboxylic acid ethyl ester;
Pyrazine-2,5-dicarboxylic acid;
Furo[2,3-c]pyridine-5-carboxylic acid ethyl ester;
2,4,6-Trimethyl-benzoic acid;
Benzofuran-2-carboxylic acid;
2,5-Dimethoxy-benzoic acid;
(2,5-Dimethoxy-phenyl)-acetic acid;
6-Hydroxy-nicotinic acid;
3,4-Dimethoxy-benzoic acid; and
1H-Benzoimidazole-5-carboxylic acid.

EXAMPLE 8

Sulfonamide Formation

The following procedure is used for preparation of certain sulfonamides of the present invention, i.e., where X of Formulas (I) to (VI) is —S(O)$_2$—.

Weigh 0.125 mmol of tetrafluorophenol resin (PL-TFP 009) into fritted polypropylene syringe tubes. Add 1 mL DMF to swell the resin. Add 0.250 mmol of an appropriate sulfonyl chloride and 0.500 mmol of N,N'diisopropylethylamine. Cap and shake on a platform shaker overnight at room temperature. Using a luer lock vacuum box, aspirate reaction liquor and wash three times each with DMF and TIF, and alternate DCM and methanol washes (three times), and follow with one DCM and two DMF washes. Add 1 mL DMF and 0.075 mmol of one of the amine intermediate selected from Intermediates 3 to 8 or 11 to 16 to the sulfone-loaded resin. Cap and shake on a platform shaker overnight at 50° C. Collect the reaction liquor, rinse twice with DCM, collecting both rinses. Add 1% triethylamine (TEA) in DCM, cap and shake approx. 1 hour at room temperature on a platform shaker. Collect this wash and add to the original collection. Dry in a Genevac centrifugal evaporator.

Scheme 17:
General Sulfonification Formation

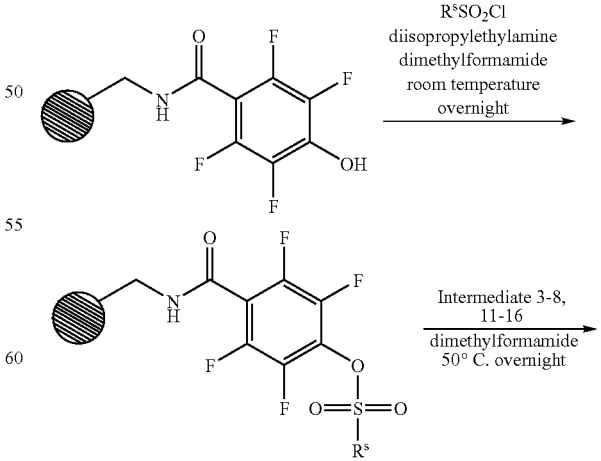

-continued

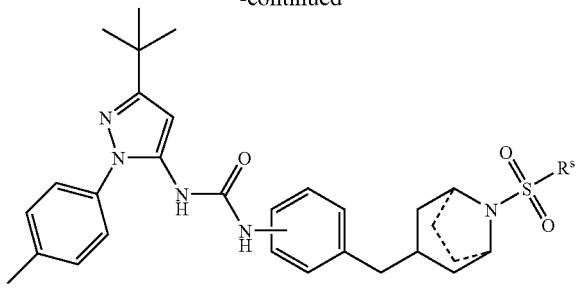

Appropriate sulfonyl chlorides, i.e. R$^s$SO$_2$Cl, which are used for the procedure of Example 8, to prepare compounds of the invention include:
Thiophene-3-sulfonyl chloride;
Benzo[1,2,5]thiadiazole-5-sulfonyl chloride;
5-Methyl-isoxazole-4-sulfonyl chloride;
5-Oxazol-5-yl-thiophene-2-sulfonyl chloride;
6-Morpholin-4-yl-pyridine-3-sulfonyl chloride;
4-Methyl-3,4-dihydro-2H-benzo[1,4]oxazine-7-sulfonyl chloride;
2,3-Dihydro-benzofuran-5-sulfonyl chloride;
2,3-Dihydro-benzo[1,4]dioxine-6-sulfonyl chloride;
5-Isoxazol-5-yl-furan-2-sulfonyl chloride;
5-Isoxazol-5-yl-thiophene-2-sulfonyl chloride;
1,3,5-Trimethyl-1H-pyrazole-4-sulfonyl chloride;
5-Chlorosulfonyl-1-methyl-1H-pyrrole-2-carboxylic acid methyl ester;
5-Chlorosulfonyl-furan-2-carboxylic acid methyl ester;
4-Chlorosulfonyl-2,5-dimethyl-furan-3-carboxylic acid methyl ester;
3-Fluoro-4-methoxy-benzenesulfonyl chloride;
2-Oxo-2H-chromene-6-sulfonyl chloride;
4'-Methoxy-biphenyl-3-sulfonyl chloride;
3-Methoxy-benzenesulfonyl chloride;
1,2-Dimethyl-1H-imidazole-4-sulfonyl chloride;
5-(2-Methyl-thiazol-4-yl)-thiophene-2-sulfonyl chloride;
5-[1,2,3]Thiadiazol-4-yl-thiophene-2-sulfonyl chloride;
6-Methyl-2,4-dioxo-1,2,3,4-tetrahydro-pyrimidine-5-sulfonyl chloride;
Isoquinoline-5-sulfonyl chloride;
4-Methoxy-2,6-dimethyl-benzenesulfonyl chloride;
5-Chlorosulfonyl-4-methoxy-thiophene-3-carboxylic acid methyl ester;
3,4-Difluoro-benzenesulfonyl chloride;
4-Vinyl-benzenesulfonyl chloride;
5-Isoxazol-3-yl-thiophene-2-sulfonyl chloride;
Benzo[1,2,5]oxadiazole-4-sulfonyl chloride;
1-Methyl-1H-imidazole-4-sulfonyl chloride;
Benzo[1,2,5]thiadiazole-4-sulfonyl chloride;
2,2,5,7,8-Pentamethyl-chroman-6-sulfonyl chloride;
2-Chloro-4-fluoro-benzenesulfonyl chloride;
2,4-Dichloro-benzenesulfonyl chloride;
3,5-Dimethyl-isoxazole-4-sulfonyl chloride;
3,4-Dimethoxy-benzenesulfonyl chloride;
2-Chloro-benzenesulfonyl chloride;
4-Chloro-2,5-dimethyl-benzenesulfonyl chloride;
4-Trifluoromethoxy-benzenesulfonyl chloride;
3-Fluoro-benzenesulfonyl chloride;
2-Fluoro-benzenesulfonyl chloride;
3-Chloro-4-fluoro-benzenesulfonyl chloride;
3,4-Dichloro-benzenesulfonyl chloride;
2,5-Dimethoxy-benzenesulfonyl chloride;
3-Trifluoromethyl-benzenesulfonyl chloride;
2-Chlorosulfonyl-benzoic acid methyl ester;
Butane-1-sulfonyl chloride;
Ethanesulfonyl chloride;
2-Phenyl-ethenesulfonyl chloride;
Phenyl-methanesulfonyl chloride;
Methanesulfonyl chloride;
4-Methyl-benzenesulfonyl chloride;
4-tert-Butyl-benzenesulfonyl chloride;
4-Methoxy-benzenesulfonyl chloride;
4-Acetylamino-benzenesulfonyl chloride;
4-Chloro-benzenesulfonyl chloride;
4-Fluoro-benzenesulfonyl chloride;
2,4,6-Trimethyl-benzenesulfonyl chloride;
2,5-Dichloro-benzenesulfonyl chloride;
Benzenesulfonyl chloride;
Quinoline-8-sulfonyl chloride;
Thiophene-2-sulfonyl chloride;
Naphthalene-2-sulfonyl chloride;
5-Dimethylamino-naphthalene-1-sulfonyl chloride;
Naphthalene-1-sulfonyl chloride; and
2-Trifluoromethoxy-benzenesulfonyl chloride.

EXAMPLE 9

Urea Formation

The following procedure is used for preparation of certain ureas of the present invention, i.e., where X of Formulas (I) to (VI) is —NHC(O)—.

Weigh 0.112 mmol of one of the amine intermediates selected from Internediate 3 to 8 or 11 to 16 starting material into fritted teflon Argonaut Quest tubes. Dissolve in 5 mL in chloroform and treat with 1.20 eq of an appropriate isocyanate (0.135 mmol). Agitate overnight at room temperature under a nitrogen atmosphere. Add 1.25 eq. of polymer-bound trisamine (0.140 mmol) and agitate at room temperature 5 hours. Collect the reaction liquor, rinse with 5 mL of dichloromethane, collecting both in the same vial. Dry in a Genevac centrifugal evaporator.

Scheme 18:
General Urea Formation

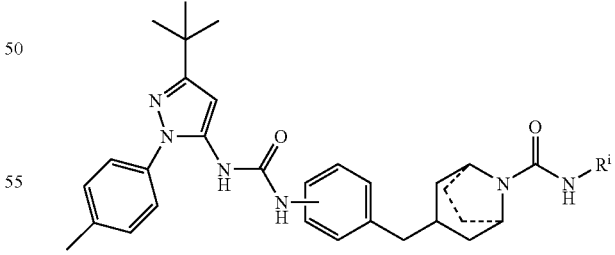

Appropriate isocyanates, i.e. R$^i$NCO, which are used in the procedure of Example 9, to prepare compounds of the invention include:
2-(5-Isocyanato-4-methyl-thiazol-2-yl)-pyrazine;
4-Isocyanato-2-phenyl-thiazole;
4-Isocyanato-5-methyl-1-phenyl-1H-pyrazole;
3-Isocyanato-2-methyl-5-phenyl-furan;
4-Isocyanato-benzo[1,2,5]thiadiazole;

3-Isocyanato-thiophene;
6-Fluoro-8-isocyanato-4H-benzo[1,3]dioxine;
5-Isocyanato-2,3-dihydro-benzofuran;
3-Isocyanato-5-methyl-2-trifluoromethyl-furan;
6-Isocyanato-2,3-dihydro-benzo[1,4]dioxine;
4-Isocyanato-5-methyl-3-phenyl-isoxazole;
2-Chloro-4-isocyanato-1-methoxy-benzene;
5-Isocyanato-benzo[1,3]dioxole;
4-Isocyanato-benzoic acid methyl ester;
4-Isocyanato-1,2-dimethoxy-benzene;
3-Isocyanato-pyridine;
1-Difluoromethoxy-4-isocyanato-benzene;
(4-Isocyanato-phenyl)-dimethyl-amine;
4-Isocyanato-3,5dimethyl-isoxazole;
1-Isocyanato-4-trifluoromethoxy-benzene;
1-(4-Isocyanato-phenyl)-ethanone;
3-Isocyanato-benzoic acid ethyl ester;
1-Isocyanato-3,5-dimethoxy-benzene;
5-Isocyanato-1,2,3-trimethoxy-benzene;
1-Chloro-5-isocyanato-2,4-dimethoxy-benzene;
1-Isocyanato-4-methoxy-2-methyl-benzene;
2-Isocyanato-1,4-dimethoxy-benzene; and
1-Isocyanato-2,4-dimethoxy-benzene.

EXAMPLE 10

Ketone Formation

The following procedure is used for preparation of certain ketones of the present invention, i.e., where X of Formulas (I) to (VI) is —C(O)CH$_2$—.

Weigh 0.112 mmol of one of the amine intermediate selected from Intermediate 3 to 8 or 11 to 16 starting material into fritted teflon Argonaut Quest tubes. Dissolve in 5 mL in chloroform and add 1.20 eq. of polymer-bound diisopropylamine (0.135 mmol). Treat with 1.00 eq of an appropriate alpha-halocarbonyl compound (0.112 mmol) and agitate overnight at 50° C. under a nitrogen atmosphere. Add 1.25 eq. of polymer-bound trisamine(0.140 mmol) and agitate at room temperature 5 hours. Collect the reaction liquor, rinse with 5 mL of dichloromethane, collecting both in the same vial. Dry in a Genevac centrifugal evaporator.

Scheme 19:
General Ketone Formation

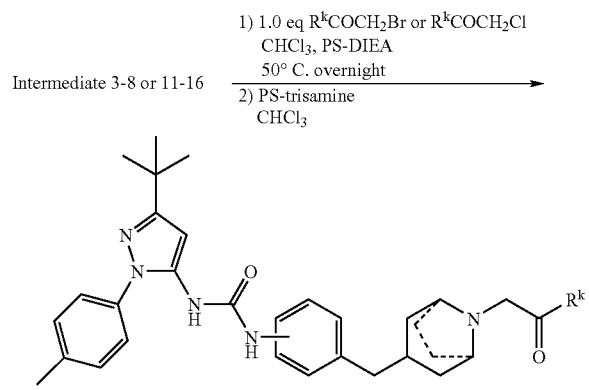

Intermediate 3-8 or 11-16
1) 1.0 eq R$^k$COCH$_2$Br or R$^k$COCH$_2$Cl
CHCl$_3$, PS-DIEA
50° C. overnight
2) PS-trisamine
CHCl$_3$ Appropriate alpha-halocarbonyl compounds, i.e. R$^k$COCH$_2$Br or R$^k$COCH$_2$Cl, which are used in the procedure of Example 10, to prepare compounds of the present invention include:

2-Bromo-1-(5-methyl-1-phenyl-1H-pyrazol-4-yl)-ethanone;
2-Bromo-1-pyridin-4-yl-ethanone hydrobromide;
2-Bromo-1-(5-pyridin-2-yl-thiophen-2-yl)-ethanone;
2-Bromo-6-methoxy-indan-1-one;
1-Benzo[1,3]dioxol-5-yl-2-bromo-ethanone;
1-(5-tert-Butyl-isoxazol-3-yl)-2-chloro-ethanone;
2-Bromo-1-(4-pyrrolidin-1-yl-phenyl)-ethanone;
2-Bromo-1-(4-methoxy-phenyl)-propan-1-one;
2-Bromo-1-(4-methanesulfonyl-phenyl)-ethanone;
2-Bromo-1-(6-dimethylamino-naphthalen-2-yl)-ethanone;
3-(2-Bromo-acetyl)-7-diethylamino-chromen-2-one;
1-Benzo[b]thiophen-3-yl-2-bromo-ethanone;
2-Bromo-1-(5-methyl-3-phenyl-isoxazol-4-yl)-ethanone;
2-Bromo-1-(3-phenyl-isoxazol-5-yl)-ethanone;
5-(2-Bromo-acetyl)-isoxazole-3-carboxylic acid ethyl ester;
6-(2-Bromo-acetyl)-3,4-dihydro-1H-quinolin-2-one;
5-Bromo-6,7-dihydro-5H-benzo[1,2,5]oxadiazol-4-one;
2-Bromo-1-(4-diethylamino-phenyl)-ethanone;
N-[4-(2-Chloro-acetyl)-phenyl]-methanesulfonamide;
2-Bromo-1-(2,3-dihydro-benzo[1,4]dioxin-6-yl)-ethanone;
2-Bromo-1-dibenzofuran-2-yl-ethanone;
2-Bromo-7-methoxy-3,4-dihydro-2H-naphthalen-1-one;
1-Benzo[b]thiophen-3-yl-2-chloro-ethanone;
2-Bromo-1-(4-trifluoromethoxy-phenyl)-ethanone;
2-Bromo-1-(4-difluoromethoxy-phenyl)-ethanone;
2-Bromo-1-pyridin-3-yl-ethanone hydrobromide;
4-(2-Chloro-acetyl)-1,5-dimethyl-2-phenyl-1,2-dihydro-pyrazol-3-one;
2-Bromo-1-(4-methoxy-phenyl)-ethanone;
2-Bromo-1-(3-methoxy-phenyl)-ethanone;
2-Bromo-1-(2,5-dimethoxy-phenyl)-ethanone; and
2-Bromo-1-(2,4-dimethoxy-phenyl)-ethanone.

EXAMPLE 11

Carbamate Formation

Method A

The following procedure is used for preparation of certain carbamates of the present invention, i.e., where X of Formulas (I) to (VI) is —C(O)—, and A is such that there is an oxygen attached directly to X.

50 mg of(4-bromomethylphenoxy)methyl polystyrene (Novabiochem, 01-64-0186, 1.10 mmol/g) is swelled in 2.5 mL of dimethylformamide and treated with 5.0 equivalents of diisopropylethylamine (48 µL), followed by 1.0 equivalent of amine Intermediate 3 to 8 or 11 to 16. Agitate at room temperature overnight, drain the vessel and wash the resin with DMF (three times), MeOH (twice), and DCM (three times). Swell the resin in 2.5 mL of dichloromethane and treat with 0.9 equivalents of an appropriate chloroformate. Agitate at room temperature overnight, add 1.0 equivalent of tris-(2-aminoethyl) amine polystyrene (Novabiochem, 01-64-0170, 3.40 mmol/g) and agitate at room temperature four hours. Drain the vessel into a vial and evaporate to dryness.

Scheme 20:
General Carbamate Formation, Method A

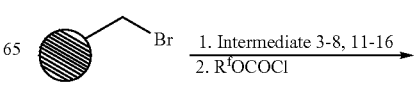

1. Intermediate 3-8, 11-16
2. R$^l$OCOCl

-continued

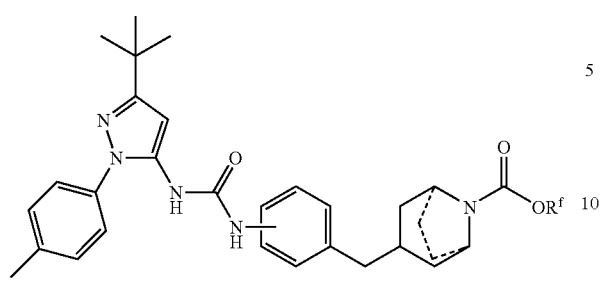

Method B

Weigh 0.104 mmol of one of the amine intermediates selected from Intermediate 3 or 4 starting material into scintillation vials. Dissolve in 5 mL in dichloromethane and 3.50 eq of N,N'-diisopropylethylamine(3.64 mmol). Treat with 1.00 eq of chloroformate(0.104 mmol) and shake overnight at room temperature. Pour the vial contents onto SPE cartridges containing 2 g of silica. Place the SPE cartridges on an Isco CombiFlash OptiX10 fitted with 4 g silica columns and elute with a 10-100% ethyl acetate-heptane linear gradient. The appropriate fractions were dried in a Savant centrifugal evaporator.

Scheme 21:
General Carbamate Formation, Method B

Intermediate 3 or 4  $\xrightarrow{\text{R}^f\text{OCOCl}}_{\text{DIEA, RT, CH}_2\text{Cl}_2}$

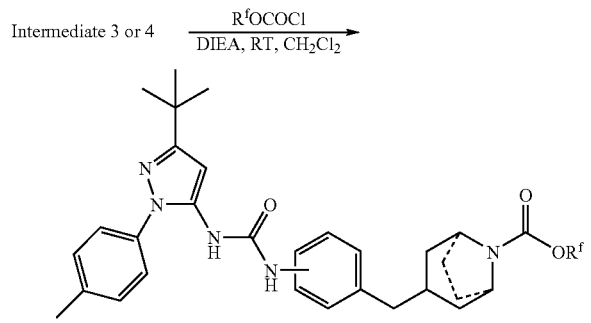

Appropriate chloroformates, i.e. R$^f$OCOCl, which are used in the procedure of Example 11, METHOD A or METHOD B, to prepare compounds of the invention include:
Ethyl chloroformate
Isobutyl chloroformate
Menthyl chloroformate
Benzyl chloroformate
Phenyl chloroformate
4-methylphenyl chloroformate
4-methoxyphenyl chloroformate
2-methoxyphenyl chloroformate*
4-methoxycarbonylphenyl chloroformate
1,1-dioxobenzo[b]thiophene-2-methyl chloroformate

EXAMPLE 12

1-(5-tertiary-Butyl-2-p-tolyl-2H-pyrazol-3-yl)-3{4-[1-(1-oxo-pyridine-3-carbonyl)-piperidine-4-ylmethyl]-phenyl}-urea, Compound A1645

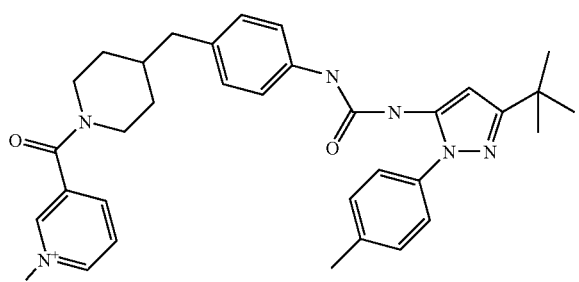

A mixture of intermediate 4 (200 mg, 0.39 mmol) nicotinic acid N-oxide (64 mg, 0.46 mmol), TEA (1.84 mmol, 256 uL) and EDCI (88 mg, 0.46 mmol) in DCM was stirred at room temperature overnight. The reaction mixture was loaded onto a silica gel column (10 g) and was eluted initially with ethyl acetate, then with a mixture of ethyl acetate and methanol (80/20, v/v) and then with a mixture of ethyl acetate and methanol (70/30, v/v) containing 1% ammonium hydroxide to give 62 mg of 1-(5-tert-Butyl-2-p-tolyl-2H-pyrazol-3-yl)-3-{4-[1-(1-oxy-pyridine-3-carbonyl)-piperidin-4-ylmethyl]-phenyl}-urea, Compound A1645, as a beige solid.

The following compounds are prepared by methods and procedures substantially similar to those as described in the Examples hereinabove, or by methods and procedures known to those skilled in the art. The compounds of the Examples described hereinabove, and the following compounds are particularly preferred embodiments of the present invention.

In the following list of compounds, the data is arranged as follows: compound name (amount synthesized), molecular formula, calculated molecular weight, observed molecular ion, observed molecular ion type, and High Performance Liquid Chromatography (HPLC) retention time in minutes.

The data are collected using a mass spectrometer liquid chromatograph using a Micromass LCT Time-of-Flight detector, scanning M/Z of 100-1000, using electrospray ionization (ESI$^+$), with a Hewlett-Packard Series 1100 HPLC and Sedex 75 evaporative light scattering detector (ELSD) at a wavelength of 220 nM. HPLC conditions are use of a Synergi 2 μm Hydro-RP 20×4.0 mm column using elution solvents of 0.1% formic acid in water (solvent A) and 0.1% formic acid in acetonitrile (solvent B), running a gradient of 30%-90% Solvent B in Solvent A over 3 minutes, then 90%-100% B over the next two minutes.

1-(5-tert-Butyl-2-p-tolyl-2H-pyrazol-3-yl)-3-(3-{1-[2-(2,4-dimethoxy-phenyl)-acetyl]-piperidin-4-ylmethyl}-phenyl)-urea (0.0215 g), C37H45N5O4, 623.80, 624.37, M+H, 4.07, Compound A1;
1-(5-tert-Butyl-2-p-tolyl-2H-pyrazol-3-yl)-3-{3-[1-((R)-5-oxo-tetrahydro-furan-2-carbonyl) -piperidin-4-ylmethyl]-phenyl}-urea (0.004 g), C32H39N5O4, 557.70, 558.32, M+H, 3.23, Compound A2;
1-(5-tert-Butyl-2-p-tolyl-2H-pyrazol-3-yl)-3-{3-[1-((R)-2-methoxy-2-phenyl-acetyl)-piperidin -4-ylmethyl]-phenyl}-urea (0.0036 g), C36H43N5O3, 593.77, 594.35, M+H, 3.95, Compound A3;

1-(5-tert-Butyl-2-p-tolyl-2H-pyrazol-3-yl)-3-{3-[1-((S)-2-methoxy-2-phenyl-acetyl)-piperidin-4-ylmethyl]-phenyl}-urea (0.0205g), C36H43N5O3, 593.77, 594.37, M+H, 4.15, Compound A4;

1-(5-tert-Butyl-2-p-tolyl-2H-pyrazol-3-yl)-3-{3-[1-(1,2,3,4-tetrahydro-naphthalene-2-carbonyl}-piperidin-4-ylmethyl]-phenyl}-urea (0.0184 g), C38H45N5O2, 603.81, 604.39, M+H, 4.77, Compound A5;

1-(5-tert-Butyl-2-p-tolyl-2H-pyrazol-3-yl)-3-{3-[1-([1,2,3]thiadiazole-4-carbonyl)-piperidin-4-ylmethyl]-phenyl}-urea (0.0178 g), C30H35N7O2S, 557.72, 558.28, M+H, 3.78, Compound A6;

1-(5-tert-Butyl-2-p-tolyl-2H-pyrazol-3-yl)-3-{3-[1-([1,6]naphthyridine-2-carbonyl)-piperidin-4-ylmethyl]-phenyl}-urea (0.0075 g), C36H39N7O2, 601.75, 602.35, M+H, 3.42, Compound A7;

1-(5-tert-Butyl-2-p-tolyl-2H-pyrazol-3-yl)-3-{3-[1-([1,8]naphthyridine-2-carbonyl)-piperidin-4-ylmethyl]-phenyl}-urea (0.0216 g), C36H39N7O2, 601.75, 602.35, M+H, 3.27, Compound A8;

1-(5-tert-Butyl-2-p-tolyl-2H-pyrazol-3-yl)-3-{3-[1-(3-thioureido-benzoyl)-piperidin-4-ylmethyl]-phenyl}-urea, C35H41N7O2S, 623.82, 624.35, M+H, 3.15, Compound A9;

1-(5-tert-Butyl-2-p-tolyl-2H-pyrazol-3-yl)-3-(3-{1-[1-(4-methoxy-phenyl)-cyclopropanecarbonyl]-piperidin-4-ylmethyl}-phenyl)-urea (0.0182 g), C38H45N5O3, 619.81, 620.38, M+H, 4.43, Compound A10;

1-(3-{1-[1-(5-Bromo-pyrimidin-2-yl)-piperidine-3-carbonyl]-piperidin-4-ylmethyl}-phenyl)-3-(5-tert-butyl-2-p-tolyl-2H-pyrazol-3-yl)-urea (0.0212 g), C37H45Br1N8O2, 712.28, 713.35, M+H, 3.57, Compound A11;

1-(3-{1-[1-(5-Bromo-pyrimidin-2-yl)-piperidine-4-carbonyl]-piperidin-4-ylmethyl}-phenyl)-3-(5-tert-butyl-2-p-tolyl-2H-pyrazol-3-yl)-urea (0.0074 g), C37H45Br1N8O2, 712.28, 713.31, M+H, 4.62, Compound A12;

1-(5-tert-Butyl-2-p-tolyl-2H-pyrazol-3-yl)-3-{3-[1-(isoquinoline-1-carbonyl)-piperidin-4-ylmethyl]-phenyl}-urea (0.0125 g), C37H40N6O2, 600.77, 601.32, M+H, 3.83, Compound A13;

1-(5-tert-Butyl-2-p-tolyl-2H-pyrazol-3-yl)-3-{3-[1-(1-methyl-cyclohexanecarbonyl)-piperidin-4-ylmethyl]-phenyl}-urea (0.001 g), C35H47N5O2, 569.79, 570.39, M+H, 4.80, Compound A14;

1-(5-tert-Butyl-2-p-tolyl-2H-pyrazol-3-yl)-3-(3-{1-[2-(1-methyl-1H-indol-3-yl)-acetyl]-piperidin-4-ylmethyl}-phenyl)-urea (0.0227 g), C38H44N6O2, 616.81, 617.34, M+H, 4.28, Compound A15;

1-(5-tert-Butyl-2-p-tolyl-2H-pyrazol-3-yl)-3-{3-[1-(1-methyl-cyclopropanecarbonyl)-piperidin-4-ylmethyl]-phenyl}-urea (0.0126 g), C32H41N5O2, 527.71, 528.35, M+H, 4.05, Compound A16;

1-(5-tert-Butyl-2-p-tolyl-2H-pyrazol-3-yl)-3-{3-[1-(2-naphthalen-1-yl-acetyl)-piperidin-4-ylmethyl]-phenyl}-urea (0.0108 g), C39H43N5O2, 613.81, 614.37, M+H, 4.40, Compound A17;

1-(5-tert-Butyl-2-p-tolyl-2H-pyrazol-3-yl)-3-{3-[1-(1-phenyl-cyclopentanecarbonyl)-piperidin-4-ylmethyl]-phenyl}-urea (0.0098 g), C39H47N5O2, 617.84, 618.43, M+H, 3.47, Compound A18;

1-(5-tert-Butyl-2-p-tolyl-2H-pyrazol-3-yl)-3-{3-[1-(2,2-difluoro-benzo[1,3]dioxole-5-carbonyl)-piperidin-4-ylmethyl]-phenyl}-urea (0.0196 g), C35H37F2N5O4, 629.71, 630.30, M+H, 4.30, Compound A19;

1-(5-tert-Butyl-2-p-tolyl-2H-pyrazol-3-yl)-3-{3-[1-(2,2-dimethyl-pentanoyl)-piperidin-4-ylmethyl]-phenyl}-urea, C34H47N5O2, 557.78, 558.38, M+H, 4.67, Compound A20;

1-(5-tert-Butyl-2-p-tolyl-2H-pyrazol-3-yl)-3-{3-[1-(2,3-dimethoxy-benzoyl)piperidin-4-ylmethyl]-phenyl}-urea (0.0144 g), C36H43N5O4, 609.77, 610.35, M+H, 4.08, Compound A21;

1-(5-tert-Butyl-2-p-tolyl-2H-pyrazol-3-yl)-3-(3-{1-[2-(2,3-dimethoxy-phenyl)-acetyl]-piperidin-4-ylmethyl}-phenyl)-urea (0.0231 g), C37H45N5O4, 623.80, 624.37, M+H, 4.25, Compound A22;

1-(5-tert-Butyl-2-p-tolyl-2H-pyrazol-3-yl)-3-(3-{1-[2-(2,3-dimethyl-phenoxy)-acetyl]-piperidin-4-ylmethyl}-phenyl)-urea (0.0227 g), C37H45N5O3, 607.80, 608.37, M+H, 4.72, Compound A23;

1-(5-tert-Butyl-2-p-tolyl-2H-pyrazol-3-yl)-3-{3-[1-(2,4,6-trimethoxy-benzoyl)-piperidin-4-ylmethyl]-phenyl}-urea (0.0067 g), C37H45N5O5, 639.80, 640.36, M+H, 4.02, Compound A24;

1-(5-tert-Butyl-2-p-tolyl-2H-pyrazol-3-yl)-3-{3-[1-(2,4,6-trimethyl-benzoyl)-piperidin-4-ylmethyl]-phenyl}-urea (0.0043 g), C37H45N5O2, 591.80, 592.37, M+H, 4.65, Compound A25;

1-(5-tert-Butyl-2-p-tolyl-2H-pyrazol-3-yl)-3-(3-{1-[2-(2,4-difluoro-phenyl)-acetyl]-piperidin-4-ylmethyl}-phenyl)-urea (0.0113 g), C35H39F2N5O2, 599.73, 600.32, M+H, 4.37, Compound A26;

1-(5-tert-Butyl-2-p-tolyl-2H-pyrazol-3-yl)-3-{3-[1-(2,4-dimethoxy-benzoyl)-piperidin-4-ylmethyl]-phenyl}-urea, C36H43N5O4 (0.165 g), 609.77, 610.35, M+H, 4.10, Compound A27;

1-(5-tert-Butyl-2-p-tolyl-2H-pyrazol-3-yl)-3-{3-[1-(2,4-dimethyl-thiazole-5-carbonyl)-piperidin-4-ylmethyl]-phenyl}-urea (0.0138 g), C33H40N6O2S, 584.79, 585.31, M+H, 3.90, Compound A28;

1-(5-tert-Butyl-2-p-tolyl-2H-pyrazol-3-yl)-3-{3-[1-(2,5-dimethyl-furan-3-carbonyl)-piperidin-4-ylmethyl]-phenyl}-urea (0.0158 g), C34H41N5O3, 567.73, 568.34, M+H, 4.08, Compound A29;

4-(4-{3-[3-(5-tert-Butyl-2-p-tolyl-2H-pyrazol-3-yl)-ureido]-benzyl}-piperidine-1-carbonyl)-2,5-dimethyl-furan-3-sulfonic acid (thiophen-2-ylmethyl)-amide (0.0218 g), C39H46N6O5S2, 742.96, 743.32, M+H, 4.7, Compound A30;

1-(5-tert-Butyl-2-p-tolyl-2H-pyrazol-3-yl)-3-{3-[1-(2,6-dimethoxy-pyridine-3-carbonyl)-piperidin-4-ylmethyl]-phenyl}-urea (0.0204 g), C35H42N6O4, 610.76, 611.34, M+H, 4.32, Compound A31;

1-(5-tert-Butyl-2-p-tolyl-2H-pyrazol-3-yl)-3-{3-[1-(2-pyridin-3-yl-thiazole-4-carbonyl)-piperidin-4-ylmethyl]-phenyl}-urea (0.0018 g), C36H39N7O2S, 633.82, 634.31, M+H, 3.88, Compound A32;

1-(5-tert-Butyl-2-p-tolyl-2H-pyrazol-3-yl)-3-(3-{1-[2-(4,6-dimethoxy-pyrimidin-2-yloxy)-benzoyl]-piperidin-4-ylmethyl}-phenyl)-urea (0.0246 g), C40H45N7O5, 703.84, 704.36, M+H, 4.47, Compound A33;

1-(5-tert-Butyl-2-p-tolyl-2H-pyrazol-3-yl)-3-{3-[1-(2-pyridin-4-yl-thiazole-4-carbonyl)-piperidin-4-ylmethyl]-phenyl}-urea (0.0149 g), C36H39N7O2S, 633.82, 634.3 1, M+H, 3.68, Compound A34;

1-(5-tert-Butyl-2-p-tolyl-2H-pyrazol-3-yl)-3-(3-{1-[2-(5-chloro-3-methyl-benzo[b]thiophen-2-yl)-acetyl]-piperidin-4-ylmethyl}-phenyl)-urea, C38H42ClN5O2S, 667.27, 668.39, M+H, 3.90, Compound A35;

1-(5-tert-Butyl-2-p-tolyl-2H-pyrazol-3-yl)-3-(3-{1-[2-(6-methoxy-benzofuran-3-yl)-acetyl]-piperidin-4-ylmethyl}-phenyl)-urea (0.0203 g), C38H43N5O4, 633.79, 634.34, M+H, 4.28, Compound A36;

1-(5-tert-Butyl-2-p-tolyl-2H-pyrazol-3-yl)-3-{3-[1-(2-trifluoromethyl-[1,6]naphthyridine-3-carbonyl)-piperidin-4-ylmethyl]-phenyl}-urea (0.0091 g), C37H38F3N7O2, 669.75, 670.30, M+H, 3.92, Compound A37;

1-(5-tert-Butyl-2-p-tolyl-2H-pyrazol-3-yl)-3-{3-[1-(2-trifluoromethyl-[1,8]naphthyridine-3-carbonyl)-piperidin-4-ylmethyl]-phenyl}-urea (0.018 g), C37H38F3N7O2, 669.75, 670.32, M+H, 3.82, Compound 38;

1-{3-[1(2-Amino-pyridine-3-carbonyl)-piperidin-4-ylmethyl]-phenyl}-3-(5-tert-butyl-2-p-tolyl-2H-pyrazol-3-yl)-urea (0.0106 g), C33H39N7O2, 565.72, 566.33, M+H, 2.18, Compound A39;

1-(5-tert-Butyl-2-p-tolyl-2H-pyrazol-3-yl)-3-{3-[1-(2-chloro-4-methanesulfonyl-benzoyl)-piperidin-4-ylmethyl]-phenyl}-urea (0.0234 g), C35H40ClN5O4S, 661.25, 662.22, M+H, 3.68, Compound A40;

1-(5-tert-Butyl-2-p-tolyl-2H-pyrazol-3-yl)-3-{3-[1-(2-chloro-6-methoxy-pyridine-4-carbonyl)-piperidin-4-ylmethyl]-phenyl}-urea (0.0193 g), C34H39ClN6O3, 615.18, 615.28, M+H, 4.45, Compound A41;

1-(5-tert-Butyl-2-p-tolyl-2H-pyrazol-3-yl)-3-{3-[1-(2-chloro-pyridine-3-carbonyl)-piperidin-4-ylmethyl]-phenyl}-urea (0.0155 g), C33H37ClN6O2, 584.27, 585.27, M+H, 3.78, Compound A42;

1-(5-tert-Butyl-2-p-tolyl-2H-pyrazol-3-yl)-3-(3-{1-[2-(2-fluoro-phenyl)-acetyl]-piperidin-4-ylmethyl}-phenyl)-urea (0.0118 g), C35H40FN5O2, 581.74, 582.32, M+H, 4.30, Compound A43;

1-(5-tert-Butyl-2-p-tolyl-2H-pyrazol-3-yl)-3-{3-[1(2-furan-2-yl-2-oxo-acetyl)-piperidin-4-ylmethyl]-phenyl}-urea, C33H37N5O4, 567.69, 568.30, M+H, 3.68, Compound A44;

1-(5-tert-Butyl-2-p-tolyl-2H-pyrazol-3-yl)-3-{3-[1-(furan-2-carbonyl)-piperidin-4-ylmethyl]-phenyl}-urea (0.0139 g), C32H37N5O3, 539.68, 540.30, M+H, 3.73, Compound A45;

1-(5-tert-Butyl-2-p-tolyl-2H-pyrazol-3-yl)-3-[3-(1-hept-2-ynoyl-piperidin-4-ylmethyl)-phenyl]-urea (0.0105 g), C34H43N5O2, 553.75, 554.35, M+H, 4.68, Compound A46;

1-(5-tert-Butyl-2-p-tolyl-2H-pyrazol-3-yl)-3-{3-[1-(2-hydroxy-6-methyl-pyridine-4-carbonyl)-piperidin-4-ylmethyl]-phenyl}-urea (0.0041 g), C34H40N6O3, 580.73, 581.33, M+H, 2.87, Compound A47;

1-(5-tert-Butyl-2-p-tolyl-2H-pyrazol-3-yl)-3-{3-[1-(2-hydroxy-quinoline-4-carbonyl)-piperidin-4-ylmethyl]-phenyl}-urea, C37H40N6O3, 616.77, 617.34, M+H, 3.15, Compound A48;

1-(5-tert-Butyl-2-p-tolyl-2H-pyrazol-3-yl)-3-{3-[1-(2-indan-2-yl-acetyl)-piperidin-4-ylmethyl]-phenyl}-urea (0.0219 g), C38H45N5O2, 603.81, 604.37, M+H, 4.77, Compound A49;

1-(5-tert-Butyl-2-p-tolyl-2H-pyrazol-3-yl)-3-(3-{1-[2-(2-methoxy-phenyl)-acetyl]-piperidin-4-ylmethyl}-phenyl)-urea (0.0132 g), C36H43N5O3, 593.77, 594.35, M+H, 4.08, Compound A50;

1-(5-tert-Butyl-2-p-tolyl-2H-pyrazol-3-yl)-3-{3-[1-(2-methyl-[1,6]naphthyridine-3-carbonyl)-piperidin-4-ylmethyl]-phenyl}-urea (0.0186 g), C37H41N7O2, 615.78, 616.36, M+H, 3.37, Compound A51;

1-(5-tert-Butyl-2-p-tolyl-2H-pyrazol-3-yl)-3-{3-[1-(2-methyl-furan-3-carbonyl)-piperidin-4-ylmethyl]-phenyl}-urea (0.0144 g), C33H39N5O3, 553.71, 554.31, M+H, 4.05, Compound A52;

1-(5-tert-Butyl-2-p-tolyl-2H-pyrazol-3-yl)-3-(3-{1-[2-(2-methyl-1H-indol-3-yl)- -acetyl]-piperidin-4-ylmethyl}-phenyl)-urea (0.0095 g), C38H44N6O2, 616.81, 617.37, M+H, 4.15, Compound A53;

1-(5-tert-Butyl-2-p-tolyl-2H-pyrazol-3-yl)-3-(3-{1-[2-methyl-5-(piperidine-1-sulfonyl)- -furan-3-carbonyl]-piperidin-4-ylmethyl}-phenyl)-urea (0.0229 g) (0.0141 g), C38H48N6O5S, 700.90, 701.36, M+H, 4.43, Compound A54;

1-(5-tert-Butyl-2-p-tolyl-2H-pyrazol-3-yl)-3-{3-[1-(2-methyl-5-trifluoromethyl-oxazole-4-carbonyl)-piperidin-4-ylmethyl]-phenyl}-urea (0.0141 g), C33H37F3N6O3, 622.69, 623.30, M+H, 4.20, Compound A55;

1-(5-tert-Butyl-2-p-tolyl-2H-pyrazol-3-yl)-3-{3-[1-(2-methyl-5-phenyl-furan-3-carbonyl) -piperidin-4-ylmethyl]-phenyl}-urea (0.0184 g), C39H43N5O3, 629.81, 630.35, M+H, 4.93, Compound A56;

1-(5-tert-Butyl-2-p-tolyl-2H-pyrazol-3-yl)-3-{3-[1-(2-methyl-[1,8]naphthyridine-3-carbonyl)-piperidin-4-ylmethyl]-phenyl}-urea (0.0136 g), C37H41N7O2, 615.78, 616.35, M+H, 3.15, Compound A57;

1-(5-tert-Butyl-2-p-tolyl-2H-pyrazol-3-yl)-3-{3-[1-(2-methyl-imidazo[1,2-a]pyridine-3-carbonyl)-piperidin-4-ylmethyl]-phenyl}-urea (0.0089 g), C36H41N7O2, 603.77, 604.36, M+H, 2.65, Compound A58;

1-(5-tert-Butyl-2-p-tolyl-2H-pyrazol-3-yl)-3-{3-[1-(2-methyl-pyridine-3-carbonyl)-piperidin-4-ylmethyl]-phenyl}-urea (0.0127 g), C34H40N6O2, 564.73, 565.34, M+H, 2.78, Compound A59;

1-(5-tert-Butyl-2-p-tolyl-2H-pyrazol-3-yl)-3-{3-[1-(2-naphthalen-2-yl-acetyl)-piperidin-4-ylmethyl]-phenyl}-urea, C39H43N5O2, 613.81, 614.36, M+H, 4.42, Compound A60;

1-(5-tert-Butyl-2-p-tolyl-2H-pyrazol-3-yl)-3-{3-[1-(2-phenyl-5-trifluoromethyl-oxazole-4-carbonyl)-piperidin-4-ylmethyl]-phenyl}-urea, C38H39F3N6O3, 684.76, 685.31, M+H, 4.67, Compound A61;

1-(5-tert-Butyl-2-p-tolyl-2H-pyrazol-3-yl)-3-{3-[1-(4-oxo-2-phenyl-pentanoyl)-piperidin-4-ylmethyl]-phenyl}-urea, C38H45N5O3, 619.81, 620.37, M+H, 4.18, Compound A62;

1-(5-tert-Butyl-2-p-tolyl-2H-pyrazol-3-yl)-3-{3-[1-(2-phenyl-propionyl)-piperidin-4-ylmethyl]-phenyl}-urea, C36H43N5O2, 577.77, 578.36, M+H, 4.25, Compound A63;

1-(5-tert-Butyl-2-p-tolyl-2H-pyrazol-3-yl)-3-{3-[1-(pyrazine-2-carbonyl)-piperidin-4-ylmethyl]-phenyl}-urea (0.0127 g), C32H37N7O2, 551.69, 552.32, M+H, 3.52, Compound A64;

1-(5-tert-Butyl-2-p-tolyl-2H-pyrazol-3-yl)-3-{3-[1-(quinoxaline-2-carbonyl)-piperidin-4-ylmethyl]-phenyl}-urea, C36H39N7O2, 601.75, 602.33, M+H, 4.22, Compound A65;

1-(5-tert-Butyl-2-p-tolyl-2H-pyrazol-3-yl)-3-{3-[1-(tetrahydro-furan-2-carbonyl)-piperidin-4-ylmethyl]-phenyl}-urea (0.0159 g), C32H41N5O3, 543.71, 544.34, M+H, 3.62, Compound A66;

1-(5-tert-Butyl-2-p-tolyl-2H-pyrazol-3-yl)-3-(3-{1-[2-(4,6-dimethoxy-pyrimidin-2-ylsulfanyl)-benzoyl]-piperidin-4-ylmethyl}-phenyl)-urea, C40H45N7O4S, 719.91, 720.35, M+H, 4.67, Compound A67;

1-(5-tert-Butyl-2-p-tolyl-2H-pyrazol-3-yl)3-(3-{1-[2-(3,4-difluoro-phenyl)-acetyl]-piperidin-4-ylmethyl}-phenyl)-urea, C35H39F2N5O2, 599.73, 600.32, M+H, 4.30, Compound A68;

1-(5-tert-Butyl-2-p-tolyl-2H-pyrazol-3-yl)-3-(3-{1-[2-(3,4-dimethoxy-phenyl)-acetyl]-piperidin-4-ylmethyl}-phenyl)-urea (0.0172 g), C37H45N5O4, 623.80, 624.36, M+H, 3.90, Compound A69;

1-{3-[1-(2-Benzo[1,3]dioxol-5-yl-acetyl)-piperidin-4-ylmethyl]-phenyl}-3-(5-tert-butyl-2-p-tolyl-2H-pyrazol-3-yl)-urea (0.0122 g), C36H41N5O4, 607.76, 608.33, M+H, 4.08, Compound A70;

1-{3-[1-(3,5-Bis-trifluoromethyl-benzoyl)-piperidin-4-ylmethyl]-phenyl}-3-(5-tert-butyl-2-p-tolyl-2H-pyrazol-3-yl)-urea, C36H37F6N5O2, 685.72, 686.32, M+H, 3.30, Compound A71;

1-(5-tert-Butyl-2-p-tolyl-2H-pyrazol-3-yl)-3-(3-{1-[2-(3,5-difluoro-phenyl)-acetyl]-piperidin-4-ylmethyl}-phenyl)-urea, C35H39F2N5O2, 599.73, 600.32, M+H, 4.20, Compound A72;

1-(5-tert-Butyl-2-p-tolyl-2H-pyrazol-3-yl)-3-{3-[1-(3,5-dimethoxy-benzoyl)-piperidin-4-ylmethyl]-phenyl}-urea (0.0148 g), C36H43N5O4, 609.77, 610.35, M+H, 4.23, Compound A73;

1-(5-tert-Butyl-2-p-tolyl-2H-pyrazol-3-yl)-3-(3-{1-[2-(3,5-dimethoxy-phenyl)-acetyl]-piperidin-4-ylmethyl}-phenyl)urea, C37H45N5O4, 623.80, 624.37, M+H, 4.20, Compound A74;

1-(5-tert-Butyl-2-p-tolyl-2H-pyrazol-3-yl)3-{3-[1-(3,5-dimethyl-1H-pyrazole-4-carbonyl)- -piperidin-4-ylmethyl]-phenyl}-urea, C33H41N7O2, 567.74, 568.36, M+H, 3.08, Compound A75;

1-(5-tert-Butyl-2-p-tolyl-2H-pyrazol-3-yl)-3-{3-[1-(3,5-dimethyl-isoxazole-4-carbonyl)- -piperidin-4-ylmethyl]-phenyl}-urea, C33H40N6O3, 568.72, 569.33, M+H, 3.78, Compound A76;

1-(5-tert-Butyl-2-p-tolyl-2H-pyrazol-3-yl)-3-(3-{1-[2-(3,5-dimethyl-phenyl)-acetyl]-piperidin-4-ylmethyl}-phenyl)-urea, C37H45N5O2, 591.80, 592.37, M+H, 4.72, Compound A77;

1-(5-tert-Butyl-2-p-tolyl-2H-pyrazol-3-yl)-3-(3-{1-[3-(1,1,2,2-tetrafluoro-ethoxy)-benzoyl]-piperidin-4-ylmethyl}-phenyl)-urea, C36H39F4N5O3, 665.73, 666.32, M+H, 4.45, Compound A78;

1-(5-tert-Butyl-2-p-tolyl-2H-pyrazol-3-yl)-3-(3-{1-[3-(cyano-methyl-methyl)-benzoyl]-piperidin-4-ylmethyl}-phenyl)-urea (0.0179 g), C37H42N6O2, 602.78, 603.35, M+H, 4.07, Compound A79;

1-(5-tert-Butyl-2-p-tolyl-2H-pyrazol-3-yl)-3-(3-{1-[3-(2,2-difluoro-benzo[1,3]dioxol-5-yl)-acryloyl]-piperidin-4-ylmethyl}-phenyl)-urea, C37H39F2N5O4, 655.75, 656.31, M+H, 4.85, Compound A80;

1-(5-tert-Butyl-2-p-tolyl-2H-pyrazol-3-yl)-3-{3-[1-(3-furan-2-yl-propionyl)-piperidin-4-ylmethyl]-phenyl}-urea (0.0193 g), C34H41N5O3, 567.73, 568.34, M+H, 4.22, Compound A81;

1-(5-tert-Butyl-2-p-tolyl-2H-pyrazol-3-yl)-3-(3-{1-[3-(2-methoxy-phenyl)propionyl]-piperidin-4-ylmethyl}-phenyl)-urea (0.0173 g), C37H45N5O3, 607.80, 608.37, M+H, 4.55, Compound A82;

1-(5-tert-Butyl-2-p-tolyl-2H-pyrazol-3-yl)-3-{3-[1-(3-thiophen-2-yl-propionyl)-piperidin-4-ylmethyl]-phenyl}-urea (0.0199 g), C34H41N5O2S, 583.80, 584.32, M+H, 4.42, Compound A83;

1-(5-tert-Butyl-2-p-tolyl-2H-pyrazol-3-yl)-3-(3-{1-[4-(4-fluoro-phenyl)-4-oxo-butyryl]-piperidin-4-ylmethyl}-phenyl)-urea, C37H42FN5O3, 623.77, 624.34, M+H, 4.33, Compound A84;

1-(5-tert-Butyl-2-p-tolyl-2H-pyrazol-3-yl)-3-(3-{1-[3-(4-fluoro-phenyl)-propionyl]-piperidin-4-ylmethyl}-phenyl)-urea, C36H42FN5O2, 595.76, 596.35, M+H, 4.5, Compound A85;

1-(5-tert-Butyl-2-p-tolyl-2H-pyrazol-3-yl)-3-{3-[1-(3-p-tolyl-propionyl)-piperidin-4-ylmethyl]-phenyl}-urea, C37H45N5O2, 591.80, 592.37, M+H, 4.73, Compound A86;

1-(5-tert-Butyl-2-p-tolyl-2H-pyrazol-3-yl)-3-{3-[1-(3-methanesulfonyl-6,7-dihydro-benzo[c]thiophene-1-carbonyl)-piperidin-4-ylmethyl]-phenyl}-urea, C37H43N5O4S2, 685.28, 686.27, M+H, 3.95, Compound A87;

N-[3-(4-{3-[3-(5-tert-Butyl-2-p-tolyl-2H-pyrazol-3-yl)-ureido]-benzyl}-piperidine-1-carbonyl)-phenyl]-acetamide (0.0057 g), C36H42N6O3, 606.33, 607.33, M+H, 3.30, Compound A88;

1-{3-[1-(3-Amino-pyrazine-2-carbonyl)-piperidin-4-ylmethyl]-phenyl}-3-(5-tert-butyl-2-p-tolyl- -2H-pyrazol-3-yl)-urea, C32H38N8O2, 566.31, 567.34, M+H, 3.25, Compound A89;

1-{3-[1-(3-Butoxy-4-methoxy-benzoyl)-piperidin-4-ylmethyl]-phenyl}-3-(5-tert-butyl-2-p-tolyl-2H-pyrazol-3-yl)-urea, C39H49N5O4, 651.38, 652.36, M+H, 4.43, Compound A90;

1-(5-tert-Butyl-2-p-tolyl-2H-pyrazol-3-yl)-3-(3-{1-[2-(3-fluoro-phenyl)-acetyl]-piperidin-4-ylmethyl}-phenyl)-urea, C35H40FN5O2, 581.32, 582.34, M+H, 4.08, Compound A91;

1-(5-tert-Butyl-2-p-tolyl-2H-pyrazol-3-yl)-3-{3-[1-(furan-3-carbonyl)-piperidin-4-ylmethyl]-phenyl}-urea (0.0183 g), C32H37N5O3, 539.29, 540.26, M+H, 3.70, Compound A92;

1-(5-tert-Butyl-2-p-tolyl-2H-pyrazol-3-yl)-3-{3-[1-(3-1H-indol-3-yl-propionyl)- -piperidin-4-ylmethyl]-phenyl}-urea, C38H44N6O2, 616.35, 617.35, M+H, 4.03, Compound A93;

1-(5-tert-Butyl-2-p-tolyl-2H-pyrazol-3-yl)-3-(3-{1-[2-(3-methoxy-phenyl)-acetyl]-piperidin- -4-ylmethyl}-phenyl)-urea, C36H43N5O3, 593.34, 594.31, M+H, 4.07, Compound A94;

1-(5-tert-Butyl-2-p-tolyl-2H-pyrazol-3-yl)-3-{3-[1-(3-methyl-furan-2-carbonyl)-piperidin-4-ylmethyl]-phenyl}-urea (0.0183 g), C33H39N5O3, 553.31, 590.34, M+H, 3.45, Compound A95;

1-(5-tert-Butyl-2-p-tolyl-2H-pyrazol-3-yl)-3-{3-[1-(3-methyl-isoxazole-4-carbonyl)-piperidin- -4-ylmethyl]-phenyl}-urea, C32H38N6O3, 554.30, 555.32, M+H, 3.73, Compound A96;

1-(5-tert-Butyl-2-p-tolyl-2H-pyrazol-3-yl)-3-{3-[1-(3-phenoxy-propionyl)-piperidin-4-ylmethyl]-phenyl}-urea, C36H43N5O3, 593.34, 594.35, M+H, 4.43, Compound A97;

1-(5-tert-Butyl-2-p-tolyl-2H-pyrazol-3-yl)-3-{3-[1-(3-pyridin-3-yl-propionyl)-piperidin-4-ylmethyl]-phenyl}-urea, C35H42N6O2, 578.34, 579.36, M+H, 2.35, Compound A98;

1-(5-tert-Butyl-2-p-tolyl-2H-pyrazol-3-yl)-3-{3-[1-(thiophene-3-carbonyl)-piperidin-4-ylmethyl]-phenyl}-urea (0.0141 g), C32H37N5O2S, 555.27, 556.25, M+H, 3.92, Compound A99;

1-(5-tert-Butyl-2-p-tolyl-2H-pyrazol-3-yl)-3-(3-{1-[3-(4,6-dimethoxy-pyrimidin-2-yloxy)- -benzoyl]-piperidin-4-yl-methyl}-phenyl)-urea, C40H45N7O5, 703.35, 704.33, M+H, 4.32, Compound A100;

1-(5-tert-Butyl-2-p-tolyl-2H-pyrazol-3-yl)-3-{3-[1-(3a,4,5,7a-tetrahydro-benzofuran-6-carbonyl)-piperidin-4-ylmethyl]-phenyl}-urea, C36H41N5O3, 591.76, 592.30, M+H, 4.20, Compound A101;

1-(5-tert-Butyl-2-p-tolyl-2H-pyrazol-3-yl)-3-{3-[1-(4,5-dihydro-benzo[b]thiophene-6-carbonyl)-piperidin-4-ylmethyl]-phenyl}-urea (0.0158 g), C36H41N5O2S, 607.30, 608.28, M+H, 4.38, Compound A102;

1-(5-tert-Butyl-2-p-tolyl-2H-pyrazol-3-yl)-3-{3-[1-(4,5-dimethyl-furan-2-carbonyl)-piperidin- -4-ylmethyl]-phenyl}-urea, C34H41N5O3, 567.32, 568.34, M+H, 4.26, Compound A103;

1-(5-tert-Butyl-2-p-tolyl-2H-pyrazol-3-yl)3-(3-{1-[4-(1,1,2,2-tetrafluoro-ethoxy)-benzoyl]-piperidin-4-ylmethyl}-phenyl)-urea, C36H39F4N5O3, 665.30, 666.27, M+H, 4.26, Compound A104;

1-(5-tert-Butyl-2-p-tolyl-2H-pyrazol-3-yl)-3-{3-[1-(4-[1,2,3]thiadiazol-4-yl -benzoyl)-piperidin-4- ylmethyl]-phenyl}-urea, C36H39N7O2S, 633.29, 634.31, M+H, 4.00, Compound A105;

1-(5-tert-Butyl-2-p-tolyl-2H-pyrazol-3-yl)-3-{3-[1-(4-oxazol-5-yl-benzoyl)-piperidin-4-ylmethyl]-phenyl}-urea (0.0166 g), C37H40N6O3, 616.32, 617.29, M+H, 3.85, Compound A106;

1-(5-tert-Butyl-2-p-tolyl-2H-pyrazol-3-yl)-3-{3-[1-(4-thiophen-2-yl-benzoyl)-piperidin-4-ylmethyl]-phenyl}-urea, C38H41N5O2S, 631.30, 632.32, M+H, 4.78, Compound A107;

1-(5-tert-Butyl-2-p-tolyl-2H-pyrazol-3-yl)-3-(3-{1-[4-(4-chloro-phenyl)-thiophene-2-carbonyl]-piperidin-4-ylmethyl}-phenyl)-urea, C38H40ClN5O2S, 665.26, 666.27, M+H, 3.50, Compound A108;

1-(5-tert-Butyl-2-p-tolyl-2H-pyrazol-3-yl)-3-(3-{1-[4-(4-methoxy-phenyl)-butyryl]-piperidin- -4-ylmethyl}-phenyl)-urea, C38H47N5O3, 621.37, 622.38, M+H, 4.35, Compound A109;

1-(5-tert-Butyl-2-p-tolyl-2H-pyrazol-3-yl)-3-(3-{1-[4-(4-methoxy-phenyl)-thiophene-2-carbonyl]-piperidin-4-ylmethyl}-phenyl)-urea, C39H43N5O3S, 661.31, 662.33, M+H, 4.80, Compound A110;

1-(5-tert-Butyl-2-p-tolyl-2H-pyrazol-3-yl)-3-{3-[1-(4-difluoromethoxy-benzoyl)-piperidin-4-ylmethyl]-phenyl}-urea (0.0165 g), C35H39F2N5O3, 615.30, 616.32, M+H, 4.25, Compound A111;

1-(5-tert-Butyl-2-p-tolyl-2H-pyrazol-3-yl)-3-{3-[1-(4-ethylamino-benzoyl)-piperidin-4-ylmethyl]-phenyl}-urea, C36H44N6O2, 592.35, 593.38, M+H, 3.85, Compound A112;

1-{3-[1-(4-tert-Butoxymethyl-benzoyl)-piperidin-4-ylmethyl]-phenyl}-3-(5-tert-butyl-2-p-tolyl-2H-pyrazol-3-yl)-urea, C39H49N5O3, 635.38, 636.39, M+H, 4.53, Compound A113;

1-{3-[1-(4-Amino-3-trifluoromethoxy-benzoyl)-piperidin-4-ylmethyl]-phenyl}-3-(5-tert-butyl-2-p -tolyl-2H-pyrazol-3-yl)-urea (0.014 g), C35H39F3N6O3, 648.30, 649.28, M+H, 3.95, Compound A114;

1-(5-tert-Butyl-2-p-tolyl-2H-pyrazol-3-yl)-3-{3-[1-(5-oxo-5-phenyl-pentanoyl)-piperidin-4-ylmethyl]-phenyl}-urea, C38H45N5O3, 619.35, 620.36, M+H, 4.10, Compound A115;

1-(5-tert-Butyl-2-p-tolyl-2H-pyrazol-3-yl)-3-(3-{1-[2-(4-chloro-phenyl)-propionyl]-piperidin-4-ylmethyl}-phenyl)-urea, C36H42ClN5O2, 611.30, 612.31, M+H, 4.77, Compound A116;

1-(5-tert-Butyl-2-p-tolyl-2H-pyrazol-3-yl)-3-(3-{1-[2-(4-fluoro-phenyl)-acetyl]-piperidin-4-ylmethyl}-phenyl)urea, C35H40FN5O2, 581.32, 582.33, M+H, 4.27,, Compound A117;

1-(5-tert-Butyl-2-p-tolyl-2H-pyrazol-3-yl)-3-{3-[1-(4-hydroxymethyl-benzoyl)-piperidin-4-ylmethyl]-phenyl}-urea (0.0098 g), C35H41N5O3, 579.32, 580.32, M+H, 3.25, Compound A118;

1-(5-tert-Butyl-2-p-tolyl-2H-pyrazol-3-yl)-3-{3-[1-(4-isobutyl-benzoyl)-piperidin-4-ylmethyl]-phenyl}-urea, C38H47N5O2, 605.37, 606.42, M+H, 3.47, Compound A119;

1-(5-tert-Butyl-2-p-tolyl-2H-pyrazol-3-yl)-3-{3-[1-(4-methoxy-2-methyl-benzoyl)-piperidin-4-ylmethyl]-phenyl}-urea (0.0094 g), C36H43N5O3, 593.34, 594.35, M+H, 4.20, Compound A120;

1-(5-tert-Butyl-2-p-tolyl-2H-pyrazol-3-yl)-3-(3-{1-[2-(4-methoxy-phenoxy)acetyl]-piperidin- -4-ylmethyl}-phenyl)-urea (0.0243g), C36H43N5O4, 609.33, 610.34, M+H, 3.92, Compound A121;

1-(5-tert-Butyl-2-p-tolyl-2H-pyrazol-3-yl)-3-(3-{1-[2-(4-methoxy-phenyl)-acetyl]-piperidin- -4-ylmethyl}-phenyl)-urea (0.0151 g), C36H43N5O3, 593.34, 594.35, M+H, 4.17, Compound A122;

1-(5-tert-Butyl-2-p-tolyl-2H-pyrazol-3-yl)-3-{3-[1-(4-methoxy-thiophene-3-carbonyl)-piperidin- -4-ylmethyl]-phenyl}-urea (0.0163 g), C33H39N5O3S, 585.28, 586.28, M+H, 3.88, Compound A123;

1-(5-tert-Butyl-2-p-tolyl-2H-pyrazol-3-yl)-3-{3-[1-(4-phenyl-butyryl)-piperidin-4-ylmethyl]-phenyl}-urea, C37H45N5O2, 591.36, 592.36, M+H, 4.43, Compound A124;

1-(5-tert-Butyl-2-p-tolyl-2H-pyrazol-3-yl)-3-{3-[1-(1H-pyrazole-4-carbonyl)piperidin-4-ylmethyl]-phenyl}-urea, C31H37N7O2, 539.30, 540.32, M+H, 2.92, Compound A125;

1-(5-tert-Butyl-2-p-tolyl-2H-pyrazol-3-yl)-3-{3-[1-(4-trifluoromethyl-pyridine-3-carbonyl)- -piperidin-4-ylmethyl]-phenyl}-urea (0.0186 g), C34H37F3N6O2, 618.29, 619.31, M+H, 3.95, Compound A126;

1-(5-tert-Butyl-2-p-tolyl-2H-pyrazol-3-yl)-3-[3-(1-{4-[(4,6-dimethyl-pyrimidin-2-yl) -methyl-amino]-benzoyl}-piperidin-4-ylmethyl)-phenyl]-urea, C41H48N8O2, 684.39, 685.42, M+H, 4.10, Compound A127;

1-(5-tert-Butyl-2-p-tolyl-2H-pyrazol-3-yl)-3-{3-[1-(5,6-dichloro-pyridine-3-carbonyl)- -piperidin-4-ylmethyl]-phenyl}-urea, C33H36Cl2N6O2, 618.23, 619.24, M+H, 4.40, Compound A128;

1-(5-tert-Butyl-2-p-tolyl-2H-pyrazol-3-yl)-3-{3-[1-(5-chloro-6-hydroxy-pyridine-3-carbonyl)-piperidin-4-ylmethyl]-phenyl}-urea, C33H37ClN6O3, 600.26, 601.28, M+H, 3.00, Compound A129;

1-(5-tert-Butyl-2-p-tolyl-2H-pyrazol-3-yl)-3-(3-{1-[2-(5-chloro-benzo[b]thiophen-3-yl)-acetyl]-piperidin-4-ylmethyl}-phenyl)-urea, C37H40ClN5O2S, 653.26, 654.27, M+H, 4.63, Compound A130;

1-(5-tert-Butyl-2-p-tolyl-2H-pyrazol-3-yl)-3-{3-[1-(5-chloro-thiophene-2-carbonyl)-piperidin- -4-ylmethyl]-phenyl}-urea (0.0108 g), C32H36ClN5O2S, 589.23, 590.24, M+H, 4.62, Compound A131;

1-(5-tert-Butyl-2-p-tolyl-2H-pyrazol-3-yl)-3-(3-{1-[5-methoxy-2-(2,2,2-trifluoro- -ethoxy)-benzoyl]-piperidin-4-ylmethyl}-phenyl)-urea (0.0214 g), C37H42F3N5O4, 677.32, 678.29, M+H, 4.18, Compound A132;

1-(5-tert-Butyl-2-p-tolyl-2H-pyrazol-3-yl)-3-{3-[1-(5-methoxy-benzofuran-2-carbonyl)- -piperidin-4-ylmethyl]-phenyl}-urea, C37H41N5O4, 619.32, 620.32, M+H, 4.55, Compound A133;

1-(5-tert-Butyl-2-p-tolyl-2H-pyrazol-3-yl)-3-{3-[1-(5-methyl-1-phenyl-1H-pyrazole-4-carbonyl)-piperidin-4-ylmethyl]-phenyl}-urea, C38H43N7O2, 629.35, 630.36, M+H, 4.15, Compound A134;

1-(5-tert-Butyl-2-p-tolyl-2H-pyrazol-3-yl)-3-{3-[1-(5-methyl-2-trifluoromethyl-furan-3-carbonyl)-piperidin-4-ylmethyl]-phenyl}-urea, C34H38F3N5O3, 621.29, 622.27, M+H, 3.12, Compound A135;

1-(5-tert-Butyl-2-p-tolyl-2H-pyrazol-3-yl)-3-{3-[1-(5-methyl-2-phenyl-2H-[1,2,3]triazole-4-carbonyl)-piperidin-4-ylmethyl]-phenyl}-urea, C37H42N8O2, 630.34, 631.33, M+H, 3.37, Compound A136;

1-(5-tert-Butyl-2-p-tolyl-2H-pyrazol-3-yl)-3-{3-[1-(5-methyl-thiophene-2-carbonyl)-piperidin- -4-ylmethyl]-phenyl}-urea (0.0153 g), C33H39N5O2S, 569.28, 570.28, M+H, 3.08, Compound A137;

1-(5-tert-Butyl-2-p-tolyl-2H-pyrazol-3-yl)-3-{3-[1-(5-methyl-3-phenyl-isoxazole-4-carbonyl)-piperidin-4-ylmethyl]-phenyl}-urea, C38H42N6O3, 630.33, 631.33, M+H, 3.02, Compound A138;

1-(5-tert-Butyl-2-p-tolyl-2H-pyrazol-3-yl)-3-{3-[1-(5-methyl-isoxazole-4-carbonyl)-piperidin- -4-ylmethyl]-phenyl}-urea, C32H38N6O3, 554.30, 555.30, M+H, 2.72, Compound A139;

1-(5-tert-Butyl-2-p-tolyl-2H-pyrazol-3-yl)-3-{3-[1-(5-methyl-pyrazine-2-carbonyl)-piperidin-4-ylmethyl]-phenyl}-urea (0.0192 g), C33H39N7O2, 565.32, 566.31, M+H, 2.65, Compound A140;

1-{3-[1-(Bicyclo[2.2.1]hept-5-ene-2-carbonyl)-piperidin-4-ylmethyl]-phenyl}-3-(5-tert- -butyl-2-p-tolyl-2H-pyrazol-3-yl)-urea, C35H43N5O2, 565.34, 566.35, M+H, 3.30, Compound A141;

1-(5-tert-Butyl-2-p-tolyl-2H-pyrazol-3-yl)3-(3-{1-[6-(2,2, 2-trifluoro-ethoxy)-pyridine-3-carbonyl]-piperidin-4-ylmethyl}-phenyl)-urea, C35H39F3N6O3, 648.30, 649.24, M+H, 3.10, Compound A142;

1-(5-tert-Butyl-2-p-tolyl-2H-pyrazol-3-yl)-3-{3-[1-(6-trifluoromethyl-pyridine-3-carbonyl)- -piperidin-4-ylmethyl]-phenyl}-urea, C34H37F3N6O2, 618.29, 619.26, M+H, 2.93, Compound A143;

1-{3-[1-(6-Amino-pyridine-3-carbonyl)-piperidin-4-ylmethyl]-phenyl}-3-(5-tert-butyl-2-p-tolyl -2H-pyrazol-3-yl)-urea (0.0089 g), C33H39N7O2, 565.32, 566.33, M+H, 1.97, Compound A144;

1-(5-tert-Butyl-2-p-tolyl-2H-pyrazol-3-yl)3-{3-[1-(6-chloro-pyridine-3-carbonyl)-piperidin-4-ylmethyl]-phenyl}-urea, C33H37ClN6O2, 584.27, 585.23, M+H, 2.85, Compound A145;

1-(5-tert,-Butyl-2-p-tolyl-2H-pyrazol-3-yl)-3-{3-[1-(6-methyl-pyridine-2-carbonyl)-piperidin- -4-ylmethyl]-phenyl}-urea (0.0161 g), C34H40N6O2, 564.32, 565.29, M+H, 2.72, Compound A146;

1-(5-tert-Butyl-2-p-tolyl-2H-pyrazol-3-yl)-3-{3-[1-(7-methoxy-benzofuran-2-carbonyl) -piperidin-4-ylmethyl]-phenyl}-urea, C37H41N5O4, 619.32, 620.29, M+H, 3.18, Compound A147;

Acetic acid 4-(4-{3-[3-(5-tert-butyl-2-p-tolyl-2H-pyrazol-3-yl)-ureido]-benzyl}-piperidine-1-carbonyl)-benzyl ester (0.0197 g), C37H43N5O4, 621.33, 622.31, M+H, 2.85, Compound A148;

1-(5-tert-Butyl-2-p-tolyl-2H-pyrazol-3-yl)-3-{3-[1(2-methyl-2-phenyl-propionyl)-piperidin-4-ylmethyl]-phenyl}-urea (0.0085 g), C37H45N5O2, 591.36, 592.35, M+H, 3.42, Compound A149;

1-{3-[1-(Benzothiazole-6-carbonyl)-piperidin-4-ylmethyl]-phenyl}-3-(5-tert-butyl-2-p-tolyl-2H -pyrazol-3-yl)-urea (0.0047 g), C35H38N6O2S, 606.28, 607.28, M+H, 2.83, Compound A150;

1-{3-[1-(1H-Benzotriazole-5-carbonyl)-piperidin-4-ylmethyl]-phenyl}-3-(5-tert-butyl-2-p-tolyl- -2H-pyrazol-3-yl)-urea, C34H38N8O2, 590.31, 591.33, M+H, 2.40, Compound A151;

1-{3-[1-(Benzo[b]thiophene-2-carbonyl)-piperidin-4-ylmethyl]-phenyl}-3-(5-tert-butyl-2-p-tolyl-2H-pyrazol-3-yl)-urea, C36H39N5O2S, 605.28, 606.28, M+H, 3.25, Compound A152;

1-(5-tert-Butyl-2-p-tolyl-2H-pyrazol-3-yl)-3-{3-[1-(2,3-dihydro-benzofuran-5-carbonyl)- -piperidin-4-ylmethyl]-phenyl}-urea, C36H41N5O3, 591.32, 592.31, M+H, 2.95, Compound A153;

1-(5-tert-Butyl-2-p-tolyl-2H-pyrazol-3-yl)-3-{3-[1(4-oxo-4, 5,6,7-tetrahydro-benzofuran-3-carbonyl)-piperidin-4-ylmethyl]-phenyl}-urea (0.0205 g), C36H41N5O4, 607.32, 608.31, M+H, 2.67, Compound A154;

1-(5-tert-Butyl-2-p-tolyl-2H-pyrazol-3-yl)-3-[3-(1-butyryl-piperidin-4-ylmethyl)-phenyl]-urea, C31H41N5O2, 515.33, 516.30, M+H, 2.92, Compound A155;

1-(5-tert-Butyl-2-p-tolyl-2H-pyrazol-3-yl)-3-[3-(1-cyclobutanecarbonyl-piperidin-4-ylmethyl)-phenyl]-urea, C32H41N5O2, 527.33, 528.31, M+H, 2.98, Compound A156;

1-(5-tert-Butyl-2-p-tolyl-2H-pyrazol-3-yl)-3-[3-(1-cyclohexanecarbonyl-piperidin-4-ylmethyl)-phenyl]-urea, C34H45N5O2, 555.36, 556.37, M+H, 3.27, Compound A157;

1-(5-tert-Butyl-2-p-tolyl-2H-pyrazol-3-yl)-3-{3-[1-(2-cyclohexyl-acetyl)-piperidin-4-ylmethyl]-phenyl}-urea, C35H47N5O2, 569.37, 570.37, M+H, 3.35, Compound A158;

1-(5-tert-Butyl-2-p-tolyl-2H-pyrazol-3-yl)-3-[3-(1-cyclopentanecarbonyl-piperidin-4-ylmethyl)-phenyl]-urea, C33H43N5O2, 541.34, 542.32, M+H, 3.15, Compound A159;

1-(5-tert-Butyl-2-p-tolyl-2H-pyrazol-3-yl)-3-{3-[1-(2-cyclopentyl-acetyl)-piperidin-4-ylmethyl]-phenyl}-urea, C34H45N5O2, 555.36, 556.35, M+H, 3.23, Compound A160;

1-(5-tert-Butyl-2-p-tolyl-2H-pyrazol-3-yl)-3-{3-[1-(5-oxopyrrolidine-2-carbonyl)-piperidin-4-ylmethyl]-phenyl}-urea (0.0083g), C32H40N6O3, 556.32, 557.36, M+H, 2.18, Compound A161;

1-(5-tert-Butyl-2-p-tolyl-2H-pyrazol-3-yl)-3-[3-(1-heptanoyl-piperidin-4-ylmethyl)-phenyl]-urea, C34H47N5O2, 557.37, 558.35, M+H, 3.38, Compound A162;

N-[2-(4-{3-[3-(5-tert-Butyl-2-p-tolyl-2H-pyrazol-3-yl)-ureido]-benzyl}-piperidin-1-yl)-2-oxo-ethyl]-benzamide (0.0165 g), C36H42N6O3, 606.33, 607.31, M+H, 2.72, Compound A163;

1-(5-tert-Butyl-2-p-tolyl-2H-pyrazol-3-yl)-3-(3-{1-[2-(2,5-dioxo-imidazolidin-4-y)- -acetyl]-piperidin-4-ylmethyl}-phenyl)-urea, C32H39N7O4, 585.31, 586.27, M+H, 2.35, Compound A164;

1-(5-tert-Butyl-2-p-tolyl-2H-pyrazol-3-yl)-3-{3-[1-(3-phenyl-propionyl)-piperidin-4-ylmethyl]-phenyl}-urea, C36H43N5O2, 577.34, 578.33, M+H, 3.40, Compound A165;

1-{3-[1-(Benzo[d]imidazo[2,1-b]thiazole-2-carbonyl)-piperidin-4-ylmethyl]-phenyl}-3-(5-tert- -butyl-2-p-tolyl-2H-pyrazol-3-yl)-urea, C37H39N7O2S, 645.83, 646.26, M+H, 3.55, Compound A166;

1-(5-tert-Butyl-2-p-tolyl-2H-pyrazol-3-yl)-3-{3-[1-(1H-indazole-3-carbonyl)-piperidin-4-ylmethyl]-phenyl}-urea (0.0118 g), C35H39N7O2, 589.32, 590.27, M+H,3.03, Compound A167;

1-(5-tert-Butyl-2-p-tolyl-2H-pyrazol-3-yl)-3-{3-[1-(2-1H-indol-3-yl-acetyl)-piperidin-4-ylmethyl]-phenyl}-urea (0.0121 g), C37H42N6O2, 602.34, 603.30, M+H, 3.10, Compound A168;

1-(5-tert-Butyl-2-p-tolyl-2H-pyrazol-3-yl)-3-{3-[1-(pyridine-4-carbonyl)-piperidin-4-ylmethyl]-phenyl}-urea (0.0111 g), C33H38N6O2, 550.30, 551.27, M+H, 2.63, Compound A170;

1-(5-tert-Butyl-2-p-tolyl-2H-pyrazol-3-yl)-3-{3-[1-((S)-2,6-dioxo-hexahydro-pyrimidine-4-carbonyl)-piperidin-4-ylmethyl]-phenyl}-urea (0.0081 g), C32H39N7O4, 585.31, 586.26, M+H, 2.28, Compound A171;

1-(5-tert-Butyl-2-p-tolyl-2H-pyrazol-3-yl)-3-{3-[1-((S)-5-oxo-pyrrolidine-2-carbonyl)-piperidin-4-ylmethyl]-phenyl}-urea (0.0122 g), C32H40N6O3, 556.32, 557.27, M+H, 4.70, Compound A161A;

1-(5-tert-Butyl-2-p-tolyl-2H-pyrazol-3-yl)-3-{3-[1-(2-methoxy-acetyl)-piperidin-4-ylmethyl]-phenyl}-urea (0.0181 g), C30H39N5O3, 517.30, 518.25, M+H, 2.72, Compound A173;

4-(4-{3-[3-(5-tert-Butyl-2-p-tolyl-2H-pyrazol-3-yl)-urido]-benzyl}-piperidin-1-yl)-4-oxo- -butyric acid methyl ester (0.0142 g), C32H41N5O4, 559.31, 560.25, M+H, 2.88, Compound A174;

1-(5-tert-Butyl-2-p-tolyl-2H-pyrazol-3-yl)-3-{3-[1-(2-dimethylamino-acetyl)-piperidin-4-ylmethyl]-phenyl}-urea, C31H42N6O2, 530.34, 531.31, M+H, 1.97, Compound A175;

1-(5-tert-Butyl-2-p-tolyl-2H-pyrazol-3-yl)-3-(3-{1-[4-(4,6-dimethyl-pyrimidin-2-ylamino)-benzoyl]-piperidin-4-ylmethyl}-phenyl)-urea, C40H46N8O2, 670.37, 671.34, M+H, 3.43, Compound A176;

1-(5-tert-Butyl-2-p-tolyl-2H-pyrazol-3-yl)-3-[3-(1-{3-[(4,6-dimethyl-pyrimidin-2-yl)- -methyl-amino]-benzoyl}-piperidin-4-ylmethyl)-phenyl]-urea, C41H48N8O2, 684.39, 685.35, M+H, 3.35, Compound A177;

N-[2-(4-{3-[3-(5-tert-Butyl-2-p-tolyl-2H-pyrazol-3-yl)-ureido]-benzyl}-piperidin-1-yl)-1-methyl-2-oxo-ethyl]-acetamide, C32H42N6O3, 558.33, 559.27, M+H, 2.53, Compound A178;

N-[2-(4-{3-[3-(5-tert-Butyl-2-p-tolyl-2H-pyrazol-3-yl)-ureido]-benzyl}-piperidin-1-yl)-2-oxo-ethyl]-acetamide (0.0158 g), C31H40N6O3, 544.32, 545.26, M+H, 2.40, Compound A179;

1-(5-tert-Butyl-2-p-tolyl-2H-pyrazol-3-yl)-3-{3-[1-(2-phenylamino-acetyl)-piperidin-4-ylmethyl]-phenyl}-urea, C35H42N6O2, 578.34, 579.29, M+H, 3.35, Compound A180;

1-(5-tert-Butyl-2-p-tolyl-2H-pyrazol-3-yl)-3-{3-[1-(pyridine-3-carbonyl)-piperidin-4-ylmethyl]-phenyl}-urea (0.017 g), C33H38N6O2, 550.30, 551.25, M+H, 2.73, Compound A181;

1-(5-tert-Butyl-2-p-tolyl-2H-pyrazol-3-yl)-3-{3-[1-(2-o-tolyl-acetyl)-piperidin-4-ylmethyl]-phenyl}-urea (0.0199 g), C36H43N5O2, 577.34, 578.29, M+H, 3.37, Compound A182;

1-(5-tert-Butyl-2-p-tolyl-2H-pyrazol-3-yl)-3-{3-[1-(2-phenoxy-acetyl)-piperidin-4-ylmethyl]-phenyl}-urea, C35H41N5O3, 579.32, 580.25, M+H, 3.25, Compound A183;

1-(5-tert-Butyl-2-p-tolyl-2H-pyrazol-3-yl)-3-{3-[1-(quinoline-2-carbonyl)-piperidin-4-ylmethyl]-phenyl}-urea (0.023 g), C37H40N6O2, 600.32, 601.28, M+H, 3.23, Compound A184;

1-(5-tert-Butyl-2-p-tolyl-2H-pyrazol-3-yl)-3-{3-[1-(quinoline-3-carbonyl)-piperidin-4-ylmethyl]-phenyl}-urea, C37H40N6O2, 600.32, 601.28, M+H, 3.17, Compound A185;

1-(5-tert-Butyl-2-p-tolyl-2H-pyrazol-3-yl)-3-{3-[1-(quinoline-4-carbonyl)-piperidin-4-ylmethyl]-phenyl}-urea (0.0223 g), C37H40N6O2, 600.32, 601.29, M+H, 3.00, Compound A186;

1-(5-tert-Butyl-2-p-tolyl-2H-pyrazol-3-yl)-3-{3-[1-(quinoline-6-carbonyl)-piperidin-4-ylmethyl]-phenyl}-urea, C37H40N6O2, 600.32, 601.28, M+H, 2.88, Compound A187;

1-{3-[1-(2-Benzo[b]thiophen-3-yl-acetyl)-piperidin-4-ylmethyl]-phenyl}-3-(5-tert-butyl-2-p -tolyl-2H-pyrazol-3-yl)urea, C37H41N5O2S, 619.30, 620.24, M+H, 3.17, Compound A188;

1-(5-tert-Butyl-2-p-tolyl-2H-pyrazol-3-yl)-3-{3-[1-(2-thiophen-2-yl-acetyl)-piperidin-4-ylmethyl]-phenyl}-urea (0.0065 g), C33H39N5O2S, 569.28, 570.22, M+H, 3.23, Compound A189;

1-(5-tert-Butyl-2-p-tolyl-2H-pyrazol-3-yl)-3-{3-[1-(2-thiophen-3-yl-acetyl)-piperidin-4-ylmethyl]-phenyl}-urea (0.0194 g), C33H39N5O2S, 569.28, 570.22, M+H, 3.23, Compound A190;

1-(5-tert-Butyl-2-p-tolyl-2H-pyrazol-3-yl)-3-(4-{1-[2-(2,4-dimethoxy-phenyl)acetyl]-piperidin-4-ylmethyl}-phenyl)-urea, C37H45N5O4, 623.35, 624.35, M+H, 3.28, Compound A191;

1-(5-tert-Butyl-2-p-tolyl-2H-pyrazol-3-yl)-3-{4-[1-((R)-5-oxo-tetrahydro-furan-2-carbonyl)- -piperidin-4-ylmethyl]-phenyl}-urea (13 mg), C32H39N5O4, 557.30, 558.34, M+H, 3.67, Compound A192;

1-(5-tert-Butyl-2-p-tolyl-2H-pyrazol-3-yl)-3-{4-[1-((R)-2-methoxy-2-phenyl-acetyl)-piperidin- -4-ylmethyl]-phenyl}-urea (0.0197 g), C36H43N5O3, 593.34, 594.34, M+H, 3.18, Compound A193;

1-(5-tert-Butyl-2-p-tolyl-2H-pyrazol-3-yl)-3-{4-[1-((S)-2-methoxy-2-phenyl-acetyl)-piperidin- -4-ylmethyl]-phenyl}-urea (0.0129 g), C36H43N5O3, 593.34, 594.34, M+H, 3.18, Compound A194;

1-(5-tert-Butyl-2-p-tolyl-2H-pyrazol-3-yl)-3-{4-[1-(1,2,3,4-tetrahydro-naphthalene-2-carbonyl)-piperidin-4-ylmethyl]-phenyl}-urea (0.0184 g), C38H45N5O2, 603.36, 604.36, M+H, 3.62, Compound A195;

1-(5-tert-Butyl-2-p-tolyl-2H-pyrazol-3-yl)-3-{4-[1-([1,2,3]thiadiazole-4-carbonyl)- -piperidin-4-ylmethyl]-phenyl}-urea (0.021 g), C30H35N7O2S, 557.26, 558.26, M+H, 2.93, Compound A196;

1-(5-tert-Butyl-2-p-tolyl-2H-pyrazol-3-yl)-3-{4-[1-([1,6]naphthyridine-2-carbonyl)- -piperidin-4-ylmethyl]-phenyl}-urea (0.0071 g), C36H39N7O2, 601.32, 602.35, M+H, 2.92, Compound A197;

1-(5-tert-Butyl-2-p-tolyl-2H-pyrazol-3-yl)-3-{4-[1-([1,8]naphthyridine-2-carbonyl)- -piperidin-4-ylmethyl]-phenyl}-urea, C36H39N7O2, 601.32, 602.34, M+H, 2.70, Compound A198;

1-(5-tert-Butyl-2-p-tolyl-2H-pyrazol-3-y)-3-{4-[1-(3-thioureido-benzoyl)-piperidin-4-ylmethyl]-phenyl}-urea, C35H41N7O2S, 623.30, 624.35, M+H, 2.63, Compound A199;

1-(5-tert-Butyl-2-p-tolyl-2H-pyrazol-3-yl)-3-(4-{1-[1-(4-methoxy-phenyl) -cyclopropanecarbonyl]-piperidin-4-ylmethyl}-phenyl)-urea, C38H45N5O3, 619.35, 620.38, M+H, 3.38, Compound A200;

1-(4-{1-[1-(5-Bromo-pyriridin-2-yl)-piperidine-3-carbonyl]-piperidin-4-ylmethyl}-phenyl)-3-(5-tert-butyl-2-p-tolyl-2H-pyrazol-3-yl)-urea, C37H45BrN8O2, 712.28, 713.35, M+H, 3.97, Compound A201;

1-(4-{1-[1-(5-Bromo-pyrimidin-2-yl)-piperidine-4-carbonyl]-piperidin-4-ylmethyl}-phenyl)-3-(5-tert-butyl-2-p- tolyl-2H-pyrazol-3-yl)-urea, C37H45Br1N8O2, 712.28, 713.35, M+H, 3.83, Compound A202;

1-(5-tert-Butyl-2-p-tolyl-2H-pyrazol-3-yl)-3-{4-[1-(isoquinoline-1-carbonyl)-piperidin-4-ylmethyl]-phenyl}-urea, C37H40N6O2, 600.32, 601.37, M+H, 3.24, Compound A203;

1-(5-tert-Butyl-2-p-tolyl-2H-pyrazol-3-yl)-3-{4-[1-(1-methyl-cyclohexanecarbonyl)piperidin-4-ylmethyl]-phenyl}-urea, C35H47N5O2, 569.37, 570.41, M+H, 3.83, Compound A204;

1-(5-tert-Butyl-2-p-tolyl-2H-pyrazol-3-yl)-3(4-{1-[2-(1-methyl-1H-indol-3-yl) -acetyl]-piperidin-4-ylmethyl}-phenyl)-urea, C38H44N6O2, 616.35, 617.37, M+H, 3.85, Compound A205;

1-(5-tert-Butyl-2-p-tolyl-2H-pyrazol-3-yl)-3-{4-[1-(1-methyl-cyclopropanecarbonyl)-piperidin-4-ylmethyl]-phenyl}-urea (0.0123 g), C32H41N5O2, 527.33, 528.34, M+H, 3.15, Compound A206;

1-(5-tert-Butyl-2-p-tolyl-2H-pyrazol-3-yl)-3-{4-[1-(2-naphthalen-1-yl-acetyl)-piperidin-4-ylmethyl]-phenyl}-urea, C39H43N5O2, 613.34, 614.35, M+H, 3.65, Compound A207;

1-(5-tert-Butyl-2-p-tolyl-2H-pyrazol-3-yl)-3-{4-[1-(1-phenyl-cyclopentanecarbonyl)-piperidin-4-ylmethyl]-phenyl}-urea, C39H47N5O2, 617.37, 618.37, M+H, 3.97, Compound A208;

1-(5-tert-Butyl-2-p-tolyl-2H-pyrazol-3-yl}3-{4-[1-(3-piperidin-1-yl-propionyl)-piperidin-4-ylmethyl]-phenyl}-urea, C35H48N6O2, 584.38, 585.41, M+H, 2.27, Compound A209;

1-(5-tert-Butyl-2-p-tolyl-2H-pyrazol-3-yl)-3-{4-[1-(2,2-difluoro-benzo[1,3]dioxole-5-carbonyl)-piperidin-4-ylmethyl]-phenyl}-urea, C35H37F2N5O4, 629.28, 630.26, M+H, 3.60, Compound A210;

1-(5-tert-Butyl-2-p-tolyl-2H-pyrazol-3-yl)-3-{4-[1-(2,2-dimethyl-pentanoyl)-piperidin-4-ylmethyl]-phenyl}-urea, C34H47N5O2, 557.37, 558.40, M+H, 6.49, Compound A211;

1-(5-tert-Butyl-2-p-tolyl-2H-pyrazol-3-yl)-3-{4-[1-(2,3-dimethoxy-benzoyl)-piperidin-4-ylmethyl]-phenyl}-urea (0.0187 g), C36H43N5O4, 609.33, 610.33, M+H, 3.12, Compound A212;

1-(5-tert-Butyl-2-p-tolyl-2H-pyrazol-3-yl)-3-(4-{1-[2-(2,3-dimethoxy-phenyl)-acetyl]-piperidin-4-ylmethyl}-phenyl)-urea (0.0188 g), C37H45N5O4, 623.35, 624.33, M+H, 3.23, Compound A213;

1-(5-tert-Butyl-2-p-tolyl-2H-pyrazol-3-yl)-3-(4-{1-[2-(2,3-dimethyl-phenoxy)-acetyl]-piperidin-4-ylmethyl}-phenyl)-urea, C37H45N5O3, 607.35, 608.33, M+H, 3.58, Compound A214;

1-(5-tert-Butyl-2-p-tolyl-2H-pyrazol-3-yl)-3-{4-[1-(2,4,6-trimethoxy-benzoyl)-piperidin-4-ylmethyl]-phenyl}-urea (0.0059 g), C37H45N5O5, 639.34, 640.35, M+H, 3.15, Compound A215;

1-(5-tert-Butyl-2-p-tolyl-2H-pyrazol-3-yl)-3-{4-[1-(2,4,6-trimethyl-benzoyl)-piperidin-4-ylmethyl]-phenyl}-urea (11 mg), C37H45N5O2, 591.36, 592.37, M+H, 3.6, Compound A216;

1-(5-tert-Butyl-2-p-tolyl-2H-pyrazol-3-yl)-3-(4-{1-[2-(2,4-difluoro-phenyl)-acetyl]-piperidin-4-ylmethyl}-phenyl)-urea (0.013 g), C35H39F2N5O2, 599.31, 600.31, M+H, 3.32, Compound A217;

1-(5-tert-Butyl-2-p-tolyl-2H-pyrazol-3-yl)-3-{4-[1-(2,4-dimethoxy-benzoyl)-piperidin-4-ylmethyl]-phenyl}-urea (0.121 g), C36H43N5O4, 609.33, 610.33, M+H, 3.17, Compound A218;

1-(5-tert-Butyl-2-p-tolyl-2H-pyrazol-3-yl)-3-{4-[1-(2,4-dimethyl-thiazole-5-carbonyl)- -piperidin-4-ylmethyl]-phenyl}-urea (0.0167 g), C33H40N6O2S, 584.29, 585.31, M+H, 3.08, Compound A219;

1-(5-tert-Butyl-2-p-tolyl-2H-pyrazol-3-yl)-3-{4-[1-(2,5-dimethoxy-benzoyl)-piperidin-4-ylmethyl]-phenyl}-urea (0.0224 g), C36H43N5O4, 609.33, 610.34, M+H, 3.17, Compound A220;

1-(5-tert-Butyl-2-p-tolyl-2H-pyrazol-3-yl)-3-(4-{1-[2-(2,5-dimethoxy-phenyl)-acetyl]-piperidin-4-ylmethyl}-phenyl)-urea, C37H45N5O4, 623.35, 624.38, M+H, 3.28, Compound A221;

1-(5-tert-Butyl-2-p-tolyl-2H-pyrazol-3-yl)-3-{4-[1-(2,5-dimethyl-furan-3-carbonyl)-piperidin- -4-ylmethyl]-phenyl}-urea (0.0157 g), C34H41N5O3, 567.32, 568.33, M+H, 3.33, Compound A222;

4-(4-{4-[3-(5-tert-Butyl-2-p-tolyl-2H-pyrazol-3-yl)-ureido]-benzyl}-piperidine-1-carbonyl)-2,5-dimethyl-furan-3-sulfonic acid (thiophen-2-ylmethyl)-amide, C39H46N6O5S2, 742.30, 743.33, M+H, 3.52, Compound A223;

1-(5-tert-Butyl-2-p-tolyl-2H-pyrazol-3-yl)-3-{4-[1-(2,6-dimethoxy-pyridine-3-carbonyl)- -piperidin-4-ylmethyl]-phenyl}-urea (0.0166 g), C35H42N6O4, 610.33, 611.35, M+H, 3.30, Compound A224;

1-(5-tert-Butyl-2-p-tolyl-2H-pyrazol-3-yl)3-{4-[1-(2-pyridin-3-yl-thiazole-4-carbonyl)- -piperidin-4-ylmethyl]-phenyl}-urea (0.0186 g), C36H39N7O2S, 633.29, 634.33, M+H, 3.18, Compound A225;

1-(5-tert-Butyl-2-p-tolyl-2H-pyrazol-3-yl)-3-(4-{1-[2-(4,6-dimethoxy-pyrimidin-2-yloxy)- -benzoyl]-piperidin-4-ylmethyl}-phenyl)-urea, C40H45N7O5, 703.35, 704.38, M+H, 3.38, Compound A226;

1-(5-tert-Butyl-2-p-tolyl-2H-pyrazol-3-yl)-3-{4-[1-(2-pyridin-4-yl-thiazole-4-carbonyl)- -piperidin-4-ylmethyl]-phenyl}-urea (0.0291g), C36H39N7O2S, 633.29, 634.33, M+H, 2.95, Compound A227;

1-(5-tert-Butyl-2-p-tolyl-2H-pyrazol-3-yl)-3-(4-{1-[2-(6-methoxy-benzofuran-3-yl) -acetyl]-piperidin-4-ylmethyl}-phenyl)-urea, C38H43N5O4, 633.33, 634.36, M+H, 3.35, Compound A228;

1-(5-tert-Butyl-2-p-tolyl-2H-pyrazol-3-yl)-3-{4-[1-(2-trifluoromethyl-[1,6]naphthyridine- -3-carbonyl)-piperidin-4-ylmethyl]-phenyl}-urea, C37H38F3N7O2, 669.30, 670.36, M+H, 3.18, Compound A229;

1-(5-tert-Butyl-2-p-tolyl-2H-pyrazol-3-yl)-3-{4-[1-(2-trifluoromethyl-[1,8]naphthyridine- -3-carbonyl)-piperidin-4-ylmethyl]-phenyl}-urea, C37H38F3N7O2, 669.30, 670.34, M+H, 2.97, Compound A230;

1-{4-[1-(2-Amino-pyridine-3-carbonyl)-piperidin-4-ylmethyl]-phenyl}-3-(5-tert-butyl-2-p-tolyl- -2H-pyrazol-3-yl)-urea (0.0138 g), C33H39N7O2, 565.32, 566.37, M+H, 2.10, Compound A231;

1-{4-[1-(Benzofuran-2-carbonyl)-piperidin-4-ylmethyl]-phenyl-3-(5-tert-butyl-2-p-tolyl-2H-pyrazol- -3-yl)-urea (0.017 g), C36H39N5O3, 589.31, 590.32, M+H, 3.50, Compound A232;

1-(5-tert-Butyl-2-p-tolyl-2H-pyrazol-3-yl)-3-{4-[1-(2-chloro-4-methanesulfonyl-benzoyl)- -piperidin-4-ylmethyl]-phenyl}-urea (0.0178 g), C35H40ClN5O4S, 661.25, 662.28, M+H, 3.05, Compound A233;

1-(5-tert-Butyl-2-p-tolyl-2H-pyrazol-3-yl)-3-{4-[1-(2-chloro-6-methoxy-pyridine-4-carbonyl)-piperidin-4-ylmethyl]-phenyl}-urea, C34H39ClN6O3, 614.28, 615.29, M+H, 3.40, Compound A234;

1-(5-tert-Butyl-2-p-tolyl-2H-pyrazol-3-yl)-3-{4-[1-(2-chloro-pyridine-3-carbonyl)-piperidin-4-ylmethyl]-phenyl}-urea (0.0194 g), C33H37ClN6O2, 584.27, 585.28, M+H, 2.95, Compound A235;

1-(5-tert-Butyl-2-p-tolyl-2H-pyrazol-3-yl)-3-(4-{1-[2-(2-fluoro-phenyl)-acetyl]-piperidin-4-ylmethyl}-phenyl)-urea (0.0128 g), C35H40FN5O2, 581.32, 582.32, M+H, 3.30, Compound A236;

1-(5-tert-Butyl-2-p-tolyl-2H-pyrazol-3-yl)-3-{4-[1-(furan-2-carbonyl)-piperidin-4-ylmethyl]-phenyl}-urea (0.0047 g), C32H37N5O3, 539.29, 540.30, M+H, 3.13, Compound A237;

1-(5-tert-Butyl-2-p-tolyl-2H-pyrazol-3-yl)-3-[4-(1-hept-2-ynoyl-piperidin-4-ylmethyl)-phenyl]-urea (0.0202 g), C34H43N5O2, 553.34, 554.35, M+H, 3.55, Compound A238;

1-(5-tert-Butyl-2-p-tolyl-2H-pyrazol-3-yl)-3-{4-[1-(2-hydroxy-6-methyl-pyridine-4-carbonyl)-piperidin-4-ylmethyl]-phenyl}-urea, C34H40N6O3, 580.32, 581.32, M+H, 2.42, Compound A239;

1-(5-tert-Butyl-2-p-tolyl-2H-pyrazol-3-yl)-3-{4-[1-(2-hydroxy-quinoline-4-carbonyl)-piperidin-4-ylmethyl]-phenyl}-urea (0.0097 g), C37H40N6O3, 616.32, 617.33, M+H, 2.78, Compound A240;

1-(5-tert-Butyl-2-p-tolyl-2H-pyrazol-3-yl)-3-{4-[1-(2-indan-2-yl-acetyl)-piperidin-4-ylmethyl]-phenyl}-urea, C38H45N5O2, 603.36, 604.34, M+H, 3.62, Compound A241;

1-(5-tert-Butyl-2-p-tolyl-2H-pyrazol-3-yl)-3-(4-{1-[2-(2-methoxy-phenyl)-acetyl]-piperidin-4-ylmethyl}-phenyl)-urea, C36H43N5O3, 593.34, 594.32, M+H, 3.32, Compound A242;

1-(5-tert-Butyl-2-p-tolyl-2H-pyrazol-3-yl)-3-{4-[1-(2-methyl-[1,6]naphthyridine-3-carbonyl)-piperidin-4-ylmethyl]-phenyl}-urea (0.0169 g), C37H41N7O2, 615.33, 616.34, M+H, 2.82, Compound A243;

1-(5-tert-Butyl-2-p-tolyl-2H-pyrazol-3-yl)-3-{4-[1-(2-methyl-furan-3-carbonyl)-piperidin-4-ylmethyl]-phenyl}-urea (0.0136 g), C33H39N5O3, 553.31, 554.28, M+H, 3.15, Compound A244;

1-(5-tert-Butyl-2-p-tolyl-2H-pyrazol-3-yl)-3-(4-{1-[2-(2-methyl-1H-indol-3-yl)-acetyl]-piperidin-4-ylmethyl}-phenyl)-urea, C38H44N6O2, 616.35, 617.35, M+H, 3.22, Compound A245;

1-(5-tert-Butyl-2-p-tolyl-2H-pyrazol-3-yl)-3-(4-{1-[2-methyl-5-(piperidine-1-sulfonyl)-furan-3-carbonyl]-piperidin-4-ylmethyl}-phenyl)-urea, C38H48N6O5S, 700.34, 701.32, M+H, 3.38, Compound A246;

1-(5-tert-Butyl-2-p-tolyl-2H-pyrazol-3-yl)-3-{4-[1-(2-methyl-5-trifluoromethyl-oxazole-4-carbonyl)-piperidin-4-ylmethyl]-phenyl}-urea, C33H37F3N6O3, 622.29, 623.26, M+H, 3.23, Compound A247;

1-(5-tert-Butyl-2-p-tolyl-2H-pyrazol-3-yl)-3-{4-[1-(2-methyl-5-phenyl-furan-3-carbonyl)-piperidin-4-ylmethyl]-phenyl}-urea, C39H43N5O3, 629.34, 630.31, M+H, 3.82, Compound A248;

1-(5-tert-Butyl-2-p-tolyl-2H-pyrazol-3-yl)-3-{4-[1-(2-methyl-[1,8]naphthyridine-3-carbonyl)-piperidin-4-ylmethyl]-phenyl}-urea (0.0237 g), C37H41N7O2, 615.33, 616.34, M+H, 2.70, Compound A249;

1-(5-tert-Butyl-2-p-tolyl-2H-pyrazol-3-yl)-3-{4-[1-(2-methyl-imidazo[1,2-a]pyridine-3-carbonyl)-piperidin-4-ylmethyl]-phenyl}-urea, C36H41N7O2, 603.33, 604.35, M+H, 2.25, Compound A250;

1-(5-tert-Butyl-2-p-tolyl-2H-pyrazol-3-yl)-3-{4-[1-(2-methyl-pyridine-3-carbonyl)-piperidin-4-ylmethyl]-phenyl}-urea (0.0061 g), C34H40N6O2, 564.32, 565.34, M+H, 2.48, Compound A251;

1-(5-tert-Butyl-2-p-tolyl-2H-pyrazol-3-yl)-3-{4-[1-(2-naphthalen-2-yl-acetyl)-piperidin-4-ylmethyl]-phenyl}-urea, C39H43N5O2, 613.34, 614.33, M+H, 3.55, Compound A252;

1-(5-tert-Butyl-2-p-tolyl-2H-pyrazol-3-yl)-3-{4-[1-(2-phenyl-5-trifluoromethyl-oxazole-4-carbonyl)-piperidin-4-ylmethyl]-phenyl}-urea, C38H39F3N6O3, 684.30, 685.30, M+H, 3.87, Compound A253;

1-(5-tert-Butyl-2-p-tolyl-2H-pyrazol-3-yl)-3-{4-[1-(4-oxo-2-phenyl-pentanoyl)piperidin-4-ylmethyl]-phenyl}-urea (0.0115g), C38H45N5O3, 619.35, 620.35, M+H, 3.23, Compound A254;

1-(5-tert-Butyl-2-p-tolyl-2H-pyrazol-3-yl)-3-{4-[1-(2-phenyl-propionyl)-piperidin-4-ylmethyl]-phenyl}-urea, C36H43N5O2, 577.34, 578.34, M+H, 3.63, Compound A255;

1-(5-tert-Butyl-2-p-tolyl-2H-pyrazol-3-yl)-3-{4-[1-(pyrazine-2-carbonyl)-piperidin-4-ylmethyl]-phenyl}-urea (0.0172 g), C32H37N7O2, 551.30, 552.28, M+H, 2.77, Compound A256;

1-(5-tert-Butyl-2-p-tolyl-2H-pyrazol-3-yl)-3-{4-[1-(quinoxaline-2-carbonyl)-piperidin-4-ylmethyl]-phenyl}-urea (0.0237 g), C36H39N7O2, 601.32, 602.28, M+H, 3.27, Compound A257;

1-(5-tert-Butyl-2-p-tolyl-2H-pyrazol-3-yl)-3-{4-[1-(tetrahydro-furan-2-carbonyl)-piperidin-4-ylmethyl]-phenyl}-urea (0.0167 g), C32H41N5O3, 543.32, 544.30, M+H, 2.95, Compound A258;

1-(5-tert-Butyl-2-p-tolyl-2H-pyrazol-3-yl)-3-(4-{1-[2-(4,6-dimethoxy-pyrimidin-2-ylsulfanyl)-benzoyl]-piperidin-4-ylmethyl}-phenyl)-urea, C40H45N7O4S, 719.33, 720.29, M+H, 3.53, Compound A259;

1-(5-tert-Butyl-2-p-tolyl-2H-pyrazol-3-yl)-3-(4-{1-[2-(3,4-difluoro-phenyl)-acetyl]-piperidin-4-ylmethyl}-phenyl)-urea, C35H39F2N5O2, 599.31, 600.27, M+H, 3.33, Compound A260;

1-(5-tert-Butyl-2-p-tolyl-2H-pyrazol-3-yl)-3-{4-[1-(3,4-dimethoxy-benzoyl)-piperidin-4-ylmethyl]-phenyl}-urea (0.0171 g), C36H43N5O4, 609.33, 610.29, M+H, 3.12, Compound A261;

1-(5-tert-Butyl-2-p-tolyl-2H-pyrazol-3-yl)-3-(4-{1-[2-(3,4-dimethoxy-phenyl)-acetyl]-piperidin-4-ylmethyl}-phenyl)-urea (0.0226 g), C37H45N5O4, 623.35, 624.32, M+H, 3.17, Compound A262;

1-{4-[1-(2-Benzo[1,3]dioxol-5-yl-acetyl)-piperidin-4-ylmethyl]-phenyl}-3-(5-tert-butyl-2-p-tolyl-2H-pyrazol-3-yl)-urea (0.0213 g), C36H41N5O4, 607.32, 608.29, M+H, 3.15, Compound A263;

1-{4-[1-(3,5-Bis-trifluoromethyl-benzoyl)-piperidin-4-ylmethyl]-phenyl}-3-(5-tert-butyl-2-p-tolyl-2H-pyrazol-3-yl)-urea, C36H37F6N5O2, 685.29, 686.25, M+H, 3.82, Compound A264;

1-(5-tert-Butyl-2-p-tolyl-2H-pyrazol-3-yl)-3-(4-{1-[2-(3,5-difluoro-phenyl)-acetyl]-piperidin-4-ylmethyl}-phenyl)-urea, C35H39F2N5O2, 599.31, 600.03, M+H, 3.35, Compound A265;

1-(5-tert-Butyl-2-p-tolyl-2H-pyrazol-3-yl)-3-{4-[1-(3,5-dimethoxy-benzoyl)-piperidin-4-ylmethyl]-phenyl}-urea (0.018 g), C36H43N5O4, 609.33, 610.29, M+H, 3.38, Compound A266;

1-(5-tert-Butyl-2-p-tolyl-2H-pyrazol-3-yl)-3-(4-{1-[2-(3,5-dimethoxy-phenyl)-acetyl]-piperidin-4-ylmethyl}-phenyl)urea, C37H45N5O4, 623.35, 624.30, M+H, 3.23, Compound A267;

1-(5-tert-Butyl-2-p-tolyl-2H-pyrazol-3-yl)-3-{4-[1-(3,5-dimethyl-1H-pyrazole-4-carbonyl)-piperidin-4-ylmethyl]-phenyl}-urea, C33H41N7O2, 567.33, 568.37, M+H, 2.97, Compound A268;

1-(5-tert-Butyl-2-p-tolyl-2H-pyrazol-3-yl)-3-{4-[1-(3,5-dimethyl-isoxazole-4-carbonyl)- -piperidin-4-ylmethyl]-phenyl}-urea, C33H40N6O3, 568.32, 569.29, M+H, 2.97, Compound A269;

1-(5-tert-Butyl-2-p-tolyl-2H-pyrazol-3-yl}3-(4-{1-[2-(3,5-dimethyl-phenyl)-acetyl]-piperidin-4-ylmethyl}-phenyl)-urea, C37H45N5O2, 591.36, 592.32, M+H, 3.58, Compound A270;

1-(5-tert-Butyl-2-p-tolyl-2H-pyrazol-3-yl)-3-(4-{1-[3-(1,1,2,2-tetrafluoro-ethoxy)-benzoyl]-piperidin-4-ylmethyl}-phenyl)-urea, C36H39F4N5O3, 665.30, 666.26, M+H, 3.42, Compound A271;

1-(5-tert-Butyl-2-p-tolyl-2H-pyrazol-3-yl)-3-(4-{1-[3-(cyano-methyl-methyl)-benzoyl]-piperidin-4-ylmethyl}-phenyl)-urea (0.0199 g), C37H42N6O2, 602.34, 603.29, M+H, 3.15, Compound A272;

1-(5-tert-Butyl-2-p-tolyl-2H-pyrazol-3-yl)-3-(4-{1-[3-(2,2-difluoro-benzo[1,3]dioxol-5-yl)-acryloyl]-piperidin-4-ylmethyl}-phenyl)-urea, C37H39F2N5O4, 655.30, 656.26, M+H, 3.67, Compound A273;

1-(5-tert-Butyl-2-p-tolyl-2H-pyrazol-3-yl)-3-{4-[1-(3-furan-2-yl-propionyl)-piperidin-4-ylmethyl]-phenyl}-urea (0.0196 g), C34H41N5O3, 567.32, 568.29, M+H, 3.23, Compound A274;

1-(5-tert-Butyl-2-p-tolyl-2H-pyrazol-3-yl)-3-(4-{1-[3-(2-methoxy-phenyl)-propionyl]-piperidin-4-ylmethyl}-phenyl)-urea, C37H45N5O3, 607.35, 608.33, M+H, 3.48, Compound A275;

1-(5-tert-Butyl-2-p-tolyl-2H-pyrazol-3-yl)-3-{4-[1-(3-thiophen-2-yl-propionyl)-piperidin-4-ylmethyl]-phenyl}-urea, C34H41N5O2S, 583.2980976, 584.25, M+H, 3.72, Compound A276;

1-(5-tert-Butyl-2-p-tolyl-2H-pyrazol-3-yl)-3-(4-{1-[4-(4-fluoro-phenyl)-4-oxo-butyryl]-piperidin-4-ylmethyl}-phenyl)-urea, C377H42FN5O3, 623.3271688, 624.28, M+H, 3.67, Compound A277;

1-(5-tert-Butyl-2-p-tolyl-2H-pyrazol-3-yl)-3-(4-{1-[3-(4-fluoro-phenyl)-propionyl]-piperidin-4-ylmethyl}-phenyl)-urea, C36H42FN5O2, 595.3322541, 596.28, M+H, 3.77, Compound A278;

1-(5-tert-Butyl-2-p-tolyl-2H-pyrazol-3-yl)-3-{4-[1-(3-p-tolyl-propionyl)-piperidin-4-ylmethyl]-phenyl}-urea, C37H45N5O2, 591.357326, 592.33, M+H, 3.83, Compound A279;

1-(5-tert-Butyl-2-p-tolyl-2H-pyrazol-3-yl)-3-{4-[1-(3-methanesulfonyl-6,7-dihydro-benzo[c]thiophene-1-carbonyl)-piperidin-4-ylmethyl]-phenyl}-urea, C37H43N5O4S2, 685.2756488, 686.22, M+H, 3.58, Compound A280;

N-[3-(4-{4-[3-(5-tert-Butyl-2-p-tolyl-2H-pyrazol-3-yl)-ureido]-benzyl}-piperidine-1-carbonyl)-phenyl]-acetamide, C36H42N6O3, 606.3318395, 607.30, M+H, 3.20, Compound A281;

1-{4-[1-(3-Amino-4-hydroxy-benzoyl)-piperidin-4-ylmethyl]-phenyl}-3-(5-tert-butyl-2-p-tolyl-2H-pyrazol-3-yl)-urea, C34H40N6O3, 580.3161894, 581.33, M+H, 2.27, Compound A282;

1-{4-[1-(3-Amino-pyrazine-2-carbonyl)-piperidin-4-ylmethyl]-phenyl}-3-(5-tert-butyl-2-p-tolyl- -2H-pyrazol-3-yl)-urea (0.0133 g), C32H38N8O2, 566.3117728, 567.27, M+H, 3.23, Compound A283;

1-{4-[1-(3-Butoxy-4-methoxy-benzoyl)-piperidin-4-ylmethyl]-phenyl}-3-(5-tert-butyl-2-p-tolyl-2H-pyrazol-3-yl) urea, C39H49N5O4, 651.3784554, 652.31, M+H, 3.82, Compound A284;

1-(5-tert-Butyl-2-p-tolyl-2H-pyrazol-3-yl)-3-(4-{1-[2-(3-fluoro-phenyl)-acetyl]-piperidin-4-ylmethyl}-phenyl)-urea, C35H40FN5O2, 581.3166041, 582.28, M+H, 3.63, Compound A285;

1-(5-tert-Butyl-2-p-tolyl-2H-pyrazol-3-yl)-3-{4-[1-(furan-3-carbonyl)-piperidin-4-ylmethyl]-phenyl}-urea (0.019 g), C32H37N5O3, 539.2896403, 540.25, M+H, 3.43, Compound A286;

1-(5-tert-Butyl-2-p-tolyl-2H-pyrazol-3-yl)-3-{4-[1-(3-1H-indol-3-yl-propionyl) -piperidin-4-ylmethyl]-phenyl}-urea, C38H44N6O2, 616.352575, 617.33, M+H, 3.63, Compound A287;

1-(5-tert-Butyl-2-p-tolyl-2H-pyrazol-3-yl)-3-(4-{1-[2-(3-methoxy-phenyl)-acetyl]-piperidin- -4-ylmethyl}-phenyl)-urea (0.0224 g), C36H43N5O3, 593.3365906, 594.32, M+H, 3.55, Compound A288;

1-(5-tert-Butyl-2-p-tolyl-2H-pyrazol-3-yl)-3-{4-[1-(3-methyl-furan-2-carbonyl)-piperidin-4-ylmethyl]-phenyl}-urea (0.0117 g), C33H39N5O3, 553.3052904, 554.26, M+H, 3.63, Compound A289;

1-(5-tert-Butyl-2-p-tolyl-2H-pyrazol-3-yl)-3-{4-[1-(3-methyl-benzofuran-2-carbonyl)-piperidin- -4-ylmethyl]-phenyl}-urea (0.0207 g), C37H41N5O3, 603.3209405, 604.30, M+H, 3.87, Compound A290;

1-(5-tert-Butyl-2-p-tolyl-2H-pyrazol-3-yl)-3-{4-[1-(3-methyl-isoxazole-4-carbonyl)-piperidin- -4-ylmethyl]-phenyl}-urea, C32H38N6O3, 554.3005394, 555.28, M+H, 3.30, Compound A291;

1-(5-tert-Butyl-2-p-tolyl-2H-pyrazol-3-yl)-3-{4-[1-(3-phenoxy-propionyl)-piperidin-4-ylmethyl]-phenyl}-urea (0.017 g), C36H43N5O3, 593.3365906, 594.31, M+H, 3.67, Compound A292;

1-(5-tert-Butyl-2-p-tolyl-2H-pyrazol-3-yl)-3-{4-[1-(3-pyridin-3-yl-propionyl)-piperidin-4-ylmethyl]-phenyl}-urea, C35H42N6O2, 578.3369249, 579.36, M+H, 2.75, Compound A293;

1-(5-tert-Butyl-2-p-tolyl-2H-pyrazol-3-yl)-3-{4-[1-(thiophene-3-carbonyl)-piperidin-4-ylmethyl]-phenyl}-urea (0.0139 g), C32H37N5O2S, 555.2667975, 556.23, M+H, 3.50, Compound A294;

1-(5-tert-Butyl-2-p-tolyl-2H-pyrazol-3-yl)-3-(4-{1-[3-(4,6-dimethoxy-pyrimidin-2-yloxy)- -benzoyl]-piperidin-4-ylmethyl}-phenyl)-urea, C40H45N7O5, 703.3482179, 704.30, M+H, 3.72, Compound A295;

1-(5-tert-Butyl-2-p-tolyl-2H-pyrazol-3-yl)-3-{4-[1-(3a,4,5,7a-tetrahydro-benzofuran-6-carbonyl)-piperidin-4-ylmethyl]-phenyl}-urea (0.0126 g), C36H41N5O3, 591.76, 592.26, M+H, 3.70, Compound A296;

1-(5-tert-Butyl-2-p-tolyl-2H-pyrazol-3-yl)-3-{4-[1-(4,5-dihydro-benzo[b]thiophene-6-carbonyl)-piperidin-4-ylmethyl]-phenyl}-urea, C36H41N5O2S, 607.2980976, 608.24, M+H, 3.77, Compound A297;

1-(5-tert-Butyl-2-p-tolyl-2H-pyrazol-3-yl)-3-{4-[1-(4,5-dimethyl-furan-2-carbonyl)-piperidin- -4-ylmethyl]-phenyl}-urea, C34H41N5O3, 567.3209405, 568.25, M+H, 3.78, Compound A298;

1-(5-tert-Butyl-2-p-tolyl-2H-pyrazol-3-yl)-3-(4-{1-[4-(1,1,2,2-tetrafluoro-ethoxy)-benzoyl]-piperidin-4-ylmethyl}-phenyl)-urea, C36H39F4N5O3, 665.2989034, 666.21, M+H, 3.75, Compound A299;

1-(5-tert-Butyl-2-p-tolyl-2H-pyrazol-3-yl)-3-{4-[1-(4-[1,2,3]thiadiazol-4-yl -benzoyl)-piperidin-4-ylmethyl]-phenyl}-urea, C36H39N7O2S, 633.2885956, 634.25, M+H, 3.62, Compound A300;

1-(5-tert-Butyl-2-p-tolyl-2H-pyrazol-3-yl)-3-{4-[1-(4-oxazol-5-yl-benzoyl)-piperidin-4-ylmethyl]-phenyl}-urea (0.0226 g), C37H40N6O3, 616.3161894, 617.28, M+H, 3.65, Compound A301;

1-(5-tert-Butyl-2-p-tolyl-2H-pyrazol-3-yl)-3-{4-[1-(4-thiophen-2-yl-benzoyl)-piperidin-4-ylmethyl]-phenyl}-urea, C38H41N5O2S, 631.2980976, 632.26, M+H, 4.02, Compound A302;

1-(5-tert-Butyl-2-p-tolyl-2H-pyrazol-3-yl)-3-(4-{1-[4-(4-chloro-phenyl)-thiophene-2-carbonyl]-piperidin-4-ylmethyl}-phenyl)-urea, C38H40ClN5O2S, 665.2591253, 666.22, M+H, 4.05, Compound A303;

1-(5-tert-Butyl-2-p-tolyl-2H-pyrazol-3-yl)-3-(4-{1-[4-(4-methoxy-phenyl)-butyryl]-piperidin--4-ylmethyl}-phenyl)-urea, C38H47N5O3, 621.3678907, 622.31, M+H, 3.82, Compound A304;

1-(5-tert-Butyl-2-p-tolyl-2H-pyrazol-3-yl)-3-(4-{1-[4-(4-methoxy-phenyl)-thiophene-2-carbonyl]-piperidin-4-ylmethyl}-phenyl)-urea, C39H43N5O3S, 661.3086624, 662.28, M+H, 3.87, Compound A305;

1-(5-tert-Butyl-2-p-tolyl-2H-pyrazol-3-yl)-3-{4-[1-(4-difluoromethoxy-benzoyl)-piperidin-4-ylmethyl]-phenyl}-urea, C35H39F2N5O3, 615.3020969, 616.24, M+H, 3.62, Compound A306;

1-(5-tert-Butyl-2-p-tolyl-2H-pyrazol-3-yl)-3-{4-[1-(4-ethylamino-benzoyl)-piperidin-4-ylmethyl]-phenyl}-urea, C36H44N6O2, 592.352575, 593.35, M+H, 3.17, Compound A307;

1-{4-[1-(4-tert-Butoxymethyl-benzoyl)-piperidin-4-ylmethyl]-phenyl}-3-(5-tert-butyl-2-p-tolyl-2H-pyrazol-3-yl) urea, C39H49N5O3, 635.3835408, 636.35, M+H, 4.05, Compound A308;

1-{4-[1-(4-Amino-3-trifluoromethoxy-benzoyl)-piperidin-4-ylmethyl]-phenyl}-3-(5-tert-butyl-2-p--tolyl-2H-pyrazol-3-yl)-urea (0.0196 g), C35H39F3N6O3, 648.3035742, 649.24, M+H, 3.57, Compound A309;

1-{4-[1-(4-Amino-5-chloro-2-methoxy-benzoyl)-piperidin-4-ylmethyl]-phenyl}-3-(5-tert-butyl-2-p-tolyl-2H-pyrazol-3-yl)-urea, C35H41CN6O3, 628.2928672, 629.28, M+H, 3.47, Compound A310;

1-(4-{1-[2-(4-Amino-phenyl)-acetyl]-piperidin-4-ylmethyl}-phenyl)-3-(5-tert-butyl-2-p-tolyl-2H-pyrazol-3-yl)-urea, C35H42N6O2, 578.3369249, 579.33, M+H, 2.25, Compound A311;

1-(5-tert-Butyl-2-p-tolyl-2H-pyrazol-3-yl)-3-{4-[1-(5-oxo-5-phenyl-pentanoyl)-piperidin-4-ylmethyl]-phenyl}-urea, C38H45N5O3, 619.3522406, 620.33, M+H, 3.62, Compound A312;

1-(5-tert-Butyl-2-p-tolyl-2H-pyrazol-3-yl)-3-(4-{1-[2-(4-chloro-phenyl)-propionyl]-piperidin-4-ylmethyl}-phenyl)-urea, C36H42ClN5O2, 611.3027036, 612.29, M+H, 3.83, Compound A313;

1-(5-tert-Butyl-2-p-tolyl-2H-pyrazol-3-yl)3-(4-{1-[2-(4-fluoro-phenyl)-acetyl]-piperidin-4-ylmethyl}-phenyl)-urea (0.0194 g), C35H40FN5O2, 581.3166041, 582.28, M+H, 3.60, Compound A314;

1-(5-tert-Butyl-2-p-tolyl-2H-pyrazol-3-yl)-3-{4-[1-(4-hydroxymethyl-benzoyl)-piperidin-4-ylmethyl]-phenyl}-urea (0.0076 g), C35H41N5O3, 579.3209405, 580.29, M+H, 3.15, Compound A315;

1-(5-tert-Butyl-2-p-tolyl-2H-pyrazol-3-yl)-3-{4-[1-(4-isobutyl-benzoyl)-piperidin-4-ylmethyl]-phenyl}-urea, C38H47N5O2, 605.3729761, 606.35, M+H, 4.05, Compound A316;

1-(5-tert-Butyl-2-p-tolyl-2H-pyrazol-3-yl)-3-{4-[1-(4-methoxy-2-methyl-benzoyl)-piperidin-4-ylmethyl]-phenyl}-urea, C36H43N5O3, 593.3365906, 594.30, M+H, 3.60, Compound A317;

1-(5-tert-Butyl-2-p-tolyl-2H-pyrazol-3-yl)-3-(4-{1-[2-(4-methoxy-phenoxy)-acetyl]-piperidin- -4-ylmethyl}-phenyl)-urea, C36H43N5O4, 609.3315052, 610.29, M+H, 3.53, Compound A318;

1-(5-tert-Butyl-2-p-tolyl-2H-pyrazol-3-yl)-3-(4-{1-[2-(4-methoxy-phenyl)-acetyl]-piperidin- -4-ylmethyl}-phenyl)-urea (0.0118 g), C36H43N5O3, 593.3365906, 594.30, M+H, 3.57, Compound A319;

1-(5-tert-Butyl-2-p-tolyl-2H-pyrazol-3-yl)-3-{4-[1-(4-methoxy-thiophene-3-carbonyl)-piperidin- -4-ylmethyl]-phenyl}-urea, C33H39N5O3S, 585.2773622, 586.24, M+H, 3.50, Compound A320;

1-(5-tert-Butyl-2-p-tolyl-2H-pyrazol-3-yl)-3-{4-[1-(4-phenyl-butyryl)-piperidin-4-ylmethyl]-phenyl}-urea, C37H45N5O2, 591.357326, 592.31, M+H, 3.83, Compound A321;

1-(5-tert-Butyl-2-p-tolyl-2H-pyrazol-3-yl)-3-{4-[1-(4-trifluoromethyl-pyridine-3-carbonyl)-piperidin-4-ylmethyl]-phenyl}-urea, C34H37F3N6O2, 618.2930094, 619.27, M+H, 3.62, Compound A322;

1-(5-tert-Butyl-2-p-tolyl-2H-pyrazol-3-yl)-3-[4-(1-{4-[(4,6-dimethyl-pyrimidin-2-yl) -methyl-amino]-benzoyl}-piperidin-4-ylmethyl)-phenyl]-urea, C41H48N8O2, 684.3900231, 685.38, M+H, 3.70, Compound A323;

1-(5-tert-Butyl-2-p-tolyl-2H-pyrazol-3-yl)-3-{4-[1-(5,6-dichloro-pyridine-3-carbonyl) -piperidin-4-ylmethyl]-phenyl}-urea, C33H36Cl2N6O2, 618.2276801, 619.19, M+H, 3.70, Compound A324;

1-{4-[1-(3H-Benzoimidazole-5-carbonyl)-piperidin-4-ylmethyl]-phenyl}-3-(5-tert-butyl-2-p-tolyl--2H-pyrazol-3-yl)-urea, C35H39N7O2, 589.3165238, 590.31, M+H, 2.12, Compound A325;

1-(5-tert-Butyl-2-p-tolyl-2H-pyrazol-3-yl)-3-{4-[1-(5-chloro-6-hydroxy-pyridine-3-carbonyl)-piperidin-4-ylmethyl]-phenyl}-urea (0.0096 g), C33H37ClN6O3, 600.2615671, 601.24, M+H, 3.07, Compound A326;

1-(5-tert-Butyl-2-p-tolyl-2H-pyrazol-3-yl)-3-(4-{1-[2-(5-chloro-benzo[b]thiophen-3-yl)-acetyl]- piperidin-4-ylmethyl}-phenyl)-urea (0.0151 g), C37H40ClN5O2S, 653.2591253, 654.25, M+H, 3.88, Compound A327;

1-(5-tert-Butyl-2-p-tolyl-2H-pyrazol-3-yl)-3-{4-[1-(5-chloro-thiophene-2-carbonyl)-piperidin-4-ylmethyl]-phenyl}-urea, C32H36ClN5O2S, 589.2278252, 590.19, M+H, 3.87, Compound A328;

1-(5-tert-Butyl-2-p-tolyl-2H-pyrazol-3-yl)-3-(4-{1-[5-methoxy-2-(2,2,2-trifluoro-ethoxy)-benzoyl]-piperidin-4-ylmethyl}-phenyl)-urea, C37H42F3N5O4, 677.3188899, 678.26, M+H, 3.67, Compound A329;

1-(5-tert-Butyl-2-p-tolyl-2H-pyrazol-3-yl)-3-{4-[1-(5-methoxy-benzofuran-2-carbonyl)-piperidin-4-ylmethyl]-phenyl}-urea, C37H41N5O4, 619.3158551, 620.28, M+H, 3.77, Compound A330;

1-(5-tert-Butyl-2-p-tolyl-2H-pyrazol-3-yl)-3-{4-[1-(5-methyl-1-phenyl-1H-pyrazole-4-carbonyl)-piperidin-4-ylmethyl]-phenyl}-urea (0.0113 g), C38H43N7O2, 629.3478239, 630.32, M+H, 3.67, Compound A331;

1-(5-tert-Butyl-2-p-tolyl-2H-pyrazol-3-yl)-3-{4-[1-(5-methyl-2-trifluoromethyl-furan-3-carbonyl)-piperidin-4-ylmethyl]-phenyl}-urea, C34H38F3N5O3, 621.2926751, 622.24, M+H, 3.72, Compound A322A;

1-(5-tert-Butyl-2-p-tolyl-2H-pyrazol-3-yl)-3-{4-[1-(5-methyl-2-phenyl-2H-[1,2,3]triazole-4-carbonyl)-piperidin- 4-ylmethyl]-phenyl}-urea, C37H42N8O2, 630.3430729, 631.32, M+H, 4.13, Compound A323A;

1-(5-tert-Butyl-2-p-tolyl-2H-pyrazol-3-yl)-3-{4-[1-(5-methyl-thiophene-2-carbonyl)-piperidin-4-ylmethyl]-phenyl}-urea, C33H39N5O2S, 569.2824476, 570.25, M+H, 3.85, Compound A324A;

1-(5-tert-Butyl-2-p-tolyl-2H-pyrazol-3-yl)-3-{4-[1-(5-methyl-3-phenyl-isoxazole-4-carbonyl)-piperidin-4-ylmethyl]-phenyl}-urea, C38H42N6O3, 630.3318395, 631.31, M+H, 3.73, Compound A325A;

1-(5-tert-Butyl-2-p-tolyl-2H-pyrazol-3-yl)-3-{4-[1-(5-methyl-isoxazole-4-carbonyl)-piperidin-4-ylmethyl]-phenyl}-urea, C32H38N6O3, 554.3005394, 555.27, M+H, 3.35, Compound A326A;

1-(5-tert-Butyl-2-p-tolyl-2H-pyrazol-3-yl)-3-{4-[1-(5-methyl-pyrazine-2-carbonyl)-piperidin-4-ylmethyl]-phenyl}-urea (0.0151 g), C33H39N7O2, 565.3165238, 566.29, M+H, 3.45, Compound A327A;

1-{4-[1-(Bicyclo[2.2.1]hept-5-ene-2-carbonyl)-piperidin-4-ylmethyl]-phenyl}-3-(5-tert-butyl-2-p-tolyl-2H-pyrazol-3-yl)-urea, C35H43N5O2, 565.3416759, 566.33, M+H, 4.00, Compound A328A;

1-(5-tert-Butyl-2-p-tolyl-2H-pyrazol-3-yl)-3-(4-{1-[6-(2,2,2-trifluoro-ethoxy)-pyridine-3-carbonyl]-piperidin-4-ylmethyl}-phenyl)-urea, C35H39F3N6O3, 648.3035742, 649.26, M+H, 3.68, Compound A329A;

1-(5-tert-Butyl-2-p-tolyl-2H-pyrazol-3-yl)-3-{4-[1-(6-trifluoromethyl-pyridine-3-carbonyl)-piperidin-4-ylmethyl]-phenyl}-urea, C34H37F3N6O2, 618.2930094, 619.25, M+H, 3.53, Compound A330A;

1-{4-[1-(6-Amino-pyridine-3-carbonyl)-piperidin-4-ylmethyl]-phenyl}-3-(5-tert-butyl-2-p-tolyl-2H-pyrazol-3-yl)-urea (0.0086 g), C33H39N7O2, 565.3165238, 566.32, M+H, 2.72, Compound A331A;

1-(5-tert-Butyl-2-p-tolyl-2H-pyrazol-3-yl)-3-{4-[1-(6-chloro-pyridine-3-carbonyl)-piperidin-4-ylmethyl]-phenyl}-urea (0.0208 g), C33H37ClN6O2, 584.2666524, 585.23, M+H, 3.47, Compound A332;

1-(5-tert-Butyl-2-p-tolyl-2H-pyrazol-3-yl)-3-{4-[1-(6-hydroxy-pyridine-3-carbonyl)-piperidin-4-ylmethyl]-phenyl}-urea (0.0009 g), C33H38N6O3, 566.3005394, 567.29, M+H, 2.90, Compound A333;

1-(5-tert-Butyl-2-p-tolyl-2H-pyrazol-3-yl)-3-{4-[1-(6-methyl-pyridine-2-carbonyl)-piperidin-4-ylmethyl]-phenyl}-urea (0.0184 g), C34H40N6O2, 564.3212748, 565.30, M+H, 3.35, Compound A334;

1-(5-tert-Butyl-2-p-tolyl-2H-pyrazol-3-yl)-3-{4-[1-(7-methoxy-benzofuran-2-carbonyl)-piperidin-4-ylmethyl]-phenyl}-urea, C37H41N5O4, 619.3158551, 620.30, M+H, 3.72, Compound A335;

Acetic acid 4-(4-{4-[3-(5-tert-butyl-2-p-tolyl-2H-pyrazol-3-yl)-ureido]-benzyl-piperidine-1-carbonyl)-benzyl ester (0.0227 g), C37H43N5O4, 621.3315052, 622.30, M+H, 3.60, Compound A336;

1-(5-tert-Butyl-2-p-tolyl-2H-pyrazol-3-yl)-3-{4-[1-(2-methyl-2-phenyl-propionyl)-piperidin-4-ylmethyl]-phenyl}-urea, C37H45N5O2, 591.357326, 592.35, M+H, 3.92, Compound A337;

1-{4-[1-(Benzothiazole-6-carbonyl)-piperidin-4-ylmethyl]-phenyl}-3-(5-tert-butyl-2-p-tolyl-2H-pyrazol-3-yl)-urea (0.0229 g), C35H38N6O2S, 606.2776965, 607.26, M+H, 3.48, Compound A338;

1-{4-[1-(3H-Benzotriazole-5-carbonyl)-piperidin-4-ylmethyl]-phenyl}-3-(5-tert-butyl-2-p-tolyl-2H-pyrazol-3-yl)-urea, C34H38N8O2, 590.3117728, 591.31, M+H, 3.08, Compound A339;

1-{4-[1-(Benzo[b]thiophene-2-carbonyl)-piperidin-4-ylmethyl]-phenyl}-3-(5-tert-butyl-2-p-tolyl-2H-pyrazol-3-yl)-urea, C36H39N5O2S, 605.2824476, 606.27, M+H, 4.00, Compound A340;

1-(5-tert-Butyl-2-p-tolyl-2H-pyrazol-3-yl)-3-{4-[1-(2,3-dihydro-benzofuran-5-carbonyl)-piperidin-4-ylmethyl]-phenyl}-urea, C36H41N5O3, 591.3209405, 592.31, M+H, 3.70, Compound A341;

1-(5-tert-Butyl-2-p-tolyl-2H-pyrazol-3-yl)-3-{4-[1-(4-oxo-4,5,6,7-tetrahydro-benzofuran-3-carbonyl)-piperidin-4-ylmethyl]-phenyl}-urea (0.0207 g), C36H41N5O4, 607.3158551, 608.31, M+H, 3.47, Compound A342;

1-(5-tert-Butyl-2-p-tolyl-2H-pyrazol-3-yl)-3-[4-(1-butyryl-piperidin-4-ylmethyl)-phenyl]-urea (0.0138 g), C31H41N5O2, 515.3260258, 516.32, M+H, 3.70, Compound A343;

1-(5-tert-Butyl-2-p-tolyl-2H-pyrazol-3-yl)-3-[4-(1-cyclobutanecarbonyl-piperidin-4-ylmethyl)-phenyl]-urea, C32H41N5O2, 527.3260258, 528.31, M+H, 3.75, Compound A344;

1-(5-tert-Butyl-2-p-tolyl-2H-pyrazol-3-yl)-3-[4-(1-cycloheptanecarbonyl-piperidin-4-ylmethyl)-phenyl]-urea, C35H47N5O2, 569.3729761, 570.36, M+H, 4.10, Compound A345;

1-(5-tert-Butyl-2-p-tolyl-2H-pyrazol-3-yl)-3-[4-(1-cyclohexanecarbonyl-piperidin-4-ylmethyl)-phenyl]-urea, C34H45N5O2, 555.357326, 556.35, M+H, 3.97, Compound A346;

1-(5-tert-Butyl-2-p-tolyl-2H-pyrazol-3-yl)-3-{4-[1-(2-cyclohexyl-acetyl)-piperidin-4-ylmethyl]-phenyl}-urea, C35H47N5O2, 569.3729761, 570.34, M+H, 3.68, Compound A347;

1-(5-tert-Butyl-2-p-tolyl-2H-pyrazol-3-yl)-3-[4-(1-cyclopentanecarbonyl-piperidin-4-ylmethyl)-phenyl]-urea, C33H43N5O2, 541.3416759, 542.30, M+H, 3.42, Compound A348;

1-(5-tert-Butyl-2-p-tolyl-2H-pyrazol-3-yl)-3-{4-[1-(2-cyclopentyl-acetyl)-piperidin-4-ylmethyl]-phenyl}-urea (0.0165 g), C34H45N5O2, 555.357326, 556.33, M+H, 3.53, Compound A349;

1-(5-tert-Butyl-2-p-tolyl-2H-pyrazol-3-yl)-3-{4-[1-(5-oxo-pyrrolidine-2-carbonyl)-piperidin-4-ylmethyl]-phenyl}-urea (0.0119 g), C32H40N6O3, 556.3161894, 557.29, M+H, 2.35, Compound A350;

1-(5-tert-Butyl-2-p-tolyl-2H-pyrazol-3-yl)-3-[4-(1-heptanoyl-piperidin-4-ylmethyl)-phenyl]-urea, C34H47N5O2, 557.3729761, 558.32, M+H, 3.75, Compound A351;

N-[2-(4-{4-[3-(5-tert-Butyl-2-p-tolyl-2H-pyrazol-3-yl)-ureido]-benzyl}-piperidin-1-yl)-2-oxo-ethyl]-benzamide (0.0165 g), C36H42N6O3, 606.3318395, 607.30, M+H, 2.90, Compound A352;

1-(5-tert-Butyl-2-p-tolyl-2H-pyrazol-3-yl)-3-(4-{1-[2-(2,5-dioxo-imidazolidin-4-yl)-acetyl]-piperidin-4-ylmethyl}-phenyl)-urea (0.008 g), C32H39N7O4, 585.3063531, 586.27, M+H, 2.32, Compound A353;

1-(5-tert-Butyl-2-p-tolyl-2H-pyrazol-3-yl)-3-{4-[1-(3-phenyl-propionyl)-piperidin-4-ylmethyl]-phenyl}-urea (0.0233 g), C36H43N5O2, 577.3416759, 578.32, M+H, 3.62, Compound A354;

1-(5-tert-Butyl-2-p-tolyl-2H-pyrazol-3-yl)-3-{4-[1-(3H-imidazole-4-carbonyl)piperidin-4-ylmethyl]-phenyl}-urea, C31H37N7O2, 539.3008737, 540.29, M+H, 2.03, Compound A355;

1-{4-[1-(Benzo[d]imidazo[2,1-b]thiazole-2-carbonyl)-piperidin-4-ylmethyl]-phenyl}-3-(5-tert-butyl-2-p-tolyl-2H- pyrazol-3-yl)-urea, C37H39N7O2S, 645.83, 646.26, M+H, 3.55, Compound A356;

1-(5-tert-Butyl-2-p-tolyl-2H-pyrazol-3-yl)-3-{4-[1-(2H-indazole-3-carbonyl)-piperidin-4-ylmethyl]-phenyl}-urea, C35H39N7O2, 589.3165238, 590.27, M+H, 3.00, Compound A357;

1-(5-tert-Butyl-2-p-tolyl-2H-pyrazol-3-yl)-3-{4-[1-(2-1H-indol-3-yl-acetyl)-piperidin-4-ylmethyl]-phenyl}-urea (0.0116 g), C37H42N6O2, 602.3369249, 603.30, M+H, 3.26, Compound A358;

1-(5-tert-Butyl-2-p-tolyl-2H-pyrazol-3-yl)-3-{4-[1-(1H-indole-3-carbonyl)-piperidin-4-ylmethyl]-phenyl}-urea, C36H40N6O2, 588.3212748, 589.31, M+H, 3.10, Compound A359;

1-(5-tert-Butyl-2-p-tolyl-2H-pyrazol-3-yl)-3-(4-{1-[2(1H-indol-3-yl)-2-oxo-acetyl]-piperidin-4-ylmethyl}-phenyl)-urea, C37H40N6O3, 616.3161894, 617.30, M+H, 3.05, Compound A360;

1-(5-tert-Butyl-2-p-tolyl-2H-pyrazol-3-yl)-3-{4-[1-(1H-indole-5-carbonyl)-piperidin-4-ylmethyl]-phenyl}-urea (0.0131 g), C36H40N6O2, 588.3212748, 589.29, M+H, 3.07, Compound A361;

1-(5-tert-Butyl-2-p-tolyl-2H-pyrazol-3-yl)-3-{4-[1-(1H-indole-6-carbonyl)-piperidin-4-ylmethyl]-phenyl}-urea (0.0084g), C36H40N6O2, 588.3212748, 589.30, M+H, 3.25, Compound A362;

1-(5-tert-Butyl-2-p-tolyl-2H-pyrazol-3-yl)-3-{4-[1-(pyridine-4-carbonyl)-piperidin-4-ylmethyl]-phenyl}-urea (0.0199 g), C33H38N6O2, 550.3056247, 551.28, M+H, 2.65, Compound A364;

1-(5-tert-Butyl-2-p-tolyl-2H-pyrazol-3-yl)-3-{4-[1(2,6-dioxo-hexahydro-pyrimidine-4-carbonyl)-piperidin-4-ylmethyl]-phenyl}-urea, C32H39N7O4, 585.3063531, 586.29, M+H, 2.27, Compound A365;

1-(5-tert-Butyl-2-p-tolyl-2H-pyrazol-3-yl)-3-{4-[1-((S)-5-oxo-pyrrolidine-2-carbonyl)-piperidin-4-ylmethyl]-phenyl}-urea (0.0226 g), C32H40N6O3, 556.3161894, 557.27, M+H, 2.37, Compound A366;

1-(5-tert-Butyl-2-p-tolyl-2H-pyrazol-3-yl)-3-{4-[1-(2-methoxy-acetyl)-piperidin-4-ylmethyl]-phenyl}-urea (0.0177 g), C30H39N5O3, 517.3052904, 518.25, M+H, 2.73, Compound A367;

4-(4-{4-[3-(5-tert-Butyl-2-p-tolyl-2H-pyrazol-3-yl)-ureido]-benzyl}-piperidin-1-yl)-4-oxo-butyric acid methyl ester, C32H41N5O4, 559.3158551, 560.29, M+H, 3.08, Compound A368;

1-(5-tert-Butyl-2-p-tolyl-2H-pyrazol-3-yl)-3-{4-[1-(2-dimethylamino-acetyl)-piperidin-4-ylmethyl]-phenyl}-urea, C31H42N6O2, 530.3369249, 531.33, M+H, 2.05, Compound A369;

1-(5-tert-Butyl-2-p-tolyl-2H-pyrazol-3-yl)-3-(4-{1-[2-(4,6-dimethyl-pyrimidin-2-ylamino)-benzoyl]-piperidin-4-ylmethyl}-phenyl)-urea, C40H46N8O2, 670.374373, 671.36, M+H, 3.58, Compound A370;

1-(5-tert-Butyl-2-p-tolyl-2H-pyrazol-3-yl)-3-(4-{1-[3-(4,6-dimethyl-pyrimidin-2-ylamino)-benzoyl]-piperidin-4-ylmethyl}-phenyl)-urea (0.0163 g), C40H46N8O2, 670.374373, 671.34, M+H, 3.42, Compound A371;

1-(5-tert-Butyl-2-p-tolyl-2H-pyrazol-3-yl)-3-(4-{1-[4-(4,6-dimethyl-pyrimidin-2-ylamino)-benzoyl]-piperidin-4-ylmethyl}-phenyl)-urea, C40H46N8O2, 670.374373, 671.34, M+H, 3.47, Compound A372;

1-(5-tert-Butyl-2-p-tolyl-2H-pyrazol-3-yl)-3-[4-(1-{3-[(4,6-dimethyl-pyrimidin-2-yl)-methyl-amino]-benzoyl}-piperidin-4-ylmethyl)-phenyl]-urea, C41H48N8O2, 684.3900231, 685.35, M+H, 3.45, Compound A373;

N-[2-(4-{4-[3-(5-tert-Butyl-2-p-tolyl-2H-pyrazol-3-yl)-ureido]-benzyl}-piperidin-1-yl)-1-methyl-2-oxo-ethyl]-acetamide (0.0076 g), C32H42N6O3, 558.3318395, 559.29, M+H, 2.52, Compound A374;

N-[2-(4-{4-[3-(5-tert-Butyl-2-p-tolyl-2H-pyrazol-3-yl)-ureido]-benzyl}-piperidin-1-yl)-2-oxo-ethyl]-acetamide (0.0149 g), C31H40N6O3, 544.3161894, 545.26, M+H, 2.43, Compound A375;

1-(5-tert-Butyl-2-p-tolyl-2H-pyrazol-3-yl)-3-{4-[1-(2-phenylamino-acetyl)-piperidin-4-ylmethyl]-phenyl}-urea, C35H42N6O2, 578.3369249, 579.30, M+H, 3.35, Compound A376;

1-(5-tert-Butyl-2-p-tolyl-2H-pyrazol-3-yl)-3-{4-[1-(pyridine-3-carbonyl)-piperidin-4-ylmethyl]-phenyl}-urea (0.0188 g), C33H38N6O2, 550.3056247, 551.27, M+H, 2.82, Compound A377;

1-(5-tert-Butyl-2-p-tolyl-2H-pyrazol-3-yl)3-{4-[1-(2-o-tolyl-acetyl)-piperidin-4-ylmethyl]-phenyl}-urea, C36H43N5O2, 577.3416759, 578.29, M+H, 3.50, Compound A378;

1-(5-tert-Butyl-2-p-tolyl-2H-pyrazol-3-yl)-3-{4-[1-(2-phenoxy-acetyl)-piperidin-4-ylmethyl]-phenyl}-urea, C35H41N5O3, 579.3209405, 580.27, M+H, 3.38, Compound A379;

1-(5-tert-Butyl-2-p-tolyl-2H-pyrazol-3-yl)-3-{4-[1-(pyridine-2-carbonyl)piperidin-4-ylmethyl]-phenyl}-urea (0.0159 g), C33H38N6O2, 550.3056247, 551.27, M+H, 2.95, Compound A380;

1-(5-tert-Butyl-2-p-tolyl-2H-pyrazol-3-yl)-3-{4-[1-(2,2-dimethyl-propionyl)-piperidin-4-ylmethyl]-phenyl}-urea, C32H43N5O2, 529.3416759, 530.29, M+H, 3.40, Compound A381;

1-(5-tert-Butyl-2-p-tolyl-2H-pyrazol-3-yl)-3-{4-[1-(1H-pyrrole-3-carbonyl)-piperidin-4-ylmethyl]-phenyl}-urea, C32H38N6O2, 538.3056247, 539.28, M+H, 2.80, Compound A382;

1-(5-tert-Butyl-2-p-tolyl-2H-pyrazol-3-yl)-3-{4-[1-(quinoline-2-carbonyl)-piperidin-4-ylmethyl]-phenyl}-urea (0.017 g), C37H40N6O2, 600.3212748, 601.27, M+H, 3.32, Compound A383;

1-(5-tert-Butyl-2-p-tolyl-2H-pyrazol-3-yl)-3-{4-[1-(quinoline-3-carbonyl)-piperidin-4-ylmethyl]-phenyl}-urea (0.021 g), C37H40N6O2, 600.3212748, 601.29, M+H, 3.33, Compound A384;

1-(5-tert-Butyl-2-p-tolyl-2H-pyrazol-3-yl)-3-{4-[1-(quinoline-4-carbonyl)-piperidin-4-ylmethyl]-phenyl}-urea (0.0186 g), C37H40N6O2, 600.3212748, 601.29, M+H, 3.08, Compound A385;

1-(5-tert-Butyl-2-p-tolyl-2H-pyrazol-3-yl)-3-{4-[1-(quinoline-6-carbonyl)-piperidin-4-ylmethyl]-phenyl}-urea (0.0223 g), C37H40N6O2, 600.3212748, 601.29, M+H, 2.98, Compound A386;

1-{4-[1-(2-Benzo[b]thiophen-3-yl-acetyl)-piperidin-4-ylmethyl]-phenyl}-3-(5-tert-butyl-2-p-tolyl-2H-pyrazol-3-yl)-urea, C37H41N5O2S, 619.2980976, 620.25, M+H, 3.63, Compound A387;

1-(5-tert-Butyl-2-p-tolyl-2H-pyrazol-3-yl)-3-{4-[1-(2-thiophen-2-yl-acetyl)-piperidin-4-ylmethyl]-phenyl}-urea (0.0151 g), C33H39N5O2S, 569.2824476, 570.25, M+H, 3.27, Compound A388;

1-(5-tert-Butyl-2-p-tolyl-2H-pyrazol-3-yl)-3-{4-[1-(2-thiophen-3-yl-acetyl)-piperidin-4-ylmethyl]-phenyl}-urea (0.0143 g), C33H39N5O2S, 569.2824476, 570.24, M+H, 3.23, Compound A389;

4-{3-[3-(5-tert-Butyl-2-p-tolyl-2H-pyrazol-3-yl)-ureido]-benzyl}-piperidine-1-carboxylic acid (2,3-dihydro-benzo

[1,4]dioxin-6-yl)-amide, C36H42N6O4, 622.33, 623.28, M+H, 3.08, Compound A390;

4-{3-[3-(5-tert-Butyl-2-p-tolyl-2H-pyrazol-3-yl)-ureido]-benzyl}-piperidine-1-carboxylic acid (2,3-dihydro-benzofuran-5-yl)-amide, C36H42N6O3, 606.33, 607.29, M+H, 3.10, Compound A391;

4-{3-[3-(5-tert-Butyl-2-p-tolyl-2H-pyrazol-3-yl)-ureido]-benzyl}-piperidine-1-carboxylic acid (2,5-dimethoxyphenyl)-amide, C36H44N6O4, 624.3424, 625.28, M+H, 3.4, Compound A392;

4-{3-[3-(5-tert-Butyl-2-p-tolyl-2H-pyrazol-3-yl)-ureido]-benzyl}-piperidine-1-carboxylic acid (3,4,5-trimethoxyphenyl)-amide, C37H46N6O5, 654.3530, 655.32, M+H, 3.02, Compound A393;

4-{3-[3-(5-tert-Butyl-2-p-tolyl-2H-pyrazol-3-yl)-ureido]-benzyl}-piperidine-1-carboxylic acid benzo[1,3]dioxol-5-ylamide, C35H40N6O4, 608.3111, 609.27, M+H, 3.10, Compound A394;

4-{3-[3-(5-tert-Butyl-2-p-tolyl-2H-pyrazol-3-yl)-ureido]-benzyl}-piperidine-1-carboxylic acid (3,4-dimethoxyphenyl)amide, C36H44N6O4, 624.3424, 625.28, M+H, 2.98, Compound A395;

4-{3-[3-(5-tert-Butyl-2-p-tolyl-2H-pyrazol-3-yl)-ureido]-benzyl}-piperidine-1-carboxylic acid (3,5-dimethoxyphenyl)-amide, C36H44N6O4, 624.3424, 625.29, M+H, 3.20, Compound A396;

4-{3-[3-(5-tert-Butyl-2-p-tolyl-2H-pyrazol-3-yl)-ureido]-benzyl}-piperidine-1-carboxylic acid (3,5-dimethyl-isoxazol-4-yl)-amide, C33H41N7O3, 583.3271, 584.28, M+H, 2.77, Compound A397;

4-{3-[3-(5-tert-Butyl-2-p-tolyl-2H-pyrazol-3-yl)-ureido]-benzyl}-piperidine-1-carboxylic acid (3-chloro-4-methoxy-phenyl)-amide, C35H41ClN6O3, 628.29, 629.24, M+H, 3.32, Compound A398;

4-{3-[3-(5-tert-Butyl-2-p-tolyl-2H-pyrazol-3-yl)-ureido]-benzyl}-piperidine-1-carboxylic acid thiophen-3-ylamide, C32H38N6O2S, 570.28, 571.23, M+H, 3.18, Compound A399;

4-{3-[3-(5-tert-Butyl-2-p-tolyl-2H-pyrazol-3-yl)-ureido]-benzyl}-piperidine-1-carboxylic acid (4-difluoromethoxy-phenyl)-amide, C35H40F2N6O3, 630.31, 631.26, M+H, 3.27, Compound A400;

4-{3-[3-(5-tert-Butyl-2-p-tolyl-2H-pyrazol-3-yl)-ureido]-benzyl}-piperidine-1-carboxylic acid (4-dimethylaminophenyl)-amide, C36H45N7O2, 607.3635, 608.34, M+H, 2.15, Compound A401;

4-{3-[3-(5-tert-Butyl-2-p-tolyl-2H-pyrazol-3-yl)-ureido]-benzyl}-piperidine-1-carboxylic acid (4-trifluoromethoxy-phenyl)-amide, C35H39F3N6O3, 648.30, 649.23, M+H, 3.52, Compound A402;

4-{3-[3-(5-tert-Butyl-2-p-tolyl-2H-pyrazol-3-yl)-ureido]-benzyl}-piperidine-1-carboxylic acid (4-acetyl-phenyl)-amide (16 mg), C36H42N6O3, 606.33, 607.28, M+H, 3.07, Compound A403;

4-{3-[3-(5-tert-Butyl-2-p-tolyl-2H-pyrazol-3-yl)-ureido]-benzyl}-piperidine-1-carboxylic acid benzo[1,2,5]thiadiazol-4-ylamide, C34H38N8O2S, 622.2838, 623.23, M+H, 3.55, Compound A404;

4-{3-[3-(5-tert-Butyl-2-p-tolyl-2H-pyrazol-3-yl)-ureido]-benzyl}-piperidine-1-carboxylic acid (4-methoxy-2-methyl-phenyl)-amide, C36H44N6O3, 608.3475, 609.30, M+H, 3.10, Compound A405;

4-{3-[3-(5-tert-Butyl-2-p-tolyl-2H-pyrazol-3-yl)-ureido]-benzyl}-piperidine-1-carboxylic acid (5-chloro-2,4-dimethoxy-phenyl)-amide, C36H43ClN6O4, 658.30, 659.25, M+H, 3.40, Compound A406;

4-{3-[3-(5-tert-Butyl-2-p-tolyl-2H-pyrazol-3-yl)-ureido]-benzyl}-piperidine-1-carboxylic acid (5-methyl-2-trifluoromethyl-furan-3-yl)-amide, C34H39F3N6O3, 636.30, 637.23, M+H, 3.43, Compound A407;

4-{3-[3-(5-tert-Butyl-2-p-tolyl-2H-pyrazol-3-yl)-ureido]-benzyl}-piperidine-1-carboxylic acid (5-methyl-3-phenyl-isoxazol-4-yl)-amide, C38H43N7O3, 645.3427, 646.27, M+H, 3.12, Compound A408;

4-{3-[3-(5-tert-Butyl-2-p-tolyl-2H-pyrazol-3-yl)-ureido]-benzyl}-piperidine-1-carboxylic acid (6-fluoro-4H-benzo[1,3]dioxin-8-yl)-amide, C36H41FN6O4, 640.32, 641.25, M+H, 3.37, Compound A409;

3-[(4-{3-[3-(5-tert-Butyl-2-p-tolyl-2H-pyrazol-3-yl)-ureido]-benzyl}-piperidine-1-carbonyl)-amino]-benzoic acid ethyl ester, C37H44N6O4, 636.3424, 637.29, M+H, 3.37, Compound A410;

4-[(4-{3-[3-(5-tert-Butyl-2-p-tolyl-2H-pyrazol-3-yl)-ureido]-benzyl}-piperidine-1-carbonyl)-amino]-benzoic acid methyl ester, C36H42N6O4, 622.33, 623.28, M+H, 3.22, Compound A411;

3-{3-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzo[1,4]dioxin-6-yl)-amide, a mixture of endo- and exo-isomers, (0.0153 g), C38H44N6O4, 648.3424042, 649.27, M+H, 3.20, Compound A412;

3-{4-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzo[1,4]dioxin-6-yl)-amide, a mixture of endo- and exo-isomers, C38H44N6O4, 648.3424042, 649.27, M+H, 3.18, Compound A413;

4-{4-[3-(5-tert-Butyl-2-p-tolyl-2H-pyrazol-3-yl)-ureido]-benzyl}-piperidine-1-carboxylic acid (2,3-dihydro-benzo[1,4]dioxin-6-yl)-amide, C36H42N6O4, 622.3267542, 623.36, M+H, 3.08, Compound A414;

3-{3-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzofuran-5-yl)-amide, a mixture of endo- and exo-isomers, C38H44N6O3, 632.3474896, 633.29, M+H, 3.25, Compound A415;

3-{4-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzofuran-5-yl)-amide, C38H44N6O3, 632.3474896, 633.28, M+H, 3.23, Compound A416;

4-{4-[3-(5-tert-Butyl-2-p-tolyl-2H-pyrazol-3-yl)-ureido]-benzyl}-piperidine-1-carboxylic acid (2,3-dihydro-benzofuran-5-yl)-amide, C36H42N6O3, 606.3318395, 607.26, M+H, 3.15, Compound A417;

3-{3-[3-(5-tert-Butyl-2-p-tolyl-2H-pyrazol-3-yl)ureido]-benzyl}-8-aza-bicyclo[3.2.1]octane-8-carboxylic acid (2,5-dimethoxy-phenyl)-amide, a mixture of endo- and exo-isomers, C38H46N6O4, 650.3580543, 651.29, M+H, 3.58, Compound A418;

3-{4-[3-(5-tert-Butyl-2-p-tolyl-2H-pyrazol-3-yl)-ureido]-benzyl}-8-aza-bicyclo[3.2.1]octane-8-carboxylic acid (2,5-dimethoxy-phenyl)-amide, a mixture of endo- and exo-isomers, C38H46N6O4, 650.3580543, 651.27, M+H, 3.48, Compound A419;

4-{4-[3-(5-tert-Butyl-2-p-tolyl-2H-pyrazol-3-yl)-ureido]-benzyl}-piperidine-1-carboxylic acid (2,5-dimethoxyphenyl)amide, C36H44N6O4, 624.3424042, 625.27, M+H, 3.37, Compound A420;

3-{3-[3-(5-tert-Butyl-2-p-tolyl-2H-pyrazol-3-yl)-ureido]-benzyl}-8-aza-bicyclo[3.2.1]octane-8-carboxylic acid (2-methyl-5-phenyl-furan-3-yl)-amide, a mixture of endo- and exo-isomers, C41H46N6O3, 670.3631397, 371.30, M+H, 3.58, Compound A421;

3-{4-[3-(5-tert-Butyl-2-p-tolyl-2H-pyrazol-3-yl)-ureido]-benzyl}-8-aza-bicyclo[3.2.1]octane-8-carboxylic acid (2-methyl-5-phenyl-furan-3-yl)-amide, a mixture of endo- and exo-isomers, C41H46N6O3, 670.3631397, 671.29, M+H, 3.58, Compound A422;

4-{4-[3-(5-tert-Butyl-2-p-tolyl-2H-pyrazol-3-y)-ureido]-benzyl -piperidine-1-carboxylic acid (2-methyl-5-phenyl-furan-3-yl)-amide, C39H44N6O3, 644.3474896, 645.27, M+H, 3.48, Compound A423;

3-{3-[3-(5-tert-Butyl-2-p-tolyl-2H-pyrazol-3-yl)-ureido]-benzyl}-8-aza-bicyclo[3.2.1]octane-8-carboxylic acid (3,4,5-trimethoxy-phenyl)-amide, a mixture of endo- and exo-isomers, C39H48N6O5, 680.368619, 681.30, M+H, 3.23, Compound A424;

3-{4-[3-(5-tert-Butyl-2-p-tolyl-2H-pyrazol-3-yl)-ureido]-benzyl }-8-aza-bicyclo[3.2.1]octane-8-carboxylic acid (3,4,5-trimethoxy-phenyl)-amide, a mixture of endo- and exo-isomers, C39H48N6O5, 680.368619, 681.29, M+H, 3.23, Compound A425;

4-{4-[3-(5-tert-Butyl-2-p-tolyl-2H-pyrazol-3-yl)-ureido]-benzyl}-piperidine-1-carboxylic acid (3,4,5-trimethoxy-phenyl)-amide, C37H46N6O5, 654.352969, 655.26, M+H, 3.05, Compound A426;

3-{3-[3-(5-tert-Butyl-2-p-tolyl-2H-pyrazol-3-yl)-ureido]-benzyl}-8-aza-bicyclo[3.2.1]octane-8-carboxylic acid benzo[1,3]dioxol-5-ylamide, a mixture of endo- and exo-isomers, C37H42N6O4, 634.3267542, 635.25, M+H, 3.23, Compound A427;

3-{4-[3-(5-tert-Butyl-2-p-tolyl-2H-pyrazol-3-yl)-ureido]-benzyl}-8-aza-bicyclo[3.2.1]octane-8-carboxylic acid benzo[1,3]dioxol-5-ylamide, a mixture of endo- and exo-isomers, C37H42N6O4, 634.3267542, 635.26, M+H, 3.22, Compound A428;

4-{4-[3-(5-tert-Butyl-2-p-tolyl-2H-pyrazol-3-yl)-ureido]-benzyl}-piperidine-1-carboxylic acid benzo[1,3]dioxol-5-ylamide (0.013 g), C35H40N6O4, 608.3111041, 609.26, M+H, 3.10, Compound A429;

3-{3-[3-(5-tert-Butyl-2-p-tolyl-2H-pyrazol-3-yl)-ureido]-benzyl}-8-aza-bicyclo[3.2.1]octane-8-carboxylic acid (3,4-dimethoxy-phenyl)-amide, a mixture of endo- and exo-isomers, C38H46N6O4, 650.3580543, 651.30, M+H, 3.13, Compound A430;

3-{4-[3-(5-tert-Butyl-2-p-tolyl-2H-pyrazol-3-yl)-ureido]-benzyl}-8-aza-bicyclo[3.2.1]octane-8-carboxylic acid (3,4-dimethoxy-phenyl)-amide, a mixture of endo- and exo-isomers, C38H46N6O4, 650.3580543, 651.30, M+H, 3.08, Compound A431;

4-{4-[3-(5-tert-Butyl-2-p-tolyl-2H-pyrazol-3-yl)-ureido]-benzyl}-piperidine-1-carboxylic acid (3,4-dimethoxy-phenyl)-amide, C36H44N6O4, 624.3424042, 625.28, M+H, 2.98, Compound A432;

3-{3-[3-(5-tert-Butyl-2-p-tolyl-2H-pyrazol-3-yl)-ureido]-benzyl}-8-aza-bicyclo[3.2.1]octane-8-carboxylic acid (3,5-dimethoxy-phenyl)-amide, a mixture of endo- and exo-isomers, C38H46N6O4, 650.3580543, 651.31, M+H, 3.30, Compound A433;

3-{4-[3-(5-tert-Butyl-2-p-tolyl-2H-pyrazol-3-yl)-ureido]-benzyl}-8-aza-bicyclo[3.2.1]octane-8-carboxylic acid (3,5-dimethoxy-phenyl)amide, a mixture of endo- and exo-isomers, C38H46N6O4, 650.3580543, 651.29, M+H, 3.32, Compound A434;

4-{4-[3-(5-tert-Butyl-2-p-tolyl-2H-pyrazol-3-yl)-ureido]-benzyl}-piperidine-1-carboxylic acid (3,5-dimethoxy-phenyl)-amide, C36H44N6O4, 624.3424042, 625.30, M+H, 3.20, Compound A435;

3-{3-[3-(5-tert-Butyl-2-p-tolyl-2H-pyrazol-3-yl)-ureido]-benzyl}-8-aza-bicyclo[3.2.1]octane-8-carboxylic acid (3,5-dimethyl-isoxazol-4-yl)-amide, a mixture of endo- and exo-isomers, C35H43N7O3, 609.3427386, 610.29, M+H, 2.90, Compound A436;

3-{4-[3-(5-tert-Butyl-2-p-tolyl-2H-pyrazol-3-yl)-ureido]-benzyl}-8-aza-bicyclo[3.2.1]octane-8-carboxylic acid (3,5-dimethyl-isoxazol-4-yl)-amide, a mixture of endo- and exo-isomers, C35H43N7O3, 609.3427386, 610.29, M+H, 2.90, Compound A437;

4-{4-[3-(5-tert-Butyl-2-p-tolyl-2H-pyrazol-3-yl)-ureido]-benzyl}-piperidine-1-carboxylic acid (3,5-dimethyl-isoxazol-4-yl)amide, C33H41N7O3, 583.3270885, 584.27, M+H, 2.78, Compound A438;

3-{3-[3-(5-tert-Butyl-2-p-tolyl-2H-pyrazol-3-yl)-ureido]-benzyl}-8-aza-bicyclo[3.2.1]octane-8-carboxylic acid (3-chloro-4-methoxy-phenyl)-amide, a mixture of endo- and exo-isomers, C37H43ClN6O3, 654.3085173, 655.27, M+H, 3.40, Compound A439;

3-{4-[3-(5-tert-Butyl-2-p-tolyl-2H-pyrazol-3-yl)-ureido]-benzyl}-8-aza-bicyclo[3.2.1 ]octane-8-carboxylic acid (3-chloro-4-methoxy-phenyl)-amide, a mixture of endo- and exo-isomers, C37H43ClN6O3, 654.3085173, 655.26, M+H, 3.38, Compound A440;

4-{4-[3-(5-tert-Butyl-2-p-tolyl-2H-pyrazol-3-yl)-ureido]-benzyl}-piperidine-1-carboxylic acid (3-chloro-4-methoxy-phenyl)-amide, C35H41ClN6O3, 628.2928672, 629.25, M+H, 3.30, Compound A441;

3-{3-[3-(5-tert-Butyl-2-p-tolyl-2H-pyrazol-3-yl)-ureido]-benzyl}-8-aza-bicyclo[3.2.1 ]octane-8-carboxylic acid thiophen-3-ylamide, a mixture of endo- and exo-isomers, C34H40N6O2S, 596.2933466, 597.24, M+H, 3.25, Compound A442;

3-{4-[3-(5-tert-Butyl-2-p-tolyl-2H-pyrazol-3-yl)-ureido]-benzyl}-8-aza-bicyclo[3.2.1 ]octane-8-carboxylic acid thiophen-3-ylamide, a mixture of endo- and exo-isomers, C34H40N6O2S, 596.2933466, 597.24, M+H, 3.25, Compound A443;

4-{4-[3-(5-tert-Butyl-2-p-tolyl-2H-pyrazol-3-yl)-ureido]-benzyl}-piperidine-1-carboxylic acid thiophen-3-ylamide, C32H38N6O2S, 570.2776965, 571.23, M+H, 3.15, Compound A444;

3-{3-[3-(5-tert-Butyl-2-p-tolyl-2H-pyrazol-3-yl)-ureido]-benzyl}-8-aza-bicyclo[3.2.1]octane-8-carboxylic acid (4-difluoromethoxy-phenyl)-amide, a mixture of endo- and exo-isomers, C37H42F2N6O3, 656.328646, 657.27, M+H, 3.38, Compound A445;

3-{4-[3-(5-tert-Butyl-2-p-tolyl-2H-pyrazol-3-yl)-ureido]-benzyl}-8-aza-bicyclo[3.2.1]octane-8-carboxylic acid (4-difluoromethoxy-phenyl)-amide, a mixture of endo- and exo-isomers, C37H42F2N6O3, 656.328646, 657.27, M+H, 3.33, Compound A446;

4-{4-[3-(5-tert-Butyl-2-p-tolyl-2H-pyrazol-3-yl)-ureido]-benzyl}-piperidine-1-carboxylic acid (4-difluoromethoxy-phenyl)-amide, C35H40F2N6O3, 630.3129959, 631.27, M+H, 3.27, Compound A447;

3-{3-[3-(5-tert-Butyl-2-p-tolyl-2H-pyrazol-3-yl)-ureido]-benzyl}-8-aza-bicyclo[3.2.1]octane-8-carboxylic acid (4-dimethylamino-phenyl)-amide, a mixture of endo- and exo-isomers, C38H47N7O2, 633.3791241, 634.36, M+H, 2.33, Compound A448;

3-4-[3-(5-tert-Butyl-2-p-tolyl-2H-pyrazol-3-yl)-ureido]-benzyl -8-aza-bicyclo[3.2.1]octane-8-carboxylic acid (4-dimethylamino-phenyl)-amide, a mixture of endo- and exo-isomers, C38H47N7O2, 633.3791241, 634.36, M+H, 2.33, Compound A449;

4-{4-[3-(5-tert-Butyl-2-p-tolyl-2H-pyrazol-3-yl)-ureido]-benzyl}-piperidine-1-carboxylic acid (4-dimethylaminophenyl)-amide (0.0157 g), C36H45N7O2, 607.363474, 608.34, M+H, 2.22, Compound A450;

3-{3-[3-(5-tert-Butyl-2-p-tolyl-2H-pyrazol-3-yl)-ureido]-benzyl}-8-aza-bicyclo[3.2.1]octane-8-carboxylic acid (4-trifluoromethoxy-phenyl)-amide, a mixture of endo- and exo-isomers, C37H41F3N6O3, 674.3192242, 675.27, M+H, 3.63, Compound A451;

3-{4-[3-(5-tert-Butyl-2-p-tolyl-2H-pyrazol-3-yl)-ureido]-benzyl}-8-aza-bicyclo[3.2.1]octane-8-carboxylic acid (4-trifluoromethoxy-phenyl)-amide, a mixture of endo- and exo-isomers, C37H41F3N6O3, 674.3192242, 675.26, M+H, 3.62, Compound A452;

3-{3-[3-(5-tert-Butyl-2-p-tolyl-2H-pyrazol-3-yl)-ureido]-benzyl}-8-aza-bicyclo[3.2.1]octane-8-carboxylic acid (4-acetyl-phenyl)-amide, a mixture of endo- and exo-isomers, C38H44N6O3, 632.3474896, 633.31, M+H, 3.20, Compound A453;

3-{4-[3-(5-tert-Butyl-2-p-tolyl-2H-pyrazol-3-yl)-ureido]-benzyl}-8-aza-bicyclo[3.2.1]octane-8-carboxylic acid (4-acetyl-phenyl)-amide, a mixture of endo- and exo-isomers, C38H44N6O3, 632.3474896, 633.31, M+H, 3.18, Compound A454;

4-{4-[3-(5-tert-Butyl-2-p-tolyl-2H-pyrazol-3-yl)-ureido]-benzyl}-piperidine-1-carboxylic acid (4-acetyl-phenyl)-amide, C36H42N6O3, 606.3318395, 607.30, M+H, 3.07, Compound A455;

3-{3-[3-(5-tert-Butyl-2-p-tolyl-2H-pyrazol-3-yl)ureido]-benzyl}-8-aza-bicyclo[3.2.1]octane-8-carboxylic acid benzo[1,2,5]thiadiazol-4-ylamide, a mixture of endo- and exo-isomers, C3 6H40N8O2S, 648.2994946, 649.26, M+H, 3.68, Compound A456;

3-4-[3-(5-tert-Butyl-2-p-tolyl-2H-pyrazol-3-yl)-ureido]-benzyl}-8-aza-bicyclo[3.2.1]octane-8-carboxylic acid benzo[1,2,5]thiadiazol-4-ylamide, a mixture of endo- and exo-isomers, C36H40N8O2S, 648.2994946, 649.26, M+H, 3.68, Compound A457;

4-{4-[3-(5-tert-Butyl-2-p-tolyl-2H-pyrazol-3-yl)-ureido]-benzyl}-piperidine-1-carboxylic acid benzo[1,2,5]thiadiazol-4-ylamide, C34H38N8O2S, 622.2838446, 623.26, M+H, 3.57, Compound A458;

3-{3-[3-(5-tert-Butyl-2-p-tolyl-2H-pyrazol-3-yl)-ureido]-benzyl}-8-aza-bicyclo[3.2.1]octane-8-carboxylic acid (4-methoxy-2-methyl-phenyl)-amide, a mixture of endo- and exo-isomers, C38H46N6O3, 634.3631397, 635.32, M+H, 3.22, Compound A459;

3-{4-[3-(5-tert-Butyl-2-p-tolyl-2H-pyrazol-3-yl)-ureido]-benzyl}-8-aza-bicyclo[3.2.1]octane-8-carboxylic acid (4-methoxy-2-methyl-phenyl)-amide, a mixture of endo- and exo-isomers, C38H46N6O3, 634.3631397, 635.32, M+H, 3.28, Compound A460;

4-{4-[3-(5-tert-Butyl-2-p-tolyl-2H-pyrazol-3-yl)-ureido]-benzyl}-piperidine-1-carboxylic acid (4-methoxy-2-methyl-phenyl)-amide, C36H44N6O3, 608.3474896, 609.30, M+H, 3.13, Compound A461;

3-{3-[3-(5-tert-Butyl-2-p-tolyl-2H-pyrazol-3-yl)-ureido]-benzyl}-8-aza-bicyclo[3.2.1]octane-8-carboxylic acid (5-chloro-2,4-dimethoxy-phenyl)amide, a mixture of endo- and exo-isomers, C38H45ClN6O4, 684.319082, 685.29, M+H, 3.52, Compound A462;

3-{4-[3-(5-tert-Butyl-2-p-tolyl-2H-pyrazol-3-yl)-ureido]-benzyl}-8-aza-bicyclo[3.2.1]octane-8-carboxylic acid (5-chloro-2,4-dimethoxy-phenyl)-amide, a mixture of endo- and exo-isomers, C38H45ClN6O4, 684.319082, 685.29, M+H, 3.53, Compound A463;

4-{4-[3-(5-tert-Butyl-2-p-tolyl-2H-pyrazol-3-yl)-ureido]-benzyl}-piperidine-1-carboxylic acid (5-chloro-2,4-dimethoxy-phenyl)-amide, C36H43ClN6O4, 658.3034319, 659.27, M+H, 3.40, Compound A464;

3-{3-[3-(5-tert-Butyl-2-p-tolyl-2H-pyrazol-3-yl)-ureido]-benzyl}-8-aza-bicyclo[3.2.1]octane-8-carboxylic acid (5-methyl-2-trifluoromethyl-furan-3-yl)-amide, a mixture of endo- and exo-isomers, C36H41F3N6O3, 662.3192242, 663.27, M+H, 3.57, Compound A465;

3-{4-[3-(5-tert-Butyl-2-p-tolyl-2H-pyrazol-3-yl)-ureido]-benzyl}-8-aza-bicyclo[3.2.1]octane-8-carboxylic acid (5-methyl-2-trifluoromethyl-furan-3-yl)-amide, a mixture of endo- and exo-isomers, C36H41F3N6O3, 662.3192242, 663.29, M+H, 3.63, Compound A466;

4-{4-[3-(5-tert-Butyl-2-p-tolyl-2H-pyrazol-3-yl)-ureido]-benzyl}-piperidine-1-carboxylic acid (5-methyl-2-trifluoromethyl-furan-3-yl)-amide, C34H39F3N6O3, 636.3035742, 637.24, M+H, 3.45, Compound A467;

3-{3-[3-(5-tert-Butyl-2-p-tolyl-2H-pyrazol-3-yl)-ureido]-benzyl}-8-aza-bicyclo[3.2.1]octane-8-carboxylic acid (5-methyl-3-phenyl-isoxazol-4-yl)-amide, a mixture of endo- and exo-isomers, C40H45N7O3, 671.3583886, 672.31, M+H, 3.20, Compound A468;

3-{4-[3-(5-tert-Butyl-2-p-tolyl-2H-pyrazol-3-yl)-ureido]-benzyl}-8-aza-bicyclo[3.2.1 ]octane-8-carboxylic acid (5-methyl-3-phenyl-isoxazol-4-yl)-amide, a mixture of endo- and exo-isomers, C40H45N7O3, 671.3583886, 672.32, M+H, 3.20, Compound A469;

4-{4-[3-(5-tert-Butyl-2-p-tolyl-2H-pyrazol-3-yl)-ureido]-benzyl}-piperidine-1-carboxylic acid (5-methyl-3-phenyl-isoxazol-4-yl)-amide, C38H43N7O3, 645.3427386, 646.29, M+H, 3.08, Compound A470;

3-{3-[3-(5-tert-Butyl-2-p-tolyl-2H-pyrazol-3-yl)-ureido]-benzyl}-8-aza-bicyclo[3.2.1]octane-8-carboxylic acid (6-fluoro-4H-benzo[1,3]dioxin-8-yl)-amide, a mixture of endo- and exo-isomers, C38H43FN6O4, 666.3329824, 667.29, M+H, 3.48, Compound A471;

3-{4-[3-(5-tert-Butyl-2-p-tolyl-2H-pyrazol-3-yl)-ureido]-benzyl}-8-aza-bicyclo[3.2.1 ]octane-8-carboxylic acid (6-fluoro-4H-benzo[1,3]dioxin-8-yl)-amide, a mixture of endo- and exo-isomers, C38H43FN6O4, 666.3329824, 667.30, M+H, 3.50, Compound A472;

4-{4-[3-(5-tert-Butyl-2-p-tolyl-2H-pyrazol-3-yl)-ureido]-benzyl}-piperidine-1-carboxylic acid (6-fluoro-4H-benzo[1,3]dioxin-8-yl)-amide, C36H41FN6O4, 640.3173324, 641.28, M+H, 3.42, Compound A473;

3-[(3-{3-[3-(5-tert-Butyl-2-p-tolyl-2H-pyrazol-3-yl)-ureido]-benzyl}-8-aza-bicyclo[3.2.1]octane-8-carbonyl)-amino]-benzoic acid ethyl ester, a mixture of endo- and exo-isomers, C39H46N6O4, 662.3580543, 663.32, M+H, 3.48, Compound A474;

3-[(3-{4-[3-(5-tert-Butyl-2-p-tolyl-2H-pyrazol-3-yl)-ureido]-benzyl}-8-aza-bicyclo[3.2.1]octane-8-carbonyl)-amino]-benzoic acid ethyl ester, a mixture of endo- and exo-isomers, C39H46N6O4, 662.3580543, 663.32, M+H, 3.52, Compound A475;

3-[(4-{4-[3-(5-tert-Butyl-2-p-tolyl-2H-pyrazol-3-yl)-ureido]-benzyl}-piperidine-1-carbonyl)-amino]-benzoic acid ethyl ester, C37H44N6O4, 636.3424042, 637.31, M+H, 3.38, Compound A476;

4-[(3-{3-[3-(5-tert-Butyl-2-p-tolyl-2H-pyrazol-3-yl)-ureido]-benzyl}-8-aza-bicyclo[3.2.1]octane-8-carbonyl)-amino]-benzoic acid methyl ester, a mixture of endo- and exo-isomers, C38H44N6O4, 648.3424042, 649.29, M+H, 3.38, Compound A477;

4-[(3-{4-[3-(5tert-Butyl-2-p-tolyl-2H-pyrazol-3-yl)-ureidol-benzyl}-8-aza-bicyclo[3.2.1]octane-8-carbonyl)- amino]-benzoic acid methyl ester, a mixture of endo- and exo-isomers, C38H44N6O4, 648.3424042, 649.31, M+H, 3.38, Compound A478;

4-[(4-{4-[3-(5-tert-Butyl-2-p-tolyl-2H-pyrazol-3-yl)-ureido]-benzyl}-piperidine-1-carbonyl)-amino]-benzoic acid methyl ester, C36H42N6O4, 622.3267542, 623.30, M+H, 3.22, Compound A479;

1-(5-tert-Butyl-2-p-tolyl-2H-pyrazol-3-yl)-3-{3-[1-(1,3,5-trimethyl-1H-pyrazole-4-sulfonyl)-piperidin-4-ylmethyl]-phenyl}-urea, C33H43N7O3S, 617.3148104, 618.26, M+H, 3.18, Compound A480;

1-{3-[1-(Butane-1-sulfonyl)piperidin-4-ylmethyl]-phenyl}-3-(5-tert-butyl-2-p-tolyl-2H-pyrazol-3-yl)-urea, C31H43N5O3S, 565.3086624, 566.25, M+H, 3.42, Compound A481;

1-(5-tert-Butyl-2-p-tolyl-2H-pyrazol-3-yl)-3-{3-[1-(naphthalene-1-sulfonyl)-piperidin-4-ylmethyl]-phenyl}-urea, C37H41N5O3S, 635.2930123, 636.23, M+H, 3.73, Compound A482;

1-{3-[1-(Benzo[1,2,5]thiadiazole-5-sulfonyl)-piperidin-4-ylmethyl]-phenyl}-3-(5-tert-butyl-2-p-tolyl-2H-pyrazol-3-yl)-urea, C33H37N7O3S2, 643.2399319, 644.19, M+H, 3.52, Compound A483;

1-(5-tert-Butyl-2-p-tolyl-2H-pyrazol-3-yl)-3-{3-[1-(2,3-dihydro-benzo[1,4]dioxine-6-sulfonyl)-piperidin-4-ylmethyl]-phenyl}-urea, C35H41N5O5S, 643.2828416, 644.22, M+H, 3.42, Compound A484;

1-(5-tert-Butyl-2-p-tolyl-2H-pyrazol-3-yl)-3-{3-[1-(2,3-dihydro-benzofuran-5-sulfonyl)-piperidin-4-ylmethyl]-phenyl}-urea, C35H41N5O4S, 627.2879269, 628.23, M+H, 3.45, Compound A485;

1-(5-tert-Butyl-2-p-tolyl-2H-pyrazol-3-yl)-3-{3-[1-(2,4-dichloro-benzenesulfonyl)-piperidin-4-ylmethyl]-phenyl}-urea, C33H37Cl2N5O3S, 653.1994176, 654.16, M+H, 3.80, Compound A486;

1-(5-tert-Butyl-2-p-tolyl-2H-pyrazol-3-yl)-3-{3-[1-(2,4-difluoro-benzenesulfonyl)-piperidin-4-ylmethyl]-phenyl}-urea, C33H37F2N5O3S, 621.2585186, 622.19, M+H, 3.53, Compound A487;

1-(5-tert-Butyl-2-p-tolyl-2H-pyrazol-3-yl)-3-{3-[1-(2,5-dichloro-benzenesulfonyl)-piperidin-4-ylmethyl]-phenyl}-urea, C33H37Cl2N5O3S, 653.1994176, 654.16, M+H, 3.80, Compound A488;

1-(5-tert-Butyl-2-p-tolyl-2H-pyrazol-3-yl)-3-{3-[1-(2,5-dimethoxy-benzenesulfonyl)piperidin-4-ylmethyl]-phenyl}-urea, C35H43N5O5S, 645.2984916, 646.24, M+H, 3.40, Compound A489;

3-(4-{3-[3-(5-tert-Butyl-2-p-tolyl-2H-pyrazol-3-yl)-ureido]-benzyl}-piperidine-1-sulfonyl)-thiophene-2-carboxylic acid methyl ester, C33H39N5O5S2, 649.2392633, 650.18, M+H, 3.35, Compound A490;

1-(5-tert-Butyl-2-p-tolyl-2H-pyrazol-3-yl)-3-{3-[1-(2-chloro-4-fluoro-benzenesulfonyl)-piperidin-4-ylmethyl]-phenyl}-urea, C33H37ClFN5O3S, 637.2289681, 638.18, M+H, 3.67, Compound A491;

1-(5-tert-Butyl-2-p-tolyl-2H-pyrazol-3-yl)-3-{3-[1-(2-chloro-benzenesulfonyl)-piperidin-4-ylmethyl]-phenyl}-urea, C33H38ClN5O3S, 619.2383899, 620.20, M+H, 3.60, Compound A492;

1-(5-tert-Butyl-2-p-tolyl-2H-pyrazol-3-yl}-3-{3-[1-(2-fluoro-benzenesulfonyl)-piperidin-4-ylmethyl]-phenyl}-urea, C33H38FN5O3S, 603.2679404, 604.24, M+H, 3.43, Compound A493;

1-(5-tert-Butyl-2-p-tolyl-2H-pyrazol-3-yl)-3-{3-[1-(2,4,6-trimethyl-benzenesulfonyl)-piperidin-4-ylmethyl]-phenyl}-urea, C36H45N5O3S, 627.3243124, 628.29, M+H, 3.92, Compound A494;

1-(5-tert-Butyl-2-p-tolyl-2H-pyrazol-3-yl)-3-{3-[1-(naphthalene-2-sulfonyl)-piperidin-4-ylmethyl]-phenyl}-urea, C37H41N5O3S, 635.2930123, 636.27, M+H, 3.73, Compound A495;

1-(5-tert-Butyl-2-p-tolyl-2H-pyrazol-3-yl)-3-{3-[1-(thiophene-2-sulfonyl)-piperidin-4-ylmethyl]-phenyl}-urea, C31H37N5O3S2, 591.2337839, 592.21, M+H, 3.42, Compound A496;

1-(5-tert-Butyl-2-p-tolyl-2H-pyrazol-3-yl)-3-{3-[1-(2-trifluoromethoxy-benzenesulfonyl)-piperidin-4-ylmethyl]-phenyl}-urea, C34H38F3N5O4S, 669.2596616, 670.23, M+H, 3.67, Compound A497;

1-(5-tert-Butyl-2-p-tolyl-2H-pyrazol-3-yl)-3-{3-[1-(3,4-dichloro-benzenesulfonyl)-piperidin-4-ylmethyl]-phenyl}-urea, C33H37Cl2N5O3S, 653.1994176, 654.21, M+H, 3.85, Compound A498;

1-(5-tert-Butyl-2-p-tolyl-2H-pyrazol-3-yl)-3-{3-[1-(3,4-difluoro-benzenesulfonyl)-piperidin-4-ylmethyl]-phenyl}-urea, C33H37F2N5O3S, 621.2585186, 622.26, M+H, 3.53, Compound A499;

1-(5-tert-Butyl-2-p-tolyl-2H-pyrazol-3-yl)-3-{3-[1-(3,4-dimethoxy-benzenesulfonyl)-piperidin-4-ylmethyl]-phenyl}-urea, C35H43N5O5S, 645.2984916, 646.31, M+H, 3.33, Compound A500;

1-(5-tert-Butyl-2-p-tolyl-2H-pyrazol-3-yl)-3-{3-[1-(3,5-dimethyl-isoxazole-4-sulfonyl)-piperidin-4-ylmethyl]-phenyl}-urea, C32H40N6O4S, 604.2831759, 605.30, M+H, 3.37, Compound A501;

1-(5-tert-Butyl-2-p-tolyl-2H-pyrazol-3-yl)-3-{3-[1-(3-chloro-4-fluoro-benzenesulfonyl)-piperidin-4-ylmethyl]-phenyl}-urea, C33H37ClFN5O3S, 637.2289681, 638.25, M+H, 3.67, Compound A502;

1-(5-tert-Butyl-2-p-tolyl-2H-pyrazol-3-yl)-3-{3-[1-(3-fluoro-benzenesulfonyl)-piperidin-4-ylmethyl]-phenyl}-urea, C33H38FN5O3S, 603.2679404, 604.28, M+H, 3.50, Compound A503;

5-(4-{3-[3-(5-tert-Butyl-2-p-tolyl-2H-pyrazol-3-yl)-ureido]-benzyl}-piperidine-1-sulfonyl)-4-methoxy-thiophene-3-carboxylic acid methyl ester, C34H41N5O6S2, 679.249828, 680.26, M+H, 3.47, Compound A504;

1-(5-tert-Butyl-2-p-tolyl-2H-pyrazol-3-yl)-3-{3-[1-(3-methoxy-benzenesulfonyl)-piperidin-4-ylmethyl]-phenyl}-urea, C34H41N5O4S, 615.2879269, 616.30, M+H, 3.50, Compound A505;

1-(5-tert-Butyl-2-p-tolyl-2H-pyrazol-3-yl)-3-{3-[1-(thiophene-3-sulfonyl)-piperidin-4-ylmethyl]-phenyl}-urea, C31H37N5O3S2, 591.2337839, 592.24, M+H, 3.38, Compound A506;

1-(5-tert-Butyl-2-p-tolyl-2H-pyrazol-3-yl)-3-{3-[1-(3-trifluoromethyl-benzenesulfonyl)-piperidin-4-ylmethyl]-phenyl}-urea, C34H38F3N5O3S, 653.2647469, 654.26, M+H, 3.70, Compound A507;

1-(5-tert-Butyl-2-p-tolyl-2H-pyrazol-3-yl)-3-{3-[1-(4-chloro-2,5-dimethyl-benzenesulfonyl)-piperidin-4-ylmethyl]-phenyl}-urea, C35H42ClN5O3S, 647.26969, 648.28, M+H, 4.00, Compound A508;

1-(5-tert-Butyl-2-p-tolyl-2H-pyrazol-3-yl)-3-{3-[1-(4-chloro-benzenesulfonyl)-piperidin-4-ylmethyl]-phenyl}-urea, C33H38ClN5O3S, 619.2383899, 620.25, M+H, 3.67, Compound A509;

1-(5-tert-Butyl-2-p-tolyl-2H-pyrazol-3-yl)-3-{3-[1-(4-fluoro-benzenesulfonyl)-piperidin-4-ylmethyl]-phenyl}-urea, C33H38FN5O3S, 603.2679404, 604.25, M+H, 3.50, Compound A510;

1-(5-tert-Butyl-2-p-tolyl-2H-pyrazol-3-yl)-3-{3-[1-(4-methoxy-benzenesulfonyl)-piperidin-4-ylmethyl]-phenyl}-urea, C34H41N5O4S, 615.2879269, 616.30, M+H, 3.47, Compound A511;

1-(5-tert-Butyl-2-p-tolyl-2H-pyrazol-3-yl)-3-{3-[1-(4-methyl-3,4-dihydro-2H-benzo[1,4]oxazine-7-sulfonyl)-piperidin-4-ylmethyl]-phenyl}-urea, C36H44N6O4S, 656.314476, 657.31, M+H, 3.52, Compound A512;

1-{3-[1-(4-tert-Butyl-benzenesulfonyl)-piperidin-4-ylmethyl]-phenyl}-3-(5-tert-butyl-2-p-tolyl-2H-pyrazol-3-yl)-urea, C37H47N5O3S, 641.3399625, 642.34, M+H, 3.95, Compound A513;

1-(5-tert-Butyl-2-p-tolyl-2H-pyrazol-3-yl)-3-{3-[1-(4-trifluoromethoxy-benzenesulfonyl)-piperidin-4-ylmethyl]-phenyl}-urea, C34H38F3N5O4S, 669.2596616, 670.23, M+H, 3.72, Compound A514;

1-(5-tert-Butyl-2-p-tolyl-2H-pyrazol-3-yl)-3-{3-[1-(5-oxazol-5-yl-thiophene-2-sulfonyl)-piperidin-4-ylmethyl]-phenyl}-urea, C34H38N6O4S2, 658.2395976, 659.23, M+H, 3.47, Compound A515;

1-(5-tert-Butyl-2-p-tolyl-2H-pyrazol-3-yl)-3-{3-[1-(5-chloro-3-methyl-benzo[b]thiophene-2-sulfonyl)-piperidin-4-ylmethyl]-phenyl}-urea, C36H40ClN5O3S2, 689.2261118, 690.22, M+H, 4.05, Compound A516;

1-(5-tert-Butyl-2-p-tolyl-2H-pyrazol-3-yl)-3-{3-[1-(2-methoxy-5-methyl-benzenesulfonyl)-piperidin-4-ylmethyl]-phenyl}-urea, C35H43N5O4S, 629.303577, 630.27, M+H, 3.52, Compound A517;

1-(5-tert-Butyl-2-p-tolyl-2H-pyrazol-3-yl)-3-{3-[1-(6-morpholin-4-yl-pyridine-3-sulfonyl)-piperidin-4-ylmethyl]-phenyl}-urea, C36H45N7O4S, 671.3253751, 672.33, M+H, 3.32, Compound A518;

1-(5-tert-Butyl-2-p-tolyl-2H-pyrazol-3-yl)-3-{3-[1-(quinoline-8-sulfonyl)-piperidin-4-ylmethyl]-phenyl}-urea, C36H40N6O3S, 636.2882612, 637.29, M+H, 3.35, Compound A519;

1-(5-tert-Butyl-2-p-tolyl-2H-pyrazol-3-yl)-3-[3-(1-phenylmethanesulfonyl-piperidin-4-ylmethyl)-phenyl]-urea, C34H41N5O3S, 599.2930123, 600.27, M+H, 3.43, Compound A520;

1-[3-(1-Benzenesulfonyl-piperidin-4-ylmethyl)-phenyl]-3-(5-tert-butyl-2-p-tolyl-2H-pyrazol-3-yl)-urea, C33H39N5O3S, 585.2773622, 586.24, M+H, 3.47, Compound A521;

1-(5-tert-Butyl-2-p-tolyl-2H-pyrazol-3-yl)-3-{3-[1-(2-phenyl-ethenesulfonyl)-piperidin-4-ylmethyl]-phenyl}-urea, C35H41N5O3S, 611.2930123, 612.27, M+H, 3.57, Compound A522;

1-{3-[1-(Benzo[1,2,5]oxadiazole-4-sulfonyl)-piperidin-4-ylmethyl]-phenyl}-3-(5-tert-butyl-2-p-tolyl-2H-pyrazol-3-yl)-urea, C33H37N7O4S, 627.2627748, 628.27, M+H, 3.37, Compound A523;

1-{3-[1(Benzo[1,2,5]thiadiazole-4-sulfonyl)-piperidin-4-ylmethyl]-phenyl}-3-(5-tert-butyl-2-p-tolyl-2H-pyrazol-3-yl)-urea, C33H37N7O3S2, 643.2399319, 644.23, M+H, 3.45, Compound A524;

1-(5-tert-Butyl-2-p-tolyl-2H-pyrazol-3-yl)-3-{3-[1-(1-methyl-1H-imidazole-4-sulfonyl)-piperidin-4-ylmethyl]-phenyl}-urea, C31H39N7O3S, 589.2835102, 590.30, M+H, 2.78, Compound A525;

1-(5-tert-Butyl-2-p-tolyl-2H-pyrazol-3-yl)-3-{3-[1-(1,2-dimethyl-1H-imidazole-4-sulfonyl)-piperidin-4-ylmethyl]-phenyl}-urea, C32H41N7O3S, 603.2991603, 604.30, M+H, 2.78, Compound A526;

1-(5-tert-Butyl-2-p-tolyl-2H-pyrazol-3-yl)-3-{3-[1-(5-isoxazol-3-yl-thiophene-2-sulfonyl)-piperidin-4-ylmethyl]-phenyl}-urea, C34H38N6O4S2, 658.2395976, 659.25, M+H, 3.28, Compound A527;

1-(5-tert-Butyl-2-p-tolyl-2H-pyrazol-3-yl)-3-(3-{1-[5-(2-methyl-thiazol-4-yl)-thiophene-2-sulfonyl]-piperidin-4-ylmethyl}-phenyl)-urea, C35H40N6O3S3, 688.2324048, 689.24, M+H, 3.73, Compound A528;

1-(5-tert-Butyl-2-p-tolyl-2H-pyrazol-3-yl)-3-{3-[1-(2-oxo-2H-chromene-6-sulfonyl)-piperidin-4-ylmethyl]-phenyl}-urea, C36H39N5O5S, 653.2671915, 654.29, M+H, 3.30, Compound A529;

1-(5-tert-Butyl-2-p-tolyl-2H-pyrazol-3-yl)-3-{3-[1-(5-dimethylamino-naphthalene-1-sulfonyl)-piperidin-4-ylmethyl]-phenyl}-urea, C39H46N6O3S, 678.3352115, 679.35, M+H, 3.92, Compound A530;

1-(5-tert-Butyl-2-p-tolyl-2H-pyrazol-3-yl)-3-[3-(1-ethanesulfonyl-piperidin-4-ylmethyl)-phenyl]-urea, C29H39N5O3S, 537.2773622, 538.27, M+H, 3.12, Compound A531;

1-(5-tert-Butyl-2-p-tolyl-2H-pyrazol-3-yl)-3-{3-[1-(isoquinoline-5-sulfonyl)-piperidin-4-ylmethyl]-phenyl}-urea, C36H40N6O3S, 636.2882612, 637.30, M+H, 3.33, Compound A532;

1-(5-tert-Butyl-2-p-tolyl-2H-pyrazol-3-yl)-3-[3-(1-methanesulfonyl-piperidin-4-ylmethyl)-phenyl]-urea, C28H37N5O3S, 523.2617121, 524.24, M+H, 3.00, Compound A533;

2-(4-{3-[3-(5-tert-Butyl-2-p-tolyl-2H-pyrazol-3-yl)-ureido]-benzyl}-piperidine-1-sulfonyl)-benzoic acid methyl ester, C35H41N5O5S, 643.2828416, 644.27, M+H, 3.35, Compound A534;

4-(4-{3-[3-(5-tert-Butyl-2-p-tolyl-2H-pyrazol-3-yl)-ureido]-benzyl}-piperidine-1-sulfonyl)-2,5-dimethyl-furan-3-carboxylic acid methyl ester, C35H43N5O6S, 661.2934063, 662.26, M+H, 3.53, Compound A535;

5-(4-{3-[3-(5-tert-Butyl-2-p-tolyl-2H-pyrazol-3-yl)-ureido]-benzyl}-piperidine-1-sulfonyl)-1-methyl-1H-pyrrole-2-carboxylic acid methyl ester, C34H42N6O5S, 646.2937406, 647.28, M+H, 3.30, Compound A536;

5-(4-{3-[3-(5-tert-Butyl-2-p-tolyl-2H-pyrazol-3-yl)-ureido]-benzyl}-piperidine-1-sulfonyl)-furan-2-carboxylic acid methyl ester, C33H39N5O6S, 633.2621061, 634.24, M+H, 3.37, Compound A537;

N-[4-(4-{3-[3-(5-tert-Butyl-2-p-tolyl-2H-pyrazol-3-yl)-ureido]-benzyl}-piperidine-1-sulfonyl)-phenyl]-acetamide, C35H42N6O4S, 642.298826, 643.32, M+H, 3.07, Compound A538;

1-(5-tert-Butyl-2-p-tolyl-2H-pyrazol-3-yl)-3-{3-[1-(4-vinyl-benzenesulfonyl)-piperidin-4-ylmethyl]-phenyl}-urea, C35H41N5O3S, 611.2930123, 612.29, M+H, 3.63, Compound A539;

1-(5-tert-Butyl-2-p-tolyl-2H-pyrazol-3-yl)-3-{3-[1-(toluene-4-sulfonyl)-piperidin-4-ylmethyl]-phenyl}-urea, C34H41N5O3S, 599.2930123, 600.28, M+H, 3.58, Compound A540;

1-{3-[1-(2-Benzo[1,3]dioxol-5-yl-2-oxo-ethyl)-piperidin-4-ylmethyl]-phenyl}-3-(5-tert-butyl-2-p-tolyl-2H-pyrazol-3-yl)-urea, C36H41N5O4, 607.3159, 608.29, M+H, 2.18, Compound A541;

1-{3-[1-(2-Benzo[b]thiophen-3-yl-2-oxo-ethyl)-piperidin-4-ylmethyl]-phenyl}-3-(5-tert-butyl-2-p-tolyl-2H-pyrazol-3-yl)-urea, C37H41N5O2S, 619.2981, 620.27, M+H, 2.43, Compound A542;

1-(5-tert-Butyl-2-p-tolyl-2H-pyrazol-3-yl)-3-(3-{1-[2-(5-methyl-1-phenyl-1H-pyrazol-4-yl)-2-oxo-ethyl]-piperidin-4-ylmethyl}-phenyl)-urea, C39H45N7O2, 643.3635, 644.33, M+H, 2.22, Compound A543;

1-(5-tert-Butyl-2-p-tolyl-2H-pyrazol-3-yl)-3-(3-{1-[2-(5-methyl-3-phenyl-isoxazol-4-yl)-2-oxo-ethyl]-piperidin-4-ylmethyl}-phenyl)-urea, C39H44N6O3, 644.3475, 645.33, M+H, 2.45, Compound A544;

1-(5-tert-Butyl-2-p-tolyl-2H-pyrazol-3-yl)-3-(3-{1-[2-oxo-2-(5-pyridin-2-yl-thiophen-2-yl)-ethyl]-piperidin-4-ylmethyl}-phenyl)-urea, C38H42N6O2S, 646.31, 647.29, M+H, 2.32, Compound A545;

1-(5-tert-Butyl-2-p-tolyl-2H-pyrazol-3-yl)-3-(3-{1-[2-(2,4-dimethoxy-phenyl)-2-oxo-ethyl]-piperidin-4-ylmethyl}-phenyl)-urea, C37H45N5O4, 623.3472, 624.32, M+H, 2.48, Compound A546;

1-(5-tert-Butyl-2-p-tolyl-2H-pyrazol-3-yl)-3-(3-{1-[2-(2,5-dimethoxy-phenyl)-2-oxo-ethyl]-piperidin-4-ylmethyl}-phenyl)-urea, C37H45N5O4, 623.3472, 624.34, M+H, 3.55, Compound A547;

1(5-tert-Butyl-2-p-tolyl-2H-pyrazol-3-yl)-3-(3-{1-[2-(3-methoxy-phenyl)-2-oxo-ethyl]-piperidin-4-ylmethyl}-phenyl)-urea, C36H43N5O3, 593.3366, 594.32, M+H, 2.28, Compound A548;

1-(5-tert-Butyl-2-p-tolyl-2H-pyrazol-3-yl)3-(3-{1-[2-(4-difluoromethoxy-phenyl)-2-oxo-ethyl]-piperidin-4-ylmethyl}-phenyl)-urea, C36H41F2N5O3, 629.32, 630.30, M+H, 2.38, Compound A549;

1-(5-tert-Butyl-2-p-tolyl-2H-pyrazol-3-yl)-3-(3-{1-[2-oxo-2-(4-trifluoromethoxy-phenyl)-ethyl]-piperidin-4-ylmethyl}-phenyl)-urea, C36H40F3N5O3, 647.31, 648.29, M+H, 2.50, Compound A550;

1-(5-tert-Butyl-2-p-tolyl-2H-pyrazol-3-yl)3-(3-{1-[2-(4-methoxy-phenyl)-2-oxo-ethyl]-piperidin-4-ylmethyl}-phenyl)-urea, C36H43N5O3, 593.3366, 594.32, M+H, 2.15, Compound A551;

1-(5-tert-Butyl-2-p-tolyl-2H-pyrazol-3-yl)-3-(3-{1-[2-oxo-2-(2-oxo-1,2,3,4-tetrahydro-quinolin-6-yl)-ethyl]-piperidin-4-ylmethyl}-phenyl)-urea, C38H44N6O3, 632.3475, 633.33, M+H, 2.02, Compound A552;

1-(5-tert-Butyl-2-p-tolyl-2H-pyrazol-3-yl)-3-(3-{1-[2-oxo-2-(4-pyrrolidin-1-yl-phenyl)-ethyl]-piperidin-4-ylmethyl}-phenyl)-urea, C39H48N6O2, 632.3839, 633.36, M+H, 2.47, Compound A553;

1-(5-tert-Butyl-2-p-tolyl-2H-pyrazol-3-yl)-3-(3-{1-[2-(4-diethylamino-phenyl)-2-oxo-ethyl]-piperidin-4-ylmethyl}-phenyl)-urea, C39H50N6O2, 634.3995, 635.38, M+H, 2.42, Compound A554;

1-(5-tert-Butyl-2-p-tolyl-2H-pyrazol-3-yl)3-{4-[1-(1,3,5-trimethyl-1H-pyrazole-4-sulfonyl)-piperidin-4-ylmethyl]-phenyl}-urea, C33H43N7O3S, 617.31, 618.28, M+H, 3.13, Compound A555;

1-{4-[1-(Butane-1-sulfonyl)-piperidin-4-ylmethyl]-phenyl}-3-(5-tert-butyl-2-p-tolyl-2H-pyrazol-3-yl)-urea, C31H43N5O3S, 565.31, 566.26, M+H, 3.40, Compound A556;

1-(5-tert-Butyl-2-p-tolyl-2H-pyrazol-3-yl)-3-{4-[1-(naphthalene-1-sulfonyl)-piperidin-4-ylmethyl]-phenyl}-urea, C37H41N5O3S, 635.29, 636.24, M+H, 3.77, Compound A557;

1-{4-[1-(Benzo[1,2,5]thiadiazole-5-sulfonyl)-piperidin-4-ylmethyl]-phenyl}-3-(5-tert-butyl-2-p-tolyl-2H-pyrazol-3-yl)-urea, C33H37N7O3S2, 643.24, 644.18, M+H, 3.55, Compound A558;

1-(5-tert-Butyl-2-p-tolyl-2H-pyrazol-3-yl)-3-{4-[1-(2,3-dihydro-benzo[1,4]dioxine-6-sulfonyl)-piperidin-4-ylmethyl]-phenyl}-urea, C35H41N5O5S, 643.28, 644.22, M+H, 3.40, Compound A559;

1-(5-tert-Butyl-2-p-tolyl-2H-pyrazol-3-yl)-3-{4-[1-(2,3-dihydro-benzofuran-5-sulfonyl)-piperidin-4-ylmethyl]-phenyl}-urea, C35H41N5O4S, 627.29, 628.23, M+H, 3.47, Compound A560;

1-(5-tert-Butyl-2-p-tolyl-2H-pyrazol-3-yl)-3-{4-[1-(2,4-dichloro-benzenesulfonyl)-piperidin-4-ylmethyl]-phenyl}-urea, C33H37Cl2N5O3S, 653.20, 654.15, M+H, 3.85, Compound A561;

1-(5-tert-Butyl-2-p-tolyl-2H-pyrazol-3-yl)-3-{4-[1-(2,4-difluoro-benzenesulfonyl)-piperidin-4-ylmethyl]-phenyl}-urea, C33H37F2N5O3S, 621.26, 622.19, M+H, 3.53, Compound A562;

1-(5-tert-Butyl-2-p-tolyl-2H-pyrazol-3-yl)-3-{4-[1-(2,5-dichloro-benzenesulfonyl)-piperidin-4-ylmethyl]-phenyl}-urea, C33H37Cl2N5O3S, 653.20, 654.14, M+H, 3.80, Compound A563;

1-(5-tert-Butyl-2-p-tolyl-2H-pyrazol-3-yl)-3-{4-[1-(2,5-dimethoxy-benzenesulfonyl)-piperidin-4-ylmethyl]-phenyl}-urea (0.0211 g), C35H43N5O5SO 645.30, 646.22, M+H, 3.38, Compound A564;

3-(4-{4-[3-(5-tert-Butyl-2-p-tolyl-2H-pyrazol-3-yl)-ureido]-benzyl}-piperidine-1-sulfonyl)-thiophene-2-carboxylic acid methyl ester, C33H39N5O5S2, 649.24, 650.16, M+H, 3.35, Compound A565;

1-(5-tert-Butyl-2-p-tolyl-2H-pyrazol-3-yl)-3-{4-[1-(2-chloro-4-fluoro-benzenesulfonyl)-piperidin-4-ylmethyl]-phenyl}-urea, C33H37ClFN5O3S, 637.23, 638.15, M+H, 3.65, Compound A566;

1-(5-tert-Butyl-2-p-tolyl-2H-pyrazol-3-yl)-3-{4-[1-(2-chloro-benzenesulfonyl)-piperidin-4-ylmethyl]-phenyl}-urea (0.0165 g), C33H38ClN5O3S, 619.24, 620.18, M+H, 3.60, Compound A567;

1-(5-tert-Butyl-2-p-tolyl-2H-pyrazol-3-yl)-3-{4-[1-(2-fluoro-benzenesulfonyl)-piperidin-4-ylmethyl]-phenyl}-urea, C33H38FN5O3S, 603.27, 604.19, M+H, 3.47, Compound A568;

1-(5-tert-Butyl-2-p-tolyl-2H-pyrazol-3-yl)-3-{4-[1-(2,4,6-trimethyl-benzenesulfonyl)-piperidin-4-ylmethyl]-phenyl}-urea, C36H45N5O3S, 627.32, 628.25, M+H, 3.92, Compound A569;

1-(5-tert-Butyl-2-p-tolyl-2H-pyrazol-3-yl)-3-{4-[1-(naphthalene-2-sulfonyl)-piperidin-4-ylmethyl]-phenyl}-urea, C37H41N5O3S, 635.29, 636.23, M+H, 3.75, Compound A570;

1-(5-tert-Butyl-2-p-tolyl-2H-pyrazol-3-yl)-3-{4-[1-(thiophene-2-sulfonyl)-piperidin-4-ylmethyl]-phenyl}-urea, C31H37N5O3S2, 591.23, 592.16, M+H, 3.43, Compound A571;

1-(5-tert-Butyl-2-p-tolyl-2H-pyrazol-3-yl)-3-{4-[1-(2-trifluoromethoxy-benzenesulfonyl)-piperidin-4-ylmethyl]-phenyl}-urea, C34H38F3N5O4S, 669.26, 670.17, M+H, 3.68, Compound A572;

1-(5-tert-Butyl-2-p-tolyl-2H-pyrazol-3-yl)-3-{4-[1-(3,4-dichloro-benzenesulfonyl)-piperidin-4-ylmethyl]-phenyl}-urea, C33H37Cl2N5O3S, 653.20, 654.14, M+H, 3.85, Compound A573;

1-(5-tert-Butyl-2-p-tolyl-2H-pyrazol-3-yl)-3-{4-[1-(3,4-difluoro-benzenesulfonyl)-piperidin-4-ylmethyl]-phenyl}-urea, C33H37F2N5O3S, 621.26, 622.17, M+H, 3.55, Compound A574;

1-(5-tert-Butyl-2-p-tolyl-2H-pyrazol-3-yl)-3-{4-[1-(3,4-dimethoxy-benzenesulfonyl)-piperidin-4-ylmethyl]-phenyl}-urea, C35H43N5O5S, 645.30, 646.22, M+H, 3.32, Compound A575;

1-(5-tert-Butyl-2-p-tolyl-2H-pyrazol-3-yl)-3-{4-[1-(3,5-dimethyl-isoxazole-4-sulfonyl)-piperidin-4-ylmethyl]-phenyl}-urea, C32H40N6O4S, 604.28, 605.21, M+H, 3.38, Compound A576;

1-(5-tert-Butyl-2-p-tolyl-2H-pyrazol-3-yl)-3-{4-[1-(3-chloro-4-fluoro-benzenesulfonyl)-piperidin-4-ylmethyl]-phenyl}-urea, C33H37ClFN5O3S, 637.23, 638.16, M+H, 3.65, Compound A577;

1-(5-tert-Butyl-2-p-tolyl-2H-pyrazol-3-yl)-3-{4-[1-(3-fluoro-benzenesulfonyl)-piperidin-4-ylmethyl]-phenyl}-urea, C33H38FN5O3S, 603.27, 604.19, M+H, 3.48, Compound A578;

5-(4-{4-[3-(5-tert-Butyl-2-p-tolyl-2H-pyrazol-3-yl)-ureido]-benzyl}-piperidine-1-sulfonyl)-4-methoxy-thiophene-3-carboxylic acid methyl ester, C34H41N5O6S2, 679.25, 680.19, M+H, 3.55, Compound A579;

1-(5-tert-Butyl-2-p-tolyl-2H-pyrazol-3-yl)-3-{4-[1-(3-methoxy-benzenesulfonyl)-piperidin-4-ylmethyl]-phenyl}-urea, C34H41N5O4S, 615.29, 616.23, M+H, 3.50, Compound A580;

1-(5-tert-Butyl-2-p-tolyl-2H-pyrazol-3-yl)-3-{4-[1-(thiophene-3-sulfonyl)-piperidin-4-ylmethyl]-phenyl}-urea, C31H37N5O3S2, 591.23, 592.18, M+H, 3.35, Compound A581;

1-(5-tert-Butyl-2-p-tolyl-2H-pyrazol-3-yl)-3-{4-[1-(3-trifluoromethyl-benzenesulfonyl)-piperidin-4-ylmethyl]-phenyl}-urea, C34H38F3N5O3S, 653.26, 654.20, M+H, 3.65, Compound A582;

1-(5-tert-Butyl-2-p-tolyl-2H-pyrazol-3-yl)-3-{4-[1-(4-chloro-2,5-dimethyl-benzenesulfonyl)-piperidin-4-ylmethyl]-phenyl}-urea, C35H42ClN5O3S, 647.27, 648.23, M+H, 4.02, Compound A583;

1-(5-tert-Butyl-2-p-tolyl-2H-pyrazol-3-yl)-3-{4-[1-(4-chloro-benzenesulfonyl)-piperidin-4-ylmethyl]-phenyl}-urea, C33H38ClN5O3S, 619.24, 620.20, M+H, 3.65, Compound A584;

1-(5-tert-Butyl-2-p-tolyl-2H-pyrazol-3-yl)-3-{4-[1-(4-fluoro-benzenesulfonyl)-piperidin-4-ylmethyl]-phenyl}-urea, C33H38FN5O3S, 603.27, 604.22, M+H, 3.48, Compound A585;

1-(5-tert-Butyl-2-p-tolyl-2H-pyrazol-3-yl)-3-{4-[1-(4-methoxy-benzenesulfonyl)-piperidin-4-ylmethyl]-phenyl}-urea, C34H41N5O4S, 615.29, 616.27, M+H, 3.45, Compound A586;

1-(5-tert-Butyl-2-p-tolyl-2H-pyrazol-3-yl)-3-{4-[1-(4-methyl-3,4-dihydro-2H-benzo[1,4]oxazine-7-sulfonyl)-piperidin-4-ylmethyl]-phenyl}-urea, C36H44N6O4S, 656.31, 657.29, M+H, 3.52, Compound A587;

1-{4-[1(4-tert-Butyl-benzenesulfonyl)-piperidin-4-ylmethyl]-phenyl}-3-(5-tert-butyl-2-p-tolyl-2H-pyrazol-3-yl)-urea, C37H47N5O3S, 641.34, 642.30, M+H, 3.93, Compound A588;

1-(5-tert-Butyl-2-p-tolyl-2H-pyrazol-3-yl)-3-{4-[1-(4-trifluoromethoxy-benzenesulfonyl)-piperidin-4-ylmethyl]-phenyl}-urea, C34H38F3N5O4S, 669.26, 670.19, M+H, 3.70, Compound A589;

1-(5-tert-Butyl-2-p-tolyl-2H-pyrazol-3-yl)-3-{4-[1-(5-oxazol-5-yl-thiophene-2-sulfonyl)-piperidin-4-ylmethyl]-phenyl}-urea, C34H38N6O4S2, 658.24, 659.21, M+H, 3.43, Compound A590;

1-(5-tert-Butyl-2-p-tolyl-2H-pyrazol-3-yl)-3-{4-[1-(5-chloro-3-methyl-benzo[b]thiophene-2-sulfonyl)-piperidin-4-ylmethyl]-phenyl}-urea, C36H40ClN5O3S2, 689.23, 690.19, M+H, 4.12, Compound A591;

1-(5-tert-Butyl-2-p-tolyl-2H-pyrazol-3-yl)-3-{4-[1-(2-methoxy-5-methyl-benzenesulfonyl)-piperidin-4-ylmethyl]-phenyl}-urea (0.0177 g), C35H43N5O4S, 629.30, 630.26, M+H, 3.50, Compound A592;

1-(5-tert-Butyl-2-p-tolyl-2H-pyrazol-3-yl)-3-{4-[1-(6-morpholin-4-yl-pyridine-3-sulfonyl)-piperidin-4-ylmethyl]-phenyl}-urea, C36H45N7O4S, 671.33, 672.30, M+H, 3.28, Compound A593;

1-(5-tert-Butyl-2-p-tolyl-2H-pyrazol-3-yl)-3-{4-[1-(quinoline-8-sulfonyl)-piperidin-4-ylmethyl]-phenyl}-urea, C36H40N6O3S, 636.29, 637.26, M+H, 3.37, Compound A594;

1-(5-tert-Butyl-2-p-tolyl-2H-pyrazol-3-yl)-3-[4-(1-phenylmethanesulfonyl-piperidin-4-ylmethyl)-phenyl]-urea, C34H41N5O3S, 599.29, 600.27, M+H, 3.37, Compound A595;

1-[4-(1-Benzenesulfonyl-piperidin-4-ylmethyl)-phenyl]-35-tert-butyl-2-p-tolyl-2H-pyrazol-3-yl)-urea, C33H39N5O3S, 585.28, 586.22, M+H, 3.45, Compound A596;

1-(5-tert-Butyl-2-p-tolyl-2H-pyrazol-3-yl)-3-{4-[1-(2-phenyl-ethenesulfonyl)-piperidin-4-ylmethyl]-phenyl}-urea, C35H41N5O3S, 611.29, 612.25, M+H, 3.58, Compound A597;

1-{4-[1-(Benzo[1,2,5]oxadiazole-4-sulfonyl)-piperidin-4-ylmethyl]-phenyl}-3-(5-tert-butyl-2-p-tolyl-2H-pyrazol-3-yl)-urea, C33H37N7O4S, 627.26, 628.22, M+H, 3.43, Compound A598;

1-{4-[1-(Benzo[1,2,5]thiadiazole-4-sulfonyl)-piperidin-4-ylmethyl]-phenyl}-3-(5-tert-butyl-2-p-tolyl-2H-pyrazol-3-yl)-urea, C33H37N7O3S2, 643.24, 644.19, M+H, 3.43, Compound A599;

1-(5-tert-Butyl-2-p-tolyl-2H-pyrazol-3-yl)-3-{4-[1-(1-methyl-1H-imidazole-4-sulfonyl)-piperidin-4-ylmethyl]-phenyl}-urea, C31H39N7O3S, 589.28, 590.26, M+H, 2.77, Compound A600;

1-(5-tert-Butyl-2-p-tolyl-2H-pyrazol-3-yl)-3-{4-[1-(1,2-dimethyl-1H-imidazole-4-sulfonyl)-piperidin-4-ylmethyl]-phenyl}-urea, C32H41N7O3S, 603.30, 604.27, M+H, 2.77, Compound A601;

1-(5-tert-Butyl-2-p-tolyl-2H-pyrazol-3-yl)-3-{4-[1-(5-isoxazol-3-yl-thiophene-2-sulfonyl)-piperidin-4-ylmethyl]-phenyl}-urea, C34H38N6O4S2, 658.24, 659.20, M+H, 3.25, Compound A602;

1-(5-tert-Butyl-2-p-tolyl-2H-pyrazol-3-yl)-3-(4-{1-[5-(2-methyl-thiazol-4-yl)-thiophene-2-sulfonyl]-piperidin-4-ylmethyl}-phenyl)-urea, C35H40N6O3S3, 688.23, 689.21, M+H, 3.70, Compound A603;

1-(5-tert-Butyl-2-p-tolyl-2H-pyrazol-3-yl)-3-{4-[1-(2-oxo-2H-chromene-6-sulfonyl)-piperidin-4-ylmethyl]-phenyl}-urea, C36H39N5O5S, 653.27, 654.23, M+H, 3.27, Compound A604;

1-(5-tert-Butyl-2-p-tolyl-2H-pyrazol-3-yl)-3-{4-[1-(5-dimethylamino-naphthalene-1-sulfonyl)-piperidin-4-ylmethyl]-phenyl}-urea, C39H46N6O3S, 678.34, 679.32, M+H, 3.92, Compound A605;

1-(5-tert-Butyl-2-p-tolyl-2H-pyrazol-3-yl)-3-[4-(1-ethanesulfonyl-piperidin-4-ylmethyl)-phenyl]-urea (0.01 g), C29H39N5O3S, 537.28, 538.25, M+H, 3.10, Compound A606;

1-(5-tert-Butyl-2-p-tolyl-2H-pyrazol-3-yl)3-{4-[1-(isoquinoline-5-sulfonyl)-piperidin-4-ylmethyl]-phenyl}-urea, C36H40N6O3S, 636.29, 637.27, M+H, 3.33, Compound A607;

1-(5-tert-Butyl-2-p-tolyl-2H-pyrazol-3-yl)-3-[4-(1-methanesulfonyl-piperidin-4-ylmethyl)-phenyl]-urea, C28H37N5O3S (0.0102g), 523.26, 524.23, M+H, 2.93, Compound A608;

2-(4-{4-[3-(5-tert-Butyl-2-p-tolyl-2H-pyrazol-3-yl)-ureido]-benzyl}-piperidine-1-sulfonyl)-benzoic acid methyl ester (0.0198 g), C35H41N5O5S, 643.28, 644.24, M+H, 3.38, Compound A609;

4-(4-{4-[3-(5-tert-Butyl-2-p-tolyl-2H-pyrazol-3-yl)-ureido]-benzyl}-piperidine-1-sulfonyl)-2,5-dimethyl-furan-3-carboxylic acid methyl ester, C35H43N5O6S, 661.29, 662.24, M+H, 3.50, Compound A610;

5-(4-{4-[3-(5-tert-Butyl-2-p-tolyl-2H-pyrazol-3-yl)-ureido]-benzyl}-piperidine-1-sulfonyl)-1-methyl-1H-pyrrole-2-carboxylic acid methyl ester, C34H42N6O5S, 646.29, 647.26, M+H, 3.30, Compound A611;

5-(4-{4-[3-(5-tert-Butyl-2-p-tolyl-2H-pyrazol-3-yl)-ureido]-benzyl}-piperidine-1-sulfonyl)-furan-2-carboxylic acid methyl ester, C33H39N5O6S, 633.26, 634.22, M+H, 3.32, Compound A612;

N-[4-(4-{4-[3-(5-tert-Butyl-2-p-tolyl-2H-pyrazol-3-yl)-ureido]-benzyl}-piperidine-1-sulfonyl)-phenyl]-acetamide, C35H42N6O4S, 642.30, 643.29, M+H, 3.03, Compound A613;

1-(5-tert-Butyl-2-p-tolyl-2H-pyrazol-3-yl)-3-{4-[1-(4-vinyl-benzenesulfonyl)-piperidin-4-ylmethyl]-phenyl}-urea, C35H41N5O3S, 611.29, 612.27, M+H, 3.63, Compound A614; and 1-(5-tert-Butyl-2-p-tolyl-2H-pyrazol-3-yl)-3-{4-[1-(toluene-4-sulfonyl)-piperidin-4-ylmethyl]-phenyl}-urea, C34H41N5O3S, 599.29, 600.26, M+H, 3.58, Compound A615.

Particular embodiments of the present invention include: unless otherwise stated compounds in the following list that are 8-aza-bicyclo[3.2.1]octyl derivatives may be prepared as a mixture of endo- and exo-isomers, and the individual exo- and endo-isomers can be separated by HPLC;

1-(5-tert-Butyl-2-p-tolyl-2H-pyrazol-3-yl)-3-{3-[8-(4-oxazol-5-yl-benzoyl)-8-aza-bicyclo[3.2.1]oct-3-ylmethyl]-phenyl}-urea, Compound A616;

1-(5-tert-Butyl-2-p-tolyl-2H-pyrazol-3-yl)-3-{3-[8-(2-hydroxy-6-methyl-pyridine-4-carbonyl)-8-aza-bicyclo[3.2.1]oct-3-ylmethyl]-phenyl}-urea, Compound A617;

1-(5-tert-Butyl-2-p-tolyl-2H-pyrazol-3-yl)-3-(3-{8-[2-(6-methoxy-benzofuran-3-yl)-acetyl]-8-aza-bicyclo[3.2.1]oct-3-ylmethyl}-phenyl)-urea (0.0178 g), C40H45N5O4, 660.33, M+H, 3.45, Compound A618;

1-(5-tert-Butyl-2-p-tolyl-2H-pyrazol-3-yl)-3-(3-{8-[2-methyl-5-(piperidine-1-sulfonyl)-furan-3-carbonyl]-8-aza-bicyclo[3.2.1]oct-3-ylmethyl}-phenyl)-urea, Compound A619;

1-{3-[8-(4-tert-Butoxymethyl-benzoyl)-8-aza-bicyclo[3.2.1]oct-3-ylmethyl]-phenyl}-3-(5-tert-butyl-2-p-tolyl-2H-pyrazol-3-yl)-urea; Compound A620;

1-(5-tert-Butyl-2-p-tolyl-2H-pyrazol-3-yl)-3-{3-[8-(3-methyl-isoxazole-4-carbonyl)-8-aza-bicyclo[3.2.1]oct-3-ylmethyl]-phenyl}-urea; Compound A621;

Acetic acid 4-(3-{3-[3-(5-tert-butyl-2-p-tolyl-2H-pyrazol-3-yl)-ureido]-benzyl}-8-aza-bicyclo[3.2.1]octane-8-carbonyl)-benzyl ester, Compound A622;

1-(5-tert-Butyl-2-p-tolyl-2H-pyrazol-3-yl)-3-{3-[8-(5-methyl-isoxazole-4-carbonyl)-8-aza-bicyclo[3.2.1]oct-3-ylmethyl]-phenyl}-urea, Compound A623;

1-{3-[8-(3-Butoxy-4-methoxy-benzoyl)-8-aza-bicyclo[3.2.1]oct-3-ylmethyl]-phenyl}-3-(5-tert-butyl-2-p-tolyl-2H-pyrazol-3-yl)-urea, Compound A624;

1-(5-tert-Butyl-2-p-tolyl-2H-pyrazol-3-yl)-3-{3-[8-(4-thiophen-2-yl-benzoy)-8-aza-bicyclo[3.2.1]oct-3-ylmethyl]-phenyl}-urea, Compound A625;

1-(5-tert-Butyl-2-p-tolyl-2H-pyrazol-3-yl)-3-{3-[8-(5-methyl-2-trifluoromethyl-furan-3-carbonyl)-8-aza-bicyclo[3.2.1]oct-3-ylmethyl]-phenyl}-urea, Compound A626;

1-(5-tert-Butyl-2-p-tolyl-2H-pyrazol-3-yl)-3-3-[8-(3-pyridin-3-yl-propionyl)-8-aza-bicyclo[3.2.1]oct-3-ylmethyl]-phenyl}-urea, Compound A627;

1-(5-tert-Butyl-2-p-tolyl-2H-pyrazol-3-yl)-3-{3-[8-(2-methyl-imidazo[1,2-a]pyridine-3-carbonyl)-8-aza-bicyclo[3.2.1]oct-3-ylmethyl]-phenyl}-urea, Compound A628;

1-(5-tert-Butyl-2-p-tolyl-2H-pyrazol-3-yl)-3-{3-[8-(4-difluoromethoxy-benzoyl)-8-aza-bicyclo[3.2.1]oct-3-ylmethyl]-phenyl}-urea, Compound A629;

1-(5-tert-Butyl-2-p-tolyl-2H-pyrazol-3-yl)-3-{3-[8-(2-methyl-5-phenyl-furan-3-carbonyl)-8-aza-bicyclo[3.2.1]oct-3-ylmethyl]-phenyl}-urea, Compound A630;

1-(5-tert-Butyl-2-p-tolyl-2H-pyrazol-3-yl)-3-(3-{8-[5-methoxy-2-(2,2,2-trifluoro-ethoxy)-benzoyl]-8-aza-bicyclo[3.2.1]oct-3-ylmethyl}-phenyl)urea, Compound A631;

1-(5-tert-Butyl-2-p-tolyl-2H-pyrazol-3-yl)-3-{3-[8-(2H-indazole-3-carbonyl)-8-aza-bicyclo[3.2.1]oct-3-ylmethyl]-phenyl}-urea, Compound A632;

1-{3-[8-(4-Amino-3-trifluoromethoxy-benzoyl)-8-aza-bicyclo[3.2.1]oct-3-ylmethyl]-phenyl}-3-(5-tert-butyl-2-p-tolyl-2H-pyrazol-3-yl)-urea, Compound A633;

1-(5-tert-Butyl-2-p-tolyl-2H-pyrazol-3-yl)-3-{3-[8-(4-isobutyl-benzoyl)-8-aza-bicyclo[3.2.1]oct-3-ylmethyl]-phenyl}-urea, Compound A634;

1-(5-tert-Butyl-2-p-tolyl-2H-pyrazol-3-yl)-3-(3-{8-[2-(2,4-dimethoxy-phenyl)-acetyl]-8-aza-bicyclo[3.2.1]oct-3-ylmethyl}-phenyl)-urea, Compound A635;

1-(5-tert-Butyl-2-p-tolyl-2H-pyrazol-3-yl)-3-{3-[8-(2-chloro-6-methoxy-pyridine-4-carbonyl)-8-aza-bicyclo[3.2.1]oct-3-ylmethyl]-phenyl}-urea, Compound A636;

1-(5-tert-Butyl-2-p-tolyl-2H-pyrazol-3-yl)-3-{3-[8-(2-pyridin-4-yl-thiazole-4-carbonyl)-8-aza-bicyclo[3.2.1]oct-3-ylmethyl]-phenyl}-urea, Compound A637;

1-(5-tert-Butyl-2-p-tolyl-2H-pyrazol-3-yl)-3-{3-[8-(3,5-dimethyl-1H-pyrazole-4-carbonyl)-8-aza-bicyclo[3.2.1]oct-3-ylmethyl]-phenyl}-urea, Compound A638;

1-(5-tert-Butyl-2-p-tolyl-2H-pyrazol-3-yl)-3-(3-{8-[4-(1,1,2,2-tetrafluoro-ethoxy)-benzoyl]-8-aza-bicyclo[3.2.1]oct-3-ylmethyl}-phenyl)-urea, Compound A639;

1-(5-tert-Butyl-2-p-tolyl-2H-pyrazol-3-yl)-3-(3-{8-[3-(1,1,2,2-tetrafluoro-ethoxy)-benzoyl]-8-aza-bicyclo[3.2.1]oct-3-ylmethyl}-phenyl)-urea, Compound A640;

1-(5-tert-Butyl-2-p-tolyl-2H-pyrazol-3-yl)-3-(3-{8-[2-(1-methyl-1H-indol-3-yl)-acetyl]-8-aza-bicyclo[3.2.1]oct-3-ylmethyl}-phenyl)-urea (0.0196 g), C40H46N6O2, 643.35, M+H, 3.50, Compound A641;

1-{3-[8-(Benzothiazole-6-carbonyl)-8-aza-bicyclo[3.2.1]oct-3-ylmethyl]-phenyl}-3-(5-tert-butyl-2-p-tolyl-2H-pyrazol-3-yl)-urea, Compound A642;

1-(5-tert-Butyl-2-p-tolyl-2H-pyrazol-3-yl)-3-(3-{8-[6-(2,2,2-trifluoro-ethoxy)-pyridine-3-carbonyl]-8-aza-bicyclo[3.2.1]oct-3-ylmethyl}-phenyl)-urea, Compound A643;

1-(5-tert-Butyl-2-p-tolyl-2H-pyrazol-3-yl)-3-3-[8-(4-ethylamino-benzoyl)-8-aza-bicyclo[3.2.1]oct-3-ylmethyl]-phenyl}-urea, Compound A644;

1-(5-tert-Butyl-2-p-tolyl-2H-pyrazol-3-yl)-3-{3-[8-(2-methyl-furan-3-carbonyl)-8-aza-bicyclo[3.2.1]oct-3-ylmethyl]-phenyl}-urea, Compound A645;

1-{3-[8-(Bicyclo[2.2.1]hept-5-ene-2-carbonyl)-8-aza-bicyclo[3.2.1]oct-3-ylmethyl]-phenyl}-3-(5-tert-butyl-2-p-tolyl-2H-pyrazol-3-yl)-urea, Compound A646;

1-(5-tert-Butyl-2-p-tolyl-2H-pyrazol-3-yl)-3-{3-[8-((S)-2,6-dioxo-hexahydro-pyrimidine-4-carbonyl)-8-aza-bicyclo

[3.2.1]oct-3-ylmethyl]-phenyl}-urea (0.0094 g), C34H41N7O4, 621.34, M+H, 2.38, Compound A647;

1-(5-tert-Butyl-2-p-tolyl-2H-pyrazol-3-yl)-3-{3-[8-(4-[1,2,3]thiadiazol-4-yl-benzoyl)-8-aza-bicyclo[3.2.1]oct-3-ylmethyl]-phenyl}-urea, Compound A648;

1-(5-tert-Butyl-2-p-tolyl-2H-pyrazol-3-yl)-3-{3-[8-(4,5-dimethyl-furan-2-carbonyl)-8-aza-bicyclo[3.2.1]oct-3-ylmethyl]-phenyl}-urea, Compound A649;

1-(5-tert-Butyl-2-p-tolyl-2H-pyrazol-3-yl)-3-{3-[8-(3-methanesulfonyl-6,7-dihydro-benzo[c]thiophene-1-carbonyl)-8-aza-bicyclo[3.2.1]oct-3-ylmethyl]-phenyl}-urea, Compound A650; 1-(5-tert-Butyl-2-p-tolyl-2H-pyrazol-3-yl)-3-{3-[8-(2,3-dihydro-benzofuran-5-carbonyl)-8-aza-bicyclo[3.2.1]oct-3-ylmethyl]-phenyl}-urea, Compound A651;

1-(5-tert-Butyl-2-p-tolyl-2H-pyrazol-3-yl)-3-(3-{8-[2-(3,5-dimethyl-phenyl)-acetyl]-8-aza-bicyclo[3.2.1]oct-3-ylmethyl}-phenyl)-urea, Compound A652;

1-(5-tert-Butyl-2-p-tolyl-2H-pyrazol-3-yl)-3-{3-[8-(2-indan-2-yl-acetyl)-8-aza-bicyclo[3.2.1]oct-3-ylmethyl]-phenyl}-urea, Compound A653;

1-(5-tert-Butyl-2-p-tolyl-2H-pyrazol-3-yl)-3-{3-[8-(3H-imidazole-4-carbonyl)-8-aza-bicyclo[3.2.1]oct-3-ylmethyl]-phenyl}-urea, Compound A654;

1-(5-tert-Butyl-2-p-tolyl-2H-pyrazol-3-yl)-3-{3-[8-(2,5-dimethyl-furan-3-carbonyl)-8-aza-bicyclo[3.2.1]oct-3-ylmethyl]-phenyl}-urea, Compound A655;

1-(5-tert-Butyl-2-p-tolyl-2H-pyrazol-3-yl)-3-{3-[8-(5-methoxy-benzofuran-2-carbonyl)-8-aza-bicyclo[3.2.1]oct-3-ylmethyl]-phenyl}-urea, Compound A656;

1-(5-tert-Butyl-2-p-tolyl-2H-pyrazol-3-yl)-3-{3-[8-(2,6-dimethoxy-pyridine-3-carbonyl)-8-aza-bicyclo[3.2.1]oct-3-ylmethyl]-phenyl}-urea, Compound A657;

1-(5-tert-Butyl-2-p-tolyl-2H-pyrazol-3-yl)-3-{3-[8-(5,6-dichloro-pyridine-3-carbonyl)-8-aza-bicyclo[3.2.1]oct-3-ylmethyl]-phenyl}-urea, Compound A658;

1-(5-tert-Butyl-2-p-tolyl-2H-pyrazol-3-yl)-3-(3-{8-[2-(2-methyl-1H-indol-3-yl)acetyl]-8-aza-bicyclo[3.2.1]oct-3-ylmethyl}-phenyl)-urea, Compound A659;

1-(5-tert-Butyl-2-p-tolyl-2H-pyrazol-3-yl)-3-{3-[8-(5-methyl-pyrazine-2-carbonyl)-8-aza-bicyclo[3.2.1]oct-3-ylmethyl]-phenyl}-urea, Compound A660;

1-(5-tert-Butyl-2-p-tolyl-2H-pyrazol-3-yl)-3-{3-[8-(4-methoxy-thiophene-3-carbonyl}8-aza-bicyclo[3.2.1]oct-3-ylmethyl]-phenyl}-urea, Compound A661;

1-(5-tert-Butyl-2-p-tolyl-2H-pyrazol-3-yl)-3-{3-[8-(5-methyl-1-phenyl-1H-pyrazole-4-carbonyl)-8-aza-bicyclo[3.2.1]oct-3-ylmethyl]-phenyl}-urea, Compound A662;

1-(5-tert-Butyl-2-p-tolyl-2H-pyrazol-3-yl)-3-{3-[8-(5oxo-pyrrolidine-2-carbonyl)-8-aza-bicyclo[3.2.1]oct-3-ylmethyl]-phenyl}-urea (0.012 g), C34H42N6O3, 583.34, M+H, 2.47, Compound A663;

1-(5-tert-Butyl-2-p-tolyl-2H-pyrazol-3-yl)-3-{3-[8-(2-methoxy-2-phenyl-acetyl)-8-aza-bicyclo[3.2.1]oct-3-ylmethyl]-phenyl}-urea, Compound A664;

1-(5-tert-Butyl-2-p-tolyl-2H-pyrazol-3-yl)-3-{3-[8-(7-methoxy-benzofuran-2-carbonyl)-8-aza-bicyclo[3.2.1]oct-3-ylmethyl]-phenyl}-urea, Compound A665;

1-(5-tert-Butyl-2-p-tolyl-2H-pyrazol-3-yl)-3-{3-[8-(3-methyl-benzofuran-2-carbonyl)-8-aza-bicyclo[3.2.1]oct-3-ylmethyl]-phenyl}-urea, Compound A666;

1-(5-tert-Butyl-2-p-tolyl-2H-pyrazol-3-yl)-3-{3-[8-(3-thioureido-benzoyl)-8-aza-bicyclo[3.2.1]oct-3-ylmethyl]-phenyl}-urea, Compound A667;

1-(5-tert-Butyl-2-p-tolyl-2H-pyrazol-3-yl)-3-(3-{8-[2-(2,3-dimethoxy-phenyl)-acetyl]-8-aza-bicyclo[3.2.1]oct-3-ylmethyl}-phenyl)urea, Compound A668;

1-(5-tert-Butyl-2-p-tolyl-2H-pyrazol-3-yl)-3-(3-{8-[3-(4-fluoro-phenyl)-propionyl]-8-aza-bicyclo[3.2.1]oct-3-ylmethyl}-phenyl)-urea, Compound A669;

1-(5-tert-Butyl-2-p-tolyl-2H-pyrazol-3-yl)-3-{3-[8-(5-chloro-6-hydroxy-pyridine-3-carbonyl)-8-aza-bicyclo[3.2.1]oct-3-ylmethyl]-phenyl}-urea, Compound A670;

1-(5-tert-Butyl-2-p-tolyl-2H-pyrazol-3-yl)-3-{3-[8-(2,4-dimethyl-thiazole-5-carbonyl)-8-aza-bicyclo[3.2.1]oct-3-ylmethyl]-phenyl}-urea, Compound A671;

1-(5-tert-Butyl-2-p-tolyl-2H-pyrazol-3-yl)-3-(3-{8-[4-(2,2,2-trifluoro-acetyl)-benzoyl]-8-aza-bicyclo[3.2.1]oct-3-ylmethyl}-phenyl)-urea, Compound A672;

1-(5-tert-Butyl-2-p-tolyl-2H-pyrazol-3-yl)-3-(3-{8-[2-(5-chloro-benzo[b]thiophen-3-yl)-acetyl]-8-aza-bicyclo[3.2.1]oct-3-ylmethyl}-phenyl)-urea, Compound A673;

1-(5-tert-Butyl-2-p-tolyl-2H-pyrazol-3-yl)-3-{3-[8-(2-pyridin-3-yl-thiazole-4-carbonyl)-8-aza-bicyclo[3.2.1]oct-3-ylmethyl]-phenyl}-urea, Compound A674;

1-(5-tert-Butyl-2-p-tolyl-2H-pyrazol-3-yl)-3-(3-{8-[2-(5-chloro-3-methyl-benzo[b]thiophen-2-yl)-acetyl]-8-aza-bicyclo[3.2.1]oct-3-ylmethyl}-phenyl)-urea, Compound A675;

1-(5-tert-Butyl-2-p-tolyl-2H-pyrazol-3-yl)-3-{3-[8-(4-oxo-4,5,6,7-tetrahydro-benzofuran-3-carbonyl)-8-aza-bicyclo[3.2.1]oct-3-ylmethyl]-phenyl}-urea, Compound A676;

1-(5-tert-Butyl-2-p-tolyl-2H-pyrazol-3-yl)-3-{3-[8-([1,2,3]thiadiazole-4-carbonyl)-8-aza-bicyclo[3.2.1]oct-3-ylmethyl]-phenyl}-urea, Compound A677;

1-(5-tert-Butyl-2-p-tolyl-2H-pyrazol-3-yl)-3-{3-[8-(3,5-dimethyl-isoxazole-4-carbonyl)-8-aza-bicyclo[3.2.1]oct-3-ylmethyl]-phenyl}-urea, Compound A678;

1-(5-tert-Butyl-2-p-tolyl-2H-pyrazol-3-yl)-3-{3-[8-(5-methyl-2-phenyl-2H-[1,2,3]triazole-4-carbonyl)-8-aza-bicyclo[3.2.1]oct-3-ylmethyl]-phenyl}-urea, Compound A679;

1-{3-[8-(2-Benzo[b]thiophen-3-yl-acetyl)-8-aza-bicyclo[3.2.1]oct-3-ylmethyl]-phenyl}-3-(5-tert-butyl-2-p-tolyl-2H-pyrazol-3-yl)-urea, Compound A680;

1-{3-[8-(Benzo[b]thiophene-2-carbonyl)-8-aza-bicyclo[3.2.1]oct-3-ylmethyl]-phenyl}-3-(5-tert-butyl-2-p-tolyl-2H-pyrazol-3-yl)-urea, Compound A681;

1-(5-tert-Butyl-2-p-tolyl-2H-pyrazol-3-yl)-3-{3-[8-(quinoline-6-carbonyl)-8-aza-bicyclo[3.2.1]oct-3-ylmethyl]-phenyl}-urea, Compound A682;

1-(5-tert-Butyl-2-p-tolyl-2H-pyrazol-3-yl)-3-{3-[8-(3-thiophen-2-yl-propionyl)-8-aza-bicyclo[3.2.1]oct-3-ylmethyl]-phenyl}-urea, Compound A683;

1-(5-tert-Butyl-2-p-tolyl-2H-pyrazol-3-yl)-3-(3-{8-[2-(4-chloro-phenyl)-propionyl]-8-aza-bicyclo[3.2.1]oct-3-ylmethyl}-phenyl)-urea, Compound A684;

1-(5-tert-Butyl-2-p-tolyl-2H-pyrazol-3-yl)-3-{3-[8-(2-furan-2-yl-2-oxo-acetyl)-8-aza-bicyclo[3.2.1]oct-3-ylmethyl]-phenyl}-urea, Compound A685;

1-(5-tert-Butyl-2-p-tolyl-2H-pyrazol-3-yl)-3-{3-[8-(5-chloro-thiophene-2-carbonyl)-8-aza-bicyclo[3.2.1]oct-3-ylmethyl]-phenyl }-urea, Compound A686;

1-{3-[8-(3-1H-Benzoimidazol-2-yl-propionyl)-8-aza-bicyclo[3.2.1]oct-3-ylmethyl]-phenyl}-3-(5-tert-butyl-2-p-tolyl-2H-pyrazol-3-yl)-urea, Compound A687;

N-[2-(3-{3-[3-(5-tert-Butyl-2-p-tolyl-2H-pyrazol-3-yl)-ureido]-benzyl}-8-aza-bicyclo[3.2.1]oct-8-yl)-1-methyl-2-oxo-ethyl]-acetamide, Compound A688;

1-(5-tert-Butyl-2-p-tolyl-2H-pyrazol-3-yl)-3-{3-[8-(2-hydroxy-quinoline-4-carbonyl)-8-aza-bicyclo[3.2.1]oct-3-ylmethyl]-phenyl }-urea, Compound A689;

1-(5-tert-Butyl-2-p-tolyl-2H-pyrazol-3yl)-3-{3-[8-(6-methyl-pyridine-2-carbonyl)-8-aza-bicyclo[3.2.1]oct-3-ylmethyl]-phenyl}-urea, Compound A690;

1-(5-tert-Butyl-2-p-tolyl-2H-pyrazol-3-yl)-3-{3-[8-(tetrahydro-furan-2-carbonyl)-8-aza-bicyclo[3.2.1]oct-3-ylmethyl]-phenyl}-urea, Compound A691;

1-(5-tert-Butyl-2-p-tolyl-2H-pyrazol-3-yl)-3-{3-[8-(4-oxo-2-phenyl-pentanoyl)-8-aza-bicyclo[3.2.1]oct-3-ylmethyl]-phenyl}-urea, Compound A692;

1-(5-tert-Butyl-2-p-tolyl-2H-pyrazol-3-yl)-3-{3-[8-(2,2-dimethyl-pentanoyl)-8-aza-bicyclo[3.2.1]oct-3-ylmethyl]-phenyl}-urea, Compound A693;

1-(5-tert-Butyl-2-p-tolyl-2H-pyrazol-3-yl)-3-{3-[8-(4-methoxy-2-methyl-benzoyl)-8-aza-bicyclo[3.2.1]oct-3-ylmethyl]-phenyl}-urea, Compound A694;

1-(5-tert-Butyl-2-p-tolyl-2H-pyrazol-3-yl)-3-(3-{8-[1-(4-methoxy-phenyl)-cyclopropanecarbonyl]-8-aza-bicyclo[3.2.1]oct-3-ylmethyl}-phenyl)-urea, Compound A695;

1-(5-tert-Butyl-2-p-tolyl-2H-pyrazol-3-yl)-3-{3-[8-(4-hydroxymethyl-benzoyl)-8-aza-bicyclo[3.2.1]oct-3-ylmethyl]-phenyl}-urea, Compound A696;

1-(5-tert-Butyl-2-p-tolyl-2H-pyrazol-3-yl)-3-(3-{8-[2-(3,5-dimethoxy-phenyl)-acetyl]-8-aza-bicyclo[3.2.1]oct-3-ylmethyl}-phenyl)-urea, Compound A697;

1-(5-tert-Butyl-2-p-tolyl-2H-pyrazol-3-yl)-3-(3-{8-[2-(2,3-dimethyl-phenoxy)-acetyl]-8-aza-bicyclo[3.2.1]oct-3-ylmethyl}-phenyl)-urea, Compound A698;

1-(5-tert-Butyl-2-p-tolyl-2H-pyrazol-3-yl)-3-{3-[8-(3-p-tolyl-propionyl)-8-aza-bicyclo[3.2.1]oct-3-ylmethyl]-phenyl}-urea, Compound A699;

1-(5-tert-Butyl-2-p-tolyl-2H-pyrazol-3-yl)-3-{3-[8-(2,4,6-trimethoxy-benzoyl)-8-aza-bicyclo[3.2.1]oct-3-ylmethyl]-phenyl}-urea, Compound A700;

1-{3-[8-(2-Benzo[1,3]dioxol-5-yl-acetyl)-8-aza-bicyclo[3.2.1]oct-3-ylmethyl]-phenyl}-3-(5-tert-butyl-2-p-tolyl-2H-pyrazol-3-yl)-urea, Compound A701;

1-(5-tert-Butyl-2-p-tolyl-2H-pyrazol-3-yl)-3-[3-(8-hept-2-ynoyl-8-aza-bicyclo[3.2.1]oct-3-ylmethyl)-phenyl]-urea, Compound A702;

1-(5-tert-Butyl-2-p-tolyl-2H-pyrazol-3-yl)-3-(3-{8-[2-(4-methoxy-phenoxy)-acetyl]-8-aza-bicyclo[3.2.1]oct-3-ylmethyl}-phenyl)-urea, Compound A703;

1-(5-tert-Butyl-2-p-tolyl-2H-pyrazol-3-yl)-3-{3-[8-(2-methyl-2-phenyl-propionyl)-8-aza-bicyclo[3.2.1]oct-3-ylmethyl]-phenyl}-urea, Compound A704;

1-(5-tert-Butyl-2-p-tolyl-2H-pyrazol-3-yl)-3-{3-[8-(3-methyl-furan-2-carbonyl)-8-aza-bicyclo[3.2.1]oct-3-ylmethyl]-phenyl}-urea, Compound A705;

1-(5-tert-Butyl-2-p-tolyl-2H-pyrazol-3-yl)-3-{3-[8-(2-phenylamino-acetyl)-8-aza-bicyclo[3.2.1]oct-3-ylmethyl]-phenyl}-urea, Compound A706;

N-[3-(3-{3-[3-(5-tert-Butyl-2-p-tolyl-2H-pyrazol-3-yl)-ureido]-benzyl}-8-aza-bicyclo[3.2.1]octane-8-carbonyl)-phenyl]-acetamide (0.026 g), C38H44N6O3, 633.26, M+H, 2.83, Compound A707;

1-(5-tert-Butyl-2-p-tolyl-2H-pyrazol-3-yl)-3-{3-[8-(2-methyl-pyridine-3-carbonyl)-8-aza-bicyclo[3.2.1]oct-3-ylmethyl]-phenyl}-urea, Compound A708;

1-(5-tert-Butyl-2-p-tolyl-2H-pyrazol-3-yl)-3-{3-[8-(2-pyridin-4-yl-acetyl)-8-aza-bicyclo[3.2.1]oct-3-ylmethyl]-phenyl}-urea, Compound A709;

1-(5-tert-Butyl-2-p-tolyl-2H-pyrazol-3-yl)-3-{3-[8-(2-pyridin-3-yl-acetyl)-8-aza-bicyclo[3.2.1]oct-3-ylmethyl]-phenyl}-urea, Compound A710;

1-(5-tert-Butyl-2-p-tolyl-2H-pyrazol-3-yl)-3-{3-[8-(2-3H-imidazol-4-yl-acetyl)-8-aza-bicyclo[3.2.1]oct-3-ylmethyl]-phenyl}-urea, Compound A711;

1-(5-tert-Butyl-2-p-tolyl-2H-pyrazol-3-y)-3-{3-[8-(quinoxaline-2-carbonyl)-8-aza-bicyclo[3.2.1]oct-3-ylmethyl]-phenyl}-urea, Compound A712;

1-{3-[8-(3H-Benzotriazole-5-carbonyl)-8-aza-bicyclo[3.2.1]oct-3-ylmethyl]-phenyl}-3-(5-tert-butyl-2-p-tolyl-2H-pyrazol-3-yl)-urea, Compound A713;

1-(5-tert-Butyl-2-p-tolyl-2H-pyrazol-3-yl)-3-{3-[8-(5-oxo-tetrahydro-furan-2-carbonyl)-8-aza-bicyclo[3.2.1]oct-3-ylmethyl]-phenyl}-urea, Compound A714;

1-(5-tert-Butyl-2-p-tolyl-2H-pyrazol-3-yl)-3-{3-[8-(1H-pyrazole-4-carbonyl)-8-aza-bicyclo[3.2.1]oct-3-ylmethyl]-phenyl}-urea, Compound A715;

1-(5-tert-Butyl-2-p-tolyl-2H-pyrazol-3-yl)-3-{3-[8-(2,3-dihydro-1H-indole-2-carbonyl)-8-aza-bicyclo[3.2.1]oct-3-ylmethyl]-phenyl}-urea, Compound A716;

1-(5-tert-Butyl-2-p-tolyl-2H-pyrazol-3-yl)-3-(3-{8-[2-(3,5-difluoro-phenyl)-acetyl]-8-aza-bicyclo[3.2.1]oct-3-ylmethyl}-phenyl)-urea, Compound A717;

1-{3-[8-(4-Aminomethyl-benzoyl)-8-aza-bicyclo[3.2.1]oct-3-ylmethyl]-phenyl}-3-(5-tert-butyl-2-p-tolyl-2H-pyrazol-3-yl)-urea, Compound A718;

1-(5-tert-Butyl-2-p-tolyl-2H-pyrazol-3-yl)-3-(3-{8-[2-(3,4-difluoro-phenyl)-acetyl]-8-aza-bicyclo[3.2.1]oct-3-ylmethyl}-phenyl)-urea (0.0087 g), C37H41F2N5O2, 626.32, M+H, 3.40, Compound A719;

1-(5-tert-Butyl-2-p-tolyl-2H-pyrazol-3-yl)-3-(3-{8-[2-(2,4-difluoro-phenyl)-acetyl]-8-aza-bicyclo[3.2.1]oct-3-ylmethyl}-phenyl)-urea (0.0137 g), C37H41F2N5O2, 626.30, M+H, 3.47, Compound A720;

1-(3-{8-[2-(4-Amino-phenyl)-acetyl]-8-aza-bicyclo[3.2.1]oct-3-ylmethyl}-phenyl)-3-(5-tert-butyl-2-p-tolyl-2H-pyrazol-3-yl)urea, Compound A721;

4-Amino-N-[2-(3-{3-[3-(5-tert-butyl-2-p-tolyl-2H-pyrazol-3-yl)-ureido]-benzyl}-8-aza-bicyclo[3.2.1]oct-8-yl)-2-oxo-ethyl]-benzamide, Compound A722;

1-{3-[8-(3-Amino-4-hydroxy-benzoyl)-8-aza-bicyclo[3.2.1]oct-3-ylmethyl]-phenyl}-3-(5-tert-butyl-2-p-tolyl-2H-pyrazol-3-yl)-urea, Compound A723;

1-(5-tert-Butyl-2-p-tolyl-2H-pyrazol-3-yl)-3-{3-[8-(isoquinoline-1-carbonyl)-8-aza-bicyclo[3.2.1]oct-3-ylmethyl]-phenyl}-urea, Compound A724;

1-(5-tert-Butyl-2-p-tolyl-2H-pyrazol-3-yl)-3-{3-[8-(quinoline-4-carbonyl)-8-aza-bicyclo[3.2.1]oct-3-ylmethyl]-phenyl}-urea, Compound A725;

1-(5-tert-Butyl-2-p-tolyl-2H-pyrazol-3-yl)-3-{3-[8-(quinoline-3-carbonyl)8-aza-bicyclo[3.2.1]oct-3-ylmethyl]-phenyl}-urea, Compound A726;

1-(5-tert-Butyl-2-p-tolyl-2H-pyrazol-3-yl)-3-{3-[8quinoline-2-carbonyl)-8-aza-bicyclo[3.2.1]oct-3-ylmethyl]-phenyl}-urea, Compound A727;

1-(5-tert-Butyl-2-p-tolyl-2H-pyrazol-3-yl)-3-{3-[8-(3-piperidin-1-yl-propionyl)-8-aza-bicyclo[3.2.1]oct-3-ylmethyl]-phenyl}-urea, Compound A728;

1-(5-tert-Butyl-2-p-tolyl-2H-pyrazol-3-yl)-3-{3-[8-(pyridine-4-carbonyl)-8-aza-bicyclo[3.2.1]oct-3-ylmethyl]-phenyl}-urea, Compound A729;

1-(5-tert-Butyl-2-p-tolyl-2H-pyrazol-3-yl)-3-{3-[8-(pyridine-3-carbonyl)-8-aza-bicyclo[3.2.1]oct-3-ylmethyl]-phenyl}-urea, Compound A730;

1-{3-[8-(6-Amino-pyridine-3-carbonyl)-8-aza-bicyclo[3.2.1]oct-3-ylmethyl]-phenyl}-3-(5-tert-butyl-2-p-tolyl-2H-pyrazol-3-yl)-urea, Compound A731;

1-{3-[8-(2-Amino-pyridine-3-carbonyl)-8-aza-bicyclo[3.2.1]oct-3-ylmethyl]-phenyl}-3-(5-tert-butyl-2-p-tolyl-2H-pyrazol-3-yl)-urea, Compound A732;

1-(5-tert-Butyl-2-p-tolyl-2H-pyrazol-3-yl)-3-{3-[8-(pyridine-2-carbonyl)-8-aza-bicyclo[3.2.1]oct-3-ylmethyl]-phenyl}-urea, Compound A733;

1-(5-tert-Butyl-2-p-tolyl-2H-pyrazol-3-yl)-3-{3-[8-(6-chloro-pyridine-3-carbonyl)-8-aza-bicyclo[3.2.1]oct-3-ylmethyl]-phenyl}-urea, Compound A734;

1-(5-tert-Butyl-2-p-tolyl-2H-pyrazol-3-yl)-3-{3-[8-(2-chloro-pyridine-3-carbonyl)-8-aza-bicyclo[3.2.1]oct-3-ylmethyl]-phenyl}-urea, Compound A735;

1-{3-[8-(3-Amino-pyrazine-2-carbonyl)-8-aza-bicyclo[3.2.1]oct-3-ylmethyl]-phenyl}-3-(5-tert-butyl-2-p-tolyl-2H-pyrazol-3-yl)-urea, Compound A736;

1-(5-tert-Butyl-2-p-tolyl-2H-pyrazol-3-yl)-3-{3-[8-(pyrazine-2-carbonyl)-8-aza-bicyclo[3.2.1]oct-3-ylmethyl]-phenyl}-urea, Compound A737;

1-(5-tert-Butyl-2-p-tolyl-2H-pyrazol-3-yl)3-{3-[8-(1H-indole-5-carbonyl)-8-aza-bicyclo[3.2.1]oct-3-ylmethyl]-phenyl}-urea, Compound A738;

1-(5-tert-Butyl-2-p-tolyl-2H-pyrazol-3-yl)-3-{3-[8-(3-1H-indol-3-yl-propionyl)-8-aza-bicyclo[3.2.1]oct-3-ylmethyl]-phenyl}-urea, Compound A739;

1-(5-tert-Butyl-2-p-tolyl-2H-pyrazol-3-yl)-3-{3-[8-(2-1H-indol-3-yl-acetyl)-8-aza-bicyclo[3.2.1]oct-3-ylmethyl]-phenyl}-urea, Compound A740;

1-(5-tert-Butyl-2-p-tolyl-2H-pyrazol-3-yl)-3-(3-{8-[2-(1H-indol-3-yl)-2-oxo-acetyl]-8-aza-bicyclo[3.2.1]oct-3-ylmethyl}-phenyl)-urea, Compound A741;

1-(5-tert-Butyl-2-p-tolyl-2H-pyrazol-3-yl)-3-{3-[8-(1H-indole-3-carbonyl)-8-aza-bicyclo[3.2.1]oct-3-ylmethyl]-phenyl}-urea, Compound A742;

1-(5-tert-Butyl-2-p-tolyl-2H-pyrazol-3-yl)-3-{3-[8-(2-thiophen-3-yl-acetyl)-8-aza-bicyclo[3.2.1]oct-3-ylmethyl]-phenyl}-urea, Compound A743;

1-(5-tert-Butyl-2-p-tolyl-2H-pyrazol-3-yl)-3-{3-[8-(thiophene-3-carbonyl)-8-aza-bicyclo[3.2.1]oct-3-ylmethyl]-phenyl}-urea, Compound A744;

1-(5-tert-Butyl-2-p-tolyl-2H-pyrazol-3-yl)-3-{3-[8-(2-thiophen-2-yl-acetyl)-8-aza-bicyclo[3.2.1]oct-3-ylmethyl]-phenyl}-urea, Compound A745;

1-(5-tert-Butyl-2-p-tolyl-2H-pyrazol-3-yl)-3-{3-[8-(5-methyl-thiophene-2-carbonyl)-8-aza-bicyclo[3.2.1]oct-3-ylmethyl]-phenyl}-urea, Compound A746;

1-(5-tert-Butyl-2-p-tolyl-2H-pyrazol-3-yl)-3-{3-[8-(furan-3-carbonyl)-8-aza-bicyclo[3.2.1]oct-3-ylmethyl]-phenyl}-urea, Compound A747;

1-(5-tert-Butyl-2-p-tolyl-2H-pyrazol-3-yl)-3-{3-[8-(3-furan-2-yl-propionyl)-8-aza-bicyclo[3.2.1]oct-3-ylmethyl]-phenyl}-urea, Compound A748;

1-(5-tert-Butyl-2-p-tolyl-2H-pyrazol-3-yl)-3-{3-[8-((S)-5-oxo-pyrrolidine-2-carbonyl)-8-aza-bicyclo[3.2.1]oct-3-ylmethyl]-phenyl}-urea (0.0045 g), C34H42N6O3, 583.35, M+H, 2.48, Compound A663A;

1-(5-tert-Butyl-2-p-tolyl-2H-pyrazol-3-yl)-3-(3-{8-[2-(2,5-dioxo-imidazolidin-4-yl)-acetyl]-8-aza-bicyclo[3.2.1]oct-3-ylmethyl}-phenyl)-urea, Compound A749;

1-(5-tert-Butyl-2-p-tolyl-2H-pyrazol-3-yl)-3-[3-(8-heptanoyl-8-aza-bicyclo[3.2.1]oct-3-ylmethyl)-phenyl]-urea, Compound A750;

1-(5-tert-Butyl-2-p-tolyl-2H-pyrazol-3-yl)-3-{3-[8-(5-oxo-5-phenyl-pentanoyl)-8-aza-bicyclo[3.2.1]oct-3-ylmethyl]-phenyl}-urea, Compound A751;

1-(5-tert-Butyl-2-p-tolyl-2H-pyrazol-3-yl)-3-(3-{8-[4-(4-methoxy-phenyl)-butyryl]-8-aza-bicyclo[3.2.1]oct-3-ylmethyl}-phenyl)-urea, Compound A752;

1-(5-tert-Butyl-2-p-tolyl-2H-pyrazol-3-yl)-3-{3-[8-(4-phenyl-butyryl)-8-aza-bicyclo[3.2.1]oct-3-ylmethyl]-phenyl}-urea, Compound A753;

1-(5-tert-Butyl-2-p-tolyl-2H-pyrazol-3-yl)-3-(3-{8-[2-(4-methoxy-phenyl)-acetyl]-8-aza-bicyclo[3.2.1]oct-3-ylmethyl}-phenyl)-urea, Compound A754;

1-(5-tert-Butyl-2-p-tolyl-2H-pyrazol-3-yl)-3-(3-{8-[2-(4-fluoro-phenyl)-acetyl]-8-aza-bicyclo[3.2.1]oct-3-ylmethyl}-phenyl)-urea, Compound A755;

1-(5-tert-Butyl-2-p-tolyl-2H-pyrazol-3-yl)-3-(3-{8-[2-(3,4-dimethoxy-phenyl)-acetyl]-8-aza-bicyclo[3.2.1]oct-3-ylmethyl}-phenyl)-urea, Compound A756;

1-(5-tert-Butyl-2-p-tolyl-2H-pyrazol-3-yl)-3-(3-{8-[2-(3-methoxy-phenyl)-acetyl]-8-aza-bicyclo[3.2.1]oct-3-ylmethyl)}-phenyl)-urea, Compound A757;

1-(5-tert-Butyl-2-p-tolyl-2H-pyrazol-3-yl)-3-(3-{8-[2-(3-fluoro-phenyl)-acetyl]-8-aza-bicyclo[3.2.1]oct-3-ylmethyl}-phenyl)-urea, Compound A758;

1-(-tert-Butyl-2-p-tolyl-2H-pyrazol-3-yl)-3-{3-[8-(2-o-tolyl-acetyl)-8-aza-bicyclo[3.2.1]oct-3-ylmethyl]-phenyl}-urea, Compound A759;

1-(5-tert-Butyl-2-p-tolyl-2H-pyrazol-3-yl)-3-(3-{8-[2-(2-methoxy-phenyl)-acetyl]-8-aza-bicyclo[3.2.1]oct-3-ylmethyl}-phenyl)-urea, Compound A760;

1-(5-tert-Butyl-2-p-tolyl-2H-pyrazol-3-yl)-3-(3-{8-[2-(2-fluoro-phenyl)-acetyl]-8-aza-bicyclo[3.2.1]oct-3-ylmethyl}-phenyl)-urea (0.0155 g), C37H42N5O2, 608.30, M+H, 3.40, Compound A761;

1-(5-tert-Butyl-2-p-tolyl-2H-pyrazol-3-yl)-3-{3-[8-(2-methoxy-acetyl)-8-aza-bicyclo[3.2.1]oct-3-ylmethyl]-phenyl}-urea, Compound A762;

1-(5-tert-Butyl-2-p-tolyl-2H-pyrazol-3-yl)-3-{3-[8-(2-phenoxy-acetyl)-8-aza-bicyclo[3.2.1]oct-3-ylmethyl]-phenyl}-urea, Compound A763;

1-(5-tert-Butyl-2-p-tolyl-2H-pyrazol-3-yl)-3-{3-[8-(2-dimethylamino-acetyl)-8-aza-bicyclo[3.2.1]oct-3-ylmethyl]-phenyl}-urea, Compound A764;

1-(5-tert-Butyl-2-p-tolyl-2H-pyrazol-3-yl)-3-(3-{8-[2-(N-methyl-guanidino)-acetyl]-8-aza-bicyclo[3.2.1]oct-3-ylmethyl}-phenyl)-urea, Compound A765;

N-[2-(3-{3-[3-(5-tert-Butyl-2-p-tolyl-2H-pyrazol-3-yl)-ureido]-benzyl}-8-aza-bicyclo[3.2.1]oct-8-yl)-2-oxo-ethyl]-acetamide (0.0205 g), C33H42N6O3, 571.34, M+H, 2.52, Compound A766;

1-(5-tert-Butyl-2-p-tolyl-2H-pyrazol-3-yl)-3-{3-[8-(2,2-dimethyl-propionyl)-8-aza-bicyclo[3.2.1]oct-3-ylmethyl]-phenyl}-urea, Compound A767;

1-(5-tert-Butyl-2-p-tolyl-2H-pyrazol-3-yl)-3-[3-(8-cycloheptanecarbonyl-8-aza-bicyclo[3.2.1]oct-3-ylmethyl)-phenyl]-urea, Compound A768;

1-(5-tert-Butyl-2-p-tolyl-2H-pyrazol-3-yl)-3-{3-[8-(2-naphthalen-2-yl-acetyl)-8-aza-bicyclo[3.2.1]oct-3-ylmethyl]-phenyl}-urea, Compound A769;

1-(5-tert-Butyl-2-p-tolyl-2H-pyrazol-3-yl)-3-{3-[8-(2-naphthalen-1-yl-acetyl)-8-aza-bicyclo[3.2.1]oct-3-ylmethyl]-phenyl}-urea, Compound A770;

1-(5-tert-Butyl-2-p-tolyl-2H-pyrazol-3-yl)-3-{3-[8-(furan-2-carbonyl)-8-aza-bicyclo[3.2.1]oct-3-ylmethyl]-phenyl}-urea, Compound A771;

1-(5-tert-Butyl-2-p-tolyl-2H-pyrazol-3-yl)-3-{3-[8-(5-methyl-3-phenyl-isoxazole-4-carbonyl)-8-aza-bicyclo[3.2.1]oct-3-ylmethyl]-phenyl}-urea, Compound A772;

1-(5-tert-Butyl-2-p-tolyl-2H-pyrazol-3-yl)-3-[3-(8-butyryl-8-aza-bicyclo[3.2.1]oct-3-ylmethyl)-phenyl]-urea, Compound A773;

1-(5-tert-Butyl-2-p-tolyl-2H-pyrazol-3-yl)-3-(3-{8-[4-(4-fluoro-phenyl)-4-oxo-butyryl]-8-aza-bicyclo[3.2.1]oct-3-ylmethyl}-phenyl)-urea, Compound A774;

4-(3-{3-[3-(5-tert-Butyl-2-p-tolyl-2H-pyrazol-3-yl)-ureido]-benzyl}-8-aza-bicyclo[3.2.1]oct-8-yl)-4-oxo-butyric acid methyl ester, Compound A775;

1-(5-tert-Butyl-2-p-tolyl-2H-pyrazol-3-yl)-3-(3-{8-[3-(2-methoxy-phenyl)propionyl]-8-aza-bicyclo[3.2.1]oct-3-ylmethyl}-phenyl)-urea, Compound A776;

1-(5-tert-Butyl-2-p-tolyl-2H-pyrazol-3-yl)-3-{3-[8-(3-phenyl-propionyl)-8-aza-bicyclo[3.2.1]oct-3-ylmethyl]-phenyl}-urea, Compound A777;

1-(5-tert-Butyl-2-p-tolyl-2H-pyrazol-3-yl)-3-3-[8-(3-phenoxy-propionyl)-8-aza-bicyclo[3.2.1]oct-3-ylmethyl]-phenyl}-urea, Compound A778;

N-[2-(3-{3-[3-(5-tert-Butyl-2-p-tolyl-2H-pyrazol-3-yl)-ureido]-benzyl}-8-aza-bicyclo[3.2.1]oct-8-yl)-2-oxo-ethyl]-benzamide, Compound A779;

1-(5-tert-Butyl-2-p-tolyl-2H-pyrazol-3-yl)-3-{3-[8-(2-phenyl-propionyl)-8-aza-bicyclo[3.2.1]oct-3-ylmethyl]-phenyl}-urea, Compound A780;

1-(5-tert-Butyl-2-p-tolyl-2H-pyrazol-3-yl)-3-{3-[8-(2-oxo-3-phenyl-propionyl)-8-aza-bicyclo[3.2.1]oct-3-ylmethyl]-phenyl}-urea, Compound A781;

1-(5-tert-Butyl-2-p-tolyl-2H-pyrazol-3-yl)-3-{3-[8-(2-oxo-propionyl)-8-aza-bicyclo[3.2.1]oct-3-ylmethyl]-phenyl}-urea, Compound A782;

1-(5-tert-Butyl-2-p-tolyl-2H-pyrazol-3-yl)-3-(3-{8-[3-(cyano-methyl-methyl)-benzoyl]-8-aza-bicyclo[3.2.1]oct-3-ylmethyl}-phenyl)-urea, Compound A783;

1-(5-tert-Butyl-2-p-tolyl-2H-pyrazol-3-yl)-3-3-[8-(3,5-dimethoxy-benzoyl)-8-aza-bicyclo[3.2.1]oct-3-ylmethyl]-phenyl}-urea, Compound A784;

1-(5-tert-Butyl-2-p-tolyl-2H-pyrazol-3-yl)-3-3-[8-(2,4-dimethoxy-benzoyl)-8-aza-bicyclo[3.2.1]oct-3-ylmethyl]-phenyl}-urea, Compound A785;

1-(5-tert-Butyl-2-p-tolyl-2H-pyrazol-3-yl)-3-3-[8-(2,3-dimethoxy-benzoyl)-8-aza-bicyclo[3.2.1]oct-3-ylmethyl]-phenyl}-urea (0.0245 g), C38H45N5O4, 636.29, M+H, 3.30, Compound A786;

1-(5-tert-Butyl-2-p-tolyl-2H-pyrazol-3-yl)-3-{3-[8-(1,2,3,4-tetrahydro-naphthalene-2-carbonyl)-8-aza-bicyclo[3.2.1]oct-3-ylmethyl]-phenyl}-urea, Compound A787;

1-(5-tert-Butyl-2-p-tolyl-2H-pyrazol-3-yl)-3-{3-[8-(2-cyclohexyl-acetyl)-8-aza-bicyclo[3.2.1]oct-3-ylmethyl]-phenyl}-urea, Compound A788;

1-(5-tert-Butyl-2-p-tolyl-2H-pyrazol-3-yl)-3-{3-[8-(1-methyl-cyclohexanecarbonyl)-8-aza-bicyclo[3.2.1]oct-3-ylmethyl]-phenyl}-urea, Compound A789;

1-(5-tert-Butyl-2-p-tolyl-2H-pyrazol-3-yl)-3-[3-(8-cyclohexanecarbonyl-8-aza-bicyclo[3.2.1]oct-3-ylmethyl)-phenyl]-urea, Compound A790;

1-(5-tert-Butyl-2-p-tolyl-2H-pyrazol-3-yl)-3-3-[8-(2-cyclopentyl-acetyl)-8-aza-bicyclo[3.2.1]oct-3-ylmethyl]-phenyl}-urea, Compound A791;

1-(5-tert-Butyl-2-p-tolyl-2H-pyrazol-3-yl)-3-{3-[8-(1-phenyl-cyclopentanecarbonyl)-8-aza-bicyclo[3.2.1]oct-3-ylmethyl]-phenyl}-urea, Compound A792;

1-(5-tert-Butyl-2-p-tolyl-2H-pyrazol-3-yl)-3-[3-(8-cyclopentanecarbonyl-8-aza-bicyclo[3.2.1]oct-3-ylmethyl)-phenyl]-urea, Compound A793;

1-(5-tert-Butyl-2-p-tolyl-2H-pyzol-3-yl)-3-[3-(8-cyclobutanecarbonyl-8-aza-bicyclo[3.2.1]oct-3-ylmethyl)-phenyl]-urea, Compound A794;

1-(5-tert-Butyl-2-p-tolyl-2H-pyrazol-3-yl)-3-{3-[8-(1-methyl-cyclopropanecarbonyl)-8-aza-bicyclo[3.2.1]oct-3-ylmethyl]-phenyl}-urea, Compound A795;

1-{3-[8-(3,5-Bis-trifluoromethyl-benzoyl)-8-aza-bicyclo[3.2.1]oct-3-ylmethyl]-phenyl}-3-(5-tert-butyl-2-p-tolyl-2H-pyrazol-3-yl)-urea, Compound A796;

1-{3-[8-(4-Amino-5-chloro-2-methoxy-benzoyl)-8-aza-bicyclo[3.2.1]oct-3-ylmethyl]-phenyl}-3-(5-tert-butyl-2-p-tolyl-2H-pyrazol-3-yl)-urea, Compound A797;

1-(5-tert-Butyl-2-p-tolyl-2H-pyrazol-3-yl)-3-{3-[8-(imidazo[2,1-b]benzothiazole-2-carbonyl)-8-aza-bicyclo[3.2.1]oct-3-ylmethyl]-phenyl}-urea, Compound A798;

1-(5-tert-Butyl-2-p-tolyl-2H-pyrazol-3-yl)-3-{3-[8-([1,6]naphthyridine-2-carbonyl)-8-aza-bicyclo[3.2.1]oct-3-ylmethyl]-phenyl}-urea, Compound A799;

1-(5-tert-Butyl-2-p-tolyl-2H-pyrazol-3-yl)-3-{3-[8-(2-methyl-5-trifluoromethyl-oxazole-4-carbonyl)-8-aza-bicyclo[3.2.1]oct-3-ylmethyl]-phenyl}-urea, Compound A800;

1-(5-tert-Butyl-2-p-tolyl-2H-pyrazol-3-yl)-3-(3-{8-[4-(4-chloro-phenyl)-thiophene-2-carbonyl]-8-aza-bicyclo[3.2.1]oct-3-ylmethyl}-phenyl)-urea, Compound A801;

1-(5-tert-Butyl-2-p-tolyl-2H-pyrazol-3-yl)-3-{3-[8-(2-trifluoromethyl-[1,8]naphthyridine-3-carbonyl)-8-aza-bicyclo[3.2.1]oct-3-ylmethyl]-phenyl}-urea, Compound A802;

1-(5-tert-Butyl-2-p-tolyl-2H-pyrazol-3-yl)-3-(3-{8-[4-(4-methoxy-phenyl)-thiophene-2-carbonyl]-8-aza-bicyclo[3.2.1]oct-3-ylmethyl}-phenyl)-urea, Compound A803;

1-(5-tert-Butyl-2-p-tolyl-2H-pyrazol-3-yl)-3-(3-{8-[2-(4,6-dimethyl-pyrimidin-2-ylamino)-benzoyl]-8-aza-bicyclo[3.2.1]oct-3-ylmethyl}-phenyl)-urea, Compound A804;

1-(5-tert-Butyl-2-p-tolyl-2H-pyrazol-3-yl)-3-(3-{8-[3-(4,6-dimethyl-pyrimidin-2-ylamino)-benzoyl]-8-aza-bicyclo[3.2.1]oct-3-ylmethyl}-phenyl)-urea, Compound A805;

1-(5-tert-Butyl-2-p-tolyl-2H-pyrazol-3-yl)-3-(3-{8-[4-(4,6-dimethyl-pyrimidin-2-ylamino)-benzoyl]-8-aza-bicyclo[3.2.1]oct-3-ylmethyl}-phenyl)-urea, Compound A806;

1-(5-tert-Butyl-2-p-tolyl-2H-pyrazol-3-yl)-3-(3-{8-[3-(2,2-difluoro-benzo[1,3]dioxol-5-yl)-acryloyl]-8-aza-bicyclo[3.2.1]oct-3-ylmethyl}-phenyl)-urea, Compound A807;

1-(5-tert-Butyl-2-p-tolyl-2H-pyrazol-3-yl)-3-{3-[8-(2-phenyl-5-trifluoromethyl-oxazole-4-carbonyl)-8-aza-bicyclo[3.2.1]oct-3-ylmethyl]-phenyl}-urea, Compound A808;

1-(5-tert-Butyl-2-p-tolyl-2H-pyrazol-3-yl)-3-{3-[8-(6-trifluoromethyl-pyridine-3-carbonyl)-8-aza-bicyclo[3.2.1]oct-3-ylmethyl]-phenyl}-urea, Compound A809;

1-(5-tert-Butyl-2-p-tolyl-2H-pyrazol-3-yl)-3-(3-{8-[2-(4,6-dimethoxy-pyrimidin-2-ylsulfanyl)-benzoyl]-8-aza-bicyclo[3.2.1]oct-3-ylmethyl}-phenyl)-urea, Compound A810;

1-(5-tert-Butyl-2-p-tolyl-2H-pyrazol-3-yl)-3-(3-{8-[3-(4,6-dimethoxy-pyrimidin-2-yloxy)-benzoyl]-8-aza-bicyclo[3.2.1]oct-3-ylmethyl}-phenyl)-urea, Compound A811;

1-(5-tert-Butyl-2-p-tolyl-2H-pyrazol-3-yl)-3-{3-[8-(2-trifluoromethyl-[1,6]naphthyridine-3-carbonyl)-8-aza-bicyclo[3.2.1]oct-3-ylmethyl]-phenyl}-urea, Compound A812;

1-(5-tert-Butyl-2-p-tolyl-2H-pyrazol-3-yl)-3-{3-[8-(2-chloro-4-methanesulfonyl-benzoyl)-8-aza-bicyclo[3.2.1]oct-3-ylmethyl]-phenyl}-urea, Compound A813;

1-(5-tert-Butyl-2-p-tolyl-2H-pyrazol-3-yl)-3-{3-[8-(1H-indole-6-carbonyl)-8-aza-bicyclo[3.2.1]oct-3-ylmethyl]-phenyl}-urea, Compound A814;

1-(5-tert-Butyl-2-p-tolyl-2H-pyrazol-3-yl)-3-[3-(8-{3-[(4,6-dimethyl-pyrimidin-2-yl)-methyl-amino]-benzoyl}-8-aza-bicyclo[3.2.1]oct-3-ylmethyl)-phenyl]-urea, Compound A815;

1-(5-tert-Butyl-2-p-tolyl-2H-pyrazol-3-yl)-3-{3-[8-(2-methyl-[1,6]naphthyridine-3-carbonyl)-8-aza-bicyclo[3.2.1]oct-3-ylmethyl]-phenyl}-urea, Compound A816;

1-(5-tert-Butyl-2-p-tolyl-2H-pyrazol-3-yl)-3-{3-[8-([1,8]naphthyridine-2-carbonyl)-8-aza-bicyclo[3.2.1]oct-3-ylmethyl]-phenyl}-urea, Compound A817;

1-(5-tert-Butyl-2-p-tolyl-2H-pyrazol-3-yl)-3-{3-[8-(4,5-dihydro-benzo[b]thiophene-6-carbonyl)-8-aza-bicyclo[3.2.1]oct-3-ylmethyl]-phenyl}-urea, Compound A818;

1-(5-tert-Butyl-2-p-tolyl-2H-pyrazol-3-yl)-3-{3-[8-(3a,4,5,7a-tetrahydro-benzofuran-6-carbonyl)-8-aza-bicyclo[3.2.1]oct-3-ylmethyl]-phenyl}-urea, Compound A819;

1-(3-{8-[1-(5-Bromo-pyrimidin-2-yl)-piperidine-4-carbonyl]-8-aza-bicyclo[3.2.1]oct-3-ylmethyl}-phenyl)-3-(5-tert-butyl-2-p-tolyl-2H-pyrazol-3-yl)-urea, Compound A820;

1-(5-tert-Butyl-2-p-tolyl-2H-pyrazol-3-yl)-3-(3-{8-[2-(4,6-dimethoxy-pyrimidin-2-yloxy)-benzoyl]-8-aza-bicyclo[3.2.1]oct-3-ylmethyl-3-phenyl)-urea, Compound A821;

1-(3-{8-[1-(5-Bromo-pyrimidin-2-yl)-piperidine-3-carbonyl]-8-aza-bicyclo[3.2.1]oct-3-ylmethyl}-phenyl)-3-(5-tert-butyl-2-p-tolyl-2H-pyrazol-3-yl)urea, Compound A822;

1-(5-tert-Butyl-2-p-tolyl-2H-pyrazol-3-yl)-3-[3-(8-{4-[(4,6-dimethyl-pyrimidin-2-yl)-methyl-amino]-benzoyl}-8-aza-bicyclo[3.2.1]oct-3-ylmethyl)-phenyl]-urea, Compound A823;

1-(5-tert-Butyl-2-p-tolyl-2H-pyrazol-3-yl)-3-{3-[8-(1H-pyrrole-3-carbonyl)-8-aza-bicyclo[3.2.1]oct-3-ylmethyl]-phenyl}-urea, Compound A824;

1-(5-tert-Butyl-2-p-tolyl-2H-pyrazol-3-yl)-3-{3-[8-(4-trifluoromethyl-pyridine-3-carbonyl)-8-aza-bicyclo[3.2.1]oct-3-ylmethyl]-phenyl}-urea, Compound A825;

1-(5-tert-Butyl-2-p-tolyl-2H-pyrazol-3-yl)-3-{3-[8-(2-methyl-[1,8]naphthyridine-3-carbonyl)-8-aza-bicyclo[3.2.1]oct-3-ylmethyl]-phenyl}-urea, Compound A826;

1-(5-tert-Butyl-2-p-tolyl-2H-pyrazol-3-yl)-3-{3-[8-(2,4,6-trimethyl-benzoyl)-8-aza-bicyclo[3.2.1]oct-3-ylmethyl]-phenyl}-urea, Compound A827;

1-(5-tert-Butyl-2-p-tolyl-2H-pyrazol-3-yl)-3-{3-[8-(2,2-difluoro-benzo[1,3]dioxole-5-carbonyl)-8-aza-bicyclo[3.2.1]oct-3-ylmethyl]-phenyl}-urea, Compound A828;

4-(3-{3-[3-(5-tert-Butyl-2-p-tolyl-2H-pyrazol-3-yl)-ureido]-benzyl}-8-aza-bicyclo[3.2.1]octane-8-carbonyl)-2,5-dimethyl-furan-3-sulfonic acid (thiophen-2-ylmethyl)-amide, Compound A829;

1-{3-[8-(2-Benzo[1,3]dioxol-5-yl-2-oxo-ethyl)-8-aza-bicyclo[3.2.1]oct-3-ylmethyl]-phenyl}-3-(5-tert-butyl-2-p-tolyl-2H-pyrazol-3-yl)-urea, Compound A830;

1-{3-[8-(2-Benzo[b]thiophen-3-yl-2-oxo-ethyl)-8-aza-bicyclo[3.2.1]oct-3-ylmethyl]-phenyl}-3-(5-tert-butyl-2-p-tolyl-2H-pyrazol-3-yl)-urea, Compound A831;

1-(5-tert-Butyl-2-p-tolyl-2H-pyrazol-3-yl)3-(3-{8-[2-oxo-2-(3-phenyl-isoxazol-5-yl)-ethyl]-8-aza-bicyclo[3.2.1]oct-3-ylmethyl}-phenyl)-urea, Compound A832;

1-(5-tert-Butyl-2-p-tolyl-2H-pyrazol-3-yl)-3-(3-{8-[2-(4-methanesulfonyl-phenyl)-2-oxo-ethyl]-8-aza-bicyclo[3.2.1]oct-3-ylmethyl}-phenyl)-urea, Compound A833;

1-(5-tert-Butyl-2-p-tolyl-2H-pyrazol-3-yl)-3-{3-[8-(2-oxo-2-pyridin-4-yl-ethyl)-8-aza-bicyclo[3.2.1]oct-3-ylmethyl]-phenyl}-urea, Compound A834;

1-(5-tert-Butyl-2-p-tolyl-2H-pyrazol-3-yl)3-(3-{8-[2-(5-methyl-1-phenyl-1H-pyrazol-4-yl)2-oxo-ethyl]-8-aza-bicyclo[3.2.1]oct-3-ylmethyl}-phenyl)-urea, Compound A835;

1-(5-tert-Butyl-2-p-tolyl-2H-pyrazol-3-yl)-3-(3-{8-[2-(5-methyl-3-phenyl-isoxazol-4-yl)-2-oxo-ethyl]-8-aza-bicyclo[3.2.1]oct-3-ylmethyl}-phenyl)-urea, Compound A836;

1-(5-tert-Butyl-2-p-tolyl-2H-pyrazol-3-yl)-3-(3-{8-[2-oxo-2-(5-pyridin-2-yl-thiophen-2-yl)-ethyl]-8-aza-bicyclo[3.2.1]oct-3-ylmethyl}-phenyl)-urea, Compound A837;

1-(5-tert-Butyl-2-p-tolyl-2H-pyrazol-3-yl)-3-(3-{8-[2-(2,4-dimethoxy-phenyl)-2-oxo-ethyl]-8-aza-bicyclo[3.2.1]oct-3-ylmethyl}-phenyl)-urea, Compound A838;

1-(5-tert-Butyl-2-p-tolyl-2H-pyrazol-3-yl)-3-(3-{8-[2-(2,5-dimethoxy-phenyl)-2-oxo-ethyl]-8-aza-bicyclo[3.2.1]oct-3-ylmethyl}-phenyl)-urea, Compound A839;

1-(5-tert-Butyl-2-p-tolyl-2H-pyrazol-3-yl)-3-(3-{8-[2-(3-methoxy-phenyl)-2-oxo-ethyl]-8-aza-bicyclo[3.2.1]oct-3-ylmethyl}-phenyl)-urea, Compound A840;

1-(5-tert-Butyl-2-p-tolyl-2H-pyrazol-3-yl)-3-{3-{8-[2-oxo-2-pyridin-3-yl-ethyl)-8-aza-bicyclo[3.2.1]oct-3-ylmethyl]-phenyl}-urea, Compound A841;

1-(5-tert-Butyl-2-p-tolyl-2H-pyrazol-3-yl)-3-(3-{8-[2-(4-difluoromethoxy-phenyl)-2-oxo-ethyl]-8-aza-bicyclo[3.2.1]oct-3-ylmethyl}-phenyl)-urea, Compound A842;

1-(5-tert-Butyl-2-p-tolyl-2H-pyrazol-3-yl)-3-(3-{8-[2-oxo-2-(4-trifluoromethoxy-phenyl)-ethyl]-8-aza-bicyclo[3.2.1]oct-3-ylmethyl}-phenyl)-urea, Compound A843;

1-(5-tert-Butyl-2-p-tolyl-2H-pyrazol-3-yl)-3-(3-{8-[2-(4-methoxy-phenyl)-2-oxo-ethyl]-8-aza-bicyclo[3.2.1]oct-3-ylmethyl}-phenyl)-urea, Compound A844;

1-(5-tert-Butyl-2-p-tolyl-2H-pyrazol-3-yl)-3-{3-[8-(4-oxo-4,5,6,7-tetrahydro-benzo[1,2,5]oxadiazol-5-yl)-8-aza-bicyclo[3.2.1]oct-3-ylmethyl]-phenyl}-urea, Compound A845;

1-(5-tert-Butyl-2-p-tolyl-2H-pyrazol-3-yl)-3-(3-{8-[2-oxo-2-(2-oxo-1,2,3,4-tetrahydro-quinolin-6-yl)-ethyl]-8-aza-bicyclo[3.2.1]oct-3-ylmethyl}-phenyl)-urea, Compound A846;

1-(5-tert-Butyl-2-p-tolyl-2H-pyrazol-3-yl)-3-(3-{8-[2-oxo-2-(4-pyrrolidin-1-yl-phenyl)-ethyl]-8-aza-bicyclo[3.2.1]oct-3-ylmethyl}-phenyl)-urea, Compound A847;

1-(5-tert-Butyl-2-p-tolyl-2H-pyrazol-3-yl)-3-(3-{8-[2-(4-diethylamino-phenyl)-2-oxo-ethyl]-8-aza-bicyclo[3.2.1]oct-3-ylmethyl}-phenyl)-urea, Compound A848;

5-[2-(3-{3-[3-(5-tert-Butyl-2-p-tolyl-2H-pyrazol-3-yl)-ureido]-benzyl}-8-aza-bicyclo[3.2.1]oct-8-yl)-acetyl]-isoxazole-3-carboxylic acid ethyl ester, Compound A849;

1-(5-tert-Butyl-2-p-tolyl-2H-pyrazol-3-yl)-3-{3-[8-(1,3,5-trimethyl-1H-pyrazole-4-sulfonyl)-8-aza-bicyclo[3.2.1]oct-3-ylmethyl]-phenyl}-urea, Compound A850;

1-{3-[8-(Butane-1-sulfonyl)-8-aza-bicyclo[3.2.1]oct-3-ylmethyl]-phenyl}-3-(5-tert-butyl-2-p-tolyl-2H-pyrazol-3-yl)-urea, Compound A851;

1-(5-tert-Butyl-2-p-tolyl-2H-pyrazol-3-yl)-3-{3-[8-(naphthalene-1-sulfonyl)-8-aza-bicyclo[3.2.1]oct-3-ylmethyl]-phenyl}-urea, Compound A852;

1-{3-[8-(Benzo[1,2,5]thiadiazole-5-sulfonyl)-8-aza-bicyclo[3.2.1]oct-3-ylmethyl]-phenyl}-3-(5-tert-butyl-2-p-tolyl-2H-pyrazol-3-yl)-urea, Compound A853;

1-(5-tert-Butyl-2-p-tolyl-2H-pyrazol-3-yl)3-{3-[8-(2,3-dihydro-benzo[1,4]dioxine-6-sulfonyl)-8-aza-bicyclo[3.2.1]oct-3-ylmethyl]-phenyl}-urea, Compound A854;

1-(5-tert-Butyl-2-p-tolyl-2H-pyrazol-3-yl)-3-{3-[8-(2,3-dihydro-benzofuran-5-sulfonyl)-8-aza-bicyclo[3.2.1]oct-3-ylmethyl]-phenyl}-urea, Compound A855;

1-(5-tert-Butyl-2-p-tolyl-2H-pyrazol-3-yl)-3-{3-[8-(2,4-dichloro-benzenesulfonyl)-8-aza-bicyclo[3.2.1]oct-3-ylmethyl]-phenyl}-urea, Compound A856;

1-(5-tert-Butyl-2-p-tolyl-2H-pyrazol-3-yl)-3-{3-[8-(2,5-dichloro-benzenesulfonyl)-8-aza-bicyclo[3.2.1]oct-3-ylmethyl]-phenyl}-urea, Compound A857;

1-(5-tert-Butyl-2-p-tolyl-2H-pyrazol-3-yl)-3-{3-[8-(2,5-dimethoxy-benzenesulfonyl)-8-aza-bicyclo[3.2.1]oct-3-ylmethyl]-phenyl}-urea, Compound A858;

1-(5-tert-Butyl-2-p-tolyl-2H-pyrazol-3-yl)-3-{3-[8-(2-chloro-4-fluoro-benzenesulfonyl)-8-aza-bicyclo[3.2.1]oct-3-ylmethyl]-phenyl}-urea, Compound A859;

1-(5-tert-Butyl-2-p-tolyl-2H-pyrazol-3-yl)-3-{3-[8-(2-chloro-benzenesulfonyl)-8-aza-bicyclo[3.2.1]oct-3-ylmethyl]-phenyl}-urea, Compound A860;

1-(5-tert-Butyl-2-p-tolyl-2H-pyrazol-3-yl)3-{3-[8-(2-fluoro-benzenesulfonyl)-8-aza-bicyclo[3.2.1]oct-3-ylmethyl]-phenyl}-urea, Compound A861;

1-(5-tert-Butyl-2-p-tolyl-2H-pyrazol-3-yl)-3-{3-[8-(2,4,6-trimethyl-benzenesulfonyl)-8-aza-bicyclo[3.2.1]oct-3-ylmethyl]-phenyl}-urea, Compound A862;

1-(5-tert-Butyl-2-p-tolyl-2H-pyrazol-3-yl)-3-{3-[8-(naphthalene-2-sulfonyl)-8-aza-bicyclo[3.2.1]oct-3-ylmethyl]-phenyl}-urea, Compound A863;

1-(5-tert-Butyl-2-p-tolyl-2H-pyrazol-3-yl)-3-{3-[8thiophene-2-sulfonyl)-8-aza-bicyclo[3.2.1]oct-3-ylmethyl]-phenyl}-urea, Compound A864;

1-(5-tert-Butyl-2-p-tolyl-2H-pyrazol-3-yl)-3-{3-[8-(2-trifluoromethoxy-benzenesulfonyl)-8-aza-bicyclo[3.2.1]oct-3-ylmethyl]-phenyl}-urea, Compound A865;

1-(5-tert-Butyl-2-p-tolyl-2H-pyrazol-3-yl)-3-{3-[8-(3,4-dichloro-benzenesulfonyl)-8-aza-bicyclo[3.2.1]oct-3-ylmethyl]-phenyl}-urea, Compound A866;

1-(5-tert-Butyl-2-p-tolyl-2H-pyrazol-3-yl)-3-{3-[8-(3,4-difluoro-benzenesulfonyl)-8-aza-bicyclo[3.2.1]oct-3-ylmethyl]-phenyl}-urea, Compound A867;

1-(5-tert-Butyl-2-p-tolyl-2H-pyrazol-3-yl)-3-{3-[8-(3,4-dimethoxy-benzenesulfonyl)-8-aza-bicyclo[3.2.1 ]oct-3-ylmethyl]-phenyl}-urea, Compound A868;

1-(5-tert-Butyl-2-p-tolyl-2H-pyrazol-3-yl)-3-{3-[8-(3,5-dimethyl-isoxazole-4-sulfonyl)-8-aza-bicyclo[3.2.1]oct-3-ylmethyl]-phenyl}-urea, Compound A869;

1-(5-tert-Butyl-2-p-tolyl-2H-pyrazol-3-yl)-3-{3-[8-(3-chloro-4-fluoro-benzenesulfonyl)-8-aza-bicyclo[3.2.1]oct-3-ylmethyl]-phenyl}-urea, Compound A870;

1-(5-tert-Butyl-2-p-tolyl-2H-pyrazol-3-yl)-3-{3-[8-(3-fluoro-benzenesulfonyl)-8-aza-bicyclo[3.2.1]oct-3-ylmethyl]-phenyl}-urea, Compound A871;

5-(3-{3-[3-(5-tert-Butyl-2-p-tolyl-2H-pyrazol-3-yl)-ureido]-benzyl}-8-aza-bicyclo[3.2.1]octane-8-sulfonyl)-4-methoxy-thiophene-3-carboxylic acid methyl ester, Compound A872;

1-(5-tert-Butyl-2-p-tolyl-2H-pyrazol-3-yl-)3-{3-[8-(3-methoxy-benzenesulfonyl)-8-aza-bicyclo[3.2.1]oct-3-ylmethyl]-phenyl}-urea, Compound A873;

1-(5-tert-Butyl-2-p-tolyl-2H-pyrazol-3-yl)-3-{3-[8-(thiophene-3-sulfonyl)-8-aza-bicyclo[3.2.1]oct-3-ylmethyl]-phenyl}-urea, Compound A874;

1-(5-tert-Butyl-2-p-tolyl-2H-pyrazol-3-yl)-3-{3-[8-(3-trifluoromethyl-benzenesulfonyl)-8-aza-bicyclo[3.2.1]oct-3-ylmethyl]-phenyl}-urea, Compound A875;

1-(5-tert-Butyl-2-p-tolyl-2H-pyrazol-3-yl)-3-{3-[8-(4-chloro-2,5-dimethyl-benzenesulfonyl)-8-aza-bicyclo[3.2.1]oct-3-ylmethyl]-phenyl}-urea, Compound A876;

1-(5-tert-Butyl-2-p-tolyl-2H-pyrazol-3-yl)-3-{3-[8-(4-chloro-benzenesulfonyl)-8-aza-bicyclo[3.2.1]oct-3-ylmethyl]-phenyl}-urea, Compound A877;

1-(5-tert-Butyl-2-p-tolyl-2H-pyrazol-3-yl)-3-{3-[8-(4-fluoro-benzenesulfonyl)-8-aza-bicyclo[3.2.1]oct-3-ylmethyl]-phenyl}-urea, Compound A878;

1-(5-tert-Butyl-2-p-tolyl-2H-pyrazol-3-yl)-3-{3-[8-(4-methoxy-benzenesulfonyl)-8-aza-bicyclo[3.2.1]oct-3-ylmethyl]-phenyl}-urea, Compound A879;

1-(5-tert-Butyl-2-p-tolyl-2H-pyrazol-3-yl)-3-{3-[8-(4-methyl-3,4-dihydro-2H-benzo[1,4]oxazine-7-sulfonyl)-8-aza-bicyclo[3.2.1]oct-3-ylmethyl]-phenyl}-urea (0.0198 g), C3 8H46N6O4S, 683.3, M+H, 3.55, Compound A880;

1-{3-[8-(4-tert-Butyl-benzenesulfonyl)-8-aza-bicyclo[3.2.1]oct-3-ylmethyl]-phenyl}-3-(5-tert-butyl-2-p-tolyl-2H-pyrazol-3-yl)-urea, Compound A881;

1-(5-tert-Butyl-2-p-tolyl-2H-pyrazol-3-yl)-3-{3-[8-(4-trifluoromethoxy-benzenesulfonyl)-8-aza-bicyclo[3.2.1]oct-3-ylmethyl]-phenyl}-urea, Compound A882;

1-(5-tert-Butyl-2-p-tolyl-2H-pyrazol-3-yl)-3-{3-[8-(5-oxazol-5-yl-thiophene-2-sulfonyl)-8-aza-bicyclo[3.2.1]oct-3-ylmethyl]-phenyl}-urea, Compound A883;

1-(5-tert-Butyl-2-p-tolyl-2H-pyrazol-3-yl)-3-{3-[8-(6-morpholin-4-yl-pyridine-3-sulfonyl)-8-aza-bicyclo[3.2.1]oct-3-ylmethyl]-phenyl}-urea, Compound A884;

1-(5-tert-Butyl-2-p-tolyl-2H-pyrazol-3-yl)-3-{3-[8-(quinoline-8-sulfonyl)-8-aza-bicyclo[3.2.1]oct-3-ylmethyl]-phenyl}-urea, Compound A885;

1-(5-tert-Butyl-2-p-tolyl-2H-pyrazol-3-yl)-3-[3-(8-phenylmethanesulfonyl-8-aza-bicyclo[3.2.1]oct-3-ylmethyl)-phenyl]-urea, Compound A886;

1-[3-(8-Benzenesulfonyl-8-aza-bicyclo[3.2.1]oct-3-ylmethyl)-phenyl]-3-(5-tert-butyl-2-p-tolyl-2H-pyrazol-3-yl)-urea, Compound A887;

1-(5-tert-Butyl-2-p-tolyl-2H-pyrazol-3-yl)-3-{3-[8-(2-phenyl-ethenesulfonyl)-8-aza-bicyclo[3.2.1 ]oct-3-ylmethyl]-phenyl}-urea, Compound A888;

1-{3-[8-(Benzo[1,2,5]oxadiazole-4-sulfonyl)-8-aza-bicyclo[3.2.1]oct-3-ylmethyl]-phenyl}-3-(5-tert-butyl-2-p-tolyl-2H-pyrazol-3-yl)-urea, Compound A889;

1-{3-[8-(Benzo[1,2,5]thiadiazole-4-sulfonyl)-8-aza-bicyclo[3.2.1]oct-3-ylmethyl]-phenyl}-3-(5-tert-butyl-2-p-tolyl-2H-pyrazol-3-yl)-urea, Compound A890;

1-(5-tert-Butyl-2-p-tolyl-2H-pyrazol-3-yl)-3-{3-[8-(1-methyl-1H-imidazole-4-sulfonyl)-8-aza-bicyclo[3.2.1]oct-3-ylmethyl]-phenyl}-urea, Compound A891;

1-(5-tert-Butyl-2-p-tolyl-2H-pyrazol-3-yl)-3-{3-[8-(1,2-dimethyl-1H-imidazole-4-sulfonyl)-8-aza-bicyclo[3.2.1]oct-3-ylmethyl]-phenyl}-urea, Compound A892;

1-(5-tert-Butyl-2-p-tolyl-2H-pyrazol-3-yl)-3-{3-[8-(5-isoxazol-3-yl-thiophene-2-sulfonyl)-8-aza-bicyclo[3.2.1]oct-3-ylmethyl]-phenyl}-urea, Compound A893;

1-(5-tert-Butyl-2-p-tolyl-2H-pyrazol-3-yl)-3-(3-{8-[5-(2-methyl-thiazol-4-y)-thiophene-2-sulfonyl]-8-aza-bicyclo[3.2.1]oct-3-ylmethyl}-phenyl)-urea, Compound A894;

1-(5-tert-Butyl-2-p-tolyl-2H-pyrazol-3-yl)-3-{3-[8-(2-oxo-2H-chromene-6-sulfonyl)-8-aza-bicyclo[3.2.1]oct-3-ylmethyl]-phenyl}-urea, Compound A895;

1-(5-tert-Butyl-2-p-tolyl-2H-pyrazol-3-yl)-3-{3-[8-(5-dimethylamino-naphthalene-1-sulfonyl)-8-aza-bicyclo[3.2.1]oct-3-ylmethyl]-phenyl}-urea, Compound A896;

1-(5-tert-Butyl-2-p-tolyl-2H-pyrazol-3-yl)-3-[3-(8-ethanesulfonyl-8-aza-bicyclo[3.2.1]oct-3-ylmethyl)-phenyl]-urea, Compound A897;

1-(5-tert-Butyl-2-p-tolyl-2H-pyrazol-3-yl)-3-{3-[8-(isoquinoline-5-sulfonyl)-8-aza-bicyclo[3.2.1]oct-3-ylmethyl]-phenyl}-urea, Compound A898;

1-(5-tert-Butyl-2-p-tolyl-2H-pyrazol-3-yl)-3-[3-(8-methanesulfonyl-8-aza-bicyclo[3.2.1]oct-3-ylmethyl)-phenyl]-urea, Compound A899;

2-(3-{3-[3-(5-tert-Butyl-2-p-tolyl-2H-pyrazol-3-yl)-ureido]-benzyl}-8-aza-bicyclo[3.2.1]octane-8-sulfonyl)-benzoic acid methyl ester, Compound A900;

4-(3-{3-[3-(5-tert-Butyl-2-p-tolyl-2H-pyrazol-3-yl)-ureido]-benzyl}-8-aza-bicyclo[3.2.1]octane-8-sulfonyl)-2,5-dimethyl-furan-3-carboxylic acid methyl ester, Compound A901;

5-(3-{3-[3-(5-tert-Butyl-2-p-tolyl-2H-pyrazol-3-yl)-ureido]-benzyl}-8-aza-bicyclo[3.2.1]octane-8-sulfonyl)-1-methyl-1H-pyrrole-2-carboxylic acid methyl ester, Compound A902;

5-(3-{3-[3-(5-tert-Butyl-2-p-tolyl-2H-pyrazol-3-yl)-ureido]-benzyl}-8-aza-bicyclo[3.2.1]octane-8-sulfonyl)-furan-2-carboxylic acid methyl ester, Compound A903;

N-[4-(3-{3-[3-(5-tert-Butyl-2-p-tolyl-2H-pyrazol-3-yl)-ureido]-benzyl}-8-aza-bicyclo[3.2.1]octane-8-sulfonyl)-phenyl]-acetamide, Compound A904;

1-(5-tert-Butyl-2-p-tolyl-2H-pyrazol-3-yl)-3-{3-[8-(4-vinyl-benzenesulfonyl)-8-aza-bicyclo[3.2.1]oct-3-ylmethyl]-phenyl}-urea, Compound A905;

1-(5-tert-Butyl-2-p-tolyl-2H-pyrazol-3-yl)-3-{3-[8-(toluene-4-sulfonyl)-8-aza-bicyclo[3.2.1]oct-3-ylmethyl]-phenyl}-urea, Compound A906;

endo-3-{3-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzo[1,4]dioxin-6-yl)-amide, Compound A412A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzo[1,4]dioxin-6-yl)-amide, Compound A412B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzofuran-5-yl)-amide, Compound A415A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzofuran-5-yl)-amide, Compound A415B;

3-{3-[3-(5-tert-Butyl-2-p-tolyl-2H-pyrazol-3-yl)-ureido]-benzyl}-8-aza-bicyclo[3.2.1]octane-8-carboxylic acid (2,4-dimethoxy-phenyl)-amide, Compound A907;

endo-3-{3-[3-(5-tert-Butyl-2-p-tolyl-2H-pyrazol-3-yl)-ureido]-benzyl}-8-aza-bicyclo[3.2.1]octane-8-carboxylic acid (2,5-dimethoxy-phenyl)-amide, Compound A418A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (2,5-dimethoxy-phenyl)-amide, Compound A418B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (2-methyl-5-phenyl-furan-3-yl)-amide, Compound A421A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (2-methyl-5-phenyl-furan-3-yl)-amide, Compound A421B;

endo-3-{3-[3-(5-tert-Butyl-2-p-tolyl-2H-pyrazol-3-yl)-ureido]-benzyl}-8-aza-bicyclo[3.2.1]octane-8-carboxylic acid benzo[1,3]dioxol-5-ylamide, Compound A427A;

exo-3-{3-[3-(5-tert-Butyl-2-p-tolyl-2H-pyrazol-3-yl)-ureido]-benzyl}-8-aza-bicyclo[3.2.1]octane-8-carboxylic acid benzo[1,3]dioxol-5-ylamide, Compound A427B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (3,4,5-trimethoxy-phenyl)-amide, Compound A424A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (3,4,5-trimethoxy-phenyl)-amide, Compound A424B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (3,4-dimethoxy-phenyl)-amide, Compound A430A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (3,4-dimethoxy-phenyl)-amide, Compound A430B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (3,5-dimethoxy-phenyl)-amide, Compound A433A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (3,5-dimethoxy-phenyl)-amide, Compound A433B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (3,5-dimethyl-isoxazol-4-yl)-amide, Compound A436A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (3,5-dimethyl-isoxazol-4-yl)-amide, Compound A436B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (3-chloro-4-methoxy-phenyl)-amide, Compound A439A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (3-chloro-4-methoxy-phenyl)-amide, Compound A439B;

endo-3-{3-[3-(5-tert-Butyl-2-p-tolyl-2H-pyrazol-3-yl)-ureido]-benzyl}-8-aza-bicyclo[3.2.1]octane-8-carboxylic acid thiophen-3-ylamide, Compound A442A;

exo-3-{3-[3-(5-tert-Butyl-2-p-tolyl-2H-pyrazol-3-yl)-ureido]-benzyl}-8-aza-bicyclo[3.2.1]octane-8-carboxylic acid thiophen-3-ylamide, Compound A442B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (4-difluoromethoxy-phenyl)-amide, Compound A445A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (4-difluoromethoxy-phenyl)-amide, Compound A445B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (4-dimethylamino-phenyl)-amide, Compound A448A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (4-dimethylamino-phenyl)-amide, Compound A448B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (4-trifluoromethoxy-phenyl)-amide, Compound A451A;

exo-3-{3-[35-tert-Butyl-2-p-tolyl-2H-pyrazol-3-yl)-ureido]-benzyl}-8-aza-bicyclo[3.2.1]octane-8-carboxylic acid (4-trifluoromethoxy-phenyl)-amide, Compound A451B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (4-acetyl-phenyl)-amide, Compound A453A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (4-acetyl-phenyl)-amide, Compound A453B;

endo-3-{3-[3-(5-tert-Butyl-2-p-tolyl-2H-pyrazol-3-yl)-ureido]-benzyl}-8-aza-bicyclo[3.2.1]octane-8-carboxylic acid benzo[1,2,5]thiadiazol-4-ylamide, Compound A456A;

exo-3-{3-[3-(5-tert-Butyl-2-p-tolyl-2H-pyrazol-3-yl)-ureido]-benzyl}-8-aza-bicyclo[3.2.1]octane-8-carboxylic acid benzo[1,2,5]thiadiazol4-ylamide, Compound A456B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (4-methoxy-2-methyl-phenyl)-amide, Compound A459A;

exo-3-{3-[3-(5-tert-Butyl-2-p-tolyl-2H-pyrazol-3-yl)-ureido]-benzyl }-8-aza-bicyclo[3.2.1]octane-8-carboxylic acid (4-methoxy-2-methyl-phenyl)-amide, Compound A459B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (5-chloro-2,4-dimethoxy-phenyl)-amide, Compound A462A;

exo-3-{3-[3-(5-tert-Butyl-2-p-tolyl-2H-pyrazol-3-y)-ureido]-benzyl}-8-aza-bicyclo[3.2.1]octane-8-carboxylic acid (5chloro-2,4-dimethoxy-phenyl)-amide, Compound A462B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (5-methyl-2-trifluoromethyl-furan-3-yl)-amide, Compound A465A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (5-methyl-2-trifluoromethyl-furan-3-yl)-amide, Compound A465B;

endo-3-{3-[3-(5-tert-Butyl-2-p-tolyl-2H-pyrazol-3-yl)-ureido]-benzyl}-8-aza-bicyclo[3.2.1]octane-8-carboxylic acid (5-methyl-3-phenyl-isoxazol-4-yl)-amide, Compound A468A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (5-methyl-3-phenyl-isoxazol4-yl)-amide, Compound A468B;

endo-3-3-[3-(5-tert-Butyl-2-p-tolyl-2H-pyrazol-3-yl)-ureido]-benzyl}-8-aza-bicyclo[3.2.1]octane-8-carboxylic acid (6-fluoro-4H-benzo[1,3]dioxin-8-yl)-amide, Compound A471A;

exo-3-{3-[3-(5-tert-Butyl-2-p-tolyl-2H-pyrazol-3-yl)-ureido]-benzyl}-8-aza-bicyclo[3.2.1]octane-8-carboxylic acid (6-fluoro4H-benzo[1,3]dioxin-8-yl)-amide, Compound A471B;

endo-3-[(3-{3-[3-(5-tert-Butyl-2-p-tolyl-2H-pyrazol-3-yl)-ureido]-benzyl}-8-aza-bicyclo[3.2.1]octane-8-carbonyl)-amino]-benzoic acid ethyl ester, Compound A474A;

exo-3-[(3-{3-[3-(5-tert-Butyl-2-p-tolyl-2H-pyrazol-3-yl)-ureido]-benzyl}-8-aza-bicyclo[3.2.1]octane-8-carbonyl)-amino]-benzoic acid ethyl ester, Compound A474B;

endo-4-[(3-{3-[3-(5-tert-Butyl-2-p-tolyl-2H-pyrazol-3-yl)-ureido]-benzyl}-8-aza-bicyclo[3.2.1]octane-8-carbonyl)-amino]-benzoic acid methyl ester, Compound A477A;

exo-4-[(3-{3-[3-(5-tert-Butyl-2-p-tolyl-2H-pyrazol-3-yl)-ureido]-benzyl}-8-aza-bicyclo[3.2.1]octane-8-carbonyl)-amino]-benzoic acid methyl ester, Compound A477B;

1-(5-tert-Butyl-2-p-tolyl-2H-pyrazol-3-yl)-3-{3-[1-(2H-indazole-3-carbonyl)-piperidin-4-ylmethyl]-phenyl}-urea, Compound A908;

1-(5-tert-Butyl-2-p-tolyl-2H-pyrazol-3-yl)-3-{3-[1-(3H-imidazole-4-carbonyl)-piperidin-4-ylmethyl]-phenyl}-urea, Compound A909;

1-(5-tert-Butyl-2-p-tolyl-2H-pyrazol-3-yl)-3-{3-[1-((R)-5-oxo-pyrrolidine-2-carbonyl)-piperidin-4-ylmethyl]-phenyl}-urea, Compound A161B;

1-(5-tert-Butyl-2-p-tolyl-2H-pyrazol-3-yl)-3-{3-[1-((S)-2-methoxy-2-phenyl-acetyl)-piperidin-4-ylmethyl]-phenyl}-urea, Compound A3B;

1-(5-tert-Butyl-2-p-tolyl-2H-pyrazol-3-yl)-3-{3-[1-(3-methyl-benzofuran-2-carbonyl)-piperidin-4-ylmethyl]-phenyl}-urea, Compound A910;

1-(5-tert-Butyl-2-p-tolyl-2H-pyrazol-3-yl)-3-(3-{1-[4-(2,2,2-trifluoro-acetyl)-benzoyl]-piperidin-4-ylmethyl}-phenyl)-urea, Compound A911;

1-(5-tert-Butyl-2-p-tolyl-2H-pyrazol-3-yl)-3-(3-{1-[2-(4-chloro-phenyl)-propionyl]-piperidin-4-ylmethyl}-phenyl)-urea, (R)-isomer, Compound A116A;

1-(5-tert-Butyl-2-p-tolyl-2H-pyrazol-3-yl)-3-(3-{1-[2-(4-chloro-phenyl)-propionyl]-piperidin-4-ylmethyl}-phenyl)-urea, (S)-isomer, Compound A116B;

1-{3-[1-(3-1H-Benzoimidazol-2-yl-propionyl)-piperidin-4-ylmethyl]-phenyl}-3-(5-tert-butyl-2-p-toyl-2H-pyrazol-3-yl)-urea, Compound A912;

N-[2-(4-{3-[3-(5-tert-Butyl-2-p-tolyl-2H-pyrazol-3-yl)-ureido]-benzyl}-piperidin-1-yl)-1-methyl-2-oxo-ethyl]-acetamide, (R)-isomer, Compound A178A;

N-[2-(4-{3-[3-(5-tert-Butyl-2-p-tolyl-2H-pyrazol-3-yl)-ureido-benzyl}-piperidin-1-yl)-1-methyl-2-oxo-ethyl]-acetamide, Compound A178B;

1-(5-tert-Butyl-2-p-tolyl-2H-pyrazol-3-yl)-3-{3-[1-((R)-tetrahydro-furan-2-carbonyl)-piperidin-4-ylmethyl]-phenyl}-urea, (R)isomer, Compound A66A;

1-(5-tert-Butyl-2-p-tolyl-2H-pyrazol-3-yl)-3-{3-[1-((S)-tetrahydro-furan-2-carbonyl)-piperidin-4-ylmethyl]-phenyl}-urea, Compound A66B;

1-(5-tert-Butyl-2-p-tolyl-2H-pyrazol-3-yl)-3-{3-[1-(4-oxo-2-phenyl-pentanoyl)-piperidin-4-ylmethyl]-phenyl}-urea, (R)-isomer, Compound A62A;

1-(5-tert-Butyl-2-p-tolyl-2H-pyrazol-3-yl)-3-{3-[1-(4-oxo-2-phenyl-pentanoyl)-piperidin-4-ylmethyl]-phenyl}-urea, (S)-isomer, Compound A62B;

1-(5-tert-Butyl-2-p-tolyl-2H-pyrazol-3-yl)-3-{3-[1-(2-pyridin-4-yl-acetyl)-piperidin-4-ylmethyl]-phenyl}-urea, Compound A913;

1-(5-tert-Butyl-2-p-tolyl-2H-pyrazol-3-yl)-3-{3-[1-(2-pyridin-3-yl-acetyl)-piperidin-4-ylmethyl]-phenyl}-urea, Compound A914;

1-(5-tert-Butyl-2-p-tolyl-2H-pyrazol-3-yl)-3-{3-[1-(2-3H-imidazol-4-yl-acetyl)-piperidin-4-ylmethyl]-phenyl}-urea, Compound A915;

1-{3-[1-(3H-Benzotriazole-5-carbonyl)-piperidin-4-ylmethyl]-phenyl}-3-(5-tert-butyl-2-p-tolyl-2H-pyrazol-3-yl)-urea, Compound A916;

1-(5-tert-Butyl-2-p-tolyl-2H-pyrazol-3-yl)-3-{3-[1-((S)-5-oxo-tetrahydro-furan-2-carbonyl)-piperidin-4-ylmethyl]-phenyl}-urea, Compound A2;

1-{3-1-(4-Aminomethyl-benzoyl)-piperidin-4-ylmethyl]-phenyl}-3-(5-tert-butyl-2-p-tolyl-2H-pyrazol-3-yl)-urea, Compound A917;

1-(3-{1-[2-(4-Amino-phenyl)-acetyl]-piperidin-4-ylmethyl}-phenyl)-3-(5-tert-butyl-2-p-tolyl-2H-pyrazol-3-yl)-urea, Compound A918;

4-Amino-N-[2-(4-{3-[3-(5-tert-butyl-2-p-tolyl-2H-pyrazol-3-yl)-ureido]-benzyl}-piperidin-1-yl)-2-oxo-ethyl]-benzamide, Compound A919;

1-{3-[1-(3-Amino-4-hydroxy-benzoyl)-piperidin-4-ylmethyl]-phenyl}-3-(5-tert-butyl-2-p-tolyl-2H-pyrazol-3-yl)-urea, Compound A920;

1-(5-tert-Butyl-2-p-tolyl-2H-pyrazol-3-yl)-3-{3-[1-(3-piperidin-1-yl-propionyl)-piperidin-4-ylmethyl]-phenyl}-urea, Compound A921;

1-(5-tert-Butyl-2-p-tolyl-2H-pyrazol-3-yl)-3-{3-[1-(pyridine-2-carbonyl)-piperidin-4-ylmethyl]-phenyl}-urea, Compound A922;

1-(5-tert-Butyl-2-p-tolyl-2H-pyrazol-3-yl)-3-{3-[1-(1H-indole-5-carbonyl)-piperidin-4-ylmethyl]-phenyl}-urea, Compound A923;

1-(5-tert-Butyl-2-p-tolyl-2H-pyrazol-3-yl)-3-(3-{1-[2-(1H-indol-3-yl)-2-oxo-acetyl]-piperidin-4-ylmethyl}-phenyl)-urea, Compound A924;

1-(5-tert-Butyl-2-p-tolyl-2H-pyrazol-3-yl)-3-{3-[1-(1H-indole-3-carbonyl)-piperidin-4-ylmethyl]-phenyl}-urea, Compound A925;

1-(5-tert-Butyl-2-p-tolyl-2H-pyrazol-3-yl)-3-(3-{1-[2-(N-methyl-guanidino)-acetyl]-piperidin-4-ylmethyl}-phenyl)-urea, Compound A926;

1-(5-tert-Butyl-2-p-tolyl-2H-pyrazol-3-yl)-3-{3-[1-(2,2-dimethyl-propionyl)-piperidin-4-ylmethyl]-phenyl}-urea, Compound A927;

1-(5-tert-Butyl-2-p-tolyl-2H-pyrazol-3-yl)-3-[3-(1-cycloheptanecarbonyl-piperidin-4-ylmethyl)-phenyl]-urea, Compound A928;

1-(5-tert-Butyl-2-p-tolyl-2H-pyrazol-3-yl)-3-{3-[1-(2-phenyl-propionyl)-piperidin-4-ylmethyl]-phenyl}-urea, (R)-isomer, Compound A63A;

1-(5-tert-Butyl-2-p-tolyl-2H-pyrazol-3-yl)-3-{3-[1-(2-phenyl-propionyl)-piperidin-4-ylmethyl]-phenyl}-urea, (S)isomer, Compound A63B;

1-(5-tert-Butyl-2-p-tolyl-2H-pyrazol-3-yl)-3-{3-[1-(2-oxo-3-phenyl-propionyl)-piperidin-4-ylmethyl]-phenyl}-urea, Compound A929;

1-(5-tert-Butyl-2-p-tolyl-2H-pyrazol-3-yl)-3-{3-[1-(2-oxo-propionyl)-piperidin-4-ylmethyl]-phenyl}-urea, Compound A930;

1-(5-tert-Butyl-2-p-tolyl-2H-pyrazol-3-yl)-3-(3-{1-[3-((R)-cyano-methyl-methyl)-benzoyl]-piperidin-4-ylmethyl}-phenyl)-urea, Compound A79A;

1-(5-tert-Butyl-2-p-tolyl-2H-pyrazol-3-yl)-3-(3-{1-[3-((S)-cyano-methyl-methyl)-benzoyl]-piperidin-4-ylmethyl}-phenyl)-urea, Compound A79B;

1-(5-tert-Butyl-2-p-tolyl-2H-pyrazol-3-yl)-3-{3-[1-((R)-1,2,3,4-tetrahydro-naphthalene-2-carbonyl)-piperidin-4-ylmethyl]-phenyl}-urea, Compound A5A;

1-(5-tert-Butyl-2-p-tolyl-2H-pyrazol-3-yl)-3-{3-[1-((S)-1,2,3,4-tetrahydro-naphthalene-2-carbonyl)-piperidin-4-ylmethyl]-phenyl}-urea, Compound A5B;

1-(5-tert-Butyl-2-p-tolyl-2H-pyrazol-3-yl)-3-{3-[1-((R)-1-phenyl-cyclopentanecarbonyl)-piperidin-4-ylmethyl]-phenyl}-urea, Compound A18A;

1-(5-tert-Butyl-2-p-tolyl-2H-pyrazol-3-yl)-3-{3-[1-((S)-1-phenyl-cyclopentanecarbonyl)-piperidin-4-ylmethyl]-phenyl}-urea, Compound A18B;

1-{3-[1(4-Amino-5-chloro-2-methoxy-benzoyl)-piperidin-4-ylmethyl]-phenyl}-3-(5-tert-butyl-2-p-tolyl-2H-pyrazol-3-yl)-urea, Compound A931;

1-(5-tert-Butyl-2-p-tolyl-2H-pyrazol-3-yl)-3-(3-{1-[2-(4,6-dimethyl-pyrimidin-2-ylamino)-benzoyl]-piperidin-4-ylmethyl}-phenyl)-urea, Compound A932;

1-(5-tert-Butyl-2-p-tolyl-2H-pyrazol-3-yl)-3-(3-{1-[3-(4,6-dimethyl-pyrimidin-2-ylamino)-benzoyl]-piperidin-4-ylmethyl}-phenyl)-urea, Compound A933;

1-(5-tert-Butyl-2-p-tolyl-2H-pyrazol-3-yl)-3-{3-[1-(1H-indole-6-carbonyl)-piperidin-4-ylmethyl]-phenyl}-urea, Compound A934;

1-(5-tert-Butyl-2-p-tolyl-2H-pyrazol-3-yl)-3-{3-[1-(1H-pyrrole-3-carbonyl)-piperidin-4-ylmethyl]-phenyl}-urea, Compound A935;

1-(5-tert-Butyl-2-p-tolyl-2H-pyrazol-3-yl)-3-(3-{1-[2-oxo-2-(3-phenyl-isoxazol-5-yl)-ethyl]-piperidin-4-ylmethyl}-phenyl)-urea, Compound A936;

1-(5-tert-Butyl-2-p-tolyl-2H-pyrazol-3-yl)-3-(3-{1-[2-(4-methanesulfonyl-phenyl)-2-oxo-ethyl]-piperidin-4-ylmethyl}-phenyl)-urea, Compound A937;

1-(5-tert-Butyl-2-p-tolyl-2H-pyrazol-3-yl)-3-{3-[1-(2-oxo-2-pyridin-4-yl-ethyl)-piperidin-4-ylmethyl]-phenyl}-urea, Compound A938;

1-(5-tert-Butyl-2-p-tolyl-2H-pyrazol-3-yl)-3-{3-[1-(2-oxo-2-pyridin-3-yl-ethyl)piperidin-4-ylmethyl]-phenyl}-urea, Compound A939;

1-(5-tert-Butyl-2-p-tolyl-2H-pyrazol-3-yl)-3-{3-[1-(4-oxo-4,5,6,7-tetrahydro-benzo[1,2,5]oxadiazol-5-yl)-piperidin-4-ylmethyl]-phenyl}-urea, Compound A940;

5-[2-(4-{3-[3-(5-tert-Butyl-2-p-tolyl-2H-pyrazol-3-yl)-ureido]-benzyl}-piperidin-1-yl)-acetyl]-isoxazole-3-carboxylic acid ethyl ester, Compound A941;

4-{3-[3-(5-tert-Butyl-2-p-tolyl-2H-pyrazol-3-yl)-ureido]-benzyl}-piperidine-1-carboxylic acid (2,4-dimethoxy-phenyl)-amide, Compound A942;

4-{3-[3-(5-tert-Butyl-2-p-tolyl-2H-pyrazol-3-yl)-ureido]-benzyl}-piperidine-1-carboxylic acid (2-methyl-5-phenyl-furan-3-yl)-amide, Compound A943;

1-(5-tert-Butyl-2-p-tolyl-2H-pyrazol-3-yl)-3-{2-[1-(4-oxazol-5-yl-benzoyl)-piperidin-4-ylmethyl]-phenyl}-urea, Compound A944;

1-(5-tert-Butyl-2-p-tolyl-2H-pyrazol-3-yl)-3-{2-[1(2-hydroxy-6-methyl-pyridine-4-carbonyl)-piperidin-4-ylmethyl]-phenyl}-urea, Compound A945;

1-(5-tert-Butyl-2-p-tolyl-2H-pyrazol-3-yl)-3-(2-{1-[2-(6-methoxy-benzofuran-3-yl)-acetyl]-piperidin-4-ylmethyl}-phenyl)-urea, Compound A946;

1-(5-tert-Butyl-2-p-tolyl-2H-pyrazol-3-yl)-3-(2-{1-[2-methyl-5-(piperidine-1-sulfonyl)-furan-3-carbonyl]-piperidin-4-ylmethyl}-phenyl)-urea, Compound A947;

1-{2-[1-(4-tert-Butoxymethyl-benzoyl)-piperidin-4-ylmethyl]-phenyl}-3-(5-tert-butyl-2-p-tolyl-2H-pyrazol-3-yl)-urea, Compound A948;

1-(5-tert-Butyl-2-p-tolyl-2H-pyrazol-3-yl)-3-{2-[1-(3-methyl-isoxazole-4-carbonyl)-piperidin-4-ylmethyl]-phenyl}-urea, Compound A949;

Acetic acid 4-(4-{2-[3-(5-tert-butyl-2-p-tolyl-2H-pyrazol-3-yl)-ureido]-benzyl}-piperidine-1-carbonyl)-benzyl ester, Compound A950;

1-(5-tert-Butyl-2-p-tolyl-2H-pyrazol-3-yl)-3-{2-[1-(5-methyl-isoxazole-4-carbonyl)-piperidin-4-ylmethyl]-phenyl}-urea, Compound A951;

1-{2-[1-(3-Butoxy-4-methoxy-benzoyl)-piperidin-4-ylmethyl]-phenyl}-3-(5-tert-butyl-2-p-tolyl-2H-pyrazol-3-yl)-urea, Compound A952;

1-(5-tert-Butyl-2-p-tolyl-2H-pyrazol-3-yl)-3-{2-[1-(4-thiophen-2-yl-benzoyl)-piperidin-4-ylmethyl]-phenyl}-urea, Compound A953;

1-(5-tert-Butyl-2-p-tolyl-2H-pyrazol-3-yl)-3-{2-[1-(5-methyl-2-trifluoromethyl-furan-3-carbonyl)-piperidin-4-ylmethyl]-phenyl}-urea, Compound A954;

1-(5-tert-Butyl-2-p-tolyl-2H-pyrazol-3-yl)-3-{2-[1-(3-pyridin-3-yl-propionyl)-piperidin-4-ylmethyl]-phenyl}-urea, Compound A955;

1-(5-tert-Butyl-2-p-tolyl-2H-pyrazol-3-yl)-3-{2-[1-(2-methyl-imidazo[1,2-a]pyridine-3-carbonyl)-piperidin-4-ylmethyl]-phenyl}-urea, Compound A956;

1-(5-tert-Butyl-2-p-tolyl-2H-pyrazol-3-yl)-3-{2-[1-(4-difluoromethoxy-benzoyl)-piperidin-4-ylmethyl]-phenyl}-urea, Compound A957;

1-(5-tert-Butyl-2-p-tolyl-2H-pyrazol-3-yl)-3-{2-[1-(2-methyl-5-phenyl-furan-3-carbonyl)-piperidin-4-ylmethyl]-phenyl}-urea, Compound A958;

1-(5-tert-Butyl-2-p-tolyl-2H-pyrazol-3-yl)-3-(2-{1-[5-methoxy-2-(2,2,2-trifluoro-ethoxyl)-benzoyl]-piperidin-4-ylmethyl}-phenyl)-urea, Compound A959;

1-(5-tert-Butyl-2-p-tolyl-2H-pyrazol-3-yl)-3-{2-[1-(2H-indazole-3-carbonyl)-piperidin-4-ylmethyl]-phenyl}-urea, Compound A960;

1-{2-[1-(4-Amino-3-trifluoromethoxy-benzoyl)-piperidin-4-ylmethyl]-phenyl}-3-(5-tert-butyl-2-p-tolyl-2H-pyrazol-3-yl)-urea, Compound A961;

1-(5-tert-Butyl-2-p-tolyl-2H-pyrazol-3-yl)-3-{2-1-(4-isobutyl-benzoyl)-piperidin-4-ylmethyl]-phenyl}-urea, Compound A962;

1-(5-tert-Butyl-2-p-tolyl-2H-pyrazol-3-yl)-3-(2-{1-[2-(2,4-dimethoxy-phenyl)-acetyl]-piperidin-4-ylmethyl}-phenyl)-urea, Compound A963;

1-(5-tert-Butyl-2-p-tolyl-2H-pyrazol-3-yl)-3-{2-[1-(2-chloro-6-methoxy-pyridine-4-carbonyl)-piperidin-4-ylmethyl]-phenyl}-urea, Compound A964;

1-(5-tert-Butyl-2-p-tolyl-2H-pyrazol-3-yl)-3-{2-[1-(2-pyridin-4-yl-thiazole-4-carbonyl)-piperidin-4-ylmethyl]-phenyl}-urea, Compound A965;

1-(5-tert-Butyl-2-p-tolyl-2H-pyrazol-3-yl)-3-{2-[1-(3,5-dimethyl-1H-pyrazole-4-carbonyl)-piperidin-4-ylmethyl]-phenyl}-urea, Compound A966;

1-(5-tert-Butyl-2-p-tolyl-2H-pyrazol-3-yl)-3-(2-{1-[4-(1,1,2,2-tetrafluoro-ethoxyl)-benzoyl]-piperidin-4-ylmethyl}-phenyl)-urea, Compound A967;

1-(5-tert-Butyl-2-p-tolyl-2H-pyrazol-3-yl)-3-(2-{1-[3-(1,1,2,2-tetrafluoro-ethoxyl)-benzoyl]-piperidin-4-ylmethyl}-phenyl)-urea, Compound A968;

1-(5-tert-Butyl-2-p-tolyl-2H-pyrazol-3-yl)-3-(2-{1-[2-(1-methyl-1H-indol-3-yl)-acetyl]-piperidin-4-ylmethyl}-phenyl)-urea, Compound A969;

1-{2-[1-(Benzothiazole-6-carbonyl)-piperidin-4-ylmethyl]-phenyl}-3-(5-tert-butyl-2-p-tolyl-2H-pyrazol-3-yl)-urea, Compound A970;

1-(5-tert-Butyl-2-p-tolyl-2H-pyrazol-3-yl)-3-(2-{1-[6-(2,2,2-trifluoro-ethoxyl)-pyridine-3-carbonyl]-piperidin-4-ylmethyl}-phenyl)-urea, Compound A971;

1-(5-tert-Butyl-2-p-tolyl-2H-pyrazol-3-yl)-3-{2-[1(4-ethylamino-benzoyl)-piperidin-4-ylmethyl]-phenyl}-urea, Compound A972;

1-(5-tert-Butyl-2-p-tolyl-2H-pyrazol-3-yl)-3-{2-[1-(2-methyl-furan-3-carbonyl)-piperidin-4-ylmethyl]-phenyl}-urea, Compound A973;

1-{2-[1-(Bicyclo[2.2.1]hept-5-ene-2-carbonyl)-piperidin-4-ylmethyl]-phenyl}-3-(5-tert-butyl-2-p-tolyl-2H-pyrazol-3-yl)-urea, Compound A974;

1-(5-tert-Butyl-2-p-tolyl-2H-pyrazol-3-yl)-3-{2-[1-(2,6-dioxo-hexahydro-pyrimidine-4-carbonyl)-piperidin-4-ylmethyl]-phenyl}-urea, Compound A975;

1-(5-tert-Butyl-2-p-tolyl-2H-pyrazol-3-yl)-3-{2-[1-(4-[1,2,3]thiadiazol-4-yl-benzoyl)-piperidin-4-ylmethyl]-phenyl}-urea, Compound A976;

1-(5-tert-Butyl-2-p-tolyl-2H-pyrazol-3-yl)-3-{2-[1-(4,5-dimethyl-furan-2-carbonyl)-piperidin-4-ylmethyl]-phenyl}-urea, Compound A977;

1-(5-tert-Butyl-2-p-tolyl-2H-pyrazol-3-yl)-3-{2-[1-(3-methanesulfonyl-6,7-dihydro-benzo[c]thiophene-1-carbonyl)-piperidin-4-ylmethyl]-phenyl}-urea, Compound A978;

1-(5-tert-Butyl-2-p-tolyl-2H-pyrazol-3-yl)-3-{2-[1-(2,3-dihydro-benzofuran-5-carbonyl)-piperidin-4-ylmethyl]-phenyl}-urea, Compound A979;

1-(5-tert-Butyl-2-p-tolyl-2H-pyrazol-3-yl)-3-(2-{1-[2-(3,5-dimethyl-phenyl)-acetyl]-piperidin-4-ylmethyl}-phenyl)-urea, Compound A980;

1-(5-tert-Butyl-2-p-tolyl-2H-pyrazol-3-yl)-3-{2-[1-(2-indan-2-yl-acetyl)-piperidin-4-ylmethyl]-phenyl}-urea, Compound A981;

1-(5-tert-Butyl-2-p-tolyl-2H-pyrazol-3-yl)-3-{2-[1-(3H-imidazole-4-carbonyl)-piperidin-4-ylmethyl]-phenyl}-urea, Compound A982;

1-(5-tert-Butyl-2-p-tolyl-2H-pyrazol-3-yl)-3-{2-[1-(2,5-dimethyl-furan-3-carbonyl)-piperidin-4-ylmethyl]-phenyl}-urea, Compound A983;

1-(5-tert-Butyl-2-p-tolyl-2H-pyrazol-3-yl)-3-{2-[1-(5-methoxy-benzofuran-2-carbonyl)-piperidin-4-ylmethyl]-phenyl}-urea, Compound A984;

1-(5-tert-Butyl-2-p-tolyl-2H-pyrazol-3-yl)-3-{2-[1-(2,6-dimethoxy-pyridine-3-carbonyl)-piperidin-4-ylmethyl]-phenyl}-urea, Compound A985;

1-(5-tert-Butyl-2-p-tolyl-2H-pyrazol-3-yl)-3-{2-[1-(5,6-dichloro-pyridine-3-carbonyl)-piperidin-4-ylmethyl]-phenyl}-urea, Compound A986;

1-(5-tert-Butyl-2-p-tolyl-2H-pyrazol-3-yl)-3-(2-{1-[2-(2-methyl-1H-indol-3-yl)-acetyl]-piperidin-4-ylmethyl}-phenyl)-urea, Compound A987;

1-(5-tert-Butyl-2-p-tolyl-2H-pyrazol-3-yl)-3-{2-[1-(5-methyl-pyrazine-2-carbonyl)-piperidin-4-ylmethyl]-phenyl}-urea, Compound A988;

1-(5-tert-Butyl-2-p-tolyl-2H-pyrazol-3-yl)-3-{2-[1-(4-methoxy-thiophene-3-carbonyl)-piperidin-4-ylmethyl]-phenyl}-urea, Compound A989;

1-(5-tert-Butyl-2-p-tolyl-2H-pyrazol-3-yl)-3-{2-[1-(5-methyl-1-phenyl-1H-pyrazole-4-carbonyl)-piperidin-4-ylmethyl]-phenyl}-urea, Compound A990;

1-(5-tert-Butyl-2-p-tolyl-2H-pyrazol-3-yl)-3-{2-[1-(5-oxo-pyrrolidine-2-carbonyl)-piperidin-4-ylmethyl]-phenyl}-urea, Compound A991;

1-(5-tert-Butyl-2-p-tolyl-2H-pyrazol-3-yl)-3-{2-[1-(2-methoxy-2-phenyl-acetyl)-piperidin-4-ylmethyl]-phenyl}-urea, Compound A992;

1-(5-tert-Butyl-2-p-tolyl-2H-pyrazol-3-yl)-3-{2-[1-(7-methoxy-benzofuran-2-carbonyl)-piperidin-4-ylmethyl]-phenyl}-urea, Compound A993;

1-(5-tert-Butyl-2-p-tolyl-2H-pyrazol-3-yl)-3-{2-[1-(3-methyl-benzofuran-2-carbonyl)-piperidin-4-ylmethyl]-phenyl}-urea, Compound A994;

1-(5-tert-Butyl-2-p-tolyl-2H-pyrazol-3-yl)-3-{2-[1-(3-thioureido-benzoyl)-piperidin-4-ylmethyl]-phenyl}-urea, Compound A995;

1-(5-tert-Butyl-2-p-tolyl-2H-pyrazol-3-yl)-3-(2-{1-[2-(2,3-dimethoxy-phenyl)-acetyl]-piperidin-4-ylmethyl}-phenyl)-urea, Compound A996;

1-(5-tert-Butyl-2-p-tolyl-2H-pyrazol-3-yl)-3-(2-{1-[3-(4-fluoro-phenyl)-propionyl]-piperidin-4-ylmethyl}-phenyl)-urea, Compound A997;

1-(5-tert-Butyl-2-p-tolyl-2H-pyrazol-3-yl)-3-{2-[1-(5-chloro-6-hydroxy-pyridine-3-carbonyl)-piperidin-4-ylmethyl]-phenyl}-urea, Compound A998;

1-(5-tert-Butyl-2-p-tolyl-2H-pyrazol-3-yl)-3-{2-[1-(2,4-dimethyl-thiazole-5-carbonyl)-piperidin-4-ylmethyl]-phenyl}-urea, Compound A999;

1-(5-tert-Butyl-2-p-tolyl-2H-pyrazol-3-yl)-3-(2-{1-[4-(2,2,2-trifluoro-acetyl)-benzoyl]-piperidin-4-ylmethyl}-phenyl)-urea, Compound 1000;

1-(5-tert-Butyl-2-p-tolyl-2H-pyrazol-3-yl)-3-(2-{1-[2-(5-chloro-benzo[b]thiophen-3-yl)-acetyl]-piperidin-4-ylmethyl}-phenyl)-urea, Compound 1001;

1-(5-tert-Butyl-2-p-tolyl-2H-pyrazol-3-yl)-3-{2-[1-(2-pyridin-3-yl-thiazole-4-carbonyl)-piperidin-4-ylmethyl]-phenyl}-urea, Compound 1002;

1-(5-tert-Butyl-2-p-tolyl-2H-pyrazol-3-yl)-3-(2-{1-[2-(5-chloro-3-methyl-benzo[b]thiophen-2-yl)-acetyl]-piperidin-4-ylmethyl}-phenyl)-urea, Compound 1003;

1-(5-tert-Butyl-2-p-tolyl-2H-pyrazol-3-yl)-3-{2-[1-(4-oxo-4,5,6,7-tetrahydro-benzofuran-3-carbonyl)-piperidin-4-ylmethyl]-phenyl}-urea, Compound 1004;

1-(5-tert-Butyl-2-p-tolyl-2H-pyrazol-3-yl)-3-{2-[1-([1,2,3]thiadiazole-4-carbonyl)-piperidin-4-ylmethyl]-phenyl}-urea, Compound 1005;

1-(5-tert-Butyl-2-p-tolyl-2H-pyrazol-3-yl)-3-{2-[1-(3,5-dimethyl-isoxazole-4-carbonyl)-piperidin-4-ylmethyl]-phenyl}-urea, Compound 1006;

1-(5-tert-Butyl-2-p-tolyl-2H-pyrazol-3-yl)-3-{2-[1-(5-methyl-2-phenyl-2H-[1,2,3]triazole-4-carbonyl)-piperidin-4-ylmethyl]-phenyl}-urea, Compound 1007;

1-{2-[1-(2-Benzo[b]thiophen-3-yl-acetyl)-piperidin-4-ylmethyl]-phenyl}-3-(5-tert-butyl-2-p-tolyl-2H-pyrazol-3-yl)-urea, Compound 1008;

1-{2-[1-(Benzo[b]thiophene-2-carbonyl)-piperidin-4-ylmethyl]-phenyl}-3-(5-tert-butyl-2-p-tolyl-2H-pyrazol-3-yl)-urea, Compound 1009;

1-(5-tert-Butyl-2-p-tolyl-2H-pyrazol-3-yl)-3-{2-[1-(quinoline-6-carbonyl)-piperidin-4-ylmethyl]-phenyl}-urea, Compound 1010;

1-(5-tert-Butyl-2-p-tolyl-2H-pyrazol-3-yl)-3-{2-[1-(3-thiophen-2-yl-propionyl)-piperidin-4-ylmethyl]-phenyl}-urea, Compound 1011;

1-(5-tert-Butyl-2-p-tolyl-2H-pyrazol-3-yl)-3-(2-{1-[2-(4-chloro-phenyl)-propionyl]-piperidin-4-ylmethyl}-phenyl)-urea, Compound 1012;

1-(5-tert-Butyl-2-p-tolyl-2H-pyrazol-3-yl)-3-{2-[1-(2-furan-2-yl-2-oxo-acetyl)-piperidin-4-ylmethyl]-phenyl}-urea, Compound 1013;

1-(5-tert-Butyl-2-p-tolyl-2H-pyrazol-3-yl)-3-{2-[1-(5-chloro-thiophene-2-carbonyl)-piperidin-4-ylmethyl]-phenyl}-urea, Compound 1014;

1-{2-[1-(3-1H-Benzoimidazol-2-yl-propionyl)-piperidin-4-ylmethyl]-phenyl}-3-(5-tert-butyl-2-p-tolyl-2H-pyrazol-3-yl)-urea, Compound 1015;

N-[2-(4-{2-[3-(5-tert-Butyl-2-p-tolyl-2H-pyrazol-3-yl)-ureido]-benzyl}-piperidin-1-yl)-1-methyl-2-oxo-ethyl]-acetamide, Compound 1016;

1-(5-tert-Butyl-2-p-tolyl-2H-pyrazol-3-yl)-3-{2-[1-(2-hydroxy-quinoline-4-carbonyl)-piperidin-4-ylmethyl]-phenyl}-urea, Compound 1017;

1-(5-tert-Butyl-2-p-tolyl-2H-pyrazol-3-yl)-3-{2-[1-(6-methyl-pyridine-2-carbonyl)-piperidin-4-ylmethyl]-phenyl}-urea, Compound A1018;

1-(5-tert-Butyl-2-p-tolyl-2H-pyrazol-3-yl)-3-{2-[1-(tetrahydro-furan-2-carbonyl)-piperidin-4-ylmethyl]-phenyl}-urea, Compound A1019;

1-(5-tert-Butyl-2-p-tolyl-2H-pyrazol-3-yl)-3-{2-[1-(4-oxo-2-phenyl-pentanoyl)-piperidin-4-ylmethyl]-phenyl}-urea, Compound A1020;

1-(5-tert-Butyl-2-p-tolyl-2H-pyrazol-3-yl)-3-{2-[1-(2,2-dimethyl-pentanoyl)-piperidin-4-ylmethyl]-phenyl}-urea, Compound A1021;

1-(5-tert-Butyl-2-p-tolyl-2H-pyrazol-3-yl)-3-{2-[1-(4-methoxy-2-methyl-benzoyl)-piperidin-4-ylmethyl]-phenyl}-urea, Compound A1022;

1-(5-tert-Butyl-2-p-tolyl-2H-pyrazol-3-yl)-3-(2-{1-[1-(4-methoxy-phenyl)-cyclopropanecarbonyl]-piperidin-4-ylmethyl}-phenyl)-urea, Compound A1023;

1-(5-tert-Butyl-2-p-tolyl-2H-pyrazol-3-yl)-3-{2-[1-(4-hydroxymethyl-benzoyl)-piperidin-4-ylmethyl]-phenyl}-urea, Compound A1024;

1-(5-tert-Butyl-2-p-tolyl-2H-pyrazol-3-yl)-3-(2-{1-[2-(3,5-dimethoxy-phenyl)-acetyl]-piperidin-4-ylmethyl}-phenyl)-urea, Compound A1025;

1-(5-tert-Butyl-2-p-tolyl-2H-pyrazol-3-yl)-3-(2-{1-[2-(2,3-dimethyl-phenoxyl)-acetyl]-piperidin-4-ylmethyl}-phenyl)-urea, Compound A1026;

1-(5-tert-Butyl-2-p-tolyl-2H-pyrazol-3-yl)-3-{2-[1-(3-p-tolyl-propionyl)-piperidin-4-ylmethyl]-phenyl}-urea, Compound A1027;

1-(5-tert-Butyl-2-p-tolyl-2H-pyrazol-3-yl)-3-{2-[1-(2,4,6-trimethoxy-benzoyl)-piperidin-4-ylmethyl]-phenyl}-urea, Compound A1028;

1-{2-[1-(2-Benzo[1,3]dioxol-5-yl-acetyl)-piperidin-4-ylmethyl]-phenyl}-3-(5-tert-butyl-2-p-tolyl-2H-pyrazol-3-yl)-urea, Compound A1029;

1-(5-tert-Butyl-2-p-tolyl-2H-pyrazol-3-yl)-3-[2-(1-hept-2-ynoyl-piperidin-4-ylmethyl)-phenyl]-urea, Compound A1030;

1-(5-tert-Butyl-2-p-tolyl-2H-pyrazol-3-yl)-3-(2-{1-[2-(4-methoxy-phenoxyl)-acetyl]-piperidin-4-ylmethyl}-phenyl)-urea, Compound A1031;

1-(5-tert-Butyl-2-p-tolyl-2H-pyrazol-3-yl)-3-{2-[1-(2-methyl-2-phenyl-propionyl)-piperidin-4-ylmethyl]-phenyl}-urea, Compound A1032;

1-(5-tert-Butyl-2-p-tolyl-2H-pyrazol-3-yl)-3-{2-[1-(3-methyl-furan-2-carbonyl)-piperidin-4-ylmethyl]-phenyl}-urea, Compound A1033;

1-(5-tert-Butyl-2-p-tolyl-2H-pyrazol-3-yl)-3-{2-[1-(2-phenylamino-acetyl)-piperidin-4-ylmethyl]-phenyl}-urea, Compound A1034;

N-[3-(4-{2-[3-(5-tert-Butyl-2-p-tolyl-2H-pyrazol-3-yl)-ureido]-benzyl}-piperidine-1-carbonyl)-phenyl]-acetamide, Compound A1035;

1-(5-tert-Butyl-2-p-tolyl-2H-pyrazol-3-yl)-3-{2-[1-(2-methyl-pyridine-3-carbonyl)-piperidin-4-ylmethyl]-phenyl}-urea, Compound A1036;

1-(5-tert-Butyl-2-p-tolyl-2H-pyrazol-3-yl)-3-{2-[1-(2-pyridin-4-yl-acetyl)-piperidin-4-ylmethyl]-phenyl}-urea, Compound A1037;

1-(5-tert-Butyl-2-p-tolyl-2H-pyrazol-3-yl)-3-{2-[1-(2-pyridin-3-yl-acetyl)-piperidin-4-ylmethyl]-phenyl}-urea, Compound A1038;

1-(5-tert-Butyl-2-p-tolyl-2H-pyrazol-3-yl)-3-{2-[1-(2-3H-imidazol-4-yl-acetyl)-piperidin-4-ylmethyl]-phenyl}-urea, Compound A1039;

1-(5-tert-Butyl-2-p-tolyl-2H-pyrazol-3-yl)-3-{2-[1-(quinoxaline-2-carbonyl)-piperidin-4-ylmethyl]-phenyl}-urea, Compound A1040;

1-{2-[1-(3H-Benzotriazole-5-carbonyl)-piperidin-4-ylmethyl]-phenyl}-3-(5-tert-butyl-2-p-tolyl-2H-pyrazol-3-yl)-urea, Compound A1041;

1-(5-tert-Butyl-2-p-tolyl-2H-pyrazol-3-yl)-3-{2-[1-(5-oxo-tetrahydro-furan-2-carbonyl)-piperidin-4-ylmethyl]-phenyl}-urea, Compound A1042;

1-(5-tert-Butyl-2-p-tolyl-2H-pyrazol-3-yl)-3-{2-[1-(1H-pyrazole-4-carbonyl)-piperidin-4-ylmethyl]-phenyl}-urea, Compound A1043;

1-(5-tert-Butyl-2-p-tolyl-2H-pyrazol-3-yl)-3-{2-[1-(2,3-dihydro-1H-indole-2-carbonyl)-piperidin-4-ylmethyl]-phenyl}-urea, Compound A1044;

1-(5-tert-Butyl-2-p-tolyl-2H-pyrazol-3-yl)-3-(2-{1-[2-(3,5-difluoro-phenyl)-acetyl]-piperidin-4-ylmethyl}-phenyl)-urea, Compound A1045;

1-{2-[1-(4-Aminomethyl-benzoyl)-piperidin-4-ylmethyl]-phenyl}-3-(5-tert-butyl-2-p-tolyl-2H-pyrazol-3-yl)-urea, Compound A1046;

1-(5-tert-Butyl-2-p-tolyl-2H-pyrazol-3-yl)-3-(2-{1-[2-(3,4-difluoro-phenyl)-acetyl]-piperidin-4-ylmethyl}-phenyl)-urea, Compound A1047;

1-(5-tert-Butyl-2-p-tolyl-2H-pyrazol-3-yl)-3-(2-{1-[2-(2,4-difluoro-phenyl)-acetyl]-piperidin-4-ylmethyl}-phenyl)-urea, Compound A1048;

1-(2-{1-[2-(4-Amino-phenyl)-acetyl]-piperidin-4-ylmethyl}-phenyl)-3-(5-tert-butyl-2-p-tolyl-2H-pyrazol-3-yl)-urea, Compound A1049;

4-Amino-N-[2-(4-{2-[3-(5-tert-butyl-2-p-tolyl-2H-pyrazol-3-yl)-ureido]-benzyl}-piperidin-1-yl)-2-oxo-ethyl]-benzamide, Compound A1050;

1-{2-[1-(3-Amino-4-hydroxy-benzoyl)-piperidin-4-ylmethyl]-phenyl}-3-(5-tert-butyl-2-p-tolyl-2H-pyrazol-3-yl)-urea, Compound A1051;

1-(5-tert-Butyl-2-p-tolyl-2H-pyrazol-3-yl)-3-{2-[1-(isoquinoline-1-carbonyl)-piperidin-4-ylmethyl]-phenyl}-urea, Compound A1052;

1-(5-tert-Butyl-2-p-tolyl-2H-pyrazol-3-yl)-3-{2-[1-(quinoline-4-carbonyl)-piperidin-4-ylmethyl]-phenyl}-urea, Compound A1053;

1-(5-tert-Butyl-2-p-tolyl-2H-pyrazol-3-yl)-3-{2-[1-(quinoline-3-carbonyl)-piperidin-4-ylmethyl]-phenyl}-urea, Compound A1054;

1-(5-tert-Butyl-2-p-tolyl-2H-pyrazol-3-yl)-3-{2-(quinoline-2-carbonyl)-piperidin-4-ylmethyl]-phenyl}-urea, Compound A1055;

1-(5-tert-Butyl-2-p-tolyl-2H-pyrazol-3-yl)-3-{2-[1-(3-piperidin-1-yl-propionyl)-piperidin-4-ylmethyl]-phenyl}-urea, Compound A1056;

1-(5-tert-Butyl-2-p-tolyl-2H-pyrazol-3-yl)-3-{2-[1-(pyridine-4-carbonyl)-piperidin-4-ylmethyl]-phenyl}-urea, Compound A1057;

1-(5-tert-Butyl-2-p-tolyl-2H-pyrazol-3-yl)-3-{2-[1-(pyridine-3-carbonyl)-piperidin-4-ylmethyl]-phenyl}-urea, Compound A1058;

1-{2-[1-(6-Amino-pyridine-3-carbonyl)-piperidin-4-ylmethyl]-phenyl}-3-(5-tert-butyl-2-p-tolyl-2H-pyrazol-3-yl)-urea, Compound A1059;

1-{2-[1-(2-Amino-pyridine-3-carbonyl)-piperidin-4-ylmethyl]-phenyl}-3-(5-tert-butyl-2-p-tolyl-2H-pyrazol-3-yl)-urea, Compound A1060;

1-(5-tert-Butyl-2-p-tolyl-2H-pyrazol-3-yl)-3-{2-[1-(pyridine-2-carbonyl)-piperidin-4-ylmethyl]-phenyl}-urea, Compound A1061;

1-(5-tert-Butyl-2-p-tolyl-2H-pyrazol-3-yl)-3-{2-[1-(6-chloro-pyridine-3-carbonyl)-piperidin-4-ylmethyl]-phenyl}-urea, Compound A1062;

1-(5-tert-Butyl-2-p-tolyl-2H-pyrazol-3-yl)-3-{2-[1-(2-chloro-pyridine-3-carbonyl)-piperidin-4-ylmethyl]-phenyl}-urea, Compound A1063;

1-{2-[1-(3-Amino-pyrazine-2-carbonyl)-piperidin-4-ylmethyl]-phenyl}-3-(5-tert-butyl-2-p-tolyl-2H-pyrazol-3-yl)-urea, Compound A1064;

1-(5-tert-Butyl-2-p-tolyl-2H-pyrazol-3-yl)-3-{2-[1-(pyrazine-2-carbonyl)-piperidin-4-ylmethyl]-phenyl}-urea, Compound A1065;

1-(5-tert-Butyl-2-p-tolyl-2H-pyrazol-3-yl)-3-{2-[1-(1H-indole-5-carbonyl)-piperidin-4-ylmethyl]-phenyl}-urea, Compound A1066;

1-(5-tert-Butyl-2-p-tolyl-2H-pyrazol-3-yl)-3-{2-[1-(3-1H-indol-3-yl-propionyl)-piperidin-4-ylmethyl]-phenyl}-urea, Compound A1067;

1-(5-tert-Butyl-2-p-tolyl-2H-pyrazol-3-yl)-3-{2-[1-(2-1H-indol-3-yl-acetyl)-piperidin-4-ylmethyl]-phenyl}-urea, Compound A1068;

1-(5-tert-Butyl-2-p-tolyl-2H-pyrazol-3-yl)-3-(2-{1-[2-(1H-indol-3-yl)-2-oxo-acetyl]-piperidin-4-ylmethyl}-phenyl)-urea, Compound A1069;

1-(5-tert-Butyl-2-p-tolyl-2H-pyrazol-3-yl)-3-{2-[1-(1H-indole-3-carbonyl)-piperidin-4-ylmethyl]-phenyl}-urea, Compound A1070;

1-(5-tert-Butyl-2-p-tolyl-2H-pyrazol-3-yl)-3-{2-[1-(2-thiophen-3-yl-acetyl)-piperidin-4-ylmethyl]-phenyl}-urea, Compound A1071;

1-(5-tert-Butyl-2-p-tolyl-2H-pyrazol-3-yl)-3-{2-[1-(thiophene-3-carbonyl)-piperidin-4-ylmethyl]-phenyl}-urea, Compound A1072;

1-(5-tert-Butyl-2-p-tolyl-2H-pyrazol-3-yl)-3-{2-[1-(2-thiophen-2-yl-acetyl)-piperidin-4-ylmethyl]-phenyl}-urea, Compound A1073;

1-(5-tert-Butyl-2-p-tolyl-2H-pyrazol-3-yl)-3-{2-[1-(5-methyl-thiophene-2-carbonyl)-piperidin-4-ylmethyl]-phenyl}-urea, Compound A1074;

1-(5-tert-Butyl-2-p-tolyl-2H-pyrazol-3-yl)-3-{2-[1-(furan-3-carbonyl)-piperidin-4-ylmethyl]-phenyl}-urea, Compound A1075;

1-(5-tert-Butyl-2-p-tolyl-2H-pyrazol-3-yl)-3-{2-[1-(3-furan-2-yl-propionyl)-piperidin-4-ylmethyl]-phenyl}-urea, Compound A1076;

1-(5-tert-Butyl-2-p-tolyl-2H-pyrazol-3-yl)-3-{2-[1-((R)-5-oxo-pyrrolidine-2-carbonyl)-piperidin-4-ylmethyl]-phenyl}-urea, Compound A991A;

1-(5-tert-Butyl-2-p-tolyl-2H-pyrazol-3-yl)-3-{2-[1-((S)-5-oxo-pyrrolidine-2-carbonyl)-piperidin-4-ylmethyl]-phenyl}-urea, Compound A991B;

1-(5-tert-Butyl-2-p-tolyl-2H-pyrazol-3-yl)-3-(2-{1-[2-(2,5-dioxo-imidazolidin-4-yl)-acetyl]-piperidin-4-ylmethyl}-phenyl)-urea, Compound A1077;

1-(5-tert-Butyl-2-p-tolyl-2H-pyrazol-3-yl)-3-[2-(1-heptanoyl-piperidin-4-ylmethyl)-phenyl]-urea, Compound A1078;

1-(5-tert-Butyl-2-p-tolyl-2H-pyrazol-3-yl)-3-{2-[1-(5-oxo-5-phenyl-pentanoyl)piperidin-4-ylmethyl]-phenyl}-urea, Compound A1079;

1-(5-tert-Butyl-2-p-tolyl-2H-pyrazol-3-yl)-3-(2-{1-[4-(4-methoxy-phenyl)-butyryl]-piperidin-4-ylmethyl}-phenyl)-urea, Compound A1080;

1-(5-tert-Butyl-2-p-tolyl-2H-pyrazol-3-yl)-3-(2-{1-[2-(4-phenyl-butyryl)-piperidin-4-ylmethyl]-phenyl}-urea, Compound A1081;

1-(5-tert-Butyl-2-p-tolyl-2H-pyrazol-3-yl)-3-(2-{1-[2-(4-methoxy-phenyl)-acetyl]-piperidin-4-ylmethyl}-phenyl)-urea, Compound A1082;

1-(5-tert-Butyl-2-p-tolyl-2H-pyrazol-3-yl)-3-(2-{1-[2-(4-fluoro-pbenyl)-acetyl]-piperidin-4-ylmethyl}-phenyl)-urea, Compound A1083;

1-(5-tert-Butyl-2-p-tolyl-2H-pyrazol-3-yl)-3-(2-{1-[2-(3,4-dimethoxy-phenyl)-acetyl]-piperidin-4-ylmethyl}-phenyl)-urea, Compound A1084;

1-(5-tert-Butyl-2-p-tolyl-2H-pyrazol-3-yl)-3-(2-{1-[2-(3-methoxy-phenyl)-acetyl]-piperidin-4-ylmethyl}-phenyl)-urea, Compound A1085;

1-(5-tert-Butyl-2-p-tolyl-2H-pyrazol-3-yl)-3-(2-{1-[2-(3-fluoro-phenyl)-acetyl]-piperidin-4-ylmethyl}-phenyl)-urea, Compound A1086;

1-(5-tert-Butyl-2-p-tolyl-2H-pyrazol-3-yl)-3-{2-[1-(2-o-tolyl-acetyl)-piperidin-4-ylmethyl]-phenyl}-urea, Compound A1087;

1-(5-tert-Butyl-2-p-tolyl-2H-pyrazol-3-yl)-3-(2-{1-[2-(2-methoxy-phenyl)-acetyl]-piperidin-4-ylmethyl}-phenyl)-urea, Compound A1088;

1-(5-tert-Butyl-2-p-tolyl-2H-pyrazol-3-yl)-3-(2-{1-[2-(2-fluoro-phenyl)-acetyl]-piperidin-4-ylmethyl}-phenyl)-urea, Compound A1089;

1-(5-tert-Butyl-2-p-tolyl-2H-pyrazol-3-yl)-3-{2-[1-(2-methoxy-acetyl)-piperidin-4-ylmethyl]-phenyl}-urea, Compound A1090;

1-(5-tert-Butyl-2-p-tolyl-2H-pyrazol-3-yl)-3-{2-[1-(2-phenoxy-acetyl)-piperidin-4-ylmethyl]-phenyl}-urea, Compound A1091;

1-(5-tert-Butyl-2-p-tolyl-2H-pyrazol-3-yl)-3-{2-[1-(2-dimethylamino-acetyl)-piperidin-4-ylmethyl]-phenyl}-urea, Compound A1092;

1-(5-tert-Butyl-2-p-tolyl-2H-pyrazol-3-yl)-3-(2-{1-[2-(N-methyl-guanidino)-acetyl]-piperidin-4-ylmethyl}-phenyl)-urea, Compound A1093;

N-[2-(4-{2-[3-(5-tert-Butyl-2-p-tolyl-2H-pyrazol-3-yl)-ureido]-benzyl}-piperidin-1-yl)-2-oxo-ethyl]-acetamide, Compound A1094;

1-(5-tert-Butyl-2-p-tolyl-2H-pyrazol-3-yl)-3-{2-[1-((R)-2-methoxy-2-phenyl-acetyl)-piperidin-4-ylmethyl]-phenyl}-urea, Compound A992A;

1-(5-tert-Butyl-2-p-tolyl-2H-pyrazol-3-yl)-3-{2-[1-((S)-2-methoxy-2-phenyl-acetyl)-piperidin-4-ylmethyl]-phenyl}-urea, Compound A992B;

1-(5-tert-Butyl-2-p-tolyl-2H-pyrazol-3-yl)-3-{2-[1-(2,2-dimethyl-propionyl)-piperidin-4-ylmethyl]-phenyl}-urea, Compound A1095;

1-(5-tert-Butyl-2-p-tolyl-2H-pyrazol-3-yl)-3-[2-(1-cycloheptanecarbonyl-piperidin-4-ylmethyl)-phenyl]-urea, Compound A1096;

1-(5-tert-Butyl-2-p-tolyl-2H-pyrazol-3-yl)-3-{2-[1-(2-naphthalen-2-yl-acetyl)-piperidin-4-ylmethyl]-phenyl}-urea, Compound A1097;

1-(5-tert-Butyl-2-p-tolyl-2H-pyrazol-3-yl)-3-{2-[1-(2-naphthalen-1-yl-acetyl)-piperidin-4-ylmethyl]-phenyl}-urea, Compound A1098;

1-(5-tert-Butyl-2-p-tolyl-2H-pyrazol-3-yl)-3-{2-[1-(furan-2-carbonyl)-piperidin-4-ylmethyl]-phenyl}-urea, Compound A1099;

1-(5-tert-Butyl-2-p-tolyl-2H-pyrazol-3-yl)-3-{2-[1-(5-methyl-3-phenyl-isoxazole-4-carbonyl)-piperidin-4-ylmethyl]-phenyl}-urea, Compound A1100;

1-(5-tert-Butyl-2-p-tolyl-2H-pyrazol-3-yl)-3-[2-(1-butyryl-piperidin-4-ylmethyl)-phenyl]-urea, Compound A1101;

1-(5-tert-Butyl-2-p-tolyl-2H-pyrazol-3-yl)-3-(2-{1-[4-(4-fluoro-phenyl)-4-oxo-butyryl]-piperidin-4-ylmethyl}-phenyl)-urea, Compound A1102;

4-(4-{2-[3-(5-tert-Butyl-2-p-tolyl-2H-pyrazol-3-yl)-ureido]-benzyl}-piperidin-1-yl)-4-oxo-butyric acid methyl ester, Compound A1103;

1-(5-tert-Butyl-2-p-tolyl-2H-pyrazol-3-yl)-3-(2-{1-[3-(2-methoxy-phenyl)-propionyl]-piperidin-4-ylmethyl}-phenyl)-urea, Compound A1104;

1-(5-tert-Butyl-2-p-tolyl-2H-pyrazol-3-yl)-3-{2-[1(3-phenyl-propionyl)-piperidin-4-ylmethyl]-phenyl}-urea, Compound A1105;

1-(5-tert-Butyl-2-p-tolyl-2H-pyrazol-3-yl)-3-{2-[1-(3-phenoxy-propionyl)-piperidin-4-ylmethyl]-phenyl}-urea, Compound A1106;

N-[2-(4-{2-[3-(5-tert-Butyl-2-p-tolyl-2H-pyrazol-3-yl)-ureido]-benzyl}-piperidin-1-yl)-2-oxo-ethyl]-benzamide, Compound A1107;

1-(5-tert-Butyl-2-p-tolyl-2H-pyrazol-3-yl)-3-{2-[1-(2-phenyl-propionyl)-piperidin-4-ylmethyl]-phenyl}-urea, Compound A1108;

1-(5-tert-Butyl-2-p-tolyl-2H-pyrazol-3-yl)-3-{2-[1-(2-oxo-3-phenyl-propionyl)-piperidin-4-ylmethyl]-phenyl}-urea, Compound A1109;

1-(5-tert-Butyl-2-p-tolyl-2H-pyrazol-3-yl)-3-{2-[1-(2-oxo-propionyl)-piperidin-4-ylmethyl]-phenyl}-urea, Compound A1110;

1-(5-tert-Butyl-2-p-tolyl-2H-pyrazol-3-yl)-3-(2-{1-[3-(cyano-methyl-methyl)-benzoyl]-piperidin-4-ylmethyl}-phenyl)-urea, Compound A1111;

1-(5-tert-Butyl-2-p-tolyl-2H-pyrazol-3-yl)-3-{2-[1-(3,5-dimethoxy-benzoyl)-piperidin-4-ylmethyl]-phenyl}-urea, Compound A1112;

1-(5-tert-Butyl-2-p-tolyl-2H-pyrazol-3-yl)-3-{2-[1-(2,4-dimethoxy-benzoyl)-piperidin-4-ylmethyl]-phenyl}-urea, Compound A1113;

1-(5-tert-Butyl-2-p-tolyl-2H-pyrazol-3-yl)-3-{2-[1-(2,3-dimethoxy-benzoyl)-piperidin-4-ylmethyl]-phenyl}-urea, Compound A1114;

1-(5-tert-Butyl-2-p-tolyl-2H-pyrazol-3-yl)-3-{2-[1-(1,2,3,4-tetrahydro-naphthalene-2-carbonyl)-piperidin-4-ylmethyl]-phenyl}-urea, Compound A1115;

1-(5-tert-Butyl-2-p-tolyl-2H-pyrazol-3-yl)-3-{2-[1-(2-cyclohexyl-acetyl)-piperidin-4-ylmethyl]-phenyl}-urea, Compound A1116;

1-(5-tert-Butyl-2-p-tolyl-2H-pyrazol-3-yl)-3-{2-[1-(1-methyl-cyclohexanecarbonyl)-piperidin-4-ylmethyl]-phenyl}-urea, Compound A1117;

1-(5-tert-Butyl-2-p-tolyl-2H-pyrazol-3-yl)-3-[2-(1-cyclohexanecarbonyl-piperidin-4-ylmethyl)-phenyl]-urea, Compound A1118;

1-(5-tert-Butyl-2-p-tolyl-2H-pyrazol-3-yl)-3-{2-[1-(2-cyclopentyl-acetyl)-piperidin-4-ylmethyl]-phenyl}-urea, Compound A1119;

1-(5-tert-Butyl-2-p-tolyl-2H-pyrazol-3-yl)-3-{2-[1-(1-phenyl-cyclopentanecarbonyl)-piperidin-4-ylmethyl]-phenyl}-urea, Compound A1120;

1-(5-tert-Butyl-2-p-tolyl-2H-pyrazol-3-yl)-3-[2-(1-cyclopentanecarbonyl-piperidin-4-ylmethyl)-phenyl]-urea, Compound A1121;

1-(5-tert-Butyl-2-p-tolyl-2H-pyrazol-3-yl)-3-[2-(1-cyclobutanecarbonyl-piperidin-4-ylmethyl)-phenyl]-urea, Compound A1122;

1-(5-tert-Butyl-2-p-tolyl-2H-pyrazol-3-yl)-3-{2-[1-(1-methyl-cyclopropanecarbonyl)-piperidin-4-ylmethyl]-phenyl}-urea, Compound A1123;

1-{2-[1-(3,5-Bis-trifluoromethyl-benzoyl)-piperidin-4-ylmethyl]-phenyl}-3-(5-tert-butyl-2-p-tolyl-2H-pyrazol-3-yl)-urea, Compound A1124;

1-{2-[1-(4-Amino-5-chloro-2-methoxy-benzoyl)-piperidin-4-ylmethyl]-phenyl}-3-(5-tert-butyl-2-p-tolyl-2H-pyrazol-3-yl)-urea, Compound A1125;

1-{2-[1-(Benzo[d]imidazo[2,1-b]thiazole-2-carbonyl)-piperidin-4-ylmethyl]-phenyl}-3-(5-tert-butyl-2-p-tolyl-2H-pyrazol-3-yl)-urea, Compound A1126;

1-(5-tert-Butyl-2-p-tolyl-2H-pyrazol-3-yl)-3-{2-[1-([1,6]naphthyridine-2-carbonyl)-piperidin-4-ylmethyl]-phenyl}-urea, Compound A1127;

1-(5-tert-Butyl-2-p-tolyl-2H-pyrazol-3-yl)-3-{2-[1-(2-methyl-5-trifluoromethyl-oxazole-4-carbonyl)-piperidin-4-ylmethyl]-phenyl}-urea, Compound A1128;

1-(5-tert-Butyl-2-p-tolyl-2H-pyrazol-3-yl)-3-(2-{1-[4-(4-chloro-phenyl)-thiophene-2-carbonyl]-piperidin-4-ylmethyl}-phenyl)-urea, Compound A1129;

1-(5-tert-Butyl-2-p-tolyl-2H-pyrazol-3-yl)-3-{2-[1-(2-trifluoromethyl-[1,8]naphthyridine-3-carbonyl)-piperidin-4-ylmethyl]-phenyl}-urea, Compound A1130;

1-(5-tert-Butyl-2-p-tolyl-2H-pyrazol-3-yl)-3-(2-{1-[4-(4-methoxy-phenyl)-thiophene-2-carbonyl]-piperidin-4-ylmethyl}-phenyl)-urea, Compound A1131;

1-(5-tert-Butyl-2-p-tolyl-2H-pyrazol-3-yl)-3-(2-{1-[2-(4,6-dimethyl-pyrimidin-2-ylamino)-benzoyl]-piperidin-4-ylmethyl}-phenyl)-urea, Compound A1132;

1-(5-tert-Butyl-2-p-tolyl-2H-pyrazol-3-yl)-3-(2-{1-[3-(4,6-dimethyl-pyrimidin-2-ylamino)-benzoyl]-piperidin-4-ylmethyl}-phenyl)-urea, Compound A1133;

1-(5-tert-Butyl-2-p-tolyl-2H-pyrazol-3-yl)-3-(2-{1-[4-(4,6-dimethyl-pyrimidin-2-ylamino)-benzoyl]-piperidin-4-ylmethyl}-phenyl)-urea, Compound A1134;

1-(5-tert-Butyl-2-p-tolyl-2H-pyrazol-3-yl)-3-(2-{1-[3-(2,2-difluoro-benzo[1,3]dioxol-5-yl)-acryloyl]-piperidin-4-ylmethyl}-phenyl)-urea, Compound A1135;

1-(5-tert-Butyl-2-p-tolyl-2H-pyrazol-3-yl)-3-{2-[1-(2-phenyl-5-trifluoromethyl-oxazole-4-carbonyl)-piperidin-4-ylmethyl]-phenyl}-urea, Compound A1136;

1-(5-tert-Butyl-2-p-tolyl-2H-pyrazol-3-yl)-3-{2-[1-(6-trifluoromethyl-pyridine-3-carbonyl)-piperidin-4-ylmethyl]-phenyl}-urea, Compound A1137;

1-(5-tert-Butyl-2-p-tolyl-2H-pyrazol-3-yl)-3-(2-{1-[2-(4,6-dimethoxy-pyrimidin-2-ylsulfanyl)-benzoyl]-piperidin-4-ylmethyl}-phenyl)-urea, Compound A1138;

1-(5-tert-Butyl-2-p-tolyl-2H-pyrazol-3-yl)-3-(2-{1-[3-(4,6-dimethoxy-pyrimidin-2-yloxyl)-benzoyl]-piperidin-4-ylmethyl}-phenyl)-urea, Compound A1139;

1-(5-tert-Butyl-2-p-tolyl-2H-pyrazol-3-yl)-3-{2-[1-(2-trifluoromethyl-[1,6]naphthyridine-3-carbonyl)-piperidin-4-ylmethyl]-phenyl}-urea, Compound A1140;

1-(5-tert-Butyl-2-p-tolyl-2H-pyrazol-3-yl)-3-{2-[1-(2-chloro-4-methanesulfonyl-benzoyl)-piperidin-4-ylmethyl]-phenyl}-urea, Compound A1141;

1-(5-tert-Butyl-2-p-tolyl-2H-pyrazol-3-yl)-3-{2-[1-(1H-indole-6-carbonyl)-piperidin-4-ylmethyl]-phenyl}-urea, Compound A1142;

1-(5-tert-Butyl-2-p-tolyl-2H-pyrazol-3-yl)-3-[2-(1-{3-[(4,6-dimethyl-pyrimidin-2-yl)-methyl-amino]-benzoyl}-piperidin-4-ylmethyl)-phenyl]-urea, Compound A1143;

1-(5-tert-Butyl-2-p-tolyl-2H-pyrazol-3-yl)-3-{2-[1-(2-methyl-[1,6]naphthyridine-3-carbonyl)-piperidin-4-ylmethyl]-phenyl}-urea, Compound A1144;

1-(5-tert-Butyl-2-p-tolyl-2H-pyrazol-3-yl)-3-{2-[1-([1,8]naphthyridine-2-carbonyl)-piperidin-4-ylmethyl]-phenyl}-urea, Compound A1145;

1-(5-tert-Butyl-2-p-tolyl-2H-pyrazol-3-yl)-3-{2-[1-(4,5-dihydro-benzo[b]thiophene-6-carbonyl)-piperidin-4-ylmethyl]-phenyl}-urea, Compound A1146;

1-(5-tert-Butyl-2-p-tolyl-2H-pyrazol-3-yl)-3-{2-[1-(3a,4,5,7a-tetrahydro-benzofuran-6-carbonyl)-piperidin-4-ylmethyl]-phenyl}-urea, Compound A1147;

1-(2-{1-[1-(5-Bromo-pyrimidin-2-yl)-piperidine-4-carbonyl]-piperidin-4-ylmethyl}-phenyl)-3-(5-tert-butyl-2-p-tolyl-2H-pyrazol-3-yl)-urea, Compound A1148;

1-(5-tert-Butyl-2-p-tolyl-2H-pyrazol-3-yl)-3-(2-{1-[2-(4,6-dimethoxy-pyrimidin-2-yloxyl)-benzoyl]-piperidin-4-ylmethyl}-phenyl)-urea, Compound A1149;

1-(2-{1-[1-(5-Bromo-pyrimidin-2-yl)-piperidine-3-carbonyl]-piperidin-4-ylmethyl}-phenyl)-3-(5-tert-butyl-2-p-tolyl-2H-pyrazol-3-yl)-urea, Compound A1150;

1-(5-tert-Butyl-2-p-tolyl-2H-pyrazol-3-yl)-3-[2-(1-{4-[(4,6-dimethyl-pyrimidin-2-yl)-methyl-amino]-benzoyl}-piperidin-4-ylmethyl)-phenyl]-urea, Compound A1151;

1-(5-tert-Butyl-2-p-tolyl-2H-pyrazol-3-yl)-3-{2-[1-(1H-pyrrole-3-carbonyl)-piperidin-4-ylmethyl]-phenyl}-urea, Compound A1152;

1-(5-tert-Butyl-2-p-tolyl-2H-pyrazol-3-yl)-3-{2-[1-(4-trifluoromethyl-pyridine-3-carbonyl)-piperidin-4-ylmethyl]-phenyl}-urea, Compound A1153;

1-(5-tert-Butyl-2-p-tolyl-2H-pyrazol-3-yl)-3-{2-[1-(2-methyl-[1,8]naphthyridine-3-carbonyl)-piperidin-4-ylmethyl]-phenyl}-urea, Compound A1154;

1-(5-tert-Butyl-2-p-tolyl-2H-pyrazol-3-yl)-3-{2-[1-(2,4,6-trimethyl-benzoyl)-piperidin-4-ylmethyl]-phenyl}-urea, Compound A1155;

1-(5-tert-Butyl-2-p-tolyl-2H-pyrazol-3-yl)-3-{2-[1-(2,2-difluoro-benzo[1,3]dioxole-5-carbonyl)-piperidin-4-ylmethyl]-phenyl}-urea, Compound A1156;

4-(4-{2-[3-(5-tert-Butyl-2-p-tolyl-2H-pyrazol-3-yl)-ureido]-benzyl}-piperidine-1-carbonyl)-2,5-dimethyl-furan-3-sulfonic acid (thiophen-2-ylmethyl)-amide, Compound A1157;

1-{2-[1-(2-Benzo[1,3]dioxol-5-yl-2-oxo-ethyl)-piperidin-4-ylmethyl]-phenyl}-3-(5-tert-butyl-2-p-tolyl-2H-pyrazol-3-yl)-urea, Compound A1158;

1-{2-[1-(2-Benzo[b]thiophen-3-yl-2-oxo-ethyl)-piperidin-4-ylmethyl]-phenyl}-3-(5-tert-butyl-2-p-tolyl-2H-pyrazol-3-yl)-urea, Compound A1159;

1-(5-tert-Butyl-2-p-tolyl-2H-pyrazol-3-yl)-3-(2-{1-[2-oxo-2-(3-phenyl-isoxazol-5-yl)-ethyl]-piperidin-4-ylmethyl}-phenyl)-urea, Compound A1160;

1-(5-tert-Butyl-2-p-tolyl-2H-pyrazol-3-yl)-3-(2-{1-[2-(4-methanesulfonyl-phenyl)-2-oxo-ethyl]-piperidin-4-ylmethyl}-phenyl)-urea, Compound A1161;

1-(5-tert-Butyl-2-p-tolyl-2H-pyrazol-3-yl)-3-{2-[1-(2-oxo-2-pyridin-4-yl-ethyl)-piperidin-4-ylmethyl]-phenyl}-urea, Compound A1162;

1-(5-tert-Butyl-2-p-tolyl-2H-pyrazol-3-yl)-3-(2-{1-[2-(5-methyl-1-phenyl-1H-pyrazol-4-yl)-2-oxo-ethyl]-piperidin-4-ylmethyl}-phenyl)-urea, Compound A1163;

1-(5-tert-Butyl-2-p-tolyl-2H-pyrazol-3-yl)-3-(2-{1-[2-(5-methyl-3-phenyl-isoxazol-4-yl)-2-oxo-ethyl]-piperidin-4-ylmethyl}-phenyl)-urea, Compound A1164;

1-(5-tert-Butyl-2-p-tolyl-2H-pyrazol-3-yl)-3-(2-{1-[2-oxo-2-(5-pyridin-2-yl-thiophen-2-yl)-ethyl]-piperidin-4-ylmethyl}-phenyl)-urea, Compound A1165;

1-(5-tert-Butyl-2-p-tolyl-2H-pyrazol-3-yl)-3-(2-{1-[2-(2,4-dimethoxy-phenyl)-2-oxo-ethyl]-piperidin-4-ylmethyl}-phenyl)-urea, Compound A1166;

1-(5-tert-Butyl-2-p-tolyl-2H-pyrazol-3-yl)-3-(2-{1-[2-(2,5-dimethoxy-phenyl)-2-oxo-ethyl]-piperidin-4-ylmethyl}-phenyl)-urea, Compound A1167;

1-(5-tert-Butyl-2-p-tolyl-2H-pyrazol-3-yl)-3-(2-{1-[2-(3-methoxy-phenyl)-2-oxo-ethyl]-piperidin-4-ylmethyl}-phenyl)-urea, Compound A1168;

1-(5-tert-Butyl-2-p-tolyl-2H-pyrazol-3-yl)-3-{2-[1-(2-oxo-2-pyridin-3-yl-ethyl)-piperidin-4-ylmethyl]-phenyl}-urea, Compound A1169;

1-(5-tert-Butyl-2-p-tolyl-2H-pyrazol-3-yl)-3-(2-{1-[2-(4-difluoromethoxy-phenyl)-2-oxo-ethyl]-piperidin-4-ylmethyl}-phenyl)-urea, Compound A1170;

1-(5-tert-Butyl-2-p-tolyl-2H-pyrazol-3-yl)-3-(2-{1-[2-oxo-2-(4-trifluoromethoxy-phenyl)-ethyl]-piperidin-4-ylmethyl}-phenyl)-urea, Compound A1171;

1-(5-tert-Butyl-2-p-tolyl-2H-pyrazol-3-yl)-3-(2-{1-[2-(4-methoxy-phenyl)-2-oxo-ethyl]-piperidin-4-ylmethyl}-phenyl)-urea, Compound A1172;

1-(5-tert-Butyl-2-p-tolyl-2H-pyrazol-3-yl)-3-{2-[1-(4-oxo-4,5,6,7-tetrahydro-benzo[1,2,5]oxadiazol-5-yl)-piperidin-4-ylmethyl]-phenyl}-urea, Compound A1173;

1-(5-tert-Butyl-2-p-tolyl-2H-pyrazol-3-yl)-3-(2-{1-[2-oxo-2-(2-oxo-1,2,3,4-tetrahydro-quinolin-6-yl)-ethyl]-piperidin-4-ylmethyl}-phenyl)-urea, Compound A1174;

1-(5-tert-Butyl-2-p-tolyl-2H-pyrazol-3-yl)-3-(2-{1-[2-oxo-2-(4-pyrrolidin-1-yl-phenyl)-ethyl]-piperidin-4-ylmethyl}-phenyl)-urea, Compound A1175;

1-(5-tert-Butyl-2-p-tolyl-2H-pyrazol-3-yl)-3-(2-{1-[2-(4-diethylamino-phenyl)-2-oxo-ethyl]-piperidin-4-ylmethyl}-phenyl)-urea, Compound A1176;

5-[2-(4-{2-[3-(5-tert-Butyl-2-p-tolyl-2H-pyrazol-3-yl)-ureido]-benzyl}-piperidin-1-yl)-acetyl]-isoxazole-3-carboxylic acid ethyl ester, Compound A1177;

1-(5-tert-Butyl-2-p-tolyl-2H-pyrazol-3-yl)-3-{2-[1-(1,3,5-trimethyl-1H-pyrazole-4-sulfonyl)-piperidin-4-ylmethyl]-phenyl}-urea, Compound A1178;

1-{2-[1-(Butane-1-sulfonyl)-piperidin-4-ylmethyl]-phenyl}-3-(5-tert-butyl-2-p-tolyl-2H-pyrazol-3-yl)-urea, Compound A1179;

1-(5-tert-Butyl-2-p-tolyl-2H-pyrazol-3-yl)-3-{2-[1-(naphthalene-1-sulfonyl)-piperidin-4-ylmethyl]-phenyl}-urea, Compound A1180;

1-{2-[1-(Benzo[1,2,5]thiadiazole-5-sulfonyl)-piperidin-4-ylmethyl]-phenyl}-3-(5-tert-butyl-2-p-tolyl-2H-pyrazol-3-yl)-urea, Compound A1181;

1-(5-tert-Butyl-2-p-tolyl-2H-pyrazol-3-yl)-3-{2-[1-(2,3-dihydro-benzo[1,4]dioxine-6-sulfonyl)-piperidin-4-ylmethyl]-phenyl}-urea, Compound A1182;

1-(5-tert-Butyl-2-p-tolyl-2H-pyrazol-3-yl)-3-{2-[1-(2,3-dihydro-benzofuran-5-sulfonyl)-piperidin-4-ylmethyl]-phenyl}-urea, Compound A1183;

1-(5-tert-Butyl-2-p-tolyl-2H-pyrazol-3-yl)-3-{2-[1-(2,4-dichloro-benzenesulfonyl)-piperidin-4-ylmethyl]-phenyl}-urea, Compound A1184;

1-(5-tert-Butyl-2-p-tolyl-2H-pyrazol-3-yl)-3-{2-[1-(2,5-dichloro-benzenesulfonyl)-piperidin-4-ylmethyl]-phenyl}-urea, Compound A1185;

1-(5-tert-Butyl-2-p-tolyl-2H-pyrazol-3-yl)-3-{2-[1-(2,5-dimethoxy-benzenesulfonyl)-piperidin-4-ylmethyl]-phenyl}-urea, Compound A1186;

1-(5-tert-Butyl-2-p-tolyl-2H-pyrazol-3-yl)-3-{2-[1-(2-chloro-4-fluoro-benzenesulfonyl)-piperidin-4-ylmethyl]-phenyl}-urea, Compound A1187;

1-(5-tert-Butyl-2-p-tolyl-2H-pyrazol-3-yl)-3-{2-[1-(2-chloro-benzenesulfonyl)-piperidin-4-ylmethyl]-phenyl}-urea, Compound A1188;

1-(5-tert-Butyl-2-p-tolyl-2H-pyrazol-3-yl)-3-{2-[1-(2-fluoro-benzenesulfonyl)-piperidin-4-ylmethyl]-phenyl}-urea, Compound A1189;

1-(5-tert-Butyl-2-p-tolyl-2H-pyrazol-3-yl)-3-{2-[1-(2,4,6-trimethyl-benzenesulfonyl)-piperidin-4-ylmethyl]-phenyl}-urea, Compound A1190;

1-(5-tert-Butyl-2-p-tolyl-2H-pyrazol-3-yl)-3-{2-[1-(naphthalene-2-sulfonyl)-piperidin-4-ylmethyl]-phenyl}-urea, Compound A1191;

1-(5-tert-Butyl-2-p-tolyl-2H-pyrazol-3-yl)-3-{2-[1-(thiophene-2-sulfonyl)-piperidin-4-ylmethyl]-phenyl}-urea, Compound A1192;

1-(5-tert-Butyl-2-p-tolyl-2H-pyrazol-3-yl)-3-{2-[1-(2-trifluoromethoxy-benzenesulfonyl)-piperidin-4-ylmethyl]-phenyl}-urea, Compound A1193;

1-(5-tert-Butyl-2-p-tolyl-2H-pyrazol-3-yl)-3-{2-[1-(3,4-dichloro-benzenesulfonyl)-piperidin-4-ylmethyl]-phenyl}-urea, Compound A1194;

1-(5-tert-Butyl-2-p-tolyl-2H-pyrazol-3-yl)-3-{2-[1-(3,4-difluoro-benzenesulfonyl)-piperidin-4-ylmethyl]-phenyl}-urea, Compound A1195;

1-(5-tert-Butyl-2-p-tolyl-2H-pyrazol-3-yl)-3-{2-[1-(3,4-dimethoxy-benzenesulfonyl)-piperidin-4-ylmethyl]-phenyl}-urea, Compound A1196;

1-(5-tert-Butyl-2-p-tolyl-2H-pyrazol-3-yl)-3-{2-[1-(3,5-dimethyl-isoxazole-4-sulfonyl)-piperidin-4-ylmethyl]-phenyl}-urea, Compound A1197;

1-(5-tert-Butyl-2-p-tolyl-2H-pyrazol-3-yl)-3-{2-[1-(3-chloro-4-fluoro-benzenesulfonyl)-piperidin-4-ylmethyl]-phenyl}-urea, Compound A1198;

1-(5-tert-Butyl-2-p-tolyl-2H-pyrazol-3-yl)-3-{2-[1-(3-fluoro-benzenesulfonyl)-piperidin-4-ylmethyl]-phenyl}-urea, Compound A1199;

5-(4-{2-[3-(5-tert-Butyl-2-p-tolyl-2H-pyrazol-3-yl)-ureido]-benzyl}-piperidine-1-sulfonyl)-4-methoxy-thiophene-3-carboxylic acid methyl ester, Compound A1200;

1-(5-tert-Butyl-2-p-tolyl-2H-pyrazol-3-yl)-3-{2-[1-(3-methoxy-benzenesulfonyl)-piperidin-4-ylmethyl]-phenyl}-urea, Compound A1201;

1-(5-tert-Butyl-2-p-tolyl-2H-pyrazol-3-yl)-3-{2-[1-(thiophene-3-sulfonyl)-piperidin-4-ylmethyl]-phenyl}-urea, Compound A1202;

1-(5-tert-Butyl-2-p-tolyl-2H-pyrazol-3-yl)-3-{2-[1-(3-trifluoromethyl-benzenesulfonyl)-piperidin-4-ylmethyl]-phenyl}-urea, Compound A1203;

1-(5-tert-Butyl-2-p-tolyl-2H-pyrazol-3-yl)-3-{2-[1-(4-chloro-2,5-dimethyl-benzenesulfonyl)-piperidin-4-ylmethyl]-phenyl}-urea, Compound A1204;

1-(5-tert-Butyl-2-p-tolyl-2H-pyrazol-3-yl)-3-{2-[1-(4-chloro-benzenesulfonyl)-piperidin-4-ylmethyl]-phenyl}-urea, Compound A1205;

1-(5-tert-Butyl-2-p-tolyl-2H-pyrazol-3-yl)-3-{2-[1-(4-fluoro-benzenesulfonyl)-piperidin-4-ylmethyl]-phenyl}-urea, Compound A1206;

1-(5-tert-Butyl-2-p-tolyl-2H-pyrazol-3-yl)-3-{2-[1-(4-methoxy-benzenesulfonyl)-piperidin-4-ylmethyl]-phenyl}-urea, Compound A1207;

1-(5-tert-Butyl-2-p-tolyl-2H-pyrazol-3-yl)-3-{2-[1-(4-methyl-3,4-dihydro-2H-benzo[1,4]oxazine-7-sulfonyl)-piperidin-4-ylmethyl]-phenyl}-urea, Compound A1208;

1-{2-[1-(4-tert-Butyl-benzenesulfonyl)-piperidin-4-ylmethyl]-phenyl}-3-(5-tert-butyl-2-p-tolyl-2H-pyrazol-3-yl)-urea, Compound A1209;

1-(5-tert-Butyl-2-p-tolyl-2H-pyrazol-3-yl)-3-{2-[1-(4-trifluoromethoxy-benzenesulfonyl)-piperidin-4-ylmethyl]-phenyl}-urea, Compound A1210;

1-(5-tert-Butyl-2-p-tolyl-2H-pyrazol-3-yl)-3-{2-[1-(5-oxazol-5-yl-thiophene-2-sulfonyl)-piperidin-4-ylmethyl]-phenyl}-urea, Compound A1212;

1-(5-tert-Butyl-2-p-tolyl-2H-pyrazol-3-yl)-3-{2-[1-(6-morpholin-4-yl-pyridine-3-sulfonyl)-piperidin-4-ylmethyl]-phenyl}-urea, Compound A1213;

1-(5-tert-Butyl-2-p-tolyl-2H-pyrazol-3-yl)-3-{2-[1-(quinoline-8-sulfonyl)-piperidin-4-ylmethyl]-phenyl}-urea, Compound A1214;

1-(5-tert-Butyl-2-p-tolyl-2H-pyrazol-3-yl)-3-[2-(1-phenylmethanesulfonyl-piperidin-4-ylmethyl)-phenyl]-urea, Compound A1215;

1-[2-(1-Benzenesulfonyl-piperidin-4-ylmethyl)-phenyl]-3-(5-tert-butyl-2-p-tolyl-2H-pyrazol-3-yl)-urea, Compound A1216;

1-(5-tert-Butyl-2-p-tolyl-2H-pyrazol-3-yl)-3-{2-[1-(2-phenyl-ethenesulfonyl)-piperidin-4-ylmethyl]-phenyl}-urea, Compound A1217;

1-{2-[1-(Benzo[1,2,5]oxadiazole-4-sulfonyl)-piperidin-4-ylmethyl]-phenyl}-3-(5-tert-butyl-2-p-tolyl-2H-pyrazol-3-yl)-urea, Compound A1218;

1-{2-[1-(Benzo[1,2,5]thiadiazole-4-sulfonyl)-piperidin-4-ylmethyl]-phenyl}-3-(5-tert-butyl-2-p-tolyl-2H-pyrazol-3-yl)-urea, Compound A1219;

1-(5-tert-Butyl-2-p-tolyl-2H-pyrazol-3-yl)-3-{2-[1-(1-methyl-1H-imidazole-4-sulfonyl)-piperidin-4-ylmethyl]-phenyl}-urea, Compound A1220;

1-(5-tert-Butyl-2-p-tolyl-2H-pyrazol-3-yl)-3-{2-[1-(1,2-dimethyl-1H-imidazole-4-sulfonyl)-piperidin-4-ylmethyl]-phenyl}-urea, Compound A1221;

1-(5-tert-Butyl-2-p-tolyl-2H-pyrazol-3-yl)-3-{2-[1-(5-isoxazol-3-yl-thiophene-2-sulfonyl)-piperidin-4-ylmethyl]-phenyl}-urea, Compound A1222;

1-(5-tert-Butyl-2-p-tolyl-2H-pyrazol-3-yl)-3-(2-{1-[5-(2-methyl-thiazol-4-yl)-thiophene-2-sulfonyl]-piperidin-4-ylmethyl}-phenyl)-urea, Compound A1223;

1-(5-tert-Butyl-2-p-tolyl-2H-pyrazol-3-yl)-3-{2-[1-(2-oxo-2H-chromene-6-sulfonyl)-piperidin-4-ylmethyl]-phenyl}-urea, Compound A1224;

1-(5-tert-Butyl-2-p-tolyl-2H-pyrazol-3-yl)-3-{2-[1-(5-dimethylamino-naphthalene-1-sulfonyl)-piperidin-4-ylmethyl]-phenyl}-urea, Compound A1225;

1-(5-tert-Butyl-2-p-tolyl-2H-pyrazol-3-yl)-3-[2-(1-ethanesulfonyl-piperidin-4-ylmethyl)-phenyl]-urea, Compound A1226;

1-(5-tert-Butyl-2-p-tolyl-2H-pyrazol-3-yl)-3-{2-[1-(isoquinoline-5-sulfonyl)-piperidin-4-ylmethyl]-phenyl}-urea, Compound A1227;

1-(5-tert-Butyl-2-p-tolyl-2H-pyrazol-3-yl)-3-[2-(1-methanesulfonyl-piperidin-4-ylmethyl)-phenyl]-urea, Compound A1228;

2-(4-{2-[3-(5-tert-Butyl-2-p-tolyl-2H-pyrazol-3-yl)-ureido]-benzyl}-piperidine-1-sulfonyl)-benzoic acid methyl ester, Compound A1229;

4-(4-{2-[3-(5-tert-Butyl-2-p-tolyl-2H-pyrazol-3-yl)-ureido]-benzyl}-piperidine-1-sulfonyl)-2,5-dimethyl-furan-3-carboxylic acid methyl ester, Compound A1230;

5-(4-{2-[3-(5-tert-Butyl-2-p-tolyl-2H-pyrazol-3-yl)-ureido]-benzyl}-piperidine-1-sulfonyl)-1-methyl-1H-pyrrole-2-carboxylic acid methyl ester, Compound A1231;

5-(4-{2-[3-(5-tert-Butyl-2-p-tolyl-2H-pyrazol-3-yl)-ureido]-benzyl}-piperidine-1-sulfonyl)-furan-2-carboxylic acid methyl ester, Compound A1232;

N-[4-(4-{2-[3-(5-tert-Butyl-2-p-tolyl-2H-pyrazol-3-yl)-ureido]-benzyl}-piperidine-1-sulfonyl)-phenyl]-acetamide, Compound A1233;

1-(5-tert-Butyl-2-p-tolyl-2H-pyrazol-3-yl)-3-{2-[1-(4-vinyl-benzenesulfonyl)-piperidin-4-ylmethyl]-phenyl}-urea, Compound A1234;

1-(5-tert-Butyl-2-p-tolyl-2H-pyrazol-3-yl)-3-{2-[1-(toluene-4-sulfonyl)-piperidin-4-ylmethyl]-phenyl}-urea, Compound A1235;

4-{2-[3-(5-tert-Butyl-2-p-tolyl-2H-pyrazol-3-yl)-ureido]-benzyl}-piperidine-1-carboxylic acid (2,3-dihydro-benzo[1,4]dioxin-6-yl)-amide, Compound A1236;

4-{2-[3-(5-tert-Butyl-2-p-tolyl-2H-pyrazol-3-yl)-ureido]-benzyl}-piperidine-1-carboxylic acid (2,3-dihydro-benzofuran-5-yl)-amide, Compound A1237;

4-{2-[3-(5-tert-Butyl-2-p-tolyl-2H-pyrazol-3-yl)-ureido]-benzyl}-piperidine-1-carboxylic acid (2,4-dimethoxy-phenyl)-amide, Compound A1238;

4-{2-[3-(5-tert-Butyl-2-p-tolyl-2H-pyrazol-3-yl)-ureido]-benzyl}-piperidine-1-carboxylic acid (2,5-dimethoxy-phenyl)-amide, Compound A1239;

4-{2-[3-(5-tert-Butyl-2-p-tolyl-2H-pyrazol-3-yl)-ureido]-benzyl}-piperidine-1-carboxylic acid (2-methyl-5-phenyl-furan-3-yl)-amide, Compound A1240;

4-{2-[3-(5-tert-Butyl-2-p-tolyl-2H-pyrazol-3-yl)-ureido]-benzyl}-piperidine-1-carboxylic acid benzo[1,3]dioxol-5-ylamide, Compound A1241;

4-{2-[3-(5-tert-Butyl-2-p-tolyl-2H-pyrazol-3-yl)-ureido]-benzyl}-piperidine-1-carboxylic acid (3,4,5-trimethoxypbenyl)-amide, Compound A1242;

4-{2-[3-(5-tert-Butyl-2-p-tolyl-2H-pyrazol-3-yl)-ureido]-benzyl}-piperidine-1-carboxylic acid (3,4-dimethoxy-phenyl)-amide, Compound A1243;

4-{2-[3-(5-tert-Butyl-2-p-tolyl-2H-pyrazol-3-yl)-ureido]-benzyl}-piperidine-1-carboxylic acid (3,5-dimethoxy-phenyl)-amide, Compound A1244;

4-{2-[3-(5-tert-Butyl-2-p-tolyl-2H-pyrazol-3-yl)-ureido]-benzyl}-piperidine-1-carboxylic acid (3,5-dimethyl-isoxazol-4-yl)-amide, Compound A1245;

4-{2-[3-(5-tert-Butyl-2-p-tolyl-2H-pyrazol-3-yl)-ureido]-benzyl}-piperidine-1-carboxylic acid (3-chloro-4-methoxy-phenyl)-amide, Compound A1246;

4-{2-[3-(5-tert-Butyl-2-p-tolyl-2H-pyrazol-3-yl)-ureido]-benzyl}-piperidine-1-carboxylic acid thiopben-3-ylamide, Compound A1247;

4-{2-[3-(5-tert-Butyl-2-p-tolyl-2H-pyrazol-3-yl)-ureido]-benzyl}-piperidine-1-carboxylic acid (4-difluorometboxy-phenyl)-amide, Compound A1248;

4-{2-[3-(5-tert-Butyl-2-p-tolyl-2H-pyrazol-3-yl)-ureido]-benzyl}-piperidine-1-carboxylic acid (4-dimethylamino-phenyl)-amide, Compound A1249;

4-{2-[3-(5-tert-Butyl-2-p-tolyl-2H-pyrazol-3-yl)-ureido]-benzyl}-piperidine-1-carboxylic acid (4-trifluoromethoxy-phenyl)-amide, Compound A1250;

4-{2-[3-(5-tert-Butyl-2-p-tolyl-2H-pyrazol-3-yl)-ureido]-benzyl}-piperidine-1-carboxylic acid (4-acetyl-phenyl)-amide, Compound A1251;

4-{2-[3-(5-tert-Butyl-2-p-tolyl-2H-pyrazol-3-yl)-ureido]-benzyl}-piperidine-1-carboxylic acid benzo[1,2,5]thiadiazol-4-ylamide, Compound A1252;

4-{2-[3-(5-tert-Butyl-2-p-tolyl-2H-pyrazol-3-yl)-ureido]-benzyl}-piperidine-1-carboxylic acid (4-methoxy-2-methyl-phenyl)amide, Compound A1253;

4-{2-[3-(5-tert-Butyl-2-p-tolyl-2H-pyrazol-3-yl)-ureido]-benzyl}-piperidine-1-carboxylic acid (5-chloro-2,4-dimethoxy-phenyl)-amide, Compound A1254;

4-{2-[3-(5-tert-Butyl-2-p-tolyl-2H-pyrazol-3-yl)-ureido]-benzyl}-piperidine-1-carboxylic acid (5-methyl-2-trifluoromethyl-furan-3-yl)-amide, Compound A1255;

4-{2-[3-(5-tert-Butyl-2-p-tolyl-2H-pyrazol-3-yl)-ureido]-benzyl}-piperidine-1-carboxylic acid (5-methyl-3-phenyl-isoxazol-4-yl)-amide, Compound A1256;

4-{2-[3-(5-tert-Butyl-2-p-tolyl-2H-pyrazol-3-yl)-ureido]-benzyl}-piperidine-1-carboxylic acid (6-fluoro-4H-benzo[1,3]dioxin-8-yl)-amide, Compound A1257;

3-[(4-{2-[3-(5-tert-Butyl-2-p-tolyl-2H-pyrazol-3-yl)-ureido]-benzyl}-piperidine-1-carbonyl)-amino]-benzoic acid ethyl ester, Compound A1258;

4-[(4-{2-[3-(5-tert-Butyl-2-p-tolyl-2H-pyrazol-3-yl)-ureido]-benzyl}-piperidine-1-carbonyl)-amino]-benzoic acid methyl ester, Compound A1259;

1-(5-tert-Butyl-2-p-tolyl-2H-pyrazol-3-yl)-3-{4-[8-(4-oxazol-5-yl-benzoyl)-8-aza-bicyclo[3.2.1]oct-3-ylmethyl]-phenyl}-urea, Compound A1260;

1-(5-tert-Butyl-2-p-tolyl-2H-pyrazol-3-yl)-3-{4-[8-(2-hydroxy-6-methyl-pyridine-4-carbonyl)-8-aza-bicyclo[3.2.1]oct-3-ylmethyl]-phenyl}-urea, Compound A1261;

1-(5-tert-Butyl-2-p-tolyl-2H-pyrazol-3-yl)-3-(4-{8-[2-(6-methoxy-benzofuran-3-yl)-acetyl]-8-aza-bicyclo[3.2.1]oct-3-ylmethyl}-phenyl)-urea, Compound A1262;

1-(5-tert-Butyl-2-p-tolyl-2H-pyrazol-3-yl)-3-(4-{8-[2-methyl-5-(piperidine-1-sulfonyl)-furan-3-carbonyl]-8-aza-bicyclo[3.2.1]oct-3-ylmethyl}-phenyl)-urea, Compound A1263;

1-{4-[8-(4-tert-Butoxymethyl-benzoyl)-8-aza-bicyclo[3.2.1]oct-3-ylmethyl]-phenyl}-3-(5-tert-butyl-2-p-tolyl-2H-pyrazol-3-yl)-urea, Compound A1264;

1-(5-tert-Butyl-2-p-tolyl-2H-pyrazol-3-yl)-3-{4-[8-(3-methyl-isoxazole-4-carbonyl)-8-aza-bicyclo[3.2.1]oct-3-ylmethyl]-phenyl}-urea, Compound A1265;

Acetic acid 4-(3-{4-[3-(5-tert-butyl-2-p-tolyl-2H-pyrazol-3-yl)-ureido]-benzyl}-8-aza-bicyclo[3.2.1]octane-8-carbonyl)-benzyl ester, Compound A1266;

1-(5-tert-Butyl-2-p-tolyl-2H-pyrazol-3-yl)-3-{4-[8-(5-methyl-isoxazole-4-carbonyl)-8-aza-bicyclo[3.2.1]oct-3-ylmethyl]-phenyl}-urea, Compound A1267;

1-{4-[8-(3-Butoxy-4-methoxy-benzoyl)-8-aza-bicyclo[3.2.1]oct-3-ylmethyl]-phenyl}-3-(5-tert-butyl-2-p-tolyl-2H-pyrazol-3-yl)-urea, Compound A1268;

1-(5-tert-Butyl-2-p-tolyl-2H-pyrazol-3-yl)-3-{4-[8-(4-thiophen-2-yl-benzoyl)-8-aza-bicyclo[3.2.1]oct-3-ylmethyl]-phenyl}-urea, Compound A1269;

1-(5-tert-Butyl-2-p-tolyl-2H-pyrazol-3-yl)-3-{4-[8-(5-methyl-2-trifluoromethyl-furan-3-carbonyl)-8-aza-bicyclo[3.2.1]oct-3-ylmethyl]-phenyl}-urea, Compound A1270;

1-(5-tert-Butyl-2-p-tolyl-2H-pyrazol-3-yl)-3-{4-[8-(3-pyridin-3-yl-propionyl)-8-aza-bicyclo[3.2.1]oct-3-ylmethyl]-phenyl}-urea, Compound A1271;

1-(5-tert-Butyl-2-p-tolyl-2H-pyrazol-3-yl)-3-{4-[8-(2-methyl-imidazo[1,2-a]pyridine-3-carbonyl)-8-aza-bicyclo[3.2.1]oct-3-ylmethyl]-phenyl}-urea, Compound A1272;

1-(5-tert-Butyl-2-p-tolyl-2H-pyrazol-3-yl)-3-{4-[8-(4-difluoromethoxy-benzoyl)-8-aza-bicyclo[3.2.1]oct-3-ylmethyl]-phenyl}-urea, Compound A1273;

1-(5-tert-Butyl-2-p-tolyl-2H-pyrazol-3-yl)-3-{4-[8-(2-methyl-5-phenyl-furan-3-carbonyl)-8-aza-bicyclo[3.2.1]oct-3-ylmethyl]-phenyl}-urea, Compound A1274;

1-(5-tert-Butyl-2-p-tolyl-2H-pyrazol-3-yl)-3-(4-{8-[5-methoxy-2-(2,2,2-trifluoro-ethoxyl)-benzoyl]-8-aza-bicyclo[3.2.1]oct-3-ylmethyl}-phenyl)-urea, Compound A1275;

1-(5-tert-Butyl-2-p-tolyl-2H-pyrazol-3-yl)-3-{4-[8-(2H-indazole-3-carbonyl)-8-aza-bicyclo[3.2.1]oct-3-ylmethyl]-phenyl}-urea, Compound A1276;

1-{4-[8-(4-Amino-3-trifluoromethoxy-benzoyl)-8-aza-bicyclo[3.2.1]oct-3-ylmethyl]-phenyl}-3-(5-tert-butyl-2-p-tolyl-2H-pyrazol-3-yl)-urea, Compound A1277;

1-(5-tert-Butyl-2-p-tolyl-2H-pyrazol-3-yl)-3-{4-[8-(4-isobutyl-benzoyl)-8-aza-bicyclo[3.2.1]oct-3-ylmethyl]-phenyl}-urea, Compound A1278;

1-(5-tert-Butyl-2-p-tolyl-2H-pyrazol-3-yl)-3-(4-{8-[2-(2,4-dimethoxy-phenyl)-acetyl]-8-aza-bicyclo[3.2.1]oct-3-ylmethyl}-phenyl)-urea, Compound A1279;

1-(5-tert-Butyl-2-p-tolyl-2H-pyrazol-3-yl)-3-{4-[8-(2-chloro-6-methoxy-pyridine-4-carbonyl)-8-aza-bicyclo[3.2.1]oct-3-ylmethyl]-phenyl}-urea, Compound A1280;

1-(5-tert-Butyl-2-p-tolyl-2H-pyrazol-3-yl)-3-{4-[8-(2-pyridin-4-yl-thiazole-4-carbonyl)-8-aza-bicyclo[3.2.1]oct-3-ylmethyl]-phenyl}-urea, Compound A1281;

1-(5-tert-Butyl-2-p-tolyl-2H-pyrazol-3-yl)-3-{4-[8-(3,5-dimethyl-1H-pyrazole-4-carbonyl)-8-aza-bicyclo[3.2.1]oct-3-ylmethyl]-phenyl}-urea, Compound A1282;

1-(5-tert-Butyl-2-p-tolyl-2H-pyrazol-3-yl)-3-(4-{8-[4-(1,1,2,2-tetrafluoro-ethoxyl)-benzoyl]-8-aza-bicyclo[3.2.1]oct-3-ylmethyl}-phenyl)-urea, Compound A1283;

1-(5-tert-Butyl-2-p-tolyl-2H-pyrazol-3-yl)-3-(4-{8-[3-(1,1,2,2-tetrafluoro-ethoxyl)-benzoyl]-8-aza-bicyclo[3.2.1]oct-3-ylmethyl}-phenyl)-urea, Compound A1284;

1-(5-tert-Butyl-2-p-tolyl-2H-pyrazol-3-yl)-3-(4-{8-[2-(1-methyl-1H-indol-3-yl)-acetyl]-8-aza-bicyclo[3.2.1]oct-3-ylmethyl}-phenyl)-urea, Compound A1285;

1-{4-[8-(Benzothiazole-6-carbonyl)-8-aza-bicyclo[3.2.1]oct-3-ylmethyl]-phenyl}-3-(5-tert-butyl-2-p-tolyl-2H-pyrazol-3-yl)-urea, Compound A1286;

1-(5-tert-Butyl-2-p-tolyl-2H-pyrazol-3-yl)-3-(4-{8-[6-(2,2,2-trifluoro-ethoxyl)-pyridine-3-carbonyl]-8-aza-bicyclo[3.2.1]oct-3-ylmethyl}-phenyl)-urea, Compound A1287;

1-(5-tert-Butyl-2-p-tolyl-2H-pyrazol-3-yl)-3-{4-[8-(4-ethylamino-benzoyl)-8-aza-bicyclo[3.2.1]oct-3-ylmethyl]-phenyl}-urea, Compound A1288;

1-(5-tert-Butyl-2-p-tolyl-2H-pyrazol-3-yl)-3-{4-[8-(2-methyl-furan-3-carbonyl)-8-aza-bicyclo[3.2.1]oct-3-ylmethyl]-phenyl}-urea, Compound A1289;

1-{4-[8-(Bicyclo[2.2.1]hept-5-ene-2-carbonyl)-8-aza-bicyclo[3.2.1]oct-3-ylmethyl]-phenyl}-3-(5-tert-butyl-2-p-tolyl-2H-pyrazol-3-yl)-urea, Compound A1290;

1-(5-tert-Butyl-2-p-tolyl-2H-pyrazol-3-yl)-3-{4-[8-(2,6-dioxo-hexahydro-pyrimidine-4-carbonyl)-8-aza-bicyclo[3.2.1]oct-3-ylmethyl]-phenyl}-urea, Compound A1291;

1-(5-tert-Butyl-2-p-tolyl-2H-pyrazol-3-yl)-3-{4-[8-(4-[1,2,3]thiadiazol-4-yl-benzoyl)-8-aza-bicyclo[3.2.1]oct-3-ylmethyl]-phenyl}-urea, Compound A1292;

1-(5-tert-Butyl-2-p-tolyl-2H-pyrazol-3-yl)-3-{4-[8-(4,5-dimethyl-furan-2-carbonyl)-8-aza-bicyclo[3.2.1]oct-3-ylmethyl]-phenyl}-urea, Compound A1293;

1-(5-tert-Butyl-2-p-tolyl-2H-pyrazol-3-yl)-3-{4-[8-(3-methanesulfonyl-6,7-dihydro-benzo[c]thiophene-1-carbonyl)-8-aza-bicyclo[3.2.1]oct-3-ylmethyl]-phenyl}-urea, Compound A1294;

1-(5-tert-Butyl-2-p-tolyl-2H-pyrazol-3-yl)-3-{4-[8-(2,3-dihydro-benzofuran-5-carbonyl)-8-aza-bicyclo[3.2.1]oct-3-ylmethyl]-phenyl}-urea, Compound A1295;

1-(5-tert-Butyl-2-p-tolyl-2H-pyrazol-3-yl)-3-(4-{8-[2-(3,5-dimethyl-phenyl)-acetyl]-8-aza-bicyclo[3.2.1]oct-3-ylmethyl}-phenyl)-urea, Compound A1296;

1-(5-tert-Butyl-2-p-tolyl-2H-pyrazol-3-yl)-3-{4-[8-(2-indan-2-yl-acetyl)-8-aza-bicyclo[3.2.1]oct-3-ylmethyl]-phenyl}-urea, Compound A1297;

1-(5-tert-Butyl-2-p-tolyl-2H-pyrazol-3-yl)-3-{4-[8-(3H-imidazole-4-carbonyl)-8-aza-bicyclo[3.2.1]oct-3-ylmethyl]-phenyl}-urea, Compound A1298;

1-(5-tert-Butyl-2-p-tolyl-2H-pyrazol-3-yl)-3-{4-[8-(2,5-dimethyl-furan-3-carbonyl)-8-aza-bicyclo[3.2.1]oct-3-ylmethyl]-phenyl}-urea, Compound A1299;

1-(5-tert-Butyl-2-p-tolyl-2H-pyrazol-3-yl)-3-{4-[8-(5-methoxy-benzofuran-2-carbonyl)-8-aza-bicyclo[3.2.1]oct-3-ylmethyl]-phenyl}-urea, Compound A1300;

1-(5-tert-Butyl-2-p-tolyl-2H-pyrazol-3-yl)-3-{4-[8-(2,6-dimethoxy-pyridine-3-carbonyl)-8-aza-bicyclo[3.2.1]oct-3-ylmethyl]-phenyl}-urea, Compound A1301;

1-(5-tert-Butyl-2-p-tolyl-2H-pyrazol-3-yl)-3-{4-[8-(5,6-dichloro-pyridine-3-carbonyl)-8-aza-bicyclo[3.2.1]oct-3-ylmethyl]-phenyl}-urea, Compound A1302;

1-(5-tert-Butyl-2-p-tolyl-2H-pyrazol-3-yl)-3-(4-{8-[2-(2-methyl-1H-indol-3-yl)-acetyl]-8-aza-bicyclo[3.2.1]oct-3-ylmethyl}-phenyl)-urea, Compound A1303;

1-(5-tert-Butyl-2-p-tolyl-2H-pyrazol-3-yl)-3-{4-[8-(5-methyl-pyrazine-2-carbonyl)-8-aza-bicyclo[3.2.1]oct-3-ylmethyl]-phenyl}-urea, Compound A1304;

1-(5-tert-Butyl-2-p-tolyl-2H-pyrazol-3-yl)-3-{4-[8-(4-methoxy-thiophene-3-carbonyl)-8-aza-bicyclo[3.2.1]oct-3-ylmethyl]-phenyl}-urea, Compound A1305;

1-(5-tert-Butyl-2-p-tolyl-2H-pyrazol-3-yl)-3-{4-[8-(5-methyl-1-phenyl-1H-pyrazole-4-carbonyl)-8-aza-bicyclo[3.2.1]oct-3-ylmethyl]-phenyl}-urea, Compound A1306;

1-(5-tert-Butyl-2-p-tolyl-2H-pyrazol-3-yl)-3-{4-[8-(5-oxo-pyrrolidine-2-carbonyl)-8-aza-bicyclo[3.2.1]oct-3-ylmethyl]-phenyl}-urea, a mixture of endo- and exo-isomers, (0.0254 g), C34H42N6O3, 583.34, M+H, 2.45, Compound A1307;

endo-1-(5-tert-Butyl-2-p-tolyl-2H-pyrazol-3-yl)-3-{4-[8-((R)-5-oxo-pyrrolidine-2-carbonyl)-8-aza-bicyclo[3.2.1]oct-3-ylmethyl]-phenyl}-urea, Compound A1307A;

exo-1-(5-tert-Butyl-2-p-tolyl-2H-pyrazol-3-yl)-3-{4-[8-((R)-5-oxo-pyrrolidine-2-carbonyl)-8-aza-bicyclo[3.2.1]oct-3-ylmethyl]-phenyl}-urea, Compound A1307B;

endo-1-(5-tert-Butyl-2-p-tolyl-2H-pyrazol-3-yl)-3-{4-[8-((S)-5-oxo-pyrrolidine-2-carbonyl)-8-aza-bicyclo[3.2.1]oct-3-ylmethyl]-phenyl}-urea, Compound A1307C;

exo-1-(5-tert-Butyl-2-p-tolyl-2H-pyrazol-3-yl)-3-{4-[8-((S)-5-oxo-pyrrolidine-2-carbonyl)-8-aza-bicyclo[3.2.1]oct-3-ylmethyl]-phenyl}-urea, Compound A1307D;

1-(5-tert-Butyl-2-p-tolyl-2H-pyrazol-3-yl)-3-{4-[8-((R)-2-methoxy-2-phenyl-acetyl)-8-aza-bicyclo[3.2.1]oct-3-ylmethyl]-phenyl}-urea, a mixture of endo- and exo-isomers, (0.0381 g), C38H45N5O3, 620.30, M+H, 3.38, Compound A1308;

endo-1-(5-tert-Butyl-2-p-tolyl-2H-pyrazol-3-yl)-3-{4-[8-((R)-2-methoxy-2-phenyl-acetyl)-8-aza-bicyclo[3.2.1]oct-3-ylmethyl]-phenyl}-urea, Compound A1308A;

exo-1-(5-tert-Butyl-2-p-tolyl-2H-pyrazol-3-yl)-3-{4-[8-((R)-2-methoxy-2-phenyl-acetyl)-8-aza-bicyclo[3.2.1]oct-3-ylmethyl]-phenyl}-urea, Compound A1308B;

endo-1-(5-tert-Butyl-2-p-tolyl-2H-pyrazol-3-yl)-3-{4-[8-((S)-2-methoxy-2-phenyl-acetyl)-8-aza-bicyclo[3.2.1]oct-3-ylmethyl]-phenyl}-urea, Compound A1308C;

exo-1-(5-tert-Butyl-2-p-tolyl-2H-pyrazol-3-yl)-3-{4-[8-((S)-2-methoxy-2-phenyl-acetyl)-8-aza-bicyclo[3.2.1]oct-3-ylmethyl]-phenyl}-urea, Compound A1308D;

1-(5-tert-Butyl-2-p-tolyl-2H-pyrazol-3-yl)-3-{4-[8-(7-methoxy-benzofuran-2-carbonyl)-8-aza-bicyclo[3.2.1]oct-3-ylmethyl]-phenyl}-urea, Compound A1309;

1-(5-tert-Butyl-2-p-tolyl-2H-pyrazol-3-yl)-3-{4-[8-(3-methyl-benzofuran-2-carbonyl)-8-aza-bicyclo[3.2.1]oct-3-ylmethyl]-phenyl}-urea, Compound A1310;

1-(5-tert-Butyl-2-p-tolyl-2H-pyrazol-3-yl)-3-{4-[8-(3-thioureido-benzoyl)-8-aza-bicyclo[3.2.1]oct-3-ylmethyl]-phenyl}-urea, Compound A1311;

1-(5-tert-Butyl-2-p-tolyl-2H-pyrazol-3-yl)-3-(4-{8-[2-(2,3-dimethoxy-phenyl)-acetyl]-8-aza-bicyclo[3.2.1]oct-3-ylmethyl}-phenyl)-urea (0.0289 g), C39H47N5O4, 650.28, M+H, 3.32, Compound A1312;

1-(5-tert-Butyl-2-p-tolyl-2H-pyrazol-3-yl)-3-(4-{8-[3-(4-fluoro-phenyl)-propionyl]-8-aza-bicyclo[3.2.1]oct-3-ylmethyl}-phenyl)-urea, Compound A1313;

1-(5-tert-Butyl-2-p-tolyl-2H-pyrazol-3-yl)-3-{4-[8-(5-chloro-6-hydroxy-pyridine-3-carbonyl)-8-aza-bicyclo[3.2.1]oct-3-ylmethyl]-phenyl}-urea, Compound A1314;

1-(5-tert-Butyl-2-p-tolyl-2H-pyrazol-3-yl)-3-{4-[8-(2,4-dimethyl-thiazole-5-carbonyl)-8-aza-bicyclo[3.2.1]oct-3-ylmethyl]-phenyl}-urea, Compound A1315;

1-(5-tert-Butyl-2-p-tolyl-2H-pyrazol-3-yl)-3-(4-{8-[4-(2,2,2-trifluoro-acetyl)-benzoyl]-8-aza-bicyclo[3.2.1]oct-3-ylmethyl}-phenyl)-urea, Compound A1316;

1-(5-tert-Butyl-2-p-tolyl-2H-pyrazol-3-yl)-3-(4-{8-[2-(5-chloro-benzo[b]thiophen-3-yl)-acetyl]-8-aza-bicyclo[3.2.1]oct-3-ylmethyl}-phenyl)-urea, Compound A1317;

1-(5-tert-Butyl-2-p-tolyl-2H-pyrazol-3-yl)-3-{4-[8-(2-pyridin-3-yl-thiazole-4-carbonyl)-8-aza-bicyclo[3.2.1]oct-3-ylmethyl]-phenyl}-urea, Compound A1318;

1-(5-tert-Butyl-2-p-tolyl-2H-pyrazol-3-yl)-3-(4-{8-[2-(5-chloro-3-methyl-benzo[b]thiophen-2-yl)-acetyl]-8-aza-bicyclo[3.2.1]oct-3-ylmethyl}-phenyl)-urea, Compound A1319;

1-(5-tert-Butyl-2-p-tolyl-2H-pyrazol-3-yl)-3-{4-[8-(4-oxo-4,5,6,7-tetrahydro-benzofuran-3-carbonyl)-8-aza-bicyclo[3.2.1]oct-3-ylmethyl]-phenyl}-urea, Compound A1320;

1-(5-tert-Butyl-2-p-tolyl-2H-pyrazol-3-yl)-3-{4-[8-([1,2,3]thiadiazole-4-carbonyl)-8-aza-bicyclo[3.2.1]oct-3-ylmethyl]-phenyl}-urea, Compound A1321;

1-(5-tert-Butyl-2-p-tolyl-2H-pyrazol-3-yl)-3-{4-[8-(3,5-dimethyl-isoxazole-4-carbonyl)-8-aza-bicyclo[3.2.1]oct-3-ylmethyl]-phenyl}-urea, Compound A1322;

1-(5-tert-Butyl-2-p-tolyl-2H-pyrazol-3-yl)-3-{4-[8-(5-methyl-2-phenyl1-2H-[1,2,3]triazole-4-carbonyl)-8-aza-bicyclo[3.2.1]oct-3-ylmethyl]-phenyl}-urea, Compound A1323;

1-{4-[8-(2-Benzo[b]thiophen-3-yl-acetyl)-8-aza-bicyclo[3.2.1]oct-3-ylmethyl]-phenyl}-3-(5-tert-butyl-2-p-tolyl-2H-pyrazol-3-yl)-urea, Compound A1324;

1-{4-[8-(Benzo[b]thiophene-2-carbonyl)-8-aza-bicyclo[3.2.1]oct-3-ylmethyl]-phenyl}-3-(5-tert-butyl-2-p-tolyl-2H-pyrazol-3-yl)-urea, Compound A1325;

1-(5-tert-Butyl-2-p-tolyl-2H-pyrazol-3-yl)-3-{4-[8-(quinoline-6-carbonyl)-8-aza-bicyclo[3.2.1]oct-3-ylmethyl]-phenyl}-urea, Compound A1326;

1-(5-tert-Butyl-2-p-tolyl-2H-pyrazol-3-yl)-3-{4-[8-(3-thiophen-2-yl-propionyl)-8-aza-bicyclo[3.2.1]oct-3-ylmethyl]-phenyl}-urea, Compound A1327;

1-(5-tert-Butyl-2-p-tolyl-2H-pyrazol-3-yl)-3-(4-{8-[2-(4-chloro-phenyl)-propionyl]-8-aza-bicyclo[3.2.1]oct-3-ylmethyl}-phenyl)-urea, Compound A1328;

1-(5-tert-Butyl-2-p-tolyl-2H-pyrazol-3-yl)-3-{4-[8-(2-furan-2-yl-2-oxo-acetyl)-8-aza-bicyclo[3.2.1]oct-3-ylmethyl]-phenyl}-urea, Compound A1329;

1-(5-tert-Butyl-2-p-tolyl-2H-pyrazol-3-yl)-3-{4-[8-(5-chloro-thiophene-2-carbonyl)-8-aza-bicyclo[3.2.1]oct-3-ylmethyl]-phenyl}-urea, Compound A1330;

1-{4-[8-(3-1H-Benzoimidazol-2-yl-propionyl)-8-aza-bicyclo[3.2.1]oct-3-ylmethyl]-phenyl}-3-(5-tert-butyl-2-p-tolyl-2H-pyrazol-3-yl)-urea, Compound A1331;

N-[2-(3-{4-[3-(5-tert-Butyl-2-p-tolyl-2H-pyrazol-3-yl)-ureido]-benzyl}-8-aza-bicyclo[3.2.1]oct-8-yl)-1-methyl-2-oxo-ethyl]-acetamide, Compound A1332;

1-(5-tert-Butyl-2-p-tolyl-2H-pyrazol-3-yl)-3-{4-[8-(2-hydroxyquinoline-4-carbonyl)-8-aza-bicyclo[3.2.1]oct-3-ylmethyl]-phenyl}-urea, Compound A1333;

1-(5-tert-Butyl-2-p-tolyl-2H-pyrazol-3-yl)-3-{4-[8-(6-methyl-pyridine-2-carbonyl)-8-aza-bicyclo[3.2.1]oct-3-ylmethyl]-phenyl}-urea, Compound A1334;

1-(5-tert-Butyl-2-p-tolyl-2H-pyrazol-3-yl)-3-{4-[8-(tetrahydro-furan-2-carbonyl)-8-aza-bicyclo[3.2.1]oct-3-ylmethyl]-phenyl}-urea, Compound A1335;

1-(5-tert-Butyl-2-p-tolyl-2H-pyrazol-3-yl)-3-{4-[8-(4-oxo-2-phenyl-pentanoyl)-8-aza-bicyclo[3.2.1]oct-3-ylmethyl]-phenyl}-urea, Compound A1336;

1-(5-tert-Butyl-2-p-tolyl-2H-pyrazol-3-yl)-3-{4-[8-(2,2-dimethyl-pentanoyl)-8-aza-bicyclo[3.2.1]oct-3-ylmethyl]-phenyl}-urea, Compound A1337;

1-(5-tert-Butyl-2-p-tolyl-2H-pyrazol-3-yl)-3-{4-[8-(4-methoxy-2-methyl-benzoyl)-8-aza-bicyclo[3.2.1]oct-3-ylmethyl]-phenyl}-urea, Compound A1338;

1-(5-tert-Butyl-2-p-tolyl-2H-pyrazol-3-yl)-3-(4-{8-[1-(4-methoxy-phenyl)-cyclopropanecarbonyl]-8-aza-bicyclo[3.2.1]oct-3-ylmethyl}-phenyl)-urea, Compound A1339;

1-(5-tert-Butyl-2-p-tolyl-2H-pyrazol-3-yl)-3-{4-[8-(4-hydroxymethyl-benzoyl)-8-aza-bicyclo[3.2.1]oct-3-ylmethyl]-phenyl}-urea, Compound A1340;

1-(5-tert-Butyl-2-p-tolyl-2H-pyrazol-3-yl)-3-(4-{8-[2-(3,5-dimethoxy-phenyl)-acetyl]-8-aza-bicyclo[3.2.1]oct-3-ylmethyl}-phenyl)-urea, Compound A1341;

1-(5-tert-Butyl-2-p-tolyl-2H-pyrazol-3-yl)-3-(4-{8-[2-(2,3-dimethyl-phenoxyl)-acetyl]-8-aza-bicyclo[3.2.1]oct-3-ylmethyl}-phenyl)-urea, Compound A1342;

1-(5-tert-Butyl-2-p-tolyl-2H-pyrazol-3-yl)-3-{4-[8-(3-p-tolyl-propionyl)-8-aza-bicyclo[3.2.1]oct-3-ylmethyl]-phenyl}-urea, Compound A1343;

1-(5-tert-Butyl-2-p-tolyl-2H-pyrazol-3-yl)-3-{4-[8-(2,4,6-trimethoxy-benzoyl)-8-aza-bicyclo[3.2.1]oct-3-ylmethyl]-phenyl}-urea, Compound A1344;

1-{4-[8-(2-Benzo[1,3]dioxol-5-yl-acetyl)-8-aza-bicyclo[3.2.1]oct-3-ylmethyl]-phenyl}-3-(5-tert-butyl-2-p-tolyl-2H-pyrazol-3-yl)-urea, Compound A1345;

1-(5-tert-Butyl-2-p-tolyl-2H-pyrazol-3-yl)-3-[4-(8-hept-2-ynoyl-8-aza-bicyclo[3.2.1]oct-3-ylmethyl)-phenyl]-urea, Compound A1346;

1-(5-tert-Butyl-2-p-tolyl-2H-pyrazol-3-yl)-3-(4-{8-[2-(4-methoxy-phenoxyl)-acetyl]-8-aza-bicyclo[3.2.1]oct-3-ylmethyl}-phenyl)-urea, Compound A1347;

1-(5-tert-Butyl-2-p-tolyl-2H-pyrazol-3-yl)-3-{4-[8-(2-methyl-2-phenyl-propionyl)-8-aza-bicyclo[3.2.1]oct-3-ylmethyl]-phenyl}-urea, Compound A1348;

1-(5-tert-Butyl-2-p-tolyl-2H-pyrazol-3-yl)-3-{4-[8-(3-methyl-furan-2-carbonyl)-8-aza-bicyclo[3.2.1]oct-3-ylmethyl]-phenyl}-urea, Compound A1349;

1-(5-tert-Butyl-2-p-tolyl-2H-pyrazol-3-yl)-3-{4-[8-(2-phenylamino-acetyl)-8-aza-bicyclo [3.2.1]oct-3-ylmethyl]-phenyl}-urea, Compound A1350;

N-[3-(3-{4-[3-(5-tert-Butyl-2-p-tolyl-2H-pyrazol-3-yl)-ureido]-benzyl}-8-aza-bicyclo[3.2.1]octane-8-carbonyl)-phenyl]-acetamide, Compound A1351;

1-(5-tert-Butyl-2-p-tolyl-2H-pyrazol-3-yl)-3-{4-[8-(2-methyl-pyridine-3-carbonyl)-8-aza-bicyclo[3.2.1]oct-3-ylmethyl]-phenyl}-urea, Compound A1352;

1-(5-tert-Butyl-2-p-tolyl-2H-pyrazol-3-yl)-3-{4-[8-(2-pyridin-4-yl-acetyl)-8-aza-bicyclo[3.2.1]oct-3-ylmethyl]-phenyl}-urea, Compound A1353;

1-(5-tert-Butyl-2-p-tolyl-2H-pyrazol-3-yl)-3-{4-[8-(2-pyridin-3-yl-acetyl)-8-aza-bicyclo[3.2.1]oct-3-ylmethyl]-phenyl}-urea, Compound A1354;

1-(5-tert-Butyl-2-p-tolyl-2H-pyrazol-3-yl)-3-{4-[8-(2-3H-imidazol-4-yl-acetyl)-8-aza-bicyclo[3.2.1]oct-3-ylmethyl]-phenyl}-urea, Compound A1355;

1-(5-tert-Butyl-2-p-tolyl-2H-pyrazol-3-yl)-3-{4-[8-(quinoxaline-2-carbonyl)-8-aza-bicyclo[3.2.1]oct-3-ylmethyl]-phenyl}-urea, Compound A1356;

1-{4-[8-(3H-Benzotriazole-5-carbonyl)-8-aza-bicyclo[3.2.1]oct-3-ylmethyl]-phenyl}-3-(5-tert-butyl-2-p-tolyl-2H-pyrazol-3-yl)-urea, Compound A1357;

1-(5-tert-Butyl-2-p-tolyl-2H-pyrazol-3-yl)-3-{4-[8-(5-oxo-tetrahydro-furan-2-carbonyl)-8-aza-bicyclo[3.2.1]oct-3-ylmethyl]-phenyl}-urea, Compound A1358;

1-(5-tert-Butyl-2-p-tolyl-2H-pyrazol-3-yl)-3-{4-[8-(1H-pyrazole-4-carbonyl)-8-aza-bicyclo[3.2.1]oct-3-ylmethyl]-phenyl}-urea, Compound A1359;

1-(5-tert-Butyl-2-p-tolyl-2H-pyrazol-3-yl)-3-{4-[8-(2,3-dihydro-1H-indole-2-carbonyl)-8-aza-bicyclo[3.2.1]oct-3-ylmethyl]-phenyl}-urea, Compound A1360;

1-(5-tert-Butyl-2-p-tolyl-2H-pyrazol-3-yl)-3-(4-{8-[2-(3,5-difluoro-phenyl)acetyl]-8-aza-bicyclo[3.2.1]oct-3-ylmethyl}-phenyl)-urea, Compound A1361;

1-{4-[8-(4-Aminomethyl-benzoyl)-8-aza-bicyclo[3.2.1]oct-3-ylmethyl]-phenyl}-3-(5-tert-butyl-2-p-tolyl-2H-pyrazol-3-yl)-urea, Compound A1362;

1-(5-tert-Butyl-2-p-tolyl-2H-pyrazol-3-yl)-3-(4-{8-[2-(3,4-difluoro-phenyl)-acetyl]-8-aza-bicyclo[3.2.1]oct-3-ylmethyl}-phenyl)-urea, Compound A1363;

1-(5-tert-Butyl-2-p-tolyl-2H-pyrazol-3-yl)-3-(4-{8-[2-(2,4-difluoro-phenyl)-acetyl]-8-aza-bicyclo[3.2.1]oct-3-ylmethyl}-phenyl)-urea (0.0111 g), C37H41F2N5O2, 626.26, M+H, 3.40, Compound A1364;

1-(4-{8-[2-(4-Amino-phenyl)-acetyl]-8-aza-bicyclo[3.2.1]oct-3-ylmethyl}-phenyl)-3-(5-tert-butyl-2-p-tolyl-2H-pyrazol-3-yl)-urea, Compound A1365;

4-Amino-N-[2-(3-{4-[3-(5-tert-butyl-2-p-tolyl-2H-pyrazol-3-yl)-ureido]-benzyl}-8-aza-bicyclo[3.2.1]oct-8-yl)-2-oxo-ethyl]-benzamide, Compound A1366;

1-{4-[8-(3-Amino-4-hydroxy-benzoyl)-8-aza-bicyclo[3.2.1]oct-3-ylmethyl]-phenyl}-3-(5-tert-butyl-2-p-tolyl-2H-pyrazol-3-yl)-urea, Compound A1367;

1-(5-tert-Butyl-2-p-tolyl-2H-pyrazol-3-yl)-3-{4-[8-(isoquinoline-1-carbonyl)-8-aza-bicyclo[3.2.1]oct-3-ylmethyl]-phenyl}-urea, Compound A1368;

1-(5-tert-Butyl-2-p-tolyl-2H-pyrazol-3-yl)-3-{4-[8-(quinoline-4-carbonyl)-8-aza-bicyclo[3.2.1]oct-3-ylmethyl]-phenyl}-urea, Compound A1369;

1-(5-tert-Butyl-2-p-tolyl-2H-pyrazol-3-yl)-3-{4-[8-(quinoline-3-carbonyl)-8-aza-bicyclo[3.2.1]oct-3-ylmethyl]-phenyl}-urea, Compound A1370;

1-(5-tert-Butyl-2-p-tolyl-2H-pyrazol-3-yl)-3-{4-[8-(quinoline-2-carbonyl)-8-aza-bicyclo[3.2.1]oct-3-ylmethyl]-phenyl}-urea, Compound A1371;

1-(5-tert-Butyl-2-p-tolyl-2H-pyrazol-3-yl)-3-{4-[8-(3-piperidin-1-yl-propionyl)-8-aza-bicyclo[3.2.1]oct-3-ylmethyl]-phenyl}-urea, Compound A1372;

1-(5-tert-Butyl-2-p-tolyl-2H-pyrazol-3-yl)-3-{4-[8-(pyridine-4-carbonyl)-8-aza-bicyclo[3.2.1]oct-3-ylmethyl]-phenyl}-urea, Compound A1373;

1-(5-tert-Butyl-2-p-tolyl-2H-pyrazol-3-yl)-3-{4-[8-(pyridine-3-carbonyl)-8-aza-bicyclo[3.2.1]oct-3-ylmethyl]-phenyl}-urea, Compound A1374;

1-{4-[8-(6-Amino-pyridine-3-carbonyl)-8-aza-bicyclo[3.2.1]oct-3-ylmethyl]-phenyl}-3-(5-tert-butyl-2-p-tolyl-2H-pyrazol-3-yl)-urea, Compound A1375;

1-{4-[8-(2-Amino-pyridine-3-carbonyl)-8-aza-bicyclo[3.2.1]oct-3-ylmethyl]-phenyl}-3-(5-tert-butyl-2-p-tolyl-2H-pyrazol-3-yl)-urea, Compound A1376;

1-(5-tert-Butyl-2-p-tolyl-2H-pyrazol-3-yl)-3-{4-[8-(pyridine-2-carbonyl)-8-aza-bicyclo[3.2.1]oct-3-ylmethyl]-phenyl}-urea, Compound A1377;

1-(5-tert-Butyl-2-p-tolyl-2H-pyrazol-3-yl)-3-{4-[8-(6-chloro-pyridine-3-carbonyl}8-aza-bicyclo[3.2.1]oct-3-ylmethyl]-phenyl}-urea, Compound A1378;

1-(5-tert-Butyl-2-p-tolyl-2H-pyrazol-3-yl)-3-{4-[8-(2-chloro-pyridine-3-carbonyl)-8-aza-bicyclo[3.2.1]oct-3-ylmethyl]-phenyl}-urea, Compound A1379;

1-{4-[8-(3-Amino-pyrazine-2-carbonyl)-8-aza-bicyclo[3.2.1]oct-3-ylmethyl]-phenyl}-3-(5-tert-butyl-2-p-tolyl-2H-pyrazol-3-yl)-urea, Compound A1380;

1-(5-tert-Butyl-2-p-tolyl-2H-pyrazol-3-yl)-3-{4-[8-(pyrazine-2-carbonyl)-8-aza-bicyclo[3.2.1]oct-3-ylmethyl]-phenyl}-urea, Compound A1381;

1-(5-tert-Butyl-2-p-tolyl-2H-pyrazol-3-yl)-3-{4-[8-(1H-indole-5-carbonyl)-8-aza-bicyclo[3.2.1]oct-3-ylmethyl]-phenyl}-urea, Compound A1382;

1-(5-tert-Butyl-2-p-tolyl-2H-pyrazol-3-yl)-3-{4-[8-(3-1H-indol-3-yl-propionyl)-8-aza-bicyclo[3.2.1]oct-3-ylmethyl]-phenyl}-urea, Compound A1383;

1-(5-tert-Butyl-2-p-tolyl-2H-pyrazol-3-yl)-3-{4-[8-(2-1H-indol-3-yl-acetyl)-8-aza-bicyclo[3.2.1]oct-3-ylmethyl]-phenyl}-urea, Compound A1384;

1-(5-tert-Butyl-2-p-tolyl-2H-pyrazol-3-yl)-3-(4-{8-[2-(1H-indol-3-yl)-2-oxo-acetyl]-8-aza-bicyclo[3.2.1]oct-3-ylmethyl}-phenyl)-urea, Compound A1385;

1-(5-tert-Butyl-2-p-tolyl-2H-pyrazol-3-yl)-3-{4-[8-(1H-indole-3-carbonyl)-8-aza-bicyclo[3.2.1]oct-3-ylmethyl]-phenyl}-urea, Compound A1386;

1-(5-tert-Butyl-2-p-tolyl-2H-pyrazol-3-yl)-3-{4-[8-(2-thiophen-3-yl-acetyl)-8-aza-bicyclo[3.2.1]oct-3-ylmethyl]-phenyl}-urea, Compound A1387;

1-(5-tert-Butyl-2-p-tolyl-2H-pyrazol-3-yl)-3-{4-[8-(thiophene-3-carbonyl)-8-aza-bicyclo[3.2.1]oct-3-ylmethyl]-phenyl}-urea, Compound A1388;

1-(5-tert-Butyl-2-p-tolyl-2H-pyrazol-3-yl)-3-{4-[8-(2-thiophen-2-yl-acetyl)-8-aza-bicyclo[3.2.1]oct-3-ylmethyl]-phenyl}-urea, Compound A1389;

1-(5-tert-Butyl-2-p-tolyl-2H-pyrazol-3-yl)-3-{4-[8-(5-methyl-thiophene-2-carbonyl)-8-aza-bicyclo[3.2.1]oct-3-ylmethyl]-phenyl}-urea, Compound A1390;

1-(5-tert-Butyl-2-p-tolyl-2H-pyrazol-3-yl)-3-{4-[8-(furan-3-carbonyl)-8-aza-bicyclo[3.2.1]oct-3-ylmethyl]-phenyl}-urea, Compound A1391;

1-(5-tert-Butyl-2-p-tolyl-2H-pyrazol-3-yl)-3-{4-[8-(3-furan-2-yl-propionyl)-8-aza-bicyclo[3.2.1]oct-3-ylmethyl]-phenyl}-urea, Compound A1392;

1-(5-tert-Butyl-2-p-tolyl-2H-pyrazol-3-yl)-3-(4-{8-[2-(2,5-dioxo-imidazolidin-4-yl)-acetyl]-8-aza-bicyclo[3.2.1]oct-3-ylmethyl}-phenyl)-urea, Compound A1393;

1-(5-tert-Butyl-2-p-tolyl-2H-pyrazol-3-yl)-3-[4-(8-heptanoyl-8-aza-bicyclo[3.2.1]oct-3-ylmethyl)-phenyl]-urea, Compound A1394;

1-(5-tert-Butyl-2-p-tolyl-2H-pyrazol-3-yl)-3-{4-[8-(5-oxo-5-phenyl-pentanoyl)-8-aza-bicyclo[3.2.1]oct-3-ylmethyl]-phenyl}-urea, Compound A1395;

1-(5-tert-Butyl-2-p-tolyl-2H-pyrazol-3-yl)-3-(4-{8-[4-(4-methoxy-phenyl)-butyryl]-8-aza-bicyclo[3.2.1]oct-3-ylmethyl}-phenyl)-urea, Compound A1396;

1-(5-tert-Butyl-2-p-tolyl-2H-pyrazol-3-yl)-3-{4-[8-(4-phenyl-butyryl)-8-aza-bicyclo[3.2.1]oct-3-ylmethyl]-phenyl}-urea, Compound A1397;

1-(5-tert-Butyl-2-p-tolyl-2H-pyrazol-3-yl)-3-(4-{8-[2-(4-methoxy-phenyl)-acetyl]-8-aza-bicyclo[3.2.1]oct-3-ylmethyl}-phenyl)-urea, Compound A1398;

1-(5-tert-Butyl-2-p-tolyl-2H-pyrazol-3-yl)-3-(4-{8-[2-(4-fluoro-phenyl)-acetyl]-8-aza-bicyclo[3.2.1]oct-3-ylmethyl}-phenyl)-urea, Compound A1399;

1-(5-tert-Butyl-2-p-tolyl-2H-pyrazol-3-yl)-3-(4-{8-[2-(3,4-dimethoxy-phenyl)-acetyl]-8-aza-bicyclo[3.2.1]oct-3-ylmethyl}-phenyl)-urea, Compound A1400;

1-(5-tert-Butyl-2-p-tolyl-2H-pyrazol-3-yl)-3-(4-{8-[2-(3-methoxy-phenyl)-acetyl]-8-aza-bicyclo[3.2.1]oct-3-ylmethyl}-phenyl)-urea, Compound A1401;

1-(5-tert-Butyl-2-p-tolyl-2H-pyrazol-3-yl)-3-(4-{8-[2-(3-fluoro-phenyl)-acetyl]-8-aza-bicyclo[3.2.1]oct-3-ylmethyl}-phenyl)-urea, Compound A1402;

1-(5-tert-Butyl-2-p-tolyl-2H-pyrazol-3-yl)-3-{4-[8-(2-o-tolyl-acetyl)-8-aza-bicyclo[3.2.1]oct-3-ylmethyl]-phenyl}-urea, Compound A1403;

1-(5-tert-Butyl-2-p-tolyl-2H-pyrazol-3-yl)-3-(4-{8-[2-(2-methoxy-phenyl)-acetyl]-8-aza-bicyclo[3.2.1]oct-3-ylmethyl}-phenyl)-urea (0.0309 g), C38H45N5O3, 620.32, M+H, 3,45, Compound A1404;

1-(5-tert-Butyl-2-p-tolyl-2H-pyrazol-3-yl)-3-(4-{8-[2-(2-fluoro-phenyl)-acetyl]-8-aza-bicyclo[3.2.1]oct-3-ylmethyl}-phenyl)-urea, Compound A1405;

1-(5-tert-Butyl-2-p-tolyl-2H-pyrazol-3-yl)-3-{4-[8-(2-methoxy-acetyl)-8-aza-bicyclo[3.2.1]oct-3-ylmethyl]-phenyl}-urea, Compound A1406;

1-(5-tert-Butyl-2-p-tolyl-2H-pyrazol-3-yl)-3-{4-[8-(2-phenoxy-acetyl)-8-aza-bicyclo[3.2.1]oct-3-ylmethyl]-phenyl}-urea, Compound A1407;

1-(5-tert-Butyl-2-p-tolyl-2H-pyrazol-3-yl)-3-{4-[8-(2-dimethylamino-acetyl)-8-aza-bicyclo[3.2.1]oct-3-ylmethyl]-phenyl}-urea, Compound A1408;

1-(5-tert-Butyl-2-p-tolyl-2H-pyrazol-3-yl)-3-(4-{8-[2-(N-methyl-guanidino)-acetyl]-8-aza-bicyclo[3.2.1]oct-3-ylmethyl}-phenyl)-urea, Compound A1409;

N-[2-(3-{4-[3-(5-tert-Butyl-2-p-tolyl-2H-pyrazol-3-yl)-ureido]-benzyl}-8-aza-bicyclo[3.2.1]oct-8-yl)-2-oxo-ethyl]-acetamide, Compound A1410;

1-(5-tert-Butyl-2-p-tolyl-2H-pyrazol-3-yl)-3-{4-[8-(2,2-dimethyl-propionyl)-8-aza-bicyclo[3.2.1]oct-3-ylmethyl]-phenyl}-urea, Compound A1411;

1-(5-tert-Butyl-2-p-tolyl-2H-pyrazol-3-yl)-3-[4-(8-cycloheptanecarbonyl-8-aza-bicyclo[3.2.1]oct-3-ylmethyl)-phenyl]-urea, Compound A1412;

1-(5-tert-Butyl-2-p-tolyl-2H-pyrazol-3-yl)-3-{4-[8-(2-naphthalen-2-yl-acetyl)-8-aza-bicyclo[3.2.1]oct-3-ylmethyl]-phenyl}-urea, Compound A1413;

1-(5-tert-Butyl-2-p-tolyl-2H-pyrazol-3-yl)-3-{4-[8-(2-naphthalen-1-yl-acetyl)-8-aza-bicyclo[3.2.1]oct-3-ylmethyl]-phenyl}-urea, Compound A1414;

1-(5-tert-Butyl-2-p-tolyl-2H-pyrazol-3-yl)-3-{4-[8-(furan-2-carbonyl)-8-aza-bicyclo[3.2.1]oct-3-ylmethyl]-phenyl}-urea, Compound A1415;

1-(5-tert-Butyl-2-p-tolyl-2H-pyrazol-3-yl)-3-{4-[8-(5-methyl-3-phenyl-isoxazole-4-carbonyl)-8-aza-bicyclo[3.2.1]oct-3-ylmethyl]-phenyl}-urea, Compound A1416;

1-(5-tert-Butyl-2-p-tolyl-2H-pyrazol-3-yl)-3-[4-(8-butyryl-8-aza-bicyclo[3.2.1]oct-3-ylmethyl)-phenyl]-urea, Compound A1417;

1-(5-tert-Butyl-2-p-tolyl-2H-pyrazol-3-yl)-3-(4-{8-[4-(4-fluoro-phenyl)-4-oxo-butyryl]-8-aza-bicyclo[3.2.1]oct-3-ylmethyl}-phenyl)-urea, Compound A1418;

4-(3-{4-[3-(5-tert-Butyl-2-p-tolyl-2H-pyrazol-3-yl)-ureido]-benzyl}-8-aza-bicyclo[3.2.1]oct-8-yl)-4-oxo-butyric acid methyl ester, Compound A1419;

1-(5-tert-Butyl-2-p-tolyl-2H-pyrazol-3-yl)-3-(4-{8-[3-(2-methoxy-phenyl)-propionyl]-8-aza-bicyclo[3.2.1]oct-3-ylmethyl}-phenyl)-urea, Compound A1420;

1-(5-tert-Butyl-2-p-tolyl-2H-pyrazol-3-yl)-3-{4-[8-(3-phenyl-propionyl)-8-aza-bicyclo[3.2.1]oct-3-ylmethyl]-phenyl}-urea, Compound A1421;

1-(5-tert-Butyl-2-p-tolyl-2H-pyrazol-3-yl)-3-{4-[8-(3-phenoxy-propionyl)-8-aza-bicyclo[3.2.1]oct-3-ylmethyl]-phenyl}-urea, Compound A1422;

N-[2-(3-{4-[3-(5-tert-Butyl-2-p-tolyl-2H-pyrazol-3-yl)-ureido]-benzyl}-8-aza-bicyclo[3.2.1]oct-8-yl)-2-oxo-ethyl]-benzamide, Compound A1423;

1-(5-tert-Butyl-2-p-tolyl-2H-pyrazol-3-yl)-3-{4-[8-(2-phenyl-propionyl)-8-aza-bicyclo[3.2.1]oct-3-ylmethyl]-phenyl}-urea, Compound A1424;

1-(5-tert-Butyl-2-p-tolyl-2H-pyrazol-3-yl)-3-{4-[8-(2-oxo-3-phenyl-propionyl)-8-aza-bicyclo[3.2.1]oct-3-ylmethyl]-phenyl}-urea, Compound A1425;

1-(5-tert-Butyl-2-p-tolyl-2H-pyrazol-3-yl)-3-{4-[8-(2-oxo-propionyl)-8-aza-bicyclo[3.2.1]oct-3-ylmethyl]-phenyl}-urea, Compound A1426;

1-(5-tert-Butyl-2-p-tolyl-2H-pyrazol-3-yl)-3-(4-{8-[3-(cyano-methyl-methyl)-benzoyl]-8-aza-bicyclo[3.2.1]oct-3-ylmethyl}-phenyl)-urea, Compound A1427;

1-(5-tert-Butyl-2-p-tolyl-2H-pyrazol-3-yl)-3-{4-[8-(3,5-dimethoxy-benzoyl)-8-aza-bicyclo[3.2.1]oct-3-ylmethyl]-phenyl}-urea, Compound A1428;

1-(5-tert-Butyl-2-p-tolyl-2H-pyrazol-3-yl)-3-{4-[8-(2,4-dimethoxy-benzoyl)-8-aza-bicyclo[3.2.1]oct-3-ylmethyl]-phenyl}-urea, Compound A1429;

1-(5-tert-Butyl-2-p-tolyl-2H-pyrazol-3-yl)-3-{4-[8-(2,3-dimethoxy-benzoyl)-8-aza-bicyclo[3.2.1]oct-3-ylmethyl]-phenyl}-urea, Compound A1430;

1-(5-tert-Butyl-2-p-tolyl-2H-pyrazol-3-yl)-3-{4-[8-(1,2,3,4-tetrahydro-naphthalene-2-carbonyl)-8-aza-bicyclo[3.2.1]oct-3-ylmethyl]-phenyl}-urea, Compound A1431;

1-(5-tert-Butyl-2-p-tolyl-2H-pyrazol-3-yl)-3-{4-[8-(2-cyclohexyl-acetyl)-8-aza-bicyclo[3.2.1]oct-3-ylmethyl]-phenyl}-urea, Compound A1432;

1-(5-tert-Butyl-2-p-tolyl-2H-pyrazol-3-yl)-3-{4-[8-(1-methyl-cyclohexanecarbonyl)-8-aza-bicyclo[3.2.1]oct-3-ylmnethyl]-phenyl}-urea, Compound A1433;

1-(5-tert-Butyl-2-p-tolyl-2H-pyrazol-3-yl)-3-[4-(8-cyclohexanecarbonyl-8-aza-bicyclo [3.2.1]oct-3-ylmethyl)-phenyl]-urea, Compound A1434;

1-(5-tert-Butyl-2-p-tolyl-2H-pyrazol-3-yl)-3-{4-[8-(2-cyclopentyl-acetyl)-8-aza-bicyclo[3.2.1]oct-3-ylmethyl]-phenyl}-urea, Compound A1435;

1-(5-tert-Butyl-2-p-tolyl-2H-pyrazol-3-yl)-3-{4-[8-(1-phenyl-cyclopentanecarbonyl)-8-aza-bicyclo[3.2.1]oct-3-ylmethyl]-phenyl}-urea, Compound A1436;

1-(5-tert-Butyl-2-p-tolyl-2H-pyrazol-3-yl)-3-[4-(8-cyclopentanecarbonyl-8-aza-bicyclo[3.2.1]oct-3-ylmethyl)-phenyl]-urea, Compound A1437;

1-(5-tert-Butyl-2-p-tolyl-2H-pyrazol-3-yl)-3-[4-(8-cyclobutanecarbonyl-8-aza-bicyclo[3.2.1]oct-3-ylmethyl)-phenyl]-urea, Compound A1438;

1-(5-tert-Butyl-2-p-tolyl-2H-pyrazol-3-yl)-3-{4-[8-(1-methyl-cyclopropanecarbonyl)-8-aza-bicyclo[3.2.1]oct-3-ylmethyl]-phenyl}-urea, Compound A1439;

1-{4-[8-(3,5-Bis-trifluoromethyl-benzoyl)-8-aza-bicyclo[3.2.1]oct-3-ylmethyl]-phenyl}-3-(5-tert-butyl-2-p-tolyl-2H-pyrazol-3-yl)-urea, Compound A1440;

1-{4-[8-(4-Amino-5-chloro-2-methoxy-benzoyl)-8-aza-bicyclo[3.2.1]oct-3-ylmethyl]-phenyl}-3-(5-tert-butyl-2-p-tolyl-2H-pyrazol-3-yl)-urea (60 mg), C37H43ClN6O3, 656.32, M+H, 3.50, Compound A1441;

1-(5-tert-Butyl-2-p-tolyl-2H-pyrazol-3-yl)-3-{4-[8-([1,6]naphthyridine-2-carbonyl)-8-aza-bicyclo[3.2.1]oct-3-ylmethyl]-phenyl}-urea, Compound A1442;

1-(5-tert-Butyl-2-p-tolyl-2H-pyrazol-3-yl)-3-{4-[8-(2-methyl-5-trifluoromethyl-oxazole-4-carbonyl)-8-aza-bicyclo[3.2.1]oct-3-ylmethyl]-phenyl}-urea, Compound A1443;

1-(5-tert-Butyl-2-p-tolyl-2H-pyrazol-3-yl)-3-(4-{8-[4-(4-chloro-phenyl)-thiophene-2-carbonyl]-8-aza-bicyclo[3.2.1]oct-3-ylmethyl}-phenyl)-urea, Compound A1444;

1-(5-tert-Butyl-2-p-tolyl-2H-pyrazol-3-yl)-3-{4-[8-(2-trifluoromethyl-[1,8]naphthyridine-3-carbonyl)-8-aza-bicyclo[3.2.1]oct-3-ylmethyl]-phenyl}-urea, Compound A1445;

1-(5-tert-Butyl-2-p-tolyl-2H-pyrazol-3-yl)-3-(4-{8-[4-(4-methoxy-phenyl)-thiophene-2-carbonyl]-8-aza-bicyclo[3.2.1]oct-3-ylmethyl}-phenyl)-urea, Compound A1446;

1-(5-tert-Butyl-2-p-tolyl-2H-pyrazol-3-yl)-3-(4-{8-[2-(4,6-dimethyl-pyrimidin-2-ylamino)-benzoyl]-8-aza-bicyclo[3.2.1]oct-3-ylmethyl}-phenyl)-urea, Compound A1447;

1-(5-tert-Butyl-2-p-tolyl-2H-pyrazol-3-yl)-3-(4-{8-[3-(4,6-dimethyl-pyrimidin-2-ylamino)-benzoyl]-8-aza-bicyclo[3.2.1]oct-3-ylmethyl}-phenyl)-urea, Compound A1448;

1-(5-tert-Butyl-2-p-tolyl-2H-pyrazol-3-yl)-3-(4-{8-[4-(4,6-dimethyl-pyrimidin-2-ylamino)-benzoyl]-8-aza-bicyclo[3.2.1]oct-3-ylmethyl}-phenyl)-urea, Compound A1449;

1-(5-tert-Butyl-2-p-tolyl-2H-pyrazol-3-yl)-3-(4-{8-[3-(2,2-difluoro-benzo[1,3]dioxol-5-yl)-acryloyl]-8-aza-bicyclo[3.2.1]oct-3-ylmethyl}-phenyl)-urea, Compound A1450;

1-(5-tert-Butyl-2-p-tolyl-2H-pyrazol-3-yl)-3-{4-[8-(2-phenyl-5-trifluoromethyl-oxazole-4-carbonyl)-8-aza-bicyclo[3.2.1]oct-3-ylmethyl]-phenyl}-urea, Compound A1451;

1-(5-tert-Butyl-2-p-tolyl-2H-pyrazol-3-yl)-3-{4-[8-(6-trifluoromethyl-pyridine-3-carbonyl)-8-aza-bicyclo[3.2.1]oct-3-ylmethyl]-phenyl}-urea, Compound A1452;

1-(5-tert-Butyl-2-p-tolyl-2H-pyrazol-3-yl)-3-(4-{8-[2-(4,6-dimethoxy-pyrimidin-2-ylsulfanyl)-benzoyl]-8-aza-bicyclo[3.2.1]oct-3-ylmethyl}-phenyl)-urea, Compound A1453;

1-(5-tert-Butyl-2-p-tolyl-2H-pyrazol-3-yl)-3-(4-{8-[3-(4,6-dimethoxy-pyrimidin-2-yloxy)-benzoyl]-8-aza-bicyclo[3.2.1]oct-3-ylmethyl}-phenyl)-urea, Compound A1454;

1-(5-tert-Butyl-2-p-tolyl-2H-pyrazol-3-yl)-3-{4-[8-(2-trifluoromethyl-[1,6]naphthyridine-3-carbonyl)-8-aza-bicyclo[3.2.1]oct-3-ylmethyl]-phenyl}-urea, Compound A1455;

1-(5-tert-Butyl-2-p-tolyl-2H-pyrazol-3-yl)-3-{4-[8-(2-chloro-4-methanesulfonyl-benzoyl)-8-aza-bicyclo[3.2.1]oct-3-ylmethyl]-phenyl}-urea, Compound A1456;

1-(5-tert-Butyl-2-p-tolyl-2H-pyrazol-3-yl)-3-{4-[8-(1H-indole-6-carbonyl)-8-aza-bicyclo[3.2.1]oct-3-ylmethyl]-phenyl}-urea, Compound A1457;

1-(5-tert-Butyl-2-p-tolyl-2H-pyrazol-3-yl)-3-[4-(8-{3-[(4,6-dimethyl-pyrimidin-2-yl)-methyl-amino]-benzoyl}-8-aza-bicyclo[3.2.1]oct-3-ylmethyl)-phenyl]-urea, Compound A1458;

1-(5-tert-Butyl-2-p-tolyl-2H-pyrazol-3-yl)-3-{4-[8-(2-methyl-[1,6]naphthyridine-3-carbonyl)-8-aza-bicyclo[3.2.1]oct-3-ylmethyl]-phenyl}-urea, Compound A1459;

1-(5-tert-Butyl-2-p-tolyl-2H-pyrazol-3-yl)-3-{4-[8-([1,8]naphthyridine-2-carbonyl)-8-aza-bicyclo[3.2.1]oct-3-ylmethyl]-phenyl}-urea, Compound A1460;

1-(5-tert-Butyl-2-p-tolyl-2H-pyrazol-3-yl)-3-{4-[8-(4,5-dihydro-benzo[b]thiophene-6-carbonyl)-8-aza-bicyclo[3.2.1]oct-3-ylmethyl]-phenyl}-urea, Compound A1461;

1-(5-tert-Butyl-2-p-tolyl-2H-pyrazol-3-yl)-3-{4-[8-(3a,4,5,7a-tetrahydro-benzofuran-6-carbonyl)-8-aza-bicyclo[3.2.1]oct-3-ylmethyl]-phenyl}-urea, Compound A1462;

1-(4-{8-[1-(5-Bromo-pyrimidin-2-yl)-piperidine-4-carbonyl]-8-aza-bicyclo[3.2.1]oct-3-ylmethyl}-phenyl)-3-(5-tert-butyl-2-p-tolyl-2H-pyrazol-3-yl)-urea, Compound A1463;

1-(5-tert-Butyl-2-p-tolyl-2H-pyrazol-3-yl)-3-(4-{8-[2-(4,6-dimethoxy-pyrimidin-2-yloxy)-benzoyl]-8-aza-bicyclo[3.2.1]oct-3-ylmethyl}-phenyl)-urea, Compound A1464;

1-(4-{8-[1-(5-Bromo-pyrimidin-2-yl)-piperidine-3-carbonyl]-8-aza-bicyclo[3.2.1]oct-3-ylmethyl}-phenyl)-3-(5-tert-butyl-2-p-tolyl-2H-pyrazol-3-yl)-urea, Compound A1465;

1-(5-tert-Butyl-2-p-tolyl-2H-pyrazol-3-yl)-3-[4-(8-{4-[(4,6-dimethyl-pyrimidin-2-yl)-methyl-amino]-benzoyl}-8-aza-bicyclo[3.2.1]oct-3-ylmethyl)-phenyl]-urea, Compound A1466;

1-(5-tert-Butyl-2-p-tolyl-2H-pyrazol-3-yl)-3-{4-[8-(1H-pyrrole-3-carbonyl)-8-aza-bicyclo[3.2.1]oct-3-ylmethyl]-phenyl}-urea, Compound A1467;

1-(5-tert-Butyl-2-p-tolyl-2H-pyrazol-3-yl)-3-{4-[8-(4-trifluoromethyl-pyridine-3-carbonyl)-8-aza-bicyclo[3.2.1]oct-3-ylmethyl]-phenyl}-urea, Compound A1468;

1-(5-tert-Butyl-2-p-tolyl-2H-pyrazol-3-yl)-3-{4-[8-(2-methyl-[1,8]naphthyridine-3-carbonyl)-8-aza-bicyclo[3.2.1]oct-3-ylmethyl]-phenyl}-urea, Compound A1469;

1-(5-tert-Butyl-2-p-tolyl-2H-pyrazol-3-yl)-3-{4-[8-(2,4,6-trimethyl-benzoyl)-8-aza-bicyclo[3.2.1]oct-3-ylmethyl]-phenyl}-urea, Compound A1470;

1-(5-tert-Butyl-2-p-tolyl-2H-pyrazol-3-yl)-3-{4-[8-(2,2-difluoro-benzo[1,3]dioxole-5-carbonyl)-8-aza-bicyclo[3.2.1]oct-3-ylmethyl]-phenyl}-urea, Compound A1471;

4-(3-{4-[3-(5-tert-Butyl-2-p-tolyl-2H-pyrazol-3-yl)-ureido]-benzyl}-8-aza-bicyclo[3.2.1]octane-8-carbonyl)-2,5-dimethyl-furan-3-sulfonic acid (thiophen-2-ylmethyl)-amide, Compound A1472;

1-{4-[8-(2-Benzo[1,3]dioxol-5-yl-2-oxo-ethyl)-8-aza-bicyclo[3.2.1]oct-3-ylmethyl]-phenyl}-3-(5-tert-butyl-2-p-tolyl-2H-pyrazol-3-yl)-urea, Compound A1473;

1-{4-[8-(2-Benzo[b]thiophen-3-yl-2-oxo-ethyl)-8-aza-bicyclo[3.2.1]oct-3-ylmethyl]-phenyl}-3-(5-tert-butyl-2-p-tolyl-2H-pyrazol-3-yl)-urea, Compound A1474;

1-(5-tert-Butyl-2-p-tolyl-2H-pyrazol-3-yl)-3-(4-{8-[2-oxo-2-(3-phenyl-isoxazol-5-yl)-ethyl]-8-aza-bicyclo[3.2.1]oct-3-ylmethyl}-phenyl)-urea, Compound A1475;

1-(5-tert-Butyl-2-p-tolyl-2H-pyrazol-3-yl)-3-(4-{8-[2-(4-methanesulfonyl-phenyl)-2-oxo-ethyl]-8-aza-bicyclo[3.2.1]oct-3-ylmethyl]-phenyl)-urea, Compound A1476;

1-(5-tert-Butyl-2-p-tolyl-2H-pyrazol-3-yl)-3-{4-[8-(2-oxo-2-pyridin-4-yl-ethyl)-8-aza-bicyclo[3.2.1]oct-3-ylmethyl]-pbenyl}-urea, Compound A1477;

1-(5-tert-Butyl-2-p-tolyl-2H-pyrazol-3-yl)-3-(4-{8-[2-(5-methyl-1-phenyl-1H-pyrazol-4-yl)-2-oxo-ethyl]-8-aza-bicyclo[3.2.1]oct-3-ylmethyl}-phenyl)-urea, Compound A1478;

1-(5-tert-Butyl-2-p-tolyl-2H-pyrazol-3-yl)-3-(4-{8-[2-(5-methyl-3-phenyl-isoxazol-4-yl)-2-oxo-ethyl]-8-aza-bicyclo[3.2.1]oct-3-ylmethyl}-phenyl)-urea, Compound A1479;

1-(5-tert-Butyl-2-p-tolyl-2H-pyrazol-3-yl)-3-(4-{8-[2-oxo-2-(5-pyridin-2-yl-thiophen-2-yl)-ethyl]-8-aza-bicyclo[3.2.1]oct-3-ylmethyl]-phenyl)-urea, Compound A1480;

1-(5-tert-Butyl-2-p-tolyl-2H-pyrazol-3-yl)-3-(4-{8-[2-(2,4-dimethoxy-phenyl)-2-oxo-ethyl]-8-aza-bicyclo[3.2.1]oct-3-ylmethyl}-phenyl)-urea, Compound A1481;

1-(5-tert-Butyl-2-p-tolyl-2H-pyrazol-3-yl)-3-(4-{8-[2-(2,5-dimethoxy-phenyl)-2-oxo-ethyl]-8-aza-bicyclo[3.2.1]oct-3-ylmethyl}-phenyl)-urea, Compound A1482;

1-(5-tert-Butyl-2-p-tolyl-2H-pyrazol-3-yl)-3-(4-{8-[2-(3-methoxy-phenyl)-2-oxo-ethyl]-8-aza-bicyclo[3.2.1]oct-3-ylmethyl}-phenyl)-urea, Compound A1483;

1-(5-tert-Butyl-2-p-tolyl-2H-pyrazol-3-yl)-3-{4-[8-(2-oxo-2-pyridin-3-yl-ethyl)-8-aza-bicyclo[3.2.1]oct-3-ylmethyl]-phenyl}-urea, Compound A1484;

1-(5-tert-Butyl-2-p-tolyl-2H-pyrazol-3-yl)-3-(4-{8-[2-(4-difluoromethoxy-phenyl)-2-oxo-ethyl]-8-aza-bicyclo[3.2.1]oct-3-ylmethyl}-phenyl)-urea, Compound A1485;

1-(5-tert-Butyl-2-p-tolyl-2H-pyrazol-3-yl)-3-(4-{8-[2-oxo-2-(4-trifluoromethoxy-phenyl)-ethyl]-8-aza-bicyclo[3.2.1]oct-3-ylmethyl}-phenyl)-urea, Compound A1486;

1-(5-tert-Butyl-2-p-tolyl-2H-pyrazol-3-yl)-3-(4-{8-[2-(4-methoxy-phenyl)-2-oxo-ethyl]-8-aza-bicyclo[3.2.1]oct-3-ylmethyl}-phenyl)-urea, Compound A1487;

1-(5-tert-Butyl-2-p-tolyl-2H-pyrazol-3-yl)-3-{4-[8-(4-oxo-4,5,6,7-tetrahydro-benzo[1,2,5]oxadiazol-5-yl)-8-aza-bicyclo[3.2.1]oct-3-ylmethyl]-phenyl}-urea, Compound A1488;

1-(5-tert-Butyl-2-p-tolyl-2H-pyrazol-3-yl)-3-(4-{8-[2-oxo-2-(2-oxo-1,2,3,4-tetrahydro-quinolin-6-yl)-ethyl]-8-aza-bicyclo[3.2.1]oct-3-ylmethyl}-phenyl)-urea, Compound A1489;

1-(5-tert-Butyl-2-p-tolyl-2H-pyrazol-3-yl)-3-(4-{8-[2-(4-diethylamino-phenyl)-2-oxo-ethyl]-8-aza-bicyclo[3.2.1]oct-3-ylmethyl}-phenyl)-urea, Compound A1490;

5-[2-(3-{4-[3-(5-tert-Butyl-2-p-tolyl-2H-pyrazol-3-yl)-ureido]-benzyl}-8-aza-bicyclo[3.2.1]oct-8-yl)-acetyl]-isoxazole-3-carboxylic acid ethyl ester, Compound A1491;

1-(5-tert-Butyl-2-p-tolyl-2H-pyrazol-3-yl)-3-{4-[8-(1,3,5-trimethyl-1H-pyrazole-4-sulfonyl)-8-aza-bicyclo[3.2.1]oct-3-ylmethyl]-phenyl}-urea, Compound A1492;

1-{4-[8-(Butane-1-sulfonyl)-8-aza-bicyclo[3.2.1]oct-3-ylmethyl]-phenyl}-3-(5-tert-butyl-2-p-tolyl-2H-pyrazol-3-yl)-urea, Compound A1493;

1-(5-tert-Butyl-2-p-tolyl-2H-pyrazol-3-yl)-3-{4-[8-(naphthalene-1-sulfonyl)-8-aza-bicyclo[3.2.1]oct-3-ylmethyl]-phenyl}-urea, Compound A1494;

1-{4-[8-(Benzo[1,2,5]thiadiazole-5-sulfonyl)-8-aza-bicyclo[3.2.1]oct-3-ylmethyl]-phenyl}-3-(5-tert-butyl-2-p-tolyl-2H-pyrazol-3-yl)-urea, Compound A1495;

1-(5-tert-Butyl-2-p-tolyl-2H-pyrazol-3-yl)-3-{4-[8-(2,3-dihydro-benzo[1,4]dioxine-6-sulfonyl)-8-aza-bicyclo[3.2.1]oct-3-ylmethyl]-phenyl}-urea, Compound A1496;

1-(5-tert-Butyl-2-p-tolyl-2H-pyrazol-3-yl)-3-{4-[8-(2,3-dihydro-benzofuran-5-sulfonyl)-8-aza-bicyclo[3.2.1]oct-3-ylmethyl]-phenyl}-urea, Compound A1497;

1-(5-tert-Butyl-2-p-tolyl-2H-pyrazol-3-yl)-3-{4-[8-(2,4-dichloro-benzenesulfonyl)-8-aza-bicyclo[3.2.1]oct-3-ylmethyl]-phenyl}-urea, Compound A1498;

1-(5-tert-Butyl-2-p-tolyl-2H-pyrazol-3-yl)-3-{4-[8-(2,5-dichloro-benzenesulfonyl)-8-aza-bicyclo[3.2.1]oct-3-ylmethyl]-phenyl}-urea, Compound A1499;

1-(5-tert-Butyl-2-p-tolyl-2H-pyrazol-3-yl)-3-{4-[8-(2,5-dimethoxy-benzenesulfonyl)-8-aza-bicyclo[3.2.1]oct-3-ylmethyl]-phenyl}-urea, Compound A1500;

1-(5-tert-Butyl-2-p-tolyl-2H-pyrazol-3-yl)-3-{4-[8-(2-chloro-4-fluoro-benzenesulfonyl)-8-aza-bicyclo[3.2.1]oct-3-ylmethyl]-phenyl}-urea, Compound A1501;

1-(5-tert-Butyl-2-p-tolyl-2H-pyrazol-3-yl)-3-{4-[8-(2-chloro-benzenesulfonyl)-8-aza-bicyclo[3.2.1]oct-3-ylmethyl]-phenyl}-urea, Compound A1502;

1-(5-tert-Butyl-2-p-tolyl-2H-pyrazol-3-yl)-3-{4-[8-(2-fluoro-benzenesulfonyl)-8-aza-bicyclo[3.2.1]oct-3-ylmethyl]-phenyl}-urea, Compound A1503;

1-(5-tert-Butyl-2-p-tolyl-2H-pyrazol-3-yl)-3-{4-[8-(2,4,6-trimethyl-benzenesulfonyl)-8-aza-bicyclo[3.2.1]oct-3-ylmethyl]-phenyl}-urea, Compound A1504;

1-(5-tert-Butyl-2-p-tolyl-2H-pyrazol-3-yl)-3-{4-[8-(naphthalene-2-sulfonyl)-8-aza-bicyclo[3.2.1]oct-3-ylmethyl]-phenyl}-urea, Compound A1505;

1-(5-tert-Butyl-2-p-tolyl-2H-pyrazol-3-yl)-3-{4-[8-(thiophene-2-sulfonyl)-8-aza-bicyclo[3.2.1]oct-3-ylmethyl]-phenyl}-urea, Compound A1506;

1-(5-tert-Butyl-2-p-tolyl-2H-pyrazol-3-yl)-3-{4-[8-(2-trifluoromethoxy-benzenesulfonyl)-8-aza-bicyclo[3.2.1]oct-3-ylmethyl]-phenyl}-urea, Compound A1507;

1-(5-tert-Butyl-2-p-tolyl-2H-pyrazol-3-yl)-3-{4-[8-(3,4-dichloro-benzenesulfonyl)-8-aza-bicyclo[3.2.1]oct-3-ylmethyl]-phenyl}-urea, Compound A1508;

1-(5-tert-Butyl-2-p-tolyl-2H-pyrazol-3-yl)-3-{4-[8-(3,4-difluoro-benzenesulfonyl)-8-aza-bicyclo[3.2.1]oct-3-ylmethyl]-phenyl}-urea, Compound A1509;

1-(5-tert-Butyl-2-p-tolyl-2H-pyrazol-3-yl)-3-{4-[8-(3,4-dimethoxy-benzenesulfonyl)-8-aza-bicyclo[3.2.1]oct-3-ylmethyl]-phenyl}-urea, Compound A1510;

1-(5-tert-Butyl-2-p-tolyl-2H-pyrazol-3-yl)-3-{4-[8-(3,5-dimethyl-isoxazole-4-sulfonyl)-8-aza-bicyclo[3.2.1]oct-3-ylmethyl]-phenyl}-urea, Compound A1511;

1-(5-tert-Butyl-2-p-tolyl-2H-pyrazol-3-yl)-3-{4-[8-(3-chloro-4-fluoro-benzenesulfonyl)-8-aza-bicyclo[3.2.1]oct-3-ylmethyl]-phenyl}-urea, Compound A1512;

1-(5-tert-Butyl-2-p-tolyl-2H-pyrazol-3-yl)-3-{4-[8-(3-fluoro-benzenesulfonyl)-8-aza-bicyclo[3.2.1]oct-3-ylmethyl]-phenyl}-urea, Compound A1513;

5-(3-{4-[3-(5-tert-Butyl-2-p-tolyl-2H-pyrazol-3-yl)-ureido]-benzyl}-8-aza-bicyclo[3.2.1]octane-8-sulfonyl)-4-methoxy-thiophene-3-carboxylic acid methyl ester, Compound A1514;

1-(5-tert-Butyl-2-p-tolyl-2H-pyrazol-3-yl)-3-{4-[8-(3-methoxy-benzenesulfonyl)-8-aza-bicyclo[3.2.1]oct-3-ylmethyl]-phenyl}-urea, Compound A1515;

1-(5-tert-Butyl-2-p-tolyl-2H-pyrazol-3-yl)-3-{4-[8-(thiophene-3-sulfonyl)-8-aza-bicyclo[3.2.1]oct-3-ylmethyl]-phenyl}-urea, Compound A1516;

1-(5-tert-Butyl-2-p-tolyl-2H-pyrazol-3-yl)-3-{4-[8-(3-trifluoromethyl-benzenesulfonyl)-8-aza-bicyclo[3.2.1]oct-3-ylmethyl]-phenyl}-urea, Compound A1517;

1-(5-tert-Butyl-2-p-tolyl-2H-pyrazol-3-yl)-3-{4-[8-(4-chloro-2,5-dimethyl-benzenesulfonyl)-8-aza-bicyclo[3.2.1]oct-3-ylmethyl]-phenyl}-urea, Compound A1518;

1-(5-tert-Butyl-2-p-tolyl-2H-pyrazol-3-yl)-3-{4-[8-(4-chloro-benzenesulfonyl)-8-aza-bicyclo[3.2.1]oct-3-ylmethyl]-phenyl}-urea, Compound A1519;

1-(5-tert-Butyl-2-p-tolyl-2H-pyrazol-3-yl)-3-{4-[8-(4-fluoro-benzenesulfonyl)-8-aza-bicyclo[3.2.1]oct-3-ylmethyl]-phenyl}-urea, Compound A1520;

1-(5-tert-Butyl-2-p-tolyl-2H-pyrazol-3-yl)-3-{4-[8-(4-methoxy-benzenesulfonyl)-8-aza-bicyclo[3.2.1]oct-3-ylmethyl]-phenyl}-urea, Compound A1521;

1-(5-tert-Butyl-2-p-tolyl-2H-pyrazol-3-yl)-3-{4-[8-(4-methyl-3,4-dihydro-2H-benzo[1,4]oxazine-7-sulfonyl)-8-aza-bicyclo[3.2.1]oct-3-ylmethyl]-phenyl}-urea, Compound A1522;

1-{4-[8-(4-tert-Butyl-benzenesulfonyl)-8-aza-bicyclo[3.2.1]oct-3-ylmethyl]-phenyl}-3-(5-tert-butyl-2-p-tolyl-2H-pyrazol-3-yl)-urea, Compound A1523;

1-(5-tert-Butyl-2-p-tolyl-2H-pyrazol-3-yl)-3-{4-[8-(4-trifluoromethoxy-benzenesulfonyl)-8-aza-bicyclo[3.2.1]oct-3-ylmethyl]-phenyl}-urea, Compound A1524;

1-(5-tert-Butyl-2-p-tolyl-2H-pyrazol-3-yl)-3-{4-[8-(5-oxazol-5-yl-thiophene-2-sulfonyl)-8-aza-bicyclo[3.2.1]oct-3-ylmethyl]-phenyl}-urea, Compound A1525;

1-(5-tert-Butyl-2-p-tolyl-2H-pyrazol-3-yl)-3-{4-[8-(6-morpholin-4-yl-pyridine-3-sulfonyl)-8-aza-bicyclo[3.2.1]oct-3-ylmethyl]-phenyl}-urea, Compound A1526;

1-(5-tert-Butyl-2-p-tolyl-2H-pyrazol-3-yl)-3-{4-[8(quinoline-8-sulfonyl)-8-aza-bicyclo[3.2.1]oct-3-ylmethyl]-phenyl}-urea, Compound A1527;

1-(5-tert-Butyl-2-p-tolyl-2H-pyrazol-3-yl)-3-[4-(8-phenylmethanesulfonyl-8-aza-bicyclo[3.2.1]oct-3-ylmethyl)-phenyl]-urea, Compound A1528;

1-[4-(8-Benzenesulfonyl-8-aza-bicyclo[3.2.1]oct-3-ylmethyl)-phenyl]-3-(5-tert-butyl-2-p-tolyl-2H-pyrazol-3-yl)-urea, Compound A1529;

1-(5-tert-Butyl-2-p-tolyl-2H-pyrazol-3-yl)-3-{4-[8-(2-phenyl-ethenesulfonyl)-8-aza-bicyclo[3.2.1]oct-3-ylmethyl]-phenyl}-urea, Compound A1530;

1-{4-[8-(Benzo[1,2,5]oxadiazole-4-sulfonyl)-8-aza-bicyclo[3.2.1]oct-3-ylmethyl]-pbenyl}-3-(5-tert-butyl-2-p-tolyl-2H-pyrazol-3-yl)-urea, Compound A1531;

1-{4-[8-(Benzo[1,2,5]thiadiazole-4-sulfonyl)-8-aza-bicyclo[3.2.1]oct-3-ylmethyl]-pbenyl}-3-(5-tert-butyl-2-p-tolyl-2H-pyrazol-3-yl)-urea, Compound A1532;

1-(5-tert-Butyl-2-p-tolyl-2H-pyrazol-3-yl)-3-{4-[8-(1-methyl-1H-imidazole-4-sulfonyl)-8-aza-bicyclo[3.2.1]oct-3-ylmethyl]-phenyl}-urea, Compound A1533;

1-(5-tert-Butyl-2-p-tolyl-2H-pyrazol-3-yl)-3-{4-[8-(1,2-dimethyl-1H-imidazole-4-sulfonyl)-8-aza-bicyclo[3.2.1]oct-3-ylmethyl]-phenyl}-urea, Compound A1534;

1-(5-tert-Butyl-2-p-tolyl-2H-pyrazol-3-yl)-3-{4-[8-(5-isoxazol-3-yl-thiophene-2-sulfonyl)-8-aza-bicyclo[3.2.1]oct-3-ylmethyl]-phenyl}-urea, Compound A1535;

1-(5-tert-Butyl-2-p-tolyl-2H-pyrazol-3-yl)-3-(4-{8-[5-(2-methyl-thiazol-4-yl)-thiophene-2-sulfonyl]-8-aza-bicyclo[3.2.1]oct-3-ylmethyl}-phenyl)-urea, Compound A1536;

1-(5-tert-Butyl-2-p-tolyl-2H-pyrazol-3-yl)-3-{4-[8-(2-oxo-2H-chromene-6-sulfonyl)-8-aza-bicyclo[3.2.1]oct-3-ylmethyl]-phenyl}-urea, Compound A1537;

1-(5-tert-Butyl-2-p-tolyl-2H-pyrazol-3-yl)-3-{4-[8-(5-dimethylamino-naphthalene-1-sulfonyl)-8-aza-bicyclo[3.2.1]oct-3-ylmethyl]-phenyl}-urea, Compound A1538;

1-(5-tert-Butyl-2-p-tolyl-2H-pyrazol-3-yl)-3-[4-(8-ethanesulfonyl-8-aza-bicyclo[3.2.1]oct-3-ylmethyl)-phenyl]-urea, Compound A1539;

1-(5-tert-Butyl-2-p-tolyl-2H-pyrazol-3-yl)-3-{4-[8-(isoquinoline-5-sulfonyl)-8-aza-bicyclo[3.2.1]oct-3-ylmethyl]-phenyl}-urea, Compound A1540;

1-(5-tert-Butyl-2-p-tolyl-2H-pyrazol-3-yl)-3-[4-(8-methanesulfonyl-8-aza-bicyclo[3.2.1]oct-3-ylmethyl)-phenyl]-urea, Compound A1541;

2-(3-{4-[3-(5-tert-Butyl-2-p-tolyl-2H-pyrazol-3-yl)-ureido]-benzyl}-8-aza-bicyclo[3.2.1]octane-8-sulfonyl)benzoic acid methyl ester, Compound A1542;

4-(3-{4-[3-(5-tert-Butyl-2-p-tolyl-2H-pyrazol-3-yl)-ureido]-benzyl}-8-aza-bicyclo[3.2.1]octane-8-sulfonyl)-2,5-dimethyl-furan-3-carboxylic acid methyl ester, Compound A1543;

5-(3-{4-[3-(5-tert-Butyl-2-p-tolyl-2H-pyrazol-3-yl)-ureido]-benzyl}-8-aza-bicyclo[3.2.1]octane-8-sulfonyl)-1-methyl-1H-pyrrole-2-carboxylic acid methyl ester, Compound A1544;

5-(3-{4-[3-(5-tert-Butyl-2-p-tolyl-2H-pyrazol-3-yl)-ureido]-benzyl}-8-aza-bicyclo[3.2.1]octane-8-sulfonyl)-furan-2-carboxylic acid methyl ester, Compound A1545;

N-[4-(3-{4-[3-(5-tert-Butyl-2-p-tolyl-2H-pyrazol-3-yl)-ureido]-benzyl}-8-aza-bicyclo[3.2.1]octane-8-sulfonyl)-phenyl]-acetamide, Compound A1546;

1-(5-tert-Butyl-2-p-tolyl-2H-pyrazol-3-yl)-3-{4-[8-(4-vinyl-benzenesulfonyl)-8-aza-bicyclo[3.2.1]oct-3-ylmethyl]-pbenyl}-urea, Compound A1547;

1-(5-tert-Butyl-2-p-tolyl-2H-pyrazol-3-yl)-3-{4-[8-(toluene-4-sulfonyl)-8-aza-bicyclo[3.2.1]oct-3-ylmethyl]-phenyl}-urea, Compound A1548;

endo-3-{4-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzo[1,4]dioxin-6-yl)-amide, Compound A413A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzo[1,4]dioxin-6-yl)-amide, Compound A413B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzofuran-5-yl)-amide, Compound A416A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (2,3-dihydro-benzofuran-5-ylamide, Compound A416B;

3-{4-[3-(5-tert-Butyl-2-p-tolyl-2H-pyrazol-3-yl)-ureido]-benzyl}-8-aza-bicyclo[3.2.1]octane-8-carboxylic acid (2,4-dimethoxy-phenyl)-amide, Compound A1549;

endo-3-{4-[3-(5-tert-Butyl-2-p-tolyl-2H-pyrazol-3-yl)-ureido]-benzyl}-8-aza-bicyclo[3.2.1]octane-8-carboxylic acid (2,5-dimethoxy-phenyl)-amide, Compound A419A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (2,5-dimethoxy-phenyl)-amide, Compound A419B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (2-methyl-5-phenyl-furan-3-yl)-amide, Compound A422A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (2-methyl-5-phenyl-furan-3-yl)-amide, Compound A422B;

endo-3-{4-[3-(5-tert-Butyl-2-p-tolyl-2H-pyrazol-3-yl)-ureido]-benzyl}-8-aza-bicyclo[3.2.1]octane-8-carboxylic acid benzo[1,3]dioxol-5-ylamide, Compound A428A;

exo-3-{4-[3-(5-tert-Butyl-2-p-tolyl-2H-pyrazol-3-yl)-ureido]-benzyl}-8-aza-bicyclo[3.2.1]octane-8-carboxylic acid benzo[1,3]dioxol-5-ylamide, Compound A428B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (3,4,5-trimethoxy-phenyl)-amide, Compound A425A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (3,4,5-trimethoxy-phenyl)-amide, Compound A425B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (3,4-dimethoxy-phenyl)amide, Compound A431A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (3,4-dimethoxy-phenyl)-amide, Compound A431B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (3,5-dimethoxy-phenyl)-amide, Compound A434A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (3,5-dimethoxy-phenyl)-amide, Compound A434B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (3,5-dimethyl-isoxazol-4-yl)amide, Compound A437A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (3,5-dimethyl-isoxazol-4-yl)-amide, Compound A437B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (3-chloro-4-methoxy-phenyl)-amide, Compound A440A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (3-chloro-4-methoxy-phenyl)-amide, Compound A440B;

endo-3-{4-[3-(5-tert-Butyl-2-p-tolyl-2H-pyrazol-3-yl)-ureido]-benzyl}-8-aza-bicyclo[3.2.1]octane-8-carboxylic acid thiophen-3-ylamide, Compound A443A;

exo-3-{4-[3-(5-tert-Butyl-2-p-tolyl-2H-pyrazol-3-yl)-ureido]-benzyl}-8-aza-bicyclo[3.2.1]octane-8-carboxylic acid thiophen-3-ylamide, Compound A443B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (4-difluoromethoxy-phenyl)-amide, Compound A446A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (4-difluoromethoxy-phenyl)-amide, Compound A446B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (4-dimethylamino-phenyl)-amide, Compound A449A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (4-dimethylamino-phenyliamide, Compound A449B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (4-trifluoromethoxy-phenyl)-amide, Compound A452A;

exo-3-{4-[3-(5-tert-Butyl-2-p-tolyl-2H-pyrazol-3-yl)-ureido]-benzyl-}-8-aza-bicyclo[3.2.1]octane-8-carboxylic acid (4-trifluoromethoxy-phenyl)-amide, Compound A452B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (4-acetyl-phenyl)-amide, Compound A454A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (4-acetyl-phenyl)-amide, Compound A454B;

endo-3-{4-[3-(5-tert-Butyl-2-p-tolyl-2H-pyrazol-3-yl)-ureido]-benzyl}-8-aza-bicyclo[3.2.1]octane-8-carboxylic acid benzo[1,2,5]thiadiazol-4-ylamide, Compound A457A;

exo-3-{4-[3-(5-tert-Butyl-2-p-tolyl-2H-pyrazol-3-yl)-ureido]-benzyl}-8-aza-bicyclo[3.2.1]octane-8-carboxylic acid benzo[1,2,5]thiadiazol-4-ylamide, Compound A457B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (4-methoxy-2-methyl-phenyl)-amide, Compound A460A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (4-methoxy-2-methyl-phenyl)-amide, Compound A460B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (5-chloro-2,4-dimethoxy-phenyl)amide, Compound A463A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (5-chloro-2,4-dimethoxy-phenyl)-amide, Compound A463B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (5-methyl-2-trifluoromethyl-furan-3-yl)-amide, Compound A466A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (5-methyl-2-trifluoromethyl-furan-3-yl)-amide, Compound A466B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (5-methyl-3-phenyl-isoxazol-4-yl)-amide, Compound A469A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (5-methyl-3-phenyl-isoxazol-4-yl)-amide, Compound A469B;

endo-3-{4-[3-(5-tert-Butyl-2-p-tolyl-2H-pyrazol-3-yl)-ureido]-benzyl}-8-aza-bicyclo[3.2.1]octane-8-carboxylic acid (6-fluoro-4H-benzo[1,3]dioxin-8-yl)amide, Compound A472A;

exo-3-{4-[3-(5-tert-Butyl-2-p-tolyl-2H-pyrazol-3-yl)-ureido]-benzyl}-8-aza-bicyclo[3.2.1]octane-8-carboxylic acid (6-fluoro-4H-benzo[1,3]dioxin-8-yl)-amide, Compound A472B;

endo-3-[(3-{4-[3-(5-tert-Butyl-2-p-tolyl-2H-pyrazol-3-yl)-ureido]-benzyl}-8-aza-bicyclo[3.2.1]octane-8-carbonyl)-amino]-benzoic acid ethyl ester, Compound A475A;

exo-3-[(3-{4-[3-(5-tert-Butyl-2-p-tolyl-2H-pyrazol-3-yl)-ureido]-benzyl}-8-aza-bicyclo[3.2.1]octane-8-carbonyl)-amino]-benzoic acid ethyl ester, Compound A475B;

endo-4-[(3-{4-[3-(5-tert-Butyl-2-p-tolyl-2H-pyrazol-3-yl)-ureido]-benzyl}-8-aza-bicyclo[3.2.1]octane-8-carbonyl)-amino]-benzoic acid methyl ester, Compound A478A;

exo-4-[(3-{4-[3-(5-tert-Butyl-2-p-tolyl-2H-pyrazol-3-yl)-ureido]-benzyl}-8-aza-bicyclo[3.2.1]octane-8-carbonyl)-amino]-benzoic acid methyl ester, Compound A478B;

1-(5-tert-Butyl-2-p-tolyl-2H-pyrazol-3-yl)-3-{4-[1-((R)-2,6-dioxo-hexahydro-pyrimidine-4-carbonyl)-piperidin-4-ylmethyl]-phenyl}-urea, Compound A365A;

1-(5-tert-Butyl-2-p-tolyl-2H-pyrazol-3-yl)-3-{4-[1-((S)-2,6-dioxo-hexahydro-pyrimidine-4-carbonyl)-piperidin-4-ylmethyl]-phenyl}-urea, Compound A365B;

1-(5-tert-Butyl-2-p-tolyl-2H-pyrazol-3-yl)-3-{4-[1-((R)-5-oxo-pyrrolidine-2-carbonyl)-piperidin-4-ylmethyl]-phenyl}-urea, Compound A350A;

1-(5-tert-Butyl-2-p-tolyl-2H-pyrazol-3-yl)-3-(4-{1-[4-(2,2,2-trifluoro-acetyl)-benzoyl]-piperidin-4-ylmethyl}-phenyl)-urea, Compound A1550;

1-(5-tert-Butyl-2-p-tolyl-2H-pyrazol-3-yl)-3-(4-{1-[2-(5-chloro-3-methyl-benzo[b]thiophen-2-yl)-acetyl]-piperidin-4-ylmethyl}-phenyl)-urea, Compound A1551;

1-(5-tert-Butyl-2-p-tolyl-2H-pyrazol-3-yl)-3-(4-{1-[2-(4-chloro-phenyl)-propionyl]-piperidin-4-ylmethyl}-phenyl)-urea, (R)-isomer, Compound A313A;

1-(5-tert-Butyl-2-p-tolyl-2H-pyrazol-3-yl)-3-(4-{1-[2-(4-chloro-phenyl)-propionyl]-piperidin-4-ylmethyl}-phenyl)-urea, (S)-isomer, Compound A313B;

1-(5-tert-Butyl-2-p-tolyl-2H-pyrazol-3-yl)-3-{4-[1-(2-furan-2-yl-2-oxo-acetyl)-piperidin-4-ylmethyl]-phenyl}-urea, Compound A1552;

1-{4-[1-(3-1H-Benzoimidazol-2-yl-propionyl)-piperidin-4-ylmethyl]-phenyl}-3-(5-tert-butyl-2-p-tolyl-2H-pyrazol-3-yl)-urea, Compound A1553;

N—[(R)-2-(4-{4-[3-(5-tert-Butyl-2-p-tolyl-2H-pyrazol-3-yl)-ureido]-benzyl}-piperidin-1-yl)-1-methyl-2-oxo-ethyl]-acetamide, Compound A374A;

N—[(S)-2-(4-{4-[3-(5-tert-Butyl-2-p-tolyl-2H-pyrazol-3-yl)-ureido]-benzyl}-piperidin-1-yl)-1-methyl-2-oxo-ethyl]-acetamide, Compound A374B;

1-(5-tert-Butyl-2-p-tolyl-2H-pyrazol-3-yl)-3-{4-[1-((R)-tetrahydro-furan-2-carbonyl)-piperidin-4-ylmethyl]-phenyl}-urea, Compound A258A;

1-(5-tert-Butyl-2-p-tolyl-2H-pyrazol-3-yl)-3-{4-[1-((S)-tetrahydro-furan-2-carbonyl)-piperidin-4-ylmethyl]-phenyl}-urea, Compound A258B;

1-(5-tert-Butyl-2-p-tolyl-2H-pyrazol-3-yl)-3-{4-[1-((R)-4-oxo-2-phenyl-pentanoyl)-piperidin-4-ylmethyl]-phenyl}-urea, Compound A254A;

1-(5-tert-Butyl-2-p-tolyl-2H-pyrazol-3-yl)-3-{4-[1-((S)-4-oxo-2-phenyl-pentanoyl)-piperidin-4-ylmethyl]-phenyl}-urea, Compound A254B;

1-(5-tert-Butyl-2-p-tolyl-2H-pyrazol-3-yl)-3-{4-[1-(2-pyridin-4-yl-acetyl)-piperidin-4-ylmethyl]-phenyl}-urea, Compound A1554;

1-(5-tert-Butyl-2-p-tolyl-2H-pyrazol-3-yl)-3-{4-[1-(2-pyridin-3-yl-acetyl)-piperidin-4-ylmethyl]-phenyl}-urea, Compound A1555;

1-(5-tert-Butyl-2-p-tolyl-2H-pyrazol-3-yl)-3-{4-[1-(2-3H-imidazol-4-yl-acetyl)-piperidin-4-ylmethyl]-phenyl}-urea, Compound A1556;

1-(5-tert-Butyl-2-p-tolyl-2H-pyrazol-3-yl)-3-{4-[1-((S)-5-oxo-tetrahydro-furan-2-carbonyl)-piperidin-4-ylmethyl]-phenyl}-urea, Compound A192B;

1-(5-tert-Butyl-2-p-tolyl-2H-pyrazol-3-yl)-3-{4-[1-(1H-pyrazole-4-carbonyl)-piperidin-4-ylmethyl]-phenyl}-urea, Compound A1557;

1-(5-tert-Butyl-2-p-tolyl-2H-pyrazol-3-yl)-3-{4-[1-((R)-2,3-dihydro-1H-indole-2-carbonyl)-piperidin-4-ylmethyl]-phenyl}-urea, Compound A363A;

1-(5-tert-Butyl-2-p-tolyl-2H-pyrazol-3-yl)-3-{4-[1-((S)-2,3-dihydro-1H-indole-2-carbonyl)-piperidin-4-ylmethyl]-phenyl}-urea, Compound A363B;

1-{4-[1-(4-Aminomethyl-benzoyl)-piperidin-4-ylmethyl]-phenyl}-3-(5-tert-butyl-2-p-tolyl-2H-pyrazol-3-yl)-urea, Compound A1558;

4-Amino-N-[2-(4-{4-[3-(5-tert-butyl-2-p-tolyl-2H-pyrazol-3-yl)-ureido]-benzyl}-piperidin-1-yl)-2-oxo-ethyl]-benzamide, Compound A1559;

1-(5-tert-Butyl-2-p-tolyl-2H-pyrazol-3-yl)-3-(4-{1-[2-(R)-2,5-dioxo-imidazolidin-4-yl)acetyl]-piperidin-4-ylmethyl}-phenyl)-urea, Compound A353A;

1-(5-tert-Butyl-2-p-tolyl-2H-pyrazol-3-yl)-3-(4-{1-[2-(S)-2,5-dioxo-imidazolidin-4-yl)-acetyl]-piperidin-4-ylmethyl}-phenyl)-urea, Compound A353B;

1-(5-tert-Butyl-2-p-tolyl-2H-pyrazol-3-yl)-3-(4-{1-[2-(N-methyl-guanidino)-acetyl]-piperidin-4-ylmethyl}-phenyl)-urea, Compound A1560;

N-[2-(4-{4-[3-(5-tert-Butyl-2-p-tolyl-2H-pyrazol-3-yl)-ureido]-benzyl}-piperidin-1-yl)-2-oxo-ethyl]-acetamide, Compound A1561;

1-(5-tert-Butyl-2-p-tolyl-2H-pyrazol-3-yl)-3-{4-[1-((R)-2-phenyl-propionyl)-piperidin-4-ylmethyl]-phenyl}-urea, C36H43N5O2, 577.34, 578.34, M+H, 3.63, Compound A255A;

1-(5-tert-Butyl-2-p-tolyl-2H-pyrazol-3-yl)-3-{4-[1-((S)-2-phenyl-propionyl)-piperidin-4-ylmethyl]-phenyl}-urea, C36H43N5O2, 577.34, 578.34, M+H, 3.63, Compound A255B;

1-(5-tert-Butyl-2-p-tolyl-2H-pyrazol-3-yl)-3-{4-[1-(2-oxo-3-phenyl-propionyl)-piperidin-4-ylmethyl]-phenyl}-urea, Compound A1562;

1-(5-tert-Butyl-2-p-tolyl-2H-pyrazol-3-yl)-3-{4-[1-(2-oxo-propionyl)-piperidin-4-ylmethyl]-phenyl}-urea, Compound A1563;

1-(5-tert-Butyl-2-p-tolyl-2H-pyrazol-3-yl)-3-(4-{1-[3-((R)-cyano-methyl-methyl)ibenzoyl]-piperidin-4-ylmethyl}-phenyl)-urea, Compound A272A;

1-(5-tert-Butyl-2-p-tolyl-2H-pyrazol-3-yl)-3-(4-{1-[3-((S)-cyano-methyl-methyl)-benzoyl]-piperidin-4-ylmethyl}-phenyl)-urea, Compound A272B;

1-(5-tert-Butyl-2-p-tolyl-2H-pyrazol-3-yl)-3-{4-[1-((R)-1,2,3,4-tetrahydro-naphthalene-2-carbonyl)-piperidin-4-ylmethyl]-phenyl}-urea, Compound A195A;

1-(5-tert-Butyl-2-p-tolyl-2H-pyrazol-3-yl)-3-{4-[1-((S)-1,2,3,4-tetrahydro-naphthalene-2-carbonyl)-piperidin-4-ylmethyl]-phenyl}-urea, Compound A195B;

1-{4-[1-(2-Benzo[1,3]dioxol-5-yl-2-oxo-ethyl)-piperidin-4-ylmethyl]-phenyl}-3-(5-tert-butyl-2-p-tolyl-2H-pyrazol-3-yl)-urea, Compound A1564;

1-{4-[1-(2-Benzo[b]thiophen-3-yl-2-oxo-ethyl)-piperidin-4-ylmethyl]-phenyl}-3-(5-tert-butyl-2-p-tolyl-2H-pyrazol-3-yl)-urea, Compound A1565;

1-(5-tert-Butyl-2-p-tolyl-2H-pyrazol-3-yl)-3-(4-{1-[2-oxo-2-(3-phenyl-isoxazol-5-yl)-ethyl]-piperidin-4-ylmethyl}-phenyl)-urea, Compound A1566;

1-(5-tert-Butyl-2-p-tolyl-2H-pyrazol-3-yl)-3-(4-{1-[2-(4-methanesulfonyl-phenyl)-2-oxo-ethyl]-piperidin-4-ylmethyl}-phenyl)-urea, Compound A1567;

1-(5-tert-Butyl-2-p-tolyl-2H-pyrazol-3-yl)-3-{4-[1-(2-oxo-2-pyridin-4-yl-ethyl)-piperidin-4-ylmethyl]-phenyl}-urea, Compound A1568;

1-(5-tert-Butyl-2-p-tolyl-2H-pyrazol-3-yl)-3-(4-{1-[2-(5-methyl-1-phenyl-1H-pyrazol-4-yl)-2-oxo-ethyl]-piperidin-4-ylmethyl}-phenyl)-urea, Compound A1569;

1-(5-tert-Butyl-2-p-tolyl-2H-pyrazol-3-yl)-3-(4-{1-[2-(5-methyl-3-phenyl-isoxazol-4-yl)-2-oxo-ethyl]-piperidin-4-ylmethyl}-phenyl)-urea, Compound A1570;

1-(5-tert-Butyl-2-p-tolyl-2H-pyrazol-3-yl)-3-(4-{1-[2-oxo-2-(5-pyridin-2-yl-thiophen-2-yl)-ethyl]-piperidin-4-ylmethyl}-phenyl)-urea, Compound A1571;

1-(5-tert-Butyl-2-p-tolyl-2H-pyrazol-3-yl)-3-(4-{1-[2-(2,4-dimethoxy-phenyl)-2-oxo-ethyl]-piperidin-4-ylmethyl}-phenyl)-urea, Compound A1572;

1-(5-tert-Butyl-2-p-tolyl-2H-pyrazol-3-yl)-3-(4-{1-[2-(2,5-dimethoxy-phenyl)-2-oxo-ethyl]-piperidin-4-ylmethyl}-phenyl)-urea, Compound A1573;

1-(5tert-Butyl-2-p-tolyl-2H-pyrazol-3-yl)-3-(4-{1-[2-(3-methoxy-phenyl)-2-oxo-ethyl]-piperidin-4-ylmethyl}-pbenyl)-urea, Compound A1574;

1-(5-tert-Butyl-2-p-tolyl-2H-pyrazol-3-yl)-3-{4-[1-(2-oxo-2-pyridin-3-yl-ethyl)-piperidin-4-ylmethyl]-phenyl}-urea, Compound A1575;

1-(5-tert-Butyl-2-p-tolyl-2H-pyrazol-3-yl)-3-(4-{1-[2-(4-difluoromethoxy-phenyl)-2-oxo-ethyl]-piperidin-4-ylmethyl}-phenyl)-urea, Compound A1576;

1-(5-tert-Butyl-2-p-tolyl-2H-pyrazol-3-yl)-3-(4-{1-[2-oxo-2-(4-trifluoromethoxy-phenyl)-ethyl]-piperidin-4-ylmethyl}-phenyl)-urea, Compound A1577;

1-(5-tert-Butyl-2-p-tolyl-2H-pyrazol-3-yl)-3-(4-{1-[2-(4-methoxy-phenyl)-2-oxo-ethyl]-piperidin-4-ylmethyl}-phenyl)-urea, Compound A1578;

1-(5-tert-Butyl-2-p-tolyl-2H-pyrazol-3-yl)-3-{4-1-(4-oxo-4,5,6,7-tetrahydro-benzo[1,2,5]oxadiazol-5-yl)-piperidin-4-ylmethyl]-phenyl}-urea, Compound A1579;

1-(5-tert-Butyl-2-p-tolyl-2H-pyrazol-3-yl)-3-(4-{1-[2-oxo-2-(2-oxo-1,2,3,4-tetrahydro-quinolin-6-yl)-ethyl]-piperidin-4-ylmethyl}-phenyl)-urea, Compound A1580;

1-(5-tert-Butyl-2-p-tolyl-2H-pyrazol-3-yl)-3-(4-{1-[2-oxo-2-(4-pyrrolidin-1-yl-phenyl)-ethyl]-piperidin-4-ylmethyl}-phenyl)-urea, Compound A1581;

1-(5-tert-Butyl-2-p-tolyl-2H-pyrazol-3-yl)-3-(4-{1-[2-(4-diethylamino-phenyl)-2-oxo-ethyl]-piperidin-4-ylmethyl}-phenyl)-urea, Compound A1582;

5-[2-(4-{4-[3-(5-tert-Butyl-2-p-tolyl-2H-pyrazol-3-yl)-ureido]-benzyl}-piperidin-1-yl)-acetyl]-isoxazole-3-carboxylic acid ethyl ester, Compound A1583;

4-{4-[3-(5-tert-Butyl-2-p-tolyl-2H-pyrazol-3-yl)-ureido]-benzyl}-piperidine-1-carboxylic acid (2,4-dimethoxy-phenyl)-amide, Compound A1584;

4-{4-[3-(5-tert-Butyl-2-p-tolyl-2H-pyrazol-3-yl)-ureido]-benzyl}-piperidine-1-carboxylic acid (4-trifluoromethoxy-phenyl)amide, Compound A1585;

3-{3-[3-(5-tert-Butyl-2-p-tolyl-2H-pyrazol-3-yl)-ureido]-benzyl}-8-aza-bicyclo[3.2.1]octane-8-carboxylic acid 1,1,-dioxo-1H-imidazo[2,1-b]benzothiazol-2-ylmethyl ester, Compound A1586;

4-{3-[3-(5-tert-Butyl-2-p-tolyl-2H-pyrazol-3-yl)-ureido]-benzyl}-piperidine-1-carboxylic acid 1,1-dioxo-1H-1-(imidazo[2,1-b]benzothiazol-2-ylmethyl ester, Compound A1587;

4-{2-[3-(5-tert-Butyl-2-p-tolyl-2H-pyrazol-3-yl)-ureido]-benzyl}-piperidine-1-carboxylic acid 1,1-dioxo-1H-imidazo[2,1-b]benzothiazol-2-ylmethyl ester, Compound A1588;

3-{4-[3-(5-tert-Butyl-2-p-tolyl-2H-pyrazol-3-yl)-ureido]-benzyl}-8-aza-bicyclo[3.2.1]octane-8-carboxylic acid 1,1-dioxo-1H-imidazo[2,1-b]benzothiazol-2-ylmethyl ester, Compound A1589;

4-{4-[3-(5-tert-Butyl-2-p-tolyl-2H-pyrazol-3-yl)-ureido]-benzyl}-piperidine-1-carboxylic acid 1,1-dioxo-1H-imidazo[2,1-b]benzothiazol-2-ylmethyl ester, Compound A1590;

3-{3-[3-(5-tert-Butyl-2-p-tolyl-2H-pyrazol-3-yl)-ureido]-benzyl}-8-aza-bicyclo[3.2.1]octane-8-carboxylic acid 2-methoxy-phenyl ester, Compound A1591;

4-{3-[3-(5-tert-Butyl-2-p-tolyl-2H-pyrazol-3-yl)-ureido]-benzyl}-piperidine-1-carboxylic acid 2-methoxy-phenyl ester, Compound A1592;

4-{2-[3-(5-tert-Butyl-2-p-tolyl-2H-pyrazol-3-yl)-ureido]-benzyl}-piperidine-1-carboxylic acid 2-methoxy-phenyl ester, Compound A1593;

3-{4-[3-(5-tert-Butyl-2-p-tolyl-2H-pyrazol-3-yl)-ureido]-benzyl}-8-aza-bicyclo[3.2.1]octane-8-carboxylic acid 2-methoxy-phenyl ester, Compound A1594;

4-{4-[3-(5-tert-Butyl-2-p-tolyl-2H-pyrazol-3-yl)-ureido]-benzyl}-piperidine-1-carboxylic acid 2-methoxy-phenyl ester, Compound A1595;

3-{3-[3-(5-tert-Butyl-2-p-tolyl-2H-pyrazol-3-yl)-ureido]-benzyl}-8-aza-bicyclo[3.2.1]octane-8-carboxylic acid 4-methoxycarbonyl-phenyl ester, Compound A1596;

4-{3-[3-(5-tert-Butyl-2-p-tolyl-2H-pyrazol-3-yl)-ureido]-benzyl}-piperidine-1-carboxylic acid 4-methoxycarbonyl-phenyl ester, Compound A1597;

4-{2-[3-(5-tert-Butyl-2-p-tolyl-2H-pyrazol-3-yl)-ureido]-benzyl}-piperidine-1-carboxylic acid 4-methoxycarbonyl-phenyl ester, Compound A1598;

3-{4-[3-(5-tert-Butyl-2-p-tolyl-2H-pyrazol-3-yl)-ureido]-benzyl}-8-aza-bicyclo[3.2.1]octane-8-carboxylic acid 4-methoxycarbonyl-phenyl ester, Compound A1599;

4-{4-[3-(5-tert-Butyl-2-p-tolyl-2H-pyrazol-3-yl)-ureido]-benzyl}-piperidine-1-carboxylic acid 4-methoxycarbonyl-phenyl ester, Compound A1600;

3-{3-[3-(5-tert-Butyl-2-p-tolyl-2H-pyrazol-3-yl)-ureido]-benzyl}-8-aza-bicyclo[3.2.1]octane-8-carboxylic acid 4-methoxy-phenyl ester, Compound A1601;

4-{3-[3-(5-tert-Butyl-2-p-tolyl-2H-pyrazol-3-yl)-ureido]-benzyl}-piperidine-1-carboxylic acid 4-methoxy-phenyl ester, Compound A1602;

4-{2-[3-(5-tert-Butyl-2-p-tolyl-2H-pyrazol-3-yl)-ureido]-benzyl}-piperidine-carboxylic acid 4-methoxy-phenyl ester, Compound A1603;

3-{4-[3-(5-tert-Butyl-2-p-tolyl-2H-pyrazol-3-yl)-ureido]-benzyl}-8-aza-bicyclo[3.2.1]octane-8-carboxylic acid 4-methoxy-phenyl ester, Compound A1604;

4-{4-[3-(5-tert-Butyl-2-p-tolyl-2H-pyrazol-3-yl)-ureido]-benzyl}-piperidine-1-carboxylic acid 4-methoxy-phenyl ester, Compound A1605;

3-{3-[3-(5-tert-Butyl-2-p-tolyl-2H-pyrazol-3-yl)-ureido]-benzyl}-8-aza-bicyclo[3.2.1]octane-8-carboxylic acid benzyl ester, Compound A1606;

4-{3-[3-(5-tert-Butyl-2-p-tolyl-2H-pyrazol-3-yl)-ureido]-benzyl}-piperidine-1-carboxylic acid benzyl ester, Compound A1607;

4-{2-[3-(5-tert-Butyl-2-p-tolyl-2H-pyrazol-3-yl)-ureido]-benzyl}-piperidine-1-carboxylic acid benzyl ester, Compound A1608;

3-{4-[3-(5-tert-Butyl-2-p-tolyl-2H-pyrazol-3-yl)-ureido]-benzyl}-8-aza-bicyclo[3.2.1]octane-8-carboxylic acid benzyl ester, Compound A1609;

4-{4-[3-(5-tert-Butyl-2-p-tolyl-2H-pyrazol-3-yl)-ureido]-benzyl}-piperidine-1-carboxylic acid benzyl ester (4.8 mg), C35H41N5O3, 580.31, M+H, 3.75, Compound A1610;

3-{3-[3-(5-tert-Butyl-2-p-tolyl-2H-pyrazol-3-yl)-ureido]-benzyl}-8-aza-bicyclo[3.2.1]octane-8-carboxylic acid cyclopentyl ester, Compound A1611;

4-{3-[3-(5-tert-Butyl-2-p-tolyl-2H-pyrazol-3-yl)-ureido]-benzyl}-piperidine-1-carboxylic acid cyclopentyl ester, Compound A1612;

4-{2-[3-(5-tert-Butyl-2-p-tolyl-2H-pyrazol-3-yl)-ureido]-benzyl}-piperidine-1-carboxylic acid cyclopentyl ester, Compound A1613;

3-{4-[3-(5-tert-Butyl-2-p-tolyl-2H-pyrazol-3-yl)-ureido]-benzyl}-8-aza-bicyclo[3.2.1]octane-8-carboxylic acid cyclopentyl ester, Compound A1614;

4-{4-[3-(5-tert-Butyl-2-p-tolyl-2H-pyrazol-3-yl)-ureido]-benzyl}-piperidine-1-carboxylic acid cyclopentyl ester, Compound A1615;

3-{3-[3-(5-tert-Butyl-2-p-tolyl-2H-pyrazol-3-yl)-ureido]-benzyl}-8-aza-bicyclo[3.2.1]octane-8-carboxylic acid ethyl ester, Compound A1616;

4-{3-[3-(5-tert-Butyl-2-p-tolyl-2H-pyrazol-3-yl)-ureido]-benzyl}-piperidine-1-carboxylic acid ethyl ester, Compound A1617;

4-{2-[3-(5-tert-Butyl-2-p-tolyl-2H-pyrazol-3-yl)-ureido]-benzyl}-piperidine-1-carboxylic acid ethyl ester, Compound A1618;

3-{4-[3-(5-tert-Butyl-2-p-tolyl-2H-pyrazol-3-yl)-ureido]-benzyl}-8-aza-bicyclo[3.2.1]octane-8-carboxylic acid ethyl ester, Compound A1619;

4-{4-[3-(5-tert-Butyl-2-p-tolyl-2H-pyrazol-3-yl)-ureido]-benzyl}-piperidine-1-carboxylic acid ethyl ester, Compound A1620;

3-{3-[3-(5-tert-Butyl-2-p-tolyl-2H-pyrazol-3-yl)-ureido]-benzyl}-8-aza-bicyclo[3.2.1]octane-8-carboxylic acid isobutyl ester, Compound A1621;

4-{3-[3-(5-tert-Butyl-2-p-tolyl-2H-pyrazol-3-yl)-ureido]-benzyl}-piperidine-1-carboxylic acid isobutyl ester, Compound A1622;

4-{2-[3-(5-tert-Butyl-2-p-tolyl-2H-pyrazol-3-yl)-ureido]-benzyl}-piperidine-1-carboxylic acid isobutyl ester, Compound A1623;

3-{4-[3-(5-tert-Butyl-2-p-tolyl-2H-pyrazol-3-yl)-ureido]-benzyl}-8-aza-bicyclo[3.2.1]octane-8-carboxylic acid isobutyl ester, Compound A1624;

4-{4-[3-(5-tert-Butyl-2-p-tolyl-2H-pyrazol-3-yl)-ureido]-benzyl}-piperidine-1-carboxylic acid isobutyl ester (6 mg), C32H43N5O3, 546.33, M+H, 3.78, Compound A1625;

3-{3-[3-(5-tert-Butyl-2-p-tolyl-2H-pyrazol-3-yl)-ureido]-benzyl}-8-aza-bicyclo[3.2.1]octane-8-carboxylic acid p-tolyl ester, Compound A1626;

4-{3-[3-(5-tert-Butyl-2-p-tolyl-2H-pyrazol-3-yl)-ureido]-benzyl}-piperidine-1-carboxylic acid p-tolyl ester, Compound A1627;

4-{2-[3-(5-tert-Butyl-2-p-tolyl-2H-pyrazol-3-yl)-ureido]-benzyl}-piperidine-1-carboxylic acid p-tolyl ester, Compound A1628;

3-{4-[3-(5-tert-Butyl-2-p-tolyl-2H-pyrazol-3-yl)-ureido]-benzyl}-8-aza-bicyclo[3.2.1]octane-8-carboxylic acid p-tolyl ester, Compound A1629;

4-{4-[3-(5-tert-Butyl-2-p-tolyl-2H-pyrazol-3-yl)-ureido]-benzyl}-piperidine-1-carboxylic acid p-tolyl ester, Compound A1630;

3-{3-[3-(5-tert-Butyl-2-p-tolyl-2H-pyrazol-3-yl)-ureido]-benzyl}-8-aza-bicyclo[3.2.1]octane-8-carboxylic acid phenyl ester, Compound A1631;

4-{3-[3-(5-tert-Butyl-2-p-tolyl-2H-pyrazol-3-yl)-ureido]-benzyl}-piperidine-1-carboxylic acid phenyl ester, Compound A1632;

4-{2-[3-(5-tert-Butyl-2-p-tolyl-2H-pyrazol-3-yl)-ureido]-benzyl}-piperidine-1-carboxylic acid phenyl ester, Compound A1633;

3-{4-[3-(5-tert-Butyl-2-p-tolyl-2H-pyrazol-3-yl)-ureido]-benzyl}-8-aza-bicyclo[3.2.1]octane-8-carboxylic acid phenyl ester, Compound A1634;

4-{4-[3-(5-tert-Butyl-2-p-tolyl-2H-pyrazol-3-yl)-ureido]-benzyl}-piperidine-1-carboxylic acid phenyl ester, Compound A1635;

1-(5-tert-Butyl-2-p-tolyl-2H-pyrazol-3-yl)-3-{3-[1-(2,5-dimethoxy-benzoyl)-piperidin-4-ylmethyl]-phenyl}-urea, Compound A1636;

1-[4-(1-Acetyl-piperidin-4-ylmethyl)-phenyl]-3-(5-tert-butyl-2-p-tolyl-2H-pyrazol-3-yl)-urea (8 mg), C29H37N5O2, 487.65, 488.27, M+H, 3.52, Compound A1637.

1-{3-[1-(benzofuran-2-carbonyl)-piperidin-4-ylmethyl]-phenyl}-3-(5-tert-butyl-2-p-tolyl-2H-pyrazol-3-yl)-urea, Compound A1638;

1-(5-tert-Butyl-2-p-tolyl-2H-pyrazol-3-yl)-3-{3-[1-(piperidine-4-carbonyl)-piperidin-4-ylmethyl]-phenyl}-urea, Compound A1639;

1-(5-tert-Butyl-2-p-tolyl-2H-pyrazol-3-yl)-3-{4-[8-(6-methyl-pyridine-2-carbonyl)-8-aza-bicyclo[3.2.1]oct-3-ylmethyl]-phenyl}-urea (0.0332 g), C36H42N6O2, 590.78, 591.3, M+H, 3.25, Compound A1640;

4-{4-[3-(5-tert-Butyl-2-p-tolyl-2H-pyrazol-3-yl)-ureido]-benzyl}-piperidine-1-carboxylic acid (1-acetyl-3-oxo-3-phenyl-propenyl)-amide (21 mg), C39H44N6O4, 660.82, 661.36, M+H, 3.95, Compound A1641;

1-(5-tert-Butyl-2-p-tolyl-2H-pyrazol-3-yl)-3-{4-[1-(4,5-dihydro-benzofuran-6-carbonyl)-piperidin-4-ylmethyl]-phenyl}-urea (0.0126 g), C36H41N5O3, 591.76, 592.26, M+H, 3.70, Compound A1642;

1-(5-tert-Butyl-2-p-tolyl-2H-pyrazol-3-yl)-3-{2-[8-(2,4-dimethoxy-benzoyl)-8-aza-bicyclo [3.2.1] oct-3-ylmethyl]-phenyl}-urea (1.5 mg), C38H45N5O4, 635.81, 636.31, M+H, 3.61, Compound A1643;

4-{4-[3-(5-tert-Butyl-2-p-tolyl-2H-pyrazol-3-yl)-ureido]-benzyl}-piperidine-1-carboxylic acid (1R,2S,5R)-2-isopropyl-5-methyl-cyclohexyl ester(9.7 mg), C38H53N5O3, 627.88, 628.39, M+H, 4.35, Compound A1644;

1-(5-tert-Butyl-2-p-tolyl-2H-pyrazol-3-yl)-3-{4-[1-(1-oxy-pyridine-3-carbonyl)-piperidin-4-ylmethyl]-phenyl}-urea (45 mg), C33H38N6O3, 566.30, 567.28, M+H, 3.34, Compound A1645;

1-(5-tert-Butyl-2-p-tolyl-2H-pyrazol-3-yl)-3-(3-{1-[2-(2,5-dimethoxy-phenyl)-acetyl]-piperidin-4-ylmethyl}-phenyl)-urea (0.001 g), C37H45N5O4, 623.80, 624.3, M+H, 3.65, Compound A1646;

1-(5-tert-Butyl-2-p-tolyl-2H-pyrazol-3-yl)-3-{4-[8-(2,5-dimethoxy-benzoyl)-8-aza-bicyclo[3.2.1]oct-3-ylmethyl]-phenyl}-urea (0.0421 g), C38H45N5O4, 635.81, 636.28, M+H, 3.28, Compound A1647.

In vitro and In vivo Test Procedures

1. Inhibitory Effects of Compounds Against p38 in a Novel Cascade Assay

The compounds of the disclosure were tested in an assay designed to identify compounds that interact preferentially with the inactive enzyme. In this novel 'cascade' assay, compound was incubated with inactive p38 prior to addition of MKK-6 (upstream activator), substrate (ATF-2) and ATP. Theoretically, compounds that interact with the inactive enzyme would be more selective and, perhaps, demonstrate improved safety margins compared with the ATP competitive compounds.

The homogeneous time resolved fluorescence method (HTRF) assay measured the phosphorylation of human activating transcription factor (ATF)-2 protein by P38 following activation by MKK-6 and was run in A384 well plate format. Inactive N-terminal His6 tagged murine P38 (final concentration 20 mM) was incubated with compound (in 1% dimethyl sulphoxide, DMSO) for 30 minutes in kinase assay buffer (HEPES, pH 8.0, containing 0.15 M NaCl, 10 mM MgCl2, 2 mM dithiothreitol, 5% glycerol, 0.01% Triton X-100, 0.10% γ-globulins). MBP-tagged mouse MKK-6 (final concentration 50 nM), GST-tagged ATF-2 (fmal concentration 200 nM) and ATP (final concentration 50 µM) were then added and the incubation continued for 90 min. p38, MKK-6 and ATF-2 were prepared in the Protein Production Group, Aventis Pharmaceuticals. XL665 labeled anti-GST antibody (Cis Bio International) and cryptate labeled anti-pbospho-ATF2 antibody (Cis Bio International) were then added to generate the specific signal proportional to the phosphorylation of the substrate. The close proximity of XL665 labeled anti-GST antibody/phosphorylated GST-ATF2 complex and the cryptate labeled anti-phospho-ATF2 antibody results in a fluorescence transfer from cryptate to XL665. The resulting fluorescence signal was than read on a LJL Acquest set at multi-method mode using a fluorescence filter set (E=360 nm, $E_m$=615/665 nm) with UV dichroic mirror (Integration time: 300000 µs). The results are reported as $IC_{50}$ values. Compounds were tested over the concentration range of $3\times10^{-10}$M to $3\times10^{-5}$M.

1.1 Results

Compounds within the scope of the invention produce 50% inhibition in the p38 cascade assay at concentrations within the range 0.3 nanomolar to 10000 nanomolar. Preferred compounds within the scope of the invention produce 50% inhibition in the p38 cascade assay at concentrations within the range 0.3 nanomolar to 500 nanomolar. Especially preferred compounds within the scope of the invention produce 50% inhibition in the p38 cascade assay at concentrations within the range 10 nanomolar to 100 nanomolar.

2. Inhibitory Effects of Compounds on Murine p38α a in Standard Assay

Compounds of the invention were tested in a conventional assay against pre-activated p38. Murine p38 enzyme activity was determined by measuring the incorporation of the γ-phosphate of ATP into ATF-2.

Human GST-tagged ATF-2 (50 µg/ml) was coated onto 96 well plates. Assay buffer (25 mM Hepes buffer, pH 7.7 containing 25 mM magnesium chloride, 2 mM dithiothreitol, 1 mM sodium orthovanadate and 100 µM ATP) was then added to each well. Compounds were dissolved in DMSO (100%) and added to the assay buffer to give a fmal DMSO concentration of 0.3%. Murine p38 (CalBiochem Catalog # 506122; 40 ng/ml) was then added and the assay continued for 1 hour.

Phosphorylated ATF-2 was quantitated using a rabbit anti-human phospho (threonine 71)-specific ATF-2 primary antibody (Cell Signaling, Catalog # 9221B) followed by a sheep europium $N^1$-labelled anti-rabbit IgG secondary antibody (Perkin Elmer Life Sciences Catalog # AD0105) and addition of the DELFIA enhancement solution (Perkin Elmer Life Sciences) resulting.

Fluorescence was measured using a Wallac Victor² 1420 multi-label HTS counter (Perkin Elmer Life Sciences). The results are reported as $IC_{50}$ values. Compounds were tested over the concentration range of $3\times10^{-10}$M to $3>10^{-5}$M.

2.1 Results

Compounds within the scope of the invention produce 50% inhibition in the murine p38 assay at concentrations within the range 10 nanomolar to 50000 nanomolar. Preferred compounds within the scope of the invention produce 50% inhibition in the murine p38 assay at concentrations within the range 10 nanomolar to 500 nanomolar. Especially preferred compounds within the scope of the invention produce 50% inhibition in the murine p38 assay at concentrations within the range 10 nanomolar to 100 nanomolar.

3. Inhibitory Effects of Compounds on LPS-Induced TNF-Alpha Release in THP-1 Cells The effects of compounds on TNF-alpha production by lipopolysaccharide (LPS)-stimulated Tamm-Horsfall protein (THP)-1 Human monocytes were examined as follows.

3.1. Preparation of THP-1 Cells

Undifferentiated THP-1 cells were maintained in RPMI 1640 with Glutamax I containing β-mercaptoethananol (50 µM) and foetal calf serum (FCS-10%) at densities of about $1\times10^6$ cells per ml. For incubations without and with test reagents, cells were seeded at the indicated densities under serum-deprived (1% FCS) conditions. Compounds were dissolved in dimethylsulfoxide (DMSO-100%) and incubated with the cells to give a fmal DMSO concentration of 0.3%. Control and untreated cell samples were incubated with DMSO (0.3%).

3.2. Measurement of Monocyte TNF-Alpha Release

THP-1 cells ($1\times10^6$ cells/ml, total volume 150 µl) in culture medium were incubated for 1 hour (5% $CO_2$, 37° C.) with fresh medium containing compounds or vehicle (0.1-0.3% dimethylsulfoxide). LPS (20 µg/ml) was then added to the cells and the incubation continued for a fuirther 18 hours. Cell supernatants were removed into 96 well plates for storage at −20° C.

TNF-alpha concentrations in cell supernatants were quantified by sandwich ELISA. Briefly, ELISA plates were coated overnight with 2 µg/ml of mouse anti-human TNF-alpha antibody in bicarbonate buffer (pH 9.9). After washing the wells with wash buffer (0.05% (v/v) Tween in PBS)and blocking unoccupied sites (1% BSA in wash buffer), monocyte supernatant samples or human recombinant TNF-alpha standards were added into the corresponding wells of the ELISA plate at 1:10 dilution. Biotinylated rabbit polyclonal anti-human TNF-alpha antibody (3 µg/ml) was used as the second antibody and streptavidin-horseradish peroxidase was used as the detection antibody. The peroxidase substrate is 3,3',5,5'-tetramethylbenzidine (TMB) in the presence of hydrogen peroxide.

TNFα concentrations in supernatants from control and LPS-stimulated monocyte incubations were calculated by interpolation from a standard (log/log) curve (0.125-16 ng/ml) fitted by Excel Fit using the Activity Base software. Compounds were tested within the concentration range of $1 \times 10^{-9}$M to $1 \times 10^{-6}$M.

3.3 Results

Compounds within the scope of the invention produce 50% inhibition in the LPS-induced TNF-alpha release in THP-1 cells assay at concentrations within the range 10 nanomolar to 50000 nanomolar. Preferred compounds within the scope of the invention produce 50% inhibition in the LPS-induced TNF-alpha release in THP-1 cells assay at concentrations within the range 10 nanomolar to 500 nanomolar. Especially preferred compounds within the scope of the invention produce 50% inhibition in the LPS-induced TNF-alpha release in THP-1 cells assay at concentrations within the range 10 nanomolar to 100 nanomolar.

4. Inhibitory Effects of Compounds on LPS-Induced TNF-Alpha Release in Human Whole Blood Human Blood was collected from donors in heparinized vacutainer tubes and aliquoted into microtiter plates (125 μl/well). Compounds (50 □l) were incubated with the whole blood for 1 hour before lipopolysaccharide (LPS 10 ng/ml, 75 μl) was added and incubations (total volume 250 μl) continued for 5 h. At the end of the incubation, whole blood was removed and centrifuged at 2000 RPM for 5 minutes. Plasma TNF-alpha and IL-1-beta were measured by ELISA (Biosorce kits) as recommended by the manufacturer. Values for TNF-alpha were calculated from a recombinant human TNF-alpha standard curve. The results are reported as $IC_{50}$ values. Compounds were tested over the concentration range of $1 \times 10^{-9}$M to $1 \times 10^{-5}$M.

5. Inhibitory Effects of Compounds on Serum TNF-Alpha Levels in LPS-Challenged Rats 5.1 Treatment of Animals and Measurement of Murine TNF-Alpha Male Sprague Dawley rats [age 7-10 weeks, or 10-12 weeks (weight 150-200 g) from Harlan, U.S.A.] in groups of 6 or more were dosed p.o. or i.v. with compounds (1.0 to 30 mg/kg, 0.5-8 hrs) suspended in 0.5% methylcellulose containing 0.2% Tween-80 (or a suitable vehicle for i.v. dosing). The animals were then challenged with A40 μg/rat i.v. dose of LPS in 0.2 ml of 0.9% saline, usually 30 minutes after compound dosing. Ninety minutes after i.v. injection of LPS, each rat was anesthetized by isoflurane inhalation. Each rat was bled by cardiac puncture and terminated by cervical dislocation. The blood was allowed to clot, then centrifuged at 4000-5000 g for 5 minutes, and the serum taken for TNF-alpha analysis. TNF-alpha levels were measured using a commercially available rat TNF-alpha ELISA kit, purchased from R & D Systems (Cat. No. RTA00), as recommended by the manufacturer. Values for TNF-alpha were calculated from a recombinant rat TNF-alpha standard curve.

5.2 Results

Compounds within the scope of the invention inhibit TNF-alpha release in LPS challenged mice up to 90% at doses of 3 mg/kg to 30 mg/kg.

6. Inhibitory Effects of Compounds on Disease Symptoms in Rat Type II Collagen-Induced Arthritis (CIA)

Bovine Nasal Type II Collagen (Elastin Products) was dissolved in 0.45 μm vacuum-filtered 0.01 M acetic acid and stirred at 4° C. overnight for a final concentration of 2 mg/ml. 10 ml Incomplete Freund's Adjuvant (Difco) was brought to 4° C. in cold room. 10 ml collagen/acetic acid solution was added drop-wise while mixing at low speed with PowerGen Homogenizer (Fisher). The resulting emulsion was mixed at high speed for one minute, allowed to return to 4° C., and mixed at high speed for one additional minute. Final collagen concentration is 1 mg/ml.

Female Lewis rats (Charles River) weighing 140-160 g were used. Fur at base of tail was shaved and the area swabbed with ethanol. Using 25 G needle and glass syringe, 0.4 ml of collagen emulsion was injected intradermally at base of tail on Day 0 and again on Day 7.

Groups of at least 10 rats each were dosed orally with compounds typically suspended in 0.5% methylcellulose (Sigma)/0.2% Tween-80 (Acros Organics) vehicle twice daily from Day 6 through Day 21. Control groups were dosed either once daily with 3 mg/kg Leflunomide (Aventis) suspended in vehicle, or twice daily with 10 ml/kg vehicle only.

Ankle width, measured using digital calipers (Electronix Express), and individual body weights were recorded 2-3 times per week from Day 6 through Day 21. Blood plasma and/or serum was taken one hour after final dose on Day 21. Animals were then euthanized and their ankles/hindpaws were removed using a guillotine, weighed, and preserved in formalin for subsequent histological analysis. Compounds were tested at doses of 1-30 mg/kg (q.d. or b.i.d.).

7. In Vitro Inhibitory Effects of Compounds on Human HSP27 Phosphorylation

The effects of compounds on Heat Shock Protein (HSP)-27 phosphorylation in LPS stimulated THP-1 cells were examined as follows:

7.1 Preparation of THP-1 Cells

THP-1 cells were maintained as described for the TNF-alpha assay (1.1.).

7.2 Measurement of HSP27 Phosphorylation

THP-1 cells ($1 \times 10^6$ cells/ml, total volume 1 ml) in culture medium were incubated for one hour (5% $CO_2$, 37° C.) with fresh medium containing compounds (0.0001-30 μM) or vehicle (0.1% DMSO). LPS (20 μl/ml) was then added to the cells (except the untreated cell sample) and the incubation continued for a further 20 minutes. Cells were collected, centrifuiged and washed with ice-cold PBS buffer (free of $Ca^{2+}$ and $Mg^{2+}$). Cell lysates were prepared with 1× lysis buffer (Promega Catalog# E153A) for storage at −20° C.

HSP27 phosphorylation was determined by Western blot-enhanced chemi-luminescence (ECL-Amersham)). Briefly, cell lysates were electrophoresed on 12% Tris-glycine gels and transferred to nitrocellulose membranes. The membranes were then probed with primary rabbit antiphospho-HSP27 (ser82) antibody and secondary anti-rabbit antibody conjugated to horse raddish peroxidase. After addition of the ECL detection reagent, the film was developed and the p-HSP27 immunoreactivity quantified by densitometry.

Results

| Compound | Mouse p38 (nM) | THP 1 cells (nM) | HSP-27 (nM) |
| --- | --- | --- | --- |
| Example 3 | 216 | 10.6 | 27 |
| Example 1 | 229.5 | 15.5 | |
| Example 2 | 500 | 83 | |

-continued

| Compound | Mouse p38 (nM) | THP 1 cells (nM) | HSP-27 (nM) |
|---|---|---|---|
| Example 4 | 1173 | 79.5 | |
| Example 5 | 6750 | 5110 | |

What is claimed is:

1. A compound of Formula (I):

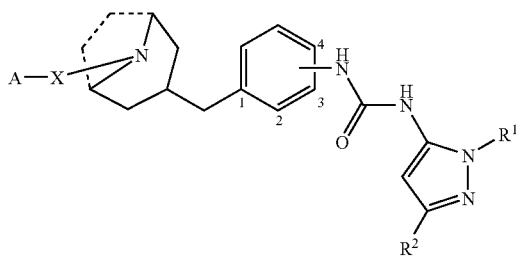

Formula (I)

wherein

is an optional ethylene bridge;

$R^1$ is alkyl, cycloalkyl, aryl or aryl substituted with one or more substituents selected from alkyl, alkoxy and amino, or $R^1$ is pyridyl or pyridyl substituted with one or more substituents selected from alkyl, alkoxy and amino;

$R^2$ is optionally substituted alkyl, alkoxyalkyl, optionally substituted cycloalkyl, optionally substituted cycloalkylalkyl, arylalkyl, or $R^2$ is arylalkyl substituted with one or more substituents selected from alkyl and alkoxy;

X is —C(O)—, —C(O)—CH$_2$—, —S(O)$_2$—, or —NHC(O)—; and

A is optionally substituted alkenyl, optionally substituted alkoxy, optionally substituted alkoxyalkyl, optionally substituted alkyl, optionally substituted alkynyl, optionally substituted aryl, optionally substituted arylalkyl, optionally substituted arylalkoxy, optionally substituted arylalkoxyalkyl, optionally substituted aryloxy, optionally substituted aryloxyalkyl, optionally substituted cycloalkenyl, optionally substituted cycloalkyl, optionally substituted cycloalkylalkyl, optionally substituted cycloalkyloxy, optionally substituted cycloalkyloxyalkyl, optionally substituted cyclalkylalkoxy, optionally substituted cycloalkylalkoxyalkyl, optionally substituted heteroaryl, optionally substituted heteroarylalkyl, optionally substituted heteroaryloxy, optionally substituted heteroaryloxyalkyl, optionally substituted heteroarylalkoxy, optionally substituted heteroarylalkoxyalkyl, optionally substituted heterocycloalkyl, optionally substituted heterocycloalkylalkyl, optionally substituted heterocycloalkyloxy, optionally substituted heterocycloalkyloxyalkyl; or a pharmaceutically acceptable salt of such compound.

2. A compound according to claim 1 of Formula (II):

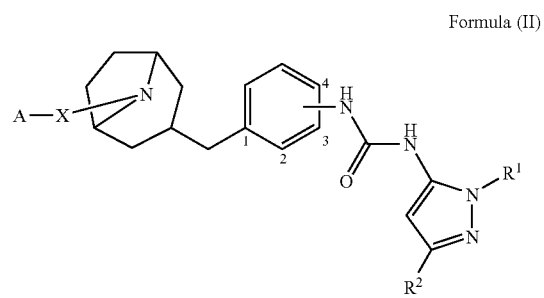

Formula (II)

wherein A, X, $R^1$ and $R^2$ are as defined in claim 1; or a pharmaceutically acceptable salt of such compound.

3. A compound according to claim 1 of Formula (III):

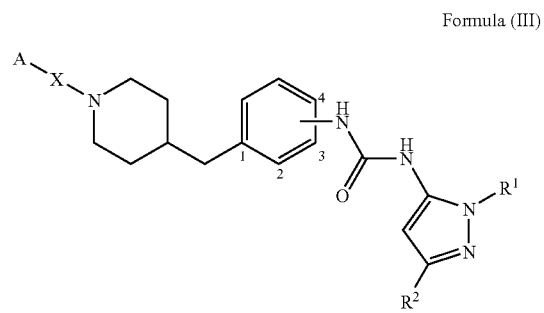

Formula (III)

wherein A, X, $R^1$ and $R^2$ are as defined in claim 1; or a pharmaceutically acceptable salt of such compound.

4. A compound according to claim 1 of Formula (IV):

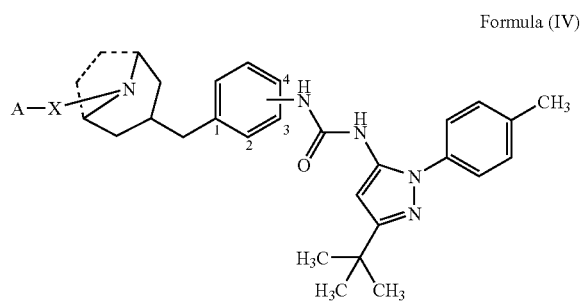

Formula (IV)

wherein

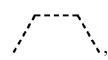

A and X are as defined in claim 1; or a pharmaceutically acceptable salt of such compound.

5. A compound according to claim 1 of Formula (V):

Formula (V)

wherein A and X are as defined in claim 1; or
a pharmaceutically acceptable salt of such compound.

6. A compound according to claim 1 of Formula (VI):

Formula (VI)

wherein A and X are as defined in claim 1; or
a pharmaceutically acceptable salt of such compound.

7. A compound according to claim 1, wherein X is —C(O)—.

8. A compound according to claim 1, wherein X is —C(O)—CH$_2$—.

9. A compound according to claim 1, wherein X is —S(O)$_2$—.

10. A compound according to claim 1, wherein X is —NHC(O)—.

11. A compound according to claim 1 wherein X is —CO—, and A is optionally substituted alkenyl, optionally substituted alkoxy, optionally substituted alkoxyalkyl, optionally substituted alkyl, optionally substituted alkynyl, optionally substituted aryl, optionally substituted arylailcyl, optionally substituted arylalkoxy, optionally substituted aryloxy, optionally substituted aryloxyalkyl, optionally substituted cycloalkenyl, optionally substituted cycloalkyl, optionally substituted cycloalkylalkyl, optionally substituted cycloalkyloxy, optionally substituted heteroaryl, optionally substituted heteroarylalkyl, optionally substituted heteroarylalkoxy, optionally substituted heterocycloalkyl or optionally substituted heterocycloalkylalkyl.

12. A compound according to claim 1 wherein X is —C(O)—CH$_2$, and A is optionally substituted aryl or optionally substituted heteroaryl.

13. A compound according to claim 1 wherein X is —S(O)$_2$—, and A is optionally substituted alkenyl, optionally substituted alkyl, optionally substituted aryl or optionally substituted heteroaryl.

14. A compound according to claim 1 wherein X is —NHC(O)—, and A is optionally substituted alkenyl, optionally substituted aryl or optionally substituted heteroaryl.

15. A compound according to claim 5 wherein X is —CO—, and A is optionally substituted alkoxyalkyl, optionally substituted alkyl, optionally substituted aryl, optionally substituted aiylalkyl, optionally substituted aryloxyalkyl, optionally substituted cycloalkyl, optionally substituted heteroaryl or optionally substituted heterocycloalkyl.

16. A compound according to claim 6 wherein X is —CO—, and A is optionally substituted alkoxyalkyl, optionally substituted alkyl, optionally substituted aryl, optionally substituted arylalkyl, optionally substituted aryloxyalkyl, optionally substituted cycloalkyl, optionally substituted heteroaryl or optionally substituted heterocycloalkyl.

17. A compound according to claim 5 wherein X is —S(O)$_2$ and A is optionally substituted alkyl, optionally substituted aryl or optionally substituted heteroaryl.

18. A compound according to claim 6 wherein X is —S(O)$_2$ and A is optionally substituted alkyl, optionally substituted aryl or optionally substituted heteroaryl.

19. A compound according to claim 5 wherein X is —NHC(O)— and A is optionally substituted alkenyl.

20. A compound according to claim 6 wherein X is —NHC(O)— and A is optionally substituted alkenyl.

21. A compound according to claim 5 wherein X is —NHC(O)— and A is 1-acetyl-3-oxo-3-phenyl-propenyl.

22. A compound according to claim 1 selected from the group consisting of:
1-(5-tert-butyl-2-p-tolyl-2H-pyrazol-3-yl)-3-{3-[1-(1-methyl-cyclopropanecarbonyl)-piperidin-4-ylmethyl]-phenyl}-urea;
1-(5-tert-butyl-2-p-tolyl-2H-pyrazol-3-yl)-3-{3-[1-(2,4-dimethoxy-benzoyl)-piperidin-4-ylmethyl]-phenyl}-urea;
1-(5-tert-butyl-2-p-tolyl-2H-pyrazol-3-yl)-3-{3-[1-(2,4-dimethyl-thiazole-5-carbonyl)-piperidin-4-ylmethyl]-phenyl}-urea;
1-(5-tert-butyl-2-p-tolyl-2H-pyrazol-3-yl)-3-{3-[1-(2-pyridin-3-yl-thiazole-4-carbonyl)-piperidin-4-ylmethyl]-phenyl}-urea;
1-(5-tert-butyl-2-p-tolyl-2H-pyrazol-3-yl)-3-{3-[1-(2-pyridin-4-yl-thiazole-4-carbonyl)-piperidin-4-ylmethyl]-phenyl}-urea;
1-(5-tert-butyl-2-p-tolyl-2H-pyrazol-3-yl)-3-{3-[1-(2-chloro-pyridine-3-carbonyl)-piperidin-4-ylmethyl]-phenyl}-urea;
1-(5-tert-butyl-2-p-tolyl-2H-pyrazol-3-yl)-3-(3-{1-[2-(2-fluoro-phenyl)-acetyl]-piperidin-4-ylmethyl}-phenyl)-urea;
1-(5-tert-butyl-2-p-tolyl-2H-pyrazol-3-yl)-3-{3-[1-(2-methyl-pyridine-3-carbonyl)-piperidin-4-ylmethyl]-phenyl}-urea;
N-[3-(4-{3-[3-(5-tert-butyl-2-p-tolyl-2H-pyrazol-3-yl)-ureido]-benzyl}-piperidine-1-carbonyl)-phenyl]-acetamide;
1-(5-tert-butyl-2-p-tolyl-2H-pyrazol-3-yl)-3-{3-[1-(4-methoxy-2-methyl-benzoyl)-piperidin-4-ylmethyl]-phenyl}-urea;
1-(5-tert-butyl-2-p-tolyl-2H-pyrazol-3-yl)-3-{3-[1-(4-methoxy-thiophene-3-carbonyl)-piperidin-4-ylmethyl]-phenyl}-urea;
1-(5-tert-butyl-2-p-tolyl-2H-pyrazol-3-yl)-3-{3-[1-(5-methyl-thiophene-2-carbonyl)-piperidin-4-ylmethyl]-phenyl}-urea;
N-[2-(4-{3-[3-(5-tert-butyl-2-p-tolyl-2H-pyrazol-3-yl)-ureido]-benzyl}-piperidin-1-yl)-2-oxo-ethyl]-benzamide;
1-(5-tert-butyl-2-p-tolyl-2H-pyrazol-3-yl)-3-{3-[1-(pyridine-4-carbonyl)-piperidin-4-ylmethyl]-phenyl}-urea;

1-(5-tert-butyl-2-p-tolyl-2H-pyrazol-3-yl)-3-{3-[1-(2-methoxy-acetyl)-piperidin-4-ylmethyl]-phenyl}-urea;

4-(4-{3-[3-(5-tert-butyl-2-p-tolyl-2H-pyrazol-3-yl)-ureido]-benzyl}-piperidin-1-yl)-4-oxo-butyric acid methyl ester;

N-[2-(4-{3-[3-(5-tert-butyl-2-p-tolyl-2H-pyrazol-3-yl)-ureido]-benzyl}-piperidin-1-yl)-2-oxo-ethyl]-acetamide;

1-(5-tert-butyl-2-p-tolyl-2H-pyrazol-3-yl)-3-{3-[1-(pyridine-3-carbonyl)-piperidin-4-ylmethyl]-phenyl}-urea;

1-(5-tert-butyl-2-p-tolyl-2H-pyrazol-3-yl)-3-(4-{1-[2-(2,4-difluoro-phenyl)-acetyl]-piperidin-4-ylinethyl}-phenyl)-urea;

1-(5-tert-butyl-2-p-tolyl-2H-pyrazol-3-yl)-3-{4-[1-(2,4-dimethoxy-benzoyl)-piperidin-4-ylmethyl]-phenyl}-urea;

1-(5-tert-butyl-2-p-tolyl-2H-pyrazol-3-yl)-3-{4-[1-(2,4-dimethyl-thiazole-5-carbonyl)-piperidin-4-ylmethyl]-phenyl}-urea;

1-(5-tert-butyl-2-p-tolyl-2H-pyrazol-3-yl)-3-{4-[1-(2,5-dimethoxy-benzoyl)-piperidin-4-ylmethyl]-phenyl}-urea;

1-(5-tert-butyl-2-p-tolyl-2H-pyrazol-3-yl)-3-{4-[1-(pyrazine-2-carbonyl)-piperidin-4-ylmethyl]-phenyl}-urea;

1-{4-[1-(3-Amino-pyrazine-2-carbonyl)-piperidin-4-ylmethyl]-phenyl}-3-(5-tert-butyl-2-p-tolyl-2H-pyrazol-3-yl)-urea;

1-(5-tert-butyl-2-p-tolyl-2H-pyrazol-3-yl)-3-{4-[1-(3-methyl-furan-2-carbonyl)-piperidin-4-ylmethyl]-phenyl}-urea;

1-(5-tert-butyl-2-p-tolyl-2H-pyrazol-3-yl)-3-{4-[1-(3-methyl-benzofuran-2-carbonyl)-piperidin-4-ylmethyl]-phenyl}-urea;

1-(5-tert-butyl-2-p-tolyl-2H-pyrazol-3-yl)-3-{4-[1-(3-phenoxy-propionyl)-piperidin-4-ylmethyl]-phenyl}-urea;

1-(5-tert-butyl-2-p-tolyl-2H-pyrazol-3-yl)-3-{4-[1-(thiophene-3-carbonyl)-piperidin-4-ylmethyl]-phenyl}-urea;

1-(5-tert-butyl-2-p-tolyl-2H-pyrazol-3-yl)-3-{4-[1-(5-chloro-6-hydroxy-pyridine-3-carhonyl)-piperidin-4-ylmethyl]-phenyl}-urea;

1-(5-tert-butyl-2-p-tolyl-2H-pyrazol-3-yl)-3-{4-[1-(5-methyl-pyrazine-2-carbonyl)-piperidin-4-ylmethyl]-phenyl}-urea;

1-(5-tert-butyl-2-p-tolyl-2H-pyrazol-3-yl)-3-{4-[1-(6-hydroxy-pyridine-3-carbonyl)-piperidin-4-ylmethyl]-phenyl}-urea;

1-(5-tert-butyl-2-p-tolyl-2H-pyrazol-3-yl)-3-{4-[1-(6-methyl-pyridine-2-carbonyl)-piperidin-4-ylmethyl]-phenyl}-urea;

Acetic acid 4-(4-{4-[3-(5-tert-butyl-2-p-tolyl-2H-pyrazol-3-yl)-ureido]-benzyl}-piperidine-1-carbonyl)-benzyl ester;

1-(5-tert-butyl-2-p-tolyl-2H-pyrazol-3-yl)-3-{4-[1-(4-oxo-4,5,6,7-tetrahydro-benzofuran-3-carbonyl)-piperidin-4-ylmethyl]-phenyl}-urea;

N-[2-(4-{4-[3-(5-tert-butyl-2-p-tolyl-2H-pyrazol-3-yl)-ureido[-benzyl}-piperidin-1-yl)-2-oxo-ethyl]-benzamide;

1-(5-tert-butyl-2-p-tolyl-2H-pyrazol-3-yl)-3-{4-[1-(1H-indole-5-carbonyl)-piperidin-4-ylmethyl]-phenyl}-urea;

1-(5-tert-butyl-2-p-tolyl-2H-pyrazol-3-yl)-3-{4-[1-(pyridine-4-carbonyl)-piperidin-4-ylmethyl]-phenyl}-urea;

1-(5-tert-butyl-2-p-tolyl-2H-pyrazol-3-yl)-3-{4-[1-(2-methoxy-acetyl)-piperidin-4-ylmethyl]-phenyl}-urea;

N-[2-(4-{4-[3-(5-tert-butyl-2-p-tolyl-2H-pyrazol-3-yl)-ureido]-benzyl}-piperidin-1-yl)-2-oxo-ethyll-acetamide;

1-(5-tert-butyl-2-p-tolyl-2H-pyrazol-3-yl)-3-{4-[1-(pyridine-3-carbonyl)-piperidin-4-ylmethyl]-phenyl}-urea;

1-(5-tert-butyl-2-p-tolyl-2H-pyrazol-3-yl)-3-{4-[1-(quinoline-6-carbonyl)-piperidin-4-ylmethyl]-phenyl}-urea;

1-(5-tert-butyl-2-p-tolyl-2H-pyrazol-3-yl)-3-[4-(1-methanesulfonyl-piperidin-4-ylmethyl)-phenyl]-urea;

N-[3-(3-{3-[3-(5-tert-butyl-2-p-tolyl-2HH-pyrazol-3-yl)-ureido]-benzyl}-8-aza-bicyclo[3,2,1]octane-8-carbonyl)-phenyl]-acetamide;

1-(5-tert-butyl-2-p-tolyl-2H-pyrazol-3-yl)-3-{3-[8-(4-methyl-3,4-dihydro-2H-benzo[1,4]oxazine-7-sulfonyl)-8-aza-bicyclo[3,2,1]oct-3-ylmethyl]-phenyl}-urea;

4-{4-[3-(5-tert-butyl-2-p-tolyl-2HH-pyrazol-3-yl)-ureido]-benzyl}-piperidine-1-carboxylic acid 4-methoxyphenyl ester;

4-{4-[3-(5-tert-butyl-2-p-tolyl-2H-pyrazol-3-yl)-ureido]-benzyl}-piperidine-1-carboxylic acid benzyl ester;

4-{4-[3-(5-tert-butyl-2-p-tolyl-2H-pyrazol-3-yl)-ureido]-benzyl}-piperidine-1-carboxylic acid isobutyl ester;

1-(5-tert-butyl-2-p-tolyl-2H-pyrazol-3-yl)-3-{3-[1-(2,5-dimethoxy-benzoyl)-piperidin-4-ylmethyl]-phenyl}-urea;

1-[4-(1-acetyl-piperidin-4-ylmethyl)-phenyl]-3-(5-tert-butyl-2-p-tolyl-2H-pyrazol-3-yl)-urea;

1-{3-[1-(benzofuran-2-carbonyl)-piperidin-4-ylmethyl]-phenyl}-3-(5-tert-butyl-2-p-tolyl-2H-pyrazol-3-yl)-urea;

1-(5-tert-butyl-2-p-tolyl-2H-pyrazol-3-yl)-3-{3-[1-(piperidine-4-carbonyl)-piperidin-4-ylmethyl]-phenyl}-urea;

1-(5-tert-butyl-2-p-tolyl-2H-pyrazol-3-yl)-3-{4-[8-(6-methyl-pyridine-2-carbonyl)-8-aza-bicyclo[3,2,1]oct-3-ylmethyl]-phenyl}-urea;

4-{4-[3-(5-tert-butyl-2-p-tolyl-2H-pyrazol-3-yl)-ureido]-benzyl}-piperidine-1-carboxylic acid (1-acetyl-3-oxo-3-phenyl-propenyl)-amide;

4-{4-[3-(5-tert-Butyl-2-p-tolyl-2H-pyrazol-3-yl)-ureido]-benzyl}-piperidine-1-carboxylic acid (1R,2S,5R)-2-isopropyl-5-methyl-cyclohexyl ester; and 1-[4-(1-Acetyl-piperidin-4-ylmethyl)-phenyl]-3-(5-tert-butyl-2-p-tolyl-2H-pyrazol-3-yl)-urea; or A pharmaceutically acceptable salt of such compound.

23. A compound according to claim 1 selected from the group consisting of:

1-(5-tert-butyl-2-p-tolyl-2H-pyrazol-3-yl)-3-{3-[1-((S)-2-methoxy-2-phenyl-acetyl)-piperidin-4-ylmethyl]-phenyl}-urea;

1-(5-tert-butyl-2-p-tolyl-2H-pyrazol-3-yl)-3-{3-[1-([1,2,3]thiadiazole-4-carbonyl)-piperidin-4-ylmethyl]-phenyl}-urea;

1-(5-tert-butyl-2-p-tolyl-2HH-pyrazol-3-yl)-3-{3-[1-(2,3-dimethoxy-benzoyl)-piperidin-4-ylmethyl]-phenyl}-urea;

1-(5-tert-butyl-2-p-tolyl-2H-pyrazol-3-yl)-3-{3-[1-(2,4,6-trimethoxy-benzoyl)-piperidin-4-ylmethyl]-phenyl}-urea;

1-(5-tert-butyl-2-p-tolyl-2H-pyrazol-3-yl)-3-{3-[1-(2,4-dimethoxy-benzoyl)-piperidin-4-ylmethyl]-phenyl}-urea;

1-(5-tert-butyl-2-p-tolyl-2H-pyrazol-3-yl)-3-{3-[1-(2,4-dimethyl-thiazole-5-carbonyl)-piperidin-4-ylmethyl[-phenyl}-urea;

1-(5-tert-butyl-2-p-tolyl-2H-pyrazol-3-yl)-3-{3-[1-(2,5-dimethyl-furan-3-carbonyl)-piperidin-4-ylmethyl]-phenyl}-urea;

1-(5-tert-butyl-2-p-tolyl-2H-pyrazol-3-yl)-3-{3-[1-(2-chloro-4-methanesulfonyl-benzoyl)-piperidin-4-ylmethyl]-phenyl}-urea;

1-(5-tert-butyl-2-p-tolyl-2H-pyrazol-3-yl)-3-{3-[1-(2-chloro-pyridine-3-carbonyl)-piperidin-4-ylmethyl]-phenyl}-urea;

1-(5-tert-butyl-2-p-tolyl-2H-pyrazol-3-yl)-3-{3-[1-(furan-2-carbonyl)-piperidin-4-ylmethyl]-phenyl}-urea;

1-(5-tert-butyl-2-p-tolyl-2H-pyrazol-3-yl)-3-{3-[1-(2-methyl-furan-3-carbonyl)-piperidin-4-ylmethyl]-phenyl}-urea;

N-[3-(4-{3-[3-(5-tert-butyl-2-p-tolyl-2H-pyrazol-3-yl)-ureido]-benzyl}-piperidine-1-carbonyl)-phenyl]-acetamide;

1-(5-tert-butyl-2-p-tolyl-2H-pyrazol-3-yl)-3-{3-[1-(furan-3-carbonyl)-piperidin-4-ylmethyl]-phenyl}-urea;

1-(5-tert-butyl-2-p-tolyl-2H-pyrazol-3-yl)-3-{3-[1-(3-methyl-furan-2-carbonyl)-piperidin-4-ylmethyl]-phenyl}-urea;

1-(5-tert-hutyl-2-p-tolyl-2H-pyrazol-3-yl)-3-{3-[1-(thiophene-3-carbonyl)-piperidin-4-ylmethyl]-phenyl}-urea;

1-(5-tert-butyl-2-p-tolyl-2H-pyrazol-3-yl)-3-{3-[1-(4-hydroxymethyl-benzoyl)-piperidin-4-ylmethyl]-phenyl}-urea;

1-(5-tert-butyl-2-p-tolyl-2H-pyrazol-3-yl)-3-{3-[1-(4-methoxy-2-methyl-benzoyl)-piperidin-4-ylmethyl]-phenyl}-urea;

1-(5-tert-butyl-2-p-tolyl-2H-pyrazol-3-yl)-3-{3-[1-(4-methoxy-thiophene-3-carbonyl)-piperidin-4-ylmethyl]-phenyl}-urea;

1-(5-tert-butyl-2-p-tolyl-2H-pyrazol-3-yl)-3-{3-[1-(5-chloro-thiophene-2-carbonyl)-piperidin-4-ylmethyl]-phenyl}-urea;

1-(5-tert-butyl-2-p-tolyl-2H-pyrazol-3-yl)-3-(3-{1-[5-methoxy-2-(2,2,2-trifluoro-ethoxy)-benzoyl]-piperidin-4-ylmethyl}-phenyl)-urea;

1-(5-tert-butyl-2-p-tolyl-2H-pyrazol-3-yl)-3-{3-[1-(5-methyl-thiophene-2-carbonyl)-piperidin-4-ylmethyl]-phenyl}-urea;

acetic acid 4-(4-{3-[3-(5-tert-butyl-2-p-tolyl-2H-pyrazol-3-yl)-ureido]-benzyl}-piperidine-1-carbonyl)-benzyl ester;

1-(5-tert-butyl-2-p-tolyl-2H-pyrazol-3-yl)-3-{4-[1-(1-methyl-cyclopropanecarbonyl)-piperidin-4-ylmethyl]-phenyl}-urea;

1-(5-tert-butyl-2-p-tolyl-2H-pyrazol-3-yl)-3-{4-[1-(2,3-dimethoxy-benzoyl)-piperidin-4ylmethyl]-phenyl}-urea;

1-(5-tert-butyl-2-p-tolyl-2H-pyrazol-3-yl)-3-{4-[1-(2,4-dimethoxy-benzoyl)-piperidin-4-ylmethyl]-phenyl}-urea;

1-(5-tert-butyl-2-p-tolyl-2H-pyrazol-3-yl)-3-{4-[1-(2,4-dimethyl-thiazole-5-carbonyl)-piperidin-4-ylmethyl]-phenyl}-urea;

1-(5-tert-butyl-2-p-tolyl-2H-pyrazol-3-yl)-3-{4-[1-(2,5-dimethoxy-benzoyl)-piperidin-4-ylmethyl]-phenyl}-urea;

1-(5-tert-butyl-2-p-tolyl-2H-pyrazol-3-yl)-3-{4-[1-(2,5-dimethyl-furan-3-carbonyl)-piperidin-4-ylmethyl]-phenyl}-urea;

1-(5-tert-butyl-2-p-tolyl-2H-pyrazol-3-yl)-3-{4-[1-(2,6-dimethoxy-pyridine-3-carbonyl)-piperidin-4-ylmethyl]-phenyl}-urea;

1-(5-tert-butyl-2-p-tolyl-2H-pyrazol-3-yl)-3-{4-[1-(2-pyridin-3-yl-thiazole-4-carbonyl)-piperidin-4-ylmethyl]-phenyl}-urea;

1-(5-tert-butyl-2-p-tolyl-2H-pyrazol-3-yl)-3-{4-[1-(2-pyridin-4-yl-thiazole-4-carbonyl)-piperidin-4-ylmethyl]-phenyl}-urea;

1-(5-tert-butyl-2-p-tolyl-2H-pyrazol-3-yl)-3-{4-[1-(2-chloro-pyridine-3-carbonyl)-piperidin-4-ylmethyl]-phenyl}-urea;

1-(5-tert-butyl-2-p-tolyl-2H-pyrazol-3-yl)-3-{4-[1-(2-methyl-furan-3-carbonyl)-piperidin-4-ylmethyl]-phenyl}-urea;

1-(5-tert-butyl-2-p-tolyl-2H-pyrazol-3-yl)-3-{4-[1-(2-methyl-[1,8]naphthyridine-3-carbonyl)-piperidin-4-ylmethyl]-phenyl}-urea;

1-(5-tert-butyl-2-p-tolyl-2H-pyrazol-3-yl)-3-{4-[1-(pyrazine-2-carbonyl)-piperidin-4-ylmethyl]-phenyl}-urea;

1-(5-tert-butyl-2-p-tolyl-2H-pyrazol-3-yl)-3-(4-{1-[3-(cyano-methyl-methyl)-benzoyl]-piperidin-4-ylmethyl}-phenyl)-urea;

1-(5-tert-butyl-2-p-tolyl-2H-pyrazol-3-yl)-3-{4-[1-(furan-3-carbonyl)-piperidin-4-ylmethyl]phenyl}-urea;

1-(5-tert-butyl-2-p-tolyl-2H-pyrazol-3-yl)-3-{4-[1-(3-methyl-furan-2-carbonyl)-piperidin-4-ylmethyl]-phenyl}-urea;

1-(5-tert-butyl-2-p-tolyl-2H-pyrazol-3-yl)-3-{4-[1-(thiophene-3-carbonyl)-piperidin-4-ylmethyl]-phenyl}-urea;

1-(5-tert-butyl-2-p-tolyl-2H-pyrazol-3-yl)-3-{4-[1-(4-oxazol-5-yl-benzoyl)-piperidin-4-ylmethyl]-phenyl}-urea;

1-(5-tert-butyl-2-p-tolyl-2H-pyrazol-3-yl)-3-{4-[1-(4-difluoromethoxy-benzoyl)-piperidin-4-ylmethyl]-phenyl}-urea;

1-(5-tert-butyl-2-p-tolyl-2H-pyrazol-3-yl)-3-{4-[1-(4-hydroxymethyl-benzoyl)-piperidin-4-ylmethyl]-phenyl}-urea;

1-(5-tert-butyl-2-p-tolyl-2H-pyrazol-3-yl)-3-(4-{1-[2-(4-methoxy-phenyl)-acetyl]-piperidin-4-ylmethyl}-phenyl)-urea;

1-{4-[1-(6-amino-pyridine-3-carbonyl)-piperidin-4-ylmethyl]-phenyl}-3-(5-tert-butyl-2-p-tolyl-2H-pyrazol-3-yl)-urea;

1-(5-tert-butyl-2-p-tolyl-2H-pyrazol-3-yl)-3-{4-[1-(6-methyl-pyridine-2-carbonyl)-piperidin-4-ylmethyl]-phenyl}-urea;

acetic acid 4-(4-{4-[3-(5-tert-butyl-2-p-tolyl-2H-pyrazol-3-yl)-ureido]-benzyl}-piperidine-1-carbonyl)-benzyl ester;

N-[2-(4-{4-[3-(5-tert-butyl-2-p-tolyl-2H-pyrazol-3-yl)-ureido]-benzyl}-piperidin-1-yl)-2-oxo-ethyl]-benzamide;

1-(5-tert-butyl-2-p-tolyl-2H-pyrazol-3-yl)-3-{4-[1-(1H-indole-5-carbonyl)-piperidin-4-ylmethyl]-phenyl}-urea;

1-(5-tert-butyl-2-p-tolyl-2H-pyrazol-3-yl)-3-{4-[1-(1H-indole-6-carbonyl)-piperidin-4-ylmethyl]-phenyl}-urea;

1-(5-tert-butyl-2-p-tolyl-2H-pyrazol-3-yl)-3-{4-[1-(pyridine-4-carbonyl)-piperidin-4-ylmethyl]-phenyl}-urea;

1-(5-tert-butyl-2-p-tolyl-2H-pyrazol-3-yl)-3-(4-{1-[3-(4,6-dimethyl-pyrimidin-2-ylaniino)-benzoyl]-piperidin-4-ylmethyl}-phenyl)-urea;

1-(5-tert-butyl-2-p-tolyl-2H-pyrazol-3-yl)-3-{4-[1-(pyridine-3-carbonyl)-piperidin-4-ylmethyl]-phenyl}-urea;

1-(5-tert-butyl-2-p-tolyl-2H-pyrazol-3-yl)-3-{4-[1-(pyridine-2-carbonyl)-piperidin-4-ylmethyl]-phenyl}-urea;

1-(5-tert-butyl-2-p-tolyl-2H-pyrazol-3-yl)-3-{4-[1-(quinoline-6-carbonyl)-piperidin-4-ylmethyl]-phenyl}-urea;

1-(5-tert-butyl-2-p-tolyl-2fl-pyrazol-3-yl)-3-{4-[1-(2,5-dimethoxy-benzenesulfonyl)-piperidin-4-ylmethyl]-phenyl}-urea;

1-(5-tert-butyl-2-p-tolyl-2H-pyrazol-3-yl)-3-{4-[1-(2-methoxy-5-methyl-benzenesulfonyl)-piperidin-4-ylmethyl]-phenyl}-urea;

1-(5-tert-butyl-2-p-tolyl-2H-pyrazol-3-yl)-3-[4-(1-methanesulfonyl-piperidin-4-ylmethyl)-phenyl]-urea;

1-(5-tert-butyl-2-p-tolyl-2H-pyrazol-3-yl)-3-{3-8-(2,3-dimethoxy-benzoyl)-8-aza-bicyclo[3,2,1]oct-3-ylmethyl]-phenyl}-urea;

1-(5-tert-butyl-2-p-tolyl-2H-pyrazol-3-yl)-3-{2-[1-(2,4-dimethoxy-benzoyl)-piperidin-4ylmethyl]-phenyl}-urea;

4-{4-[3-(5-tert-butyl-2-p-tolyl-2H-pyrazol-3-yl)-ureido]-benzyl}-piperidine-1-carboxylic acid isobutyl ester;

1-(5-tert-butyl-2-p-tolyl-2H-pyrazol-3-yl)-3-{3-[1-(2,5-dimethoxy-benzoyl)-piperidin-4-ylmethyl]-phenyl}-urea; and 1-(5-tert-butyl-2-p-tolyl-2H-pyrazol-3-yl)-3-{4-[1-(4,5-dihydro-benzofuran-6-carbonyl)-piperidin-4-ylmethyl]-phenyl}-urea; or A pharmaceutically acceptable salt of such compound.

24. A pharmaceutical composition comprising a compound according to claim 1, together with a pharmaceutically acceptable carrier or excipient.

* * * * *